United States Patent
Griffioen et al.

(10) Patent No.: US 8,722,681 B2
(45) Date of Patent: May 13, 2014

(54) N-SULFONYL THIAZOLYLPIPERAZINE DERIVATIVES AND RELATED N-SULFONYL HETEROCYCLIC DERIVATIVES FOR THE TREATMENT OF NEURO DEGENERATIVE DISEASES

(75) Inventors: Gerard Griffioen, Linden (BE); Veronica Rojas De La Parra, Haasrode (BE); Annick Lauwers, Herent (BE)

(73) Assignee: NV reMYND, Heverlee (BE)

( * ) Notice: Subject to any disclaimer, the term of this patent is extended or adjusted under 35 U.S.C. 154(b) by 176 days.

(21) Appl. No.: 12/701,361

(22) Filed: Feb. 5, 2010

(65) Prior Publication Data

US 2010/0197703 A1    Aug. 5, 2010

Related U.S. Application Data

(63) Continuation-in-part of application No. PCT/EP2008/060362, filed on Aug. 6, 2008.

(30) Foreign Application Priority Data

Aug. 6, 2007  (GB) .................................. 0715256.4
Aug. 6, 2007  (GB) .................................. 0715257.2

(51) Int. Cl.
*A61K 31/496*  (2006.01)
*C07D 277/42*  (2006.01)
*C07D 417/12*  (2006.01)
*A61K 31/454*  (2006.01)

(52) U.S. Cl.
USPC .................. 514/253.1; 514/254.02; 514/318; 514/326; 544/364; 544/369; 546/193; 546/194; 546/209

(58) Field of Classification Search
None
See application file for complete search history.

(56) References Cited

U.S. PATENT DOCUMENTS

| 2005/0234033 | A1 | 10/2005 | Anandan et al. |
| 2005/0234046 | A1 | 10/2005 | Zhao et al. |
| 2008/0255147 | A1 | 10/2008 | Wilson et al. |

FOREIGN PATENT DOCUMENTS

| WO | WO 2005/042521 A2 | 5/2005 |
| WO | WO 2006/105127 A2 | 10/2006 |
| WO | WO 2006/130493 A2 | 12/2006 |

OTHER PUBLICATIONS

Lamberto et al. Journal of Biological Chemistry,vol. 286, p. 32036-32044 (2011).*
CA Registry No. 938852-08-5, entered into the CA Registry File on May 1, 2007, supplied by TimTec, Inc.*
CA Registry No. 385375-22-4, entered into the CA Registry File on Jan. 22, 2002, supplied by Ambinter.*
CA Registry No. 606088-65-7, entered into the CA Registry File on Oct. 17, 2003, supplied by AsInEx.*
CA Registry No. 837386-06-8, entered into the CA Registry File on Feb. 25, 2005, supplied by AsInEx.*
CA Registry No. 837386-37-5, entered into the CA Registry File on Feb. 25, 2005, supplied by AsInEx.*
CA Registry No. 936074-98-5, entered into CA Registry File on May 30, 2007, supplied by Chemical Block, Ltd.*
CA Registry No. 933827-86-2, entered into CA Registry File on May 1, 2007, supplied by TimTec, Inc.*
CA Registry No. 909236-51-7, entered into CA Registry File on Oct. 2, 2006, supplied by Scientific Exchange, Inc.*
CA Registry No. 1105216-29-2, entered into CA Registry File on Feb. 13, 2009, supplied by Life Chemicals, Inc.*
CA Registry No. 1170239-17-4, entered into CA Registry File on Jul. 29, 2009, supplied by Ambinter.*
CA Registry No. 1170231-22-7, entered into CA Registry File on Jul. 29, 2009, supplied by Ambinter.*
Collins et al., "N-(2-Benzoylphenyl)-L-tyrosine PPARgamma agonists. 2. Structure-activity relationship and optimization of the phenyl alkyl ether moiety," *J. Med. Chem.* 41:5037-5054, 1998.
Hyun et al., "Receptor-based 3D QSAR Studies on PPARγ Agonists using CoMFA and CoMSIA Approaches," *QSAR Comb. Sci.* 23:637-649, 2004.
Rücker et al., "2D QSAR of PPARγ agonist binding and transactivation," *Biorg. Med. Chem.* 14:5178-5195, 2006.
U.K. Search Report (GB0715256.4) dated Dec. 10, 2007.
U.K. Search Report (GB0715257.2) dated Dec. 10, 2007.
International Search Report (PCT/EP2008/060362) mailed Aug. 31, 2009.
International Preliminary Report on Patentability for PCT/EP2008/060362, issued Mar. 1, 2010.

\* cited by examiner

*Primary Examiner* — Emily Bernhardt
(74) *Attorney, Agent, or Firm* — Clark & Elbing LLP

(57) ABSTRACT

This invention provides thiazolylpiperazine derivatives, and N-sulfonyl heterocyclic derivatives including phenyl- and benzyl-thiazolylpiperidine derivatives, and pharmaceutically acceptable salts thereof, which are useful active ingredients for administration in a method for the treatment of an α-synucleopathy such as Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease. This invention also provides methods for making such derivatives, and pharmaceutical compositions including such derivatives together with pharmaceutically acceptable excipients.

15 Claims, 8 Drawing Sheets

Scheme 1

Scheme 2

Scheme 3

Scheme 7

Scheme 8

Scheme 9

N-SULFONYL THIAZOLYLPIPERAZINE DERIVATIVES AND RELATED N-SULFONYL HETEROCYCLIC DERIVATIVES FOR THE TREATMENT OF NEURO DEGENERATIVE DISEASES

CROSS REFERENCE TO RELATED APPLICATIONS

This application is a continuation-in-part of International Patent Application No. PCT/EP2008/060362 filed on Aug. 6, 2008, which claims the benefit of UK Patent Application No. 0715257.2 filed Aug. 6, 2007 and UK Patent Application No. 0715256.4 filed Aug. 6, 2007, the disclosures of which are incorporated by reference in their entirety.

FIELD OF THE INVENTION

The present invention relates to a group of N-sulfonyl heterocyclic compounds, in particular N-sulfonyl phenylthiazolylpiperazine derivatives and N-sulfonyl benzylthiazolylpiperazine derivatives, N-sulfonyl phenylthiazolylpiperidine derivatives and N-sulfonyl benzylthiazolylpiperidine derivatives, their use as a medicament, and more particularly their use for the manufacture of a medicament useful in a method for treating certain neurological disorders characterised by cytotoxic α-synuclein amyloidogenesis. The invention further relates to pharmaceutical compositions comprising pharmaceutically acceptable excipients and a therapeutically effective amount of one or more compounds from said group of derivatives.

BACKGROUND OF THE INVENTION

α-Synuclein is a neuronal protein, which originally has been associated with neuronal plasticity during Zebra finch song learning. Although its role at the molecular level is at present largely elusive it appears to have lipid bi-layer (or membrane) with binding properties important for preserving proper transport of neurotransmitter vesicles to the axonal ends of neurons presumably to ensure proper signalling at the synapse. Apart from its physiological role in brain cells, human α-synuclein also possesses pathological features that underlies a plethora of neurodegenerative diseases including Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease. These neurological disorders are characterised by the presence of insoluble α-synuclein polymers or aggregates usually residing within neuronal cells, although in the case of Alzheimer's disease α-synuclein (or proteolytic fragments thereof) constitutes the non-amyloid component of extracellular "amyloid-β plaques". It is widely believed that the amyloidogenic properties α-synuclein disrupt cellular integrity leading to dysfunctioning or death of affected neurons resulting in cognitive and/or motoric decline as it is found in patients suffering from such diseases. The aggregation of α-synuclein is at present very poorly defined, but constitutes most likely a multi-step process wherein self-polymerization of α-synuclein into insoluble aggregates is preceded by the formation of soluble protofibrils of α-synuclein monomers. Self-association may be triggered by the formation of alternative conformations of α-synuclein monomers with high propensity to polymerize. Several studies using neuronal cell lines or whole animals have shown that formation of reactive oxygen species (hereinafter abbreviated as ROS) appear to stimulate noxious α-synuclein amyloidogenesis. For instance paraquat (an agent stimulating ROS formation within the cell) has been recognized as a stimulator of α-synuclein aggregation. Like in animals, exposure to paraquat is believed to induce the formation of synuclein inclusions, and consequently neurodegeneration, especially of dopaminergic neurons in humans. Dopaminergic neurons appear to be particularly sensitive because the concurrent dopamine metabolism may on the one hand contribute significantly to the oxidative stress load but may on the other hand result in kinetic stabilisation of highly toxic protofibrillar α-synuclein species by dopamine (or its metabolic derivatives). Parkinson's disease is characterised by a selective loss of dopaminergic substantia nigra cells and therefore treatment of animals (or neuronal cells) with paraquat is a common well-accepted experimental set-up for studying synucleopathies, in particular Parkinson's disease.

Apart from ROS, mutations in the coding region of the α-synuclein gene have also been identified as stimulators of self-polymerization resulting in early disease onset as it is observed in families afflicted by such mutations. Finally, increased expression of α-synuclein also promotes early disease onset as evidenced by a duplication or triplication of the α-synuclein gene in the genome of some individuals. The molecular mechanism by which α-synuclein self-association triggers cellular degeneration is at present largely unknown. Although it has been speculated that insoluble aggregates affect cellular integrity, it has recently been suggested that soluble protofibrillar intermediates of the aggregation process are particularly toxic for the cell as opposed to mature insoluble fibrils which may be inert end-products or may even serve as cytoprotective reservoirs of otherwise harmful soluble species. Therapeutic attempts to inhibit formation of insoluble aggregates may therefore be conceptually wrong, possibly even promoting disease progress.

While the identification of pathological α-synuclein mutations unequivocally revealed a causative factor of a plethora of neurodegenerative disorders, treatments ensuring suppression of toxic α-synuclein amyloidogenesis are presently not available. Only symptomatic treatments of Parkinson's disease exist, which aim e.g. at increasing dopamine levels in order to replenish its lowered level due to degeneration of dopaminergic neurons, for instance by administrating L-DOPA or inhibitors of dopamine breakdown. Although such treatments suppress disease symptoms to some extent, they are only temporarily effective and certainly do not slow down ongoing neuronal degeneration.

Thus there is a need in the art for designing new drugs for therapeutic treatments that target the underlying molecular mechanism of α-synuclein related pathologies in order to reduce neuronal cell death and/or degeneration.

SUMMARY OF THE INVENTION

According to a first aspect, the present invention relates a group of novel thiazolylpiperazine derivatives, in particular substituted 1-(4-phenyl-1,3-thiazol-2-yl)-4-sulfonylpiperazines, 1-(4-benzyl-1,3-thiazol-2-yl)-4-sulfonylpiperazines and N-sulfonyl heterocyclic derivatives (in particular substituted 1-(4-phenyl-1,3-thiazol-2-yl)-4-sulfonylpiperidines and 1-(4-benzyl-1,3-thiazol-2-yl)-4-sulfonylpiperidines) such as defined in the detailed description of the invention.

According to another aspect the present invention relates to a group of thiazolylpiperazine derivatives for use in the manufacture of a medicament.

According to another aspect, the present invention relates to pharmaceutical compositions comprising such compounds as active ingredients that effectively counteract or inhibit the toxic properties of α-synuclein, said compositions being useful for the prevention and/or treatment of an α-synucleopathy such as, but not limited to, Parkinson's disease, diffuse Lewy body disease, multiple system atrophy and Alzheimer's disease.

According to another aspect, the present invention relates to the use of such thiazolylpiperazine derivatives in the treatment and/or prevention of α-synucleopathies, such as, but not limited to Parkinson's disease, diffuse Lewy body disease, multiple system atrophy and Alzheimer's disease. According to another aspect, the present invention also relates to methods of treatment of α-synucleopathies, such as, but not limited to Parkinson's disease, diffuse Lewy body disease, multiple system atrophy and Alzheimer's disease, including the administration of a therapeutically effective amount of such a thiazolylpiperazine derivative to a patient in need thereof.

DEFINITIONS

Figure 1:
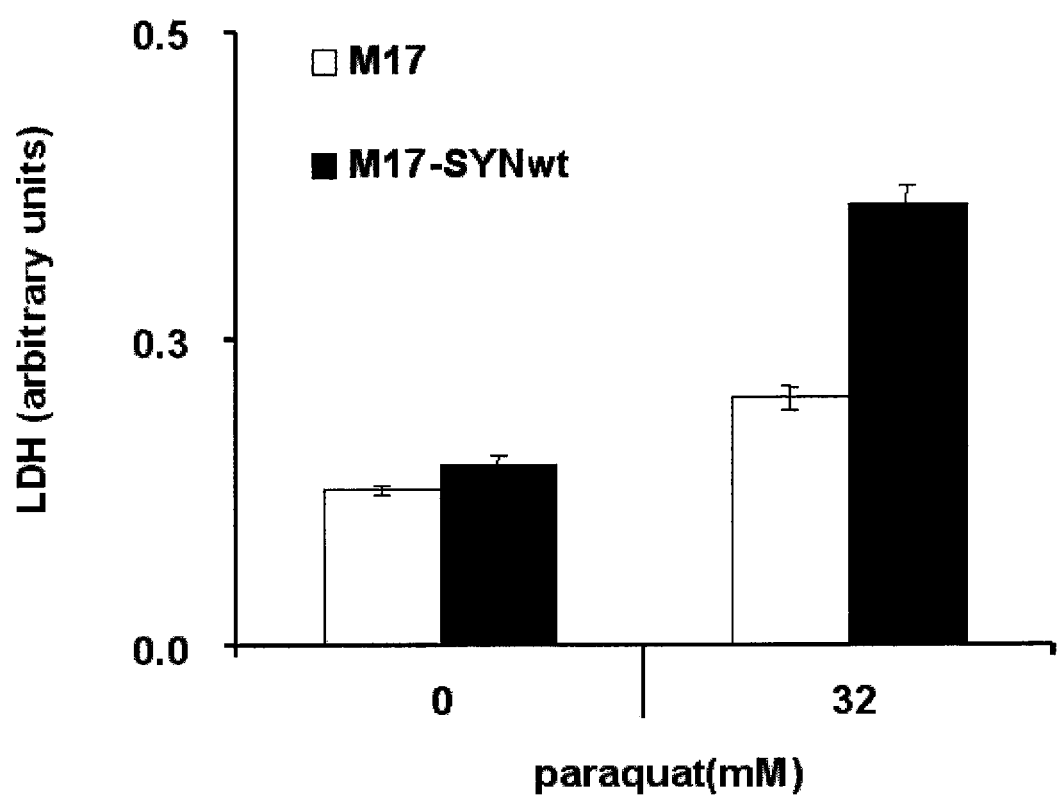
FIG. 1 shows the sensitivity of an α-synuclein expressing neuroblastoma cell line to paraquat.

As used herein with respect to a substituting group, and unless otherwise stated, the term "$C_{1-4}$ alkyl" means straight and branched chain saturated acyclic hydrocarbon monovalent groups having from 1 to 4 carbon atoms such as, for example, methyl, ethyl, propyl, n-butyl, 1-methylethyl (isopropyl), 2-methylpropyl (isobutyl) and 1,1-dimethylethyl (ter-butyl). By analogy, the term "$C_{1-6}$ alkyl" refers to such radicals having from 1 to 6 carbon atoms, including 2-methylbutyl, n-pentyl, dimethylpropyl, n-hexyl, 2-methylpentyl, 3-methylpentyl, and the like.

As used herein with respect to a substituting group, and unless otherwise stated, the term "aryl" designate any mono- or polycyclic aromatic monovalent hydrocarbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl groups such as, for instance, indanyl, tetrahydronaphtyl, fluorenyl and the like, all of the said radicals being optionally substituted with one or more substituents independently selected from the group consisting of halogen, amino, trifluoromethyl, hydroxyl, sulfhydryl and nitro and other groups exemplified herein, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting group, and unless otherwise stated, the terms "$C_{1-6}$ alkoxy" and "aryloxy", refer to substituents wherein a carbon atom of a $C_{1-6}$ alkyl, respectively or an aryl group (each of them such as defined herein), is attached to an oxygen atom through a single bond such as, but not limited to, methoxy, ethoxy, propoxy, butoxy, pentoxy, isopropoxy, sec-butoxy, tert-butoxy, isopentoxy, phenyloxy, and the like.

As used herein and unless otherwise stated, the term "stereoisomer" refers to all possible different isomeric as well as conformational forms which the compounds of structural formula may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

The term "α-synucleopathy" as used herein, unless otherwise stated, refers to a disease characterised by the presence of pathological deposition of insoluble α-synuclein polymers or aggregates intracellularly and/or extracellularly. Such diseases include, but are not limited to, Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

The term "neuroprotective" agent, as used herein, refers to drugs or chemical agents intended to prevent neurodegeneration, including drugs that slow down or stop the progression of neuronal degeneration.

As used herein with respect to a substituting group, and unless otherwise stated, the terms "heterocyclic" and "heterocyclyl" mean a mono- or polycyclic, saturated or monounsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydro-thienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl(benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrroli-dinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl(oxo), alcohol(hydroxyl), ether(alkoxy), acetal, amino, imino, oximino, alkyloximino, amino-acid, cyano, carboxylic acid ester or amide, nitro, thio $C_{1-7}$, alkyl, thio $C_{3-10}$ cycloalkyl, $C_{1-7}$ alkylamino, cycloalkylamino, alkenylamino, cycloalkenylamino, alkynylamino, arylamino, arylalkyl-amino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkyl-amino, heterocyclic amino, heterocyclic-substituted arylamino, hydrazino, alkylhydrazino, phenylhydrazino, sulfhydryl,$C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

DETAILED DESCRIPTION OF THE INVENTION

The present invention relates, to a group of 1-thiazolyl-4-sulfonylpiperazine derivatives, which have desirable biological properties such as an inhibitory effect on α-synuclein mediated toxicity. Based on this inhibitory activity, and the fact that these compounds are not toxic to neural cells, these compounds are useful for the manufacture of medicament for the prevention and/or treatment of α-synucleopathies.

The ability of the compounds of the invention to inhibit α-synuclein mediated toxicity is based on their activity in the α-synuclein cytotoxicity test described in the examples herein after. Treatment of mice with mitochondrial complex I inhibitors such as paraquat or MPTP (1-methyl-4-phenyl-1,2,3,6-tetrahydropyridine) is a well-accepted and commonly used experimental set-up to study neuronal degeneration. Paraquat triggers synuclein-aggregation, which allegedly triggers a specific loss of dopaminergic neurons and ultimately a decline in the locomotion function. Briefly, one or more compounds are administered to paraquat-receiving mice and the onset of motoric dysfunction is assessed using a rotary rod device. A delay or absence in the occurrence of motoric problems in compound treated mice (compared to control mice treated with only vehicle) indicates that the compound(s) inhibit(s) synuclein-dependent degeneration of dopaminergic cells.

According to a first aspect, the present invention provides a group of phenylthiazolylpiperazine derivatives that can be used in the treatment of an α-synucleopathy. The novel compounds according to this aspect of the present invention are represented by the structural formula (I)

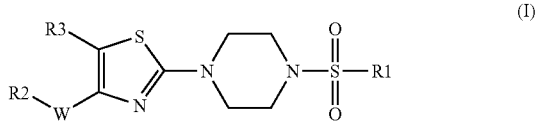

(I)

wherein:
W is selected from the group consisting of a single bond, methylene ($CH_2$), bis-methylene ($CH_2$—$CH_2$) and methylidene (vinylene) (CH=CH);

$R_1$ is selected from the group consisting of aryl$C_{1-4}$ alkyl, aryl-$C_{2-4}$ alkenyl, and $C_{3-10}$ cycloalkyl-$C_{1-6}$ alkyl, wherein said aryl-$C_{1-4}$ alkyl is optionally substituted by one or more substituents independently selected from the group consisting of halogen, cyano, nitro, aryloxy, carboxylic acid ($CO_2H$) and $C_{1-4}$ alkyl esters thereof; or $R_1$ is a phenyl ring substituted with one or more substituents independently selected from the group consisting of cyano, heterocycly, $C_{1-6}$ alkyl, $C_{1-6}$ alkoxy, aryl, aryloxy, hydroxy, acetyl, nitro, trifluoromethyl and halogen; or any two adjacent substituents of said phenyl ring form, together with the phenyl ring carbon atoms to which they are attached, a saturated or unsaturated ring fused to said phenyl ring and having from 5 to 7 ring members, said saturated or unsaturated ring optionally comprising one or two heteroatoms independently selected from the group consisting of oxygen, sulfur and nitrogen; and each of said $C_{1-6}$ alkyl, $C_{1-6}$ alkoxy, aryl or fused ring is optionally substituted with one or more halogen atoms, —C(O)—O—$R_{14}$, or —NH—C(O)—$R_{14}$; or $R_1$ is a heterocyclyl optionally substituted with one or more substituents independently selected from $R_8$ and $R_9$;

$R_2$ is a phenyl ring optionally substituted with one or more substituents independently selected from the group consisting of cyano, $C_{1-6}$ alkyl, $C_{1-6}$ alkoxy, aryl, aryloxy, acetyl, nitro, trifluoromethyl and halogen; or any two adjacent substituents of said phenyl ring form, together with the phenyl ring carbon atoms to which they are attached, a saturated or unsaturated ring fused to said phenyl ring and having from 5 to 7 ring members, said saturated or unsaturated ring optionally comprising one or two heteroatoms independently selected from the group consisting of oxygen, sulfur and nitrogen; and each of said $C_{1-6}$ alkyl, $C_{1-6}$ alkoxy, aryl or fused ring is optionally substituted with one or more halogen atoms, or $R_2$ is a heterocyclyl optionally substituted with one or more substituents independently selected from $R_8$ and $R_9$;

$R_3$ is selected form the group consisting of a hydrogen atom and $C_{1-6}$ alkyl;

each $R_8$ is independently selected from the group consisting of $C_{1-10}$ alkyl, $C_{1-6}$ alkenyl, $C_{1-6}$ alkynyl, $C_{1-6}$ alkoxy, aryl, aryloxy, aryl-$C_{1-6}$alkyl, heterocyclyl, heterocyclyl-$C_{1-6}$alkyl, heterocyclyl oxy, $C_{1-6}$ alkanoyl wherein each of said $R_8$ is optionally substituted with one or more substituents independently selected from the group consisting of halogen, oxo, thioxo, $C_{1-6}$alkyl, $C_{1-6}$alkoxy, amino, $C_{1-6}$alkyl-amino, di-$C_{1-6}$alkyl-amino, $C_{1-6}$alkylthio, —CN, —NO, —C(O)—NR$_{14}$R$_{15}$, —C(O)—R$_{15}$, —NH—C(O)—R$_{14}$, —O—C(O)—R$_{14}$, —C(O)—O—R$_{14}$, —S(O)—R$_{14}$, —S(O)$_2$—R$_{14}$, —S(O)$_2$—NR$_{14}$R$_{15}$, and each $R_9$ is independently selected from the group consisting of OH, $NO_2$, halogen, $NH_2$, $C_{1-6}$alkyl-amino, di-$C_{1-6}$alkyl-amino, —CN, —NO, —C(O)—NR$_{14}$R$_{15}$, —C(O)—R$_{15}$, —NH—C(O)—R$_{14}$, —O—C(O)—R$_{14}$, —C(O)—O—R$_{14}$, —S(O)—R$_{14}$, —S(O)$_2$—R$_{14}$, —S(O)$_2$—NR$_{14}$R$_{15}$, and $C_{1-6}$alkylthio;

each $R_{14}$ is independently selected from the group consisting of hydrogen, $C_{1-6}$ alkyl, $C_{1-6}$ alkenyl, $C_{1-6}$ alkynyl, aryl, aryl $C_{1-6}$ alkyl, $C_{3-10}$ cycloalkyl and heterocyclyl;

each $R_{15}$ is independently selected from the group consisting of hydrogen and $C_{1-6}$ alkyl;

or a stereoisomer thereof, or an enantiomer thereof, or a N-oxide thereof, or a solvate thereof, or a pharmaceutically acceptable salt thereof, provided that said derivative is not:

1-[4-(4-fluorophenyl)-1,3-thiazol-2-yl]-4-[(4-methoxyphenyl)sulfonyl]-piperazine;

1-[4-(4-fluorophenyl)-1,3-thiazol-2-yl]-4-[(4-methylphenyl)sulfonyl]-piperazine;

1-[4-(4-fluorophenyl)-1,3-thiazol-2-yl]-4-[(4-methylphenyl)sulfonyl]-piperazine;

1-(4-phenyl-3-propyl-1,3-thiazol-2-yl)-4-[(4-methylphenyl)sulfonyl]-piperazine;

1-[4-(3-methoxyphenyl)-1,3-thiazol-2-yl]-4-[(4-fluorophenyl)sulfonyl]-piperazine;

1-[4-(4-fluorophenyl)-1,3-thiazol-2-yl]-4-[(4-chlorophenyl)sulfonyl]-piperazine;

1-[4-(4-fluorophenyl)-1,3-thiazol-2-yl]-4-[(4-bromophenyl)sulfonyl]-piperazine;

1-[4-(4-fluorophenyl)-1,3-thiazol-2-yl]-4-[(2-bromophenyl)sulfonyl]-piperazine; or 1-[4-(4-fluorophenyl)-1,3-thiazol-2-yl]-4-[(4-fluorophenyl)sulfonyl]-piperazine.

A particular embodiment of the invention is a thiazolyl-piperazine derivative represented by the structural formula (I) such as above defined, wherein W is a single bond and $R_2$ is not substituted in ortho position with respect to the thiazolyl ring.

Another particular embodiment of the invention is a thiazolyl-piperazine derivative represented by the structural formula (I) such as above defined, wherein $R_1$ is phenyl substituted with $C_{1-6}$ alkyl or $C_{1-6}$ alkoxy in para position with respect to the sulfonyl moiety.

Another particular embodiment of the invention is a thiazolyl-piperazine derivative represented by the structural formula (I) such as above defined, wherein $R_1$ is phenyl substituted with two substituents which may be the same or different, but are preferably the same.

Another particular embodiment of the invention is a thiazolyl-piperazine derivative represented by the structural formula (I) such as above defined, wherein $R_1$ is phenyl substituted with three substituents which may be the same or different, but are preferably the same.

Another particular embodiment of the invention is a thiazolyl-piperazine derivative represented by the structural formula (I) such as above defined, wherein $R_1$ is benzyl, phenylethyl, phenylethenyl or cyclohexylmethyl.

Another particular embodiment of the invention is a thiazolyl-piperazine derivative represented by the structural formula (I) such as above defined, wherein W is methylene and $R_2$ is a substituted phenyl ring.

Another particular embodiment of the invention is a thiazolyl-piperazine derivative represented by the structural formula (I) such as above defined, wherein W is methylene and R₂ is phenyl substituted with two substituents which may be the same or different, but are preferably the same.

Another particular embodiment of the invention is a thiazolyl-piperazine derivative represented by the structural formula (I) such as above defined, wherein W is methylene and R₂ is phenyl substituted with three substituents which may be the same or different, but are preferably the same.

Another particular embodiment of the invention is a thiazolyl-piperazine derivative represented by the structural formula (I) such as above defined, wherein W is methylene and R₂ is thienyl or benzodioxolyl.

According to another aspect, the present invention provides a group of N-sulfonyl heterocyclic derivatives that can be used in a method for the treatment of an α-synucleopathy. The novel compounds according to this aspect of the present invention are represented by the structural formula (IV):

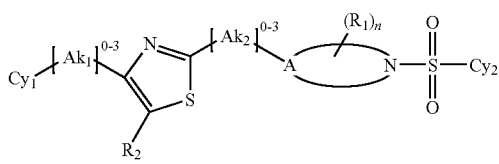

wherein:
A is CH or N and the divalent group schematically represented by the structural formula (G)

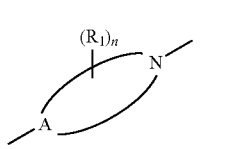

(G)

is an optionally mono-substituted or poly-substituted, saturated heterocyclic ring with one or two nitrogen atoms in the said heterocyclic ring and with a total of 5 to 7 atoms in the said heterocyclic ring,
each $R_1$ is independently selected from the group consisting of $C_{1-4}$ alkyl, $C_{2-4}$ alkenyl or $C_{2-4}$ alkynyl;
n is 0, 1, 2 or 3;
$R_2$ is hydrogen or $C_{1-6}$ alkyl;
$Ak_1$ and $Ak_2$ are linking moieties independently selected from the group consisting of a single bond; and divalent saturated, ethylenically unsaturated and acetylenically unsaturated non-cyclic hydrocarbon groups comprising from 1 to 3 atoms in the main chain;
$Cy_1$ is selected from the group consisting of $C_{3-10}$ cycloalkyl, aryl-$C_{1-4}$alkyl, aryl-$C_{2-4}$alkenyl and $C_{3-10}$cycloalkyl-$C_{1-6}$alkyl; wherein said $C_{3-10}$ cycloalkyl or aryl-$C_{1-4}$alkyl is optionally substituted with one or more substituents independently selected from the group consisting of hydroxyl, acetyl, nitro, cyano, acetamido, trifluoromethyl, $NH_2$, $SO_2$ and halogen; or $Cy_1$ is a phenyl ring optionally substituted with one or more substituents independently selected from the group consisting of $C_{1-6}$ alkyl, $C_{1-6}$ alkoxy, aryl, aryloxy, acetyl, nitro, cyano, acetamido, trifluoromethyl, $NH_2$, $SO_2$, $OCH_2COOCH_3$, heterocyclyl and halogen; and said heterocyclyl ring is optionally substituted with one or more $R_3$, or any two adjacent substituents of said phenyl ring form, together with the phenyl ring carbon atoms to which they are attached, a saturated or unsaturated ring fused to said phenyl ring and having from 5 to 7 ring members, said saturated or unsaturated ring optionally comprising one or two heteroatoms independently selected from the group consisting of O, S and N; and each of said $C_{1-6}$ alkyl, $C_{1-6}$ alkoxy, aryl or fused ring is optionally substituted with one or more substituents selected from the group consisting of $C_{1-6}$ alkyl, oxo and halogen; or $Cy_1$ is a heterocyclyl optionally substituted with one or more $R_3$;

$Cy_2$ is selected from the group consisting of aryl-$C_{1-4}$alkyl, aryl-$C_{2-4}$alkenyl and $C_{3-10}$cycloalkyl-$C_{1-6}$alkyl; wherein said aryl-$C_{1-4}$alkyl is optionally substituted with one or more substituents independently selected from the group consisting of hydroxyl, acetyl, nitro, cyano, acetamido, trifluoromethyl, $NH_2$, $SO_2$ and halogen; or $Cy_2$ is a phenyl ring substituted with one or more substituents independently selected from the group consisting of $C_{1-6}$ alkyl, $C_{1-6}$ alkoxy, aryl, aryloxy, hydroxyl, acetyl, nitro, cyano, acetamido, trifluoromethyl, $NH_2$, $SO_2$, $OCH_2COOCH_3$, heterocyclyl and halogen; and said heterocyclyl ring is optionally substituted with one or more $R_3$, or any two adjacent substituents of said phenyl ring form, together with the phenyl ring carbon atoms to which they are attached, a saturated or unsaturated ring fused to said phenyl ring and having from 5 to 7 ring members, said saturated or unsaturated ring optionally comprising one or two heteroatoms independently selected from the group consisting of O, S and N; and each of said $C_{1-6}$ alkyl, $C_{1-6}$ alkoxy, aryl or fused ring is optionally substituted with one or more substituents selected from the group consisting of $C_{1-6}$ alkyl, oxo and halogen; and
each $R_3$ is independently selected from the group consisting of $C_{1-6}$ alkyl, $C_{1-6}$ alkoxy, aryl, aryloxy, hydroxyl, acetyl, nitro, cyano, acetamido, trifluoromethyl, $NH_2$, $SO_2$, oxo and halogen;
or a stereoisomer thereof, or an enantiomer thereof, or a N-oxide thereof, or a solvate thereof, or a pharmaceutically acceptable salt thereof.
Optionally said compounds represented by the structural formula (IV) are not:
1-[4-(4-fluorophenyl)-1,3-thiazol-2-yl]-4-[(4-methoxyphenyl)sulfonyl]-piperazine;
1-[4-(4-fluorophenyl)-1,3-thiazol-2-yl]-4-[(4-methylphenyl)sulfonyl]-piperazine;
1-[4-(4-fluorophenyl)-1,3-thiazol-2-yl]-4-[(4-methylphenyl)sulfonyl]-piperazine;
1-(4-phenyl-3-propyl-1,3-thiazol-2-yl)-4-[(4-methylphenyl)sulfonyl]-piperazine;
1-[4-(3-methoxyphenyl)-1,3-thiazol-2-yl]-4-[(4-fluorophenyl)sulfonyl]-piperazine;
1-[4-(4-fluorophenyl)-1,3-thiazol-2-yl]-4-[(4-chlorophenyl)sulfonyl]-piperazine;
1-[4-(4-fluorophenyl)-1,3-thiazol-2-yl]-4-[(4-bromophenyl)sulfonyl]-piperazine;
1-[4-(4-fluorophenyl)-1,3-thiazol-2-yl]-4-[(2-bromophenyl)sulfonyl]-piperazine; or
1-[4-(4-fluorophenyl)-1,3-thiazol-2-yl]-4-[(4-fluorophenyl)sulfonyl]-piperazine.

A particular embodiment of the invention is a N-sulfonyl heterocyclic derivative represented by the structural formula (IV) as defined above, wherein said divalent group schematically represented by the structural formula (G) is an optionally substituted saturated heterocyclic ring having 6 atoms in said ring, with two non-adjacent nitrogen atoms in said ring.

Another particular embodiment of the invention is a N-sulfonyl heterocyclic derivative represented by the structural formula (IV) as defined above, wherein said divalent group schematically represented by the structural formula (G) is an optionally substituted saturated heterocyclic ring having 5, 6 or 7 atoms in said ring, with two adjacent nitrogen atoms in said ring.

Another particular embodiment of the invention is a N-sulfonyl heterocyclic derivative represented by the structural formula (IV) as defined above, wherein said divalent group schematically represented by the structural formula (G) is a non-substituted (i.e. n=0) saturated heterocyclic ring having 6 atoms in said ring, with two non-adjacent nitrogen atoms in said ring.

Another particular embodiment of the invention is a N-sulfonyl heterocyclic derivative represented by the structural formula (IV) as defined above, wherein said divalent group schematically represented by the structural formula (G) is a non-substituted (i.e. n=0) saturated heterocyclic ring having 5, 6 or 7 atoms in said ring, with two adjacent nitrogen atoms in said ring.

Representative but non-limiting examples of the nitrogen-containing heterocyclic ring included in (G) are:
- 5 to 7 membered non-substituted saturated rings with two nitrogen atoms such as pyrazolidine, imidazolidine, piperazine and diazepane (homopiperazine);
- 5 to 7 membered non-substituted saturated rings with a single nitrogen atom such as pyrrolidine, piperidine and azepane,
- 5 to 7 membered mono-substituted saturated rings with two nitrogen atoms such as, but not limited to, 3-pyrazolidinone, 2-imidazolidinone, 2-piperazinone, 2-methylpiperazine, 2-ethylpiperazine, 2-propylpiperazine, 2-butylpiperazine, 2-phenylpiperazine, 2-vinylpiperazine, 2-ethynylpiperazine, 2-(methoxymethyl)-piperazine, 2-(phenoxymethyl)piperazine, 2-(hexyloxymethyl)-piperazine, 2-(dodecyloxymethyl)piperazine, 2-[(1-methyl-ethoxy)methyl]piperazine, 2-(3-methyl-2-thienyl)piperazine, 2-(fluoromethyl)piperazine, 2-(2-furanyl)piperazine, 2-(5-methyl-2-furanyl)piperazine, 2-(2-benzofuranyl)piperazine, 2-(3,5-dimethyl-2-furanyl)piperazine, 2-(3-thienyl)piperazine, 2-(4-methyl-2-thienyl)piperazine, 2-(5-methyl-2-thienyl)piperazine, 2-(2,5-dimethyl-3-thienyl)piperazine, 2-(1H-pyrrol-1-ylmethyl)piperazine, 3-(1-methyl-1H-pyrazol-3-yl)-piperazine, and others disclosed in U.S. Pat. No. 5,210,193, the content of which is hereby incorporated by reference;
- 5 to 7 membered di-substituted saturated rings with two nitrogen atoms such as, but not limited to, 3,5-pyrazolidinedione, 2,4-imidazolidinedione (hydantoine), 2,6-piperazinedione, 2,3-dimethylpiperazine, 2,5-dimethylpiperazine, 2,6-dimethyl-piperazine, 2,3-diethylpiperazine, 2,5-diethylpiperazine, 2,6-diethylpiperazine, and 2,5-dipropylpiperazine,
- 5 to 7 membered di-substituted saturated rings with a single nitrogen atom such as, but not limited to, 2,5-pyrrolidinedione, 2,3-piperidinedione, 2,4-piperidinedione, 2,5-piperidinedione, 2,6-piperidinedione, 3,4-piperidinedione, 3,5-piperidinedione, 3-phenyl-4-(benzyloxyphenoxy)-piperidine, 4-phenyl-4-propoxy-piperidine, 4-methyl-4-methoxypiperidine, and 4-methyl-4-butoxy-piperidine;
- 5 to 7 membered mono-substituted saturated rings with a single nitrogen atom such as, but not limited to, 2-piperidinone, 4-piperidinone, 2-phenylpiperidine, 3-benzylpiperidine, 4-benzyl-piperidine, 2-benzylpiperidine, 3-methoxypiperidine, 4-methoxy-piperidine, 3-ethoxypiperidine, 4-ethoxypiperidine, 3-propoxy-piperidine, 4-propoxypiperidine, 3-butoxypiperidine, 4-butoxy-piperidine, 3-phenoxypiperidine, 4-phenoxypiperidine, 4-n-propyl-piperidine, and 2-n-propylpiperidine; and
- 5 to 7 membered tri-substituted saturated rings with a single nitrogen atom such as, but not limited to, 6,6-diphenyl-2-piperidinone and 5,5-diphenyl-2-pyrrolidinone.

Another particular embodiment of the invention is a N-sulfonyl heterocyclic derivative represented by the structural formula (IV) as defined above, wherein $Ak_2$ is selected from the group consisting of a single bond, methylene ($CH_2$), bis-methylene ($CH_2$—$CH_2$) and methylidene(vinylene) ($CH$=$CH$).

Another particular embodiment of the invention is a N-sulfonyl heterocyclic derivative represented by the structural formula (IV) as defined above, wherein $Ak_1$ is selected from the group consisting of a single bond, methylene ($CH_2$), bis-methylene ($CH_2$—$CH_2$) and methylidene(vinylene) ($CH$=$CH$).

Another particular embodiment of the invention is a N-sulfonyl heterocyclic derivative represented by the structural formula (IV) such as above defined, wherein $Cy_2$ is phenyl substituted with $C_{1-6}$ alkyl or $C_{1-6}$ alkoxy in para position with respect to the sulfonyl moiety.

Another particular embodiment of the invention is a N-sulfonyl heterocyclic derivative represented by the structural formula (IV) such as above defined, wherein $Cy_2$ is phenyl substituted with two substituents which may be the same or different, but are preferably the same.

Another particular embodiment of the invention is a N-sulfonyl heterocyclic derivative represented by the structural formula (IV) such as above defined, wherein $Cy_2$ is phenyl substituted with three substituents which may be the same or different, but are preferably the same.

Another particular embodiment of the invention is a N-sulfonyl heterocyclic derivative represented by the structural formula (IV) such as above defined, wherein $Cy_2$ is benzyl, phenylethyl, phenylethenyl or cyclohexylmethyl.

Another particular embodiment of the invention is a N-sulfonyl heterocyclic derivative represented by the structural formula (IV) such as above defined, wherein $Ak_1$ is methylene and $Cy_1$ is a substituted phenyl ring.

Another particular embodiment of the invention is a N-sulfonyl heterocyclic derivative represented by the structural formula (IV) such as above defined, wherein $Ak_1$ is methylene and $Cy_1$ is phenyl substituted with two substituents which may be the same or different, but are preferably the same.

Another particular embodiment of the invention is a N-sulfonyl heterocyclic derivative represented by the structural formula (IV) such as above defined, wherein $Ak_1$ is methylene and $Cy_1$ is phenyl substituted with three substituents which may be the same or different, but are preferably the same.

Another particular embodiment of the invention is a N-sulfonyl heterocyclic derivative represented by the structural formula (IV) such as above defined, wherein $Ak_1$ is methylene and $Cy_1$ is thienyl or benzodioxolyl.

These derivatives—being represented by the structural formula (I) or the structural formula (IV)—may also be in the form of a pharmaceutically acceptable salt. The latter include any therapeutically active non-toxic addition salt, which these compounds are able to form with a salt-forming agent. Such addition salts may conveniently be obtained by treating the derivatives of the invention with an appropriate salt-forming acid. For instance, derivatives may be converted into the corresponding therapeutically active, non-toxic acid addition salt form by treating the free base form with a suitable amount of an appropiate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like.

Reaction conditions for treating the derivatives with an appropriate salt-forming acid are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected, so as to impart greater water-solubility, lower toxicity, greater stability and/or slower dissolution rate to the derivative of this invention.

The derivatives according to both aspects of the invention, i.e. represented by both structural formulae (I) and (IV) and also including all 9 above recited (commercially available) compounds, are particularly suitable for administration in a method for treating an α-synucleopathy, e.g. Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy or Alzheimer's disease.

According to another aspect, the present invention provides pharmaceutical compositions containing at least one of the above-defined derivatives, i.e. represented by both structural formulae (I) and (IV) and including all 9 above recited (commercially available) compounds, together with one or more pharmaceutically acceptable carriers or excipients.

The term "pharmaceutically acceptable carrier or excipient" as used herein in relation to pharmaceutical compositions and combined preparations means any material or substance with which the active principle may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents may also be prepared by micronisation, for instance in view to obtain them in the form of microspheres usually having a diameter of about 1 to 10 μm, namely for the manufacture of microcapsules for controlled or sustained release of the biologically active ingredient(s).

Figure 2:
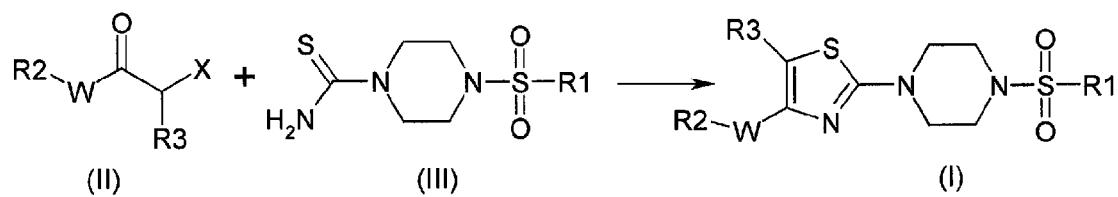
FIG. 2 shows synthetic schemes for the preparation of thiazolyl-piperazine derivatives according to this invention.
Figure 2:
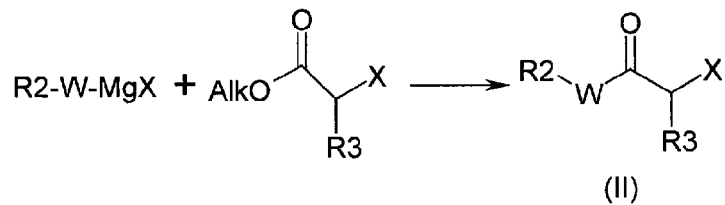
Figure 2:
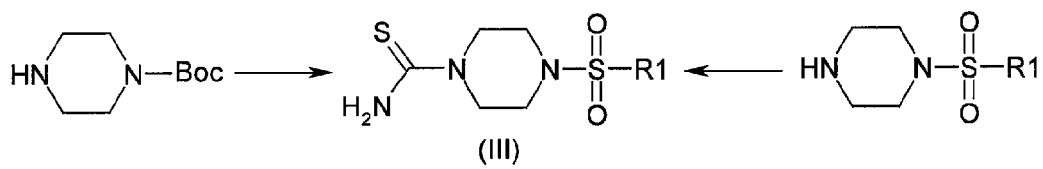

The various thiazolylpiperazine derivatives of the present invention represented by the structural formula (I) can be synthesised according to the general schemes 1, 2 and 3 represented in FIG. 2, and described hereafter. The last step, represented in scheme 1 of FIG. 2, consists in the reaction between a 2-haloketone compound represented by the structural formula (II), wherein W, $R_2$ and $R_3$ are as defined in formula (I) and X is a halogen (in particular chloro or bromo), and a 4-[($R_1$-substituted)sulfonyl]piperazine-1-carbothioamide compound represented by the structural formula (III) under reaction conditions known in the art for the formation of thiazole derivatives (i.e. Hantzch synthesis of thiazoles).

Suitable compounds represented by the structural formula (II) wherein W is a single bond include, but are not limited to, commercially available products such as 2-bromoacetophenone, 2,3'-dibromoacetophenone, 2-bromo-4'-chloroacetophenone, 2-bromo-4'-methoxyacetophenone, 2-bromo-3'-methoxyacetophenone, 2-bromo-2'-methoxyacetophenone, 2-bromo-4'-methylacetophenone, 2-bromo-3'-methyl-acetophenone, 2-bromo-2'-methylacetophenone, 2-bromo-4'-ethylacetophenone, 2-bromo-4'-propylacetophenone, 2-bromo-4'-isopropylacetophenone, 2,2',4'-trichloroacetophenone; 2-chloroacetophenone, 2-bromopropiophenone; 2,4'-dibromopropiophenone and 2-bromo-4'-n-butylacetophenone. Other compounds represented by the structural formula (II) can be obtained for example, as represented in scheme 2 of FIG. 2, by halogenation of the corresponding ketone. Conditions for halogenation of arylalkyletone derivatives are known in the art, preferably acidic conditions are used in order to limit to monohalogenation. Arylalkylketones that may be used for halogenation are, but not limited to, commercially available products such as 3'-methoxyacetophenone; 3'-chloro-acetophenone; 2'-nitroacetophenone; 3'-nitroacetophenone; 4'-nitroacetophenone; 3'-ethylacetophenone; 4'-tert-butylacetophenone; 4'-n-propylacetophenone; 4'-iso-propylacetophenone; 4'-isobutoxyacetophenone; 4'-propoxyacetophenone; 2'-methoxyacetophenone; 2'-fluoroacetophenone; 4'-fluoroacetophenone; 2',5'-dimethoxyacetophenone; 2,2-dichloroacetophenone; 3'-fluoroacetophenone; 2,4'-dibromoacetophenone; 4'-chloroacetophenone; 4'-bromoacetophenone; 3'-bromoacetophenone; acetophenone; 2',4'-difluoropropiophenone; 3'-bromo-4'-fluoropropionphenone; 3'-chloropropiophenone; 4'-methylpropiophenone; 3'-bromo-propiophenone; 4'-fluoropropiophenone; propiophenone; 4'-methoxypropiophenone; 4'-chloropropiophenone; 3'-nitropropiophenone; 4'-bromopropiophenone; 4'-chloropropiophenone; 1-(2,4-dichlorophenyl)-1-propanone; 1-(3,4-dichlorophenyl)-1-propanone; 4'-chlorobutyrophenone; 4'-methoxybutyrophenone; n-butyrophenone; 1-(2,4-dichlorophenyl)-1-propanone; and 1-phenyl-1-pentanone(valerophenone).

Alternatively, suitable compounds represented by the structural formula (II) wherein W is a single bond can also be obtained, as shown in scheme 2, by reaction of a corresponding phenylhalogenomagnesium or heterocyclylhalogenomagnesium (wherein the halogen is preferably bromo) with an adequate chloroacetate or bromoacetate derivative such as, but not limited to methyl bromoacetate, methyl chloroacetate, ethyl bromoacetate, ethyl chloroacetate, propyl bromoacetate, isopropyl bromoacetate, tert-butyl bromoacetate, tert-butyl chloroacetate, methyl 2-chloropropionate, methyl 2-bromopropionate, ethyl 2-bromopropionate, methyl 2-bromobutyrate, ethyl 2-bromobutyrate, ethyl 2-bromoisobutyrate, ethyl 2-bromovalerate, ethyl 2-bromohexanoate, ethyl 2-bromoheptanoate, and analogs thereof. Suitable phenylhalogenomagnesium and heterocyclyl-halogenomagnesium compounds for this reaction include, but are not limited to, commercially available products such as phenylmagnesium bromide, 4-methoxyphenylmagnesium bromide, 4-chlorophenyl-magnesium bromide, 4-fluorophenylmagnesium bromide, 1-naphthylmagnesium bromide, phenylmagnesium chloride, o-tolylmagnesium bromide, m-tolylmagnesium bromide, p-tolylmagnesium bromide, o-tolylmagnesium chloride, m-tolylmagnesium chloride, 3,4-dichlorophenyl-magnesium bromide, 3,5-dichlorophenylmagnesium bromide, 3,4-difluorophenylmagnesium bromide, 3,5-difluorophenylmagnesium bromide, 3-chloro-4-fluorophenylmagnesium bromide, 3-chloro-5-fluorophenylmagnesium bromide, 4-chloro-3-fluorophenylmagnesium bromide, 3,5-dimethylphenylmagnesium bromide, 3,4-dimethylphenylmagnesium bromide, 2,3-dimethylphenylmagnesium bromide, 2,4-dimethylphenylmagnesium bromide, 2,5-dimethylphenylmagnesium bromide, 2,6-dimethylphenylmagnesium bromide, 2,4-dimethoxyphenylmagnesium bromide, 2,5-dimethoxyphenylmagnesium bromide, 3,4-dimethoxyphenylmagnesium bromide, 3,5-dimethoxyphenylmagnesium bromide, 3,4,5-trimethoxyphenylmagnesium bromide, 2,4,5-trimethylphenyl-magnesium bromide, 4-ethylphenylmagnesium bromide, 4-ethoxyphenylmagnesium bromide, 2,4,6-trimethylphenylmagnesium bromide, 2-pyridylmagnesium bromide, 3-thienylmagnesium iodide.

Compounds of formula (II) wherein W is methylene, bismethylene or methylidene (vinylene) can be obtained for example, as represented in scheme 2 of FIG. 2, by reaction of an arylalkylhalogenomagnesium or arylalkenyl-halogenomagnesium compound with an adequate chloroacetate or bromoacetate derivative such as, but not limited to methyl bromoacetate, methyl chloroacetate, ethyl bromoacetate, ethyl chloroacetate, propyl bromoacetate, isopropyl bromoacetate, tert-butyl bromoacetate, tert-butyl chloroacetate, methyl 2-chloropropionate, methyl 2-bromopropionate, ethyl 2-bromopropionate, methyl 2-bromobutyrate, ethyl 2-bromobutyrate, ethyl 2-bromoisobutyrate, ethyl 2-bromovalerate, ethyl 2-bromohexanoate, ethyl 2-bromoheptanoate, and analogs thereof. Arylalkylhalogenomagnesium compounds that are suitable for this reaction include, but are not limited to, commercially available products such as benzylmagnesium chloride, 4-methylbenzylmagnesium chloride, 3-methylbenzylm agnesium chloride, 2-methylbenzylmagnesium chloride, 4-methoxybenzyl-magnesium chloride, 3-methoxybenzylmagnesium chloride, 2-methoxybenzyl-magnesium chloride, 4-chlorobenzylmagnesium chloride, 3-chlorobenzylmagnesium chloride, 2-chlorobenzylmagnesium chloride, 4-fluorobenzylmagnesium chloride, 3-fluorobenzylmagnesium chloride, 2-fluorobenzylmagnesium chloride, 4-bromobenzylmagnesium bromide, 3-bromobenzylmagnesium bromide, and 2-bromobenzylmagnesium bromide. Any arylalkyl halide or arylalkenyl halide can also be transformed in a desired arylalkylhalogenomagnesium or arylalkenyl-halogenomagnesium compound, if the latter is not commercially available, according to standard methods known in the art. For instance an arylalkyl bromide or arylalkyl chloride can be first transformed into the corresponding iodide in order to increase reactivity. Arylalkyl halides that may be used include, but are not limited to, commercially available compounds such as, benzyl iodide; 3-chlorobenzyl chloride; 3-methoxybenzyl bromide; 4-methoxybenzyl bromide; 4-ethoxybenzyl chloride; 4-isopropoxybenzyl chloride; 4-methoxybenzyl chloride; 2-iodobenzyl chloride; 2-bromobenzyl chloride; 3-bromobenzyl chloride; 4-bromobenzyl chloride; 2-chlorobenzyl chloride; 4-chlorobenzyl chloride; 2-fluoro-3-methylbenzyl bromide; 3,5-dimethylbenzyl bromide; 2,3,5,6-tetrafluorobenzyl bromide; 2,3,4,5-tetrafluorobenzyl bromide; 3,5-bis(trifluoromethyl)benzyl bromide; 4-(trifluoromethoxy)benzyl bromide; 3-nitrobenzyl bromide; 4-fluorobenzyl bromide; 2-fluorobenzyl bromide; 2-nitrobenzyl bromide; 4-nitrobenzyl bromide; 3-fluorobenzyl bromide; benzyl bromide; 2,4-dimethylbenzyl bromide, 3-phenoxybenzyl chloride; 2,6-difluorobenzyl chloride; 3-methoxybenzyl chloride; 2-methyl-3-nitrobenzyl chloride; 4-methyl-3-nitrobenzyl chloride; 5-methyl-2-nitrobenzyl chloride; 3-nitrobenzyl chloride; 3,4-dibenzyloxybenzyl chloride; benzyl chloride; 4-nitrobenzyl chloride; 2,5-dimethylbenzyl chloride; 2-nitrobenzyl chloride; 4-fluorobenzyl chloride; 3-fluorobenzyl chloride; 2-fluorobenzyl chloride; pentamethylbenzyl chloride; 2,4-dimethylbenzyl chloride; 3,4-difluorobenzyl chloride; 2-methoxybenzyl chloride; 2,5-difluorobenzyl chloride; (2-chloroethyl)benzene; 1-(2-chloroethyl)-4-methoxybenzene; (2-bromoethyl)benzene; 4-Nitrophenethyl bromide; (2-iodoethyl)benzene and beta-bromostyrene.

Figure 4:
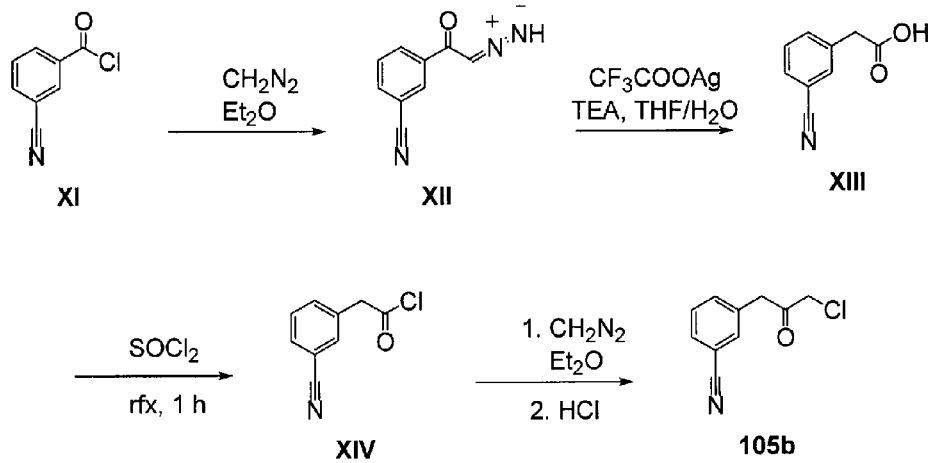
FIGS. 4 and 5 show synthetic schemes for the preparation of intermediates useful in producing benzylthiazolyl-piperazine derivatives according to this invention.
Figure 5:
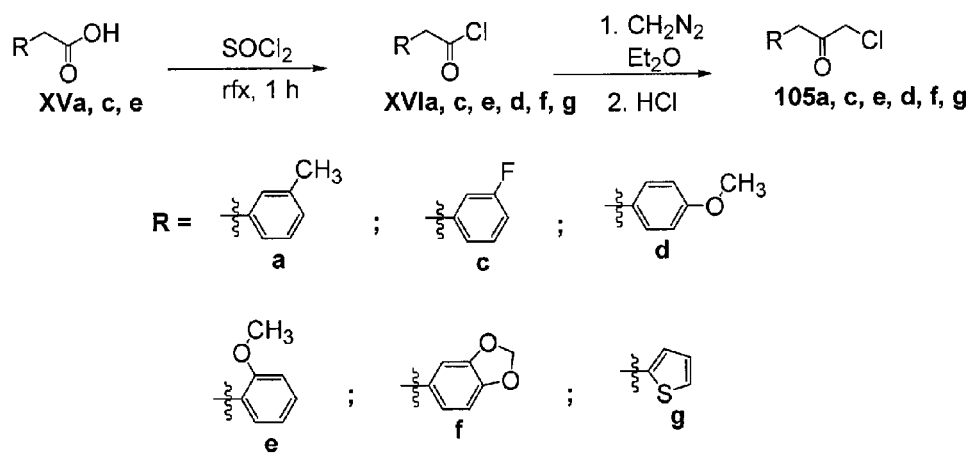

Compounds of formula (II) wherein W is methylene can also be produced according to synthetic procedures shown in FIGS. 4 and 5, details of which are provided hereinafter, i.e. starting from an arylacetyl or heteroarylacetyl chloride. Optionally substituted phenylacetyl chlorides suitable as starting materials for such synthetic procedures include, but are not limited to, acid chlorides derived from 4-bromophenylacetic acid, 3-bromophenylacetic acid, 2-bromophenylacetic acid, 4-chlorophenylacetic acid, 3-chlorophenylacetic acid, 2-chlorophenylacetic acid, 3-cyanophenylacetic acid, 4-fluorophenylacetic acid, 3-fluorophenylacetic acid, 2-fluorophenylacetic acid, 4-nitrophenylacetic acid, 3-nitrophenylacetic acid, 2-nitrophenylacetic acid, 2,4-dichlorophenylacetic acid, 2,6-dichlorophenylacetic acid, 3,4-dichlorophenylacetic acid, 4-methoxyphenylacetic acid, 3-methoxyphenylacetic acid, 2-methoxyphenylacetic acid, 4-methylphenylacetic acid (p-tolylacetic acid), 3-methylphenylacetic acid (m-tolylacetic acid), 2-methylphenylacetic acid (o-tolylacetic acid), 2,4,6-trimethylphenylacetic acid (mesitylacetic acid), 4-isopropylphenylacetic acid (cumenylacetic acid), 4-n-propylphenylacetic acid, 3,5-dimethylphenylacetic acid, 2,5-dimethylphenylacetic acid, 3,4-dimethylphenylacetic acid, 2,4-dimethylphenylacetic acid, 4-n-butoxyphenylacetic acid, 4-n-propoxyphenylacetic acid, 4-ethoxyphenylacetic acid, 2-ethoxyphenylacetic acid, 4-n-butylphenylacetic acid, 4-isobutylphenylacetic acid, 4-tert-butylphenylacetic acid, 3,4-dimethoxyphenylacetic acid, 2,5-dimethoxyphenylacetic acid, 2,3-dimethoxyphenylacetic acid, 3,5-dimethoxy-phenylacetic acid, 2,4-dimethoxyphenylacetic acid, 2-(trifluoromethyl)-phenylacetic acid, 3-(trifluoromethyl)-phenylacetic acid, 4-(trifluoromethyl)-phenylacetic acid, 2-(trifluoromethoxy)-phenylacetic acid, 3-(trifluoromethoxy)-phenylacetic acid, 4-(trifluoromethoxy)-phenylacetic acid and 3,4-diethoxyphenylacetic acid.

A few illustrative compounds of formula (II) wherein W is methylene, bismethylene or methylidene (vinylene) include, but are not limited to, 1-chloro-3-m-tolylpropan-2-one, 1-chloro-3-(4-bromophenyl)propan-2-one, 1-chloro-3-(3-bromophenyl)propan-2-one, 1-chloro-3-(2-bromophenyl)propan-2-one, 1-chloro-3-(4-chlorophenyl)propan-2-one, 1-chloro-3-(3-chlorophenyl)propan-2-one, 1-chloro-3-(2-chlorophenyl)propan-2-one, 1-chloro-3-(2,4-dichlorophenyl)propan-2-one, 1-chloro-3-(2,6-dichlorophenyl)propan-2-one, 1-chloro-3-(3,4-dichlorophenyl)propan-2-one, 1-chloro-3-(4-fluorophenyl)propan-2-one, 1-chloro-3-(3-fluorophenyl)propan-2-one, 1-chloro-3-(2-fluorophenyl)propan-2-one, 1-chloro-3-(4-methoxyphenyl)propan-2-one, 1-chloro-3-(3-methoxyphenyl)propan-2-one, 1-chloro-3-(4-ethoxyphenyl)propan-2-one, 1-chloro-3-(2-ethoxyphenyl)propan-2-one, 1-chloro-3-(2-methoxyphenyl)propan-2-one, 1-chloro-3-(4-nitrophenyl)propan-2-one, 1-chloro-3-(3-nitrophenyl)propan-2-one, 1-chloro-3-(2-nitrophenyl)propan-2-one, 1-chloro-3-(3-cyanophenyl)propan-2-one, 1-chloro-3-(2,4,6-trimethylphenyl)propan-2-one, 1-chloro-3-(2,4-dimethylphenyl)-propan-2-one, 1-chloro-3-(3,4-dimethylphenyl)propan-2-one, 1-chloro-3-(2,5-dimethylphenyl)propan-2-one, 1-chloro-3-(3,5-dimethylphenyl)propan-2-one, 1-chloro-3-(2,4-dimethoxyphenyl)propan-2-one, 1-chloro-3-(3,4-dimethoxyphenyl)-propan-2-one, 1-chloro-3-(2,5-dimethoxyphenyl)propan-2-one, 1-chloro-3-(3,5-dimethoxyphenyl)propan-2-one, 1-chloro-3-(2,3-dimethoxyphenyl)-propan-2-one, 1-(benzo[d][1,3]dioxol-5-yl)-3-chloropropan-2-one and 1-chloro-3-(thien-2-yl)propan-2-one.

Compounds represented by the structural formula (III), i.e. 4-[(R₁-substituted)sulfonyl]piperazine-1-carbothioamides, in particular 4-arylsulfonyl-piperazine-1-carbothioamides and 4-heterocyclylsulfonyl-piperazine-1-carbothioamides, can be obtained for example, as shown on the left part of scheme 3 of FIG. 2, starting with a mono-protected piperazine (such as but not limited to, a butoxycarbonyl (Boc) mono-protected piperazine), by introducing a thioamide group using ethyl chloroformate and potassium thiocyanate under conditions known in the art, followed by nitrogen deprotection (e.g. acidic deprotection of the Boc nitrogen-protecting group), and followed by reaction with a suitable corresponding arylsulfonyl chloride or heterocyclylsulfonyl chloride; or (as shown on the right part of scheme 3 in FIG. 2) simply by using ethyl chloroformate and potassium thiocyanate directly onto a suitable arylsulfonylpiperazine or heterocyclylsulfonyl derivative (the latter being e.g. obtained by reaction of piperazine and a suitable sulfonyl chloride). In the first alternative of the process, any known nitrogen-protecting group may be initially used instead of butoxycarbonyl, and the deprotection technique required in the next step may then be adapted, depending upon the type of nitrogen-protecting group, using common knowledge in the art.

Arylsulfonyl chlorides that may be used as precursors in scheme 3 of FIG. 2 include, but are not limited to, commercially available products such as 4-fluorobenzenesulfonyl chloride, 2-mesitylenesulfonyl chloride, 4-methoxybenzenesulfonyl chloride, p-toluenesulfonyl chloride, pentafluorobenzenesulfonyl chloride, benzenesulfonyl chloride, 4-bromobenzenesulfonyl chloride, N-acetylsulfanilyl chloride, 2,4,6-triisopropyl-benzenesulfonyl chloride 2-naphthalenesulfonylchloride, 4-chloro-benzenesulfonyl chloride, 2,5-dichlorobenzenesulfonyl chloride, 1-naphthalenesulfonylchloride, 4-tert-butylbenzenesulfonyl chloride, 3-(trifluoromethyl)-benzenesulfonyl chloride, 2-bromobenzenesulfonyl chloride, 2-(trifluoromethyl)-benzenesulfonyl chloride, 3,4-dichlorobenzenesulfonyl chloride, 3,4-dimethoxybenzenesulfonyl chloride, 3-chlorobenzenesulfonyl chloride, 2-chloro-4-fluorobenzenesulfonyl chloride, 3,5-dichlorobenzenesulfonyl chloride, 3-chloro-4-fluorobenzenesulfonyl chloride, 2,4-dichlorobenzenesulfonyl chloride, 2,5-dimethoxybenzenesulfonyl chloride, 3-bromobenzenesulfonyl chloride, 2,3-dichlorobenzenesulfonyl chloride, 5-fluoro-2-methylbenzenesulfonyl chloride, 3-fluorobenzenesulfonyl chloride, 2,3,5,6-tetramethylbenzenesulfonyl chloride, 3-chloro-2-methylbenzenesulfonyl chloride, 2,5-dibromo-3,6-difluorobenzenesulfonyl chloride, 2,6-difluorobenzenesulfonyl chloride, 2-chlorobenzenesulfonyl chloride, 5-bromo-2-methoxybenzenesulfonyl chloride, 5-chloro-2-methoxybenzenesulfonyl chloride, 2,4-difluorobenzenesulfonyl chloride, 2-cyanobenzenesulfonyl chloride, 2-chloro-5-(trifluoromethyl)-benzenesulfonyl chloride, 4-bromomethylbenzenesulfonyl chloride, 2,4-dimethoxybenzenesulfonyl chloride, 4-chloro-3-nitrobenzenesulfonyl chloride, 4-(chlorosulfonyl)-benzoic acid, 3-nitrobenzenesulfonyl chloride, 4-nitrobenzenesulfonyl chloride, 2-(methylsulfonyl)-benzenesulfonyl chloride, 4-(methylsulfonyl)-benzenesulfonyl chloride, 3-(chlorosulfonyl)-benzoic acid, 2,4-dichloro-5-methylbenzenesulfonyl chloride, 4-(trifluoromethoxy)-benzenesulfonyl chloride, 2-methoxy-4-nitrobenzenesulfonyl chloride, 4-bromo-2-chlorobenzene-sulfonyl chloride, 2,3-dihydro-1-benzofuran-5-sulfonyl chloride, 2,3-dihydro-1,4-benzodioxine-6-sulfonyl chloride, 1,3-benzothiazole-6-sulfonyl chloride, 2,1,3-benzothiadiazole-4-sulfonyl chloride, 2,1,3-benzothiadiazole-5-sulfonyl chloride, 2,1,3-benzoxadiazole-4-sulfonyl chloride, 3,4-dihydro-2H-1,5-benzodioxepine-7-sulfonyl chloride, 4-methyl-3,4-dihydro-2H-1,4-benzoxazine-7-sulfonyl chloride, 4-(1,3-oxazol-5-yl)benzenesulfonyl chloride, 4-(1,2,3-thiadiazol-4-yl)benzenesulfonyl chloride, 4-(1H-pyrazol-1-yl)benzenesulfonyl chloride, 4-(3-chloro-2-cyano-phenoxy)benzene-1-sulfonyl chloride, 5-chlorosulfonyl-2-hydroxybenzoic acid, 4-bromo-2,5-difluorobenzene-1-sulfonyl chloride, 4-(Acetylamino)-3-chlorobenzene-1-sulfonyl chloride, 3,5-di-(trifluoromethyl)-benzene-1-sulfonyl chloride, 2-fluorobenzenesulfonyl chloride, 4-methyl-3-nitrobenzene-1-sulfonyl chloride, 5-chloro-2,1,3-benzoxadiazole-4-sulfonyl chloride, 3-(5-methyl-1,3,4-oxadiazol-2-yl)-benzenesulfonyl chloride, methyl 3-(chlorosulfonyl)-4-methoxy-benzoate, 4-bromo-2-(trifluoromethyl)-benzenesulfonyl chloride, 2,2-dimethyl-6-chromanesulfonyl chloride, 4-(morpholine-4-sulfonyl)benzenesulfonyl chloride, 4-(pyrrolidine-1-sulfonyl)benzenesulfonyl chloride, 3-(2-methyl-4-pyrimidinyl)benzene-sulfonyl chloride, 2-cyano-5-methylbenzenesulfonyl chloride, 2,5-dimethylbenzenesulfonyl chloride, 4-chloro-3-(trifluoromethyl)-benzenesulfonyl chloride, 4-bromo-2-methylbenzene-1- sulfonyl chloride, 2-chloro-4-(trifluoromethyl)-benzene-1-sulfonyl chloride, 2-chloro-4-cyanobenzene-1-sulfonyl chloride, 2,6-dichloro-4-(trifluoro-methyl)benzene-1-sulfonyl chloride, 3,4-difluorobenzene-1-sulfonyl chloride, 2-Iodobenzene-1-sulfonyl chloride, 4-methyl-1-naphthalenesulfonyl chloride, 4-(trifluoromethyl)benzene-1-sulfonyl chloride, 2,6-dichlorobenzene-1-sulfonyl chloride, 2-(trifluoromethoxy)benzene-1-sulfonyl chloride, 4-cyanobenzene-1-sulfonyl chloride, 4-butoxybenzene-1-sulfonyl chloride, 2,3,4-trifluorobenzene-1-sulfonyl chloride, 4-bromo-2-(trifluoromethoxy)-benzene-1-sulfonyl chloride, 3-cyanobenzene-1-sulfonyl chloride, 3-chloro-4-methylbenzene-1-sulfonyl chloride, 4-bromo-2-ethylbenzene-1-sulfonyl chloride, 5,5,8,8-tetramethyl-5,6,7,8-tetrahydro-2-naphthalenesulfonyl chloride, 4-(2-chloro-6-nitrophenoxy) benzene-1-sulfonyl chloride, 3,5-dichloro-4-(2-chloro-4-nitrophenoxy)-benzene-1-sulfonyl chloride, 4-pentylbenzene-1-sulfonyl chloride, 4-ethylbenzene-1-sulfonyl chloride, 4-propylbenzene-1-sulfonyl chloride, 4-butylbenzene-1-sulfonyl chloride, 3-toluenesulfonyl chloride, 4-isopropylbenzene-sulfonyl chloride, 4-(2-oxo-1-pyrrolidinyl)benzene sulfonyl chloride, 4-(2-Methoxyphenoxy)benzenesulfonyl chloride, 4-(2-chlorophenoxy)benzenesulfonyl chloride, 4-(2-methylphenoxy)-benzenesulfonyl chloride, 4'-chloro(1,1'-biphenyl)-4-sulfonyl chloride, 4'-Fluoro(1,1'-biphenyl)-4-sulfonyl chloride, 4'-methoxy-(1,1'-biphenyl)-4-sulfonyl chloride, 3',4'-Dichloro-(1,1'-biphenyl)-4-sulfonyl chloride, 4-phenoxybenzenesulfonyl chloride, 4'-Methyl-(1,1'-biphenyl)-4-sulfonyl chloride, 5-bromo-2,3-dihydrobenzo[b]furan-7-sulphonyl chloride, 3,4,5-trifluorobenzenesulfonyl chloride, 3-(5-methyl-1,2,4-oxadiazol-3-yl)benzenesulfonyl chloride, 4-(2-methyl-1,3-thiazol-4-yl)benzenesulfonyl chloride, 1-acetyl-5-indolinesulfonyl chloride, 3-(2-methyl-1,3-thiazol-4-yl)benzene-sulfonyl chloride and 1,3-benzodioxole-5-sulfonyl chloride.

Heterocyclylsulfonyl chlorides that may be used as precursors in scheme 3 of FIG. 2 include for example, but are not limited to, commercially available products such as, 4-methyl-2-[3-(pentyloxy)phenyl]-5-thiazolesulfonyl chloride, 2-(5-chloro-2-propoxyphenyl)-4-methyl-5-thiazolesulfonyl chloride, 2-(3-chloro-4-ethoxy-5-methoxy-phenyl)-4-methyl-5-thiazolesulfonyl chloride, 2-(3-chloro-4,5-dimethoxy-phenyl)-4-methyl-5-thiazolesulfonyl chloride, 2-(2-methoxy-1-naphthalenyl)-4-methyl-5-thiazole-sulfonyl chloride, 2-[3-[2-(dimethylamino)ethoxy]-4-methoxyphenyl]-4-methyl-5-thiazolesulfonyl chloride, 2-[4-[3-(dimethylamino)propoxy]phenyl]-4-methyl-5-Thiazolesulfonyl chloride, 2-[3-(hexyloxy)phenyl]-4-methyl-5-thiazolesulfonyl chloride, 2-(5-bromo-2-ethoxyphenyl)-4-methyl-5-Thiazolesulfonyl chloride, 2-(2-butoxy-3-methoxyphenyl)-4-methyl-5-thiazolesulfonyl chloride, 2-[2-[2-(dimethyl-amino)ethoxy]-3-methoxyphenyl]-4-methyl-5-thiazolesulfonyl chloride, 2-[2-[2-(dimethylamino)-ethoxy]-4-methoxyphenyl]-4-methyl-5-thiazolesulfonyl chloride, 2-(3-ethoxy-4-methoxyphenyl)-4-methyl-5-thiazolesulfonyl chloride, 2-(3,4-diethoxyphenyl)-4-methyl-5-thiazolesulfonyl chloride, 2-(2-butoxy-4-methoxyphenyl)-4-methyl-5-thiazole-sulfonyl chloride, 2-[4-(hexyloxy)phenyl]-4-methyl-5-thiazolesulfonyl chloride, 2-(3-ethoxy-4-propoxyphenyl)-4-methyl-5-Thiazolesulfonyl chloride, 2-[3-[2-(diethylamino)-ethoxy]phenyl]-4-methyl-5-thiazolesulfonyl chloride, 2-(3-chloro-5-ethoxy-4-methoxyphenyl)-4-methyl-5-thiazolesulfonyl chloride, 2-(3-methoxy-2-propoxy-phenyl)-4-methyl-5-thiazolesulfonyl chloride, 4-methyl-2-[2-(2-phenylethoxy)-phenyl]-5-thiazolesulfonyl chloride, 2-[4-methoxy-2-(pentyloxy)phenyl]-4-methyl-5-thiazole-sulfonyl chloride, 2-[3-methoxy-4-(pentyloxy)phenyl]-4-methyl-5-thiazole-sulfonyl chloride, 2-(3-methoxy-4-propoxyphenyl)-4-methyl-5-thiazolesulfonyl chloride, 2-(3-bromo-4-hydroxy-5-methoxyphenyl)-4-methyl-5-thiazolesulfonyl chloride, 5-(chlorosulfonyl)-2-Thiopheneacetic acid methyl ester, 5-[[(2,2,2-trifluoroacetypamino]methyl]-2-thiophenesulfonyl chloride, 5-[2-[(2,2,2-trifluoroacetyl)-amino]ethyl]-2-thiophenesulfonyl chloride, 5-formyl-2-Thiophenesulfonyl chloride, 5-(3-amino-3-oxo-1-propen-1-yl)-2-thiophenesulfonyl chloride, 5-(2H-tetrazol-5-yl)-2-thiophenesulfonyl chloride, 5-(5-isoxazolyl)-2-methyl-3-furansulfonyl chloride, 3-(1,3-dioxolan-2-yl)-2-furansulfonyl chloride, 5-(chlorosulfonyl)-3-thiophenecarboxylic acid, 4-[2-(methylthio)-4-pyrimidinyl]-2-thiophenesulfonyl chloride, 5-(1,3-dioxolan-2-yl)-2-thiophenesulfonyl chloride, 5-(chlorosulfonyl)-2-thiopheneacetic acid, 5-(acetamidomethyl)-2-thiophenesulfonyl chloride, 5-(chlorosulfonyl)-3-methyl-2,4-thiophenedicarboxylic acid dimethyl ester, 4-phenyl-5-(trifluoromethyl)-3-thiophenesulfonyl chloride, 5-(5-isoxazolyl)-2-furansulfonyl chloride, 5-(5-Isoxazolyl) thiophene-2-sulfonyl chloride, 3-(chlorosulfonyl)-4-[(1-methylethyl)sulfonyl]-2-thiophenecarboxylic acid methyl ester, 5-chlorosulfonyl-4-methylthiophene-2-carboxylic acid methyl ester, 5-[5-(chloromethyl)-1,2,4-oxadiazol-3-yl]-2-thiophenesulfonyl chloride, 5-[(3-chloro-5-trifluoromethylpyridin-2-yl)methyl]-thiophene-2-sulfonyl chloride, 5-(1,2,3-thiadiazol-4-yl)-2-thiophenesulfonyl chloride, 5-(5-chloro-1,2,4-thiadiazol-3-yl)-2-thiophenesulfonyl chloride, 5-(chlorosulfonyl)-2-methyl-3-furancarboxylic acid methyl ester, 4-(chlorosulfonyl)-2,5-dimethyl-3-furancarboxylic acid methyl ester, 4-(chlorosulfonyl)-2,5-dimethyl-3-furancarboxylic acid ethyl ester, 5-(4-chlorophenyl)-4-(chlorosulfonyl)-2-methyl-3-furancarboxylic acid ethyl ester, 3-(chlorosulfonyl)-4-phenyl-5-(trifluoromethyl)-2-thiophenecarboxylic acid methyl ester, 5-methyl-2-trifluoromethylfuran-3-sulfonyl chloride, 5-(2-methyl-5-trifluoromethyl-2H-pyrazol-3-yl)thiophene-2-sulfonyl chloride, 5-(2-methyl-1,3-thiazol-4-yl)thiophene-2-sulfonyl chloride, 3-bromo-5-chloro-2-thiophenesulfonyl chloride, 5-(chlorosulfonyl)-4-methoxy-3-Thiophenecarboxylic acid methyl ester, 5-(2-methylsulfanylpyrimidin-4-yl)thiophene-2-sulfonyl chloride, 3-bromothiophene-2-sulfonyl chloride, 5-(benzenesulfonyl)thiophene-2-sulfonyl chloride, 5-[[3-chloro-5-(trifluoromethyl)-2-pyridinyl]sulfonyl]-2-thiophenesulfonyl chloride, 3-Bromo-2,5-dichlorothiophene-4-sulfonyl chloride, 4-bromo-5-chlorothiophene-2-sulfonyl chloride, 5-(((4-chlorobenzoyl)amino)methyl)-2-thiophenesulfonyl chloride, 2-[1-methyl-5-(trifluoromethyl)-3-pyrazolyl]thiophene-5-sulfonyl chloride, 2,5-dimethylfuran-3-sulfonyl chloride, 2-phenylthiophene-3-sulfonyl chloride, 4-(phenylsulfonyl)-2-thiophenesulfonyl chloride, 2-(isoxazol-3-yl)thiophene-5-sulfonyl chloride, 3-quinolinesulfonyl chloride, dimethyl 3-chlorosulfonyl-2,5-thiophenedicarboxylate, 4-chloro-3-quinolinesulfonyl chloride, 2-(2-pyridyl)thiophene-5-sulfonyl chloride, 2-(benzoylaminomethyl)thiophene-5-sulfonyl chloride, 5-chloro-3-(chlorosulfonyl)-2-thiophenecarboxylic acid methyl ester, 2,3-dichlorothiophene-5-sulfonyl chloride, 4-bromo-3-thiophenesulfonyl chloride, 3-(1,3-dioxolan-2-yl)-2-thiophenesulfonyl chloride, 2,5-dimethylthiophene-3-sulfonyl chloride, 2-chlorosulfonyl-5-phenyl-thiophene, 2,3-dibromothiophene-5-sulfonyl chloride, 2,5-dibromo-3-thiophene-sulfonyl chloride, 2,5-dichloro-4-nitro-3-thiophenesulfonyl chloride, 4-(chlorosulfonyl)-3-thiophenecarboxylic acid methyl ester, 5-chloro-4-nitro-2-thiophenesulfonyl chloride, 2,4,5-trichloro-3-thiophenesulfonyl chloride, 5-ethyl-2-thiophenesulfonyl chloride, 5-(dichloromethyl)-2-furansulfonyl chloride, 5-iodo-2-thiophenesulfonyl chloride, 5-bromo-2-Thiophenesulfonyl chloride, 1,4-dimethyl-1H-imidazole-2-sulfonyl chloride, 2-(chlorosulfonyl)-1-methyl-1H-imidazole-5-carboxylic acid methyl ester, 1,5-dimethyl-1H-Imidazole-2-sulfonyl chloride, 3-chloro-5-(2,2,2-trichloroacetyl)-1H-pyrrole-2-sulfonyl chloride, 2,3-dihydro-2-methyl-1-(methylsulfonyl)-1H-Indole-5-sulfonyl chloride, 2-methyl-1-piperidinesulfonyl chloride, 5-(2H-tetrazol-5-yl)-1H-pyrrole-2-sulfonyl chloride, 1-(chlorosulfonyl)-4-piperidinecarboxylic acid methyl ester, 3,5-dimethyl-1-piperidinesulfonyl chloride, 5-bromo-3-pyridinesulfonyl chloride, 5-chloro-3-cyano-4,6-dimethyl-2-pyridinesulfonyl chloride, 6-chloro-4-methyl-3-pyridinesulfonyl chloride, 6-chloro-2-methylpyridine-3-sulfonyl chloride, 3-bromo-4-pyridinesulfonyl chloride, 6-bromo-3-pyridinesulfonyl chloride, 3,5-dichloro-2-pyridinesulfonyl chloride, 3-(phenylmethoxy)-2-pyridinesulfonyl chloride, 5-chloro-2-pyridinesulfonyl chloride, 6-phenyl-3-pyridinesulfonyl chloride, 1-methyl-5-(trichloroacetyl)-1H-pyrrole-3-sulfonyl chloride, 5-(trichloroacetyl)-1H-pyrrole-3-sulfonyl chloride, 1,2-dimethyl-1H-Imidazole-5-sulfonyl chloride, 1-(chlorosulfonyl)-3-Piperidinecarboxylic acid ethyl ester, 1-(chlorosulfonyl)-4-Piperidinecarboxylic acid ethyl ester, 3-chloro-1,5-dimethyl-1H-pyrazole-4-sulfonyl chloride, 3-methyl-1-piperidinesulfonyl chloride, 1-methyl-3-(trifluoromethyl)-1H-pyrazole-4-sulfonyl chloride, 1-Methylimidazol-5-ylsulfonyl chloride, 2-(4-morpholinyl)-3-Pyridinesulfonyl chloride, 5-Fluoro-2-chlorosulfonyl-3-methylbenzo[b]thiophene, 6-Phenoxypyridine-3-sulfonyl chloride, 4-(Chlorosulfonyl)-3,5-dimethyl-1H-pyrrole-2-carboxylic acid ethyl ester, 5-Methyl-1-phenyl-1H-pyrazole-4-sulfonyl chloride, 4-methyl-2-Pyridinesulfonyl chloride, 5-bromo-3-methyl-Benzo[b]thiophene-2-sulfonyl chloride, 1-[3-chloro-5-(trifluoromethyl)-2-pyridinyl]-1H-pyrrole-2-sulfonyl chloride, 6-(Morpholin-4-yl)pyridine-3-sulfonyl chloride, 6-methoxypyridine-3-sulfonyl chloride, 5-(chlorosulfonyl)-1-methyl-1H-Pyrrole-2-carboxylic acid methyl ester, 3-(chlorosulfonyl)-4-pyridinecarboxylic acid ethyl ester, 1-methyl-1H-pyrazole-4-sulfonyl chloride, benzyl 4-(chlorosulfonyl)-1-piperidinecarboxylate, 6-methyl-2-Pyridinesulfonyl chloride, 2,6-dichloro-3-pyridinesulfonyl chloride, 3-bromo-2-chloropyridine-5-sulfonyl chloride, 5-methyl-2-pyridinesulfonyl chloride, 5-nitro-2-pyridinesulfonyl chloride, 5-(trifluoro-methyl)pyridine-2-sulfonyl chloride, 5-chloro-2-(chlorosulfonyl)-3-methylbenzo[b]-thiophene, 1,2-dimethyl-1H-imidazole-4-sulfonyl chloride, 5-chloro-1-methyl-1H-Imidazole-4-sulfonyl chloride, 6-chlorobenzo[b]thiophene-2-sulfonyl chloride, 4-chloro-benzo[b]thiophene-2-sulfonyl chloride, 2-pyridinesulfonyl chloride, 5,6-dichloro-3-pyridinesulfonyl chloride, ethyl 3-(chlorosulfonyl)-1-methylpyrazole-4-carboxylate, 5-methyl-benzo[b]thiophene-2-sulfonyl chloride, 1-benzothiophene-2-sulfonyl chloride, 1,3-dimethyl-1H-pyrazole-4-sulfonyl chloride, 1-methyl-1H-pyrazole-3-sulfonyl chloride, 5-chloro-1,3-dimethyl-1H-pyrazole-4-sulfonyl chloride, 3,5-dimethyl-pyrazole-4-sulfonyl chloride, 5-bromo-3-pyridinesulfonyl chloride, 3,5-dimethyl-1-phenyl-1H-pyrazole-4-sulfonyl chloride, 3-methylbenzo[b]thiophene-2-sulfonyl chloride, 1-methyl-1H-imidazole-2-sulfonyl chloride, 3-pyridinesulfonyl chloride, 4-methyl-1-piperidinesulfonyl chloride, 1-piperidinesulfonyl chloride, 4-chloro-3-pyridinesulfonyl chloride, benzo[b]thiophene-3-sulfonyl chloride, 5-(chlorosulfonyl)-1,3,4-thiadiazole-2-acetic acid methyl ester, 3,4-dihydro-4-oxo-2H-1-benzopyran-3-sulfonyl chloride, 4-isoxazolesulfonyl chloride, 5-formyl-1,3,4-thiadiazole-2-sulfonyl chloride, 5-methyl-1H-imidazole-2-sulfonyl chloride, 5-(chlorosulfonyl)-1,3,4-thiadiazole-2-carboxylic acid methyl ester, 2,3-dihydro-2-oxo-5-thiazolesulfonyl chloride, 2,3-dihydro-4-methyl-2-oxo-5-thiazolesulfonyl chloride, 6-amino-1,2,3,4-tetrahydro-1,3-dimethyl-2,4-dioxo-5-pyrimidinesulfonyl chloride, 1,2,3,4-tetrahydro-1,3,6-trimethyl-2,4-dioxo-5-pyrimidinesulfonyl chloride, 2,6-dimethyl-4-morpholinesulfonyl chloride, 2,4-dimethyl-5-pyrimidinesulfonyl chloride, 1H-indole-3-sulfonyl chloride, 5-methyl-3-phenyl-4-isoxazolesulfonyl chloride, 1,3,4-thiadiazole-2-sulfonyl chloride, 5-methyl-4-isoxazolesulfonyl chloride, 1H-imidazole-2-sulfonyl chloride, 2-methyl-1H-imidazole-5-sulfonyl chloride, 3,4-dihydro-1H-isoquinoline-2-sulfonyl chloride, 3-(chlorosulfonyl)-4-methyl-3-thiolene 1,1-dioxide, 1,2,3,4-tetrahydro-1,3-dimethyl-2,4-dioxo-5-pyrimidinesulfonyl chloride, 4-chloro-tetrahydro-3-thiophenesulfonyl chloride 1,1-dioxide, 3-(chlorosulfonyl)-3-thiolene 1,1-dioxide, tetrahydro-4-hydroxy-3-thiophenesulfonyl chloride 1,1-dioxide, 3,5-dimethyl-4-isoxazolesulfonyl chloride, 4,5,6,7-tetrahydro-5-methyl-thiazolo[5,4-c]pyridine-2-sulfonyl chloride, 4,5,6,7-tetrahydro-5-(2,2,2-trifluoroacetyl)-thiazolo[5,4-c]pyridine-2-sulfonyl chloride, and 2-(chlorosulfonyl)-4,7-dihydro-thieno[2,3-c]pyridine-6(5H)-carboxylic acid 1,1-dimethylethyl ester.

The above synthetic principles can also be applied similarly with partly aliphatic sulfonyl chlorides, such as cycloalkyl-alkyl-, arylalkyl-, and arylalkenyl-sulfonyl chlorides, for instance when $R_1$ is aryl-$C_{1-4}$ alkyl, aryl-$C_{2-4}$ alkenyl or $C_{3-10}$ cycloalkyl-$C_{1-6}$ alkyl in a derivative represented by the structural formula (I), or when $Cy_2$ is aryl-$C_{1-4}$ alkyl, aryl-$C_{2-4}$ alkenyl or $C_{3-10}$ cycloalkyl-$C_{1-6}$ alkyl in a derivative represented by the structural formula (IV).

The above synthetic principles can also be applied similarly with a higher analogue of piperazine, e.g. homopiperazine.

Figure 7:
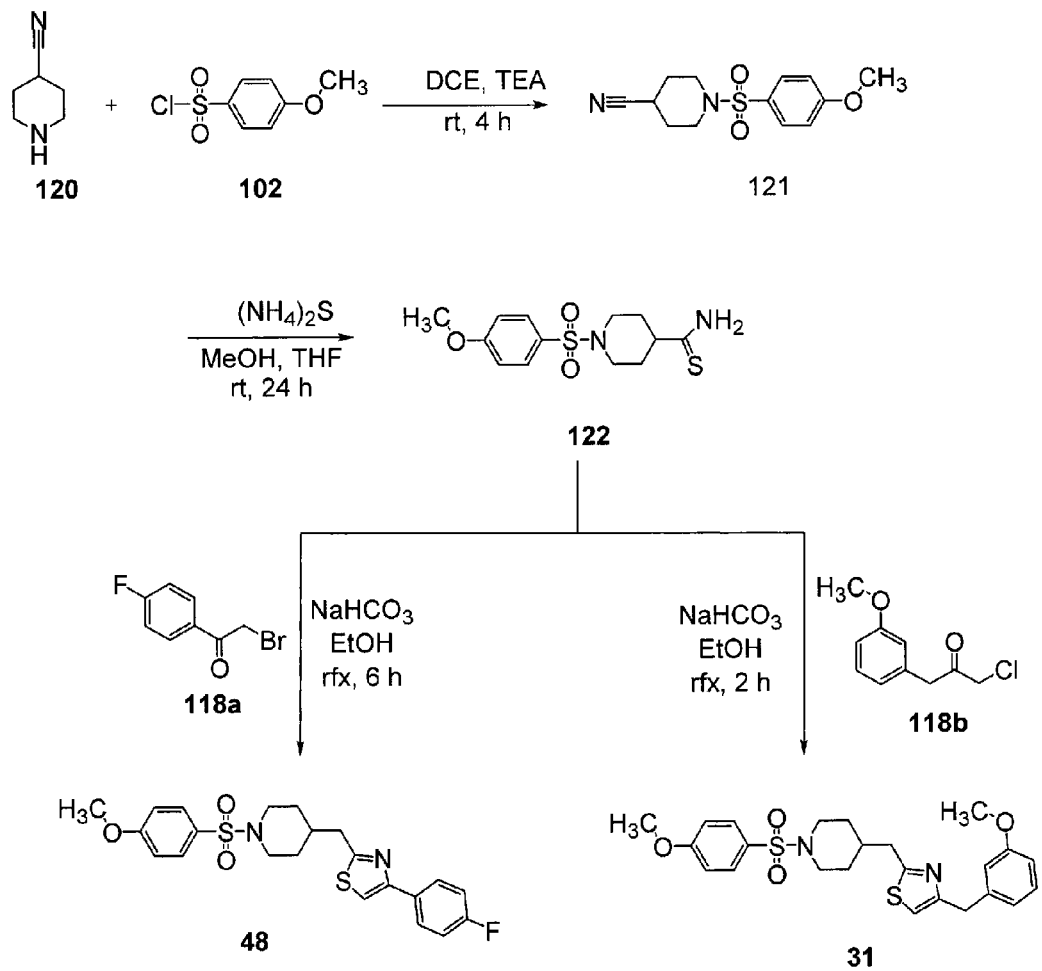
FIG. 7 shows synthetic schemes for the preparation of benzyl-thiazolylmethyl-piperidine derivatives according to this invention.
Figure 8:
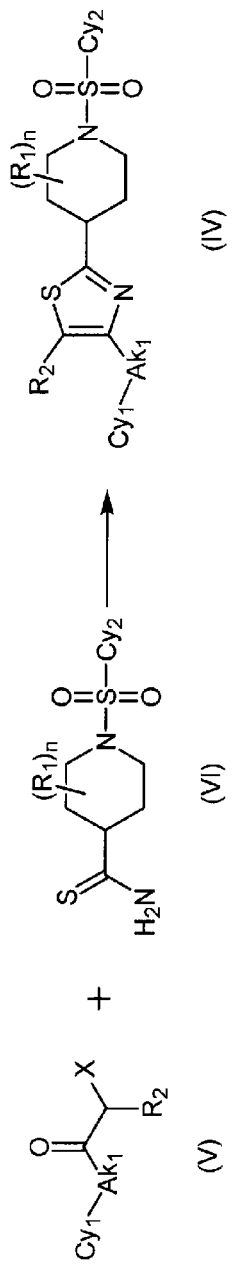
FIG. 8 shows synthetic schemes for the preparation of thiazolyl-piperidine derivatives according to this invention and intermediates therefor.
Figure 8:
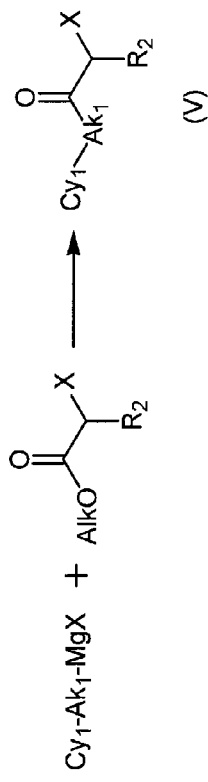
Figure 8:
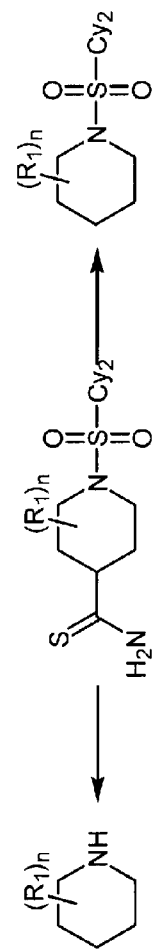
Figure 9:
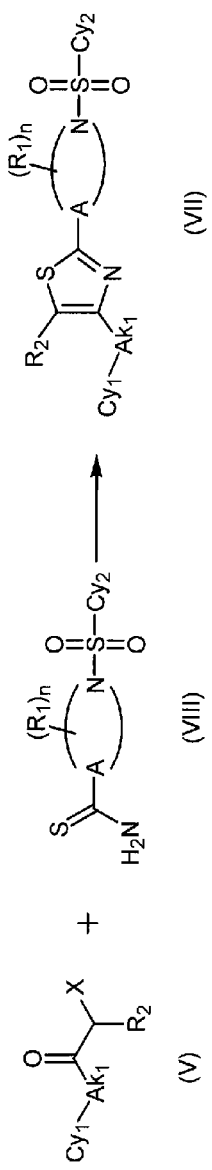
FIG. 9 shows synthetic schemes for the preparation of thiazolyl-heterocyclyl derivatives according to this invention and intermediates therefor.
Figure 9:
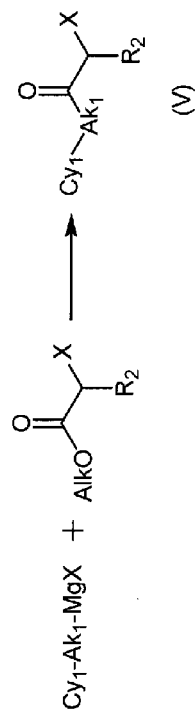
Figure 9:
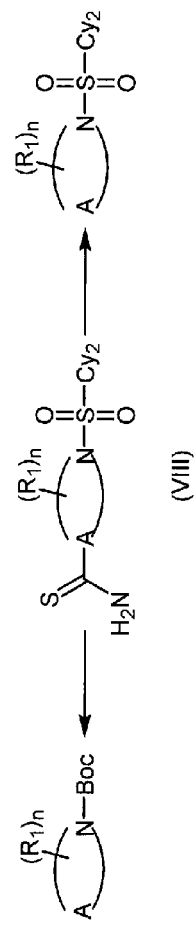

The above synthetic principles (schemes 1 and 3 of FIG. 2) can also be applied similarly when a divalent group (G), such as but not limited to a divalent group derived from an optionally substituted piperidine, is present in the final compounds instead of a divalent group derived from piperazine, i.e. when a thiazolyl derivative represented by the structural formula (IV) has to be produced, as shown in FIGS. 7, 8 and 9.

Thus, compounds represented by the structural formula (VI), i.e. 4-[(R$_1$-substituted)sulfonyl]piperidine-1-carbothioamides wherein R$_1$ is as defined in formula (I), in particular 4-arylsulfonyl-piperidine-1-carbothioamides and 4-heterocyclyl-sulfonylpiperidine-1-carbo-thioamides, can be obtained for example, as shown on the left part of the bottom scheme of FIG. 8, starting with piperidine, by introducing a thioamide group using ethyl chloroformate and potassium thiocyanate under conditions known in the art, followed by reaction with a suitable corresponding arylsulfonyl chloride or heterocyclylsulfonyl chloride; or (as shown on the right part of the bottom scheme of FIG. 8) simply by using ethyl chloroformate and potassium thiocyanate directly onto a suitable arylsulfonylpiperidine or heterocyclyl-sulfonylpiperidine derivative (the latter being e.g. obtained by reaction of piperidine and a suitable sulfonyl chloride).

More generally speaking, compounds represented by the structural formula (VIII), i.e. sulfonated heterocyclylcarbothioamides, can be obtained for example as shown in FIG. 9 and later on used as intermediates for producing derivatives of this invention represented by the structural formula (I).

Figure 6:
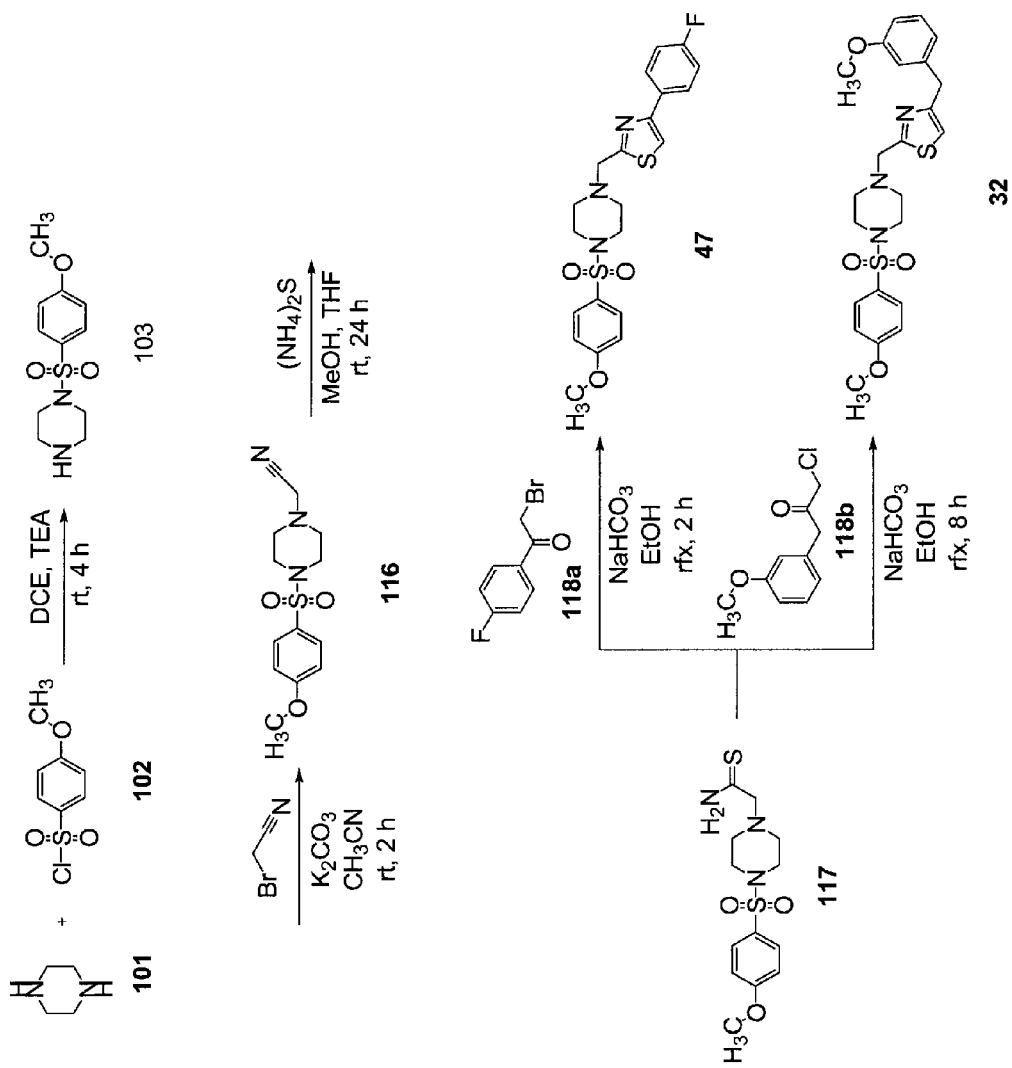
FIG. 6 shows synthetic schemes for the preparation of benzyl-thiazolylmethyl-piperazine derivatives according to this invention.

Derivatives of the present invention represented by the structural formula (I) in FIG. 2 wherein the thiazolyl group and the piperazine ring are linked via a linking moiety other than a single bond (i.e. W is a divalent non-cyclic hydrocarbyl group such as CH$_2$, (CH$_2$)$_2$, CH(CH$_3$) or (CH$_2$)$_3$, may be obtained as shown in FIG. 6 through the reaction step of an (optionally substituted)arylsulfonylpiperazine with an w-halocarbonitrile having from 2 to 4 carbon atoms wherein halo is chloro, bromo or iodo, thus producing a class of novel 2-(4-(R$_1$substituted-phenylsulfonyl)piperazin-1-yl)acetonitriles, 3-(4-(R$_1$substituted-phenylsulfonyl)piperazin-1-yl) propionitriles and 4-(4-(R$_1$substituted-phenylsulfonyl)piperazin-1-yl)butyronitriles intermediates wherein R$_1$ is as defined in formula (I). Suitable ω-halocarbonitriles for this reaction step include, but are not limited to, bromoacetonitrile, chloroacetonitrile, iodoacetonitrile, 2-bromopropionitrile, 2-chloropropionitrile, 3-bromopropionitrile, 3-chloropropionitrile, 4-bromobutyronitrile and 4-chlorobutyronitrile. These nitrile intermediates are then converted into the corresponding novel 2-(4-(R$_1$substituted-phenylsulfonyl)piperazin-1-yl)ethanethio-amides, 3-(4-(R$_1$substituted-phenylsulfonyl)piperazin-1-yl)propane-thioamides and 4-(4-(R$_1$substituted-phenylsulfonyl) piperazin-1-yl)butanethioamides (FIG. 6).

Exemplary derivatives of the present invention are shown in table 1 below with their chemical formula, the value of EC$_{50}$ (expressed in nM) and the percentage inhibition (% I) in a biological assay as explained in examples 3 and 4.

TABLE 1

| No. | Formula Name | EC$_{50}$ (nM) | % I |
|---|---|---|---|
| 1 | 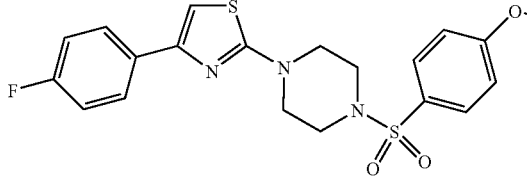 1-[4-(4-fluorophenyl)-1,3-thiazol-2-yl]-4-[(4-methoxyphenyl)sulfonyl]-piperazine | 24 | 100 |
| 2 | 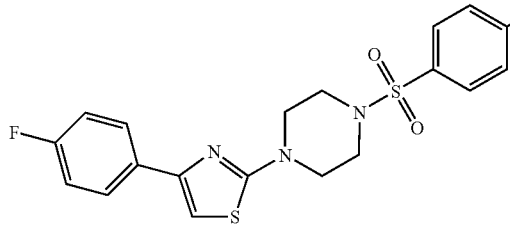 1-[4-(4-fluorophenyl)-1,3-thiazol-2-yl]-4-[(4-methylphenyl)sulfonyl]-piperazine | 160 | 70 |
| 4 | 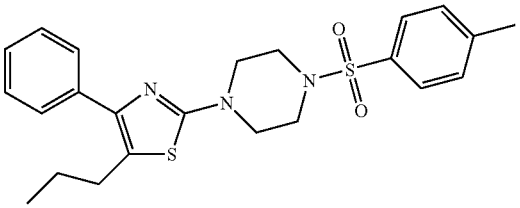 1-(4-phenyl-3-propyl-1,3-thiazol-2-yl)-4-[(4-methylphenyl)sulfonyl]-piperazine | 203 | 61 |
| 5 | 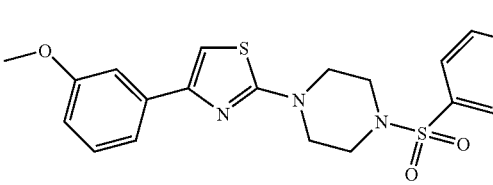 1-[4-(3-methoxyphenyl)-1,3-thiazol-2-yl]-4-[(4-fluorophenyl)sulfonyl]-piperazine | 216 | 90 |

TABLE 1-continued

| No. | Formula Name | | EC$_{50}$ (nM) | % I |
|---|---|---|---|---|
| 6 | 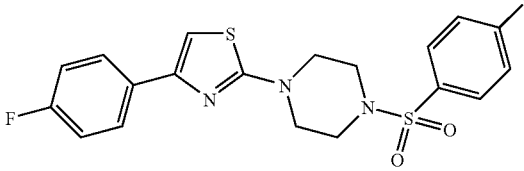 1-[4-(4-fluorophenyl)-1,3-thiazol-2-yl]-4-[(4-chlorophenyl)sulfonyl]-piperazine | | 300 | 88 |
| 7 |  1-[4-(4-fluorophenyl)-1,3-thiazol-2-yl]-4-[(4-bromophenyl)sulfonyl]-piperazine | | 327 | 94 |
| 8 | 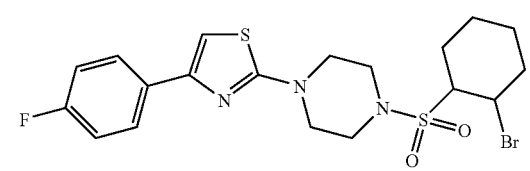 1-[4-(4-fluorophenyl)-1,3-thiazol-2-yl]-4-[(2-bromophenyl)sulfonyl]-piperazine | | 568 | 88 |
| 9 | 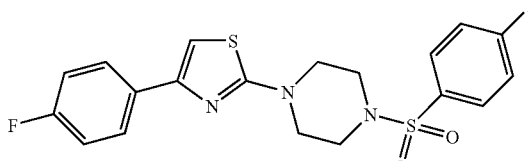 1-[4-(4-fluorophenyl)-1,3-thiazol-2-yl]-4-[(4-fluorophenyl)sulfonyl]-piperazine | | 833 | 81 |

(end of Table 1)

All stereoisomers or enantiomers thereof, or solvates thereof, or N-oxides thereof, or pharmaceutically acceptable salts thereof, are also embraced within the present invention.

Example 1

Construction of an α-synuclein Over-expressing Cell Line

An α-synuclein expression plasmid was constructed by sub-cloning the NcoI/XhoI fragment from 212T-SYN(WT) (Griffioen et al., Biochem Biophys Acta (2006) 1762(3):312-318) containing the cDNA of human wild type α-synuclein correspondingly into a standard mammalian expression vector pcDNA3.1 resulting in plasmid pcDNA3.1-SYNwt. Plasmid pcDNA3.1 and pcDNA3.1-SYNwt were transfected to human neuroblastoma cells (ATCC No. CRL-2267) and independent clonal lines with the plasmids stably integrated into the genome were selected. These resulted in cell lines named M17 (transfected with pcDNA3.1) and M17-SYNwt (transfected with pcDNA3.1-SYNwt). Over-expression of α-synuclein in M17-SYNwt cell lines was confirmed by Western analysis.

Example 2

Use of α-synuclein Expressing Cells as a Model for Neuronal Degradation

Due to the high levels of α-synuclein M17-SYNwt cells are exquisitely sensitivity to paraquat, a well-known risk factor of synuclein-dependent neuronal degeneration. In degenerated or dead cells lactate dehydrogenase (LDH) is leaked out of the cells into the extracellular environment due to a loss of plasma-membrane integrity. This principle was used to determine cytotoxicity by quantifying the level of leaked LDH into the growth medium.

The detailed method for determining α-synuclein cytotoxicity was as follows: From appropriate precultures of M17 and M17-SYN cells were seeded at 50000 cells/cm$^2$ in Optimem Reduced Serum without phenol red (InVitrogen, Cat.

31985-047) supplemented with 5% fetal calf serum, 1 mM sodium pyruvate, 1×non-essential amino acids, 500 µg/ml G418 0.5×antibiotic/antimycotic. After 3 hours of incubation at 37° C./5% $CO_2$ paraquat was added to the cells (final concentration of 32 mM), together with the test compound and the cells were further incubated for 40 hours. Subsequently, LDH activity was determined using Promega Cytotox 96 Non-Radioactive cytotoxicity assay, (Cat. G1780) according the supplier's instructions.

FIG. 1 shows that treatment of M17-SYNwt cells, but not of M17 cells with paraquat led to a relatively high level of LDH leaked into the medium demonstrating that α-synuclein mediates cellular degeneration or cell death in response to paraquat.

Example 3

Use of the α-synuclein Expressing Cells in the Screening Compounds

This α-synuclein expressing neuroblastoma cells made it possible to assess the ability of novel compounds to counteract α-synuclein cytotoxicity. Active inhibitors of α-synuclein cytotoxicity were found to provoke a decrease of LDH leakage in paraquat-treated M17-SYNwt cells. Since this method monitors leaked LDH from degenerated or dead cells only non-toxic compounds will be identified as active inhibitors of α-synuclein-mediated cytotoxicity. Lack of toxicity is an important characteristic for compounds to be used as a medicament to patients in need. A compound was considered to be active in this test when it inhibits α-synuclein cytotoxicity by more than 25% relative to untreated M17-SYNwt cells at a concentration of 20 µg/mL or lower. In the experiments, the control group consisted of M17-SYNwt cells treated with DMSO, the untreated paraquat group consisted of M17-SYNwt cells treated with paraquat and DMSO, and the treated paraquat group consisted of M17-SYNwt cells treated with paraquat and the test compound dissolved in DMSO.

In order to determine $EC_{50}$ compounds were tested at different concentrations ranging from non-effective (thus at a relatively low concentration) to an effective (relatively high) concentration of test compound. These data were also used for calculation of percent inhibition (% I). Percent inhibition was calculated as the synuclein toxicity inhibition by the compound in treated paraquat cells, relative to the synuclein cytotoxicity in untreated paraquat cells. This corresponds to the following equation:

(*LDH* release of treated paraquat cells at non-effective concentration of test cmpd)–(*LDH* release of treated paraquat cells at most effective concentration of test cmpd)/(*LDH* release of untreated paraquat cells)–(*LDH* release control cells)*100%

Example 4

Inhibition of Synuclein-mediated Toxicity

The compounds from table 1 were screened for activity using the α-synuclein cytotoxicity assay as described above. Dose responses were carried out on all compounds found to be active (10 point curves in duplicate). Although the pharmacological properties of the compounds disclosed in this invention vary with structural change as expected, active compounds most particularly possess $EC_{50}$ in a cell-based assay of synuclein cytotoxicity in a range from about 0.0001 to 10 µM.

Example 5

In vivo Inhibition of Synuclein-mediated Instigated Loss of Substantia Nigra Neurons In order to model neuronal loss in the substantia nigra region of the brain, mice are treated with paraquat (intraperitoneal) at a dose not higher than 8 mg/kg/day for a continuous period of 15-100 days. These mice are also chronically co-treated during that period with a compound from table 1 administered at a dose not higher than 20 mg/kg body weight/day), or by vehicle only (no active compound). Mice treatment by means of vehicle or a compound of the invention start 2 days before administration of paraquat.

At the end of the treatment period, mice are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosin hydroxylase), tyrosine hydroxylase containing neurons in the brains are detected. Quantitative and comparative analysis of the tyrosin hydroxylase-positive stained substantia nigra areas reveal a significantly larger TH-positive area in mice treated with compound versus vehicle treated mice.

Example 6

In vivo Inhibition of 6-hydroxydopamine (6-OHDA) Instigated Loss of Substantia Nigra Neurons Unilateral substantia nigra lesions are obtained by stereotactic striatal injections of 6-hydroxydopamine in brains of living rats as described by Vercammen et al. in *Molecular Therapy*, 14(5) 716-723 (2006). These rats are also chronically co-treated with a compound of table 1 and at the same dose as mentioned in example 5, or by vehicle only (no active compound). Daily treatment of compound or vehicle is started preferably 1 or 2 days before administration of 6-OHDA and lasts between 7 to 30 days after the 6-OHDA injection.

At the end of the treatment period, rats are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosine hydroxylase) tyrosine hydroxylase containing neurons in the brains are detected. The nigral lesion volumes and/or the tyrosine hydroxylase positive cell numbers are quantified as described in Vercammen et al. (cited supra). This analysis reveals that:

the nigral lesion volumes are significantly reduced in rats treated with a compound according to this invention, as compared to vehicle treated rats, thus indicating that the compound is able to inhibit 6-OHDA triggered degeneration of substantia nigra cells in vivo; and tyrosine hydroxylase positive cell numbers are higher in rats treated with a compound according to this invention as compared to vehicle treated rats, thus providing confirmation that the compound is able to inhibit 6-OHDA triggered degeneration of substantia nigra cells in vivo.

Example 7

In vitro Inhibition of α-synuclein Appreciation

α-Synucleinopathies are characterised by aggregation of α-synuclein in neurons. Aggregation of purified α-synuclein is performed essentially as described by Gerard et al. *FASEB*. 20(3):524-6 (2006). 20-100 μg purified α-synuclein (Sigma; S7820) at a concentration of about 2.5 μg/mL is incubated in the presence of spermin (250 μM) or paraquat (32 mM) or 6-hydroxydopamine (400 μM) or vehicle in a 384 well plate. Spermin, paraquat and 6-hydroxydopamine promote the α-synuclein aggregation process. Aggregation kinetics is determined by measuring turbidity at 340 nm, every 1-15 minutes for at least one hour. The same compounds of table 1, or vehicle only, is added to the different α-synuclein mixtures described above. This analysis reveals that, when a compound is present, the measured turbidity is lower compared to reactions containing vehicle only. This finding shows that the compound is able to inhibit aggregation of α-synuclein.

Example 8

Detailed Synthetic and Analytical Procedures

In the following examples 9 to 11 and 13 to 21, commercial grade anhydrous solvents and reagents were used without further purification or drying. For conciseness, abbreviations with the meanings summarized in the following table were used throughout the examples.

| | |
|---|---|
| atmospheric pressure chemical ionization | APCI |
| chloroform-d | $CDCl_3$ |
| trifluoroacetic acid | TFA |
| dimethyl-d6 sulfoxide | DMSO-d6 |
| ethanol | EtOH |
| ethyl acetate | EtOAc |
| high performance liquid chromatography | HPLC |
| mass spectrum | MS |
| methanol | MeOH |
| methanol-d4 | $CD_3OD$ |
| methylene chloride or dichloromethane | DCM |
| proton nuclear magnetic resonance | $^1$H NMR |
| thin layer chromatography | TLC |
| thiocarbonyl-diimidazole | thio-CDI |
| triethylamine | TEA |
| 1,2-dichloethane | DCE |
| tetrahydrofuran | THF |

TLC was performed using silica gel 60 F254 plates (available from Merck) and visualized by UV light (254 nm). Column chromatography was carried out using silica gel 60 unless otherwise specified.

Proton nuclear magnetic resonance spectra were obtained at room temperature on a Bruker Avance II 400 MHz instrument. For spectra calibration, solvent peak and tetramethylsilane signals were used. Spectral data are given in ppm (δ) with coupling constants and J values reported in Hertz.

HPLC-MS analysis was performed at room temperature on a Waters HPLC/MS instrument (with 4-channel MUX interface) with a LiChroCART 30-4 Purospher STAR RP-18, end-capped, 3 μm (Merck) column using a solvent gradient program. HPLC conditions were:
 eluent A=95:5 water/acetonitrile with 20 mM $HCOONH_4$/$NH_4OH$ buffer, pH 7.4,
 eluent B=20:80 water/acetonitrile with 20 mM $HCOONH_4$/$NH_4OH$ buffer, pH 7.4,
 gradient elution program adjusted to the compound properties,
 flow rate: 1.50 ml/minute,
 sample Concentration: 1 mg/mL,
 sample solvent: acetonitrile,
 injection: 0.1.2.5 μl, and
 detection wavelength: 220 nm MS conditions were:
 measured mass range: 150 to 750 Da,
 scan time: 0.2 s,
 ion mode: ESI+; ESI.; APCI+, and
 cone voltage: typically 30 V or lower depending on the compound properties.

Example 9

Preparation of Compound 1 and Analogues Thereof

Using the synthetic scheme shown in FIG. 2 (wherein W is a single bond), compound 1 (i.e. 1-[4-(4-fluorophenyl)-1,3-thiazol-2-yl]-4-[(4-methoxyphenyl)-sulfonyl]-piperazine) shown in table 1 has been synthesised in good yield starting from 4'-fluoroacetophenone, piperazine and (4-methoxyphenyl)sulfonyl chloride.

Using the same synthetic procedure but replacing 4'-fluoroacetophenone with another alkylarylketone, the following derivatives of this invention are prepared:
1-[4-phenyl-1,3-thiazol-2-yl]-4-[(4-methoxyphenyl)sulfonyl]-piperazine
1-[4-(2-methylphenyl)-1,3-thiazol-2-yl]-4-[(4-methoxyphenyl)sulfonyl]-piperazine
1-[4-(2-methoxyphenyl)-1,3-thiazol-2-yl]-4-[(4-methoxyphenyl)sulfonyl]-piperazine
1-[4-(3-methylphenyl)-1,3-thiazol-2-yl]-4-[(4-methoxyphenyl)sulfonyl]-piperazine
1-[4-(3-methoxyphenyl)-1,3-thiazol-2-yl]-4-[(4-methoxyphenyl)sulfonyl]-piperazine
1-[4-(3-bromophenyl)-1,3-thiazol-2-yl]-4-[(4-methoxyphenyl)sulfonyl]-piperazine
1-[4-(4-chlorophenyl)-1,3-thiazol-2-yl]-4-[(4-methoxyphenyl)sulfonyl]-piperazine
1-[4-(4-methoxyphenyl)-1,3-thiazol-2-yl]-4-[(4-methoxyphenyl)sulfonyl]-piperazine
1-[4-(4-methylphenyl)-1,3-thiazol-2-yl]-4-[(4-methoxyphenyl)sulfonyl]-piperazine
1-[4-(4-ethylphenyl)-1,3-thiazol-2-yl]-4-[(4-methoxyphenyl)sulfonyl]-piperazine
1-[4-(4-ethoxyphenyl)-1,3-thiazol-2-yl]-4-[(4-methoxyphenyl)sulfonyl]-piperazine
1-[4-(4-propylphenyl)-1,3-thiazol-2-yl]-4-[(4-methoxyphenyl)sulfonyl]-piperazine
1-[4-(2,6-dimethylphenyl)-1,3-thiazol-2-yl]-4-[(4-methoxyphenyl)sulfonyl]-piperazine
1-[4-(2,3-dimethylphenyl)-1,3-thiazol-2-yl]-4-[(4-methoxyphenyl)sulfonyl]-piperazine
1-[4-(2,5-dimethylphenyl)-1,3-thiazol-2-yl]-4-[(4-methoxyphenyl)sulfonyl]-piperazine
1-[4-(2,4-dichlorophenyl)-1,3-thiazol-2-yl]-4-[(4-methoxyphenyl)sulfonyl]-piperazine
1-[4-(2,4-dimethoxyphenyl)-1,3-thiazol-2-yl]-4-[(4-methoxyphenyl)sulfonyl]-piperazine
1-[4-(2,5-dimethoxyphenyl)-1,3-thiazol-2-yl]-4-[(4-methoxyphenyl)sulfonyl]-piperazine
1-[4-(3,4-dimethoxyphenyl)-1,3-thiazol-2-yl]-4-[(4-methoxyphenyl)sulfonyl]-piperazine
1-[4-(3,5-dimethoxyphenyl)-1,3-thiazol-2-yl]-4-[(4-methoxyphenyl)sulfonyl]-piperazine
1-[4-(3,4-dichlorophenyl)-1,3-thiazol-2-yl]-4-[(4-methoxyphenyl)sulfonyl]-piperazine
1-[4-(3,4-dimethylphenyl)-1,3-thiazol-2-yl]-4-[(4-methoxyphenyl)sulfonyl]-piperazine
1-[4-(3,4-difluorophenyl)-1,3-thiazol-2-yl]-4-[(4-methoxyphenyl)sulfonyl]-piperazine 1-[4-(3,5-difluorophenyl)-1,3-thiazol-2-yl]-4-[(4-methoxyphenyl)sulfonyl]-piperazine
1-[4-(3,5-dichlorophenyl)-1,3-thiazol-2-yl]-4-[(4-methoxyphenyl)sulfonyl]-piperazine
1-[4-(3,5-dimethylphenyl)-1,3-thiazol-2-yl]-4-[(4-methoxyphenyl)sulfonyl]-piperazine
1-[4-(3-chloro-4-fluorophenyl)-1,3-thiazol-2-yl]-4-[(4-methoxyphenyl)sulfonyl]-piperazine
1-[4-(3-chloro-5-fluorophenyl)-1,3-thiazol-2-yl]-4-[(4-methoxyphenyl)sulfonyl]-piperazine
1-[4-(4-chloro-3-fluorophenyl)-1,3-thiazol-2-yl]-4-[(4-methoxyphenyl)sulfonyl]-piperazine
1-[4-(3,4,5-trimethoxyphenyl)-1,3-thiazol-2-yl]-4-[(4-methoxyphenyl)sulfonyl]-piperazine, and
1-[4-(2,4,6-trimethylphenyl)-1,3-thiazol-2-yl]-4-[(4-methoxyphenyl)sulfonyl]-piperazine.

Example 10

Preparation of Derivatives of the Invention Wherein W is a Simile Bond

Using the same synthetic procedure (FIG. 2) and the same alkylarylketones as in example 9, but replacing (4-methoxyphenyl)sulfonyl chloride with another arylsulfonylchloride, the following derivatives are prepared:
1-[4-phenyl-1,3-thiazol-2-yl]-4-[(4-fluorophenyl)sulfonyl]-piperazine
1-[4-(2-methylphenyl)-1,3-thiazol-2-yl]-4-[(4-fluorophenyl)sulfonyl]-piperazine
1-[4-(2-methoxyphenyl)-1,3-thiazol-2-yl]-4-[(4-fluorophenyl)sulfonyl]-piperazine
1-[4-(3-methylphenyl)-1,3-thiazol-2-yl]-4-[(4-fluorophenyl)sulfonyl]-piperazine
1-[4-(3-methoxyphenyl)-1,3-thiazol-2-yl]-4-[(4-fluorophenyl)sulfonyl]-piperazine
1-[4-(3-bromophenyl)-1,3-thiazol-2-yl]-4-[(4-fluorophenyl)sulfonyl]-piperazine
1-[4-(4-chlorophenyl)-1,3-thiazol-2-yl]-4-[(4-fluorophenyl)sulfonyl]-piperazine
1-[4-(4-methoxyphenyl)-1,3-thiazol-2-yl]-4-[(4-fluorophenyl)sulfonyl]-piperazine
1-[4-(4-methylphenyl)-1,3-thiazol-2-yl]-4-[(4-fluorophenyl)sulfonyl]-piperazine
1-[4-(4-ethylphenyl)-1,3-thiazol-2-yl]-4-[(4-fluorophenyl)sulfonyl]-piperazine
1-[4-(4-ethoxyphenyl)-1,3-thiazol-2-yl]-4-[(4-fluorophenyl)sulfonyl]-piperazine
1-[4-(4-propylphenyl)-1,3-thiazol-2-yl]-4-[(4-fluorophenyl)sulfonyl]-piperazine
1-[4-(2,6-dimethylphenyl)-1,3-thiazol-2-yl]-4-[(4-fluorophenyl)sulfonyl]-piperazine
1-[4-(2,3-dimethylphenyl)-1,3-thiazol-2-yl]-4-[(4-fluorophenyl)sulfonyl]-piperazine
1-[4-(2,5-dimethylphenyl)-1,3-thiazol-2-yl]-4-[(4-fluorophenyl)sulfonyl]-piperazine
1-[4-(2,4-dichlorophenyl)-1,3-thiazol-2-yl]-4-[(4-fluorophenyl)sulfonyl]-piperazine
1-[4-(2,4-dimethoxyphenyl)-1,3-thiazol-2-yl]-4-[(4-fluorophenyl)sulfonyl]-piperazine
1-[4-(2,5-dimethoxyphenyl)-1,3-thiazol-2-yl]-4-[(4-fluorophenyl)sulfonyl]-piperazine
1-[4-(3,4-dimethoxyphenyl)-1,3-thiazol-2-yl]-4-[(4-fluorophenyl)sulfonyl]-piperazine
1-[4-(3,5-dimethoxyphenyl)-1,3-thiazol-2-yl]-4-[(4-fluorophenyl)sulfonyl]-piperazine
1-[4-(3,4-dichlorophenyl)-1,3-thiazol-2-yl]-4-[(4-fluorophenyl)sulfonyl]-piperazine
1-[4-(3,4-dimethylphenyl)-1,3-thiazol-2-yl]-4-[(4-fluorophenyl)sulfonyl]-piperazine
1-[4-(3,4-difluorophenyl)-1,3-thiazol-2-yl]-4-[(4-fluorophenyl)sulfonyl]-piperazine
1-[4-(3,5-difluorophenyl)-1,3-thiazol-2-yl]-4-[(4-fluorophenyl)sulfonyl]-piperazine
1-[4-(3,5-dichlorophenyl)-1,3-thiazol-2-yl]-4-[(4-fluorophenyl)sulfonyl]-piperazine
1-[4-(3,5-dimethylphenyl)-1,3-thiazol-2-yl]-4-[(4-fluorophenyl)sulfonyl]-piperazine
1-[4-(3-chloro-4-fluorophenyl)-1,3-thiazol-2-yl]-4-[(4-fluorophenyl)sulfonyl]-piperazine
1-[4-(3-chloro-5-fluorophenyl)-1,3-thiazol-2-yl]-4-[(4-fluorophenyl)sulfonyl]-piperazine
1-[4-(4-chloro-3-fluorophenyl)-1,3-thiazol-2-yl]-4-[(4-fluorophenyl)sulfonyl]-piperazine
1-[4-(3,4,5-trimethoxyphenyl)-1,3-thiazol-2-yl]-4-[(4-fluorophenyl)sulfonyl]-piperazine
1-[4-(2,4,6-trimethylphenyl)-1,3-thiazol-2-yl]-4-[(4-fluorophenyl)sulfonyl]-piperazine
1-[4-phenyl-1,3-thiazol-2-yl]-4-[(4-bromophenyl)sulfonyl]-piperazine
1-[4-(2-methylphenyl)-1,3-thiazol-2-yl]-4-[(4-bromophenyl)sulfonyl]-piperazine
1-[4-(2-methoxyphenyl)-1,3-thiazol-2-yl]-4-[(4-bromophenyl)sulfonyl]-piperazine
1-[4-(3-methylphenyl)-1,3-thiazol-2-yl]-4-[(4-bromophenyl)sulfonyl]-piperazine
1-[4-(3-methoxyphenyl)-1,3-thiazol-2-yl]-4-[(4-bromophenyl)sulfonyl]-piperazine
1-[4-(3-bromophenyl)-1,3-thiazol-2-yl]-4-[(4-bromophenyl)sulfonyl]-piperazine
1-[4-(4-chlorophenyl)-1,3-thiazol-2-yl]-4-[(4-bromophenyl)sulfonyl]-piperazine
1-[4-(4-methoxyphenyl)-1,3-thiazol-2-yl]-4-[(4-bromophenyl)sulfonyl]-piperazine
1-[4-(4-methylphenyl)-1,3-thiazol-2-yl]-4-[(4-bromophenyl)sulfonyl]-piperazine
1-[4-(4-ethylphenyl)-1,3-thiazol-2-yl]-4-[(4-bromophenyl)sulfonyl]-piperazine
1-[4-(4-ethoxyphenyl)-1,3-thiazol-2-yl]-4-[(4-bromophenyl)sulfonyl]-piperazine
1-[4-(4-propylphenyl)-1,3-thiazol-2-yl]-4-[(4-bromophenyl)sulfonyl]-piperazine
1-[4-(2,6-dimethylphenyl)-1,3-thiazol-2-yl]-4-[(4-bromophenyl)sulfonyl]-piperazine
1-[4-(2,3-dimethylphenyl)-1,3-thiazol-2-yl]-4-[(4-bromophenyl)sulfonyl]-piperazine
1-[4-(2,5-dimethylphenyl)-1,3-thiazol-2-yl]-4-[(4-bromophenyl)sulfonyl]-piperazine
1-[4-(2,4-dichlorophenyl)-1,3-thiazol-2-yl]-4-[(4-bromophenyl)sulfonyl]-piperazine
1-[4-(2,4-dimethoxyphenyl)-1,3-thiazol-2-yl]-4-[(4-bromophenyl)sulfonyl]-piperazine
1-[4-(2,5-dimethoxyphenyl)-1,3-thiazol-2-yl]-4-[(4-bromophenyl)sulfonyl]-piperazine
1-[4-(3,4-dimethoxyphenyl)-1,3-thiazol-2-yl]-4-[(4-bromophenyl)sulfonyl]-piperazine
1-[4-(3,5-dimethoxyphenyl)-1,3-thiazol-2-yl]-4-[(4-bromophenyl)sulfonyl]-piperazine
1-[4-(3,4-dichlorophenyl)-1,3-thiazol-2-yl]-4-[(4-bromophenyl)sulfonyl]-piperazine
1-[4-(3,4-dimethylphenyl)-1,3-thiazol-2-yl]-4-[(4-bromophenyl)sulfonyl]-piperazine 1-[4-(3,4-difluorophenyl)-1,3-thiazol-2-yl]-4-[(4-bromophenyl)sulfonyl]-piperazine
1-[4-(3,5-difluorophenyl)-1,3-thiazol-2-yl]-4-[(4-bromophenyl)sulfonyl]-piperazine
1-[4-(3,5-dichlorophenyl)-1,3-thiazol-2-yl]-4-[(4-bromophenyl)sulfonyl]-piperazine
1-[4-(3,5-dimethylphenyl)-1,3-thiazol-2-yl]-4-[(4-bromophenyl)sulfonyl]-piperazine
1-[4-(3-chloro-4-fluorophenyl)-1,3-thiazol-2-yl]-4-[(4-bromophenyl)sulfonyl]-piperazine
1-[4-(3-chloro-5-fluorophenyl)-1,3-thiazol-2-yl]-4-[(4-bromophenyl)sulfonyl]-piperazine
1-[4-(4-chloro-3-fluorophenyl)-1,3-thiazol-2-yl]-4-[(4-bromophenyl)sulfonyl]-piperazine
1-[4-(3,4,5-trimethoxyphenyl)-1,3-thiazol-2-yl]-4-[(4-bromophenyl)sulfonyl]-piperazine
1-[4-(2,4,6-trimethylphenyl)-1,3-thiazol-2-yl]-4-[(4-bromophenyl)sulfonyl]-piperazine
1-[4-phenyl-1,3-thiazol-2-yl]-4-[(4-methylphenyl)sulfonyl]-piperazine
1-[4-(2-methylphenyl)-1,3-thiazol-2-yl]-4-[(4-methylphenyl)sulfonyl]-piperazine
1-[4-(2-methoxyphenyl)-1,3-thiazol-2-yl]-4-[(4-methylphenyl)sulfonyl]-piperazine
1-[4-(3-methylphenyl)-1,3-thiazol-2-yl]-4-[(4-methylphenyl)sulfonyl]-piperazine
1-[4-(3-methoxyphenyl)-1,3-thiazol-2-yl]-4-[(4-methylphenyl)sulfonyl]-piperazine
1-[4-(3-bromophenyl)-1,3-thiazol-2-yl]-4-[(4-methylphenyl)sulfonyl]-piperazine
1-[4-(4-chlorophenyl)-1,3-thiazol-2-yl]-4-[(4-methylphenyl)sulfonyl]-piperazine
1-[4-(4-methoxyphenyl)-1,3-thiazol-2-yl]-4-[(4-methylphenyl)sulfonyl]-piperazine
1-[4-(4-methylphenyl)-1,3-thiazol-2-yl]-4-[(4-methylphenyl)sulfonyl]-piperazine
1-[4-(4-ethylphenyl)-1,3-thiazol-2-yl]-4-[(4-methylphenyl)sulfonyl]-piperazine
1-[4-(4-ethoxyphenyl)-1,3-thiazol-2-yl]-4-[(4-methylphenyl)sulfonyl]-piperazine
1-[4-(4-propylphenyl)-1,3-thiazol-2-yl]-4-[(4-methylphenyl)sulfonyl]-piperazine
1-[4-(2,6-dimethylphenyl)-1,3-thiazol-2-yl]-4-[(4-methylphenyl)sulfonyl]-piperazine
1-[4-(2,3-dimethylphenyl)-1,3-thiazol-2-yl]-4-[(4-methylphenyl)sulfonyl]-piperazine
1-[4-(2,5-dimethylphenyl)-1,3-thiazol-2-yl]-4-[(4-methylphenyl)sulfonyl]-piperazine
1-[4-(2,4-dichlorophenyl)-1,3-thiazol-2-yl]-4-[(4-methylphenyl)sulfonyl]-piperazine
1-[4-(2,4-dimethoxyphenyl)-1,3-thiazol-2-yl]-4-[(4-methylphenyl)sulfonyl]-piperazine
1-[4-(2,5-dimethoxyphenyl)-1,3-thiazol-2-yl]-4-[(4-methylphenyl)sulfonyl]-piperazine
1-[4-(3,4-dimethoxyphenyl)-1,3-thiazol-2-yl]-4-[(4-methylphenyl)sulfonyl]-piperazine
1-[4-(3,5-dimethoxyphenyl)-1,3-thiazol-2-yl]-4-[(4-methylphenyl)sulfonyl]-piperazine
1-[4-(3,4-dichlorophenyl)-1,3-thiazol-2-yl]-4-[(4-methylphenyl)sulfonyl]-piperazine
1-[4-(3,4-dimethylphenyl)-1,3-thiazol-2-yl]-4-[(4-methylphenyl)sulfonyl]-piperazine
1-[4-(3,4-difluorophenyl)-1,3-thiazol-2-yl]-4-[(4-methylphenyl)sulfonyl]-piperazine
1-[4-(3,5-difluorophenyl)-1,3-thiazol-2-yl]-4-[(4-methylphenyl)sulfonyl]-piperazine
1-[4-(3,5-dichlorophenyl)-1,3-thiazol-2-yl]-4-[(4-methylphenyl)sulfonyl]-piperazine
1-[4-(3,5-dimethylphenyl)-1,3-thiazol-2-yl]-4-[(4-methylphenyl)sulfonyl]-piperazine
1-[4-(3-chloro-4-fluorophenyl)-1,3-thiazol-2-yl]-4-[(4-methylphenyl)sulfonyl]-piperazine
1-[4-(3-chloro-5-fluorophenyl)-1,3-thiazol-2-yl]-4-[(4-methylphenyl)sulfonyl]-piperazine
1-[4-(4-chloro-3-fluorophenyl)-1,3-thiazol-2-yl]-4-[(4-methylphenyl)sulfonyl]-piperazine
1-[4-(3,4,5-trimethoxyphenyl)-1,3-thiazol-2-yl]-4-[(4-methylphenyl)sulfonyl]-piperazine
1-[4-(2,4,6-trimethylphenyl)-1,3-thiazol-2-yl]-4-[(4-methylphenyl)sulfonyl]-piperazine
1-[4-phenyl-1,3-thiazol-2-yl]-4-[(4-chlorophenyl)sulfonyl]-piperazine
1-[4-(2-methylphenyl)-1,3-thiazol-2-yl]-4-[(4-chlorophenyl)sulfonyl]-piperazine
1-[4-(2-methoxyphenyl)-1,3-thiazol-2-yl]-4-[(4-chlorophenyl)sulfonyl]-piperazine
1-[4-(3-methylphenyl)-1,3-thiazol-2-yl]-4-[(4-chlorophenyl)sulfonyl]-piperazine
1-[4-(3-methoxyphenyl)-1,3-thiazol-2-yl]-4-[(4-chlorophenyl)sulfonyl]-piperazine
1-[4-(3-bromophenyl)-1,3-thiazol-2-yl]-4-[(4-chlorophenyl)sulfonyl]-piperazine
1-[4-(4-chlorophenyl)-1,3-thiazol-2-yl]-4-[(4-chlorophenyl)sulfonyl]-piperazine
1-[4-(4-methoxyphenyl)-1,3-thiazol-2-yl]-4-[(4-chlorophenyl)sulfonyl]-piperazine
1-[4-(4-methylphenyl)-1,3-thiazol-2-yl]-4-[(4-chlorophenyl)sulfonyl]-piperazine
1-[4-(4-ethylphenyl)-1,3-thiazol-2-yl]-4-[(4-chlorophenyl)sulfonyl]-piperazine
1-[4-(4-ethoxyphenyl)-1,3-thiazol-2-yl]-4-[(4-chlorophenyl)sulfonyl]-piperazine
1-[4-(4-propylphenyl)-1,3-thiazol-2-yl]-4-[(4-chlorophenyl)sulfonyl]-piperazine
1-[4-(2,6-dimethylphenyl)-1,3-thiazol-2-yl]-4-[(4-chlorophenyl)sulfonyl]-piperazine
1-[4-(2,3-dimethylphenyl)-1,3-thiazol-2-yl]-4-[(4-chlorophenyl)sulfonyl]-piperazine
1-[4-(2,5-dimethylphenyl)-1,3-thiazol-2-yl]-4-[(4-chlorophenyl)sulfonyl]-piperazine
1-[4-(2,4-dichlorophenyl)-1,3-thiazol-2-yl]-4-[(4-chlorophenyl)sulfonyl]-piperazine
1-[4-(2,4-dimethoxyphenyl)-1,3-thiazol-2-yl]-4-[(4-chlorophenyl)sulfonyl]-piperazine
1-[4-(2,5-dimethoxyphenyl)-1,3-thiazol-2-yl]-4-[(4-chlorophenyl)sulfonyl]-piperazine
1-[4-(3,4-dimethoxyphenyl)-1,3-thiazol-2-yl]-4-[(4-chlorophenyl)sulfonyl]-piperazine
1-[4-(3,5-dimethoxyphenyl)-1,3-thiazol-2-yl]-4-[(4-chlorophenyl)sulfonyl]-piperazine
1-[4-(3,4-dichlorophenyl)-1,3-thiazol-2-yl]-4-[(4-chlorophenyl)sulfonyl]-piperazine
1-[4-(3,4-dimethylphenyl)-1,3-thiazol-2-yl]-4-[(4-chlorophenyl)sulfonyl]-piperazine
1-[4-(3,4-difluorophenyl)-1,3-thiazol-2-yl]-4-[(4-chlorophenyl)sulfonyl]-piperazine
1-[4-(3,5-difluorophenyl)-1,3-thiazol-2-yl]-4-[(4-chlorophenyl)sulfonyl]-piperazine
1-[4-(3,5-dichlorophenyl)-1,3-thiazol-2-yl]-4-[(4-chlorophenyl)sulfonyl]-piperazine
1-[4-(3,5-dimethylphenyl)-1,3-thiazol-2-yl]-4-[(4-chlorophenyl)sulfonyl]-piperazine 1-[4-(3-chloro-4-fluorophenyl)-1,3-thiazol-2-yl]-4-[(4-chlorophenyl)sulfonyl]-piperazine
1-[4-(3-chloro-5-fluorophenyl)-1,3-thiazol-2-yl]-4-[(4-chlorophenyl)sulfonyl]-piperazine
1-[4-(4-chloro-3-fluorophenyl)-1,3-thiazol-2-yl]-4-[(4-chlorophenyl)sulfonyl]-piperazine
1-[4-(3,4,5-trimethoxyphenyl)-1,3-thiazol-2-yl]-4-[(4-chlorophenyl)sulfonyl]-piperazine
1-[4-(2,4,6-trimethylphenyl)-1,3-thiazol-2-yl]-4-[(4-chlorophenyl)sulfonyl]-piperazine
1-[4-phenyl-1,3-thiazol-2-yl]-4-[(4-(trifluoromethoxy)phenyl)sulfonyl]-piperazine
1-[4-(2-methylphenyl)-1,3-thiazol-2-yl]-4-[(4-(trifluoromethoxy)phenyl)sulfonyl]-piperazine
1-[4-(2-methoxyphenyl)-1,3-thiazol-2-yl]-4-[(4-(trifluoromethoxy)phenyl)sulfonyl]-piperazine
1-[4-(3-methylphenyl)-1,3-thiazol-2-yl]-4-[(4-(trifluoromethoxy)phenyl)sulfonyl]-piperazine
1-[4-(3-methoxyphenyl)-1,3-thiazol-2-yl]-4-[(4-(trifluoromethoxy)phenyl)sulfonyl]-piperazine
1-[4-(3-bromophenyl)-1,3-thiazol-2-yl]-4-[(4-(trifluoromethoxy)phenyl)sulfonyl]-piperazine
1-[4-(4-chlorophenyl)-1,3-thiazol-2-yl]-4-[(4-(trifluoromethoxy)phenyl)sulfonyl]-piperazine
1-[4-(4-methoxyphenyl)-1,3-thiazol-2-yl]-4-[(4-(trifluoromethoxy)phenyl)sulfonyl]-piperazine
1-[4-(4-methylphenyl)-1,3-thiazol-2-yl]-4-[(4-(trifluoromethoxy)phenyl)sulfonyl]-piperazine
1-[4-(4-ethylphenyl)-1,3-thiazol-2-yl]-4-[(4-(trifluoromethoxy)phenyl)sulfonyl]-piperazine
1-[4-(4-ethoxyphenyl)-1,3-thiazol-2-yl]-4-[(4-(trifluoromethoxy)phenyl)sulfonyl]-piperazine
1-[4-(4-propylphenyl)-1,3-thiazol-2-yl]-4-[(4-(trifluoromethoxy)phenyl)sulfonyl]-piperazine
1-[4-(2,6-dimethylphenyl)-1,3-thiazol-2-yl]-4-[(4-(trifluoromethoxy)phenyl)sulfonyl]-piperazine
1-[4-(2,3-dimethylphenyl)-1,3-thiazol-2-yl]-4-[(4-(trifluoromethoxy)phenyl)sulfonyl]-piperazine
1-[4-(2,5-dimethylphenyl)-1,3-thiazol-2-yl]-4-[(4-(trifluoromethoxy)phenyl)sulfonyl]-piperazine
1-[4-(2,4-dichlorophenyl)-1,3-thiazol-2-yl]-4-[(4-(trifluoromethoxy)phenyl)sulfonyl]-piperazine
1-[4-(2,4-dimethoxyphenyl)-1,3-thiazol-2-yl]-4-[(4-(trifluoromethoxy)phenyl)sulfonyl]-piperazine
1-[4-(2,5-dimethoxyphenyl)-1,3-thiazol-2-yl]-4-[(4-(trifluoromethoxy)phenyl)sulfonyl]-piperazine
1-[4-(3,4-dimethoxyphenyl)-1,3-thiazol-2-yl]-4-[(4-(trifluoromethoxy)phenyl)sulfonyl]-piperazine
1-[4-(3,5-dimethoxyphenyl)-1,3-thiazol-2-yl]-4-[(4-(trifluoromethoxy)phenyl)sulfonyl]-piperazine
1-[4-(3,4-dichlorophenyl)-1,3-thiazol-2-yl]-4-[(4-(trifluoromethoxy)phenyl)sulfonyl]-piperazine
1-[4-(3,4-dimethylphenyl)-1,3-thiazol-2-yl]-4-[(4-(trifluoromethoxy)phenyl)sulfonyl]-piperazine
1-[4-(3,4-difluorophenyl)-1,3-thiazol-2-yl]-4-[(4-(trifluoromethoxy)phenyl)sulfonyl]-piperazine
1-[4-(3,5-difluorophenyl)-1,3-thiazol-2-yl]-4-[(4-(trifluoromethoxy)phenyl)sulfonyl]-piperazine
1-[4-(3,5-dichlorophenyl)-1,3-thiazol-2-yl]-4-[(4-(trifluoromethoxy)phenyl)sulfonyl]-piperazine
1-[4-(3,5-dimethylphenyl)-1,3-thiazol-2-yl]-4-[(4-(trifluoromethoxy)phenyl)sulfonyl]-piperazine
1-[4-(3-chloro-4-fluorophenyl)-1,3-thiazol-2-yl]-4-[(4-(trifluoromethoxy)phenyl)sulfonyl]-piperazine
1-[4-(3-chloro-5-fluorophenyl)-1,3-thiazol-2-yl]-4-[(4-(trifluoromethoxy)phenyl)sulfonyl]-piperazine
1-[4-(4-chloro-3-fluorophenyl)-1,3-thiazol-2-yl]-4-[(4-(trifluoromethoxy)phenyl)sulfonyl]-piperazine
1-[4-(3,4,5-trimethoxyphenyl)-1,3-thiazol-2-yl]-4-[(4-(trifluoromethoxy)phenyl)sulfonyl]-piperazine
1-[4-(2,4,6-trimethylphenyl)-1,3-thiazol-2-yl]-4-[(4-(trifluoromethoxy)phenyl)sulfonyl]-piperazine
1-[4-phenyl-1,3-thiazol-2-yl]-4-[(4-tert-butylphenyl)sulfonyl]-piperazine
1-[4-(2-methylphenyl)-1,3-thiazol-2-yl]-4-[(4-tert-butylphenyl)sulfonyl]-piperazine
1-[4-(2-methoxyphenyl)-1,3-thiazol-2-yl]-4-[(4-tert-butylphenyl)sulfonyl]-piperazine
1-[4-(3-methylphenyl)-1,3-thiazol-2-yl]-4-[(4-tert-butylphenyl)sulfonyl]-piperazine
1-[4-(3-methoxyphenyl)-1,3-thiazol-2-yl]-4-[(4-tert-butylphenyl)sulfonyl]-piperazine
1-[4-(3-bromophenyl)-1,3-thiazol-2-yl]-4-[(4-tert-butylphenyl)sulfonyl]-piperazine
1-[4-(4-chlorophenyl)-1,3-thiazol-2-yl]-4-[(4-tert-butylphenyl)sulfonyl]-piperazine
1-[4-(4-methoxyphenyl)-1,3-thiazol-2-yl]-4-[(4-tert-butylphenyl)sulfonyl]-piperazine
1-[4-(4-methylphenyl)-1,3-thiazol-2-yl]-4-[(4-tert-butylphenyl)sulfonyl]-piperazine
1-[4-(4-ethylphenyl)-1,3-thiazol-2-yl]-4-[(4-tert-butylphenyl)sulfonyl]-piperazine
1-[4-(4-ethoxyphenyl)-1,3-thiazol-2-yl]-4-[(4-tert-butylphenyl)sulfonyl]-piperazine
1-[4-(4-propylphenyl)-1,3-thiazol-2-yl]-4-[(4-tert-butylphenyl)sulfonyl]-piperazine
1-[4-(2,6-dimethylphenyl)-1,3-thiazol-2-yl]-4-[(4-tert-butylphenyl)sulfonyl]-piperazine
1-[4-(2,3-dimethylphenyl)-1,3-thiazol-2-yl]-4-[(4-tert-butylphenyl)sulfonyl]-piperazine
1-[4-(2,5-dimethylphenyl)-1,3-thiazol-2-yl]-4-[(4-tert-butylphenyl)sulfonyl]-piperazine
1-[4-(2,4-dichlorophenyl)-1,3-thiazol-2-yl]-4-[(4-tert-butylphenyl)sulfonyl]-piperazine
1-[4-(2,4-dimethoxyphenyl)-1,3-thiazol-2-yl]-4-[(4-tert-butylphenyl)sulfonyl]-piperazine
1-[4-(2,5-dimethoxyphenyl)-1,3-thiazol-2-yl]-4-[(4-tert-butylphenyl)sulfonyl]-piperazine
1-[4-(3,4-dimethoxyphenyl)-1,3-thiazol-2-yl]-4-[(4-tert-butylphenyl)sulfonyl]-piperazine
1-[4-(3,5-dimethoxyphenyl)-1,3-thiazol-2-yl]-4-[(4-tert-butylphenyl)sulfonyl]-piperazine
1-[4-(3,4-dichlorophenyl)-1,3-thiazol-2-yl]-4-[(4-tert-butylphenyl)sulfonyl]-piperazine
1-[4-(3,4-dimethylphenyl)-1,3-thiazol-2-yl]-4-[(4-tert-butylphenyl)sulfonyl]-piperazine
1-[4-(3,4-difluorophenyl)-1,3-thiazol-2-yl]-4-[(4-tert-butylphenyl)sulfonyl]-piperazine
1-[4-(3,5-difluorophenyl)-1,3-thiazol-2-yl]-4-[(4-tert-butylphenyl)sulfonyl]-piperazine
1-[4-(3,5-dichlorophenyl)-1,3-thiazol-2-yl]-4-[(4-tert-butylphenyl)sulfonyl]-piperazine
1-[4-(3,5-dimethylphenyl)-1,3-thiazol-2-yl]-4-[(4-tert-butylphenyl)sulfonyl]-piperazine
1-[4-(3-chloro-4-fluorophenyl)-1,3-thiazol-2-yl]-4-[(4-tert-butylphenyl)sulfonyl]-piperazine
1-[4-(3-chloro-5-fluorophenyl)-1,3-thiazol-2-yl]-4-[(4-tert-butylphenyl)sulfonyl]-piperazine
1-[4-(4-chloro-3-fluorophenyl)-1,3-thiazol-2-yl]-4-[(4-tert-butylphenyl)sulfonyl]-piperazine
1-[4-(3,4,5-trimethoxyphenyl)-1,3-thiazol-2-yl]-4-[(4-tert-butylphenyl)sulfonyl]-piperazine 1-[4-(2,4,6-trimethylphenyl)-1,3-thiazol-2-yl]-4-[(4-tert-butylphenyl)sulfonyl]-piperazine
1-[4-phenyl-1,3-thiazol-2-yl]-4-[(pentafluorophenyl)sulfonyl]-piperazine
1-[4-(2-methylphenyl)-1,3-thiazol-2-yl]-4-[(pentafluorophenyl)sulfonyl]-piperazine
1-[4-(2-methoxyphenyl)-1,3-thiazol-2-yl]-4-[(pentafluorophenyl)sulfonyl]-piperazine
1-[4-(3-methylphenyl)-1,3-thiazol-2-yl]-4-[(pentafluorophenyl)sulfonyl]-piperazine
1-[4-(3-methoxyphenyl)-1,3-thiazol-2-yl]-4-[(pentafluorophenyl)sulfonyl]-piperazine
1-[4-(3-bromophenyl)-1,3-thiazol-2-yl]-4-[(pentafluorophenyl)sulfonyl]-piperazine
1-[4-(4-chlorophenyl)-1,3-thiazol-2-yl]-4-[(pentafluorophenyl)sulfonyl]-piperazine
1-[4-(4-methoxyphenyl)-1,3-thiazol-2-yl]-4-[(pentafluorophenyl)sulfonyl]-piperazine
1-[4-(4-methylphenyl)-1,3-thiazol-2-yl]-4-[(pentafluorophenyl)sulfonyl]-piperazine
1-[4-(4-ethylphenyl)-1,3-thiazol-2-yl]-4-[(pentafluorophenyl)sulfonyl]-piperazine
1-[4-(4-ethoxyphenyl)-1,3-thiazol-2-yl]-4-[(pentafluorophenyl)sulfonyl]-piperazine
1-[4-(4-propylphenyl)-1,3-thiazol-2-yl]-4-[(pentafluorophenyl)sulfonyl]-piperazine
1-[4-(2,6-dimethylphenyl)-1,3-thiazol-2-yl]-4-[(pentafluorophenyl)sulfonyl]-piperazine
1-[4-(2,3-dimethylphenyl)-1,3-thiazol-2-yl]-4-[(pentafluorophenyl)sulfonyl]-piperazine
1-[4-(2,5-dimethylphenyl)-1,3-thiazol-2-yl]-4-[(pentafluorophenyl)sulfonyl]-piperazine
1-[4-(2,4-dichlorophenyl)-1,3-thiazol-2-yl]-4-[(pentafluorophenyl)sulfonyl]-piperazine
1-[4-(2,4-dimethoxyphenyl)-1,3-thiazol-2-yl]-4-[(pentafluorophenyl)sulfonyl]-piperazine
1-[4-(2,5-dimethoxyphenyl)-1,3-thiazol-2-yl]-4-[(pentafluorophenyl)sulfonyl]-piperazine
1-[4-(3,4-dimethoxyphenyl)-1,3-thiazol-2-yl]-4-[(pentafluorophenyl)sulfonyl]-piperazine
1-[4-(3,5-dimethoxyphenyl)-1,3-thiazol-2-yl]-4-[(pentafluorophenyl)sulfonyl]-piperazine
1-[4-(3,4-dichlorophenyl)-1,3-thiazol-2-yl]-4-[(pentafluorophenyl)sulfonyl]-piperazine
1-[4-(3,4-dimethylphenyl)-1,3-thiazol-2-yl]-4-[(pentafluorophenyl)sulfonyl]-piperazine
1-[4-(3,4-difluorophenyl)-1,3-thiazol-2-yl]-4-[(pentafluorophenyl)sulfonyl]-piperazine
1-[4-(3,5-difluorophenyl)-1,3-thiazol-2-yl]-4-[(pentafluorophenyl)sulfonyl]-piperazine
1-[4-(3,5-dichlorophenyl)-1,3-thiazol-2-yl]-4-[(pentafluorophenyl)sulfonyl]-piperazine
1-[4-(3,5-dimethylphenyl)-1,3-thiazol-2-yl]-4-[(pentafluorophenyl)sulfonyl]-piperazine
1-[4-(3-chloro-4-fluorophenyl)-1,3-thiazol-2-yl]-4-[(pentafluorophenyl)sulfonyl]-piperazine
1-[4-(3-chloro-5-fluorophenyl)-1,3-thiazol-2-yl]-4-[(pentafluorophenyl)sulfonyl]-piperazine
1-[4-(4-chloro-3-fluorophenyl)-1,3-thiazol-2-yl]-4-[(pentafluorophenyl)sulfonyl]-piperazine
1-[4-(3,4,5-trimethoxyphenyl)-1,3-thiazol-2-yl]-4-[(pentafluorophenyl)sulfonyl]-piperazine
1-[4-(2,4,6-trimethylphenyl)-1,3-thiazol-2-yl]-4-[(pentafluorophenyl)sulfonyl]-piperazine
1-[4-phenyl-1,3-thiazol-2-yl]-4-[(2,4,6-trimethylphenyl)sulfonyl]-piperazine
1-[4-(2-methylphenyl)-1,3-thiazol-2-yl]-4-[(2,4,6-trimethylphenyl)sulfonyl]-piperazine
1-[4-(2-methoxyphenyl)-1,3-thiazol-2-yl]-4-[(2,4,6-trimethylphenyl)sulfonyl]-piperazine
1-[4-(3-methylphenyl)-1,3-thiazol-2-yl]-4-[(2,4,6-trimethylphenyl)sulfonyl]-piperazine
1-[4-(3-methoxyphenyl)-1,3-thiazol-2-yl]-4-[(2,4,6-trimethylphenyl)sulfonyl]-piperazine
1-[4-(3-bromophenyl)-1,3-thiazol-2-yl]-4-[(2,4,6-trimethylphenyl)sulfonyl]-piperazine
1-[4-(4-chlorophenyl)-1,3-thiazol-2-yl]-4-[(2,4,6-trimethylphenyl)sulfonyl]-piperazine
1-[4-(4-methoxyphenyl)-1,3-thiazol-2-yl]-4-[(2,4,6-trimethylphenyl)sulfonyl]-piperazine
1-[4-(4-methylphenyl)-1,3-thiazol-2-yl]-4-[(2,4,6-trimethylphenyl)sulfonyl]-piperazine
1-[4-(4-ethylphenyl)-1,3-thiazol-2-yl]-4-[(2,4,6-trimethylphenyl)sulfonyl]-piperazine
1-[4-(4-ethoxyphenyl)-1,3-thiazol-2-yl]-4-[(2,4,6-trimethylphenyl)sulfonyl]-piperazine
1-[4-(4-propylphenyl)-1,3-thiazol-2-yl]-4-[(2,4,6-trimethylphenyl)sulfonyl]-piperazine
1-[4-(2,6-dimethylphenyl)-1,3-thiazol-2-yl]-4-[(2,4,6-trimethylphenyl)sulfonyl]-piperazine
1-[4-(2,3-dimethylphenyl)-1,3-thiazol-2-yl]-4-[(2,4,6-trimethylphenyl)sulfonyl]-piperazine
1-[4-(2,5-dimethylphenyl)-1,3-thiazol-2-yl]-4-[(2,4,6-trimethylphenyl)sulfonyl]-piperazine
1-[4-(2,4-dichlorophenyl)-1,3-thiazol-2-yl]-4-[(2,4,6-trimethylphenyl)sulfonyl]-piperazine
1-[4-(2,4-dimethoxyphenyl)-1,3-thiazol-2-yl]-4-[(2,4,6-trimethylphenyl)sulfonyl]-piperazine
1-[4-(2,5-dimethoxyphenyl)-1,3-thiazol-2-yl]-4-[(2,4,6-trimethylphenyl)sulfonyl]-piperazine
1-[4-(3,4-dimethoxyphenyl)-1,3-thiazol-2-yl]-4-[(2,4,6-trimethylphenyl)sulfonyl]-piperazine
1-[4-(3,5-dimethoxyphenyl)-1,3-thiazol-2-yl]-4-[(2,4,6-trimethylphenyl)sulfonyl]-piperazine
1-[4-(3,4-dichlorophenyl)-1,3-thiazol-2-yl]-4-[(2,4,6-trimethylphenyl)sulfonyl]-piperazine
1-[4-(3,4-dimethylphenyl)-1,3-thiazol-2-yl]-4-[(2,4,6-trimethylphenyl)sulfonyl]-piperazine
1-[4-(3,4-difluorophenyl)-1,3-thiazol-2-yl]-4-[(2,4,6-trimethylphenyl)sulfonyl]-piperazine
1-[4-(3,5-difluorophenyl)-1,3-thiazol-2-yl]-4-[(2,4,6-trimethylphenyl)sulfonyl]-piperazine
1-[4-(3,5-dichlorophenyl)-1,3-thiazol-2-yl]-4-[(2,4,6-trimethylphenyl)sulfonyl]-piperazine
1-[4-(3,5-dimethylphenyl)-1,3-thiazol-2-yl]-4-[(2,4,6-trimethylphenyl)sulfonyl]-piperazine
1-[4-(3-chloro-4-fluorophenyl)-1,3-thiazol-2-yl]-4-[(2,4,6-trimethylphenyl)sulfonyl]-piperazine
1-[4-(3-chloro-5-fluorophenyl)-1,3-thiazol-2-yl]-4-[(2,4,6-trimethylphenyl)sulfonyl]-piperazine
1-[4-(4-chloro-3-fluorophenyl)-1,3-thiazol-2-yl]-4-[(2,4,6-trimethylphenyl)sulfonyl]-piperazine
1-[4-(3,4,5-trimethoxyphenyl)-1,3-thiazol-2-yl]-4-[(2,4,6-trimethylphenyl)sulfonyl]-piperazine
1-[4-(2,4,6-trimethylphenyl)-1,3-thiazol-2-yl]-4-[(2,4,6-trimethylphenyl)sulfonyl]-piperazine
1-[4-phenyl-1,3-thiazol-2-yl]-4-[(2,4,6-tri-iso-propylphenyl)sulfonyl]-piperazine
1-[4-(2-methylphenyl)-1,3-thiazol-2-yl]-4-[(2,4,6-tri-iso-propylphenyl)sulfonyl]-piperazine
1-[4-(2-methoxyphenyl)-1,3-thiazol-2-yl]-4-[(2,4,6-tri-iso-propylphenyl)sulfonyl]-piperazine 1-[4-(3-methylphenyl)-1,3-thiazol-2-yl]-4-[(2,4,6-tri-iso-propylphenyl)sulfonyl]-piperazine
1-[4-(3-methoxyphenyl)-1,3-thiazol-2-yl]-4-[(2,4,6-tri-iso-propylphenyl)sulfonyl]-piperazine
1-[4-(3-bromophenyl)-1,3-thiazol-2-yl]-4-[(2,4,6-tri-iso-propylphenyl)sulfonyl]-piperazine
1-[4-(4-chlorophenyl)-1,3-thiazol-2-yl]-4-[(2,4,6-tri-iso-propylphenyl)sulfonyl]-piperazine
1-[4-(4-methoxyphenyl)-1,3-thiazol-2-yl]-4-[(2,4,6-tri-iso-propylphenyl)sulfonyl]-piperazine
1-[4-(4-methylphenyl)-1,3-thiazol-2-yl]-4-[(2,4,6-tri-iso-propylphenyl)sulfonyl]-piperazine
1-[4-(4-ethylphenyl)-1,3-thiazol-2-yl]-4-[(2,4,6-tri-iso-propylphenyl)sulfonyl]-piperazine
1-[4-(4-ethoxyphenyl)-1,3-thiazol-2-yl]-4-[(2,4,6-tri-iso-propylphenyl)sulfonyl]-piperazine
1-[4-(4-propylphenyl)-1,3-thiazol-2-yl]-4-[(2,4,6-tri-iso-propylphenyl)sulfonyl]-piperazine
1-[4-(2,6-dimethylphenyl)-1,3-thiazol-2-yl]-4-[(2,4,6-tri-iso-propylphenyl)sulfonyl]-piperazine
1-[4-(2,3-dimethylphenyl)-1,3-thiazol-2-yl]-4-[(2,4,6-tri-iso-propylphenyl)sulfonyl]-piperazine
1-[4-(2,5-dimethylphenyl)-1,3-thiazol-2-yl]-4-[(2,4,6-tri-iso-propylphenyl)sulfonyl]-piperazine
1-[4-(2,4-dichlorophenyl)-1,3-thiazol-2-yl]-4-[(2,4,6-tri-iso-propylphenyl)sulfonyl]-piperazine
1-[4-(2,4-dimethoxyphenyl)-1,3-thiazol-2-yl]-4-[(2,4,6-tri-iso-propylphenyl)sulfonyl]-piperazine
1-[4-(2,5-dimethoxyphenyl)-1,3-thiazol-2-yl]-4-[(2,4,6-tri-iso-propylphenyl)sulfonyl]-piperazine
1-[4-(3,4-dimethoxyphenyl)-1,3-thiazol-2-yl]-4-[(2,4,6-tri-iso-propylphenyl)sulfonyl]-piperazine
1-[4-(3,5-dimethoxyphenyl)-1,3-thiazol-2-yl]-4-[(2,4,6-tri-iso-propylphenyl)sulfonyl]-piperazine
1-[4-(3,4-dichlorophenyl)-1,3-thiazol-2-yl]-4-[(2,4,6-tri-iso-propylphenyl)sulfonyl]-piperazine
1-[4-(3,4-dimethylphenyl)-1,3-thiazol-2-yl]-4-[(2,4,6-tri-iso-propylphenyl)sulfonyl]-piperazine
1-[4-(3,4-difluorophenyl)-1,3-thiazol-2-yl]-4-[(2,4,6-tri-iso-propylphenyl)sulfonyl]-piperazine
1-[4-(3,5-difluorophenyl)-1,3-thiazol-2-yl]-4-[(2,4,6-tri-iso-propylphenyl)sulfonyl]-piperazine
1-[4-(3,5-dichlorophenyl)-1,3-thiazol-2-yl]-4-[(2,4,6-tri-iso-propylphenyl)sulfonyl]-piperazine
1-[4-(3,5-dimethylphenyl)-1,3-thiazol-2-yl]-4-[(2,4,6-tri-iso-propylphenyl)sulfonyl]-piperazine
1-[4-(3-chloro-4-fluorophenyl)-1,3-thiazol-2-yl]-4-[(2,4,6-tri-iso-propylphenyl)sulfonyl]-piperazine
1-[4-(3-chloro-5-fluorophenyl)-1,3-thiazol-2-yl]-4-[(2,4,6-tri-iso-propylphenyl)sulfonyl]-piperazine
1-[4-(4-chloro-3-fluorophenyl)-1,3-thiazol-2-yl]-4-[(2,4,6-tri-iso-propylphenyl)sulfonyl]-piperazine
1-[4-(3,4,5-trimethoxyphenyl)-1,3-thiazol-2-yl]-4-[(2,4,6-tri-iso-propylphenyl)sulfonyl]-piperazine
1-[4-(2,4,6-trimethylphenyl)-1,3-thiazol-2-yl]-4-[(2,4,6-tri-iso-propylphenyl)sulfonyl]-piperazine
1-[4-phenyl-1,3-thiazol-2-yl]-4-[(2,4-dichlorophenyl)sulfonyl]-piperazine
1-[4-(2-methylphenyl)-1,3-thiazol-2-yl]-4-[(2,4-dichlorophenyl)sulfonyl]-piperazine
1-[4-(2-methoxyphenyl)-1,3-thiazol-2-yl]-4-[(2,4-dichlorophenyl)sulfonyl]-piperazine
1-[4-(3-methylphenyl)-1,3-thiazol-2-yl]-4-[(2,4-dichlorophenyl)sulfonyl]-piperazine
1-[4-(3-methoxyphenyl)-1,3-thiazol-2-yl]-4-[(2,4-dichlorophenyl)sulfonyl]-piperazine
1-[4-(3-bromophenyl)-1,3-thiazol-2-yl]-4-[(2,4-dichlorophenyl)sulfonyl]-piperazine
1-[4-(4-chlorophenyl)-1,3-thiazol-2-yl]-4-[(2,4-dichlorophenyl)sulfonyl]-piperazine
1-[4-(4-methoxyphenyl)-1,3-thiazol-2-yl]-4-[(2,4-dichlorophenyl)sulfonyl]-piperazine
1-[4-(4-methylphenyl)-1,3-thiazol-2-yl]-4-[(2,4-dichlorophenyl)sulfonyl]-piperazine
1-[4-(4-ethylphenyl)-1,3-thiazol-2-yl]-4-[(2,4-dichlorophenyl)sulfonyl]-piperazine
1-[4-(4-ethoxyphenyl)-1,3-thiazol-2-yl]-4-[(2,4-dichlorophenyl)sulfonyl]-piperazine
1-[4-(4-propylphenyl)-1,3-thiazol-2-yl]-4-[(2,4-dichlorophenyl)sulfonyl]-piperazine
1-[4-(2,6-dimethylphenyl)-1,3-thiazol-2-yl]-4-[(2,4-dichlorophenyl)sulfonyl]-piperazine
1-[4-(2,3-dimethylphenyl)-1,3-thiazol-2-yl]-4-[(2,4-dichlorophenyl)sulfonyl]-piperazine
1-[4-(2,5-dimethylphenyl)-1,3-thiazol-2-yl]-4-[(2,4-dichlorophenyl)sulfonyl]-piperazine
1-[4-(2,4-dichlorophenyl)-1,3-thiazol-2-yl]-4-[(2,4-dichlorophenyl)sulfonyl]-piperazine
1-[4-(2,4-dimethoxyphenyl)-1,3-thiazol-2-yl]-4-[(2,4-dichlorophenyl)sulfonyl]-piperazine
1-[4-(2,5-dimethoxyphenyl)-1,3-thiazol-2-yl]-4-[(2,4-dichlorophenyl)sulfonyl]-piperazine
1-[4-(3,4-dimethoxyphenyl)-1,3-thiazol-2-yl]-4-[(2,4-dichlorophenyl)sulfonyl]-piperazine
1-[4-(3,5-dimethoxyphenyl)-1,3-thiazol-2-yl]-4-[(2,4-dichlorophenyl)sulfonyl]-piperazine
1-[4-(3,4-dichlorophenyl)-1,3-thiazol-2-yl]-4-[(2,4-dichlorophenyl)sulfonyl]-piperazine
1-[4-(3,4-dimethylphenyl)-1,3-thiazol-2-yl]-4-[(2,4-dichlorophenyl)sulfonyl]-piperazine
1-[4-(3,4-difluorophenyl)-1,3-thiazol-2-yl]-4-[(2,4-dichlorophenyl)sulfonyl]-piperazine
1-[4-(3,5-difluorophenyl)-1,3-thiazol-2-yl]-4-[(2,4-dichlorophenyl)sulfonyl]-piperazine
1-[4-(3,5-dichlorophenyl)-1,3-thiazol-2-yl]-4-[(2,4-dichlorophenyl)sulfonyl]-piperazine
1-[4-(3,5-dimethylphenyl)-1,3-thiazol-2-yl]-4-[(2,4-dichlorophenyl)sulfonyl]-piperazine
1-[4-(3-chloro-4-fluorophenyl)-1,3-thiazol-2-yl]-4-[(2,4-dichlorophenyl)sulfonyl]-piperazine
1-[4-(3-chloro-5-fluorophenyl)-1,3-thiazol-2-yl]-4-[(2,4-dichlorophenyl)sulfonyl]-piperazine
1-[4-(4-chloro-3-fluorophenyl)-1,3-thiazol-2-yl]-4-[(2,4-dichlorophenyl)sulfonyl]-piperazine
1-[4-(3,4,5-trimethoxyphenyl)-1,3-thiazol-2-yl]-4-[(2,4-dichlorophenyl)sulfonyl]-piperazine
1-[4-(2,4,6-trimethylphenyl)-1,3-thiazol-2-yl]-4-[(2,4-dichlorophenyl)sulfonyl]-piperazine
1-[4-phenyl-1,3-thiazol-2-yl]-4-[(2,5-dichlorophenyl)sulfonyl]-piperazine
1-[4-(2-methylphenyl)-1,3-thiazol-2-yl]-4-[(2,5-dichlorophenyl)sulfonyl]-piperazine
1-[4-(2-methoxyphenyl)-1,3-thiazol-2-yl]-4-[(2,5-dichlorophenyl)sulfonyl]-piperazine
1-[4-(3-methylphenyl)-1,3-thiazol-2-yl]-4-[(2,5-dichlorophenyl)sulfonyl]-piperazine
1-[4-(3-methoxyphenyl)-1,3-thiazol-2-yl]-4-[(2,5-dichlorophenyl)sulfonyl]-piperazine
1-[4-(3-bromophenyl)-1,3-thiazol-2-yl]-4-[(2,5-dichlorophenyl)sulfonyl]-piperazine
1-[4-(4-chlorophenyl)-1,3-thiazol-2-yl]-4-[(2,5-dichlorophenyl)sulfonyl]-piperazine 1-[4-(4-methoxyphenyl)-1,3-thiazol-2-yl]-4-[(2,5-dichlorophenyl)sulfonyl]-piperazine
1-[4-(4-methylphenyl)-1,3-thiazol-2-yl]-4-[(2,5-dichlorophenyl)sulfonyl]-piperazine
1-[4-(4-ethylphenyl)-1,3-thiazol-2-yl]-4-[(2,5-dichlorophenyl)sulfonyl]-piperazine
1-[4-(4-ethoxyphenyl)-1,3-thiazol-2-yl]-4-[(2,5-dichlorophenyl)sulfonyl]-piperazine
1-[4-(4-propylphenyl)-1,3-thiazol-2-yl]-4-[(2,5-dichlorophenyl)sulfonyl]-piperazine
1-[4-(2,6-dimethylphenyl)-1,3-thiazol-2-yl]-4-[(2,5-dichlorophenyl)sulfonyl]-piperazine
1-[4-(2,3-dimethylphenyl)-1,3-thiazol-2-yl]-4-[(2,5-dichlorophenyl)sulfonyl]-piperazine
1-[4-(2,5-dimethylphenyl)-1,3-thiazol-2-yl]-4-[(2,5-dichlorophenyl)sulfonyl]-piperazine
1-[4-(2,4-dichlorophenyl)-1,3-thiazol-2-yl]-4-[(2,5-dichlorophenyl)sulfonyl]-piperazine
1-[4-(2,4-dimethoxyphenyl)-1,3-thiazol-2-yl]-4-[(2,5-dichlorophenyl)sulfonyl]-piperazine
1-[4-(2,5-dimethoxyphenyl)-1,3-thiazol-2-yl]-4-[(2,5-dichlorophenyl)sulfonyl]-piperazine
1-[4-(3,4-dimethoxyphenyl)-1,3-thiazol-2-yl]-4-[(2,5-dichlorophenyl)sulfonyl]-piperazine
1-[4-(3,5-dimethoxyphenyl)-1,3-thiazol-2-yl]-4-[(2,5-dichlorophenyl)sulfonyl]-piperazine
1-[4-(3,4-dichlorophenyl)-1,3-thiazol-2-yl]-4-[(2,5-dichlorophenyl)sulfonyl]-piperazine
1-[4-(3,4-dimethylphenyl)-1,3-thiazol-2-yl]-4-[(2,5-dichlorophenyl)sulfonyl]-piperazine
1-[4-(3,4-difluorophenyl)-1,3-thiazol-2-yl]-4-[(2,5-dichlorophenyl)sulfonyl]-piperazine
1-[4-(3,5-difluorophenyl)-1,3-thiazol-2-yl]-4-[(2,5-dichlorophenyl)sulfonyl]-piperazine
1-[4-(3,5-dichlorophenyl)-1,3-thiazol-2-yl]-4-[(2,5-dichlorophenyl)sulfonyl]-piperazine
1-[4-(3,5-dimethylphenyl)-1,3-thiazol-2-yl]-4-[(2,5-dichlorophenyl)sulfonyl]-piperazine
1-[4-(3-chloro-4-fluorophenyl)-1,3-thiazol-2-yl]-4-[(2,5-dichlorophenyl)sulfonyl]-piperazine
1-[4-(3-chloro-5-fluorophenyl)-1,3-thiazol-2-yl]-4-[(2,5-dichlorophenyl)sulfonyl]-piperazine
1-[4-(4-chloro-3-fluorophenyl)-1,3-thiazol-2-yl]-4-[(2,5-dichlorophenyl)sulfonyl]-piperazine
1-[4-(3,4,5-trimethoxyphenyl)-1,3-thiazol-2-yl]-4-[(2,5-dichlorophenyl)sulfonyl]-piperazine
1-[4-(2,4,6-trimethylphenyl)-1,3-thiazol-2-yl]-4-[(2,5-dichlorophenyl)sulfonyl]-piperazine
1-[4-phenyl-1,3-thiazol-2-yl]-4-[(3,4-dichlorophenyl)sulfonyl]-piperazine
1-[4-(2-methylphenyl)-1,3-thiazol-2-yl]-4-[(3,4-dichlorophenyl)sulfonyl]-piperazine
1-[4-(2-methoxyphenyl)-1,3-thiazol-2-yl]-4-[(3,4-dichlorophenyl)sulfonyl]-piperazine
1-[4-(3-methylphenyl)-1,3-thiazol-2-yl]-4-[(3,4-dichlorophenyl)sulfonyl]-piperazine
1-[4-(3-methoxyphenyl)-1,3-thiazol-2-yl]-4-[(3,4-dichlorophenyl)sulfonyl]-piperazine
1-[4-(3-bromophenyl)-1,3-thiazol-2-yl]-4-[(3,4-dichlorophenyl)sulfonyl]-piperazine
1-[4-(4-chlorophenyl)-1,3-thiazol-2-yl]-4-[(3,4-dichlorophenyl)sulfonyl]-piperazine
1-[4-(4-methoxyphenyl)-1,3-thiazol-2-yl]-4-[(3,4-dichlorophenyl)sulfonyl]-piperazine
1-[4-(4-methylphenyl)-1,3-thiazol-2-yl]-4-[(3,4-dichlorophenyl)sulfonyl]-piperazine
1-[4-(4-ethylphenyl)-1,3-thiazol-2-yl]-4-[(3,4-dichlorophenyl)sulfonyl]-piperazine
1-[4-(4-ethoxyphenyl)-1,3-thiazol-2-yl]-4-[(3,4-dichlorophenyl)sulfonyl]-piperazine
1-[4-(4-propylphenyl)-1,3-thiazol-2-yl]-4-[(3,4-dichlorophenyl)sulfonyl]-piperazine
1-[4-(2,6-dimethylphenyl)-1,3-thiazol-2-yl]-4-[(3,4-dichlorophenyl)sulfonyl]-piperazine
1-[4-(2,3-dimethylphenyl)-1,3-thiazol-2-yl]-4-[(3,4-dichlorophenyl)sulfonyl]-piperazine
1-[4-(2,5-dimethylphenyl)-1,3-thiazol-2-yl]-4-[(3,4-dichlorophenyl)sulfonyl]-piperazine
1-[4-(2,4-dichlorophenyl)-1,3-thiazol-2-yl]-4-[(3,4-dichlorophenyl)sulfonyl]-piperazine
1-[4-(2,4-dimethoxyphenyl)-1,3-thiazol-2-yl]-4-[(3,4-dichlorophenyl)sulfonyl]-piperazine
1-[4-(2,5-dimethoxyphenyl)-1,3-thiazol-2-yl]-4-[(3,4-dichlorophenyl)sulfonyl]-piperazine
1-[4-(3,4-dimethoxyphenyl)-1,3-thiazol-2-yl]-4-[(3,4-dichlorophenyl)sulfonyl]-piperazine
1-[4-(3,5-dimethoxyphenyl)-1,3-thiazol-2-yl]-4-[(3,4-dichlorophenyl)sulfonyl]-piperazine
1-[4-(3,4-dichlorophenyl)-1,3-thiazol-2-yl]-4-[(3,4-dichlorophenyl)sulfonyl]-piperazine
1-[4-(3,4-dimethylphenyl)-1,3-thiazol-2-yl]-4-[(3,4-dichlorophenyl)sulfonyl]-piperazine
1-[4-(3,4-difluorophenyl)-1,3-thiazol-2-yl]-4-[(3,4-dichlorophenyl)sulfonyl]-piperazine
1-[4-(3,5-difluorophenyl)-1,3-thiazol-2-yl]-4-[(3,4-dichlorophenyl)sulfonyl]-piperazine
1-[4-(3,5-dichlorophenyl)-1,3-thiazol-2-yl]-4-[(3,4-dichlorophenyl)sulfonyl]-piperazine
1-[4-(3,5-dimethylphenyl)-1,3-thiazol-2-yl]-4-[(3,4-dichlorophenyl)sulfonyl]-piperazine
1-[4-(3-chloro-4-fluorophenyl)-1,3-thiazol-2-yl]-4-[(3,4-dichlorophenyl)sulfonyl]-piperazine
1-[4-(3-chloro-5-fluorophenyl)-1,3-thiazol-2-yl]-4-[(3,4-dichlorophenyl)sulfonyl]-piperazine
1-[4-(4-chloro-3-fluorophenyl)-1,3-thiazol-2-yl]-4-[(3,4-dichlorophenyl)sulfonyl]-piperazine
1-[4-(3,4,5-trimethoxyphenyl)-1,3-thiazol-2-yl]-4-[(3,4-dichlorophenyl)sulfonyl]-piperazine
1-[4-(2,4,6-trimethylphenyl)-1,3-thiazol-2-yl]-4-[(3,4-dichlorophenyl)sulfonyl]-piperazine
1-[4-phenyl-1,3-thiazol-2-yl]-4-[(3,4-dimethoxyphenyl)sulfonyl]-piperazine
1-[4-(2-methylphenyl)-1,3-thiazol-2-yl]-4-[(3,4-dimethoxyphenyl)sulfonyl]-piperazine
1-[4-(2-methoxyphenyl)-1,3-thiazol-2-yl]-4-[(3,4-dimethoxyphenyl)sulfonyl]-piperazine
1-[4-(3-methylphenyl)-1,3-thiazol-2-yl]-4-[(3,4-dimethoxyphenyl)sulfonyl]-piperazine
1-[4-(3-methoxyphenyl)-1,3-thiazol-2-yl]-4-[(3,4-dimethoxyphenyl)sulfonyl]-piperazine
1-[4-(3-bromophenyl)-1,3-thiazol-2-yl]-4-[(3,4-dimethoxyphenyl)sulfonyl]-piperazine
1-[4-(4-chlorophenyl)-1,3-thiazol-2-yl]-4-[(3,4-dimethoxyphenyl)sulfonyl]-piperazine
1-[4-(4-methoxyphenyl)-1,3-thiazol-2-yl]-4-[(3,4-dimethoxyphenyl)sulfonyl]-piperazine
1-[4-(4-methylphenyl)-1,3-thiazol-2-yl]-4-[(3,4-dimethoxyphenyl)sulfonyl]-piperazine
1-[4-(4-ethylphenyl)-1,3-thiazol-2-yl]-4-[(3,4-dimethoxyphenyl)sulfonyl]-piperazine
1-[4-(4-ethoxyphenyl)-1,3-thiazol-2-yl]-4-[(3,4-dimethoxyphenyl)sulfonyl]-piperazine 1-[4-(4-propylphenyl)-1,3-thiazol-2-yl]-4-[(3,4-dimethoxyphenyl)sulfonyl]-piperazine
1-[4-(2,6-dimethylphenyl)-1,3-thiazol-2-yl]-4-[(3,4-dimethoxyphenyl)sulfonyl]-piperazine
1-[4-(2,3-dimethylphenyl)-1,3-thiazol-2-yl]-4-[(3,4-dimethoxyphenyl)sulfonyl]-piperazine
1-[4-(2,5-dimethylphenyl)-1,3-thiazol-2-yl]-4-[(3,4-dimethoxyphenyl)sulfonyl]-piperazine
1-[4-(2,4-dichlorophenyl)-1,3-thiazol-2-yl]-4-[(3,4-dimethoxyphenyl)sulfonyl]-piperazine
1-[4-(2,4-dimethoxyphenyl)-1,3-thiazol-2-yl]-4-[(3,4-dimethoxyphenyl)sulfonyl]-piperazine
1-[4-(2,5-dimethoxyphenyl)-1,3-thiazol-2-yl]-4-[(3,4-dimethoxyphenyl)sulfonyl]-piperazine
1-[4-(3,4-dimethoxyphenyl)-1,3-thiazol-2-yl]-4-[(3,4-dimethoxyphenyl)sulfonyl]-piperazine
1-[4-(3,5-dimethoxyphenyl)-1,3-thiazol-2-yl]-4-[(3,4-dimethoxyphenyl)sulfonyl]-piperazine
1-[4-(3,4-dichlorophenyl)-1,3-thiazol-2-yl]-4-[(3,4-dimethoxyphenyl)sulfonyl]-piperazine
1-[4-(3,4-dimethylphenyl)-1,3-thiazol-2-yl]-4-[(3,4-dimethoxyphenyl)sulfonyl]-piperazine
1-[4-(3,4-difluorophenyl)-1,3-thiazol-2-yl]-4-[(3,4-dimethoxyphenyl)sulfonyl]-piperazine
1-[4-(3,5-difluorophenyl)-1,3-thiazol-2-yl]-4-[(3,4-dimethoxyphenyl)sulfonyl]-piperazine
1-[4-(3,5-dichlorophenyl)-1,3-thiazol-2-yl]-4-[(3,4-dimethoxyphenyl)sulfonyl]-piperazine
1-[4-(3,5-dimethylphenyl)-1,3-thiazol-2-yl]-4-[(3,4-dimethoxyphenyl)sulfonyl]-piperazine
1-[4-(3-chloro-4-fluorophenyl)-1,3-thiazol-2-yl]-4-[(3,4-dimethoxyphenyl)sulfonyl]-piperazine
1-[4-(3-chloro-5-fluorophenyl)-1,3-thiazol-2-yl]-4-[(3,4-dimethoxyphenyl)sulfonyl]-piperazine
1-[4-(4-chloro-3-fluorophenyl)-1,3-thiazol-2-yl]-4-[(3,4-dimethoxyphenyl)sulfonyl]-piperazine
1-[4-(3,4,5-trimethoxyphenyl)-1,3-thiazol-2-yl]-4-[(3,4-dimethoxyphenyl)sulfonyl]-piperazine
1-[4-(2,4,6-trimethylphenyl)-1,3-thiazol-2-yl]-4-[(3,4-dimethoxyphenyl)sulfonyl]-piperazine
1-[4-phenyl-1,3-thiazol-2-yl]-4-[(2,4-dimethoxyphenyl)sulfonyl]-piperazine
1-[4-(2-methylphenyl)-1,3-thiazol-2-yl]-4-[(2,4-dimethoxyphenyl)sulfonyl]-piperazine
1-[4-(2-methoxyphenyl)-1,3-thiazol-2-yl]-4-[(2,4-dimethoxyphenyl)sulfonyl]-piperazine
1-[4-(3-methylphenyl)-1,3-thiazol-2-yl]-4-[(2,4-dimethoxyphenyl)sulfonyl]-piperazine
1-[4-(3-methoxyphenyl)-1,3-thiazol-2-yl]-4-[(2,4-dimethoxyphenyl)sulfonyl]-piperazine
1-[4-(3-bromophenyl)-1,3-thiazol-2-yl]-4-[(2,4-dimethoxyphenyl)sulfonyl]-piperazine
1-[4-(4-chlorophenyl)-1,3-thiazol-2-yl]-4-[(2,4-dimethoxyphenyl)sulfonyl]-piperazine
1-[4-(4-methoxyphenyl)-1,3-thiazol-2-yl]-4-[(2,4-dimethoxyphenyl)sulfonyl]-piperazine
1-[4-(4-methylphenyl)-1,3-thiazol-2-yl]-4-[(2,4-dimethoxyphenyl)sulfonyl]-piperazine
1-[4-(4-ethylphenyl)-1,3-thiazol-2-yl]-4-[(2,4-dimethoxyphenyl)sulfonyl]-piperazine
1-[4-(4-ethoxyphenyl)-1,3-thiazol-2-yl]-4-[(2,4-dimethoxyphenyl)sulfonyl]-piperazine
1-[4-(4-propylphenyl)-1,3-thiazol-2-yl]-4-[(2,4-dimethoxyphenyl)sulfonyl]-piperazine
1-[4-(2,6-dimethylphenyl)-1,3-thiazol-2-yl]-4-[(2,4-dimethoxyphenyl)sulfonyl]-piperazine
1-[4-(2,3-dimethylphenyl)-1,3-thiazol-2-yl]-4-[(2,4-dimethoxyphenyl)sulfonyl]-piperazine
1-[4-(2,5-dimethylphenyl)-1,3-thiazol-2-yl]-4-[(2,4-dimethoxyphenyl)sulfonyl]-piperazine
1-[4-(2,4-dichlorophenyl)-1,3-thiazol-2-yl]-4-[(2,4-dimethoxyphenyl)sulfonyl]-piperazine
1-[4-(2,4-dimethoxyphenyl)-1,3-thiazol-2-yl]-4-[(2,4-dimethoxyphenyl)sulfonyl]-piperazine
1-[4-(2,5-dimethoxyphenyl)-1,3-thiazol-2-yl]-4-[(2,4-dimethoxyphenyl)sulfonyl]-piperazine
1-[4-(3,4-dimethoxyphenyl)-1,3-thiazol-2-yl]-4-[(2,4-dimethoxyphenyl)sulfonyl]-piperazine
1-[4-(3,5-dimethoxyphenyl)-1,3-thiazol-2-yl]-4-[(2,4-dimethoxyphenyl)sulfonyl]-piperazine
1-[4-(3,4-dichlorophenyl)-1,3-thiazol-2-yl]-4-[(2,4-dimethoxyphenyl)sulfonyl]-piperazine
1-[4-(3,4-dimethylphenyl)-1,3-thiazol-2-yl]-4-[(2,4-dimethoxyphenyl)sulfonyl]-piperazine
1-[4-(3,4-difluorophenyl)-1,3-thiazol-2-yl]-4-[(2,4-dimethoxyphenyl)sulfonyl]-piperazine
1-[4-(3,5-difluorophenyl)-1,3-thiazol-2-yl]-4-[(2,4-dimethoxyphenyl)sulfonyl]-piperazine
1-[4-(3,5-dichlorophenyl)-1,3-thiazol-2-yl]-4-[(2,4-dimethoxyphenyl)sulfonyl]-piperazine
1-[4-(3,5-dimethylphenyl)-1,3-thiazol-2-yl]-4-[(2,4-dimethoxyphenyl)sulfonyl]-piperazine
1-[4-(3-chloro-4-fluorophenyl)-1,3-thiazol-2-yl]-4-[(2,4-dimethoxyphenyl)sulfonyl]-piperazine
1-[4-(3-chloro-5-fluorophenyl)-1,3-thiazol-2-yl]-4-[(2,4-dimethoxyphenyl)sulfonyl]-piperazine
1-[4-(4-chloro-3-fluorophenyl)-1,3-thiazol-2-yl]-4-[(2,4-dimethoxyphenyl)sulfonyl]-piperazine
1-[4-(3,4,5-trimethoxyphenyl)-1,3-thiazol-2-yl]-4-[(2,4-dimethoxyphenyl)sulfonyl]-piperazine
1-[4-(2,4,6-trimethylphenyl)-1,3-thiazol-2-yl]-4-[(2,4-dimethoxyphenyl)sulfonyl]-piperazine
1-[4-phenyl-1,3-thiazol-2-yl]-4-[(2,5-dimethoxyphenyl)sulfonyl]-piperazine
1-[4-(2-methylphenyl)-1,3-thiazol-2-yl]-4-[(2,5-dimethoxyphenyl)sulfonyl]-piperazine
1-[4-(2-methoxyphenyl)-1,3-thiazol-2-yl]-4-[(2,5-dimethoxyphenyl)sulfonyl]-piperazine
1-[4-(3-methylphenyl)-1,3-thiazol-2-yl]-4-[(2,5-dimethoxyphenyl)sulfonyl]-piperazine
1-[4-(3-methoxyphenyl)-1,3-thiazol-2-yl]-4-[(2,5-dimethoxyphenyl)sulfonyl]-piperazine
1-[4-(3-bromophenyl)-1,3-thiazol-2-yl]-4-[(2,5-dimethoxyphenyl)sulfonyl]-piperazine
1-[4-(4-chlorophenyl)-1,3-thiazol-2-yl]-4-[(2,5-dimethoxyphenyl)sulfonyl]-piperazine
1-[4-(4-methoxyphenyl)-1,3-thiazol-2-yl]-4-[(2,5-dimethoxyphenyl)sulfonyl]-piperazine
1-[4-(4-methylphenyl)-1,3-thiazol-2-yl]-4-[(2,5-dimethoxyphenyl)sulfonyl]-piperazine
1-[4-(4-ethylphenyl)-1,3-thiazol-2-yl]-4-[(2,5-dimethoxyphenyl)sulfonyl]-piperazine
1-[4-(4-ethoxyphenyl)-1,3-thiazol-2-yl]-4-[(2,5-dimethoxyphenyl)sulfonyl]-piperazine
1-[4-(4-propylphenyl)-1,3-thiazol-2-yl]-4-[(2,5-dimethoxyphenyl)sulfonyl]-piperazine
1-[4-(2,6-dimethylphenyl)-1,3-thiazol-2-yl]-4-[(2,5-dimethoxyphenyl)sulfonyl]-piperazine
1-[4-(2,3-dimethylphenyl)-1,3-thiazol-2-yl]-4-[(2,5-dimethoxyphenyl)sulfonyl]-piperazine
1-[4-(2,5-dimethylphenyl)-1,3-thiazol-2-yl]-4-[(2,5-dimethoxyphenyl)sulfonyl]-piperazine 1-[4-(2,4-dichlorophenyl)-1,3-thiazol-2-yl]-4-[(2,5-dimethoxyphenyl)sulfonyl]-piperazine
1-[4-(2,4-dimethoxyphenyl)-1,3-thiazol-2-yl]-4-[(2,5-dimethoxyphenyl)sulfonyl]-piperazine
1-[4-(2,5-dimethoxyphenyl)-1,3-thiazol-2-yl]-4-[(2,5-dimethoxyphenyl)sulfonyl]-piperazine
1-[4-(3,4-dimethoxyphenyl)-1,3-thiazol-2-yl]-4-[(2,5-dimethoxyphenyl)sulfonyl]-piperazine
1-[4-(3,5-dimethoxyphenyl)-1,3-thiazol-2-yl]-4-[(2,5-dimethoxyphenyl)sulfonyl]-piperazine
1-[4-(3,4-dichlorophenyl)-1,3-thiazol-2-yl]-4-[(2,5-dimethoxyphenyl)sulfonyl]-piperazine
1-[4-(3,4-dimethylphenyl)-1,3-thiazol-2-yl]-4-[(2,5-dimethoxyphenyl)sulfonyl]-piperazine
1-[4-(3,4-difluorophenyl)-1,3-thiazol-2-yl]-4-[(2,5-dimethoxyphenyl)sulfonyl]-piperazine
1-[4-(3,5-difluorophenyl)-1,3-thiazol-2-yl]-4-[(2,5-dimethoxyphenyl)sulfonyl]-piperazine
1-[4-(3,5-dichlorophenyl)-1,3-thiazol-2-yl]-4-[(2,5-dimethoxyphenyl)sulfonyl]-piperazine
1-[4-(3,5-dimethylphenyl)-1,3-thiazol-2-yl]-4-[(2,5-dimethoxyphenyl)sulfonyl]-piperazine
1-[4-(3-chloro-4-fluorophenyl)-1,3-thiazol-2-yl]-4-[(2,5-dimethoxyphenyl)sulfonyl]-piperazine
1-[4-(3-chloro-5-fluorophenyl)-1,3-thiazol-2-yl]-4-[(2,5-dimethoxyphenyl)sulfonyl]-piperazine
1-[4-(4-chloro-3-fluorophenyl)-1,3-thiazol-2-yl]-4-[(2,5-dimethoxyphenyl)sulfonyl]-piperazine
1-[4-(3,4,5-trimethoxyphenyl)-1,3-thiazol-2-yl]-4-[(2,5-dimethoxyphenyl)sulfonyl]-piperazine
1-[4-(2,4,6-trimethylphenyl)-1,3-thiazol-2-yl]-4-[(2,5-dimethoxyphenyl)sulfonyl]-piperazine
1-[4-phenyl-1,3-thiazol-2-yl]-4-[(3,5-dichlorophenyl)sulfonyl]-piperazine
1-[4-(2-methylphenyl)-1,3-thiazol-2-yl]-4-[(3,5-dichlorophenyl)sulfonyl]-piperazine
1-[4-(2-methoxyphenyl)-1,3-thiazol-2-yl]-4-[(3,5-dichlorophenyl)sulfonyl]-piperazine
1-[4-(3-methylphenyl)-1,3-thiazol-2-yl]-4-[(3,5-dichlorophenyl)sulfonyl]-piperazine
1-[4-(3-methoxyphenyl)-1,3-thiazol-2-yl]-4-[(3,5-dichlorophenyl)sulfonyl]-piperazine
1-[4-(3-bromophenyl)-1,3-thiazol-2-yl]-4-[(3,5-dichlorophenyl)sulfonyl]-piperazine
1-[4-(4-chlorophenyl)-1,3-thiazol-2-yl]-4-[(3,5-dichlorophenyl)sulfonyl]-piperazine
1-[4-(4-methoxyphenyl)-1,3-thiazol-2-yl]-4-[(3,5-dichlorophenyl)sulfonyl]-piperazine
1-[4-(4-methylphenyl)-1,3-thiazol-2-yl]-4-[(3,5-dichlorophenyl)sulfonyl]-piperazine
1-[4-(4-ethylphenyl)-1,3-thiazol-2-yl]-4-[(3,5-dichlorophenyl)sulfonyl]-piperazine
1-[4-(4-ethoxyphenyl)-1,3-thiazol-2-yl]-4-[(3,5-dichlorophenyl)sulfonyl]-piperazine
1-[4-(4-propylphenyl)-1,3-thiazol-2-yl]-4-[(3,5-dichlorophenyl)sulfonyl]-piperazine
1-[4-(2,6-dimethylphenyl)-1,3-thiazol-2-yl]-4-[(3,5-dichlorophenyl)sulfonyl]-piperazine
1-[4-(2,3-dimethylphenyl)-1,3-thiazol-2-yl]-4-[(3,5-dichlorophenyl)sulfonyl]-piperazine
1-[4-(2,5-dimethylphenyl)-1,3-thiazol-2-yl]-4-[(3,5-dichlorophenyl)sulfonyl]-piperazine
1-[4-(2,4-dichlorophenyl)-1,3-thiazol-2-yl]-4-[(3,5-dichlorophenyl)sulfonyl]-piperazine
1-[4-(2,4-dimethoxyphenyl)-1,3-thiazol-2-yl]-4-[(3,5-dichlorophenyl)sulfonyl]-piperazine
1-[4-(2,5-dimethoxyphenyl)-1,3-thiazol-2-yl]-4-[(3,5-dichlorophenyl)sulfonyl]-piperazine
1-[4-(3,4-dimethoxyphenyl)-1,3-thiazol-2-yl]-4-[(3,5-dichlorophenyl)sulfonyl]-piperazine
1-[4-(3,5-dimethoxyphenyl)-1,3-thiazol-2-yl]-4-[(3,5-dichlorophenyl)sulfonyl]-piperazine
1-[4-(3,4-dichlorophenyl)-1,3-thiazol-2-yl]-4-[(3,5-dichlorophenyl)sulfonyl]-piperazine
1-[4-(3,4-dimethylphenyl)-1,3-thiazol-2-yl]-4-[(3,5-dichlorophenyl)sulfonyl]-piperazine
1-[4-(3,4-difluorophenyl)-1,3-thiazol-2-yl]-4-[(3,5-dichlorophenyl)sulfonyl]-piperazine
1-[4-(3,5-difluorophenyl)-1,3-thiazol-2-yl]-4-[(3,5-dichlorophenyl)sulfonyl]-piperazine
1-[4-(3,5-dichlorophenyl)-1,3-thiazol-2-yl]-4-[(3,5-dichlorophenyl)sulfonyl]-piperazine
1-[4-(3,5-dimethylphenyl)-1,3-thiazol-2-yl]-4-[(3,5-dichlorophenyl)sulfonyl]-piperazine
1-[4-(3-chloro-4-fluorophenyl)-1,3-thiazol-2-yl]-4-[(3,5-dichlorophenyl)sulfonyl]-piperazine
1-[4-(3-chloro-5-fluorophenyl)-1,3-thiazol-2-yl]-4-[(3,5-dichlorophenyl)sulfonyl]-piperazine
1-[4-(4-chloro-3-fluorophenyl)-1,3-thiazol-2-yl]-4-[(3,5-dichlorophenyl)sulfonyl]-piperazine
1-[4-(3,4,5-trimethoxyphenyl)-1,3-thiazol-2-yl]-4-[(3,5-dichlorophenyl)sulfonyl]-piperazine
1-[4-(2,4,6-trimethylphenyl)-1,3-thiazol-2-yl]-4-[(3,5-dichlorophenyl)sulfonyl]-piperazine
1-[4-phenyl-1,3-thiazol-2-yl]-4-[(2,3-dichlorophenyl)sulfonyl]-piperazine
1-[4-(2-methylphenyl)-1,3-thiazol-2-yl]-4-[(2,3-dichlorophenyl)sulfonyl]-piperazine
1-[4-(2-methoxyphenyl)-1,3-thiazol-2-yl]-4-[(2,3-dichlorophenyl)sulfonyl]-piperazine
1-[4-(3-methylphenyl)-1,3-thiazol-2-yl]-4-[(2,3-dichlorophenyl)sulfonyl]-piperazine
1-[4-(3-methoxyphenyl)-1,3-thiazol-2-yl]-4-[(2,3-dichlorophenyl)sulfonyl]-piperazine
1-[4-(3-bromophenyl)-1,3-thiazol-2-yl]-4-[(2,3-dichlorophenyl)sulfonyl]-piperazine
1-[4-(4-chlorophenyl)-1,3-thiazol-2-yl]-4-[(2,3-dichlorophenyl)sulfonyl]-piperazine
1-[4-(4-methoxyphenyl)-1,3-thiazol-2-yl]-4-[(2,3-dichlorophenyl)sulfonyl]-piperazine
1-[4-(4-methylphenyl)-1,3-thiazol-2-yl]-4-[(2,3-dichlorophenyl)sulfonyl]-piperazine
1-[4-(4-ethylphenyl)-1,3-thiazol-2-yl]-4-[(2,3-dichlorophenyl)sulfonyl]-piperazine
1-[4-(4-ethoxyphenyl)-1,3-thiazol-2-yl]-4-[(2,3-dichlorophenyl)sulfonyl]-piperazine
1-[4-(4-propylphenyl)-1,3-thiazol-2-yl]-4-[(2,3-dichlorophenyl)sulfonyl]-piperazine
1-[4-(2,6-dimethylphenyl)-1,3-thiazol-2-yl]-4-[(2,3-dichlorophenyl)sulfonyl]-piperazine
1-[4-(2,3-dimethylphenyl)-1,3-thiazol-2-yl]-4-[(2,3-dichlorophenyl)sulfonyl]-piperazine
1-[4-(2,5-dimethylphenyl)-1,3-thiazol-2-yl]-4-[(2,3-dichlorophenyl)sulfonyl]-piperazine
1-[4-(2,4-dichlorophenyl)-1,3-thiazol-2-yl]-4-[(2,3-dichlorophenyl)sulfonyl]-piperazine
1-[4-(2,4-dimethoxyphenyl)-1,3-thiazol-2-yl]-4-[(2,3-dichlorophenyl)sulfonyl]-piperazine
1-[4-(2,5-dimethoxyphenyl)-1,3-thiazol-2-yl]-4-[(2,3-dichlorophenyl)sulfonyl]-piperazine
1-[4-(3,4-dimethoxyphenyl)-1,3-thiazol-2-yl]-4-[(2,3-dichlorophenyl)sulfonyl]-piperazine 1-[4-(3,5-dimethoxyphenyl)-1,3-thiazol-2-yl]-4-[(2,3-dichlorophenyl)sulfonyl]-piperazine
1-[4-(3,4-dichlorophenyl)-1,3-thiazol-2-yl]-4-[(2,3-dichlorophenyl)sulfonyl]-piperazine
1-[4-(3,4-dimethylphenyl)-1,3-thiazol-2-yl]-4-[(2,3-dichlorophenyl)sulfonyl]-piperazine
1-[4-(3,4-difluorophenyl)-1,3-thiazol-2-yl]-4-[(2,3-dichlorophenyl)sulfonyl]-piperazine
1-[4-(3,5-difluorophenyl)-1,3-thiazol-2-yl]-4-[(2,3-dichlorophenyl)sulfonyl]-piperazine
1-[4-(3,5-dichlorophenyl)-1,3-thiazol-2-yl]-4-[(2,3-dichlorophenyl)sulfonyl]-piperazine
1-[4-(3,5-dimethylphenyl)-1,3-thiazol-2-yl]-4-[(2,3-dichlorophenyl)sulfonyl]-piperazine
1-[4-(3-chloro-4-fluorophenyl)-1,3-thiazol-2-yl]-4-[(2,3-dichlorophenyl)sulfonyl]-piperazine
1-[4-(3-chloro-5-fluorophenyl)-1,3-thiazol-2-yl]-4-[(2,3-dichlorophenyl)sulfonyl]-piperazine
1-[4-(4-chloro-3-fluorophenyl)-1,3-thiazol-2-yl]-4-[(2,3-dichlorophenyl)sulfonyl]-piperazine
1-[4-(3,4,5-trimethoxyphenyl)-1,3-thiazol-2-yl]-4-[(2,3-dichlorophenyl)sulfonyl]-piperazine
1-[4-(2,4,6-trimethylphenyl)-1,3-thiazol-2-yl]-4-[(2,3-dichlorophenyl)sulfonyl]-piperazine
1-[4-phenyl-1,3-thiazol-2-yl]-4-[(2,6-difluorophenyl)sulfonyl]-piperazine
1-[4-(2-methylphenyl)-1,3-thiazol-2-yl]-4-[(2,6-difluorophenyl)sulfonyl]-piperazine
1-[4-(2-methoxyphenyl)-1,3-thiazol-2-yl]-4-[(2,6-difluorophenyl)sulfonyl]-piperazine
1-[4-(3-methylphenyl)-1,3-thiazol-2-yl]-4-[(2,6-difluorophenyl)sulfonyl]-piperazine
1-[4-(3-methoxyphenyl)-1,3-thiazol-2-yl]-4-[(2,6-difluorophenyl)sulfonyl]-piperazine
1-[4-(3-bromophenyl)-1,3-thiazol-2-yl]-4-[(2,6-difluorophenyl)sulfonyl]-piperazine
1-[4-(4-chlorophenyl)-1,3-thiazol-2-yl]-4-[(2,6-difluorophenyl)sulfonyl]-piperazine
1-[4-(4-methoxyphenyl)-1,3-thiazol-2-yl]-4-[(2,6-difluorophenyl)sulfonyl]-piperazine
1-[4-(4-methylphenyl)-1,3-thiazol-2-yl]-4-[(2,6-difluorophenyl)sulfonyl]-piperazine
1-[4-(4-ethylphenyl)-1,3-thiazol-2-yl]-4-[(2,6-difluorophenyl)sulfonyl]-piperazine
1-[4-(4-ethoxyphenyl)-1,3-thiazol-2-yl]-4-[(2,6-difluorophenyl)sulfonyl]-piperazine
1-[4-(4-propylphenyl)-1,3-thiazol-2-yl]-4-[(2,6-difluorophenyl)sulfonyl]-piperazine
1-[4-(2,6-dimethylphenyl)-1,3-thiazol-2-yl]-4-[(2,6-difluorophenyl)sulfonyl]-piperazine
1-[4-(2,3-dimethylphenyl)-1,3-thiazol-2-yl]-4-[(2,6-difluorophenyl)sulfonyl]-piperazine
1-[4-(2,5-dimethylphenyl)-1,3-thiazol-2-yl]-4-[(2,6-difluorophenyl)sulfonyl]-piperazine
1-[4-(2,4-dichlorophenyl)-1,3-thiazol-2-yl]-4-[(2,6-difluorophenyl)sulfonyl]-piperazine
1-[4-(2,4-dimethoxyphenyl)-1,3-thiazol-2-yl]-4-[(2,6-difluorophenyl)sulfonyl]-piperazine
1-[4-(2,5-dimethoxyphenyl)-1,3-thiazol-2-yl]-4-[(2,6-difluorophenyl)sulfonyl]-piperazine
1-[4-(3,4-dimethoxyphenyl)-1,3-thiazol-2-yl]-4-[(2,6-difluorophenyl)sulfonyl]-piperazine
1-[4-(3,5-dimethoxyphenyl)-1,3-thiazol-2-yl]-4-[(2,6-difluorophenyl)sulfonyl]-piperazine
1-[4-(3,4-dichlorophenyl)-1,3-thiazol-2-yl]-4-[(2,6-difluorophenyl)sulfonyl]-piperazine
1-[4-(3,4-dimethylphenyl)-1,3-thiazol-2-yl]-4-[(2,6-difluorophenyl)sulfonyl]-piperazine
1-[4-(3,4-difluorophenyl)-1,3-thiazol-2-yl]-4-[(2,6-difluorophenyl)sulfonyl]-piperazine
1-[4-(3,5-difluorophenyl)-1,3-thiazol-2-yl]-4-[(2,6-difluorophenyl)sulfonyl]-piperazine
1-[4-(3,5-dichlorophenyl)-1,3-thiazol-2-yl]-4-[(2,6-difluorophenyl)sulfonyl]-piperazine
1-[4-(3,5-dimethylphenyl)-1,3-thiazol-2-yl]-4-[(2,6-difluorophenyl)sulfonyl]-piperazine
1-[4-(3-chloro-4-fluorophenyl)-1,3-thiazol-2-yl]-4-[(2,6-difluorophenyl)sulfonyl]-piperazine
1-[4-(3-chloro-5-fluorophenyl)-1,3-thiazol-2-yl]-4-[(2,6-difluorophenyl)sulfonyl]-piperazine
1-[4-(4-chloro-3-fluorophenyl)-1,3-thiazol-2-yl]-4-[(2,6-difluorophenyl)sulfonyl]-piperazine
1-[4-(3,4,5-trimethoxyphenyl)-1,3-thiazol-2-yl]-4-[(2,6-difluorophenyl)sulfonyl]-piperazine
1-[4-(2,4,6-trimethylphenyl)-1,3-thiazol-2-yl]-4-[(2,6-difluorophenyl)sulfonyl]-piperazine
1-[4-phenyl-1,3-thiazol-2-yl]-4-[(2,4-difluorophenyl)sulfonyl]-piperazine
1-[4-(2-methylphenyl)-1,3-thiazol-2-yl]-4-[(2,4-difluorophenyl)sulfonyl]-piperazine
1-[4-(2-methoxyphenyl)-1,3-thiazol-2-yl]-4-[(2,4-difluorophenyl)sulfonyl]-piperazine
1-[4-(3-methylphenyl)-1,3-thiazol-2-yl]-4-[(2,4-difluorophenyl)sulfonyl]-piperazine
1-[4-(3-methoxyphenyl)-1,3-thiazol-2-yl]-4-[(2,4-difluorophenyl)sulfonyl]-piperazine
1-[4-(3-bromophenyl)-1,3-thiazol-2-yl]-4-[(2,4-difluorophenyl)sulfonyl]-piperazine
1-[4-(4-chlorophenyl)-1,3-thiazol-2-yl]-4-[(2,4-difluorophenyl)sulfonyl]-piperazine
1-[4-(4-methoxyphenyl)-1,3-thiazol-2-yl]-4-[(2,4-difluorophenyl)sulfonyl]-piperazine
1-[4-(4-methylphenyl)-1,3-thiazol-2-yl]-4-[(2,4-difluorophenyl)sulfonyl]-piperazine
1-[4-(4-ethylphenyl)-1,3-thiazol-2-yl]-4-[(2,4-difluorophenyl)sulfonyl]-piperazine
1-[4-(4-ethoxyphenyl)-1,3-thiazol-2-yl]-4-[(2,4-difluorophenyl)sulfonyl]-piperazine
1-[4-(4-propylphenyl)-1,3-thiazol-2-yl]-4-[(2,4-difluorophenyl)sulfonyl]-piperazine
1-[4-(2,6-dimethylphenyl)-1,3-thiazol-2-yl]-4-[(2,4-difluorophenyl)sulfonyl]-piperazine
1-[4-(2,3-dimethylphenyl)-1,3-thiazol-2-yl]-4-[(2,4-difluorophenyl)sulfonyl]-piperazine
1-[4-(2,5-dimethylphenyl)-1,3-thiazol-2-yl]-4-[(2,4-difluorophenyl)sulfonyl]-piperazine
1-[4-(2,4-dichlorophenyl)-1,3-thiazol-2-yl]-4-[(2,4-difluorophenyl)sulfonyl]-piperazine
1-[4-(2,4-dimethoxyphenyl)-1,3-thiazol-2-yl]-4-[(2,4-difluorophenyl)sulfonyl]-piperazine
1-[4-(2,5-dimethoxyphenyl)-1,3-thiazol-2-yl]-4-[(2,4-difluorophenyl)sulfonyl]-piperazine
1-[4-(3,4-dimethoxyphenyl)-1,3-thiazol-2-yl]-4-[(2,4-difluorophenyl)sulfonyl]-piperazine
1-[4-(3,5-dimethoxyphenyl)-1,3-thiazol-2-yl]-4-[(2,4-difluorophenyl)sulfonyl]-piperazine
1-[4-(3,4-dichlorophenyl)-1,3-thiazol-2-yl]-4-[(2,4-difluorophenyl)sulfonyl]-piperazine
1-[4-(3,4-dimethylphenyl)-1,3-thiazol-2-yl]-4-[(2,4-difluorophenyl)sulfonyl]-piperazine
1-[4-(3,4-difluorophenyl)-1,3-thiazol-2-yl]-4-[(2,4-difluorophenyl)sulfonyl]-piperazine 1-[4-(3,5-difluorophenyl)-1,3-thiazol-2-yl]-4-[(2,4-difluorophenyl)sulfonyl]-piperazine
1-[4-(3,5-dichlorophenyl)-1,3-thiazol-2-yl]-4-[(2,4-difluorophenyl)sulfonyl]-piperazine
1-[4-(3,5-dimethylphenyl)-1,3-thiazol-2-yl]-4-[(2,4-difluorophenyl)sulfonyl]-piperazine
1-[4-(3-chloro-4-fluorophenyl)-1,3-thiazol-2-yl]-4-[(2,4-difluorophenyl)sulfonyl]-piperazine
1-[4-(3-chloro-5-fluorophenyl)-1,3-thiazol-2-yl]-4-[(2,4-difluorophenyl)sulfonyl]-piperazine
1-[4-(4-chloro-3-fluorophenyl)-1,3-thiazol-2-yl]-4-[(2,4-difluorophenyl)sulfonyl]-piperazine
1-[4-(3,4,5-trimethoxyphenyl)-1,3-thiazol-2-yl]-4-[(2,4-difluorophenyl)sulfonyl]-piperazine
1-[4-(2,4,6-trimethylphenyl)-1,3-thiazol-2-yl]-4-[(2,4-difluorophenyl)sulfonyl]-piperazine
1-[4-phenyl-1,3-thiazol-2-yl]-4-[(4-(bromomethyl)phenyl)sulfonyl]-piperazine
1-[4-(2-methylphenyl)-1,3-thiazol-2-yl]-4-[(4-(bromomethyl)phenyl)sulfonyl]-piperazine
1-[4-(2-methoxyphenyl)-1,3-thiazol-2-yl]-4-[(4-(bromomethyl)phenyl)sulfonyl]-piperazine
1-[4-(3-methylphenyl)-1,3-thiazol-2-yl]-4-[(4-(bromomethyl)phenyl)sulfonyl]-piperazine
1-[4-(3-methoxyphenyl)-1,3-thiazol-2-yl]-4-[(4-(bromomethyl)phenyl)sulfonyl]-piperazine
1-[4-(3-bromophenyl)-1,3-thiazol-2-yl]-4-[(4-(bromomethyl)phenyl)sulfonyl]-piperazine
1-[4-(4-chlorophenyl)-1,3-thiazol-2-yl]-4-[(4-(bromomethyl)phenyl)sulfonyl]-piperazine
1-[4-(4-methoxyphenyl)-1,3-thiazol-2-yl]-4-[(4-(bromomethyl)phenyl)sulfonyl]-piperazine
1-[4-(4-methylphenyl)-1,3-thiazol-2-yl]-4-[(4-(bromomethyl)phenyl)sulfonyl]-piperazine
1-[4-(4-ethylphenyl)-1,3-thiazol-2-yl]-4-[(4-(bromomethyl)phenyl)sulfonyl]-piperazine
1-[4-(4-ethoxyphenyl)-1,3-thiazol-2-yl]-4-[(4-(bromomethyl)phenyl)sulfonyl]-piperazine
1-[4-(4-propylphenyl)-1,3-thiazol-2-yl]-4-[(4-(bromomethyl)phenyl)sulfonyl]-piperazine
1-[4-(2,6-dimethylphenyl)-1,3-thiazol-2-yl]-4-[(4-(bromomethyl)phenyl)sulfonyl]-piperazine
1-[4-(2,3-dimethylphenyl)-1,3-thiazol-2-yl]-4-[(4-(bromomethyl)phenyl)sulfonyl]-piperazine
1-[4-(2,5-dimethylphenyl)-1,3-thiazol-2-yl]-4-[(4-(bromomethyl)phenyl)sulfonyl]-piperazine
1-[4-(2,4-dichlorophenyl)-1,3-thiazol-2-yl]-4-[(4-(bromomethyl)phenyl)sulfonyl]-piperazine
1-[4-(2,4-dimethoxyphenyl)-1,3-thiazol-2-yl]-4-[(4-(bromomethyl)phenyl)sulfonyl]-piperazine
1-[4-(2,5-dimethoxyphenyl)-1,3-thiazol-2-yl]-4-[(4-(bromomethyl)phenyl)sulfonyl]-piperazine
1-[4-(3,4-dimethoxyphenyl)-1,3-thiazol-2-yl]-4-[(4-(bromomethyl)phenyl)sulfonyl]-piperazine
1-[4-(3,5-dimethoxyphenyl)-1,3-thiazol-2-yl]-4-[(4-(bromomethyl)phenyl)sulfonyl]-piperazine
1-[4-(3,4-dichlorophenyl)-1,3-thiazol-2-yl]-4-[(4-(bromomethyl)phenyl)sulfonyl]-piperazine
1-[4-(3,4-dimethylphenyl)-1,3-thiazol-2-yl]-4-[(4-(bromomethyl)phenyl)sulfonyl]-piperazine
1-[4-(3,4-difluorophenyl)-1,3-thiazol-2-yl]-4-[(4-(bromomethyl)phenyl)sulfonyl]-piperazine
1-[4-(3,5-difluorophenyl)-1,3-thiazol-2-yl]-4-[(4-(bromomethyl)phenyl)sulfonyl]-piperazine
1-[4-(3,5-dichlorophenyl)-1,3-thiazol-2-yl]-4-[(4-(bromomethyl)phenyl)sulfonyl]-piperazine
1-[4-(3,5-dimethylphenyl)-1,3-thiazol-2-yl]-4-[(4-(bromomethyl)phenyl)sulfonyl]-piperazine
1-[4-(3-chloro-4-fluorophenyl)-1,3-thiazol-2-yl]-4-[(4-(bromomethyl)phenyl)sulfonyl]-piperazine
1-[4-(3-chloro-5-fluorophenyl)-1,3-thiazol-2-yl]-4-[(4-(bromomethyl)phenyl)sulfonyl]-piperazine
1-[4-(4-chloro-3-fluorophenyl)-1,3-thiazol-2-yl]-4-[(4-(bromomethyl)phenyl)sulfonyl]-piperazine
1-[4-(3,4,5-trimethoxyphenyl)-1,3-thiazol-2-yl]-4-[(4-(bromomethyl)phenyl)sulfonyl]-piperazine
1-[4-(2,4,6-trimethylphenyl)-1,3-thiazol-2-yl]-4-[(4-(bromomethyl)phenyl)sulfonyl]-piperazine
1-[4-phenyl-1,3-thiazol-2-yl]-4-[(3-(trifluoromethyl)phenyl)sulfonyl]-piperazine
1-[4-(2-methylphenyl)-1,3-thiazol-2-yl]-4-[(3-(trifluoromethyl)phenyl)sulfonyl]-piperazine
1-[4-(2-methoxyphenyl)-1,3-thiazol-2-yl]-4-[(3-(trifluoromethyl)phenyl)sulfonyl]-piperazine
1-[4-(3-methylphenyl)-1,3-thiazol-2-yl]-4-[(3-(trifluoromethyl)phenyl)sulfonyl]-piperazine
1-[4-(3-methoxyphenyl)-1,3-thiazol-2-yl]-4-[(3-(trifluoromethyl)phenyl)sulfonyl]-piperazine
1-[4-(3-bromophenyl)-1,3-thiazol-2-yl]-4-[(3-(trifluoromethyl)phenyl)sulfonyl]-piperazine
1-[4-(4-chlorophenyl)-1,3-thiazol-2-yl]-4-[(3-(trifluoromethyl)phenyl)sulfonyl]-piperazine
1-[4-(4-methoxyphenyl)-1,3-thiazol-2-yl]-4-[(3-(trifluoromethyl)phenyl)sulfonyl]-piperazine
1-[4-(4-methylphenyl)-1,3-thiazol-2-yl]-4-[(3-(trifluoromethyl)phenyl)sulfonyl]-piperazine
1-[4-(4-ethylphenyl)-1,3-thiazol-2-yl]-4-[(3-(trifluoromethyl)phenyl)sulfonyl]-piperazine
1-[4-(4-ethoxyphenyl)-1,3-thiazol-2-yl]-4-[(3-(trifluoromethyl)phenyl)sulfonyl]-piperazine
1-[4-(4-propylphenyl)-1,3-thiazol-2-yl]-4-[(3-(trifluoromethyl)phenyl)sulfonyl]-piperazine
1-[4-(2,6-dimethylphenyl)-1,3-thiazol-2-yl]-4-[(3-(trifluoromethyl)phenyl)sulfonyl]-piperazine
1-[4-(2,3-dimethylphenyl)-1,3-thiazol-2-yl]-4-[(3-(trifluoromethyl)phenyl)sulfonyl]-piperazine
1-[4-(2,5-dimethylphenyl)-1,3-thiazol-2-yl]-4-[(3-(trifluoromethyl)phenyl)sulfonyl]-piperazine
1-[4-(2,4-dichlorophenyl)-1,3-thiazol-2-yl]-4-[(3-(trifluoromethyl)phenyl)sulfonyl]-piperazine
1-[4-(2,4-dimethoxyphenyl)-1,3-thiazol-2-yl]-4-[(3-(trifluoromethyl)phenyl)sulfonyl]-piperazine
1-[4-(2,5-dimethoxyphenyl)-1,3-thiazol-2-yl]-4-[(3-(trifluoromethyl)phenyl)sulfonyl]-piperazine
1-[4-(3,4-dimethoxyphenyl)-1,3-thiazol-2-yl]-4-[(3-(trifluoromethyl)phenyl)sulfonyl]-piperazine
1-[4-(3,5-dimethoxyphenyl)-1,3-thiazol-2-yl]-4-[(3-(trifluoromethyl)phenyl)sulfonyl]-piperazine
1-[4-(3,4-dichlorophenyl)-1,3-thiazol-2-yl]-4-[(3-(trifluoromethyl)phenyl)sulfonyl]-piperazine
1-[4-(3,4-dimethylphenyl)-1,3-thiazol-2-yl]-4-[(3-(trifluoromethyl)phenyl)sulfonyl]-piperazine
1-[4-(3,4-difluorophenyl)-1,3-thiazol-2-yl]-4-[(3-(trifluoromethyl)phenyl)sulfonyl]-piperazine
1-[4-(3,5-difluorophenyl)-1,3-thiazol-2-yl]-4-[(3-(trifluoromethyl)phenyl)sulfonyl]-piperazine
1-[4-(3,5-dichlorophenyl)-1,3-thiazol-2-yl]-4-[(3-(trifluoromethyl)phenyl)sulfonyl]-piperazine
1-[4-(3,5-dimethylphenyl)-1,3-thiazol-2-yl]-4-[(3-(trifluoromethyl)phenyl)sulfonyl]-piperazine
1-[4-(3-chloro-4-fluorophenyl)-1,3-thiazol-2-yl]-4-[(3-(trifluoromethyl)phenyl)sulfonyl]-piperazine 1-[4-(3-chloro-5-fluorophenyl)-1,3-thiazol-2-yl]-4-[(3-(trifluoromethyl)phenyl)sulfonyl]-piperazine
1-[4-(4-chloro-3-fluorophenyl)-1,3-thiazol-2-yl]-4-[(3-(trifluoromethyl)phenyl)sulfonyl]-piperazine
1-[4-(3,4,5-trimethoxyphenyl)-1,3-thiazol-2-yl]-4-[(3-(trifluoromethyl)phenyl)sulfonyl]-piperazine
1-[4-(2,4,6-trimethylphenyl)-1,3-thiazol-2-yl]-4-[(3-(trifluoromethyl)phenyl)sulfonyl]-piperazine
1-[4-phenyl-1,3-thiazol-2-yl]-4-[(2-(trifluoromethyl)phenyl)sulfonyl]-piperazine
1-[4-(2-methylphenyl)-1,3-thiazol-2-yl]-4-[(2-(trifluoromethyl)phenyl)sulfonyl]-piperazine
1-[4-(2-methoxyphenyl)-1,3-thiazol-2-yl]-4-[(2-(trifluoromethyl)phenyl)sulfonyl]-piperazine
1-[4-(3-methylphenyl)-1,3-thiazol-2-yl]-4-[(2-(trifluoromethyl)phenyl)sulfonyl]-piperazine
1-[4-(3-methoxyphenyl)-1,3-thiazol-2-yl]-4-[(2-(trifluoromethyl)phenyl)sulfonyl]-piperazine
1-[4-(3-bromophenyl)-1,3-thiazol-2-yl]-4-[(2-(trifluoromethyl)phenyl)sulfonyl]-piperazine
1-[4-(4-chlorophenyl)-1,3-thiazol-2-yl]-4-[(2-(trifluoromethyl)phenyl)sulfonyl]-piperazine
1-[4-(4-methoxyphenyl)-1,3-thiazol-2-yl]-4-[(2-(trifluoromethyl)phenyl)sulfonyl]-piperazine
1-[4-(4-methylphenyl)-1,3-thiazol-2-yl]-4-[(2-(trifluoromethyl)phenyl)sulfonyl]-piperazine
1-[4-(4-ethylphenyl)-1,3-thiazol-2-yl]-4-[(2-(trifluoromethyl)phenyl)sulfonyl]-piperazine
1-[4-(4-ethoxyphenyl)-1,3-thiazol-2-yl]-4-[(2-(trifluoromethyl)phenyl)sulfonyl]-piperazine
1-[4-(4-propylphenyl)-1,3-thiazol-2-yl]-4-[(2-(trifluoromethyl)phenyl)sulfonyl]-piperazine
1-[4-(2,6-dimethylphenyl)-1,3-thiazol-2-yl]-4-[(2-(trifluoromethyl)phenyl)sulfonyl]-piperazine
1-[4-(2,3-dimethylphenyl)-1,3-thiazol-2-yl]-4-[(2-(trifluoromethyl)phenyl)sulfonyl]-piperazine
1-[4-(2,5-dimethylphenyl)-1,3-thiazol-2-yl]-4-[(2-(trifluoromethyl)phenyl)sulfonyl]-piperazine
1-[4-(2,4-dichlorophenyl)-1,3-thiazol-2-yl]-4-[(2-(trifluoromethyl)phenyl)sulfonyl]-piperazine
1-[4-(2,4-dimethoxyphenyl)-1,3-thiazol-2-yl]-4-[(2-(trifluoromethyl)phenyl)sulfonyl]-piperazine
1-[4-(2,5-dimethoxyphenyl)-1,3-thiazol-2-yl]-4-[(2-(trifluoromethyl)phenyl)sulfonyl]-piperazine
1-[4-(3,4-dimethoxyphenyl)-1,3-thiazol-2-yl]-4-[(2-(trifluoromethyl)phenyl)sulfonyl]-piperazine
1-[4-(3,5-dimethoxyphenyl)-1,3-thiazol-2-yl]-4-[(2-(trifluoromethyl)phenyl)sulfonyl]-piperazine
1-[4-(3,4-dichlorophenyl)-1,3-thiazol-2-yl]-4-[(2-(trifluoromethyl)phenyl)sulfonyl]-piperazine
1-[4-(3,4-dimethylphenyl)-1,3-thiazol-2-yl]-4-[(2-(trifluoromethyl)phenyl)sulfonyl]-piperazine
1-[4-(3,4-difluorophenyl)-1,3-thiazol-2-yl]-4-[(2-(trifluoromethyl)phenyl)sulfonyl]-piperazine
1-[4-(3,5-difluorophenyl)-1,3-thiazol-2-yl]-4-[(2-(trifluoromethyl)phenyl)sulfonyl]-piperazine
1-[4-(3,5-dichlorophenyl)-1,3-thiazol-2-yl]-4-[(2-(trifluoromethyl)phenyl)sulfonyl]-piperazine
1-[4-(3,5-dimethylphenyl)-1,3-thiazol-2-yl]-4-[(2-(trifluoromethyl)phenyl)sulfonyl]-piperazine
1-[4-(3-chloro-4-fluorophenyl)-1,3-thiazol-2-yl]-4-[(2-(trifluoromethyl)phenyl)sulfonyl]-piperazine
1-[4-(3-chloro-5-fluorophenyl)-1,3-thiazol-2-yl]-4-[(2-(trifluoromethyl)phenyl)sulfonyl]-piperazine
1-[4-(4-chloro-3-fluorophenyl)-1,3-thiazol-2-yl]-4-[(2-(trifluoromethyl)phenyl)sulfonyl]-piperazine
1-[4-(3,4,5-trimethoxyphenyl)-1,3-thiazol-2-yl]-4-[(2-(trifluoromethyl)phenyl)sulfonyl]-piperazine
1-[4-(2,4,6-trimethylphenyl)-1,3-thiazol-2-yl]-4-[(2-(trifluoromethyl)phenyl)sulfonyl]-piperazine
1-[4-phenyl-1,3-thiazol-2-yl]-4-[(4-nitrophenyl)sulfonyl]-piperazine
1-[4-(2-methylphenyl)-1,3-thiazol-2-yl]-4-[(4-nitrophenyl)sulfonyl]-piperazine
1-[4-(2-methoxyphenyl)-1,3-thiazol-2-yl]-4-[(4-nitrophenyl)sulfonyl]-piperazine
1-[4-(3-methylphenyl)-1,3-thiazol-2-yl]-4-[(4-nitrophenyl)sulfonyl]-piperazine
1-[4-(3-methoxyphenyl)-1,3-thiazol-2-yl]-4-[(4-nitrophenyl)sulfonyl]-piperazine
1-[4-(3-bromophenyl)-1,3-thiazol-2-yl]-4-[(4-nitrophenyl)sulfonyl]-piperazine
1-[4-(4-chlorophenyl)-1,3-thiazol-2-yl]-4-[(4-nitrophenyl)sulfonyl]-piperazine
1-[4-(4-methoxyphenyl)-1,3-thiazol-2-yl]-4-[(4-nitrophenyl)sulfonyl]-piperazine
1-[4-(4-methylphenyl)-1,3-thiazol-2-yl]-4-[(4-nitrophenyl)sulfonyl]-piperazine
1-[4-(4-ethylphenyl)-1,3-thiazol-2-yl]-4-[(4-nitrophenyl)sulfonyl]-piperazine
1-[4-(4-ethoxyphenyl)-1,3-thiazol-2-yl]-4-[(4-nitrophenyl)sulfonyl]-piperazine
1-[4-(4-propylphenyl)-1,3-thiazol-2-yl]-4-[(4-nitrophenyl)sulfonyl]-piperazine
1-[4-(2,6-dimethylphenyl)-1,3-thiazol-2-yl]-4-[(4-nitrophenyl)sulfonyl]-piperazine
1-[4-(2,3-dimethylphenyl)-1,3-thiazol-2-yl]-4-[(4-nitrophenyl)sulfonyl]-piperazine
1-[4-(2,5-dimethylphenyl)-1,3-thiazol-2-yl]-4-[(4-nitrophenyl)sulfonyl]-piperazine
1-[4-(2,4-dichlorophenyl)-1,3-thiazol-2-yl]-4-[(4-nitrophenyl)sulfonyl]-piperazine
1-[4-(2,4-dimethoxyphenyl)-1,3-thiazol-2-yl]-4-[(4-nitrophenyl)sulfonyl]-piperazine
1-[4-(2,5-dimethoxyphenyl)-1,3-thiazol-2-yl]-4-[(4-nitrophenyl)sulfonyl]-piperazine
1-[4-(3,4-dimethoxyphenyl)-1,3-thiazol-2-yl]-4-[(4-nitrophenyl)sulfonyl]-piperazine
1-[4-(3,5-dimethoxyphenyl)-1,3-thiazol-2-yl]-4-[(4-nitrophenyl)sulfonyl]-piperazine
1-[4-(3,4-dichlorophenyl)-1,3-thiazol-2-yl]-4-[(4-nitrophenyl)sulfonyl]-piperazine
1-[4-(3,4-dimethylphenyl)-1,3-thiazol-2-yl]-4-[(4-nitrophenyl)sulfonyl]-piperazine
1-[4-(3,4-difluorophenyl)-1,3-thiazol-2-yl]-4-[(4-nitrophenyl)sulfonyl]-piperazine
1-[4-(3,5-difluorophenyl)-1,3-thiazol-2-yl]-4-[(4-nitrophenyl)sulfonyl]-piperazine
1-[4-(3,5-dichlorophenyl)-1,3-thiazol-2-yl]-4-[(4-nitrophenyl)sulfonyl]-piperazine
1-[4-(3,5-dimethylphenyl)-1,3-thiazol-2-yl]-4-[(4-nitrophenyl)sulfonyl]-piperazine
1-[4-(3-chloro-4-fluorophenyl)-1,3-thiazol-2-yl]-4-[(4-nitrophenyl)sulfonyl]-piperazine
1-[4-(3-chloro-5-fluorophenyl)-1,3-thiazol-2-yl]-4-[(4-nitrophenyl)sulfonyl]-piperazine
1-[4-(4-chloro-3-fluorophenyl)-1,3-thiazol-2-yl]-4-[(4-nitrophenyl)sulfonyl]-piperazine
1-[4-(3,4,5-trimethoxyphenyl)-1,3-thiazol-2-yl]-4-[(4-nitrophenyl)sulfonyl]-piperazine
1-[4-(2,4,6-trimethylphenyl)-1,3-thiazol-2-yl]-4-[(4-nitrophenyl)sulfonyl]-piperazine 1-[4-phenyl-1,3-thiazol-2-yl]-4-[(2-bromophenyl)sulfonyl]-piperazine
1-[4-(2-methylphenyl)-1,3-thiazol-2-yl]-4-[(2-bromophenyl)sulfonyl]-piperazine
1-[4-(2-methoxyphenyl)-1,3-thiazol-2-yl]-4-[(2-bromophenyl)sulfonyl]-piperazine
1-[4-(3-methylphenyl)-1,3-thiazol-2-yl]-4-[(2-bromophenyl)sulfonyl]-piperazine
1-[4-(3-methoxyphenyl)-1,3-thiazol-2-yl]-4-[(2-bromophenyl)sulfonyl]-piperazine
1-[4-(3-bromophenyl)-1,3-thiazol-2-yl]-4-[(2-bromophenyl)sulfonyl]-piperazine
1-[4-(4-chlorophenyl)-1,3-thiazol-2-yl]-4-[(2-bromophenyl)sulfonyl]-piperazine
1-[4-(4-methoxyphenyl)-1,3-thiazol-2-yl]-4-[(2-bromophenyl)sulfonyl]-piperazine
1-[4-(4-methylphenyl)-1,3-thiazol-2-yl]-4-[(2-bromophenyl)sulfonyl]-piperazine
1-[4-(4-ethylphenyl)-1,3-thiazol-2-yl]-4-[(2-bromophenyl)sulfonyl]-piperazine
1-[4-(4-ethoxyphenyl)-1,3-thiazol-2-yl]-4-[(2-bromophenyl)sulfonyl]-piperazine
1-[4-(4-propylphenyl)-1,3-thiazol-2-yl]-4-[(2-bromophenyl)sulfonyl]-piperazine
1-[4-(2,6-dimethylphenyl)-1,3-thiazol-2-yl]-4-[(2-bromophenyl)sulfonyl]-piperazine
1-[4-(2,3-dimethylphenyl)-1,3-thiazol-2-yl]-4-[(2-bromophenyl)sulfonyl]-piperazine
1-[4-(2,5-dimethylphenyl)-1,3-thiazol-2-yl]-4-[(2-bromophenyl)sulfonyl]-piperazine
1-[4-(2,4-dichlorophenyl)-1,3-thiazol-2-yl]-4-[(2-bromophenyl)sulfonyl]-piperazine
1-[4-(2,4-dimethoxyphenyl)-1,3-thiazol-2-yl]-4-[(2-bromophenyl)sulfonyl]-piperazine
1-[4-(2,5-dimethoxyphenyl)-1,3-thiazol-2-yl]-4-[(2-bromophenyl)sulfonyl]-piperazine
1-[4-(3,4-dimethoxyphenyl)-1,3-thiazol-2-yl]-4-[(2-bromophenyl)sulfonyl]-piperazine
1-[4-(3,5-dimethoxyphenyl)-1,3-thiazol-2-yl]-4-[(2-bromophenyl)sulfonyl]-piperazine
1-[4-(3,4-dichlorophenyl)-1,3-thiazol-2-yl]-4-[(2-bromophenyl)sulfonyl]-piperazine
1-[4-(3,4-dimethylphenyl)-1,3-thiazol-2-yl]-4-[(2-bromophenyl)sulfonyl]-piperazine
1-[4-(3,4-difluorophenyl)-1,3-thiazol-2-yl]-4-[(2-bromophenyl)sulfonyl]-piperazine
1-[4-(3,5-difluorophenyl)-1,3-thiazol-2-yl]-4-[(2-bromophenyl)sulfonyl]-piperazine
1-[4-(3,5-dichlorophenyl)-1,3-thiazol-2-yl]-4-[(2-bromophenyl)sulfonyl]-piperazine
1-[4-(3,5-dimethylphenyl)-1,3-thiazol-2-yl]-4-[(2-bromophenyl)sulfonyl]-piperazine
1-[4-(3-chloro-4-fluorophenyl)-1,3-thiazol-2-yl]-4-[(2-bromophenyl)sulfonyl]-piperazine
1-[4-(3-chloro-5-fluorophenyl)-1,3-thiazol-2-yl]-4-[(2-bromophenyl)sulfonyl]-piperazine
1-[4-(4-chloro-3-fluorophenyl)-1,3-thiazol-2-yl]-4-[(2-bromophenyl)sulfonyl]-piperazine
1-[4-(3,4,5-trimethoxyphenyl)-1,3-thiazol-2-yl]-4-[(2-bromophenyl)sulfonyl]-piperazine
1-[4-(2,4,6-trimethylphenyl)-1,3-thiazol-2-yl]-4-[(2-bromophenyl)sulfonyl]-piperazine
1-[4-phenyl-1,3-thiazol-2-yl]-4-[(2-chlorophenyl)sulfonyl]-piperazine
1-[4-(2-methylphenyl)-1,3-thiazol-2-yl]-4-[(2-chlorophenyl)sulfonyl]-piperazine
1-[4-(2-methoxyphenyl)-1,3-thiazol-2-yl]-4-[(2-chlorophenyl)sulfonyl]-piperazine
1-[4-(3-methylphenyl)-1,3-thiazol-2-yl]-4-[(2-chlorophenyl)sulfonyl]-piperazine
1-[4-(3-methoxyphenyl)-1,3-thiazol-2-yl]-4-[(2-chlorophenyl)sulfonyl]-piperazine
1-[4-(3-bromophenyl)-1,3-thiazol-2-yl]-4-[(2-chlorophenyl)sulfonyl]-piperazine
1-[4-(4-chlorophenyl)-1,3-thiazol-2-yl]-4-[(2-chlorophenyl)sulfonyl]-piperazine
1-[4-(4-methoxyphenyl)-1,3-thiazol-2-yl]-4-[(2-chlorophenyl)sulfonyl]-piperazine
1-[4-(4-methylphenyl)-1,3-thiazol-2-yl]-4-[(2-chlorophenyl)sulfonyl]-piperazine
1-[4-(4-ethylphenyl)-1,3-thiazol-2-yl]-4-[(2-chlorophenyl)sulfonyl]-piperazine
1-[4-(4-ethoxyphenyl)-1,3-thiazol-2-yl]-4-[(2-chlorophenyl)sulfonyl]-piperazine
1-[4-(4-propylphenyl)-1,3-thiazol-2-yl]-4-[(2-chlorophenyl)sulfonyl]-piperazine
1-[4-(2,6-dimethylphenyl)-1,3-thiazol-2-yl]-4-[(2-chlorophenyl)sulfonyl]-piperazine
1-[4-(2,3-dimethylphenyl)-1,3-thiazol-2-yl]-4-[(2-chlorophenyl)sulfonyl]-piperazine
1-[4-(2,5-dimethylphenyl)-1,3-thiazol-2-yl]-4-[(2-chlorophenyl)sulfonyl]-piperazine
1-[4-(2,4-dichlorophenyl)-1,3-thiazol-2-yl]-4-[(2-chlorophenyl)sulfonyl]-piperazine
1-[4-(2,4-dimethoxyphenyl)-1,3-thiazol-2-yl]-4-[(2-chlorophenyl)sulfonyl]-piperazine
1-[4-(2,5-dimethoxyphenyl)-1,3-thiazol-2-yl]-4-[(2-chlorophenyl)sulfonyl]-piperazine
1-[4-(3,4-dimethoxyphenyl)-1,3-thiazol-2-yl]-4-[(2-chlorophenyl)sulfonyl]-piperazine
1-[4-(3,5-dimethoxyphenyl)-1,3-thiazol-2-yl]-4-[(2-chlorophenyl)sulfonyl]-piperazine
1-[4-(3,4-dichlorophenyl)-1,3-thiazol-2-yl]-4-[(2-chlorophenyl)sulfonyl]-piperazine
1-[4-(3,4-dimethylphenyl)-1,3-thiazol-2-yl]-4-[(2-chlorophenyl)sulfonyl]-piperazine
1-[4-(3,4-difluorophenyl)-1,3-thiazol-2-yl]-4-[(2-chlorophenyl)sulfonyl]-piperazine
1-[4-(3,5-difluorophenyl)-1,3-thiazol-2-yl]-4-[(2-chlorophenyl)sulfonyl]-piperazine
1-[4-(3,5-dichlorophenyl)-1,3-thiazol-2-yl]-4-[(2-chlorophenyl)sulfonyl]-piperazine
1-[4-(3,5-dimethylphenyl)-1,3-thiazol-2-yl]-4-[(2-chlorophenyl)sulfonyl]-piperazine
1-[4-(3-chloro-4-fluorophenyl)-1,3-thiazol-2-yl]-4-[(2-chlorophenyl)sulfonyl]-piperazine
1-[4-(3-chloro-5-fluorophenyl)-1,3-thiazol-2-yl]-4-[(2-chlorophenyl)sulfonyl]-piperazine
1-[4-(4-chloro-3-fluorophenyl)-1,3-thiazol-2-yl]-4-[(2-chlorophenyl)sulfonyl]-piperazine
1-[4-(3,4,5-trimethoxyphenyl)-1,3-thiazol-2-yl]-4-[(2-chlorophenyl)sulfonyl]-piperazine
1-[4-(2,4,6-trimethylphenyl)-1,3-thiazol-2-yl]-4-[(2-chlorophenyl)sulfonyl]-piperazine
1-[4-phenyl-1,3-thiazol-2-yl]-4-[(2-cyanophenyl)sulfonyl]-piperazine
1-[4-(2-methylphenyl)-1,3-thiazol-2-yl]-4-[(2-cyanophenyl)sulfonyl]-piperazine
1-[4-(2-methoxyphenyl)-1,3-thiazol-2-yl]-4-[(2-cyanophenyl)sulfonyl]-piperazine
1-[4-(3-methylphenyl)-1,3-thiazol-2-yl]-4-[(2-cyanophenyl)sulfonyl]-piperazine 1-[4-(3-methoxyphenyl)-1,3-thiazol-2-yl]-4-[(2-cyanophenyl)sulfonyl]-piperazine
1-[4-(3-bromophenyl)-1,3-thiazol-2-yl]-4-[(2-cyanophenyl)sulfonyl]-piperazine
1-[4-(4-chlorophenyl)-1,3-thiazol-2-yl]-4-[(2-cyanophenyl)sulfonyl]-piperazine
1-[4-(4-methoxyphenyl)-1,3-thiazol-2-yl]-4-[(2-cyanophenyl)sulfonyl]-piperazine
1-[4-(4-methylphenyl)-1,3-thiazol-2-yl]-4-[(2-cyanophenyl)sulfonyl]-piperazine
1-[4-(4-ethylphenyl)-1,3-thiazol-2-yl]-4-[(2-cyanophenyl)sulfonyl]-piperazine
1-[4-(4-ethoxyphenyl)-1,3-thiazol-2-yl]-4-[(2-cyanophenyl)sulfonyl]-piperazine
1-[4-(4-propylphenyl)-1,3-thiazol-2-yl]-4-[(2-cyanophenyl)sulfonyl]-piperazine
1-[4-(2,6-dimethylphenyl)-1,3-thiazol-2-yl]-4-[(2-cyanophenyl)sulfonyl]-piperazine
1-[4-(2,3-dimethylphenyl)-1,3-thiazol-2-yl]-4-[(2-cyanophenyl)sulfonyl]-piperazine
1-[4-(2,5-dimethylphenyl)-1,3-thiazol-2-yl]-4-[(2-cyanophenyl)sulfonyl]-piperazine
1-[4-(2,4-dichlorophenyl)-1,3-thiazol-2-yl]-4-[(2-cyanophenyl)sulfonyl]-piperazine
1-[4-(2,4-dimethoxyphenyl)-1,3-thiazol-2-yl]-4-[(2-cyanophenyl)sulfonyl]-piperazine
1-[4-(2,5-dimethoxyphenyl)-1,3-thiazol-2-yl]-4-[(2-cyanophenyl)sulfonyl]-piperazine
1-[4-(3,4-dimethoxyphenyl)-1,3-thiazol-2-yl]-4-[(2-cyanophenyl)sulfonyl]-piperazine
1-[4-(3,5-dimethoxyphenyl)-1,3-thiazol-2-yl]-4-[(2-cyanophenyl)sulfonyl]-piperazine
1-[4-(3,4-dichlorophenyl)-1,3-thiazol-2-yl]-4-[(2-cyanophenyl)sulfonyl]-piperazine
1-[4-(3,4-dimethylphenyl)-1,3-thiazol-2-yl]-4-[(2-cyanophenyl)sulfonyl]-piperazine
1-[4-(3,4-difluorophenyl)-1,3-thiazol-2-yl]-4-[(2-cyanophenyl)sulfonyl]-piperazine
1-[4-(3,5-difluorophenyl)-1,3-thiazol-2-yl]-4-[(2-cyanophenyl)sulfonyl]-piperazine
1-[4-(3,5-dichlorophenyl)-1,3-thiazol-2-yl]-4-[(2-cyanophenyl)sulfonyl]-piperazine
1-[4-(3,5-dimethylphenyl)-1,3-thiazol-2-yl]-4-[(2-cyanophenyl)sulfonyl]-piperazine
1-[4-(3-chloro-4-fluorophenyl)-1,3-thiazol-2-yl]-4-[(2-cyanophenyl)sulfonyl]-piperazine
1-[4-(3-chloro-5-fluorophenyl)-1,3-thiazol-2-yl]-4-[(2-cyanophenyl)sulfonyl]-piperazine
1-[4-(4-chloro-3-fluorophenyl)-1,3-thiazol-2-yl]-4-[(2-cyanophenyl)sulfonyl]-piperazine
1-[4-(3,4,5-trimethoxyphenyl)-1,3-thiazol-2-yl]-4-[(2-cyanophenyl)sulfonyl]-piperazine
1-[4-(2,4,6-trimethylphenyl)-1,3-thiazol-2-yl]-4-[(2-cyanophenyl)sulfonyl]-piperazine
1-[4-phenyl-1,3-thiazol-2-yl]-4-[(3-nitrophenyl)sulfonyl]-piperazine
1-[4-(2-methylphenyl)-1,3-thiazol-2-yl]-4-[(3-nitrophenyl)sulfonyl]-piperazine
1-[4-(2-methoxyphenyl)-1,3-thiazol-2-yl]-4-[(3-nitrophenyl)sulfonyl]-piperazine
1-[4-(3-methylphenyl)-1,3-thiazol-2-yl]-4-[(3-nitrophenyl)sulfonyl]-piperazine
1-[4-(3-methoxyphenyl)-1,3-thiazol-2-yl]-4-[(3-nitrophenyl)sulfonyl]-piperazine
1-[4-(3-bromophenyl)-1,3-thiazol-2-yl]-4-[(3-nitrophenyl)sulfonyl]-piperazine
1-[4-(4-chlorophenyl)-1,3-thiazol-2-yl]-4-[(3-nitrophenyl)sulfonyl]-piperazine
1-[4-(4-methoxyphenyl)-1,3-thiazol-2-yl]-4-[(3-nitrophenyl)sulfonyl]-piperazine
1-[4-(4-methylphenyl)-1,3-thiazol-2-yl]-4-[(3-nitrophenyl)sulfonyl]-piperazine
1-[4-(4-ethylphenyl)-1,3-thiazol-2-yl]-4-[(3-nitrophenyl)sulfonyl]-piperazine
1-[4-(4-ethoxyphenyl)-1,3-thiazol-2-yl]-4-[(3-nitrophenyl)sulfonyl]-piperazine
1-[4-(4-propylphenyl)-1,3-thiazol-2-yl]-4-[(3-nitrophenyl)sulfonyl]-piperazine
1-[4-(2,6-dimethylphenyl)-1,3-thiazol-2-yl]-4-[(3-nitrophenyl)sulfonyl]-piperazine
1-[4-(2,3-dimethylphenyl)-1,3-thiazol-2-yl]-4-[(3-nitrophenyl)sulfonyl]-piperazine
1-[4-(2,5-dimethylphenyl)-1,3-thiazol-2-yl]-4-[(3-nitrophenyl)sulfonyl]-piperazine
1-[4-(2,4-dichlorophenyl)-1,3-thiazol-2-yl]-4-[(3-nitrophenyl)sulfonyl]-piperazine
1-[4-(2,4-dimethoxyphenyl)-1,3-thiazol-2-yl]-4-[(3-nitrophenyl)sulfonyl]-piperazine
1-[4-(2,5-dimethoxyphenyl)-1,3-thiazol-2-yl]-4-[(3-nitrophenyl)sulfonyl]-piperazine
1-[4-(3,4-dimethoxyphenyl)-1,3-thiazol-2-yl]-4-[(3-nitrophenyl)sulfonyl]-piperazine
1-[4-(3,5-dimethoxyphenyl)-1,3-thiazol-2-yl]-4-[(3-nitrophenyl)sulfonyl]-piperazine
1-[4-(3,4-dichlorophenyl)-1,3-thiazol-2-yl]-4-[(3-nitrophenyl)sulfonyl]-piperazine
1-[4-(3,4-dimethylphenyl)-1,3-thiazol-2-yl]-4-[(3-nitrophenyl)sulfonyl]-piperazine
1-[4-(3,4-difluorophenyl)-1,3-thiazol-2-yl]-4-[(3-nitrophenyl)sulfonyl]-piperazine
1-[4-(3,5-difluorophenyl)-1,3-thiazol-2-yl]-4-[(3-nitrophenyl)sulfonyl]-piperazine
1-[4-(3,5-dichlorophenyl)-1,3-thiazol-2-yl]-4-[(3-nitrophenyl)sulfonyl]-piperazine
1-[4-(3,5-dimethylphenyl)-1,3-thiazol-2-yl]-4-[(3-nitrophenyl)sulfonyl]-piperazine
1-[4-(3-chloro-4-fluorophenyl)-1,3-thiazol-2-yl]-4-[(3-nitrophenyl)sulfonyl]-piperazine
1-[4-(3-chloro-5-fluorophenyl)-1,3-thiazol-2-yl]-4-[(3-nitrophenyl)sulfonyl]-piperazine
1-[4-(4-chloro-3-fluorophenyl)-1,3-thiazol-2-yl]-4-[(3-nitrophenyl)sulfonyl]-piperazine
1-[4-(3,4,5-trimethoxyphenyl)-1,3-thiazol-2-yl]-4-[(3-nitrophenyl)sulfonyl]-piperazine
1-[4-(2,4,6-trimethylphenyl)-1,3-thiazol-2-yl]-4-[(3-nitrophenyl)sulfonyl]-piperazine
1-[4-phenyl-1,3-thiazol-2-yl]-4-[(3-chlorophenyl)sulfonyl]-piperazine
1-[4-(2-methylphenyl)-1,3-thiazol-2-yl]-4-[(3-chlorophenyl)sulfonyl]-piperazine
1-[4-(2-methoxyphenyl)-1,3-thiazol-2-yl]-4-[(3-chlorophenyl)sulfonyl]-piperazine
1-[4-(3-methylphenyl)-1,3-thiazol-2-yl]-4-[(3-chlorophenyl)sulfonyl]-piperazine
1-[4-(3-methoxyphenyl)-1,3-thiazol-2-yl]-4-[(3-chlorophenyl)sulfonyl]-piperazine
1-[4-(3-bromophenyl)-1,3-thiazol-2-yl]-4-[(3-chlorophenyl)sulfonyl]-piperazine
1-[4-(4-chlorophenyl)-1,3-thiazol-2-yl]-4-[(3-chlorophenyl)sulfonyl]-piperazine
1-[4-(4-methoxyphenyl)-1,3-thiazol-2-yl]-4-[(3-chlorophenyl)sulfonyl]-piperazine 1-[4-(4-methylphenyl)-1,3-thiazol-2-yl]-4-[(3-chlorophenyl)sulfonyl]-piperazine
1-[4-(4-ethylphenyl)-1,3-thiazol-2-yl]-4-[(3-chlorophenyl)sulfonyl]-piperazine
1-[4-(4-ethoxyphenyl)-1,3-thiazol-2-yl]-4-[(3-chlorophenyl)sulfonyl]-piperazine
1-[4-(4-propylphenyl)-1,3-thiazol-2-yl]-4-[(3-chlorophenyl)sulfonyl]-piperazine
1-[4-(2,6-dimethylphenyl)-1,3-thiazol-2-yl]-4-[(3-chlorophenyl)sulfonyl]-piperazine
1-[4-(2,3-dimethylphenyl)-1,3-thiazol-2-yl]-4-[(3-chlorophenyl)sulfonyl]-piperazine
1-[4-(2,5-dimethylphenyl)-1,3-thiazol-2-yl]-4-[(3-chlorophenyl)sulfonyl]-piperazine
1-[4-(2,4-dichlorophenyl)-1,3-thiazol-2-yl]-4-[(3-chlorophenyl)sulfonyl]-piperazine
1-[4-(2,4-dimethoxyphenyl)-1,3-thiazol-2-yl]-4-[(3-chlorophenyl)sulfonyl]-piperazine
1-[4-(2,5-dimethoxyphenyl)-1,3-thiazol-2-yl]-4-[(3-chlorophenyl)sulfonyl]-piperazine
1-[4-(3,4-dimethoxyphenyl)-1,3-thiazol-2-yl]-4-[(3-chlorophenyl)sulfonyl]-piperazine
1-[4-(3,5-dimethoxyphenyl)-1,3-thiazol-2-yl]-4-[(3-chlorophenyl)sulfonyl]-piperazine
1-[4-(3,4-dichlorophenyl)-1,3-thiazol-2-yl]-4-[(3-chlorophenyl)sulfonyl]-piperazine
1-[4-(3,4-dimethylphenyl)-1,3-thiazol-2-yl]-4-[(3-chlorophenyl)sulfonyl]-piperazine
1-[4-(3,4-difluorophenyl)-1,3-thiazol-2-yl]-4-[(3-chlorophenyl)sulfonyl]-piperazine
1-[4-(3,5-difluorophenyl)-1,3-thiazol-2-yl]-4-[(3-chlorophenyl)sulfonyl]-piperazine
1-[4-(3,5-dichlorophenyl)-1,3-thiazol-2-yl]-4-[(3-chlorophenyl)sulfonyl]-piperazine
1-[4-(3,5-dimethylphenyl)-1,3-thiazol-2-yl]-4-[(3-chlorophenyl)sulfonyl]-piperazine
1-[4-(3-chloro-4-fluorophenyl)-1,3-thiazol-2-yl]-4-[(3-chlorophenyl)sulfonyl]-piperazine
1-[4-(3-chloro-5-fluorophenyl)-1,3-thiazol-2-yl]-4-[(3-chlorophenyl)sulfonyl]-piperazine
1-[4-(4-chloro-3-fluorophenyl)-1,3-thiazol-2-yl]-4-[(3-chlorophenyl)sulfonyl]-piperazine
1-[4-(3,4,5-trimethoxyphenyl)-1,3-thiazol-2-yl]-4-[(3-chlorophenyl)sulfonyl]-piperazine
1-[4-(2,4,6-trimethylphenyl)-1,3-thiazol-2-yl]-4-[(3-chlorophenyl)sulfonyl]-piperazine
1-[4-phenyl-1,3-thiazol-2-yl]-4-[(3-bromophenyl)sulfonyl]-piperazine
1-[4-(2-methylphenyl)-1,3-thiazol-2-yl]-4-[(3-bromophenyl)sulfonyl]-piperazine
1-[4-(2-methoxyphenyl)-1,3-thiazol-2-yl]-4-[(3-bromophenyl)sulfonyl]-piperazine
1-[4-(3-methylphenyl)-1,3-thiazol-2-yl]-4-[(3-bromophenyl)sulfonyl]-piperazine
1-[4-(3-methoxyphenyl)-1,3-thiazol-2-yl]-4-[(3-bromophenyl)sulfonyl]-piperazine
1-[4-(3-bromophenyl)-1,3-thiazol-2-yl]-4-[(3-bromophenyl)sulfonyl]-piperazine
1-[4-(4-chlorophenyl)-1,3-thiazol-2-yl]-4-[(3-bromophenyl)sulfonyl]-piperazine
1-[4-(4-methoxyphenyl)-1,3-thiazol-2-yl]-4-[(3-bromophenyl)sulfonyl]-piperazine
1-[4-(4-methylphenyl)-1,3-thiazol-2-yl]-4-[(3-bromophenyl)sulfonyl]-piperazine
1-[4-(4-ethylphenyl)-1,3-thiazol-2-yl]-4-[(3-bromophenyl)sulfonyl]-piperazine
1-[4-(4-ethoxyphenyl)-1,3-thiazol-2-yl]-4-[(3-bromophenyl)sulfonyl]-piperazine
1-[4-(4-propylphenyl)-1,3-thiazol-2-yl]-4-[(3-bromophenyl)sulfonyl]-piperazine
1-[4-(2,6-dimethylphenyl)-1,3-thiazol-2-yl]-4-[(3-bromophenyl)sulfonyl]-piperazine
1-[4-(2,3-dimethylphenyl)-1,3-thiazol-2-yl]-4-[(3-bromophenyl)sulfonyl]-piperazine
1-[4-(2,5-dimethylphenyl)-1,3-thiazol-2-yl]-4-[(3-bromophenyl)sulfonyl]-piperazine
1-[4-(2,4-dichlorophenyl)-1,3-thiazol-2-yl]-4-[(3-bromophenyl)sulfonyl]-piperazine
1-[4-(2,4-dimethoxyphenyl)-1,3-thiazol-2-yl]-4-[(3-bromophenyl)sulfonyl]-piperazine
1-[4-(2,5-dimethoxyphenyl)-1,3-thiazol-2-yl]-4-[(3-bromophenyl)sulfonyl]-piperazine
1-[4-(3,4-dimethoxyphenyl)-1,3-thiazol-2-yl]-4-[(3-bromophenyl)sulfonyl]-piperazine
1-[4-(3,5-dimethoxyphenyl)-1,3-thiazol-2-yl]-4-[(3-bromophenyl)sulfonyl]-piperazine
1-[4-(3,4-dichlorophenyl)-1,3-thiazol-2-yl]-4-[(3-bromophenyl)sulfonyl]-piperazine
1-[4-(3,4-dimethylphenyl)-1,3-thiazol-2-yl]-4-[(3-bromophenyl)sulfonyl]-piperazine
1-[4-(3,4-difluorophenyl)-1,3-thiazol-2-yl]-4-[(3-bromophenyl)sulfonyl]-piperazine
1-[4-(3,5-difluorophenyl)-1,3-thiazol-2-yl]-4-[(3-bromophenyl)sulfonyl]-piperazine
1-[4-(3,5-dichlorophenyl)-1,3-thiazol-2-yl]-4-[(3-bromophenyl)sulfonyl]-piperazine
1-[4-(3,5-dimethylphenyl)-1,3-thiazol-2-yl]-4-[(3-bromophenyl)sulfonyl]-piperazine
1-[4-(3-chloro-4-fluorophenyl)-1,3-thiazol-2-yl]-4-[(3-bromophenyl)sulfonyl]-piperazine
1-[4-(3-chloro-5-fluorophenyl)-1,3-thiazol-2-yl]-4-[(3-bromophenyl)sulfonyl]-piperazine
1-[4-(4-chloro-3-fluorophenyl)-1,3-thiazol-2-yl]-4-[(3-bromophenyl)sulfonyl]-piperazine
1-[4-(3,4,5-trimethoxyphenyl)-1,3-thiazol-2-yl]-4-[(3-bromophenyl)sulfonyl]-piperazine
1-[4-(2,4,6-trimethylphenyl)-1,3-thiazol-2-yl]-4-[(3-bromophenyl)sulfonyl]-piperazine
1-[4-phenyl-1,3-thiazol-2-yl]-4-[(3-fluorophenyl)sulfonyl]-piperazine
1-[4-(2-methylphenyl)-1,3-thiazol-2-yl]-4-[(3-fluorophenyl)sulfonyl]-piperazine
1-[4-(2-methoxyphenyl)-1,3-thiazol-2-yl]-4-[(3-fluorophenyl)sulfonyl]-piperazine
1-[4-(3-methylphenyl)-1,3-thiazol-2-yl]-4-[(3-fluorophenyl)sulfonyl]-piperazine
1-[4-(3-methoxyphenyl)-1,3-thiazol-2-yl]-4-[(3-fluorophenyl)sulfonyl]-piperazine
1-[4-(3-bromophenyl)-1,3-thiazol-2-yl]-4-[(3-fluorophenyl)sulfonyl]-piperazine
1-[4-(4-chlorophenyl)-1,3-thiazol-2-yl]-4-[(3-fluorophenyl)sulfonyl]-piperazine
1-[4-(4-methoxyphenyl)-1,3-thiazol-2-yl]-4-[(3-fluorophenyl)sulfonyl]-piperazine
1-[4-(4-methylphenyl)-1,3-thiazol-2-yl]-4-[(3-fluorophenyl)sulfonyl]-piperazine
1-[4-(4-ethylphenyl)-1,3-thiazol-2-yl]-4-[(3-fluorophenyl)sulfonyl]-piperazine
1-[4-(4-ethoxyphenyl)-1,3-thiazol-2-yl]-4-[(3-fluorophenyl)sulfonyl]-piperazine
1-[4-(4-propylphenyl)-1,3-thiazol-2-yl]-4-[(3-fluorophenyl)sulfonyl]-piperazine 1-[4-(2,6-dimethylphenyl)-1,3-thiazol-2-yl]-4-[(3-fluorophenyl)sulfonyl]-piperazine
1-[4-(2,3-dimethylphenyl)-1,3-thiazol-2-yl]-4-[(3-fluorophenyl)sulfonyl]-piperazine
1-[4-(2,5-dimethylphenyl)-1,3-thiazol-2-yl]-4-[(3-fluorophenyl)sulfonyl]-piperazine
1-[4-(2,4-dichlorophenyl)-1,3-thiazol-2-yl]-4-[(3-fluorophenyl)sulfonyl]-piperazine
1-[4-(2,4-dimethoxyphenyl)-1,3-thiazol-2-yl]-4-[(3-fluorophenyl)sulfonyl]-piperazine
1-[4-(2,5-dimethoxyphenyl)-1,3-thiazol-2-yl]-4-[(3-fluorophenyl)sulfonyl]-piperazine
1-[4-(3,4-dimethoxyphenyl)-1,3-thiazol-2-yl]-4-[(3-fluorophenyl)sulfonyl]-piperazine
1-[4-(3,5-dimethoxyphenyl)-1,3-thiazol-2-yl]-4-[(3-fluorophenyl)sulfonyl]-piperazine
1-[4-(3,4-dichlorophenyl)-1,3-thiazol-2-yl]-4-[(3-fluorophenyl)sulfonyl]-piperazine
1-[4-(3,4-dimethylphenyl)-1,3-thiazol-2-yl]-4-[(3-fluorophenyl)sulfonyl]-piperazine
1-[4-(3,4-difluorophenyl)-1,3-thiazol-2-yl]-4-[(3-fluorophenyl)sulfonyl]-piperazine
1-[4-(3,5-difluorophenyl)-1,3-thiazol-2-yl]-4-[(3-fluorophenyl)sulfonyl]-piperazine
1-[4-(3,5-dichlorophenyl)-1,3-thiazol-2-yl]-4-[(3-fluorophenyl)sulfonyl]-piperazine
1-[4-(3,5-dimethylphenyl)-1,3-thiazol-2-yl]-4-[(3-fluorophenyl)sulfonyl]-piperazine
1-[4-(3-chloro-4-fluorophenyl)-1,3-thiazol-2-yl]-4-[(3-fluorophenyl)sulfonyl]-piperazine
1-[4-(3-chloro-5-fluorophenyl)-1,3-thiazol-2-yl]-4-[(3-fluorophenyl)sulfonyl]-piperazine
1-[4-(4-chloro-3-fluorophenyl)-1,3-thiazol-2-yl]-4-[(3-fluorophenyl)sulfonyl]-piperazine
1-[4-(3,4,5-trimethoxyphenyl)-1,3-thiazol-2-yl]-4-[(3-fluorophenyl)sulfonyl]-piperazine
1-[4-(2,4,6-trimethylphenyl)-1,3-thiazol-2-yl]-4-[(3-fluorophenyl)sulfonyl]-piperazine
1-[4-phenyl-1,3-thiazol-2-yl]-4-[(3-chloro-4-fluorophenyl)sulfonyl]-piperazine
1-[4-(2-methylphenyl)-1,3-thiazol-2-yl]-4-[(3-chloro-4-fluorophenyl)sulfonyl]-piperazine
1-[4-(2-methoxyphenyl)-1,3-thiazol-2-yl]-4-[(3-chloro-4-fluorophenyl)sulfonyl]-piperazine
1-[4-(3-methylphenyl)-1,3-thiazol-2-yl]-4-[(3-chloro-4-fluorophenyl)sulfonyl]-piperazine
1-[4-(3-methoxyphenyl)-1,3-thiazol-2-yl]-4-[(3-chloro-4-fluorophenyl)sulfonyl]-piperazine
1-[4-(3-bromophenyl)-1,3-thiazol-2-yl]-4-[(3-chloro-4-fluorophenyl)sulfonyl]-piperazine
1-[4-(4-chlorophenyl)-1,3-thiazol-2-yl]-4-[(3-chloro-4-fluorophenyl)sulfonyl]-piperazine
1-[4-(4-methoxyphenyl)-1,3-thiazol-2-yl]-4-[(3-chloro-4-fluorophenyl)sulfonyl]-piperazine
1-[4-(4-methylphenyl)-1,3-thiazol-2-yl]-4-[(3-chloro-4-fluorophenyl)sulfonyl]-piperazine
1-[4-(4-ethylphenyl)-1,3-thiazol-2-yl]-4-[(3-chloro-4-fluorophenyl)sulfonyl]-piperazine
1-[4-(4-ethoxyphenyl)-1,3-thiazol-2-yl]-4-[(3-chloro-4-fluorophenyl)sulfonyl]-piperazine
1-[4-(4-propylphenyl)-1,3-thiazol-2-yl]-4-[(3-chloro-4-fluorophenyl)sulfonyl]-piperazine
1-[4-(2,6-dimethylphenyl)-1,3-thiazol-2-yl]-4-[(3-chloro-4-fluorophenyl)sulfonyl]-piperazine
1-[4-(2,3-dimethylphenyl)-1,3-thiazol-2-yl]-4-[(3-chloro-4-fluorophenyl)sulfonyl]-piperazine
1-[4-(2,5-dimethylphenyl)-1,3-thiazol-2-yl]-4-[(3-chloro-4-fluorophenyl)sulfonyl]-piperazine
1-[4-(2,4-dichlorophenyl)-1,3-thiazol-2-yl]-4-[(3-chloro-4-fluorophenyl)sulfonyl]-piperazine
1-[4-(2,4-dimethoxyphenyl)-1,3-thiazol-2-yl]-4-[(3-chloro-4-fluorophenyl)sulfonyl]-piperazine
1-[4-(2,5-dimethoxyphenyl)-1,3-thiazol-2-yl]-4-[(3-chloro-4-fluorophenyl)sulfonyl]-piperazine
1-[4-(3,4-dimethoxyphenyl)-1,3-thiazol-2-yl]-4-[(3-chloro-4-fluorophenyl)sulfonyl]-piperazine
1-[4-(3,5-dimethoxyphenyl)-1,3-thiazol-2-yl]-4-[(3-chloro-4-fluorophenyl)sulfonyl]-piperazine
1-[4-(3,4-dichlorophenyl)-1,3-thiazol-2-yl]-4-[(3-chloro-4-fluorophenyl)sulfonyl]-piperazine
1-[4-(3,4-dimethylphenyl)-1,3-thiazol-2-yl]-4-[(3-chloro-4-fluorophenyl)sulfonyl]-piperazine
1-[4-(3,4-difluorophenyl)-1,3-thiazol-2-yl]-4-[(3-chloro-4-fluorophenyl)sulfonyl]-piperazine
1-[4-(3,5-difluorophenyl)-1,3-thiazol-2-yl]-4-[(3-chloro-4-fluorophenyl)sulfonyl]-piperazine
1-[4-(3,5-dichlorophenyl)-1,3-thiazol-2-yl]-4-[(3-chloro-4-fluorophenyl)sulfonyl]-piperazine
1-[4-(3,5-dimethylphenyl)-1,3-thiazol-2-yl]-4-[(3-chloro-4-fluorophenyl)sulfonyl]-piperazine
1-[4-(3-chloro-4-fluorophenyl)-1,3-thiazol-2-yl]-4-[(3-chloro-4-fluorophenyl)sulfonyl]-piperazine
1-[4-(3-chloro-5-fluorophenyl)-1,3-thiazol-2-yl]-4-[(3-chloro-4-fluorophenyl)sulfonyl]-piperazine
1-[4-(4-chloro-3-fluorophenyl)-1,3-thiazol-2-yl]-4-[(3-chloro-4-fluorophenyl)sulfonyl]-piperazine
1-[4-(3,4,5-trimethoxyphenyl)-1,3-thiazol-2-yl]-4-[(3-chloro-4-fluorophenyl)sulfonyl]-piperazine
1-[4-(2,4,6-trimethylphenyl)-1,3-thiazol-2-yl]-4-[(3-chloro-4-fluorophenyl)sulfonyl]-piperazine
1-[4-phenyl-1,3-thiazol-2-yl]-4-[(2-chloro-4-fluorophenyl)sulfonyl]-piperazine
1-[4-(2-methylphenyl)-1,3-thiazol-2-yl]-4-[(2-chloro-4-fluorophenyl)sulfonyl]-piperazine
1-[4-(2-methoxyphenyl)-1,3-thiazol-2-yl]-4-[(2-chloro-4-fluorophenyl)sulfonyl]-piperazine
1-[4-(3-methylphenyl)-1,3-thiazol-2-yl]-4-[(2-chloro-4-fluorophenyl)sulfonyl]-piperazine
1-[4-(3-methoxyphenyl)-1,3-thiazol-2-yl]-4-[(2-chloro-4-fluorophenyl)sulfonyl]-piperazine
1-[4-(3-bromophenyl)-1,3-thiazol-2-yl]-4-[(2-chloro-4-fluorophenyl)sulfonyl]-piperazine
1-[4-(4-chlorophenyl)-1,3-thiazol-2-yl]-4-[(2-chloro-4-fluorophenyl)sulfonyl]-piperazin
1-[4-(4-methoxyphenyl)-1,3-thiazol-2-yl]-4-[(2-chloro-4-fluorophenyl)sulfonyl]-piperazine
1-[4-(4-methylphenyl)-1,3-thiazol-2-yl]-4-[(2-chloro-4-fluorophenyl)sulfonyl]-piperazine
1-[4-(4-ethylphenyl)-1,3-thiazol-2-yl]-4-[(2-chloro-4-fluorophenyl)sulfonyl]-piperazine
1-[4-(4-ethoxyphenyl)-1,3-thiazol-2-yl]-4-[(2-chloro-4-fluorophenyl)sulfonyl]-piperazine
1-[4-(4-propylphenyl)-1,3-thiazol-2-yl]-4-[(2-chloro-4-fluorophenyl)sulfonyl]-piperazine
1-[4-(2,6-dimethylphenyl)-1,3-thiazol-2-yl]-4-[(2-chloro-4-fluorophenyl)sulfonyl]-piperazine
1-[4-(2,3-dimethylphenyl)-1,3-thiazol-2-yl]-4-[(2-chloro-4-fluorophenyl)sulfonyl]-piperazine
1-[4-(2,5-dimethylphenyl)-1,3-thiazol-2-yl]-4-[(2-chloro-4-fluorophenyl)sulfonyl]-piperazine
1-[4-(2,4-dichlorophenyl)-1,3-thiazol-2-yl]-4-[(2-chloro-4-fluorophenyl)sulfonyl]-piperazine 1-[4-(2,4-dimethoxyphenyl)-1,3-thiazol-2-yl]-4-[(2-chloro-4-fluorophenyl)sulfonyl]-piperazine
1-[4-(2,5-dimethoxyphenyl)-1,3-thiazol-2-yl]-4-[(2-chloro-4-fluorophenyl)sulfonyl]-piperazine
1-[4-(3,4-dimethoxyphenyl)-1,3-thiazol-2-yl]-4-[(2-chloro-4-fluorophenyl)sulfonyl]-piperazine
1-[4-(3,5-dimethoxyphenyl)-1,3-thiazol-2-yl]-4-[(2-chloro-4-fluorophenyl)sulfonyl]-piperazine
1-[4-(3,4-dichlorophenyl)-1,3-thiazol-2-yl]-4-[(2-chloro-4-fluorophenyl)sulfonyl]-piperazine
1-[4-(3,4-dimethylphenyl)-1,3-thiazol-2-yl]-4-[(2-chloro-4-fluorophenyl)sulfonyl]-piperazine
1-[4-(3,4-difluorophenyl)-1,3-thiazol-2-yl]-4-[(2-chloro-4-fluorophenyl)sulfonyl]-piperazine
1-[4-(3,5-difluorophenyl)-1,3-thiazol-2-yl]-4-[(2-chloro-4-fluorophenyl)sulfonyl]-piperazine
1-[4-(3,5-dichlorophenyl)-1,3-thiazol-2-yl]-4-[(2-chloro-4-fluorophenyl)sulfonyl]-piperazine
1-[4-(3,5-dimethylphenyl)-1,3-thiazol-2-yl]-4-[(2-chloro-4-fluorophenyl)sulfonyl]-piperazine
1-[4-(3-chloro-4-fluorophenyl)-1,3-thiazol-2-yl]-4-[(2-chloro-4-fluorophenyl)sulfonyl]-piperazine
1-[4-(3-chloro-5-fluorophenyl)-1,3-thiazol-2-yl]-4-[(2-chloro-4-fluorophenyl)sulfonyl]-piperazine
1-[4-(4-chloro-3-fluorophenyl)-1,3-thiazol-2-yl]-4-[(2-chloro-4-fluorophenyl)sulfonyl]-piperazine
1-[4-(3,4,5-trimethoxyphenyl)-1,3-thiazol-2-yl]-4-[(2-chloro-4-fluorophenyl)sulfonyl]-piperazine
1-[4-(2,4,6-trimethylphenyl)-1,3-thiazol-2-yl]-4-[(2-chloro-4-fluorophenyl)sulfonyl]-piperazine
1-[4-phenyl-1,3-thiazol-2-yl]-4-[(2-chloro-2-methylphenyl)sulfonyl]-piperazine
1-[4-(2-methylphenyl)-1,3-thiazol-2-yl]-4-[(2-chloro-2-methylphenyl)sulfonyl]-piperazine
1-[4-(2-methoxyphenyl)-1,3-thiazol-2-yl]-4-[(2-chloro-2-methylphenyl)sulfonyl]-piperazine
1-[4-(3-methylphenyl)-1,3-thiazol-2-yl]-4-[(2-chloro-2-methylphenyl)sulfonyl]-piperazine
1-[4-(3-methoxyphenyl)-1,3-thiazol-2-yl]-4-[(2-chloro-2-methylphenyl)sulfonyl]-piperazine
1-[4-(3-bromophenyl)-1,3-thiazol-2-yl]-4-[(2-chloro-2-methylphenyl)sulfonyl]-piperazine
1-[4-(4-chlorophenyl)-1,3-thiazol-2-yl]-4-[(2-chloro-2-methylphenyl)sulfonyl]-piperazine
1-[4-(4-methoxyphenyl)-1,3-thiazol-2-yl]-4-[(2-chloro-2-methylphenyl)sulfonyl]-piperazine
1-[4-(4-methylphenyl)-1,3-thiazol-2-yl]-4-[(2-chloro-2-methylphenyl)sulfonyl]-piperazine
1-[4-(4-ethylphenyl)-1,3-thiazol-2-yl]-4-[(2-chloro-2-methylphenyl)sulfonyl]-piperazine
1-[4-(4-ethoxyphenyl)-1,3-thiazol-2-yl]-4-[(2-chloro-2-methylphenyl)sulfonyl]-piperazine
1-[4-(4-propylphenyl)-1,3-thiazol-2-yl]-4-[(2-chloro-2-methylphenyl)sulfonyl]-piperazine
1-[4-(2,6-dimethylphenyl)-1,3-thiazol-2-yl]-4-[(2-chloro-2-methylphenyl)sulfonyl]-piperazine
1-[4-(2,3-dimethylphenyl)-1,3-thiazol-2-yl]-4-[(2-chloro-2-methylphenyl)sulfonyl]-piperazine
1-[4-(2,5-dimethylphenyl)-1,3-thiazol-2-yl]-4-[(2-chloro-2-methylphenyl)sulfonyl]-piperazine
1-[4-(2,4-dichlorophenyl)-1,3-thiazol-2-yl]-4-[(2-chloro-2-methylphenyl)sulfonyl]-piperazine
1-[4-(2,4-dimethoxyphenyl)-1,3-thiazol-2-yl]-4-[(2-chloro-2-methylphenyl)sulfonyl]-piperazine
1-[4-(2,5-dimethoxyphenyl)-1,3-thiazol-2-yl]-4-[(2-chloro-2-methylphenyl)sulfonyl]-piperazine
1-[4-(3,4-dimethoxyphenyl)-1,3-thiazol-2-yl]-4-[(2-chloro-2-methylphenyl)sulfonyl]-piperazine
1-[4-(3,5-dimethoxyphenyl)-1,3-thiazol-2-yl]-4-[(2-chloro-2-methylphenyl)sulfonyl]-piperazine
1-[4-(3,4-dichlorophenyl)-1,3-thiazol-2-yl]-4-[(2-chloro-2-methylphenyl)sulfonyl]-piperazine
1-[4-(3,4-dimethylphenyl)-1,3-thiazol-2-yl]-4-[(2-chloro-2-methylphenyl)sulfonyl]-piperazine
1-[4-(3,4-difluorophenyl)-1,3-thiazol-2-yl]-4-[(2-chloro-2-methylphenyl)sulfonyl]-piperazine
1-[4-(3,5-difluorophenyl)-1,3-thiazol-2-yl]-4-[(2-chloro-2-methylphenyl)sulfonyl]-piperazine
1-[4-(3,5-dichlorophenyl)-1,3-thiazol-2-yl]-4-[(2-chloro-2-methylphenyl)sulfonyl]-piperazine
1-[4-(3,5-dimethylphenyl)-1,3-thiazol-2-yl]-4-[(2-chloro-2-methylphenyl)sulfonyl]-piperazine
1-[4-(3-chloro-4-fluorophenyl)-1,3-thiazol-2-yl]-4-[(2-chloro-2-methylphenyl)sulfonyl]-piperazine
1-[4-(3-chloro-5-fluorophenyl)-1,3-thiazol-2-yl]-4-[(2-chloro-2-methylphenyl)sulfonyl]-piperazine
1-[4-(4-chloro-3-fluorophenyl)-1,3-thiazol-2-yl]-4-[(2-chloro-2-methylphenyl)sulfonyl]-piperazine
1-[4-(3,4,5-trimethoxyphenyl)-1,3-thiazol-2-yl]-4-[(2-chloro-2-methylphenyl)sulfonyl]-piperazine
1-[4-(2,4,6-trimethylphenyl)-1,3-thiazol-2-yl]-4-[(2-chloro-2-methylphenyl)sulfonyl]-piperazine
1-[4-phenyl-1,3-thiazol-2-yl]-4-[(5-fluoro-2-methylphenyl)sulfonyl]-piperazine
1-[4-(2-methylphenyl)-1,3-thiazol-2-yl]-4-[(5-fluoro-2-methylphenyl)sulfonyl]-piperazine
1-[4-(2-methoxyphenyl)-1,3-thiazol-2-yl]-4-[(5-fluoro-2-methylphenyl)sulfonyl]-piperazine
1-[4-(3-methylphenyl)-1,3-thiazol-2-yl]-4-[(5-fluoro-2-methylphenyl)sulfonyl]-piperazine
1-[4-(3-methoxyphenyl)-1,3-thiazol-2-yl]-4-[(5-fluoro-2-methylphenyl)sulfonyl]-piperazine
1-[4-(3-bromophenyl)-1,3-thiazol-2-yl]-4-[(5-fluoro-2-methylphenyl)sulfonyl]-piperazine
1-[4-(4-chlorophenyl)-1,3-thiazol-2-yl]-4-[(5-fluoro-2-methylphenyl)sulfonyl]-piperazin
1-[4-(4-methoxyphenyl)-1,3-thiazol-2-yl]-4-[(5-fluoro-2-methylphenyl)sulfonyl]-piperazine
1-[4-(4-methylphenyl)-1,3-thiazol-2-yl]-4-[(5-fluoro-2-methylphenyl)sulfonyl]-piperazine
1-[4-(4-ethylphenyl)-1,3-thiazol-2-yl]-4-[(5-fluoro-2-methylphenyl)sulfonyl]-piperazine
1-[4-(4-ethoxyphenyl)-1,3-thiazol-2-yl]-4-[(5-fluoro-2-methylphenyl)sulfonyl]-piperazine
1-[4-(4-propylphenyl)-1,3-thiazol-2-yl]-4-[(5-fluoro-2-methylphenyl)sulfonyl]-piperazine
1-[4-(2,6-dimethylphenyl)-1,3-thiazol-2-yl]-4-[(5-fluoro-2-methylphenyl)sulfonyl]-piperazine
1-[4-(2,3-dimethylphenyl)-1,3-thiazol-2-yl]-4-[(5-fluoro-2-methylphenyl)sulfonyl]-piperazine
1-[4-(2,5-dimethylphenyl)-1,3-thiazol-2-yl]-4-[(5-fluoro-2-methylphenyl)sulfonyl]-piperazine
1-[4-(2,4-dichlorophenyl)-1,3-thiazol-2-yl]-4-[(5-fluoro-2-methylphenyl)sulfonyl]-piperazine
1-[4-(2,4-dimethoxyphenyl)-1,3-thiazol-2-yl]-4-[(5-fluoro-2-methylphenyl)sulfonyl]-piperazine
1-[4-(2,5-dimethoxyphenyl)-1,3-thiazol-2-yl]-4-[(5-fluoro-2-methylphenyl)sulfonyl]-piperazine
1-[4-(3,4-dimethoxyphenyl)-1,3-thiazol-2-yl]-4-[(5-fluoro-2-methylphenyl)sulfonyl]-piperazine
1-[4-(3,5-dimethoxyphenyl)-1,3-thiazol-2-yl]-4-[(5-fluoro-2-methylphenyl)sulfonyl]-piperazine 1-[4-(3,4-dichlorophenyl)-1,3-thiazol-2-yl]-4-[(5-fluoro-2-methylphenyl)sulfonyl]-piperazine
1-[4-(3,4-dimethylphenyl)-1,3-thiazol-2-yl]-4-[(5-fluoro-2-methylphenyl)sulfonyl]-piperazine
1-[4-(3,4-difluorophenyl)-1,3-thiazol-2-yl]-4-[(5-fluoro-2-methylphenyl)sulfonyl]-piperazine
1-[4-(3,5-difluorophenyl)-1,3-thiazol-2-yl]-4-[(5-fluoro-2-methylphenyl)sulfonyl]-piperazine
1-[4-(3,5-dichlorophenyl)-1,3-thiazol-2-yl]-4-[(5-fluoro-2-methylphenyl)sulfonyl]-piperazine
1-[4-(3,5-dimethylphenyl)-1,3-thiazol-2-yl]-4-[(5-fluoro-2-methylphenyl)sulfonyl]-piperazine
1-[4-(3-chloro-4-fluorophenyl)-1,3-thiazol-2-yl]-4-[(5-fluoro-2-methylphenyl)sulfonyl]-piperazine
1-[4-(3-chloro-5-fluorophenyl)-1,3-thiazol-2-yl]-4-[(5-fluoro-2-methylphenyl)sulfonyl]-piperazine
1-[4-(4-chloro-3-fluorophenyl)-1,3-thiazol-2-yl]-4-[(5-fluoro-2-methylphenyl)sulfonyl]-piperazine
1-[4-(3,4,5-trimethoxyphenyl)-1,3-thiazol-2-yl]-4-[(5-fluoro-2-methylphenyl)sulfonyl]-piperazine
1-[4-(2,4,6-trimethylphenyl)-1,3-thiazol-2-yl]-4-[(5-fluoro-2-methylphenyl)sulfonyl]-piperazine
1-[4-phenyl-1,3-thiazol-2-yl]-4-[(2,3,5,6-tetramethylphenyl)sulfonyl]-piperazine
1-[4-(2-methylphenyl)-1,3-thiazol-2-yl]-4-[(2,3,5,6-tetramethylphenyl)sulfonyl]-piperazine
1-[4-(2-methoxyphenyl)-1,3-thiazol-2-yl]-4-[(2,3,5,6-tetramethylphenyl)sulfonyl]-piperazine
1-[4-(3-methylphenyl)-1,3-thiazol-2-yl]-4-[(2,3,5,6-tetramethylphenyl)sulfonyl]-piperazine
1-[4-(3-methoxyphenyl)-1,3-thiazol-2-yl]-4-[(2,3,5,6-tetramethylphenyl)sulfonyl]-piperazine
1-[4-(3-bromophenyl)-1,3-thiazol-2-yl]-4-[(2,3,5,6-tetramethylphenyl)sulfonyl]-piperazine
1-[4-(4-chlorophenyl)-1,3-thiazol-2-yl]-4-[(2,3,5,6-tetramethylphenyl)sulfonyl]-piperazine
1-[4-(4-methoxyphenyl)-1,3-thiazol-2-yl]-4-[(2,3,5,6-tetramethylphenyl)sulfonyl]-piperazine
1-[4-(4-methylphenyl)-1,3-thiazol-2-yl]-4-[(2,3,5,6-tetramethylphenyl)sulfonyl]-piperazine
1-[4-(4-ethylphenyl)-1,3-thiazol-2-yl]-4-[(2,3,5,6-tetramethylphenyl)sulfonyl]-piperazine
1-[4-(4-ethoxyphenyl)-1,3-thiazol-2-yl]-4-[(2,3,5,6-tetramethylphenyl)sulfonyl]-piperazine
1-[4-(4-propylphenyl)-1,3-thiazol-2-yl]-4-[(2,3,5,6-tetramethylphenyl)sulfonyl]-piperazine
1-[4-(2,6-dimethylphenyl)-1,3-thiazol-2-yl]-4-[(2,3,5,6-tetramethylphenyl)sulfonyl]-piperazine
1-[4-(2,3-dimethylphenyl)-1,3-thiazol-2-yl]-4-[(2,3,5,6-tetramethylphenyl)sulfonyl]-piperazine
1-[4-(2,5-dimethylphenyl)-1,3-thiazol-2-yl]-4-[(2,3,5,6-tetramethylphenyl)sulfonyl]-piperazine
1-[4-(2,4-dichlorophenyl)-1,3-thiazol-2-yl]-4-[(2,3,5,6-tetramethylphenyl)sulfonyl]-piperazine
1-[4-(2,4-dimethoxyphenyl)-1,3-thiazol-2-yl]-4-[(2,3,5,6-tetramethylphenyl)sulfonyl]-piperazine
1-[4-(2,5-dimethoxyphenyl)-1,3-thiazol-2-yl]-4-[(2,3,5,6-tetramethylphenyl)sulfonyl]-piperazine
1-[4-(3,4-dimethoxyphenyl)-1,3-thiazol-2-yl]-4-[(2,3,5,6-tetramethylphenyl)sulfonyl]-piperazine
1-[4-(3,5-dimethoxyphenyl)-1,3-thiazol-2-yl]-4-[(2,3,5,6-tetramethylphenyl)sulfonyl]-piperazine
1-[4-(3,4-dichlorophenyl)-1,3-thiazol-2-yl]-4-[(2,3,5,6-tetramethylphenyl)sulfonyl]-piperazine
1-[4-(3,4-dimethylphenyl)-1,3-thiazol-2-yl]-4-[(2,3,5,6-tetramethylphenyl)sulfonyl]-piperazine
1-[4-(3,4-difluorophenyl)-1,3-thiazol-2-yl]-4-[(2,3,5,6-tetramethylphenyl)sulfonyl]-piperazine
1-[4-(3,5-difluorophenyl)-1,3-thiazol-2-yl]-4-[(2,3,5,6-tetramethylphenyl)sulfonyl]-piperazine
1-[4-(3,5-dichlorophenyl)-1,3-thiazol-2-yl]-4-[(2,3,5,6-tetramethylphenyl)sulfonyl]-piperazine
1-[4-(3,5-dimethylphenyl)-1,3-thiazol-2-yl]-4-[(2,3,5,6-tetramethylphenyl)sulfonyl]-piperazine
1-[4-(3-chloro-4-fluorophenyl)-1,3-thiazol-2-yl]-4-[(2,3,5,6-tetramethylphenyl)sulfonyl]-piperazine
1-[4-(3-chloro-5-fluorophenyl)-1,3-thiazol-2-yl]-4-[(2,3,5,6-tetramethylphenyl)sulfonyl]-piperazine
1-[4-(4-chloro-3-fluorophenyl)-1,3-thiazol-2-yl]-4-[(2,3,5,6-tetramethylphenyl)sulfonyl]-piperazine
1-[4-(3,4,5-trimethoxyphenyl)-1,3-thiazol-2-yl]-4-[(2,3,5,6-tetramethylphenyl)sulfonyl]-piperazine
1-[4-(2,4,6-trimethylphenyl)-1,3-thiazol-2-yl]-4-[(2,3,5,6-tetramethylphenyl)sulfonyl]-piperazine
1-[4-phenyl-1,3-thiazol-2-yl]-4-[(2,5-dibromo-3,6-difluorophenyl)sulfonyl]-piperazine
1-[4-(2-methylphenyl)-1,3-thiazol-2-yl]-4-[(2,5-dibromo-3,6-difluorophenyl)sulfonyl]-piperazine
1-[4-(2-methoxyphenyl)-1,3-thiazol-2-yl]-4-[(2,5-dibromo-3,6-difluorophenyl)sulfonyl]-piperazine
1-[4-(3-methylphenyl)-1,3-thiazol-2-yl]-4-[(2,5-dibromo-3,6-difluorophenyl)sulfonyl]-piperazine
1-[4-(3-methoxyphenyl)-1,3-thiazol-2-yl]-4-[(2,5-dibromo-3,6-difluorophenyl)sulfonyl]-piperazine
1-[4-(3-bromophenyl)-1,3-thiazol-2-yl]-4-[(2,5-dibromo-3,6-difluorophenyl)sulfonyl]-piperazine
1-[4-(4-chlorophenyl)-1,3-thiazol-2-yl]-4-[(2,5-dibromo-3,6-difluorophenyl)sulfonyl]-piperazine
1-[4-(4-methoxyphenyl)-1,3-thiazol-2-yl]-4-[(2,5-dibromo-3,6-difluorophenyl)sulfonyl]-piperazine
1-[4-(4-methylphenyl)-1,3-thiazol-2-yl]-4-[(2,5-dibromo-3,6-difluorophenyl)sulfonyl]-piperazine
1-[4-(4-ethylphenyl)-1,3-thiazol-2-yl]-4-[(2,5-dibromo-3,6-difluorophenyl)sulfonyl]-piperazine
1-[4-(4-ethoxyphenyl)-1,3-thiazol-2-yl]-4-[(2,5-dibromo-3,6-difluorophenyl)sulfonyl]-piperazine
1-[4-(4-propylphenyl)-1,3-thiazol-2-yl]-4-[(2,5-dibromo-3,6-difluorophenyl)sulfonyl]-piperazine
1-[4-(2,6-dimethylphenyl)-1,3-thiazol-2-yl]-4-[(2,5-dibromo-3,6-difluorophenyl)sulfonyl]-piperazine
1-[4-(2,3-dimethylphenyl)-1,3-thiazol-2-yl]-4-[(2,5-dibromo-3,6-difluorophenyl)sulfonyl]-piperazine
1-[4-(2,5-dimethylphenyl)-1,3-thiazol-2-yl]-4-[(2,5-dibromo-3,6-difluorophenyl)sulfonyl]-piperazine
1-[4-(2,4-dichlorophenyl)-1,3-thiazol-2-yl]-4-[(2,5-dibromo-3,6-difluorophenyl)sulfonyl]-piperazine
1-[4-(2,4-dimethoxyphenyl)-1,3-thiazol-2-yl]-4-[(2,5-dibromo-3,6-difluorophenyl)sulfonyl]-piperazine
1-[4-(2,5-dimethoxyphenyl)-1,3-thiazol-2-yl]-4-[(2,5-dibromo-3,6-difluorophenyl)sulfonyl]-piperazine
1-[4-(3,4-dimethoxyphenyl)-1,3-thiazol-2-yl]-4-[(2,5-dibromo-3,6-difluorophenyl)sulfonyl]-piperazine
1-[4-(3,5-dimethoxyphenyl)-1,3-thiazol-2-yl]-4-[(2,5-dibromo-3,6-difluorophenyl)sulfonyl]-piperazine
1-[4-(3,4-dichlorophenyl)-1,3-thiazol-2-yl]-4-[(2,5-dibromo-3,6-difluorophenyl)sulfonyl]-piperazine
1-[4-(3,4-dimethylphenyl)-1,3-thiazol-2-yl]-4-[(2,5-dibromo-3,6-difluorophenyl)sulfonyl]-piperazine
1-[4-(3,4-difluorophenyl)-1,3-thiazol-2-yl]-4-[(2,5-dibromo-3,6-difluorophenyl)sulfonyl]-piperazine
1-[4-(3,5-difluorophenyl)-1,3-thiazol-2-yl]-4-[(2,5-dibromo-3,6-difluorophenyl)sulfonyl]-piperazine 1-[4-(3,5-dichlorophenyl)-1,3-thiazol-2-yl]-4-[(2,5-dibromo-3,6-difluorophenyl)sulfonyl]-piperazine
1-[4-(3,5-dimethylphenyl)-1,3-thiazol-2-yl]-4-[(2,5-dibromo-3,6-difluorophenyl)sulfonyl]-piperazine
1-[4-(3-chloro-4-fluorophenyl)-1,3-thiazol-2-yl]-4-[(2,5-dibromo-3,6-difluorophenyl)sulfonyl]-piperazine
1-[4-(3-chloro-5-fluorophenyl)-1,3-thiazol-2-yl]-4-[(2,5-dibromo-3,6-difluorophenyl)sulfonyl]-piperazine
1-[4-(4-chloro-3-fluorophenyl)-1,3-thiazol-2-yl]-4-[(2,5-dibromo-3,6-difluorophenyl)sulfonyl]-piperazine
1-[4-(3,4,5-trimethoxyphenyl)-1,3-thiazol-2-yl]-4-[(2,5-dibromo-3,6-difluorophenyl)sulfonyl]-piperazine
1-[4-(2,4,6-trimethylphenyl)-1,3-thiazol-2-yl]-4-[(2,5-dibromo-3,6-difluorophenyl)sulfonyl]-piperazine
1-[4-phenyl-1,3-thiazol-2-yl]-4-[(5-bromo-2-methoxyphenyl)sulfonyl]-piperazine
1-[4-(2-methylphenyl)-1,3-thiazol-2-yl]-4-[(5-bromo-2-methoxyphenyl)sulfonyl]-piperazine
1-[4-(2-methoxyphenyl)-1,3-thiazol-2-yl]-4-[(5-bromo-2-methoxyphenyl)sulfonyl]-piperazine
1-[4-(3-methylphenyl)-1,3-thiazol-2-yl]-4-[(5-bromo-2-methoxyphenyl)sulfonyl]-piperazine
1-[4-(3-methoxyphenyl)-1,3-thiazol-2-yl]-4-[(5-bromo-2-methoxyphenyl)sulfonyl]-piperazine
1-[4-(3-bromophenyl)-1,3-thiazol-2-yl]-4-[(5-bromo-2-methoxyphenyl)sulfonyl]-piperazine
1-[4-(4-chlorophenyl)-1,3-thiazol-2-yl]-4-[(5-bromo-2-methoxyphenyl)sulfonyl]-piperazine
1-[4-(4-methoxyphenyl)-1,3-thiazol-2-yl]-4-[(5-bromo-2-methoxyphenyl)sulfonyl]-piperazine
1-[4-(4-methylphenyl)-1,3-thiazol-2-yl]-4-[(5-bromo-2-methoxyphenyl)sulfonyl]-piperazine
1-[4-(4-ethylphenyl)-1,3-thiazol-2-yl]-4-[(5-bromo-2-methoxyphenyl)sulfonyl]-piperazine
1-[4-(4-ethoxyphenyl)-1,3-thiazol-2-yl]-4-[(5-bromo-2-methoxyphenyl)sulfonyl]-piperazine
1-[4-(4-propylphenyl)-1,3-thiazol-2-yl]-4-[(5-bromo-2-methoxyphenyl)sulfonyl]-piperazine
1-[4-(2,6-dimethylphenyl)-1,3-thiazol-2-yl]-4-[(5-bromo-2-methoxyphenyl)sulfonyl]-piperazine
1-[4-(2,3-dimethylphenyl)-1,3-thiazol-2-yl]-4-[(5-bromo-2-methoxyphenyl)sulfonyl]-piperazine
1-[4-(2,5-dimethylphenyl)-1,3-thiazol-2-yl]-4-[(5-bromo-2-methoxyphenyl)sulfonyl]-piperazine
1-[4-(2,4-dichlorophenyl)-1,3-thiazol-2-yl]-4-[(5-bromo-2-methoxyphenyl)sulfonyl]-piperazine
1-[4-(2,4-dimethoxyphenyl)-1,3-thiazol-2-yl]-4-[(5-bromo-2-methoxyphenyl)sulfonyl]-piperazine
1-[4-(2,5-dimethoxyphenyl)-1,3-thiazol-2-yl]-4-[(5-bromo-2-methoxyphenyl)sulfonyl]-piperazine
1-[4-(3,4-dimethoxyphenyl)-1,3-thiazol-2-yl]-4-[(5-bromo-2-methoxyphenyl)sulfonyl]-piperazine
1-[4-(3,5-dimethoxyphenyl)-1,3-thiazol-2-yl]-4-[(5-bromo-2-methoxyphenyl)sulfonyl]-piperazine
1-[4-(3,4-dichlorophenyl)-1,3-thiazol-2-yl]-4-[(5-bromo-2-methoxyphenyl)sulfonyl]-piperazine
1-[4-(3,4-dimethylphenyl)-1,3-thiazol-2-yl]-4-[(5-bromo-2-methoxyphenyl)sulfonyl]-piperazine
1-[4-(3,4-difluorophenyl)-1,3-thiazol-2-yl]-4-[(5-bromo-2-methoxyphenyl)sulfonyl]-piperazine
1-[4-(3,5-difluorophenyl)-1,3-thiazol-2-yl]-4-[(5-bromo-2-methoxyphenyl)sulfonyl]-piperazine
1-[4-(3,5-dichlorophenyl)-1,3-thiazol-2-yl]-4-[(5-bromo-2-methoxyphenyl)sulfonyl]-piperazine
1-[4-(3,5-dimethylphenyl)-1,3-thiazol-2-yl]-4-[(5-bromo-2-methoxyphenyl)sulfonyl]-piperazine
1-[4-(3-chloro-4-fluorophenyl)-1,3-thiazol-2-yl]-4-[(5-bromo-2-methoxyphenyl)sulfonyl]-piperazine
1-[4-(3-chloro-5-fluorophenyl)-1,3-thiazol-2-yl]-4-[(5-bromo-2-methoxyphenyl)sulfonyl]-piperazine
1-[4-(4-chloro-3-fluorophenyl)-1,3-thiazol-2-yl]-4-[(5-bromo-2-methoxyphenyl)sulfonyl]-piperazine
1-[4-(3,4,5-trimethoxyphenyl)-1,3-thiazol-2-yl]-4-[(5-bromo-2-methoxyphenyl)sulfonyl]-piperazine
1-[4-(2,4,6-trimethylphenyl)-1,3-thiazol-2-yl]-4-[(5-bromo-2-methoxyphenyl)sulfonyl]-piperazine
1-[4-phenyl-1,3-thiazol-2-yl]-4-[(4-bromo-2-chlorophenyl)sulfonyl]-piperazine
1-[4-(2-methylphenyl)-1,3-thiazol-2-yl]-4-[(4-bromo-2-chlorophenyl)sulfonyl]-piperazine
1-[4-(2-methoxyphenyl)-1,3-thiazol-2-yl]-4-[(4-bromo-2-chlorophenyl)sulfonyl]-piperazine
1-[4-(3-methylphenyl)-1,3-thiazol-2-yl]-4-[(4-bromo-2-chlorophenyl)sulfonyl]-piperazine
1-[4-(3-methoxyphenyl)-1,3-thiazol-2-yl]-4-[(4-bromo-2-chlorophenyl)sulfonyl]-piperazine
1-[4-(3-bromophenyl)-1,3-thiazol-2-yl]-4-[(4-bromo-2-chlorophenyl)sulfonyl]-piperazine
1-[4-(4-chlorophenyl)-1,3-thiazol-2-yl]-4-[(4-bromo-2-chlorophenyl)sulfonyl]-piperazine
1-[4-(4-methoxyphenyl)-1,3-thiazol-2-yl]-4-[(4-bromo-2-chlorophenyl)sulfonyl]-piperazine
1-[4-(4-methylphenyl)-1,3-thiazol-2-yl]-4-[(4-bromo-2-chlorophenyl)sulfonyl]-piperazine
1-[4-(4-ethylphenyl)-1,3-thiazol-2-yl]-4-[(4-bromo-2-chlorophenyl)sulfonyl]-piperazine
1-[4-(4-ethoxyphenyl)-1,3-thiazol-2-yl]-4-[(4-bromo-2-chlorophenyl)sulfonyl]-piperazine
1-[4-(4-propylphenyl)-1,3-thiazol-2-yl]-4-[(4-bromo-2-chlorophenyl)sulfonyl]-piperazine
1-[4-(2,6-dimethylphenyl)-1,3-thiazol-2-yl]-4-[(4-bromo-2-chlorophenyl)sulfonyl]-piperazine
1-[4-(2,3-dimethylphenyl)-1,3-thiazol-2-yl]-4-[(4-bromo-2-chlorophenyl)sulfonyl]-piperazine
1-[4-(2,5-dimethylphenyl)-1,3-thiazol-2-yl]-4-[(4-bromo-2-chlorophenyl)sulfonyl]-piperazine
1-[4-(2,4-dichlorophenyl)-1,3-thiazol-2-yl]-4-[(4-bromo-2-chlorophenyl)sulfonyl]-piperazine
1-[4-(2,4-dimethoxyphenyl)-1,3-thiazol-2-yl]-4-[(4-bromo-2-chlorophenyl)sulfonyl]-piperazine
1-[4-(2,5-dimethoxyphenyl)-1,3-thiazol-2-yl]-4-[(4-bromo-2-chlorophenyl)sulfonyl]-piperazine
1-[4-(3,4-dimethoxyphenyl)-1,3-thiazol-2-yl]-4-[(4-bromo-2-chlorophenyl)sulfonyl]-piperazine
1-[4-(3,5-dimethoxyphenyl)-1,3-thiazol-2-yl]-4-[(4-bromo-2-chlorophenyl)sulfonyl]-piperazine
1-[4-(3,4-dichlorophenyl)-1,3-thiazol-2-yl]-4-[(4-bromo-2-chlorophenyl)sulfonyl]-piperazine
1-[4-(3,4-dimethylphenyl)-1,3-thiazol-2-yl]-4-[(4-bromo-2-chlorophenyl)sulfonyl]-piperazine
1-[4-(3,4-difluorophenyl)-1,3-thiazol-2-yl]-4-[(4-bromo-2-chlorophenyl)sulfonyl]-piperazine
1-[4-(3,5-difluorophenyl)-1,3-thiazol-2-yl]-4-[(4-bromo-2-chlorophenyl)sulfonyl]-piperazine
1-[4-(3,5-dichlorophenyl)-1,3-thiazol-2-yl]-4-[(4-bromo-2-chlorophenyl)sulfonyl]-piperazine
1-[4-(3,5-dimethylphenyl)-1,3-thiazol-2-yl]-4-[(4-bromo-2-chlorophenyl)sulfonyl]-piperazine
1-[4-(3-chloro-4-fluorophenyl)-1,3-thiazol-2-yl]-4-[(4-bromo-2-chlorophenyl)sulfonyl]-piperazine
1-[4-(3-chloro-5-fluorophenyl)-1,3-thiazol-2-yl]-4-[(4-bromo-2-chlorophenyl)sulfonyl]-piperazine 1-[4-(4-chloro-3-fluorophenyl)-1,3-thiazol-2-yl]-4-[(4-bromo-2-chlorophenyl)sulfonyl]-piperazine
1-[4-(3,4,5-trimethoxyphenyl)-1,3-thiazol-2-yl]-4-[(4-bromo-2-chlorophenyl)sulfonyl]-piperazine
1-[4-(2,4,6-trimethylphenyl)-1,3-thiazol-2-yl]-4-[(4-bromo-2-chlorophenyl)sulfonyl]-piperazine
1-[4-phenyl-1,3-thiazol-2-yl]-4-[(5-chloro-2-methoxyphenyl)sulfonyl]-piperazine
1-[4-(2-methylphenyl)-1,3-thiazol-2-yl]-4-[(5-chloro-2-methoxyphenyl)sulfonyl]-piperazine
1-[4-(2-methoxyphenyl)-1,3-thiazol-2-yl]-4-[(5-chloro-2-methoxyphenyl)sulfonyl]-piperazine
1-[4-(3-methylphenyl)-1,3-thiazol-2-yl]-4-[(5-chloro-2-methoxyphenyl)sulfonyl]-piperazine
1-[4-(3-methoxyphenyl)-1,3-thiazol-2-yl]-4-[(5-chloro-2-methoxyphenyl)sulfonyl]-piperazine
1-[4-(3-bromophenyl)-1,3-thiazol-2-yl]-4-[(5-chloro-2-methoxyphenyl)sulfonyl]-piperazine
1-[4-(4-chlorophenyl)-1,3-thiazol-2-yl]-4-[(5-chloro-2-methoxyphenyl)sulfonyl]-piperazine
1-[4-(4-methoxyphenyl)-1,3-thiazol-2-yl]-4-[(5-chloro-2-methoxyphenyl)sulfonyl]-piperazine
1-[4-(4-methylphenyl)-1,3-thiazol-2-yl]-4-[(5-chloro-2-methoxyphenyl)sulfonyl]-piperazine
1-[4-(4-ethylphenyl)-1,3-thiazol-2-yl]-4-[(5-chloro-2-methoxyphenyl)sulfonyl]-piperazine
1-[4-(4-ethoxyphenyl)-1,3-thiazol-2-yl]-4-[(5-chloro-2-methoxyphenyl)sulfonyl]-piperazine
1-[4-(4-propylphenyl)-1,3-thiazol-2-yl]-4-[(5-chloro-2-methoxyphenyl)sulfonyl]-piperazine
1-[4-(2,6-dimethylphenyl)-1,3-thiazol-2-yl]-4-[(5-chloro-2-methoxyphenyl)sulfonyl]-piperazine
1-[4-(2,3-dimethylphenyl)-1,3-thiazol-2-yl]-4-[(5-chloro-2-methoxyphenyl)sulfonyl]-piperazine
1-[4-(2,5-dimethylphenyl)-1,3-thiazol-2-yl]-4-[(5-chloro-2-methoxyphenyl)sulfonyl]-piperazine
1-[4-(2,4-dichlorophenyl)-1,3-thiazol-2-yl]-4-[(5-chloro-2-methoxyphenyl)sulfonyl]-piperazine
1-[4-(2,4-dimethoxyphenyl)-1,3-thiazol-2-yl]-4-[(5-chloro-2-methoxyphenyl)sulfonyl]-piperazine
1-[4-(2,5-dimethoxyphenyl)-1,3-thiazol-2-yl]-4-[(5-chloro-2-methoxyphenyl)sulfonyl]-piperazine
1-[4-(3,4-dimethoxyphenyl)-1,3-thiazol-2-yl]-4-[(5-chloro-2-methoxyphenyl)sulfonyl]-piperazine
1-[4-(3,5-dimethoxyphenyl)-1,3-thiazol-2-yl]-4-[(5-chloro-2-methoxyphenyl)sulfonyl]-piperazine
1-[4-(3,4-dichlorophenyl)-1,3-thiazol-2-yl]-4-[(5-chloro-2-methoxyphenyl)sulfonyl]-piperazine
1-[4-(3,4-dimethylphenyl)-1,3-thiazol-2-yl]-4-[(5-chloro-2-methoxyphenyl)sulfonyl]-piperazine
1-[4-(3,4-difluorophenyl)-1,3-thiazol-2-yl]-4-[(5-chloro-2-methoxyphenyl)sulfonyl]-piperazine
1-[4-(3,5-difluorophenyl)-1,3-thiazol-2-yl]-4-[(5-chloro-2-methoxyphenyl)sulfonyl]-piperazine
1-[4-(3,5-dichlorophenyl)-1,3-thiazol-2-yl]-4-[(5-chloro-2-methoxyphenyl)sulfonyl]-piperazine
1-[4-(3,5-dimethylphenyl)-1,3-thiazol-2-yl]-4-[(5-chloro-2-methoxyphenyl)sulfonyl]-piperazine
1-[4-(3-chloro-4-fluorophenyl)-1,3-thiazol-2-yl]-4-[(5-chloro-2-methoxyphenyl)sulfonyl]-piperazine
1-[4-(3-chloro-5-fluorophenyl)-1,3-thiazol-2-yl]-4-[(5-chloro-2-methoxyphenyl)sulfonyl]-piperazine
1-[4-(4-chloro-3-fluorophenyl)-1,3-thiazol-2-yl]-4-[(5-chloro-2-methoxyphenyl)sulfonyl]-piperazine
1-[4-(3,4,5-trimethoxyphenyl)-1,3-thiazol-2-yl]-4-[(5-chloro-2-methoxyphenyl)sulfonyl]-piperazine
1-[4-(2,4,6-trimethylphenyl)-1,3-thiazol-2-yl]-4-[(5-chloro-2-methoxyphenyl)sulfonyl]-piperazine
1-[4-phenyl-1,3-thiazol-2-yl]-4-[(2-chloro-5-(trifluoromethyl)phenyl)sulfonyl]-piperazine
1-[4-(2-methylphenyl)-1,3-thiazol-2-yl]-4-[(2-chloro-5-(trifluoromethyl)phenyl)sulfonyl]-piperazine
1-[4-(2-methoxyphenyl)-1,3-thiazol-2-yl]-4-[(2-chloro-5-(trifluoromethyl)phenyl)sulfonyl]-piperazine
1-[4-(3-methylphenyl)-1,3-thiazol-2-yl]-4-[(2-chloro-5-(trifluoromethyl)phenyl)sulfonyl]-piperazine
1-[4-(3-methoxyphenyl)-1,3-thiazol-2-yl]-4-[(2-chloro-5-(trifluoromethyl)phenyl)sulfonyl]-piperazine
1-[4-(3-bromophenyl)-1,3-thiazol-2-yl]-4-[(2-chloro-5-(trifluoromethyl)phenyl)sulfonyl]-piperazine
1-[4-(4-chlorophenyl)-1,3-thiazol-2-yl]-4-[(2-chloro-5-(trifluoromethyl)phenyl)sulfonyl]-piperazine
1-[4-(4-methoxyphenyl)-1,3-thiazol-2-yl]-4-[(2-chloro-5-(trifluoromethyl)phenyl)sulfonyl]-piperazine
1-[4-(4-methylphenyl)-1,3-thiazol-2-yl]-4-[(2-chloro-5-(trifluoromethyl)phenyl)sulfonyl]-piperazine
1-[4-(4-ethylphenyl)-1,3-thiazol-2-yl]-4-[(2-chloro-5-(trifluoromethyl)phenyl)sulfonyl]-piperazine
1-[4-(4-ethoxyphenyl)-1,3-thiazol-2-yl]-4-[(2-chloro-5-(trifluoromethyl)phenyl)sulfonyl]-piperazine
1-[4-(4-propylphenyl)-1,3-thiazol-2-yl]-4-[(2-chloro-5-(trifluoromethyl)phenyl)sulfonyl]-piperazine
1-[4-(2,6-dimethylphenyl)-1,3-thiazol-2-yl]-4-[(2-chloro-5-(trifluoromethyl)phenyl)sulfonyl]-piperazine
1-[4-(2,3-dimethylphenyl)-1,3-thiazol-2-yl]-4-[(2-chloro-5-(trifluoromethyl)phenyl)sulfonyl]-piperazine
1-[4-(2,5-dimethylphenyl)-1,3-thiazol-2-yl]-4-[(2-chloro-5-(trifluoromethyl)phenyl)sulfonyl]-piperazine
1-[4-(2,4-dichlorophenyl)-1,3-thiazol-2-yl]-4-[(2-chloro-5-(trifluoromethyl)phenyl)sulfonyl]-piperazine
1-[4-(2,4-dimethoxyphenyl)-1,3-thiazol-2-yl]-4-[(2-chloro-5-(trifluoromethyl)phenyl)sulfonyl]-piperazine
1-[4-(2,5-dimethoxyphenyl)-1,3-thiazol-2-yl]-4-[(2-chloro-5-(trifluoromethyl)phenyl)sulfonyl]-piperazine
1-[4-(3,4-dimethoxyphenyl)-1,3-thiazol-2-yl]-4-[(2-chloro-5-(trifluoromethyl)phenyl)sulfonyl]-piperazine
1-[4-(3,5-dimethoxyphenyl)-1,3-thiazol-2-yl]-4-[(2-chloro-5-(trifluoromethyl)phenyl)sulfonyl]-piperazine
1-[4-(3,4-dichlorophenyl)-1,3-thiazol-2-yl]-4-[(2-chloro-5-(trifluoromethyl)phenyl)sulfonyl]-piperazine
1-[4-(3,4-dimethylphenyl)-1,3-thiazol-2-yl]-4-[(2-chloro-5-(trifluoromethyl)phenyl)sulfonyl]-piperazine
1-[4-(3,4-difluorophenyl)-1,3-thiazol-2-yl]-4-[(2-chloro-5-(trifluoromethyl)phenyl)sulfonyl]-piperazine
1-[4-(3,5-difluorophenyl)-1,3-thiazol-2-yl]-4-[(2-chloro-5-(trifluoromethyl)phenyl)sulfonyl]-piperazine
1-[4-(3,5-dichlorophenyl)-1,3-thiazol-2-yl]-4-[(2-chloro-5-(trifluoromethyl)phenyl)sulfonyl]-piperazine
1-[4-(3,5-dimethylphenyl)-1,3-thiazol-2-yl]-4-[(2-chloro-5-(trifluoromethyl)phenyl)sulfonyl]-piperazine
1-[4-(3-chloro-4-fluorophenyl)-1,3-thiazol-2-yl]-4-[(2-chloro-5-(trifluoromethyl)phenyl)sulfonyl]-piperazine
1-[4-(3-chloro-5-fluorophenyl)-1,3-thiazol-2-yl]-4-[(2-chloro-5-(trifluoromethyl)phenyl)sulfonyl]-piperazine
1-[4-(4-chloro-3-fluorophenyl)-1,3-thiazol-2-yl]-4-[(2-chloro-5-(trifluoromethyl)phenyl)sulfonyl]-piperazine
1-[4-(3,4,5-trimethoxyphenyl)-1,3-thiazol-2-yl]-4-[(2-chloro-5-(trifluoromethyl)phenyl)sulfonyl]-piperazine
1-[4-(2,4,6-trimethylphenyl)-1,3-thiazol-2-yl]-4-[(2-chloro-5-(trifluoromethyl)phenyl)sulfonyl]-piperazine
1-[4-phenyl-1,3-thiazol-2-yl]-4-[(4-chloro-3-nitrophenyl)sulfonyl]-piperazine 1-[4-(2-methylphenyl)-1,3-thiazol-2-yl]-4-[(4-chloro-3-nitrophenyl)sulfonyl]-piperazine
1-[4-(2-methoxyphenyl)-1,3-thiazol-2-yl]-4-[(4-chloro-3-nitrophenyl)sulfonyl]-piperazine
1-[4-(3-methylphenyl)-1,3-thiazol-2-yl]-4-[(4-chloro-3-nitrophenyl)sulfonyl]-piperazine
1-[4-(3-methoxyphenyl)-1,3-thiazol-2-yl]-4-[(4-chloro-3-nitrophenyl)sulfonyl]-piperazine
1-[4-(3-bromophenyl)-1,3-thiazol-2-yl]-4-[(4-chloro-3-nitrophenyl)sulfonyl]-piperazine
1-[4-(4-chlorophenyl)-1,3-thiazol-2-yl]-4-[(4-chloro-3-nitrophenyl)sulfonyl]-piperazine
1-[4-(4-methoxyphenyl)-1,3-thiazol-2-yl]-4-[(4-chloro-3-nitrophenyl)sulfonyl]-piperazine
1-[4-(4-methylphenyl)-1,3-thiazol-2-yl]-4-[(4-chloro-3-nitrophenyl)sulfonyl]-piperazine
1-[4-(4-ethylphenyl)-1,3-thiazol-2-yl]-4-[(4-chloro-3-nitrophenyl)sulfonyl]-piperazine
1-[4-(4-ethoxyphenyl)-1,3-thiazol-2-yl]-4-[(4-chloro-3-nitrophenyl)sulfonyl]-piperazine
1-[4-(4-propylphenyl)-1,3-thiazol-2-yl]-4-[(4-chloro-3-nitrophenyl)sulfonyl]-piperazine
1-[4-(2,6-dimethylphenyl)-1,3-thiazol-2-yl]-4-[(4-chloro-3-nitrophenyl)sulfonyl]-piperazine
1-[4-(2,3-dimethylphenyl)-1,3-thiazol-2-yl]-4-[(4-chloro-3-nitrophenyl)sulfonyl]-piperazine
1-[4-(2,5-dimethylphenyl)-1,3-thiazol-2-yl]-4-[(4-chloro-3-nitrophenyl)sulfonyl]-piperazine
1-[4-(2,4-dichlorophenyl)-1,3-thiazol-2-yl]-4-[(4-chloro-3-nitrophenyl)sulfonyl]-piperazine
1-[4-(2,4-dimethoxyphenyl)-1,3-thiazol-2-yl]-4-[(4-chloro-3-nitrophenyl)sulfonyl]-piperazine
1-[4-(2,5-dimethoxyphenyl)-1,3-thiazol-2-yl]-4-[(4-chloro-3-nitrophenyl)sulfonyl]-piperazine
1-[4-(3,4-dimethoxyphenyl)-1,3-thiazol-2-yl]-4-[(4-chloro-3-nitrophenyl)sulfonyl]-piperazine
1-[4-(3,5-dimethoxyphenyl)-1,3-thiazol-2-yl]-4-[(4-chloro-3-nitrophenyl)sulfonyl]-piperazine
1-[4-(3,4-dichlorophenyl)-1,3-thiazol-2-yl]-4-[(4-chloro-3-nitrophenyl)sulfonyl]-piperazine
1-[4-(3,4-dimethylphenyl)-1,3-thiazol-2-yl]-4-[(4-chloro-3-nitrophenyl)sulfonyl]-piperazine
1-[4-(3,4-difluorophenyl)-1,3-thiazol-2-yl]-4-[(4-chloro-3-nitrophenyl)sulfonyl]-piperazine
1-[4-(3,5-difluorophenyl)-1,3-thiazol-2-yl]-4-[(4-chloro-3-nitrophenyl)sulfonyl]-piperazine
1-[4-(3,5-dichlorophenyl)-1,3-thiazol-2-yl]-4-[(4-chloro-3-nitrophenyl)sulfonyl]-piperazine
1-[4-(3,5-dimethylphenyl)-1,3-thiazol-2-yl]-4-[(4-chloro-3-nitrophenyl)sulfonyl]-piperazine
1-[4-(3-chloro-4-fluorophenyl)-1,3-thiazol-2-yl]-4-[(4-chloro-3-nitrophenyl)sulfonyl]-piperazine
1-[4-(3-chloro-5-fluorophenyl)-1,3-thiazol-2-yl]-4-[(4-chloro-3-nitrophenyl)sulfonyl]-piperazine
1-[4-(4-chloro-3-fluorophenyl)-1,3-thiazol-2-yl]-4-[(4-chloro-3-nitrophenyl)sulfonyl]-piperazine
1-[4-(3,4,5-trimethoxyphenyl)-1,3-thiazol-2-yl]-4-[(4-chloro-3-nitrophenyl)sulfonyl]-piperazine
1-[4-(2,4,6-trimethylphenyl)-1,3-thiazol-2-yl]-4-[(4-chloro-3-nitrophenyl)sulfonyl]-piperazine
1-[4-phenyl-1,3-thiazol-2-yl]-4-[(2,4-dichloro-5-methylphenyl)sulfonyl]-piperazine
1-[4-(2-methylphenyl)-1,3-thiazol-2-yl]-4-[(2,4-dichloro-5-methylphenyl)sulfonyl]-piperazine
1-[4-(2-methoxyphenyl)-1,3-thiazol-2-yl]-4-[(2,4-dichloro-5-methylphenyl)sulfonyl]-piperazine
1-[4-(3-methylphenyl)-1,3-thiazol-2-yl]-4-[(2,4-dichloro-5-methylphenyl)sulfonyl]-piperazine
1-[4-(3-methoxyphenyl)-1,3-thiazol-2-yl]-4-[(2,4-dichloro-5-methylphenyl)sulfonyl]-piperazine
1-[4-(3-bromophenyl)-1,3-thiazol-2-yl]-4-[(2,4-dichloro-5-methylphenyl)sulfonyl]-piperazine
1-[4-(4-chlorophenyl)-1,3-thiazol-2-yl]-4-[(2,4-dichloro-5-methylphenyl)sulfonyl]-piperazine
1-[4-(4-methoxyphenyl)-1,3-thiazol-2-yl]-4-[(2,4-dichloro-5-methylphenyl)sulfonyl]-piperazine
1-[4-(4-methylphenyl)-1,3-thiazol-2-yl]-4-[(2,4-dichloro-5-methylphenyl)sulfonyl]-piperazine
1-[4-(4-ethylphenyl)-1,3-thiazol-2-yl]-4-[(2,4-dichloro-5-methylphenyl)sulfonyl]-piperazine
1-[4-(4-ethoxyphenyl)-1,3-thiazol-2-yl]-4-[(2,4-dichloro-5-methylphenyl)sulfonyl]-piperazine
1-[4-(4-propylphenyl)-1,3-thiazol-2-yl]-4-[(2,4-dichloro-5-methylphenyl)sulfonyl]-piperazine
1-[4-(2,6-dimethylphenyl)-1,3-thiazol-2-yl]-4-[(2,4-dichloro-5-methylphenyl)sulfonyl]-piperazine
1-[4-(2,3-dimethylphenyl)-1,3-thiazol-2-yl]-4-[(2,4-dichloro-5-methylphenyl)sulfonyl]-piperazine
1-[4-(2,5-dimethylphenyl)-1,3-thiazol-2-yl]-4-[(2,4-dichloro-5-methylphenyl)sulfonyl]-piperazine
1-[4-(2,4-dichlorophenyl)-1,3-thiazol-2-yl]-4-[(2,4-dichloro-5-methylphenyl)sulfonyl]-piperazine
1-[4-(2,4-dimethoxyphenyl)-1,3-thiazol-2-yl]-4-[(2,4-dichloro-5-methylphenyl)sulfonyl]-piperazine
1-[4-(2,5-dimethoxyphenyl)-1,3-thiazol-2-yl]-4-[(2,4-dichloro-5-methylphenyl)sulfonyl]-piperazine
1-[4-(3,4-dimethoxyphenyl)-1,3-thiazol-2-yl]-4-[(2,4-dichloro-5-methylphenyl)sulfonyl]-piperazine
1-[4-(3,5-dimethoxyphenyl)-1,3-thiazol-2-yl]-4-[(2,4-dichloro-5-methylphenyl)sulfonyl]-piperazine
1-[4-(3,4-dichlorophenyl)-1,3-thiazol-2-yl]-4-[(2,4-dichloro-5-methylphenyl)sulfonyl]-piperazine
1-[4-(3,4-dimethylphenyl)-1,3-thiazol-2-yl]-4-[(2,4-dichloro-5-methylphenyl)sulfonyl]-piperazine
1-[4-(3,4-difluorophenyl)-1,3-thiazol-2-yl]-4-[(2,4-dichloro-5-methylphenyl)sulfonyl]-piperazine
1-[4-(3,5-difluorophenyl)-1,3-thiazol-2-yl]-4-[(2,4-dichloro-5-methylphenyl)sulfonyl]-piperazine
1-[4-(3,5-dichlorophenyl)-1,3-thiazol-2-yl]-4-[(2,4-dichloro-5-methylphenyl)sulfonyl]-piperazine
1-[4-(3,5-dimethylphenyl)-1,3-thiazol-2-yl]-4-[(2,4-dichloro-5-methylphenyl)sulfonyl]-piperazine
1-[4-(3-chloro-4-fluorophenyl)-1,3-thiazol-2-yl]-4-[(2,4-dichloro-5-methylphenyl)sulfonyl]-piperazine
1-[4-(3-chloro-5-fluorophenyl)-1,3-thiazol-2-yl]-4-[(2,4-dichloro-5-methylphenyl)sulfonyl]-piperazine
1-[4-(4-chloro-3-fluorophenyl)-1,3-thiazol-2-yl]-4-[(2,4-dichloro-5-methylphenyl)sulfonyl]-piperazine
1-[4-(3,4,5-trimethoxyphenyl)-1,3-thiazol-2-yl]-4-[(2,4-dichloro-5-methylphenyl)sulfonyl]-piperazine
1-[4-(2,4,6-trimethylphenyl)-1,3-thiazol-2-yl]-4-[(2,4-dichloro-5-methylphenyl)sulfonyl]-piperazine
1-[4-(pyridin-2-yl)-1,3-thiazol-2-yl]-4-[(4-bromophenyl)sulfonyl]-piperazine
1-[4-(thien-3-yl)-1,3-thiazol-2-yl]-4-[(4-bromophenyl)sulfonyl]-piperazine
1-[4-(pyridin-2-yl)-1,3-thiazol-2-yl]-4-[(5-chloro-4-nitrothiophen-2-yl)sulfonyl]-piperazine
1-[4-(thien-3-yl)-1,3-thiazol-2-yl]-4-[(5-chloro-4-nitrothiophen-2-yl)sulfonyl]-piperazine
1-[4-(2,4,6-trimethylphenyl)-1,3-thiazol-2-yl]-4-[(5-chloro-4-nitrothiophen-2-yl)sulfonyl]-piperazine 1-[4-(pyridin-2-yl)-1,3-thiazol-2-yl]-4-[(6-bromopyridin-3-yl)sulfonyl]-piperazine
1-[4-(thien-3-yl)-1,3-thiazol-2-yl]-4-[(6-bromopyridin-3-yl)sulfonyl]-piperazine
1-[4-(2,4,6-trimethylphenyl)-1,3-thiazol-2-yl]-4-[(6-bromopyridin-3-yl)sulfonyl]-piperazine
1-[4-(pyridin-2-yl)-1,3-thiazol-2-yl]-4-[(5-methyl-1H-imidazol-2-yl)sulfonyl]-piperazine
1-[4-(thien-3-yl)-1,3-thiazol-2-yl]-4-[(5-methyl-1H-imidazol-2-yl)sulfonyl]-piperazine
1-[4-(2,4,6-trimethylphenyl)-1,3-thiazol-2-yl]-4-[(5-methyl-1H-imidazol-2-yl)sulfonyl]-piperazine
1-[4-(pyridin-2-yl)-1,3-thiazol-2-yl]-4-[(2,4-dimethylpyrimidin-5-yl)sulfonyl]-piperazine
1-[4-(thien-3-yl)-1,3-thiazol-2-yl]-4-[(2,4-dimethylpyrimidin-5-yl)sulfonyl]-piperazine, and
1-[4-(2,4,6-trimethylphenyl)-1,3-thiazol-2-yl]-4-[(2,4-dimethylpyrimidin-5-yl)sulfonyl]-piperazine.

Example 11

Preparation of Derivatives of the Invention wherein W is methylene, Bis-methylene or Ethylidene 1-[4-(4-methylbenzyl-1,3-thiazol-2-yl]-4-[(4-propylphenyl)sulfonyl]-piperazine is prepared using the synthetic scheme shown in FIG. 2 (wherein W is methylene), starting from 4-methylbenzylmagnesium chloride, piperazine and 4-propylbenzene-1-sulfonyl chloride.

Using the same procedure, the following compounds are prepared:
1-[4-benzyl-1,3-thiazol-2-yl]-4-[(4-fluorophenyl)sulfonyl]-piperazine
1-[4-(2-methylbenzyl)-1,3-thiazol-2-yl]-4-[(4-fluorophenyl)sulfonyl]-piperazine
1-[4-(2-methoxybenzyl)-1,3-thiazol-2-yl]-4-[(4-fluorophenyl)sulfonyl]-piperazine
1-[4-(3-methylbenzyl)-1,3-thiazol-2-yl]-4-[(4-fluorophenyl)sulfonyl]-piperazine
1-[4-(3-methoxybenzyl)-1,3-thiazol-2-yl]-4-[(4-fluorophenyl)sulfonyl]-piperazine
1-[4-(3-bromobenzyl)-1,3-thiazol-2-yl]-4-[(4-fluorophenyl)sulfonyl]-piperazine
1-[4-(4-chlorobenzyl)-1,3-thiazol-2-yl]-4-[(4-fluorophenyl)sulfonyl]-piperazine
1-[4-(4-methoxybenzyl)-1,3-thiazol-2-yl]-4-[(4-fluorophenyl)sulfonyl]-piperazine
1-[4-(4-methylbenzyl)-1,3-thiazol-2-yl]-4-[(4-fluorophenyl)sulfonyl]-piperazine
1-[4-(4-ethylbenzyl)-1,3-thiazol-2-yl]-4-[(4-fluorophenyl)sulfonyl]-piperazine
1-[4-(4-ethoxybenzyl)-1,3-thiazol-2-yl]-4-[(4-fluorophenyl)sulfonyl]-piperazine
1-[4-(4-propylbenzyl)-1,3-thiazol-2-yl]-4-[(4-fluorophenyl)sulfonyl]-piperazine
1-[4-(2,6-dimethylbenzyl)-1,3-thiazol-2-yl]-4-[(4-fluorophenyl)sulfonyl]-piperazine
1-[4-(2,3-dimethylbenzyl)-1,3-thiazol-2-yl]-4-[(4-fluorophenyl)sulfonyl]-piperazine
1-[4-(2,5-dimethylbenzyl)-1,3-thiazol-2-yl]-4-[(4-fluorophenyl)sulfonyl]-piperazine
1-[4-(2,4-dichlorobenzyl)-1,3-thiazol-2-yl]-4-[(4-fluorophenyl)sulfonyl]-piperazine
1-[4-(2,4-dimethoxybenzyl)-1,3-thiazol-2-yl]-4-[(4-fluorophenyl)sulfonyl]-piperazine
1-[4-(2,5-dimethoxybenzyl)-1,3-thiazol-2-yl]-4-[(4-fluorophenyl)sulfonyl]-piperazine
1-[4-(3,4-dimethoxybenzyl)-1,3-thiazol-2-yl]-4-[(4-fluorophenyl)sulfonyl]-piperazine
1-[4-(3,5-dimethoxybenzyl)-1,3-thiazol-2-yl]-4-[(4-fluorophenyl)sulfonyl]-piperazine
1-[4-(3,4-dichlorobenzyl)-1,3-thiazol-2-yl]-4-[(4-fluorophenyl)sulfonyl]-piperazine
1-[4-(3,4-dimethylbenzyl)-1,3-thiazol-2-yl]-4-[(4-fluorophenyl)sulfonyl]-piperazine
1-[4-(3,4-difluorobenzyl)-1,3-thiazol-2-yl]-4-[(4-fluorophenyl)sulfonyl]-piperazine
1-[4-(3,5-difluorobenzyl)-1,3-thiazol-2-yl]-4-[(4-fluorophenyl)sulfonyl]-piperazine
1-[4-(3,5-dichlorobenzyl)-1,3-thiazol-2-yl]-4-[(4-fluorophenyl)sulfonyl]-piperazine
1-[4-(3,5-dimethylbenzyl)-1,3-thiazol-2-yl]-4-[(4-fluorophenyl)sulfonyl]-piperazine
1-[4-(3-chloro-4-fluorobenzyl)-1,3-thiazol-2-yl]-4-[(4-fluorophenyl)sulfonyl]-piperazine
1-[4-(3-chloro-5-fluorobenzyl)-1,3-thiazol-2-yl]-4-[(4-fluorophenyl)sulfonyl]-piperazine
1-[4-(4-chloro-3-fluorobenzyl)-1,3-thiazol-2-yl]-4-[(4-fluorophenyl)sulfonyl]-piperazine
1-[4-(3,4,5-trimethoxybenzyl)-1,3-thiazol-2-yl]-4-[(4-fluorophenyl)sulfonyl]-piperazine
1-[4-(2,4,6-trimethylbenzyl)-1,3-thiazol-2-yl]-4-[(4-fluorophenyl)sulfonyl]-piperazine
1-[4-benzyl-1,3-thiazol-2-yl]-4-[(4-bromophenyl)sulfonyl]-piperazine
1-[4-(2-methylbenzyl)-1,3-thiazol-2-yl]-4-[(4-bromophenyl)sulfonyl]-piperazine
1-[4-(2-methoxybenzyl)-1,3-thiazol-2-yl]-4-[(4-bromophenyl)sulfonyl]-piperazine
1-[4-(3-methylbenzyl)-1,3-thiazol-2-yl]-4-[(4-bromophenyl)sulfonyl]-piperazine
1-[4-(3-methoxybenzyl)-1,3-thiazol-2-yl]-4-[(4-bromophenyl)sulfonyl]-piperazine
1-[4-(3-bromobenzyl)-1,3-thiazol-2-yl]-4-[(4-bromophenyl)sulfonyl]-piperazine
1-[4-(4-chlorobenzyl)-1,3-thiazol-2-yl]-4-[(4-bromophenyl)sulfonyl]-piperazine
1-[4-(4-methoxybenzyl)-1,3-thiazol-2-yl]-4-[(4-bromophenyl)sulfonyl]-piperazine
1-[4-(4-methylbenzyl)-1,3-thiazol-2-yl]-4-[(4-bromophenyl)sulfonyl]-piperazine
1-[4-(4-ethylbenzyl)-1,3-thiazol-2-yl]-4-[(4-bromophenyl)sulfonyl]-piperazine
1-[4-(4-ethoxybenzyl)-1,3-thiazol-2-yl]-4-[(4-bromophenyl)sulfonyl]-piperazine
1-[4-(4-propylbenzyl)-1,3-thiazol-2-yl]-4-[(4-bromophenyl)sulfonyl]-piperazine
1-[4-(2,6-dimethylbenzyl)-1,3-thiazol-2-yl]-4-[(4-bromophenyl)sulfonyl]-piperazine
1-[4-(2,3-dimethylbenzyl)-1,3-thiazol-2-yl]-4-[(4-bromophenyl)sulfonyl]-piperazine
1-[4-(2,5-dimethylbenzyl)-1,3-thiazol-2-yl]-4-[(4-bromophenyl)sulfonyl]-piperazine
1-[4-(2,4-dichlorobenzyl)-1,3-thiazol-2-yl]-4-[(4-bromophenyl)sulfonyl]-piperazine
1-[4-(2,4-dimethoxybenzyl)-1,3-thiazol-2-yl]-4-[(4-bromophenyl)sulfonyl]-piperazine
1-[4-(2,5-dimethoxybenzyl)-1,3-thiazol-2-yl]-4-[(4-bromophenyl)sulfonyl]-piperazine
1-[4-(3,4-dimethoxybenzyl)-1,3-thiazol-2-yl]-4-[(4-bromophenyl)sulfonyl]-piperazine
1-[4-(3,5-dimethoxybenzyl)-1,3-thiazol-2-yl]-4-[(4-bromophenyl)sulfonyl]-piperazine 1-[4-(3,4-dichlorobenzyl)-1,3-thiazol-2-yl]-4-[(4-bromophenyl)sulfonyl]-piperazine
1-[4-(3,4-dimethylbenzyl)-1,3-thiazol-2-yl]-4-[(4-bromophenyl)sulfonyl]-piperazine
1-[4-(3,4-difluorobenzyl)-1,3-thiazol-2-yl]-4-[(4-bromophenyl)sulfonyl]-piperazine
1-[4-(3,5-difluorobenzyl)-1,3-thiazol-2-yl]-4-[(4-bromophenyl)sulfonyl]-piperazine
1-[4-(3,5-dichlorobenzyl)-1,3-thiazol-2-yl]-4-[(4-bromophenyl)sulfonyl]-piperazine
1-[4-(3,5-dimethylbenzyl)-1,3-thiazol-2-yl]-4-[(4-bromophenyl)sulfonyl]-piperazine
1-[4-(3-chloro-4-fluorobenzyl)-1,3-thiazol-2-yl]-4-[(4-bromophenyl)sulfonyl]-piperazine
1-[4-(3-chloro-5-fluorobenzyl)-1,3-thiazol-2-yl]-4-[(4-bromophenyl)sulfonyl]-piperazine
1-[4-(4-chloro-3-fluorobenzyl)-1,3-thiazol-2-yl]-4-[(4-bromophenyl)sulfonyl]-piperazine
1-[4-(3,4,5-trimethoxybenzyl)-1,3-thiazol-2-yl]-4-[(4-bromophenyl)sulfonyl]-piperazine
1-[4-(2,4,6-trimethylbenzyl)-1,3-thiazol-2-yl]-4-[(4-bromophenyl)sulfonyl]-piperazine
1-[4-benzyl-1,3-thiazol-2-yl]-4-[(4-methylphenyl)sulfonyl]-piperazine
1-[4-(2-methylbenzyl)-1,3-thiazol-2-yl]-4-[(4-methylphenyl)sulfonyl]-piperazine
1-[4-(2-methoxybenzyl)-1,3-thiazol-2-yl]-4-[(4-methylphenyl)sulfonyl]-piperazine
1-[4-(3-methylbenzyl)-1,3-thiazol-2-yl]-4-[(4-methylphenyl)sulfonyl]-piperazine
1-[4-(3-methoxybenzyl)-1,3-thiazol-2-yl]-4-[(4-methylphenyl)sulfonyl]-piperazine
1-[4-(3-bromobenzyl)-1,3-thiazol-2-yl]-4-[(4-methylphenyl)sulfonyl]-piperazine
1-[4-(4-chlorobenzyl)-1,3-thiazol-2-yl]-4-[(4-methylphenyl)sulfonyl]-piperazine
1-[4-(4-methoxybenzyl)-1,3-thiazol-2-yl]-4-[(4-methylphenyl)sulfonyl]-piperazine
1-[4-(4-methylbenzyl)-1,3-thiazol-2-yl]-4-[(4-methylphenyl)sulfonyl]-piperazine
1-[4-(4-ethylbenzyl)-1,3-thiazol-2-yl]-4-[(4-methylphenyl)sulfonyl]-piperazine
1-[4-(4-ethoxybenzyl)-1,3-thiazol-2-yl]-4-[(4-methylphenyl)sulfonyl]-piperazine
1-[4-(4-propylbenzyl)-1,3-thiazol-2-yl]-4-[(4-methylphenyl)sulfonyl]-piperazine
1-[4-(2,6-dimethylbenzyl)-1,3-thiazol-2-yl]-4-[(4-methylphenyl)sulfonyl]-piperazine
1-[4-(2,3-dimethylbenzyl)-1,3-thiazol-2-yl]-4-[(4-methylphenyl)sulfonyl]-piperazine
1-[4-(2,5-dimethylbenzyl)-1,3-thiazol-2-yl]-4-[(4-methylphenyl)sulfonyl]-piperazine
1-[4-(2,4-dichlorobenzyl)-1,3-thiazol-2-yl]-4-[(4-methylphenyl)sulfonyl]-piperazine
1-[4-(2,4-dimethoxybenzyl)-1,3-thiazol-2-yl]-4-[(4-methylphenyl)sulfonyl]-piperazine
1-[4-(2,5-dimethoxybenzyl)-1,3-thiazol-2-yl]-4-[(4-methylphenyl)sulfonyl]-piperazine
1-[4-(3,4-dimethoxybenzyl)-1,3-thiazol-2-yl]-4-[(4-methylphenyl)sulfonyl]-piperazine
1-[4-(3,5-dimethoxybenzyl)-1,3-thiazol-2-yl]-4-[(4-methylphenyl)sulfonyl]-piperazine
1-[4-(3,4-dichlorobenzyl)-1,3-thiazol-2-yl]-4-[(4-methylphenyl)sulfonyl]-piperazine
1-[4-(3,4-dimethylbenzyl)-1,3-thiazol-2-yl]-4-[(4-methylphenyl)sulfonyl]-piperazine
1-[4-(3,4-difluorobenzyl)-1,3-thiazol-2-yl]-4-[(4-methylphenyl)sulfonyl]-piperazine
1-[4-(3,5-difluorobenzyl)-1,3-thiazol-2-yl]-4-[(4-methylphenyl)sulfonyl]-piperazine
1-[4-(3,5-dichlorobenzyl)-1,3-thiazol-2-yl]-4-[(4-methylphenyl)sulfonyl]-piperazine
1-[4-(3,5-dimethylbenzyl)-1,3-thiazol-2-yl]-4-[(4-methylphenyl)sulfonyl]-piperazine
1-[4-(3-chloro-4-fluorobenzyl)-1,3-thiazol-2-yl]-4-[(4-methylphenyl)sulfonyl]-piperazine
1-[4-(3-chloro-5-fluorobenzyl)-1,3-thiazol-2-yl]-4-[(4-methylphenyl)sulfonyl]-piperazine
1-[4-(4-chloro-3-fluorobenzyl)-1,3-thiazol-2-yl]-4-[(4-methylphenyl)sulfonyl]-piperazine
1-[4-(3,4,5-trimethoxybenzyl)-1,3-thiazol-2-yl]-4-[(4-methylphenyl)sulfonyl]-piperazine
1-[4-(2,4,6-trimethylbenzyl)-1,3-thiazol-2-yl]-4-[(4-methylphenyl)sulfonyl]-piperazine
1-[4-benzyl-1,3-thiazol-2-yl]-4-[(4-chlorophenyl)sulfonyl]-piperazine
1-[4-(2-methylbenzyl)-1,3-thiazol-2-yl]-4-[(4-chlorophenyl)sulfonyl]-piperazine
1-[4-(2-methoxybenzyl)-1,3-thiazol-2-yl]-4-[(4-chlorophenyl)sulfonyl]-piperazine
1-[4-(3-methylbenzyl)-1,3-thiazol-2-yl]-4-[(4-chlorophenyl)sulfonyl]-piperazine
1-[4-(3-methoxybenzyl)-1,3-thiazol-2-yl]-4-[(4-chlorophenyl)sulfonyl]-piperazine
1-[4-(3-bromobenzyl)-1,3-thiazol-2-yl]-4-[(4-chlorophenyl)sulfonyl]-piperazine
1-[4-(4-chlorobenzyl)-1,3-thiazol-2-yl]-4-[(4-chlorophenyl)sulfonyl]-piperazine
1-[4-(4-methoxybenzyl)-1,3-thiazol-2-yl]-4-[(4-chlorophenyl)sulfonyl]-piperazine
1-[4-(4-methylbenzyl)-1,3-thiazol-2-yl]-4-[(4-chlorophenyl)sulfonyl]-piperazine
1-[4-(4-ethylbenzyl)-1,3-thiazol-2-yl]-4-[(4-chlorophenyl)sulfonyl]-piperazine
1-[4-(4-ethoxybenzyl)-1,3-thiazol-2-yl]-4-[(4-chlorophenyl)sulfonyl]-piperazine
1-[4-(4-propylbenzyl)-1,3-thiazol-2-yl]-4-[(4-chlorophenyl)sulfonyl]-piperazine
1-[4-(2,6-dimethylbenzyl)-1,3-thiazol-2-yl]-4-[(4-chlorophenyl)sulfonyl]-piperazine
1-[4-(2,3-dimethylbenzyl)-1,3-thiazol-2-yl]-4-[(4-chlorophenyl)sulfonyl]-piperazine
1-[4-(2,5-dimethylbenzyl)-1,3-thiazol-2-yl]-4-[(4-chlorophenyl)sulfonyl]-piperazine
1-[4-(2,4-dichlorobenzyl)-1,3-thiazol-2-yl]-4-[(4-chlorophenyl)sulfonyl]-piperazine
1-[4-(2,4-dimethoxybenzyl)-1,3-thiazol-2-yl]-4-[(4-chlorophenyl)sulfonyl]-piperazine
1-[4-(2,5-dimethoxybenzyl)-1,3-thiazol-2-yl]-4-[(4-chlorophenyl)sulfonyl]-piperazine
1-[4-(3,4-dimethoxybenzyl)-1,3-thiazol-2-yl]-4-[(4-chlorophenyl)sulfonyl]-piperazine
1-[4-(3,5-dimethoxybenzyl)-1,3-thiazol-2-yl]-4-[(4-chlorophenyl)sulfonyl]-piperazine
1-[4-(3,4-dichlorobenzyl)-1,3-thiazol-2-yl]-4-[(4-chlorophenyl)sulfonyl]-piperazine
1-[4-(3,4-dimethylbenzyl)-1,3-thiazol-2-yl]-4-[(4-chlorophenyl)sulfonyl]-piperazine
1-[4-(3,4-difluorobenzyl)-1,3-thiazol-2-yl]-4-[(4-chlorophenyl)sulfonyl]-piperazine
1-[4-(3,5-difluorobenzyl)-1,3-thiazol-2-yl]-4-[(4-chlorophenyl)sulfonyl]-piperazine 1-[4-(3,5-dichlorobenzyl)-1,3-thiazol-2-yl]-4-[(4-chlorophenyl)sulfonyl]-piperazine
1-[4-(3,5-dimethylbenzyl)-1,3-thiazol-2-yl]-4-[(4-chlorophenyl)sulfonyl]-piperazine
1-[4-(3-chloro-4-fluorobenzyl)-1,3-thiazol-2-yl]-4-[(4-chlorophenyl)sulfonyl]-piperazine
1-[4-(3-chloro-5-fluorobenzyl)-1,3-thiazol-2-yl]-4-[(4-chlorophenyl)sulfonyl]-piperazine
1-[4-(4-chloro-3-fluorobenzyl)-1,3-thiazol-2-yl]-4-[(4-chlorophenyl)sulfonyl]-piperazine
1-[4-(3,4,5-trimethoxybenzyl)-1,3-thiazol-2-yl]-4-[(4-chlorophenyl)sulfonyl]-piperazine
1-[4-(2,4,6-trimethylbenzyl)-1,3-thiazol-2-yl]-4-[(4-chlorophenyl)sulfonyl]-piperazine
1-[4-benzyl-1,3-thiazol-2-yl]-4-[(4-(trifluoromethoxy)phenyl)sulfonyl]-piperazine
1-[4-(2-methylbenzyl)-1,3-thiazol-2-yl]-4-[(4-(trifluoromethoxy)phenyl)sulfonyl]-piperazine
1-[4-(2-methoxybenzyl)-1,3-thiazol-2-yl]-4-[(4-(trifluoromethoxy)phenyl)sulfony]-piperazine
1-[4-(3-methylbenzyl)-1,3-thiazol-2-yl]-4-[(4-(trifluoromethoxy)phenyl)sulfonyl]-piperazine
1-[4-(3-methoxybenzyl)-1,3-thiazol-2-yl]-4-[(4-(trifluoromethoxy)phenyl)sulfonyl]-piperazine
1-[4-(3-bromobenzyl)-1,3-thiazol-2-yl]-4-[(4-(trifluoromethoxy)phenyl)sulfonyl]-piperazine
1-[4-(4-chlorobenzyl)-1,3-thiazol-2-yl]-4-[(4-(trifluoromethoxy)phenyl)sulfonyl]-piperazine
1-[4-(4-methoxybenzyl)-1,3-thiazol-2-yl]-4-[(4-(trifluoromethoxy)phenyl)sulfonyl]-piperazine
1-[4-(4-methylbenzyl)-1,3-thiazol-2-yl]-4-[(4-(trifluoromethoxy)phenyl)sulfonyl]-piperazine
1-[4-(4-ethylbenzyl)-1,3-thiazol-2-yl]-4-[(4-(trifluoromethoxy)phenyl)sulfonyl]-piperazine
1-[4-(4-ethoxybenzyl)-1,3-thiazol-2-yl]-4-[(4-(trifluoromethoxy)phenyl)sulfonyl]-piperazine
1-[4-(4-propylbenzyl)-1,3-thiazol-2-yl]-4-[(4-(trifluoromethoxy)phenyl)sulfonyl]-piperazine
1-[4-(2,6-dimethylbenzyl)-1,3-thiazol-2-yl]-4-[(4-(trifluoromethoxy)phenyl)sulfonyl]-piperazine
1-[4-(2,3-dimethylbenzyl)-1,3-thiazol-2-yl]-4-[(4-(trifluoromethoxy)phenyl)sulonyl]-piperazine
1-[4-(2,5-dimethylbenzyl)-1,3-thiazol-2-yl]-4-[(4-(trifluoromethoxy)phenyl)sulfonyl]-piperazine
1-[4-(2,4-dichlorobenzyl)-1,3-thiazol-2-yl]-4-[(4-(trifluoromethoxy)phenyl)sulfonyl]-piperazine
1-[4-(2,4-dimethoxybenzyl)-1,3-thiazol-2-yl]-4-[(4-(trifluoromethoxy)phenyl)sulfonyl]-piperazine
1-[4-(2,5-dimethoxybenzyl)-1,3-thiazol-2-yl]-4-[(4-(trifluoromethoxy)phenyl)sulfonyl]-piperazine
1-[4-(3,4-dimethoxybenzyl)-1,3-thiazol-2-yl]-4-[(4-(trifluoromethoxy)phenyl)sulfonyl]-piperazine
1-[4-(3,5-dimethoxybenzyl)-1,3-thiazol-2-yl]-4-[(4-(trifluoromethoxy)phenyl)sulfonyl]-piperazine
1-[4-(3,4-dichlorobenzyl)-1,3-thiazol-2-yl]-4-[(4-(trifluoromethoxy)phenyl)sulfonyl]-piperazine
1-[4-(3,4-dimethylbenzyl)-1,3-thiazol-2-yl]-4-[(4-(trifluoromethoxy)phenyl)sulfonyl]-piperazine
1-[4-(3,4-difluorobenzyl)-1,3-thiazol-2-yl]-4-[(4-(trifluoromethoxy)phenyl)sulfonyl]-piperazine
1-[4-(3,5-difluorobenzyl)-1,3-thiazol-2-yl]-4-[(4-(trifluoromethoxy)phenyl)sulfonyl]-piperazine
1-[4-(3,5-dichlorobenzyl)-1,3-thiazol-2-yl]-4-[(4-(trifluoromethoxy)phenyl)sulfonyl]-piperazine
1-[4-(3,5-dimethylbenzyl)-1,3-thiazol-2-yl]-4-[(4-(trifluoromethoxy)phenyl)sulfonyl]-piperazine
1-[4-(3-chloro-4-fluorobenzyl)-1,3-thiazol-2-yl]-4-[(4-(trifluoromethoxy)phenyl)sulfonyl]-piperazine
1-[4-(3-chloro-5-fluorobenzyl)-1,3-thiazol-2-yl]-4-[(4-(trifluoromethoxy)phenyl)sulfonyl]-piperazine
1-[4-(4-chloro-3-fluorobenzyl)-1,3-thiazol-2-yl]-4-[(4-(trifluoromethoxy)phenyl)sulfonyl]-piperazine
1-[4-(3,4,5-trimethoxybenzyl)-1,3-thiazol-2-yl]-4-[(4-(trifluoromethoxy)phenyl)sulfonyl]-piperazine
1-[4-(2,4,6-trimethylbenzyl)-1,3-thiazol-2-yl]-4-[(4-(trifluoromethoxy)phenyl)sulfonyl]-piperazine
1-[4-benzyl-1,3-thiazol-2-yl]-4-[(4-tert-butylphenyl)sulfonyl]-piperazine
1-[4-(2-methylbenzyl)-1,3-thiazol-2-yl]-4-[(4-tert-butylphenyl)sulfonyl]-piperazine
1-[4-(2-methoxybenzyl)-1,3-thiazol-2-yl]-4-[(4-tert-butylphenyl)sulfonyl]-piperazine
1-[4-(3-methylbenzyl)-1,3-thiazol-2-yl]-4-[(4-tert-butylphenyl)sulfonyl]-piperazine
1-[4-(3-methoxybenzyl)-1,3-thiazol-2-yl]-4-[(4-tert-butylphenyl)sulfonyl]-piperazine
1-[4-(3-bromobenzyl)-1,3-thiazol-2-yl]-4-[(4-tert-butylphenyl)sulfonyl]-piperazine
1-[4-(4-chlorobenzyl)-1,3-thiazol-2-yl]-4-[(4-tert-butylphenyl)sulfonyl]-piperazine
1-[4-(4-methoxybenzyl)-1,3-thiazol-2-yl]-4-[(4-tert-butylphenyl)sulfonyl]-piperazine
1-[4-(4-methylbenzyl)-1,3-thiazol-2-yl]-4-[(4-tert-butylphenyl)sulfonyl]-piperazine
1-[4-(4-ethylbenzyl)-1,3-thiazol-2-yl]-4-[(4-tert-butylphenyl)sulfonyl]-piperazine
1-[4-(4-ethoxybenzyl)-1,3-thiazol-2-yl]-4-[(4-tert-butylphenyl)sulfonyl]-piperazine
1-[4-(4-propylbenzyl)-1,3-thiazol-2-yl]-4-[(4-tert-butylphenyl)sulfonyl]-piperazine
1-[4-(2,6-dimethylbenzyl)-1,3-thiazol-2-yl]-4-[(4-tert-butylphenyl)sulfonyl]-piperazine
1-[4-(2,3-dimethylbenzyl)-1,3-thiazol-2-yl]-4-[(4-tert-butylphenyl)sulfonyl]-piperazine
1-[4-(2,5-dimethylbenzyl)-1,3-thiazol-2-yl]-4-[(4-tert-butylphenyl)sulfonyl]-piperazine
1-[4-(2,4-dichlorobenzyl)-1,3-thiazol-2-yl]-4-[(4-tert-butylphenyl)sulfonyl]-piperazine
1-[4-(2,4-dimethoxybenzyl)-1,3-thiazol-2-yl]-4-[(4-tert-butylphenyl)sulfonyl]-piperazine
1-[4-(2,5-dimethoxybenzyl)-1,3-thiazol-2-yl]-4-[(4-tert-butylphenyl)sulfonyl]-piperazine
1-[4-(3,4-dimethoxybenzyl)-1,3-thiazol-2-yl]-4-[(4-tert-butylphenyl)sulfonyl]-piperazine
1-[4-(3,5-dimethoxybenzyl)-1,3-thiazol-2-yl]-4-[(4-tert-butylphenyl)sulfonyl]-piperazine
1-[4-(3,4-dichlorobenzyl)-1,3-thiazol-2-yl]-4-[(4-tert-butylphenyl)sulfonyl]-piperazine
1-[4-(3,4-dimethylbenzyl)-1,3-thiazol-2-yl]-4-[(4-tert-butylphenyl)sulfonyl]-piperazine
1-[4-(3,4-difluorobenzyl)-1,3-thiazol-2-yl]-4-[(4-tert-butylphenyl)sulfonyl]-piperazine
1-[4-(3,5-difluorobenzyl)-1,3-thiazol-2-yl]-4-[(4-tert-butylphenyl)sulfonyl]-piperazine
1-[4-(3,5-dichlorobenzyl)-1,3-thiazol-2-yl]-4-[(4-tert-butylphenyl)sulfonyl]-piperazine
1-[4-(3,5-dimethylbenzyl)-1,3-thiazol-2-yl]-4-[(4-tert-butylphenyl)sulfonyl]-piperazine
1-[4-(3-chloro-4-fluorobenzyl)-1,3-thiazol-2-yl]-4-[(4-tert-butylphenyl)sulfonyl]-piperazine
1-[4-(3-chloro-5-fluorobenzyl)-1,3-thiazol-2-yl]-4-[(4-tert-butylphenyl)sulfonyl]-piperazine 1-[4-(4-chloro-3-fluorobenzyl)-1,3-thiazol-2-yl]-4-[(4-tert-butylphenyl)sulfonyl]-piperazine
1-[4-(3,4,5-trimethoxybenzyl)-1,3-thiazol-2-yl]-4-[(4-tert-butylphenyl)sulfonyl]-piperazine
1-[4-(2,4,6-trimethylbenzyl)-1,3-thiazol-2-yl]-4-[(4-tert-butylphenyl)sulfonyl]-piperazine
1-[4-benzyl-1,3-thiazol-2-yl]-4-[(pentafluorophenyl)sulfonyl]-piperazine
1-[4-(2-methylbenzyl)-1,3-thiazol-2-yl]-4-[(pentafluorophenyl)sulfonyl]-piperazine
1-[4-(2-methoxybenzyl)-1,3-thiazol-2-yl]-4-[(pentafluorophenyl)sulfonyl]-piperazine
1-[4-(3-methylbenzyl)-1,3-thiazol-2-yl]-4-[(pentafluorophenyl)sulfonyl]-piperazine
1-[4-(3-methoxybenzyl)-1,3-thiazol-2-yl]-4-[(pentafluorophenyl)sulfonyl]-piperazine
1-[4-(3-bromobenzyl)-1,3-thiazol-2-yl]-4-[(pentafluorophenyl)sulfonyl]-piperazine
1-[4-(4-chlorobenzyl)-1,3-thiazol-2-yl]-4-[(pentafluorophenyl)sulfonyl]-piperazine
1-[4-(4-methoxybenzyl)-1,3-thiazol-2-yl]-4-[(pentafluorophenyl)sulfonyl]-piperazine
1-[4-(4-methylbenzyl)-1,3-thiazol-2-yl]-4-[(pentafluorophenyl)sulfonyl]-piperazine
1-[4-(4-ethylbenzyl)-1,3-thiazol-2-yl]-4-[(pentafluorophenyl)sulfonyl]-piperazine
1-[4-(4-ethoxybenzyl)-1,3-thiazol-2-yl]-4-[(pentafluorophenyl)sulfonyl]-piperazine
1-[4-(4-propylbenzyl)-1,3-thiazol-2-yl]-4-[(pentafluorophenyl)sulfonyl]-piperazine
1-[4-(2,6-dimethylbenzyl)-1,3-thiazol-2-yl]-4-[(pentafluorophenyl)sulfonyl]-piperazine
1-[4-(2,3-dimethylbenzyl)-1,3-thiazol-2-yl]-4-[(pentafluorophenyl)sulfonyl]-piperazine
1-[4-(2,5-dimethylbenzyl)-1,3-thiazol-2-yl]-4-[(pentafluorophenyl)sulfonyl]-piperazine
1-[4-(2,4-dichlorobenzyl)-1,3-thiazol-2-yl]-4-[(pentafluorophenyl)sulfonyl]-piperazine
1-[4-(2,4-dimethoxybenzyl)-1,3-thiazol-2-yl]-4-[(pentafluorophenyl)sulfonyl]-piperazine
1-[4-(2,5-dimethoxybenzyl)-1,3-thiazol-2-yl]-4-[(pentafluorophenyl)sulfonyl]-piperazine
1-[4-(3,4-dimethoxybenzyl)-1,3-thiazol-2-yl]-4-[(pentafluorophenyl)sulfonyl]-piperazine
1-[4-(3,5-dimethoxybenzyl)-1,3-thiazol-2-yl]-4-[(pentafluorophenyl)sulfonyl]-piperazine
1-[4-(3,4-dichlorobenzyl)-1,3-thiazol-2-yl]-4-[(pentafluorophenyl)sulfonyl]-piperazine
1-[4-(3,4-dimethylbenzyl)-1,3-thiazol-2-yl]-4-[(pentafluorophenyl)sulfonyl]-piperazine
1-[4-(3,4-difluorobenzyl)-1,3-thiazol-2-yl]-4-[(pentafluorophenyl)sulfonyl]-piperazine
1-[4-(3,5-difluorobenzyl)-1,3-thiazol-2-yl]-4-[(pentafluorophenyl)sulfonyl]-piperazine
1-[4-(3,5-dichlorobenzyl)-1,3-thiazol-2-yl]-4-[(pentafluorophenyl)sulfonyl]-piperazine
1-[4-(3,5-dimethylbenzyl)-1,3-thiazol-2-yl]-4-[(pentafluorophenyl)sulfonyl]-piperazine
1-[4-(3-chloro-4-fluorobenzyl)-1,3-thiazol-2-yl]-4-[(pentafluorophenyl)sulfonyl]-piperazine
1-[4-(3-chloro-5-fluorobenzyl)-1,3-thiazol-2-yl]-4-[(pentafluorophenyl)sulfonyl]-piperazine
1-[4-(4-chloro-3-fluorobenzyl)-1,3-thiazol-2-yl]-4-[(pentafluorophenyl)sulfonyl]-piperazine
1-[4-(3,4,5-trimethoxybenzyl)-1,3-thiazol-2-yl]-4-[(pentafluorophenyl)sulfonyl]-piperazine
1-[4-(2,4,6-trimethylbenzyl)-1,3-thiazol-2-yl]-4-[(pentafluorophenyl)sulfonyl]-piperazine
1-[4-benzyl-1,3-thiazol-2-yl]-4-[(2,4,6-trimethylphenyl)sulfonyl]-piperazine
1-[4-(2-methylbenzyl)-1,3-thiazol-2-yl]-4-[(2,4,6-trimethylphenyl)sulfonyl]-piperazine
1-[4-(2-methoxybenzyl)-1,3-thiazol-2-yl]-4-[(2,4,6-trimethylphenyl)sulfonyl]-piperazine
1-[4-(3-methylbenzyl)-1,3-thiazol-2-yl]-4-[(2,4,6-trimethylphenyl)sulfonyl]-piperazine
1-[4-(3-methoxybenzyl)-1,3-thiazol-2-yl]-4-[(2,4,6-trimethylphenyl)sulfonyl]-piperazine
1-[4-(3-bromobenzyl)-1,3-thiazol-2-yl]-4-[(2,4,6-trimethylphenyl)sulfonyl]-piperazine
1-[4-(4-chlorobenzyl)-1,3-thiazol-2-yl]-4-[(2,4,6-trimethylphenyl)sulfonyl]-piperazine
1-[4-(4-methoxybenzyl)-1,3-thiazol-2-yl]-4-[(2,4,6-trimethylphenyl)sulfonyl]-piperazine
1-[4-(4-methylbenzyl)-1,3-thiazol-2-yl]-4-[(2,4,6-trimethylphenyl)sulfonyl]-piperazine
1-[4-(4-ethylbenzyl)-1,3-thiazol-2-yl]-4-[(2,4,6-trimethylphenyl)sulfonyl]-piperazine
1-[4-(4-ethoxybenzyl)-1,3-thiazol-2-yl]-4-[(2,4,6-trimethylphenyl)sulfonyl]-piperazine
1-[4-(4-propylbenzyl)-1,3-thiazol-2-yl]-4-[(2,4,6-trimethylphenyl)sulfonyl]-piperazine
1-[4-(2,6-dimethylbenzyl)-1,3-thiazol-2-yl]-4-[(2,4,6-trimethylphenyl)sulfonyl]-piperazine
1-[4-(2,3-dimethylbenzyl)-1,3-thiazol-2-yl]-4-[(2,4,6-trimethylphenyl)sulfonyl]-piperazine
1-[4-(2,5-dimethylbenzyl)-1,3-thiazol-2-yl]-4-[(2,4,6-trimethylphenyl)sulfonyl]-piperazine
1-[4-(2,4-dichlorobenzyl)-1,3-thiazol-2-yl]-4-[(2,4,6-trimethylphenyl)sulfonyl]-piperazine
1-[4-(2,4-dimethoxybenzyl)-1,3-thiazol-2-yl]-4-[(2,4,6-trimethylphenyl)sulfonyl]-piperazine
1-[4-(2,5-dimethoxybenzyl)-1,3-thiazol-2-yl]-4-[(2,4,6-trimethylphenyl)sulfonyl]-piperazine
1-[4-(3,4-dimethoxybenzyl)-1,3-thiazol-2-yl]-4-[(2,4,6-trimethylphenyl)sulfonyl]-piperazine
1-[4-(3,5-dimethoxybenzyl)-1,3-thiazol-2-yl]-4-[(2,4,6-trimethylphenyl)sulfonyl]-piperazine
1-[4-(3,4-dichlorobenzyl)-1,3-thiazol-2-yl]-4-[(2,4,6-trimethylphenyl)sulfonyl]-piperazine
1-[4-(3,4-dimethylbenzyl)-1,3-thiazol-2-yl]-4-[(2,4,6-trimethylphenyl)sulfonyl]-piperazine
1-[4-(3,4-difluorobenzyl)-1,3-thiazol-2-yl]-4-[(2,4,6-trimethylphenyl)sulfonyl]-piperazine
1-[4-(3,5-difluorobenzyl)-1,3-thiazol-2-yl]-4-[(2,4,6-trimethylphenyl)sulfonyl]-piperazine
1-[4-(3,5-dichlorobenzyl)-1,3-thiazol-2-yl]-4-[(2,4,6-trimethylphenyl)sulfonyl]-piperazine
1-[4-(3,5-dimethylbenzyl)-1,3-thiazol-2-yl]-4-[(2,4,6-trimethylphenyl)sulfonyl]-piperazine
1-[4-(3-chloro-4-fluorobenzyl)-1,3-thiazol-2-yl]-4-[(2,4,6-trimethylphenyl)sulfonyl]-piperazine
1-[4-(3-chloro-5-fluorobenzyl)-1,3-thiazol-2-yl]-4-[(2,4,6-trimethylphenyl)sulfonyl]-piperazine
1-[4-(4-chloro-3-fluorobenzyl)-1,3-thiazol-2-yl]-4-[(2,4,6-trimethylphenyl)sulfonyl]-piperazine
1-[4-(3,4,5-trimethoxybenzyl)-1,3-thiazol-2-yl]-4-[(2,4,6-trimethylphenyl)sulfonyl]-piperazine
1-[4-(2,4,6-trimethylbenzyl)-1,3-thiazol-2-yl]-4-[(2,4,6-trimethylphenyl)sulfonyl]-piperazine
1-[4-benzyl-1,3-thiazol-2-yl]-4-[(2,4,6-tri-iso-propylphenyl)sulfonyl]-piperazine 1-[4-(2-methylbenzyl)-1,3-thiazol-2-yl]-4-[(2,4,6-tri-iso-propylphenyl)sulfonyl]-piperazine
1-[4-(2-methoxybenzyl)-1,3-thiazol-2-yl]-4-[(2,4,6-tri-iso-propylphenyl)sulfonyl]-piperazine
1-[4-(3-methylbenzyl)-1,3-thiazol-2-yl]-4-[(2,4,6-tri-iso-propylphenyl)sulfonyl]-piperazine
1-[4-(3-methoxybenzyl)-1,3-thiazol-2-yl]-4-[(2,4,6-tri-iso-propylphenyl)sulfonyl]-piperazine
1-[4-(3-bromobenzyl)-1,3-thiazol-2-yl]-4-[(2,4,6-tri-iso-propylphenyl)sulfonyl]-piperazine
1-[4-(4-chlorobenzyl)-1,3-thiazol-2-yl]-4-[(2,4,6-tri-iso-propylphenyl)sulfonyl]-piperazine
1-[4-(4-methoxybenzyl)-1,3-thiazol-2-yl]-4-[(2,4,6-tri-iso-propylphenyl)sulfonyl]-piperazine
1-[4-(4-methylbenzyl)-1,3-thiazol-2-yl]-4-[(2,4,6-tri-iso-propylphenyl)sulfonyl]-piperazine
1-[4-(4-ethylbenzyl)-1,3-thiazol-2-yl]-4-[(2,4,6-tri-iso-propylphenyl)sulfonyl]-piperazine
1-[4-(4-ethoxybenzyl)-1,3-thiazol-2-yl]-4-[(2,4,6-tri-iso-propylphenyl)sulfonyl]-piperazine
1-[4-(4-propylbenzyl)-1,3-thiazol-2-yl]-4-[(2,4,6-tri-iso-propylphenyl)sulfonyl]-piperazine
1-[4-(2,6-dimethylbenzyl)-1,3-thiazol-2-yl]-4-[(2,4,6-tri-iso-propylphenyl)sulfonyl]-piperazine
1-[4-(2,3-dimethylbenzyl)-1,3-thiazol-2-yl]-4-[(2,4,6-tri-iso-propylphenyl)sulfonyl]-piperazine
1-[4-(2,5-dimethylbenzyl)-1,3-thiazol-2-yl]-4-[(2,4,6-tri-iso-propylphenyl)sulfonyl]-piperazine
1-[4-(2,4-dichlorobenzyl)-1,3-thiazol-2-yl]-4-[(2,4,6-tri-iso-propylphenyl)sulfonyl]-piperazine
1-[4-(2,4-dimethoxybenzyl)-1,3-thiazol-2-yl]-4-[(2,4,6-tri-iso-propylphenyl)sulfonyl]-piperazine
1-[4-(2,5-dimethoxybenzyl)-1,3-thiazol-2-yl]-4-[(2,4,6-tri-iso-propylphenyl)sulfonyl]-piperazine
1-[4-(3,4-dimethoxybenzyl)-1,3-thiazol-2-yl]-4-[(2,4,6-tri-iso-propylphenyl)sulfonyl]-piperazine
1-[4-(3,5-dimethoxybenzyl)-1,3-thiazol-2-yl]-4-[(2,4,6-tri-iso-propylphenyl)sulfonyl]-piperazine
1-[4-(3,4-dichlorobenzyl)-1,3-thiazol-2-yl]-4-[(2,4,6-tri-iso-propylphenyl)sulfonyl]-piperazine
1-[4-(3,4-dimethylbenzyl)-1,3-thiazol-2-yl]-4-[(2,4,6-tri-iso-propylphenyl)sulfonyl]-piperazine
1-[4-(3,4-difluorobenzyl)-1,3-thiazol-2-yl]-4-[(2,4,6-tri-iso-propylphenyl)sulfonyl]-piperazine
1-[4-(3,5-difluorobenzyl)-1,3-thiazol-2-yl]-4-[(2,4,6-tri-iso-propylphenyl)sulfonyl]-piperazine
1-[4-(3,5-dichlorobenzyl)-1,3-thiazol-2-yl]-4-[(2,4,6-tri-iso-propylphenyl)sulfonyl]-piperazine
1-[4-(3,5-dimethylbenzyl)-1,3-thiazol-2-yl]-4-[(2,4,6-tri-iso-propylphenyl)sulfonyl]-piperazine
1-[4-(3-chloro-4-fluorobenzyl)-1,3-thiazol-2-yl]-4-[(2,4,6-tri-iso-propylphenyl)sulfonyl]-piperazine
1-[4-(3-chloro-5-fluorobenzyl)-1,3-thiazol-2-yl]-4-[(2,4,6-tri-iso-propylphenyl)sulfonyl]-piperazine
1-[4-(4-chloro-3-fluorobenzyl)-1,3-thiazol-2-yl]-4-[(2,4,6-tri-iso-propylphenyl)sulfonyl]-piperazine
1-[4-(3,4,5-trimethoxybenzyl)-1,3-thiazol-2-yl]-4-[(2,4,6-tri-iso-propylphenyl)sulfonyl]-piperazine
1-[4-(2,4,6-trimethylbenzyl)-1,3-thiazol-2-yl]-4-[(2,4,6-tri-iso-propylphenyl)sulfonyl]-piperazine
1-[4-benzyl-1,3-thiazol-2-yl]-4-[(2,4-dichlorophenyl)sulfonyl]-piperazine
1-[4-(2-methylbenzyl)-1,3-thiazol-2-yl]-4-[(2,4-dichlorophenyl)sulfonyl]-piperazine
1-[4-(2-methoxybenzyl)-1,3-thiazol-2-yl]-4-[(2,4-dichlorophenyl)sulfonyl]-piperazine
1-[4-(3-methylbenzyl)-1,3-thiazol-2-yl]-4-[(2,4-dichlorophenyl)sulfonyl]-piperazine
1-[4-(3-methoxybenzyl)-1,3-thiazol-2-yl]-4-[(2,4-dichlorophenyl)sulfonyl]-piperazine
1-[4-(3-bromobenzyl)-1,3-thiazol-2-yl]-4-[(2,4-dichlorophenyl)sulfonyl]-piperazine
1-[4-(4-chlorobenzyl)-1,3-thiazol-2-yl]-4-[(2,4-dichlorophenyl)sulfonyl]-piperazine
1-[4-(4-methoxybenzyl)-1,3-thiazol-2-yl]-4-[(2,4-dichlorophenyl)sulfonyl]-piperazine
1-[4-(4-methylbenzyl)-1,3-thiazol-2-yl]-4-[(2,4-dichlorophenyl)sulfonyl]-piperazine
1-[4-(4-ethylbenzyl)-1,3-thiazol-2-yl]-4-[(2,4-dichlorophenyl)sulfonyl]-piperazine
1-[4-(4-ethoxybenzyl)-1,3-thiazol-2-yl]-4-[(2,4-dichlorophenyl)sulfonyl]-piperazine
1-[4-(4-propylbenzyl)-1,3-thiazol-2-yl]-4-[(2,4-dichlorophenyl)sulfonyl]-piperazine
1-[4-(2,6-dimethylbenzyl)-1,3-thiazol-2-yl]-4-[(2,4-dichlorophenyl)sulfonyl]-piperazine
1-[4-(2,3-dimethylbenzyl)-1,3-thiazol-2-yl]-4-[(2,4-dichlorophenyl)sulfonyl]-piperazine
1-[4-(2,5-dimethylbenzyl)-1,3-thiazol-2-yl]-4-[(2,4-dichlorophenyl)sulfonyl]-piperazine
1-[4-(2,4-dichlorobenzyl)-1,3-thiazol-2-yl]-4-[(2,4-dichlorophenyl)sulfonyl]-piperazine
1-[4-(2,4-dimethoxybenzyl)-1,3-thiazol-2-yl]-4-[(2,4-dichlorophenyl)sulfonyl]-piperazine
1-[4-(2,5-dimethoxybenzyl)-1,3-thiazol-2-yl]-4-[(2,4-dichlorophenyl)sulfonyl]-piperazine
1-[4-(3,4-dimethoxybenzyl)-1,3-thiazol-2-yl]-4-[(2,4-dichlorophenyl)sulfonyl]-piperazine
1-[4-(3,5-dimethoxybenzyl)-1,3-thiazol-2-yl]-4-[(2,4-dichlorophenyl)sulfonyl]-piperazine
1-[4-(3,4-dichlorobenzyl)-1,3-thiazol-2-yl]-4-[(2,4-dichlorophenyl)sulfonyl]-piperazine
1-[4-(3,4-dimethylbenzyl)-1,3-thiazol-2-yl]-4-[(2,4-dichlorophenyl)sulfonyl]-piperazine
1-[4-(3,4-difluorobenzyl)-1,3-thiazol-2-yl]-4-[(2,4-dichlorophenyl)sulfonyl]-piperazine
1-[4-(3,5-difluorobenzyl)-1,3-thiazol-2-yl]-4-[(2,4-dichlorophenyl)sulfonyl]-piperazine
1-[4-(3,5-dichlorobenzyl)-1,3-thiazol-2-yl]-4-[(2,4-dichlorophenyl)sulfonyl]-piperazine
1-[4-(3,5-dimethylbenzyl)-1,3-thiazol-2-yl]-4-[(2,4-dichlorophenyl)sulfonyl]-piperazine
1-[4-(3-chloro-4-fluorobenzyl)-1,3-thiazol-2-yl]-4-[(2,4-dichlorophenyl)sulfonyl]-piperazine
1-[4-(3-chloro-5-fluorobenzyl)-1,3-thiazol-2-yl]-4-[(2,4-dichlorophenyl)sulfonyl]-piperazine
1-[4-(4-chloro-3-fluorobenzyl)-1,3-thiazol-2-yl]-4-[(2,4-dichlorophenyl)sulfonyl]-piperazine
1-[4-(3,4,5-trimethoxybenzyl)-1,3-thiazol-2-yl]-4-[(2,4-dichlorophenyl)sulfonyl]-piperazine
1-[4-(2,4,6-trimethylbenzyl)-1,3-thiazol-2-yl]-4-[(2,4-dichlorophenyl)sulfonyl]-piperazine
1-[4-benzyl-1,3-thiazol-2-yl]-4-[(2,5-dichlorophenyl)sulfonyl]-piperazine
1-[4-(2-methylbenzyl)-1,3-thiazol-2-yl]-4-[(2,5-dichlorophenyl)sulfonyl]-piperazine
1-[4-(2-methoxybenzyl)-1,3-thiazol-2-yl]-4-[(2,5-dichlorophenyl)sulfonyl]-piperazine
1-[4-(3-methylbenzyl)-1,3-thiazol-2-yl]-4-[(2,5-dichlorophenyl)sulfonyl]-piperazine
1-[4-(3-methoxybenzyl)-1,3-thiazol-2-yl]-4-[(2,5-dichlorophenyl)sulfonyl]-piperazine 1-[4-(3-bromobenzyl)-1,3-thiazol-2-yl]-4-[(2,5-dichlorophenyl)sulfonyl]-piperazine
1-[4-(4-chlorobenzyl)-1,3-thiazol-2-yl]-4-[(2,5-dichlorophenyl)sulfonyl]-piperazine
1-[4-(4-methoxybenzyl)-1,3-thiazol-2-yl]-4-[(2,5-dichlorophenyl)sulfonyl]-piperazine
1-[4-(4-methylbenzyl)-1,3-thiazol-2-yl]-4-[(2,5-dichlorophenyl)sulfonyl]-piperazine
1-[4-(4-ethylbenzyl)-1,3-thiazol-2-yl]-4-[(2,5-dichlorophenyl)sulfonyl]-piperazine
1-[4-(4-ethoxybenzyl)-1,3-thiazol-2-yl]-4-[(2,5-dichlorophenyl)sulfonyl]-piperazine
1-[4-(4-propylbenzyl)-1,3-thiazol-2-yl]-4-[(2,5-dichlorophenyl)sulfonyl]-piperazine
1-[4-(2,6-dimethylbenzyl)-1,3-thiazol-2-yl]-4-[(2,5-dichlorophenyl)sulfonyl]-piperazine
1-[4-(2,3-dimethylbenzyl)-1,3-thiazol-2-yl]-4-[(2,5-dichlorophenyl)sulfonyl]-piperazine
1-[4-(2,5-dimethylbenzyl)-1,3-thiazol-2-yl]-4-[(2,5-dichlorophenyl)sulfonyl]-piperazine
1-[4-(2,4-dichlorobenzyl)-1,3-thiazol-2-yl]-4-[(2,5-dichlorophenyl)sulfonyl]-piperazine
1-[4-(2,4-dimethoxybenzyl)-1,3-thiazol-2-yl]-4-[(2,5-dichlorophenyl)sulfonyl]-piperazine
1-[4-(2,5-dimethoxybenzyl)-1,3-thiazol-2-yl]-4-[(2,5-dichlorophenyl)sulfonyl]-piperazine
1-[4-(3,4-dimethoxybenzyl)-1,3-thiazol-2-yl]-4-[(2,5-dichlorophenyl)sulfonyl]-piperazine
1-[4-(3,5-dimethoxybenzyl)-1,3-thiazol-2-yl]-4-[(2,5-dichlorophenyl)sulfonyl]-piperazine
1-[4-(3,4-dichlorobenzyl)-1,3-thiazol-2-yl]-4-[(2,5-dichlorophenyl)sulfonyl]-piperazine
1-[4-(3,4-dimethylbenzyl)-1,3-thiazol-2-yl]-4-[(2,5-dichlorophenyl)sulfonyl]-piperazine
1-[4-(3,4-difluorobenzyl)-1,3-thiazol-2-yl]-4-[(2,5-dichlorophenyl)sulfonyl]-piperazine
1-[4-(3,5-difluorobenzyl)-1,3-thiazol-2-yl]-4-[(2,5-dichlorophenyl)sulfonyl]-piperazine
1-[4-(3,5-dichlorobenzyl)-1,3-thiazol-2-yl]-4-[(2,5-dichlorophenyl)sulfonyl]-piperazine
1-[4-(3,5-dimethylbenzyl)-1,3-thiazol-2-yl]-4-[(2,5-dichlorophenyl)sulfonyl]-piperazine
1-[4-(3-chloro-4-fluorobenzyl)-1,3-thiazol-2-yl]-4-[(2,5-dichlorophenyl)sulfonyl]-piperazine
1-[4-(3-chloro-5-fluorobenzyl)-1,3-thiazol-2-yl]-4-[(2,5-dichlorophenyl)sulfonyl]-piperazine
1-[4-(4-chloro-3-fluorobenzyl)-1,3-thiazol-2-yl]-4-[(2,5-dichlorophenyl)sulfonyl]-piperazine
1-[4-(3,4,5-trimethoxybenzyl)-1,3-thiazol-2-yl]-4-[(2,5-dichlorophenyl)sulfonyl]-piperazine
1-[4-(2,4,6-trimethylbenzyl)-1,3-thiazol-2-yl]-4-[(2,5-dichlorophenyl)sulfonyl]-piperazine
1-[4-benzyl-1,3-thiazol-2-yl]-4-[(3,4-dichlorophenyl)sulfonyl]-piperazine
1-[4-(2-methylbenzyl)-1,3-thiazol-2-yl]-4-[(3,4-dichlorophenyl)sulfonyl]-piperazine
1-[4-(2-methoxybenzyl)-1,3-thiazol-2-yl]-4-[(3,4-dichlorophenyl)sulfonyl]-piperazine
1-[4-(3-methylbenzyl)-1,3-thiazol-2-yl]-4-[(3,4-dichlorophenyl)sulfonyl]-piperazine
1-[4-(3-methoxybenzyl)-1,3-thiazol-2-yl]-4-[(3,4-dichlorophenyl)sulfonyl]-piperazine
1-[4-(3-bromobenzyl)-1,3-thiazol-2-yl]-4-[(3,4-dichlorophenyl)sulfonyl]-piperazine
1-[4-(4-chlorobenzyl)-1,3-thiazol-2-yl]-4-[(3,4-dichlorophenyl)sulfonyl]-piperazine
1-[4-(4-methoxybenzyl)-1,3-thiazol-2-yl]-4-[(3,4-dichlorophenyl)sulfonyl]-piperazine
1-[4-(4-methylbenzyl)-1,3-thiazol-2-yl]-4-[(3,4-dichlorophenyl)sulfonyl]-piperazine
1-[4-(4-ethylbenzyl)-1,3-thiazol-2-yl]-4-[(3,4-dichlorophenyl)sulfonyl]-piperazine
1-[4-(4-ethoxybenzyl)-1,3-thiazol-2-yl]-4-[(3,4-dichlorophenyl)sulfonyl]-piperazine
1-[4-(4-propylbenzyl)-1,3-thiazol-2-yl]-4-[(3,4-dichlorophenyl)sulfonyl]-piperazine
1-[4-(2,6-dimethylbenzyl)-1,3-thiazol-2-yl]-4-[(3,4-dichlorophenyl)sulfonyl]-piperazine
1-[4-(2,3-dimethylbenzyl)-1,3-thiazol-2-yl]-4-[(3,4-dichlorophenyl)sulfonyl]-piperazine
1-[4-(2,5-dimethylbenzyl)-1,3-thiazol-2-yl]-4-[(3,4-dichlorophenyl)sulfonyl]-piperazine
1-[4-(2,4-dichlorobenzyl)-1,3-thiazol-2-yl]-4-[(3,4-dichlorophenyl)sulfonyl]-piperazine
1-[4-(2,4-dimethoxybenzyl)-1,3-thiazol-2-yl]-4-[(3,4-dichlorophenyl)sulfonyl]-piperazine
1-[4-(2,5-dimethoxybenzyl)-1,3-thiazol-2-yl]-4-[(3,4-dichlorophenyl)sulfonyl]-piperazine
1-[4-(3,4-dimethoxybenzyl)-1,3-thiazol-2-yl]-4-[(3,4-dichlorophenyl)sulfonyl]-piperazine
1-[4-(3,5-dimethoxybenzyl)-1,3-thiazol-2-yl]-4-[(3,4-dichlorophenyl)sulfonyl]-piperazine
1-[4-(3,4-dichlorobenzyl)-1,3-thiazol-2-yl]-4-[(3,4-dichlorophenyl)sulfonyl]-piperazine
1-[4-(3,4-dimethylbenzyl)-1,3-thiazol-2-yl]-4-[(3,4-dichlorophenyl)sulfonyl]-piperazine
1-[4-(3,4-difluorobenzyl)-1,3-thiazol-2-yl]-4-[(3,4-dichlorophenyl)sulfonyl]-piperazine
1-[4-(3,5-difluorobenzyl)-1,3-thiazol-2-yl]-4-[(3,4-dichlorophenyl)sulfonyl]-piperazine
1-[4-(3,5-dichlorobenzyl)-1,3-thiazol-2-yl]-4-[(3,4-dichlorophenyl)sulfonyl]-piperazine
1-[4-(3,5-dimethylbenzyl)-1,3-thiazol-2-yl]-4-[(3,4-dichlorophenyl)sulfonyl]-piperazine
1-[4-(3-chloro-4-fluorobenzyl)-1,3-thiazol-2-yl]-4-[(3,4-dichlorophenyl)sulfonyl]-piperazine
1-[4-(3-chloro-5-fluorobenzyl)-1,3-thiazol-2-yl]-4-[(3,4-dichlorophenyl)sulfonyl]-piperazine
1-[4-(4-chloro-3-fluorobenzyl)-1,3-thiazol-2-yl]-4-[(3,4-dichlorophenyl)sulfonyl]-piperazine
1-[4-(3,4,5-trimethoxybenzyl)-1,3-thiazol-2-yl]-4-[(3,4-dichlorophenyl)sulfonyl]-piperazine
1-[4-(2,4,6-trimethylbenzyl)-1,3-thiazol-2-yl]-4-[(3,4-dichlorophenyl)sulfonyl]-piperazine
1-[4-benzyl-1,3-thiazol-2-yl]-4-[(3,4-dimethoxyphenyl)sulfonyl]-piperazine
1-[4-(2-methylbenzyl)-1,3-thiazol-2-yl]-4-[(3,4-dimethoxyphenyl)sulfonyl]-piperazine
1-[4-(2-methoxybenzyl)-1,3-thiazol-2-yl]-4-[(3,4-dimethoxyphenyl)sulfonyl]-piperazine
1-[4-(3-methylbenzyl)-1,3-thiazol-2-yl]-4-[(3,4-dimethoxyphenyl)sulfonyl]-piperazine
1-[4-(3-methoxybenzyl)-1,3-thiazol-2-yl]-4-[(3,4-dimethoxyphenyl)sulfonyl]-piperazine
1-[4-(3-bromobenzyl)-1,3-thiazol-2-yl]-4-[(3,4-dimethoxyphenyl)sulfonyl]-piperazine
1-[4-(4-chlorobenzyl)-1,3-thiazol-2-yl]-4-[(3,4-dimethoxyphenyl)sulfonyl]-piperazine
1-[4-(4-methoxybenzyl)-1,3-thiazol-2-yl]-4-[(3,4-dimethoxyphenyl)sulfonyl]-piperazine
1-[4-(4-methylbenzyl)-1,3-thiazol-2-yl]-4-[(3,4-dimethoxyphenyl)sulfonyl]-piperazine 1-[4-(4-ethylbenzyl)-1,3-thiazol-2-yl]-4-[(3,4-dimethoxyphenyl)sulfonyl]-piperazine
1-[4-(4-ethoxybenzyl)-1,3-thiazol-2-yl]-4-[(3,4-dimethoxyphenyl)sulfonyl]-piperazine
1-[4-(4-propylbenzyl)-1,3-thiazol-2-yl]-4-[(3,4-dimethoxyphenyl)sulfonyl]-piperazine
1-[4-(2,6-dimethylbenzyl)-1,3-thiazol-2-yl]-4-[(3,4-dimethoxyphenyl)sulfonyl]-piperazine
1-[4-(2,3-dimethylbenzyl)-1,3-thiazol-2-yl]-4-[(3,4-dimethoxyphenyl)sulfonyl]-piperazine
1-[4-(2,5-dimethylbenzyl)-1,3-thiazol-2-yl]-4-[(3,4-dimethoxyphenyl)sulfonyl]-piperazine
1-[4-(2,4-dichlorobenzyl)-1,3-thiazol-2-yl]-4-[(3,4-dimethoxyphenyl)sulfonyl]-piperazine
1-[4-(2,4-dimethoxybenzyl)-1,3-thiazol-2-yl]-4-[(3,4-dimethoxyphenyl)sulfonyl]-piperazine
1-[4-(2,5-dimethoxybenzyl)-1,3-thiazol-2-yl]-4-[(3,4-dimethoxyphenyl)sulfonyl]-piperazine
1-[4-(3,4-dimethoxybenzyl)-1,3-thiazol-2-yl]-4-[(3,4-dimethoxyphenyl)sulfonyl]-piperazine
1-[4-(3,5-dimethoxybenzyl)-1,3-thiazol-2-yl]-4-[(3,4-dimethoxyphenyl)sulfonyl]-piperazine
1-[4-(3,4-dichlorobenzyl)-1,3-thiazol-2-yl]-4-[(3,4-dimethoxyphenyl)sulfonyl]-piperazine
1-[4-(3,4-dimethylbenzyl)-1,3-thiazol-2-yl]-4-[(3,4-dimethoxyphenyl)sulfonyl]-piperazine
1-[4-(3,4-difluorobenzyl)-1,3-thiazol-2-yl]-4-[(3,4-dimethoxyphenyl)sulfonyl]-piperazine
1-[4-(3,5-difluorobenzyl)-1,3-thiazol-2-yl]-4-[(3,4-dimethoxyphenyl)sulfonyl]-piperazine
1-[4-(3,5-dichlorobenzyl)-1,3-thiazol-2-yl]-4-[(3,4-dimethoxyphenyl)sulfonyl]-piperazine
1-[4-(3,5-dimethylbenzyl)-1,3-thiazol-2-yl]-4-[(3,4-dimethoxyphenyl)sulfonyl]-piperazine
1-[4-(3-chloro-4-fluorobenzyl)-1,3-thiazol-2-yl]-4-[(3,4-dimethoxyphenyl)sulfonyl]-piperazine
1-[4-(3-chloro-5-fluorobenzyl)-1,3-thiazol-2-yl]-4-[(3,4-dimethoxyphenyl)sulfonyl]-piperazine
1-[4-(4-chloro-3-fluorobenzyl)-1,3-thiazol-2-yl]-4-[(3,4-dimethoxyphenyl)sulfonyl]-piperazine
1-[4-(3,4,5-trimethoxybenzyl)-1,3-thiazol-2-yl]-4-[(3,4-dimethoxyphenyl)sulfonyl]-piperazine
1-[4-(2,4,6-trimethylbenzyl)-1,3-thiazol-2-yl]-4-[(3,4-dimethoxyphenyl)sulfonyl]-piperazine
1-[4-benzyl-1,3-thiazol-2-yl]-4-[(2,4-dimethoxyphenyl)sulfonyl]-piperazine
1-[4-(2-methylbenzyl)-1,3-thiazol-2-yl]-4-[(2,4-dimethoxyphenyl)sulfonyl]-piperazine
1-[4-(2-methoxybenzyl)-1,3-thiazol-2-yl]-4-[(2,4-dimethoxyphenyl)sulfonyl]-piperazine
1-[4-(3-methylbenzyl)-1,3-thiazol-2-yl]-4-[(2,4-dimethoxyphenyl)sulfonyl]-piperazine
1-[4-(3-methoxybenzyl)-1,3-thiazol-2-yl]-4-[(2,4-dimethoxyphenyl)sulfonyl]-piperazine
1-[4-(3-bromobenzyl)-1,3-thiazol-2-yl]-4-[(2,4-dimethoxyphenyl)sulfonyl]-piperazine
1-[4-(4-chlorobenzyl)-1,3-thiazol-2-yl]-4-[(2,4-dimethoxyphenyl)sulfonyl]-piperazine
1-[4-(4-methoxybenzyl)-1,3-thiazol-2-yl]-4-[(2,4-dimethoxyphenyl)sulfonyl]-piperazine
1-[4-(4-methylbenzyl)-1,3-thiazol-2-yl]-4-[(2,4-dimethoxyphenyl)sulfonyl]-piperazine
1-[4-(4-ethylbenzyl)-1,3-thiazol-2-yl]-4-[(2,4-dimethoxyphenyl)sulfonyl]-piperazine
1-[4-(4-ethoxybenzyl)-1,3-thiazol-2-yl]-4-[(2,4-dimethoxyphenyl)sulfonyl]-piperazine
1-[4-(4-propylbenzyl)-1,3-thiazol-2-yl]-4-[(2,4-dimethoxyphenyl)sulfonyl]-piperazine
1-[4-(2,6-dimethylbenzyl)-1,3-thiazol-2-yl]-4-[(2,4-dimethoxyphenyl)sulfonyl]-piperazine
1-[4-(2,3-dimethylbenzyl)-1,3-thiazol-2-yl]-4-[(2,4-dimethoxyphenyl)sulfonyl]-piperazine
1-[4-(2,5-dimethylbenzyl)-1,3-thiazol-2-yl]-4-[(2,4-dimethoxyphenyl)sulfonyl]-piperazine
1-[4-(2,4-dichlorobenzyl)-1,3-thiazol-2-yl]-4-[(2,4-dimethoxyphenyl)sulfonyl]-piperazine
1-[4-(2,4-dimethoxybenzyl)-1,3-thiazol-2-yl]-4-[(2,4-dimethoxyphenyl)sulfonyl]-piperazine
1-[4-(2,5-dimethoxybenzyl)-1,3-thiazol-2-yl]-4-[(2,4-dimethoxyphenyl)sulfonyl]-piperazine
1-[4-(3,4-dimethoxybenzyl)-1,3-thiazol-2-yl]-4-[(2,4-dimethoxyphenyl)sulfonyl]-piperazine
1-[4-(3,5-dimethoxybenzyl)-1,3-thiazol-2-yl]-4-[(2,4-dimethoxyphenyl)sulfonyl]-piperazine
1-[4-(3,4-dichlorobenzyl)-1,3-thiazol-2-yl]-4-[(2,4-dimethoxyphenyl)sulfonyl]-piperazine
1-[4-(3,4-dimethylbenzyl)-1,3-thiazol-2-yl]-4-[(2,4-dimethoxyphenyl)sulfonyl]-piperazine
1-[4-(3,4-difluorobenzyl)-1,3-thiazol-2-yl]-4-[(2,4-dimethoxyphenyl)sulfonyl]-piperazine
1-[4-(3,5-difluorobenzyl)-1,3-thiazol-2-yl]-4-[(2,4-dimethoxyphenyl)sulfonyl]-piperazine
1-[4-(3,5-dichlorobenzyl)-1,3-thiazol-2-yl]-4-[(2,4-dimethoxyphenyl)sulfonyl]-piperazine
1-[4-(3,5-dimethylbenzyl)-1,3-thiazol-2-yl]-4-[(2,4-dimethoxyphenyl)sulfonyl]-piperazine
1-[4-(3-chloro-4-flourobenzyl))-1,3-thiazol-2-yl]-4-[(2,4-dimethoxyphenyl)sulfonyl]-piperazine
1-[4-(3-chloro-5-fluorobenzyl)-1,3-thiazol-2-yl]-4-[(2,4-dimethoxyphenyl)sulfonyl]-piperazine
1-[4-(4-chloro-3-fluorobenzyl)-1,3-thiazol-2-yl]-4-[(2,4-dimethoxyphenyl)sulfonyl]-piperazine
1-[4-(3,4,5-trimethoxybenzyl)-1,3-thiazol-2-yl]-4-[(2,4-dimethoxyphenyl)sulfonyl]-piperazine
1-[4-(2,4,6-trimethylbenzyl)-1,3-thiazol-2-yl]-4-[(2,4-dimethoxyphenyl)sulfonyl]-piperazine
1-[4-benzyl-1,3-thiazol-2-yl]-4-[(2,5-dimethoxyphenyl)sulfonyl]-piperazine
1-[4-(2-methylbenzyl)-1,3-thiazol-2-yl]-4-[(2,5-dimethoxyphenyl)sulfonyl]-piperazine
1-[4-(2-methoxybenzyl)-1,3-thiazol-2-yl]-4-[(2,5-dimethoxyphenyl)sulfonyl]-piperazine
1-[4-(3-methylbenzyl)-1,3-thiazol-2-yl]-4-[(2,5-dimethoxyphenyl)sulfonyl]-piperazine
1-[4-(3-methoxybenzyl)-1,3-thiazol-2-yl]-4-[(2,5-dimethoxyphenyl)sulfonyl]-piperazine
1-[4-(3-bromobenzyl)-1,3-thiazol-2-yl]-4-[(2,5-dimethoxyphenyl)sulfonyl]-piperazine
1-[4-(4-chlorobenzyl)-1,3-thiazol-2-yl]-4-[(2,5-dimethoxyphenyl)sulfonyl]-piperazine
1-[4-(4-methoxybenzyl)-1,3-thiazol-2-yl]-4-[(2,5-dimethoxyphenyl)sulfonyl]-piperazine
1-[4-(4-methylbenzyl)-1,3-thiazol-2-yl]-4-[(2,5-dimethoxyphenyl)sulfonyl]-piperazine
1-[4-(4-ethylbenzyl)-1,3-thiazol-2-yl]-4-[(2,5-dimethoxyphenyl)sulfonyl]-piperazine
1-[4-(4-ethoxybenzyl)-1,3-thiazol-2-yl]-4-[(2,5-dimethoxyphenyl)sulfonyl]-piperazine
1-[4-(4-propylbenzyl)-1,3-thiazol-2-yl]-4-[(2,5-dimethoxyphenyl)sulfonyl]-piperazine
1-[4-(2,6-dimethylbenzyl)-1,3-thiazol-2-yl]-4-[(2,5-dimethoxyphenyl)sulfonyl]-piperazine 1-[4-(2,3-dimethylbenzyl)-1,3-thiazol-2-yl]-4-[(2,5-dimethoxyphenyl)sulfonyl]-piperazine
1-[4-(2,5-dimethylbenzyl)-1,3-thiazol-2-yl]-4-[(2,5-dimethoxyphenyl)sulfonyl]-piperazine
1-[4-(2,4-dichlorobenzyl)-1,3-thiazol-2-yl]-4-[(2,5-dimethoxyphenyl)sulfonyl]-piperazine
1-[4-(2,4-dimethoxybenzyl)-1,3-thiazol-2-yl]-4-[(2,5-dimethoxyphenyl)sulfonyl]-piperazine
1-[4-(2,5-dimethoxybenzyl)-1,3-thiazol-2-yl]-4-[(2,5-dimethoxyphenyl)sulfonyl]-piperazine
1-[4-(3,4-dimethoxybenzyl)-1,3-thiazol-2-yl]-4-[(2,5-dimethoxyphenyl)sulfonyl]-piperazine
1-[4-(3,5-dimethoxybenzyl)-1,3-thiazol-2-yl]-4-[(2,5-dimethoxyphenyl)sulfonyl]-piperazine
1-[4-(3,4-dichlorobenzyl)-1,3-thiazol-2-yl]-4-[(2,5-dimethoxyphenyl)sulfonyl]-piperazine
1-[4-(3,4-dimethylbenzyl)-1,3-thiazol-2-yl]-4-[(2,5-dimethoxyphenyl)sulfonyl]-piperazine
1-[4-(3,4-difluorobenzyl)-1,3-thiazol-2-yl]-4-[(2,5-dimethoxyphenyl)sulfonyl]-piperazine
1-[4-(3,5-difluorobenzyl)-1,3-thiazol-2-yl]-4-[(2,5-dimethoxyphenyl)sulfonyl]-piperazine
1-[4-(3,5-dichlorobenzyl)-1,3-thiazol-2-yl]-4-[(2,5-dimethoxyphenyl)sulfonyl]-piperazine
1-[4-(3,5-dimethylbenzyl)-1,3-thiazol-2-yl]-4-[(2,5-dimethoxyphenyl)sulfonyl]-piperazine
1-[4-(3-chloro-4-fluorobenzyl)-1,3-thiazol-2-yl]-4-[(2,5-dimethoxyphenyl)sulfonyl]-piperazine
1-[4-(3-chloro-5-fluorobenzyl)-1,3-thiazol-2-yl]-4-[(2,5-dimethoxyphenyl)sulfonyl]-piperazine
1-[4-(4-chloro-3-fluorobenzyl)-1,3-thiazol-2-yl]-4-[(2,5-dimethoxyphenyl)sulfonyl]-piperazine
1-[4-(3,4,5-trimethoxybenzyl)-1,3-thiazol-2-yl]-4-[(2,5-dimethoxyphenyl)sulfonyl]-piperazine
1-[4-(2,4,6-trimethylbenzyl)-1,3-thiazol-2-yl]-4-[(2,5-dimethoxyphenyl)sulfonyl]-piperazine
1-[4-benzyl-1,3-thiazol-2-yl]-4-[(3,5-dichlorophenyl)sulfonyl]-piperazine
1-[4-(2-methylbenzyl)-1,3-thiazol-2-yl]-4-[(3,5-dichlorophenyl)sulfonyl]-piperazine
1-[4-(2-methoxybenzyl)-1,3-thiazol-2-yl]-4-[(3,5-dichlorophenyl)sulfonyl]-piperazine
1-[4-(3-methylbenzyl)-1,3-thiazol-2-yl]-4-[(3,5-dichlorophenyl)sulfonyl]-piperazine
1-[4-(3-methoxybenzyl)-1,3-thiazol-2-yl]-4-[(3,5-dichlorophenyl)sulfonyl]-piperazine
1-[4-(3-bromobenzyl)-1,3-thiazol-2-yl]-4-[(3,5-dichlorophenyl)sulfonyl]-piperazine
1-[4-(4-chlorobenzyl)-1,3-thiazol-2-yl]-4-[(3,5-dichlorophenyl)sulfonyl]-piperazine
1-[4-(4-methoxybenzyl)-1,3-thiazol-2-yl]-4-[(3,5-dichlorophenyl)sulfonyl]-piperazine
1-[4-(4-methylbenzyl)-1,3-thiazol-2-yl]-4-[(3,5-dichlorophenyl)sulfonyl]-piperazine
1-[4-(4-ethylbenzyl)-1,3-thiazol-2-yl]-4-[(3,5-dichlorophenyl)sulfonyl]-piperazine
1-[4-(4-ethoxybenzyl)-1,3-thiazol-2-yl]-4-[(3,5-dichlorophenyl)sulfonyl]-piperazine
1-[4-(4-propylbenzyl)-1,3-thiazol-2-yl]-4-[(3,5-dichlorophenyl)sulfonyl]-piperazine
1-[4-(2,6-dimethylbenzyl)-1,3-thiazol-2-yl]-4-[(3,5-dichlorophenyl)sulfonyl]-piperazine
1-[4-(2,3-dimethylbenzyl)-1,3-thiazol-2-yl]-4-[(3,5-dichlorophenyl)sulfonyl]-piperazine
1-[4-(2,5-dimethylbenzyl)-1,3-thiazol-2-yl]-4-[(3,5-dichlorophenyl)sulfonyl]-piperazine
1-[4-(2,4-dichlorobenzyl)-1,3-thiazol-2-yl]-4-[(3,5-dichlorophenyl)sulfonyl]-piperazine
1-[4-(2,4-dimethoxybenzyl)-1,3-thiazol-2-yl]-4-[(3,5-dichlorophenyl)sulfonyl]-piperazine
1-[4-(2,5-dimethoxybenzyl)-1,3-thiazol-2-yl]-4-[(3,5-dichlorophenyl)sulfonyl]-piperazine
1-[4-(3,4-dimethoxybenzyl)-1,3-thiazol-2-yl]-4-[(3,5-dichlorophenyl)sulfonyl]-piperazine
1-[4-(3,5-dimethoxybenzyl)-1,3-thiazol-2-yl]-4-[(3,5-dichlorophenyl)sulfonyl]-piperazine
1-[4-(3,4-dichlorobenzyl)-1,3-thiazol-2-yl]-4-[(3,5-dichlorophenyl)sulfonyl]-piperazine
1-[4-(3,4-dimethylbenzyl)-1,3-thiazol-2-yl]-4-[(3,5-dichlorophenyl)sulfonyl]-piperazine
1-[4-(3,4-difluorobenzyl)-1,3-thiazol-2-yl]-4-[(3,5-dichlorophenyl)sulfonyl]-piperazine
1-[4-(3,5-difluorobenzyl)-1,3-thiazol-2-yl]-4-[(3,5-dichlorophenyl)sulfonyl]-piperazine
1-[4-(3,5-dichlorobenzyl)-1,3-thiazol-2-yl]-4-[(3,5-dichlorophenyl)sulfonyl]-piperazine
1-[4-(3,5-dimethylbenzyl)-1,3-thiazol-2-yl]-4-[(3,5-dichlorophenyl)sulfonyl]-piperazine
1-[4-(3-chloro-4-fluorobenzyl)-1,3-thiazol-2-yl]-4-[(3,5-dichlorophenyl)sulfonyl]-piperazine
1-[4-(3-chloro-5-fluorobenzyl)-1,3-thiazol-2-yl]-4-[(3,5-dichlorophenyl)sulfonyl]-piperazine
1-[4-(4-chloro-3-fluorobenzyl)-1,3-thiazol-2-yl]-4-[(3,5-dichlorophenyl)sulfonyl]-piperazine
1-[4-(3,4,5-trimethoxybenzyl)-1,3-thiazol-2-yl]-4-[(3,5-dichlorophenyl)sulfonyl]-piperazine
1-[4-(2,4,6-trimethylbenzyl)-1,3-thiazol-2-yl]-4-[(3,5-dichlorophenyl)sulfonyl]-piperazine
1-[4-benzyl-1,3-thiazol-2-yl]-4-[(2,3-dichlorophenyl)sulfonyl]-piperazine
1-[4-(2-methylbenzyl)-1,3-thiazol-2-yl]-4-[(2,3-dichlorophenyl)sulfonyl]-piperazine
1-[4-(2-methoxybenzyl)-1,3-thiazol-2-yl]-4-[(2,3-dichlorophenyl)sulfonyl]-piperazine
1-[4-(3-methylbenzyl)-1,3-thiazol-2-yl]-4-[(2,3-dichlorophenyl)sulfonyl]-piperazine
1-[4-(3-methoxybenzyl)-1,3-thiazol-2-yl]-4-[(2,3-dichlorophenyl)sulfonyl]-piperazine
1-[4-(3-bromobenzyl)-1,3-thiazol-2-yl]-4-[(2,3-dichlorophenyl)sulfonyl]-piperazine
1-[4-(4-chlorobenzyl)-1,3-thiazol-2-yl]-4-[(2,3-dichlorophenyl)sulfonyl]-piperazine
1-[4-(4-methoxybenzyl)-1,3-thiazol-2-yl]-4-[(2,3-dichlorophenyl)sulfonyl]-piperazine
1-[4-(4-methylbenzyl)-1,3-thiazol-2-yl]-4-[(2,3-dichlorophenyl)sulfonyl]-piperazine
1-[4-(4-ethylbenzyl)-1,3-thiazol-2-yl]-4-[(2,3-dichlorophenyl)sulfonyl]-piperazine
1-[4-(4-ethoxybenzyl)-1,3-thiazol-2-yl]-4-[(2,3-dichlorophenyl)sulfonyl]-piperazine
1-[4-(4-propylbenzyl)-1,3-thiazol-2-yl]-4-[(2,3-dichlorophenyl)sulfonyl]-piperazine
1-[4-(2,6-dimethylbenzyl)-1,3-thiazol-2-yl]-4-[(2,3-dichlorophenyl)sulfonyl]-piperazine
1-[4-(2,3-dimethylbenzyl)-1,3-thiazol-2-yl]-4-[(2,3-dichlorophenyl)sulfonyl]-piperazine
1-[4-(2,5-dimethylbenzyl)-1,3-thiazol-2-yl]-4-[(2,3-dichlorophenyl)sulfonyl]-piperazine
1-[4-(2,4-dichlorobenzyl)-1,3-thiazol-2-yl]-4-[(2,3-dichlorophenyl)sulfonyl]-piperazine
1-[4-(2,4-dimethoxybenzyl)-1,3-thiazol-2-yl]-4-[(2,3-dichlorophenyl)sulfonyl]-piperazine 1-[4-(2,5-dimethoxybenzyl)-1,3-thiazol-2-yl]-4-[(2,3-dichlorophenyl)sulfonyl]-piperazine
1-[4-(3,4-dimethoxybenzyl)-1,3-thiazol-2-yl]-4-[(2,3-dichlorophenyl)sulfonyl]-piperazine
1-[4-(3,5-dimethoxybenzyl)-1,3-thiazol-2-yl]-4-[(2,3-dichlorophenyl)sulfonyl]-piperazine
1-[4-(3,4-dichlorobenzyl)-1,3-thiazol-2-yl]-4-[(2,3-dichlorophenyl)sulfonyl]-piperazine
1-[4-(3,4-dimethylbenzyl)-1,3-thiazol-2-yl]-4-[(2,3-dichlorophenyl)sulfonyl]-piperazine
1-[4-(3,4-difluorobenzyl)-1,3-thiazol-2-yl]-4-[(2,3-dichlorophenyl)sulfonyl]-piperazine
1-[4-(3,5-difluorobenzyl)-1,3-thiazol-2-yl]-4-[(2,3-dichlorophenyl)sulfonyl]-piperazine
1-[4-(3,5-dichlorobenzyl)-1,3-thiazol-2-yl]-4-[(2,3-dichlorophenyl)sulfonyl]-piperazine
1-[4-(3,5-dimethylbenzyl)-1,3-thiazol-2-yl]-4-[(2,3-dichlorophenyl)sulfonyl]-piperazine
1-[4-(3-chloro-4-fluorobenzyl)-1,3-thiazol-2-yl]-4-[(2,3-dichlorophenyl)sulfonyl]-piperazine
1-[4-(3-chloro-5-fluorobenzyl)-1,3-thiazol-2-yl]-4-[(2,3-dichlorophenyl)sulfonyl]-piperazine
1-[4-(4-chloro-3-fluorobenzyl)-1,3-thiazol-2-yl]-4-[(2,3-dichlorophenyl)sulfonyl]-piperazine
1-[4-(3,4,5-trimethoxybenzyl)-1,3-thiazol-2-yl]-4-[(2,3-dichlorophenyl)sulfonyl]-piperazine
1-[4-(2,4,6-trimethylbenzyl)-1,3-thiazol-2-yl]-4-[(2,3-dichlorophenyl)sulfonyl]-piperazine
1-[4-benzyl-1,3-thiazol-2-yl]-4-[(2,6-difluorophenyl)sulfonyl]-piperazine
1-[4-(2-methylbenzyl)-1,3-thiazol-2-yl]-4-[(2,6-difluorophenyl)sulfonyl]-piperazine
1-[4-(2-methoxybenzyl)-1,3-thiazol-2-yl]-4-[(2,6-difluorophenyl)sulfonyl]-piperazine
1-[4-(3-methylbenzyl)-1,3-thiazol-2-yl]-4-[(2,6-difluorophenyl)sulfonyl]-piperazine
1-[4-(3-methoxybenzyl)-1,3-thiazol-2-yl]-4-[(2,6-difluorophenyl)sulfonyl]-piperazine
1-[4-(3-bromobenzyl)-1,3-thiazol-2-yl]-4-[(2,6-difluorophenyl)sulfonyl]-piperazine
1-[4-(4-chlorobenzyl)-1,3-thiazol-2-yl]-4-[(2,6-difluorophenyl)sulfonyl]-piperazine
1-[4-(4-methoxybenzyl)-1,3-thiazol-2-yl]-4-[(2,6-difluorophenyl)sulfonyl]-piperazine
1-[4-(4-methylbenzyl)-1,3-thiazol-2-yl]-4-[(2,6-difluorophenyl)sulfonyl]-piperazine
1-[4-(4-ethylbenzyl)-1,3-thiazol-2-yl]-4-[(2,6-difluorophenyl)sulfonyl]-piperazine
1-[4-(4-ethoxybenzyl)-1,3-thiazol-2-yl]-4-[(2,6-difluorophenyl)sulfonyl]-piperazine
1-[4-(4-propylbenzyl)-1,3-thiazol-2-yl]-4-[(2,6-difluorophenyl)sulfonyl]-piperazine
1-[4-(2,6-dimethylbenzyl)-1,3-thiazol-2-yl]-4-[(2,6-difluorophenyl)sulfonyl]-piperazine
1-[4-(2,3-dimethylbenzyl)-1,3-thiazol-2-yl]-4-[(2,6-difluorophenyl)sulfonyl]-piperazine
1-[4-(2,5-dimethylbenzyl)-1,3-thiazol-2-yl]-4-[(2,6-difluorophenyl)sulfonyl]-piperazine
1-[4-(2,4-dichlorobenzyl)-1,3-thiazol-2-yl]-4-[(2,6-difluorophenyl)sulfonyl]-piperazine
1-[4-(2,4-dimethoxybenzyl)-1,3-thiazol-2-yl]-4-[(2,6-difluorophenyl)sulfonyl]-piperazine
1-[4-(2,5-dimethoxybenzyl)-1,3-thiazol-2-yl]-4-[(2,6-difluorophenyl)sulfonyl]-piperazine
1-[4-(3,4-dimethoxybenzyl)-1,3-thiazol-2-yl]-4-[(2,6-difluorophenyl)sulfonyl]-piperazine
1-[4-(3,5-dimethoxybenzyl)-1,3-thiazol-2-yl]-4-[(2,6-difluorophenyl)sulfonyl]-piperazine
1-[4-(3,4-dichlorobenzyl)-1,3-thiazol-2-yl]-4-[(2,6-difluorophenyl)sulfonyl]-piperazine
1-[4-(3,4-dimethylbenzyl)-1,3-thiazol-2-yl]-4-[(2,6-difluorophenyl)sulfonyl]-piperazine
1-[4-(3,4-difluorobenzyl)-1,3-thiazol-2-yl]-4-[(2,6-difluorophenyl)sulfonyl]-piperazine
1-[4-(3,5-difluorobenzyl)-1,3-thiazol-2-yl]-4-[(2,6-difluorophenyl)sulfonyl]-piperazine
1-[4-(3,5-dichlorobenzyl)-1,3-thiazol-2-yl]-4-[(2,6-difluorophenyl)sulfonyl]-piperazine
1-[4-(3,5-dimethylbenzyl)-1,3-thiazol-2-yl]-4-[(2,6-difluorophenyl)sulfonyl]-piperazine
1-[4-(3-chloro-4-fluorobenzyl)-1,3-thiazol-2-yl]-4-[(2,6-difluorophenyl)sulfonyl]-piperazine
1-[4-(3-chloro-5-fluorobenzyl)-1,3-thiazol-2-yl]-4-[(2,6-difluorophenyl)sulfonyl]-piperazine
1-[4-(4-chloro-3-fluorobenzyl)-1,3-thiazol-2-yl]-4-[(2,6-difluorophenyl)sulfonyl]-piperazine
1-[4-(3,4,5-trimethoxybenzyl)-1,3-thiazol-2-yl]-4-[(2,6-difluorophenyl)sulfonyl]-piperazine
1-[4-(2,4,6-trimethylbenzyl)-1,3-thiazol-2-yl]-4-[(2,6-difluorophenyl)sulfonyl]-piperazine
1-[4-benzyl-1,3-thiazol-2-yl]-4-[(2,4-difluorophenyl)sulfonyl]-piperazine
1-[4-(2-methylbenzyl)-1,3-thiazol-2-yl]-4-[(2,4-difluorophenyl)sulfonyl]-piperazine
1-[4-(2-methoxybenzyl)-1,3-thiazol-2-yl]-4-[(2,4-difluorophenyl)sulfonyl]-piperazine
1-[4-(3-methylbenzyl)-1,3-thiazol-2-yl]-4-[(2,4-difluorophenyl)sulfonyl]-piperazine
1-[4-(3-methoxybenzyl)-1,3-thiazol-2-yl]-4-[(2,4-difluorophenyl)sulfonyl]-piperazine
1-[4-(3-bromobenzyl)-1,3-thiazol-2-yl]-4-[(2,4-difluorophenyl)sulfonyl]-piperazine
1-[4-(4-chlorobenzyl)-1,3-thiazol-2-yl]-4-[(2,4-difluorophenyl)sulfonyl]-piperazine
1-[4-(4-methoxybenzyl)-1,3-thiazol-2-yl]-4-[(2,4-difluorophenyl)sulfonyl]-piperazine
1-[4-(4-methylbenzyl)-1,3-thiazol-2-yl]-4-[(2,4-difluorophenyl)sulfonyl]-piperazine
1-[4-(4-ethylbenzyl)-1,3-thiazol-2-yl]-4-[(2,4-difluorophenyl)sulfonyl]-piperazine
1-[4-(4-ethoxybenzyl)-1,3-thiazol-2-yl]-4-[(2,4-difluorophenyl)sulfonyl]-piperazine
1-[4-(4-propylbenzyl)-1,3-thiazol-2-yl]-4-[(2,4-difluorophenyl)sulfonyl]-piperazine
1-[4-(2,6-dimethylbenzyl)-1,3-thiazol-2-yl]-4-[(2,4-difluorophenyl)sulfonyl]-piperazine
1-[4-(2,3-dimethylbenzyl)-1,3-thiazol-2-yl]-4-[(2,4-difluorophenyl)sulfonyl]-piperazine
1-[4-(2,5-dimethylbenzyl)-1,3-thiazol-2-yl]-4-[(2,4-difluorophenyl)sulfonyl]-piperazine
1-[4-(2,4-dichlorobenzyl)-1,3-thiazol-2-yl]-4-[(2,4-difluorophenyl)sulfonyl]-piperazine
1-[4-(2,4-dimethoxybenzyl)-1,3-thiazol-2-yl]-4-[(2,4-difluorophenyl)sulfonyl]-piperazine
1-[4-(2,5-dimethoxybenzyl)-1,3-thiazol-2-yl]-4-[(2,4-difluorophenyl)sulfonyl]-piperazine
1-[4-(3,4-dimethoxybenzyl)-1,3-thiazol-2-yl]-4-[(2,4-difluorophenyl)sulfonyl]-piperazine
1-[4-(3,5-dimethoxybenzyl)-1,3-thiazol-2-yl]-4-[(2,4-difluorophenyl)sulfonyl]-piperazine
1-[4-(3,4-dichlorobenzyl)-1,3-thiazol-2-yl]-4-[(2,4-difluorophenyl)sulfonyl]-piperazine 1-[4-(3,4-dimethylbenzyl)-1,3-thiazol-2-yl]-4-[(2,4-difluorophenyl)sulfonyl]-piperazine
1-[4-(3,4-difluorobenzyl)-1,3-thiazol-2-yl]-4-[(2,4-difluorophenyl)sulfonyl]-piperazine
1-[4-(3,5-difluorobenzyl)-1,3-thiazol-2-yl]-4-[(2,4-difluorophenyl)sulfonyl]-piperazine
1-[4-(3,5-dichlorobenzyl)-1,3-thiazol-2-yl]-4-[(2,4-difluorophenyl)sulfonyl]-piperazine
1-[4-(3,5-dimethylbenzyl)-1,3-thiazol-2-yl]-4-[(2,4-difluorophenyl)sulfonyl]-piperazine
1-[4-(3-chloro-4-fluorobenzyl)-1,3-thiazol-2-yl]-4-[(2,4-difluorophenyl)sulfonyl]-piperazine
1-[4-(3-chloro-5-fluorobenzyl)-1,3-thiazol-2-yl]-4-[(2,4-difluorophenyl)sulfonyl]-piperazine
1-[4-(4-chloro-3-fluorobenzyl)-1,3-thiazol-2-yl]-4-[(2,4-difluorophenyl)sulfonyl]-piperazine
1-[4-(3,4,5-trimethoxybenzyl)-1,3-thiazol-2-yl]-4-[(2,4-difluorophenyl)sulfonyl]-piperazine
1-[4-(2,4,6-trimethylbenzyl)-1,3-thiazol-2-yl]-4-[(2,4-difluorophenyl)sulfonyl]-piperazine
1-[4-benzyl-1,3-thiazol-2-yl]-4-[(4-(bromomethyl)phenyl)sulfonyl]-piperazine
1-[4-(2-methylbenzyl)-1,3-thiazol-2-yl]-4-[(4-(bromomethyl)phenyl)sulfonyl]-piperazine
1-[4-(2-methoxybenzyl)-1,3-thiazol-2-yl]-4-[(4-(bromomethyl)phenyl)sulfonyl]-piperazine
1-[4-(3-methylbenzyl)-1,3-thiazol-2-yl]-4-[(4-(bromomethyl)phenyl)sulfonyl]-piperazine
1-[4-(3-methoxybenzyl)-1,3-thiazol-2-yl]-4-[(4-(bromomethyl)phenyl)sulfonyl]-piperazine
1-[4-(3-bromobenzyl)-1,3-thiazol-2-yl]-4-[(4-(bromomethyl)phenyl)sulfonyl]-piperazine
1-[4-(4-chlorobenzyl)-1,3-thiazol-2-yl]-4-[(4-(bromomethyl)phenyl)sulfonyl]-piperazine
1-[4-(4-methoxybenzyl)-1,3-thiazol-2-yl]-4-[(4-(bromomethyl)phenyl)sulfonyl]-piperazine
1-[4-(4-methylbenzyl)-1,3-thiazol-2-yl]-4-[(4-(bromomethyl)phenyl)sulfonyl]-piperazine
1-[4-(4-ethylbenzyl)-1,3-thiazol-2-yl]-4-[(4-(bromomethyl)phenyl)sulfonyl]-piperazine
1-[4-(4-ethoxybenzyl)-1,3-thiazol-2-yl]-4-[(4-(bromomethyl)phenyl)sulfonyl]-piperazine
1-[4-(4-propylbenzyl)-1,3-thiazol-2-yl]-4-[(4-(bromomethyl)phenyl)sulfonyl]-piperazine
1-[4-(2,6-dimethylbenzyl)-1,3-thiazol-2-yl]-4-[(4-(bromomethyl)phenyl)sulfonyl]-piperazine
1-[4-(2,3-dimethylbenzyl)-1,3-thiazol-2-yl]-4-[(4-(bromomethyl)phenyl)sulfonyl]-piperazine
1-[4-(2,5-dimethylbenzyl)-1,3-thiazol-2-yl]-4-[(4-(bromomethyl)phenyl)sulfonyl]-piperazine
1-[4-(2,4-dichlorobenzyl)-1,3-thiazol-2-yl]-4-[(4-(bromomethyl)phenyl)sulfonyl]-piperazine
1-[4-(2,4-dimethoxybenzyl)-1,3-thiazol-2-yl]-4-[(4-(bromomethyl)phenyl)sulfonyl]-piperazine
1-[4-(2,5-dimethoxybenzyl)-1,3-thiazol-2-yl]-4-[(4-(bromomethyl)phenyl)sulfonyl]-piperazine
1-[4-(3,4-dimethoxybenzyl)-1,3-thiazol-2-yl]-4-[(4-(bromomethyl)phenyl)sulfonyl]-piperazine
1-[4-(3,5-dimethoxybenzyl)-1,3-thiazol-2-yl]-4-[(4-(bromomethyl)phenyl)sulfonyl]-piperazine
1-[4-(3,4-dichlorobenzyl)-1,3-thiazol-2-yl]-4-[(4-(bromomethyl)phenyl)sulfonyl]-piperazine
1-[4-(3,4-dimethylbenzyl)-1,3-thiazol-2-yl]-4-[(4-(bromomethyl)phenyl)sulfonyl]-piperazine
1-[4-(3,4-difluorobenzyl)-1,3-thiazol-2-yl]-4-[(4-(bromomethyl)phenyl)sulfonyl]-piperazine
1-[4-(3,5-difluorobenzyl)-1,3-thiazol-2-yl]-4-[(4-(bromomethyl)phenyl)sulfonyl]-piperazine
1-[4-(3,5-dichlorobenzyl)-1,3-thiazol-2-yl]-4-[(4-(bromomethyl)phenyl)sulfonyl]-piperazine
1-[4-(3,5-dimethylbenzyl)-1,3-thiazol-2-yl]-4-[(4-(bromomethyl)phenyl)sulfonyl]-piperazine
1-[4-(3-chloro-4-fluorobenzyl)-1,3-thiazol-2-yl]-4-[(4-(bromomethyl)phenyl)sulfonyl]-piperazine
1-[4-(3-chloro-5-fluorobenzyl)-1,3-thiazol-2-yl]-4-[(4-(bromomethyl)phenyl)sulfonyl]-piperazine
1-[4-(4-chloro-3-fluorobenzyl)-1,3-thiazol-2-yl]-4-[(4-(bromomethyl)phenyl)sulfonyl]-piperazine
1-[4-(3,4,5-trimethoxybenzyl)-1,3-thiazol-2-yl]-4-[(4-(bromomethyl)phenyl)sulfonyl]-piperazine
1-[4-(2,4,6-trimethylbenzyl)-1,3-thiazol-2-yl]-4-[(4-(bromomethyl)phenyl)sulfonyl]-piperazine
1-[4-benzyl-1,3-thiazol-2-yl]-4-[(3-(trifluoromethyl)phenyl)sulfonyl]-piperazine
1-[4-(2-methylbenzyl)-1,3-thiazol-2-yl]-4-[(3-(trifluoromethyl)phenyl)sulfonyl]-piperazine
1-[4-(2-methoxybenzyl)-1,3-thiazol-2-yl]-4-[(3-(trifluoromethyl)phenyl)sulfonyl]-piperazine
1-[4-(3-methylbenzyl)-1,3-thiazol-2-yl]-4-[(3-(trifluoromethyl)phenyl)sulfonyl]-piperazine
1-[4-(3-methoxybenzyl)-1,3-thiazol-2-yl]-4-[(3-(trifluoromethyl)phenyl)sulfonyl]-piperazine
1-[4-(3-bromobenzyl)-1,3-thiazol-2-yl]-4-[(3-(trifluoromethyl)phenyl)sulfonyl]-piperazine
1-[4-(4-chlorobenzyl)-1,3-thiazol-2-yl]-4-[(3-(trifluoromethyl)phenyl)sulfonyl]-piperazine
1-[4-(4-methoxybenzyl)-1,3-thiazol-2-yl]-4-[(3-(trifluoromethyl)phenyl)sulfonyl]-piperazine
1-[4-(4-methylbenzyl)-1,3-thiazol-2-yl]-4-[(3-(trifluoromethyl)phenyl)sulfonyl]-piperazine
1-[4-(4-ethylbenzyl)-1,3-thiazol-2-yl]-4-[(3-(trifluoromethyl)phenyl)sulfonyl]-piperazine
1-[4-(4-ethoxybenzyl)-1,3-thiazol-2-yl]-4-[(3-(trifluoromethyl)phenyl)sulfonyl]-piperazine
1-[4-(4-propylbenzyl)-1,3-thiazol-2-yl]-4-[(3-(trifluoromethyl)phenyl)sulfonyl]-piperazine
1-[4-(2,6-dimethylbenzyl)-1,3-thiazol-2-yl]-4-[(3-(trifluoromethyl)phenyl)sulfonyl]-piperazine
1-[4-(2,3-dimethylbenzyl)-1,3-thiazol-2-yl]-4-[(3-(trifluoromethyl)phenyl)sulfonyl]-piperazine
1-[4-(2,5-dimethylbenzyl)-1,3-thiazol-2-yl]-4-[(3-(trifluoromethyl)phenyl)sulfonyl]-piperazine
1-[4-(2,4-dichlorobenzyl)-1,3-thiazol-2-yl]-4-[(3-(trifluoromethyl)phenyl)sulfonyl]-piperazine
1-[4-(2,4-dimethoxybenzyl)-1,3-thiazol-2-yl]-4-[(3-(trifluoromethyl)phenyl)sulfonyl]-piperazine
1-[4-(2,5-dimethoxybenzyl)-1,3-thiazol-2-yl]-4-[(3-(trifluoromethyl)phenyl)sulfonyl]-piperazine
1-[4-(3,4-dimethoxybenzyl)-1,3-thiazol-2-yl]-4-[(3-(trifluoromethyl)phenyl)sulfonyl]-piperazine
1-[4-(3,5-dimethoxybenzyl)-1,3-thiazol-2-yl]-4-[(3-(trifluoromethyl)phenyl)sulfonyl]-piperazine
1-[4-(3,4-dichlorobenzyl)-1,3-thiazol-2-yl]-4-[(3-(trifluoromethyl)phenyl)sulfonyl]-piperazine
1-[4-(3,4-dimethylbenzyl)-1,3-thiazol-2-yl]-4-[(3-(trifluoromethyl)phenyl)sulfonyl]-piperazine
1-[4-(3,4-difluorobenzyl)-1,3-thiazol-2-yl]-4-[(3-(trifluoromethyl)phenyl)sulfonyl]-piperazine
1-[4-(3,5-difluorobenzyl)-1,3-thiazol-2-yl]-4-[(3-(trifluoromethyl)phenyl)sulfonyl]-piperazine
1-[4-(3,5-dichlorobenzyl)-1,3-thiazol-2-yl]-4-[(3-(trifluoromethyl)phenyl)sulfonyl]-piperazine 1-[4-(3,5-dimethylbenzyl)-1,3-thiazol-2-yl]-4-[(3-(trifluoromethyl)phenyl)sulfonyl]-piperazine
1-[4-(3-chloro-4-fluorobenzyl)-1,3-thiazol-2-yl]-4-[(3-(trifluoromethyl)phenyl)sulfonyl]-piperazine
1-[4-(3-chloro-5-fluorobenzyl)-1,3-thiazol-2-yl]-4-[(3-(trifluoromethyl)phenyl)sulfonyl]-piperazine
1-[4-(4-chloro-3-fluorobenzyl)-1,3-thiazol-2-yl]-4-[(3-(trifluoromethyl)phenyl)sulfonyl]-piperazine
1-[4-(3,4,5-trimethoxybenzyl)-1,3-thiazol-2-yl]-4-[(3-(trifluoromethyl)phenyl)sulfonyl]-piperazine
1-[4-(2,4,6-trimethylbenzyl)-1,3-thiazol-2-yl]-4-[(3-(trifluoromethyl)phenyl)sulfonyl]-piperazine
1-[4-benzyl-1,3-thiazol-2-yl]-4-[(2-(trifluoromethyl)phenyl)sulfonyl]-piperazine
1-[4-(2-methylbenzyl)-1,3-thiazol-2-yl]-4-[(2-(trifluoromethyl)phenyl)sulfonyl]-piperazine
1-[4-(2-methoxybenzyl)-1,3-thiazol-2-yl]-4-[(2-(trifluoromethyl)phenyl)sulfonyl]-piperazine
1-[4-(3-methylbenzyl)-1,3-thiazol-2-yl]-4-[(2-(trifluoromethyl)phenyl)sulfonyl]-piperazine
1-[4-(3-methoxybenzyl)-1,3-thiazol-2-yl]-4-[(2-(trifluoromethyl)phenyl)sulfonyl]-piperazine
1-[4-(3-bromobenzyl)-1,3-thiazol-2-yl]-4-[(2-(trifluoromethyl)phenyl)sulfonyl]-piperazine
1-[4-(4-chlorobenzyl)-1,3-thiazol-2-yl]-4-[(2-(trifluoromethyl)phenyl)sulfonyl]-piperazine
1-[4-(4-methoxybenzyl)-1,3-thiazol-2-yl]-4-[(2-(trifluoromethyl)phenyl)sulfonyl]-piperazine
1-[4-(4-methylbenzyl)-1,3-thiazol-2-yl]-4-[(2-(trifluoromethyl)phenyl)sulfonyl]-piperazine
1-[4-(4-ethylbenzyl)-1,3-thiazol-2-yl]-4-[(2-(trifluoromethyl)phenyl)sulfonyl]-piperazine
1-[4-(4-ethoxybenzyl)-1,3-thiazol-2-yl]-4-[(2-(trifluoromethyl)phenyl)sulfonyl]-piperazine
1-[4-(4-propylbenzyl)-1,3-thiazol-2-yl]-4-[(2-(trifluoromethyl)phenyl)sulfonyl]-piperazine
1-[4-(2,6-dimethylbenzyl)-1,3-thiazol-2-yl]-4-[(2-(trifluoromethyl)phenyl)sulfonyl]-piperazine
1-[4-(2,3-dimethylbenzyl)-1,3-thiazol-2-yl]-4-[(2-(trifluoromethyl)phenyl)sulfonyl]-piperazine
1-[4-(2,5-dimethylbenzyl)-1,3-thiazol-2-yl]-4-[(2-(trifluoromethyl)phenyl)sulfonyl]-piperazine
1-[4-(2,4-dichlorobenzyl)-1,3-thiazol-2-yl]-4-[(2-(trifluoromethyl)phenyl)sulfonyl]-piperazine
1-[4-(2,4-dimethoxybenzyl)-1,3-thiazol-2-yl]-4-[(2-(trifluoromethyl)phenyl)sulfonyl]-piperazine
1-[4-(2,5-dimethoxybenzyl)-1,3-thiazol-2-yl]-4-[(2-(trifluoromethyl)phenyl)sulfonyl]-piperazine
1-[4-(3,4-dimethoxybenzyl)-1,3-thiazol-2-yl]-4-[(2-(trifluoromethyl)phenyl)sulfonyl]-piperazine
1-[4-(3,5-dimethoxybenzyl)-1,3-thiazol-2-yl]-4-[(2-(trifluoromethyl)phenyl)sulfonyl]-piperazine
1-[4-(3,4-dichlorobenzyl)-1,3-thiazol-2-yl]-4-[(2-(trifluoromethyl)phenyl)sulfonyl]-piperazine
1-[4-(3,4-dimethylbenzyl)-1,3-thiazol-2-yl]-4-[(2-(trifluoromethyl)phenyl)sulfonyl]-piperazine
1-[4-(3,4-difluorobenzyl)-1,3-thiazol-2-yl]-4-[(2-(trifluoromethyl)phenyl)sulfonyl]-piperazine
1-[4-(3,5-difluorobenzyl)-1,3-thiazol-2-yl]-4-[(2-(trifluoromethyl)phenyl)sulfonyl]-piperazine
1-[4-(3,5-dichlorobenzyl)-1,3-thiazol-2-yl]-4-[(2-(trifluoromethyl)phenyl)sulfonyl]-piperazine
1-[4-(3,5-dimethylbenzyl)-1,3-thiazol-2-yl]-4-[(2-(trifluoromethyl)phenyl)sulfonyl]-piperazine
1-[4-(3-chloro-4-fluorobenzyl)-1,3-thiazol-2-yl]-4-[(2-(trifluoromethyl)phenyl)sulfonyl]-piperazine
1-[4-(3-chloro-5-fluorobenzyl)-1,3-thiazol-2-yl]-4-[(2-(trifluoromethyl)phenyl)sulfonyl]-piperazine
1-[4-(4-chloro-3-fluorobenzyl)-1,3-thiazol-2-yl]-4-[(2-(trifluoromethyl)phenyl)sulfonyl]-piperazine
1-[4-(3,4,5-trimethoxybenzyl)-1,3-thiazol-2-yl]-4-[(2-(trifluoromethyl)phenyl)sulfonyl]-piperazine
1-[4-(2,4,6-trimethylbenzyl)-1,3-thiazol-2-yl]-4-[(2-(trifluoromethyl)phenyl)sulfonyl]-piperazine
1-[4-benzyl-1,3-thiazol-2-yl]-4-[(4-nitrophenyl)sulfonyl]-piperazine
1-[4-(2-methylbenzyl)-1,3-thiazol-2-yl]-4-[(4-nitrophenyl)sulfonyl]-piperazine
1-[4-(2-methoxybenzyl)-1,3-thiazol-2-yl]-4-[(4-nitrophenyl)sulfonyl]-piperazine
1-[4-(3-methylbenzyl)-1,3-thiazol-2-yl]-4-[(4-nitrophenyl)sulfonyl]-piperazine
1-[4-(3-methoxybenzyl)-1,3-thiazol-2-yl]-4-[(4-nitrophenyl)sulfonyl]-piperazine
1-[4-(3-bromobenzyl)-1,3-thiazol-2-yl]-4-[(4-nitrophenyl)sulfonyl]-piperazine
1-[4-(4-chlorobenzyl)-1,3-thiazol-2-yl]-4-[(4-nitrophenyl)sulfonyl]-piperazine
1-[4-(4-methoxybenzyl)-1,3-thiazol-2-yl]-4-[(4-nitrophenyl)sulfonyl]-piperazine
1-[4-(4-methylbenzyl)-1,3-thiazol-2-yl]-4-[(4-nitrophenyl)sulfonyl]-piperazine
1-[4-(4-ethylbenzyl)-1,3-thiazol-2-yl]-4-[(4-nitrophenyl)sulfonyl]-piperazine
1-[4-(4-ethoxybenzyl)-1,3-thiazol-2-yl]-4-[(4-nitrophenyl)sulfonyl]-piperazine
1-[4-(4-propylbenzyl)-1,3-thiazol-2-yl]-4-[(4-nitrophenyl)sulfonyl]-piperazine
1-[4-(2,6-dimethylbenzyl)-1,3-thiazol-2-yl]-4-[(4-nitrophenyl)sulfonyl]-piperazine
1-[4-(2,3-dimethylbenzyl)-1,3-thiazol-2-yl]-4-[(4-nitrophenyl)sulfonyl]-piperazine
1-[4-(2,5-dimethylbenzyl)-1,3-thiazol-2-yl]-4-[(4-nitrophenyl)sulfonyl]-piperazine
1-[4-(2,4-dichlorobenzyl)-1,3-thiazol-2-yl]-4-[(4-nitrophenyl)sulfonyl]-piperazine
1-[4-(2,4-dimethoxybenzyl)-1,3-thiazol-2-yl]-4-[(4-nitrophenyl)sulfonyl]-piperazine
1-[4-(2,5-dimethoxybenzyl)-1,3-thiazol-2-yl]-4-[(4-nitrophenyl)sulfonyl]-piperazine
1-[4-(3,4-dimethoxybenzyl)-1,3-thiazol-2-yl]-4-[(4-nitrophenyl)sulfonyl]-piperazine
1-[4-(3,5-dimethoxybenzyl)-1,3-thiazol-2-yl]-4-[(4-nitrophenyl)sulfonyl]-piperazine
1-[4-(3,4-dichlorobenzyl)-1,3-thiazol-2-yl]-4-[(4-nitrophenyl)sulfonyl]-piperazine
1-[4-(3,4-dimethylbenzyl)-1,3-thiazol-2-yl]-4-[(4-nitrophenyl)sulfonyl]-piperazine
1-[4-(3,4-difluorobenzyl)-1,3-thiazol-2-yl]-4-[(4-nitrophenyl)sulfonyl]-piperazine
1-[4-(3,5-difluorobenzyl)-1,3-thiazol-2-yl]-4-[(4-nitrophenyl)sulfonyl]-piperazine
1-[4-(3,5-dichlorobenzyl)-1,3-thiazol-2-yl]-4-[(4-nitrophenyl)sulfonyl]-piperazine
1-[4-(3,5-dimethylbenzyl)-1,3-thiazol-2-yl]-4-[(4-nitrophenyl)sulfonyl]-piperazine
1-[4-(3-chloro-4-fluorobenzyl)-1,3-thiazol-2-yl]-4-[(4-nitrophenyl)sulfonyl]-piperazine
1-[4-(3-chloro-5-fluorobenzyl)-1,3-thiazol-2-yl]-4-[(4-nitrophenyl)sulfonyl]-piperazine
1-[4-(4-chloro-3-fluorobenzyl)-1,3-thiazol-2-yl]-4-[(4-nitrophenyl)sulfonyl]-piperazine 1-[4-(3,4,5-trimethoxybenzyl)-1,3-thiazol-2-yl]-4-[(4-nitrophenyl)sulfonyl]-piperazine
1-[4-(2,4,6-trimethylbenzyl)-1,3-thiazol-2-yl]-4-[(4-nitrophenyl)sulfonyl]-piperazine
1-[4-benzyl-1,3-thiazol-2-yl]-4-[(2-bromophenyl)sulfonyl]-piperazine
1-[4-(2-methylbenzyl)-1,3-thiazol-2-yl]-4-[(2-bromophenyl)sulfonyl]-piperazine
1-[4-(2-methoxybenzyl)-1,3-thiazol-2-yl]-4-[(2-bromophenyl)sulfonyl]-piperazine
1-[4-(3-methylbenzyl)-1,3-thiazol-2-yl]-4-[(2-bromophenyl)sulfonyl]-piperazine
1-[4-(3-methoxybenzyl)-1,3-thiazol-2-yl]-4-[(2-bromophenyl)sulfonyl]-piperazine
1-[4-(3-bromobenzyl)-1,3-thiazol-2-yl]-4-[(2-bromophenyl)sulfonyl]-piperazine
1-[4-(4-chlorobenzyl)-1,3-thiazol-2-yl]-4-[(2-bromophenyl)sulfonyl]-piperazine
1-[4-(4-methoxybenzyl)-1,3-thiazol-2-yl]-4-[(2-bromophenyl)sulfonyl]-piperazine
1-[4-(4-methylbenzyl)-1,3-thiazol-2-yl]-4-[(2-bromophenyl)sulfonyl]-piperazine
1-[4-(4-ethylbenzyl)-1,3-thiazol-2-yl]-4-[(2-bromophenyl)sulfonyl]-piperazine
1-[4-(4-ethoxybenzyl)-1,3-thiazol-2-yl]-4-[(2-bromophenyl)sulfonyl]-piperazine
1-[4-(4-propylbenzyl)-1,3-thiazol-2-yl]-4-[(2-bromophenyl)sulfonyl]-piperazine
1-[4-(2,6-dimethylbenzyl)-1,3-thiazol-2-yl]-4-[(2-bromophenyl)sulfonyl]-piperazine
1-[4-(2,3-dimethylbenzyl)-1,3-thiazol-2-yl]-4-[(2-bromophenyl)sulfonyl]-piperazine
1-[4-(2,5-dimethylbenzyl)-1,3-thiazol-2-yl]-4-[(2-bromophenyl)sulfonyl]-piperazine
1-[4-(2,4-dichlorobenzyl)-1,3-thiazol-2-yl]-4-[(2-bromophenyl)sulfonyl]-piperazine
1-[4-(2,4-dimethoxybenzyl)-1,3-thiazol-2-yl]-4-[(2-bromophenyl)sulfonyl]-piperazine
1-[4-(2,5-dimethoxybenzyl)-1,3-thiazol-2-yl]-4-[(2-bromophenyl)sulfonyl]-piperazine
1-[4-(3,4-dimethoxybenzyl)-1,3-thiazol-2-yl]-4-[(2-bromophenyl)sulfonyl]-piperazine
1-[4-(3,5-dimethoxybenzyl)-1,3-thiazol-2-yl]-4-[(2-bromophenyl)sulfonyl]-piperazine
1-[4-(3,4-dichlorobenzyl)-1,3-thiazol-2-yl]-4-[(2-bromophenyl)sulfonyl]-piperazine
1-[4-(3,4-dimethylbenzyl)-1,3-thiazol-2-yl]-4-[(2-bromophenyl)sulfonyl]-piperazine
1-[4-(3,4-difluorobenzyl)-1,3-thiazol-2-yl]-4-[(2-bromophenyl)sulfonyl]-piperazine
1-[4-(3,5-difluorobenzyl)-1,3-thiazol-2-yl]-4-[(2-bromophenyl)sulfonyl]-piperazine
1-[4-(3,5-dichlorobenzyl)-1,3-thiazol-2-yl]-4-[(2-bromophenyl)sulfonyl]-piperazine
1-[4-(3,5-dimethylbenzyl)-1,3-thiazol-2-yl]-4-[(2-bromophenyl)sulfonyl]-piperazine
1-[4-(3-chloro-4-fluorobenzyl)-1,3-thiazol-2-yl]-4-[(2-bromophenyl)sulfonyl]-piperazine
1-[4-(3-chloro-5-fluorobenzyl)-1,3-thiazol-2-yl]-4-[(2-bromophenyl)sulfonyl]-piperazine
1-[4-(4-chloro-3-fluorobenzyl)-1,3-thiazol-2-yl]-4-[(2-bromophenyl)sulfonyl]-piperazine
1-[4-(3,4,5-trimethoxybenzyl)-1,3-thiazol-2-yl]-4-[(2-bromophenyl)sulfonyl]-piperazine
1-[4-(2,4,6-trimethylbenzyl)-1,3-thiazol-2-yl]-4-[(2-bromophenyl)sulfonyl]-piperazine
1-[4-benzyl-1,3-thiazol-2-yl]-4-[(2-chlorophenyl)sulfonyl]-piperazine
1-[4-(2-methylbenzyl)-1,3-thiazol-2-yl]-4-[(2-chlorophenyl)sulfonyl]-piperazine
1-[4-(2-methoxybenzyl)-1,3-thiazol-2-yl]-4-[(2-chlorophenyl)sulfonyl]-piperazine
1-[4-(3-methylbenzyl)-1,3-thiazol-2-yl]-4-[(2-chlorophenyl)sulfonyl]-piperazine
1-[4-(3-methoxybenzyl)-1,3-thiazol-2-yl]-4-[(2-chlorophenyl)sulfonyl]-piperazine
1-[4-(3-bromobenzyl)-1,3-thiazol-2-yl]-4-[(2-chlorophenyl)sulfonyl]-piperazine
1-[4-(4-chlorobenzyl)-1,3-thiazol-2-yl]-4-[(2-chlorophenyl)sulfonyl]-piperazine
1-[4-(4-methoxybenzyl)-1,3-thiazol-2-yl]-4-[(2-chlorophenyl)sulfonyl]-piperazine
1-[4-(4-methylbenzyl)-1,3-thiazol-2-yl]-4-[(2-chlorophenyl)sulfonyl]-piperazine
1-[4-(4-ethylbenzyl)-1,3-thiazol-2-yl]-4-[(2-chlorophenyl)sulfonyl]-piperazine
1-[4-(4-ethoxybenzyl)-1,3-thiazol-2-yl]-4-[(2-chlorophenyl)sulfonyl]-piperazine
1-[4-(4-propylbenzyl)-1,3-thiazol-2-yl]-4-[(2-chlorophenyl)sulfonyl]-piperazine
1-[4-(2,6-dimethylbenzyl)-1,3-thiazol-2-yl]-4-[(2-chlorophenyl)sulfonyl]-piperazine
1-[4-(2,3-dimethylbenzyl)-1,3-thiazol-2-yl]-4-[(2-chlorophenyl)sulfonyl]-piperazine
1-[4-(2,5-dimethylbenzyl)-1,3-thiazol-2-yl]-4-[(2-chlorophenyl)sulfonyl]-piperazine
1-[4-(2,4-dichlorobenzyl)-1,3-thiazol-2-yl]-4-[(2-chlorophenyl)sulfonyl]-piperazine
1-[4-(2,4-dimethoxybenzyl)-1,3-thiazol-2-yl]-4-[(2-chlorophenyl)sulfonyl]-piperazine
1-[4-(2,5-dimethoxybenzyl)-1,3-thiazol-2-yl]-4-[(2-chlorophenyl)sulfonyl]-piperazine
1-[4-(3,4-dimethoxybenzyl)-1,3-thiazol-2-yl]-4-[(2-chlorophenyl)sulfonyl]-piperazine
1-[4-(3,5-dimethoxybenzyl)-1,3-thiazol-2-yl]-4-[(2-chlorophenyl)sulfonyl]-piperazine
1-[4-(3,4-dichlorobenzyl)-1,3-thiazol-2-yl]-4-[(2-chlorophenyl)sulfonyl]-piperazine
1-[4-(3,4-dimethylbenzyl)-1,3-thiazol-2-yl]-4-[(2-chlorophenyl)sulfonyl]-piperazine
1-[4-(3,4-difluorobenzyl)-1,3-thiazol-2-yl]-4-[(2-chlorophenyl)sulfonyl]-piperazine
1-[4-(3,5-difluorobenzyl)-1,3-thiazol-2-yl]-4-[(2-chlorophenyl)sulfonyl]-piperazine
1-[4-(3,5-dichlorobenzyl)-1,3-thiazol-2-yl]-4-[(2-chlorophenyl)sulfonyl]-piperazine
1-[4-(3,5-dimethylbenzyl)-1,3-thiazol-2-yl]-4-[(2-chlorophenyl)sulfonyl]-piperazine
1-[4-(3-chloro-4-fluorobenzyl)-1,3-thiazol-2-yl]-4-[(2-chlorophenyl)sulfonyl]-piperazine
1-[4-(3-chloro-5-fluorobenzyl)-1,3-thiazol-2-yl]-4-[(2-chlorophenyl)sulfonyl]-piperazine
1-[4-(4-chloro-3-fluorobenzyl)-1,3-thiazol-2-yl]-4-[(2-chlorophenyl)sulfonyl]-piperazine
1-[4-(3,4,5-trimethoxybenzyl)-1,3-thiazol-2-yl]-4-[(2-chlorophenyl)sulfonyl]-piperazine
1-[4-(2,4,6-trimethylbenzyl)-1,3-thiazol-2-yl]-4-[(2-chlorophenyl)sulfonyl]-piperazine
1-[4-benzyl-1,3-thiazol-2-yl]-4-[(2-cyanophenyl)sulfonyl]-piperazine
1-[4-(2-methylbenzyl)-1,3-thiazol-2-yl]-4-[(2-cyanophenyl)sulfonyl]-piperazine 1-[4-(2-methoxybenzyl)-1,3-thiazol-2-yl]-4-[(2-cyanophenyl)sulfonyl]-piperazine
1-[4-(3-methylbenzyl)-1,3-thiazol-2-yl]-4-[(2-cyanophenyl)sulfonyl]-piperazine
1-[4-(3-methoxybenzyl)-1,3-thiazol-2-yl]-4-[(2-cyanophenyl)sulfonyl]-piperazine
1-[4-(3-bromobenzyl)-1,3-thiazol-2-yl]-4-[(2-cyanophenyl)sulfonyl]-piperazine
1-[4-(4-chlorobenzyl)-1,3-thiazol-2-yl]-4-[(2-cyanophenyl)sulfonyl]-piperazine
1-[4-(4-methoxybenzyl)-1,3-thiazol-2-yl]-4-[(2-cyanophenyl)sulfonyl]-piperazine
1-[4-(4-methylbenzyl)-1,3-thiazol-2-yl]-4-[(2-cyanophenyl)sulfonyl]-piperazine
1-[4-(4-ethylbenzyl)-1,3-thiazol-2-yl]-4-[(2-cyanophenyl)sulfonyl]-piperazine
1-[4-(4-ethoxybenzyl)-1,3-thiazol-2-yl]-4-[(2-cyanophenyl)sulfonyl]-piperazine
1-[4-(4-propylbenzyl)-1,3-thiazol-2-yl]-4-[(2-cyanophenyl)sulfonyl]-piperazine
1-[4-(2,6-dimethylbenzyl)-1,3-thiazol-2-yl]-4-[(2-cyanophenyl)sulfonyl]-piperazine
1-[4-(2,3-dimethylbenzyl)-1,3-thiazol-2-yl]-4-[(2-cyanophenyl)sulfonyl]-piperazine
1-[4-(2,5-dimethylbenzyl)-1,3-thiazol-2-yl]-4-[(2-cyanophenyl)sulfonyl]-piperazine
1-[4-(2,4-dichlorobenzyl)-1,3-thiazol-2-yl]-4-[(2-cyanophenyl)sulfonyl]-piperazine
1-[4-(2,4-dimethoxybenzyl)-1,3-thiazol-2-yl]-4-[(2-cyanophenyl)sulfonyl]-piperazine
1-[4-(2,5-dimethoxybenzyl)-1,3-thiazol-2-yl]-4-[(2-cyanophenyl)sulfonyl]-piperazine
1-[4-(3,4-dimethoxybenzyl)-1,3-thiazol-2-yl]-4-[(2-cyanophenyl)sulfonyl]-piperazine
1-[4-(3,5-dimethoxybenzyl)-1,3-thiazol-2-yl]-4-[(2-cyanophenyl)sulfonyl]-piperazine
1-[4-(3,4-dichlorobenzyl)-1,3-thiazol-2-yl]-4-[(2-cyanophenyl)sulfonyl]-piperazine
1-[4-(3,4-dimethylbenzyl)-1,3-thiazol-2-yl]-4-[(2-cyanophenyl)sulfonyl]-piperazine
1-[4-(3,4-difluorobenzyl)-1,3-thiazol-2-yl]-4-[(2-cyanophenyl)sulfonyl]-piperazine
1-[4-(3,5-difluorobenzyl)-1,3-thiazol-2-yl]-4-[(2-cyanophenyl)sulfonyl]-piperazine
1-[4-(3,5-dichlorobenzyl)-1,3-thiazol-2-yl]-4-[(2-cyanophenyl)sulfonyl]-piperazine
1-[4-(3,5-dimethylbenzyl)-1,3-thiazol-2-yl]-4-[(2-cyanophenyl)sulfonyl]-piperazine
1-[4-(3-chloro-4-fluorobenzyl)-1,3-thiazol-2-yl]-4-[(2-cyanophenyl)sulfonyl]-piperazine
1-[4-(3-chloro-5-fluorobenzyl)-1,3-thiazol-2-yl]-4-[(2-cyanophenyl)sulfonyl]-piperazine
1-[4-(4-chloro-3-fluorobenzyl)-1,3-thiazol-2-yl]-4-[(2-cyanophenyl)sulfonyl]-piperazine
1-[4-(3,4,5-trimethoxybenzyl)-1,3-thiazol-2-yl]-4-[(2-cyanophenyl)sulfonyl]-piperazine
1-[4-(2,4,6-trimethylbenzyl)-1,3-thiazol-2-yl]-4-[(2-cyanophenyl)sulfonyl]-piperazine
1-[4-benzyl-1,3-thiazol-2-yl]-4-[(3-nitrophenyl)sulfonyl]-piperazine
1-[4-(2-methylbenzyl)-1,3-thiazol-2-yl]-4-[(3-nitrophenyl)sulfonyl]-piperazine
1-[4-(2-methoxybenzyl)-1,3-thiazol-2-yl]-4-[(3-nitrophenyl)sulfonyl]-piperazine
1-[4-(3-methylbenzyl)-1,3-thiazol-2-yl]-4-[(3-nitrophenyl)sulfonyl]-piperazine
1-[4-(3-methoxybenzyl)-1,3-thiazol-2-yl]-4-[(3-nitrophenyl)sulfonyl]-piperazine
1-[4-(3-bromobenzyl)-1,3-thiazol-2-yl]-4-[(3-nitrophenyl)sulfonyl]-piperazine
1-[4-(4-chlorobenzyl)-1,3-thiazol-2-yl]-4-[(3-nitrophenyl)sulfonyl]-piperazine
1-[4-(4-methoxybenzyl)-1,3-thiazol-2-yl]-4-[(3-nitrophenyl)sulfonyl]-piperazine
1-[4-(4-methylbenzyl)-1,3-thiazol-2-yl]-4-[(3-nitrophenyl)sulfonyl]-piperazine
1-[4-(4-ethylbenzyl)-1,3-thiazol-2-yl]-4-[(3-nitrophenyl)sulfonyl]-piperazine
1-[4-(4-ethoxybenzyl)-1,3-thiazol-2-yl]-4-[(3-nitrophenyl)sulfonyl]-piperazine
1-[4-(4-propylbenzyl)-1,3-thiazol-2-yl]-4-[(3-nitrophenyl)sulfonyl]-piperazine
1-[4-(2,6-dimethylbenzyl)-1,3-thiazol-2-yl]-4-[(3-nitrophenyl)sulfonyl]-piperazine
1-[4-(2,3-dimethylbenzyl)-1,3-thiazol-2-yl]-4-[(3-nitrophenyl)sulfonyl]-piperazine
1-[4-(2,5-dimethylbenzyl)-1,3-thiazol-2-yl]-4-[(3-nitrophenyl)sulfonyl]-piperazine
1-[4-(2,4-dichlorobenzyl)-1,3-thiazol-2-yl]-4-[(3-nitrophenyl)sulfonyl]-piperazine
1-[4-(2,4-dimethoxybenzyl)-1,3-thiazol-2-yl]-4-[(3-nitrophenyl)sulfonyl]-piperazine
1-[4-(2,5-dimethoxybenzyl)-1,3-thiazol-2-yl]-4-[(3-nitrophenyl)sulfonyl]-piperazine
1-[4-(3,4-dimethoxybenzyl)-1,3-thiazol-2-yl]-4-[(3-nitrophenyl)sulfonyl]-piperazine
1-[4-(3,5-dimethoxybenzyl)-1,3-thiazol-2-yl]-4-[(3-nitrophenyl)sulfonyl]-piperazine
1-[4-(3,4-dichlorobenzyl)-1,3-thiazol-2-yl]-4-[(3-nitrophenyl)sulfonyl]-piperazine
1-[4-(3,4-dimethylbenzyl)-1,3-thiazol-2-yl]-4-[(3-nitrophenyl)sulfonyl]-piperazine
1-[4-(3,4-difluorobenzyl)-1,3-thiazol-2-yl]-4-[(3-nitrophenyl)sulfonyl]-piperazine
1-[4-(3,5-difluorobenzyl)-1,3-thiazol-2-yl]-4-[(3-nitrophenyl)sulfonyl]-piperazine
1-[4-(3,5-dichlorobenzyl)-1,3-thiazol-2-yl]-4-[(3-nitrophenyl)sulfonyl]-piperazine
1-[4-(3,5-dimethylbenzyl)-1,3-thiazol-2-yl]-4-[(3-nitrophenyl)sulfonyl]-piperazine
1-[4-(3-chloro-4-fluorobenzyl)-1,3-thiazol-2-yl]-4-[(3-nitrophenyl)sulfonyl]-piperazine
1-[4-(3-chloro-5-fluorobenzyl)-1,3-thiazol-2-yl]-4-[(3-nitrophenyl)sulfonyl]-piperazine
1-[4-(4-chloro-3-fluorobenzyl)-1,3-thiazol-2-yl]-4-[(3-nitrophenyl)sulfonyl]-piperazine
1-[4-(3,4,5-trimethoxybenzyl)-1,3-thiazol-2-yl]-4-[(3-nitrophenyl)sulfonyl]-piperazine
1-[4-(2,4,6-trimethylbenzyl)-1,3-thiazol-2-yl]-4-[(3-nitrophenyl)sulfonyl]-piperazine
1-[4-benzyl-1,3-thiazol-2-yl]-4-[(3-chlorophenyl)sulfonyl]-piperazine
1-[4-(2-methylbenzyl)-1,3-thiazol-2-yl]-4-[(3-chlorophenyl)sulfonyl]-piperazine
1-[4-(2-methoxybenzyl)-1,3-thiazol-2-yl]-4-[(3-chlorophenyl)sulfonyl]-piperazine
1-[4-(3-methylbenzyl)-1,3-thiazol-2-yl]-4-[(3-chlorophenyl)sulfonyl]-piperazine
1-[4-(3-methoxybenzyl)-1,3-thiazol-2-yl]-4-[(3-chlorophenyl)sulfonyl]-piperazine
1-[4-(3-bromobenzyl)-1,3-thiazol-2-yl]-4-[(3-chlorophenyl)sulfonyl]-piperazine 1-[4-(4-chlorobenzyl)-1,3-thiazol-2-yl]-4-[(3-chlorophenyl)sulfonyl]-piperazine
1-[4-(4-methoxybenzyl)-1,3-thiazol-2-yl]-4-[(3-chlorophenyl)sulfonyl]-piperazine
1-[4-(4-methylbenzyl)-1,3-thiazol-2-yl]-4-[(3-chlorophenyl)sulfonyl]-piperazine
1-[4-(4-ethylbenzyl)-1,3-thiazol-2-yl]-4-[(3-chlorophenyl)sulfonyl]-piperazine
1-[4-(4-ethoxybenzyl)-1,3-thiazol-2-yl]-4-[(3-chlorophenyl)sulfonyl]-piperazine
1-[4-(4-propylbenzyl)-1,3-thiazol-2-yl]-4-[(3-chlorophenyl)sulfonyl]-piperazine
1-[4-(2,6-dimethylbenzyl)-1,3-thiazol-2-yl]-4-[(3-chlorophenyl)sulfonyl]-piperazine
1-[4-(2,3-dimethylbenzyl)-1,3-thiazol-2-yl]-4-[(3-chlorophenyl)sulfonyl]-piperazine
1-[4-(2,5-dimethylbenzyl)-1,3-thiazol-2-yl]-4-[(3-chlorophenyl)sulfonyl]-piperazine
1-[4-(2,4-dichlorobenzyl)-1,3-thiazol-2-yl]-4-[(3-chlorophenyl)sulfonyl]-piperazine
1-[4-(2,4-dimethoxybenzyl)-1,3-thiazol-2-yl]-4-[(3-chlorophenyl)sulfonyl]-piperazine
1-[4-(2,5-dimethoxybenzyl)-1,3-thiazol-2-yl]-4-[(3-chlorophenyl)sulfonyl]-piperazine
1-[4-(3,4-dimethoxybenzyl)-1,3-thiazol-2-yl]-4-[(3-chlorophenyl)sulfonyl]-piperazine
1-[4-(3,5-dimethoxybenzyl)-1,3-thiazol-2-yl]-4-[(3-chlorophenyl)sulfonyl]-piperazine
1-[4-(3,4-dichlorobenzyl)-1,3-thiazol-2-yl]-4-[(3-chlorophenyl)sulfonyl]-piperazine
1-[4-(3,4-dimethylbenzyl)-1,3-thiazol-2-yl]-4-[(3-chlorophenyl)sulfonyl]-piperazine
1-[4-(3,4-difluorobenzyl)-1,3-thiazol-2-yl]-4-[(3-chlorophenyl)sulfonyl]-piperazine
1-[4-(3,5-difluorobenzyl)-1,3-thiazol-2-yl]-4-[(3-chlorophenyl)sulfonyl]-piperazine
1-[4-(3,5-dichlorobenzyl)-1,3-thiazol-2-yl]-4-[(3-chlorophenyl)sulfonyl]-piperazine
1-[4-(3,5-dimethylbenzyl)-1,3-thiazol-2-yl]-4-[(3-chlorophenyl)sulfonyl]-piperazine
1-[4-(3-chloro-4-fluorobenzyl)-1,3-thiazol-2-yl]-4-[(3-chlorophenyl)sulfonyl]-piperazine
1-[4-(3-chloro-5-fluorobenzyl)-1,3-thiazol-2-yl]-4-[(3-chlorophenyl)sulfonyl]-piperazine
1-[4-(4-chloro-3-fluorobenzyl)-1,3-thiazol-2-yl]-4-[(3-chlorophenyl)sulfonyl]-piperazine
1-[4-(3,4,5-trimethoxybenzyl)-1,3-thiazol-2-yl]-4-[(3-chlorophenyl)sulfonyl]-piperazine
1-[4-(2,4,6-trimethylbenzyl)-1,3-thiazol-2-yl]-4-[(3-chlorophenyl)sulfonyl]-piperazine
1-[4-benzyl-1,3-thiazol-2-yl]-4-[(3-bromophenyl)sulfonyl]-piperazine
1-[4-(2-methylbenzyl)-1,3-thiazol-2-yl]-4-[(3-bromophenyl)sulfonyl]-piperazine
1-[4-(2-methoxybenzyl)-1,3-thiazol-2-yl]-4-[(3-bromophenyl)sulfonyl]-piperazine
1-[4-(3-methylbenzyl)-1,3-thiazol-2-yl]-4-[(3-bromophenyl)sulfonyl]-piperazine
1-[4-(3-methoxybenzyl)-1,3-thiazol-2-yl]-4-[(3-bromophenyl)sulfonyl]-piperazine
1-[4-(3-bromobenzyl)-1,3-thiazol-2-yl]-4-[(3-bromophenyl)sulfonyl]-piperazine
1-[4-(4-chlorobenzyl)-1,3-thiazol-2-yl]-4-[(3-bromophenyl)sulfonyl]-piperazine
1-[4-(4-methoxybenzyl)-1,3-thiazol-2-yl]-4-[(3-bromophenyl)sulfonyl]-piperazine
1-[4-(4-methylbenzyl)-1,3-thiazol-2-yl]-4-[(3-bromophenyl)sulfonyl]-piperazine
1-[4-(4-ethylbenzyl)-1,3-thiazol-2-yl]-4-[(3-bromophenyl)sulfonyl]-piperazine
1-[4-(4-ethoxybenzyl)-1,3-thiazol-2-yl]-4-[(3-bromophenyl)sulfonyl]-piperazine
1-[4-(4-propylbenzyl)-1,3-thiazol-2-yl]-4-[(3-bromophenyl)sulfonyl]-piperazine
1-[4-(2,6-dimethylbenzyl)-1,3-thiazol-2-yl]-4-[(3-bromophenyl)sulfonyl]-piperazine
1-[4-(2,3-dimethylbenzyl)-1,3-thiazol-2-yl]-4-[(3-bromophenyl)sulfonyl]-piperazine
1-[4-(2,5-dimethylbenzyl)-1,3-thiazol-2-yl]-4-[(3-bromophenyl)sulfonyl]-piperazine
1-[4-(2,4-dichlorobenzyl)-1,3-thiazol-2-yl]-4-[(3-bromophenyl)sulfonyl]-piperazine
1-[4-(2,4-dimethoxybenzyl)-1,3-thiazol-2-yl]-4-[(3-bromophenyl)sulfonyl]-piperazine
1-[4-(2,5-dimethoxybenzyl)-1,3-thiazol-2-yl]-4-[(3-bromophenyl)sulfonyl]-piperazine
1-[4-(3,4-dimethoxybenzyl)-1,3-thiazol-2-yl]-4-[(3-bromophenyl)sulfonyl]-piperazine
1-[4-(3,5-dimethoxybenzyl)-1,3-thiazol-2-yl]-4-[(3-bromophenyl)sulfonyl]-piperazine
1-[4-(3,4-dichlorobenzyl)-1,3-thiazol-2-yl]-4-[(3-bromophenyl)sulfonyl]-piperazine
1-[4-(3,4-dimethylbenzyl)-1,3-thiazol-2-yl]-4-[(3-bromophenyl)sulfonyl]-piperazine
1-[4-(3,4-difluorobenzyl)-1,3-thiazol-2-yl]-4-[(3-bromophenyl)sulfonyl]-piperazine
1-[4-(3,5-difluorobenzyl)-1,3-thiazol-2-yl]-4-[(3-bromophenyl)sulfonyl]-piperazine
1-[4-(3,5-dichlorobenzyl)-1,3-thiazol-2-yl]-4-[(3-bromophenyl)sulfonyl]-piperazine
1-[4-(3,5-dimethylbenzyl)-1,3-thiazol-2-yl]-4-[(3-bromophenyl)sulfonyl]-piperazine
1-[4-(3-chloro-4-fluorobenzyl)-1,3-thiazol-2-yl]-4-[(3-bromophenyl)sulfonyl]-piperazine
1-[4-(3-chloro-5-fluorobenzyl)-1,3-thiazol-2-yl]-4-[(3-bromophenyl)sulfonyl]-piperazine
1-[4-(4-chloro-3-fluorobenzyl)-1,3-thiazol-2-yl]-4-[(3-bromophenyl)sulfonyl]-piperazine
1-[4-(3,4,5-trimethoxybenzyl)-1,3-thiazol-2-yl]-4-[(3-bromophenyl)sulfonyl]-piperazine
1-[4-(2,4,6-trimethylbenzyl)-1,3-thiazol-2-yl]-4-[(3-bromophenyl)sulfonyl]-piperazine
1-[4-benzyl-1,3-thiazol-2-yl]-4-[(3-fluorophenyl)sulfonyl]-piperazine
1-[4-(2-methylbenzyl)-1,3-thiazol-2-yl]-4-[(3-fluorophenyl)sulfonyl]-piperazine
1-[4-(2-methoxybenzyl)-1,3-thiazol-2-yl]-4-[(3-fluorophenyl)sulfonyl]-piperazine
1-[4-(3-methylbenzyl)-1,3-thiazol-2-yl]-4-[(3-fluorophenyl)sulfonyl]-piperazine
1-[4-(3-methoxybenzyl)-1,3-thiazol-2-yl]-4-[(3-fluorophenyl)sulfonyl]-piperazine
1-[4-(3-bromobenzyl)-1,3-thiazol-2-yl]-4-[(3-fluorophenyl)sulfonyl]-piperazine
1-[4-(4-chlorobenzyl)-1,3-thiazol-2-yl]-4-[(3-fluorophenyl)sulfonyl]-piperazine
1-[4-(4-methoxybenzyl)-1,3-thiazol-2-yl]-4-[(3-fluorophenyl)sulfonyl]-piperazine
1-[4-(4-methylbenzyl)-1,3-thiazol-2-yl]-4-[(3-fluorophenyl)sulfonyl]-piperazine
1-[4-(4-ethylbenzyl)-1,3-thiazol-2-yl]-4-[(3-fluorophenyl)sulfonyl]-piperazine 1-[4-(4-ethoxybenzyl)-1,3-thiazol-2-yl]-4-[(3-fluorophenyl)sulfonyl]-piperazine
1-[4-(4-propylbenzyl)-1,3-thiazol-2-yl]-4-[(3-fluorophenyl)sulfonyl]-piperazine
1-[4-(2,6-dimethylbenzyl)-1,3-thiazol-2-yl]-4-[(3-fluorophenyl)sulfonyl]-piperazine
1-[4-(2,3-dimethylbenzyl)-1,3-thiazol-2-yl]-4-[(3-fluorophenyl)sulfonyl]-piperazine
1-[4-(2,5-dimethylbenzyl)-1,3-thiazol-2-yl]-4-[(3-fluorophenyl)sulfonyl]-piperazine
1-[4-(2,4-dichlorobenzyl)-1,3-thiazol-2-yl]-4-[(3-fluorophenyl)sulfonyl]-piperazine
1-[4-(2,4-dimethoxybenzyl)-1,3-thiazol-2-yl]-4-[(3-fluorophenyl)sulfonyl]-piperazine
1-[4-(2,5-dimethoxybenzyl)-1,3-thiazol-2-yl]-4-[(3-fluorophenyl)sulfonyl]-piperazine
1-[4-(3,4-dimethoxybenzyl)-1,3-thiazol-2-yl]-4-[(3-fluorophenyl)sulfonyl]-piperazine
1-[4-(3,5-dimethoxybenzyl)-1,3-thiazol-2-yl]-4-[(3-fluorophenyl)sulfonyl]-piperazine
1-[4-(3,4-dichlorobenzyl)-1,3-thiazol-2-yl]-4-[(3-fluorophenyl)sulfonyl]-piperazine
1-[4-(3,4-dimethylbenzyl)-1,3-thiazol-2-yl]-4-[(3-fluorophenyl)sulfonyl]-piperazine
1-[4-(3,4-difluorobenzyl)-1,3-thiazol-2-yl]-4-[(3-fluorophenyl)sulfonyl]-piperazine
1-[4-(3,5-difluorobenzyl)-1,3-thiazol-2-yl]-4-[(3-fluorophenyl)sulfonyl]-piperazine
1-[4-(3,5-dichlorobenzyl)-1,3-thiazol-2-yl]-4-[(3-fluorophenyl)sulfonyl]-piperazine
1-[4-(3,5-dimethylbenzyl)-1,3-thiazol-2-yl]-4-[(3-fluorophenyl)sulfonyl]-piperazine
1-[4-(3-chloro-4-fluorobenzyl)-1,3-thiazol-2-yl]-4-[(3-fluorophenyl)sulfonyl]-piperazine
1-[4-(3-chloro-5-fluorobenzyl)-1,3-thiazol-2-yl]-4-[(3-fluorophenyl)sulfonyl]-piperazine
1-[4-(4-chloro-3-fluorobenzyl)-1,3-thiazol-2-yl]-4-[(3-fluorophenyl)sulfonyl]-piperazine
1-[4-(3,4,5-trimethoxybenzyl)-1,3-thiazol-2-yl]-4-[(3-fluorophenyl)sulfonyl]-piperazine
1-[4-(2,4,6-trimethylbenzyl)-1,3-thiazol-2-yl]-4-[(3-fluorophenyl)sulfonyl]-piperazine
1-[4-benzyl-1,3-thiazol-2-yl]-4-[(3-chloro-4-fluorophenyl)sulfonyl]-piperazine
1-[4-(2-methylbenzyl)-1,3-thiazol-2-yl]-4-[(3-chloro-4-fluorophenyl)sulfonyl]-piperazine
1-[4-(2-methoxybenzyl)-1,3-thiazol-2-yl]-4-[(3-chloro-4-fluorophenyl)sulfonyl]-piperazine
1-[4-(3-methylbenzyl)-1,3-thiazol-2-yl]-4-[(3-chloro-4-fluorophenyl)sulfonyl]-piperazine
1-[4-(3-methoxybenzyl)-1,3-thiazol-2-yl]-4-[(3-chloro-4-fluorophenyl)sulfonyl]-piperazine
1-[4-(3-bromobenzyl)-1,3-thiazol-2-yl]-4-[(3-chloro-4-fluorophenyl)sulfonyl]-piperazine
1-[4-(4-chlorobenzyl)-1,3-thiazol-2-yl]-4-[(3-chloro-4-fluorophenyl)sulfonyl]-piperazine
1-[4-(4-methoxybenzyl)-1,3-thiazol-2-yl]-4-[(3-chloro-4-fluorophenyl)sulfonyl]-piperazine
1-[4-(4-methylbenzyl)-1,3-thiazol-2-yl]-4-[(3-chloro-4-fluorophenyl)sulfonyl]-piperazine
1-[4-(4-ethylbenzyl)-1,3-thiazol-2-yl]-4-[(3-chloro-4-fluorophenyl)sulfonyl]-piperazine
1-[4-(4-ethoxybenzyl)-1,3-thiazol-2-yl]-4-[(3-chloro-4-fluorophenyl)sulfonyl]-piperazine
1-[4-(4-propylbenzyl)-1,3-thiazol-2-yl]-4-[(3-chloro-4-fluorophenyl)sulfonyl]-piperazine
1-[4-(2,6-dimethylbenzyl)-1,3-thiazol-2-yl]-4-[(3-chloro-4-fluorophenyl)sulfonyl]-piperazine
1-[4-(2,3-dimethylbenzyl)-1,3-thiazol-2-yl]-4-[(3-chloro-4-fluorophenyl)sulfonyl]-piperazine
1-[4-(2,5-dimethylbenzyl)-1,3-thiazol-2-yl]-4-[(3-chloro-4-fluorophenyl)sulfonyl]-piperazine
1-[4-(2,4-dichlorobenzyl)-1,3-thiazol-2-yl]-4-[(3-chloro-4-fluorophenyl)sulfonyl]-piperazine
1-[4-(2,4-dimethoxybenzyl)-1,3-thiazol-2-yl]-4-[(3-chloro-4-fluorophenyl)sulfonyl]-piperazine
1-[4-(2,5-dimethoxybenzyl)-1,3-thiazol-2-yl]-4-[(3-chloro-4-fluorophenyl)sulfonyl]-piperazine
1-[4-(3,4-dimethoxybenzyl)-1,3-thiazol-2-yl]-4-[(3-chloro-4-fluorophenyl)sulfonyl]-piperazine
1-[4-(3,5-dimethoxybenzyl)-1,3-thiazol-2-yl]-4-[(3-chloro-4-fluorophenyl)sulfonyl]-piperazine
1-[4-(3,4-dichlorobenzyl)-1,3-thiazol-2-yl]-4-[(3-chloro-4-fluorophenyl)sulfonyl]-piperazine
1-[4-(3,4-dimethylbenzyl)-1,3-thiazol-2-yl]-4-[(3-chloro-4-fluorophenyl)sulfonyl]-piperazine
1-[4-(3,4-difluorobenzyl)-1,3-thiazol-2-yl]-4-[(3-chloro-4-fluorophenyl)sulfonyl]-piperazine
1-[4-(3,5-difluorobenzyl)-1,3-thiazol-2-yl]-4-[(3-chloro-4-fluorophenyl)sulfonyl]-piperazine
1-[4-(3,5-dichlorobenzyl)-1,3-thiazol-2-yl]-4-[(3-chloro-4-fluorophenyl)sulfonyl]-piperazine
1-[4-(3,5-dimethylbenzyl)-1,3-thiazol-2-yl]-4-[(3-chloro-4-fluorophenyl)sulfonyl]-piperazine
1-[4-(3-chloro-4-fluorobenzyl)-1,3-thiazol-2-yl]-4-[(3-chloro-4-fluorophenyl)sulfonyl]-piperazine
1-[4-(3-chloro-5-fluorobenzyl)-1,3-thiazol-2-yl]-4-[(3-chloro-4-fluorophenyl)sulfonyl]-piperazine
1-[4-(4-chloro-3-fluorobenzyl)-1,3-thiazol-2-yl]-4-[(3-chloro-4-fluorophenyl)sulfonyl]-piperazine
1-[4-(3,4,5-trimethoxybenzyl)-1,3-thiazol-2-yl]-4-[(3-chloro-4-fluorophenyl)sulfonyl]-piperazine
1-[4-(2,4,6-trimethylbenzyl)-1,3-thiazol-2-yl]-4-[(3-chloro-4-fluorophenyl)sulfonyl]-piperazine
1-[4-benzyl-1,3-thiazol-2-yl]-4-[(2-chloro-4-fluorophenyl)sulfonyl]-piperazine
1-[4-(2-methylbenzyl)-1,3-thiazol-2-yl]-4-[(2-chloro-4-fluorophenyl)sulfonyl]-piperazine
1-[4-(2-methoxybenzyl)-1,3-thiazol-2-yl]-4-[(2-chloro-4-fluorophenyl)sulfonyl]-piperazine
1-[4-(3-methylbenzyl)-1,3-thiazol-2-yl]-4-[(2-chloro-4-fluorophenyl)sulfonyl]-piperazine
1-[4-(3-methoxybenzyl)-1,3-thiazol-2-yl]-4-[(2-chloro-4-fluorophenyl)sulfonyl]-piperazine
1-[4-(3-bromobenzyl)-1,3-thiazol-2-yl]-4-[(2-chloro-4-fluorophenyl)sulfonyl]-piperazine
1-[4-(4-chlorobenzyl)-1,3-thiazol-2-yl]-4-[(2-chloro-4-fluorophenyl)sulfonyl]-piperazine
1-[4-(4-methoxybenzyl)-1,3-thiazol-2-yl]-4-[(2-chloro-4-fluorophenyl)sulfonyl]-piperazine
1-[4-(4-methylbenzyl)-1,3-thiazol-2-yl]-4-[(2-chloro-4-fluorophenyl)sulfonyl]-piperazine
1-[4-(4-ethylbenzyl)-1,3-thiazol-2-yl]-4-[(2-chloro-4-fluorophenyl)sulfonyl]-piperazine
1-[4-(4-ethoxybenzyl)-1,3-thiazol-2-yl]-4-[(2-chloro-4-fluorophenyl)sulfonyl]-piperazine
1-[4-(4-propylbenzyl)-1,3-thiazol-2-yl]-4-[(2-chloro-4-fluorophenyl)sulfonyl]-piperazine
1-[4-(2,6-dimethylbenzyl)-1,3-thiazol-2-yl]-4-[(2-chloro-4-fluorophenyl)sulfonyl]-piperazine
1-[4-(2,3-dimethylbenzyl)-1,3-thiazol-2-yl]-4-[(2-chloro-4-fluorophenyl)sulfonyl]-piperazine 1-[4-(2,5-dimethylbenzyl)-1,3-thiazol-2-yl]-4-[(2-chloro-4-fluorophenyl)sulfonyl]-piperazine
1-[4-(2,4-dichlorobenzyl)-1,3-thiazol-2-yl]-4-[(2-chloro-4-fluorophenyl)sulfonyl]-piperazine
1-[4-(2,4-dimethoxybenzyl)-1,3-thiazol-2-yl]-4-[(2-chloro-4-fluorophenyl)sulfonyl]-piperazine
1-[4-(2,5-dimethoxybenzyl)-1,3-thiazol-2-yl]-4-[(2-chloro-4-fluorophenyl)sulfonyl]-piperazine
1-[4-(3,4-dimethoxybenzyl)-1,3-thiazol-2-yl]-4-[(2-chloro-4-fluorophenyl)sulfonyl]-piperazine
1-[4-(3,5-dimethoxybenzyl)-1,3-thiazol-2-yl]-4-[(2-chloro-4-fluorophenyl)sulfonyl]-piperazine
1-[4-(3,4-dichlorobenzyl)-1,3-thiazol-2-yl]-4-[(2-chloro-4-fluorophenyl)sulfonyl]-piperazine
1-[4-(3,4-dimethylbenzyl)-1,3-thiazol-2-yl]-4-[(2-chloro-4-fluorophenyl)sulfonyl]-piperazine
1-[4-(3,4-difluorobenzyl)-1,3-thiazol-2-yl]-4-[(2-chloro-4-fluorophenyl)sulfonyl]-piperazine
1-[4-(3,5-difluorobenzyl)-1,3-thiazol-2-yl]-4-[(2-chloro-4-fluorophenyl)sulfonyl]-piperazine
1-[4-(3,5-dichlorobenzyl)-1,3-thiazol-2-yl]-4-[(2-chloro-4-fluorophenyl)sulfonyl]-piperazine
1-[4-(3,5-dimethylbenzyl)-1,3-thiazol-2-yl]-4-[(2-chloro-4-fluorophenyl)sulfonyl]-piperazine
1-[4-(3-chloro-4-fluorobenzyl)-1,3-thiazol-2-yl]-4-[(2-chloro-4-fluorophenyl)sulfonyl]-piperazine
1-[4-(3-chloro-5-fluorobenzyl)-1,3-thiazol-2-yl]-4-[(2-chloro-4-fluorophenyl)sulfonyl]-piperazine
1-[4-(4-chloro-3-fluorobenzyl)-1,3-thiazol-2-yl]-4-[(2-chloro-4-fluorophenyl)sulfonyl]-piperazine
1-[4-(3,4,5-trimethoxybenzyl)-1,3-thiazol-2-yl]-4-[(2-chloro-4-fluorophenyl)sulfonyl]-piperazine
1-[4-(2,4,6-trimethylbenzyl)-1,3-thiazol-2-yl]-4-[(2-chloro-4-fluorophenyl)sulfonyl]-piperazine
1-[4-benzyl-1,3-thiazol-2-yl]-4-[(2-chloro-2-methylphenyl)sulfonyl]-piperazine
1-[4-(2-methylbenzyl)-1,3-thiazol-2-yl]-4-[(2-chloro-2-methylphenyl)sulfonyl]-piperazine
1-[4-(2-methoxybenzyl)-1,3-thiazol-2-yl]-4-[(2-chloro-2-methylphenyl)sulfonyl]-piperazine
1-[4-(3-methylbenzyl)-1,3-thiazol-2-yl]-4-[(2-chloro-2-methylphenyl)sulfonyl]-piperazine
1-[4-(3-methoxybenzyl)-1,3-thiazol-2-yl]-4-[(2-chloro-2-methylphenyl)sulfonyl]-piperazine
1-[4-(3-bromobenzyl)-1,3-thiazol-2-yl]-4-[(2-chloro-2-methylphenyl)sulfonyl]-piperazine
1-[4-(4-chlorobenzyl)-1,3-thiazol-2-yl]-4-[(2-chloro-2-methylphenyl)sulfonyl]-piperazine
1-[4-(4-methoxybenzyl)-1,3-thiazol-2-yl]-4-[(2-chloro-2-methylphenyl)sulfonyl]-piperazine
1-[4-(4-methylbenzyl)-1,3-thiazol-2-yl]-4-[(2-chloro-2-methylphenyl)sulfonyl]-piperazine
1-[4-(4-ethylbenzyl)-1,3-thiazol-2-yl]-4-[(2-chloro-2-methylphenyl)sulfonyl]-piperazine
1-[4-(4-ethoxybenzyl)-1,3-thiazol-2-yl]-4-[(2-chloro-2-methylphenyl)sulfonyl]-piperazine
1-[4-(4-propylbenzyl)-1,3-thiazol-2-yl]-4-[(2-chloro-2-methylphenyl)sulfonyl]-piperazine
1-[4-(2,6-dimethylbenzyl)-1,3-thiazol-2-yl]-4-[(2-chloro-2-methylphenyl)sulfonyl]-piperazine
1-[4-(2,3-dimethylbenzyl)-1,3-thiazol-2-yl]-4-[(2-chloro-2-methylphenyl)sulfonyl]-piperazine
1-[4-(2,5-dimethylbenzyl)-1,3-thiazol-2-yl]-4-[(2-chloro-2-methylphenyl)sulfonyl]-piperazine
1-[4-(2,4-dichlorobenzyl)-1,3-thiazol-2-yl]-4-[(2-chloro-2-methylphenyl)sulfonyl]-piperazine
1-[4-(2,4-dimethoxybenzyl)-1,3-thiazol-2-yl]-4-[(2-chloro-2-methylphenyl)sulfonyl]-piperazine
1-[4-(2,5-dimethoxybenzyl)-1,3-thiazol-2-yl]-4-[(2-chloro-2-methylphenyl)sulfonyl]-piperazine
1-[4-(3,4-dimethoxybenzyl)-1,3-thiazol-2-yl]-4-[(2-chloro-2-methylphenyl)sulfonyl]-piperazine
1-[4-(3,5-dimethoxybenzyl)-1,3-thiazol-2-yl]-4-[(2-chloro-2-methylphenyl)sulfonyl]-piperazine
1-[4-(3,4-dichlorobenzyl)-1,3-thiazol-2-yl]-4-[(2-chloro-2-methylphenyl)sulfonyl]-piperazine
1-[4-(3,4-dimethylbenzyl)-1,3-thiazol-2-yl]-4-[(2-chloro-2-methylphenyl)sulfonyl]-piperazine
1-[4-(3,4-difluorobenzyl)-1,3-thiazol-2-yl]-4-[(2-chloro-2-methylphenyl)sulfonyl]-piperazine
1-[4-(3,5-difluorobenzyl)-1,3-thiazol-2-yl]-4-[(2-chloro-2-methylphenyl)sulfonyl]-piperazine
1-[4-(3,5-dichlorobenzyl)-1,3-thiazol-2-yl]-4-[(2-chloro-2-methylphenyl)sulfonyl]-piperazine
1-[4-(3,5-dimethylbenzyl)-1,3-thiazol-2-yl]-4-[(2-chloro-2-methylphenyl)sulfonyl]-piperazine
1-[4-(3-chloro-4-fluorobenzyl)-1,3-thiazol-2-yl]-4-[(2-chloro-2-methylphenyl)sulfonyl]-piperazine
1-[4-(3-chloro-5-fluorobenzyl)-1,3-thiazol-2-yl]-4-[(2-chloro-2-methylphenyl)sulfonyl]-piperazine
1-[4-(4-chloro-3-fluorobenzyl)-1,3-thiazol-2-yl]-4-[(2-chloro-2-methylphenyl)sulfonyl]-piperazine
1-[4-(3,4,5-trimethoxybenzyl)-1,3-thiazol-2-yl]-4-[(2-chloro-2-methylphenyl)sulfonyl]-piperazine
1-[4-(2,4,6-trimethylbenzyl)-1,3-thiazol-2-yl]-4-[(2-chloro-2-methylphenyl)sulfonyl]-piperazine
1-[4-benzyl-1,3-thiazol-2-yl]-4-[(5-fluoro-2-methylphenyl)sulfonyl]-piperazine
1-[4-(2-methylbenzyl)-1,3-thiazol-2-yl]-4-[(5-fluoro-2-methylphenyl)sulfonyl]-piperazine
1-[4-(2-methoxybenzyl)-1,3-thiazol-2-yl]-4-[(5-fluoro-2-methylphenyl)sulfonyl]-piperazine
1-[4-(3-methylbenzyl)-1,3-thiazol-2-yl]-4-[(5-fluoro-2-methylphenyl)sulfonyl]-piperazine
1-[4-(3-methoxybenzyl)-1,3-thiazol-2-yl]-4-[(5-fluoro-2-methylphenyl)sulfonyl]-piperazine
1-[4-(3-bromobenzyl)-1,3-thiazol-2-yl]-4-[(5-fluoro-2-methylphenyl)sulfonyl]-piperazine
1-[4-(4-chlorobenzyl)-1,3-thiazol-2-yl]-4-[(5-fluoro-2-methylphenyl)sulfonyl]-piperazine
1-[4-(4-methoxybenzyl)-1,3-thiazol-2-yl]-4-[(5-fluoro-2-methylphenyl)sulfonyl]-piperazine
1-[4-(4-methylbenzyl)-1,3-thiazol-2-yl]-4-[(5-fluoro-2-methylphenyl)sulfonyl]-piperazine
1-[4-(4-ethylbenzyl)-1,3-thiazol-2-yl]-4-[(5-fluoro-2-methylphenyl)sulfonyl]-piperazine
1-[4-(4-ethoxybenzyl)-1,3-thiazol-2-yl]-4-[(5-fluoro-2-methylphenyl)sulfonyl]-piperazine
1-[4-(4-propylbenzyl)-1,3-thiazol-2-yl]-4-[(5-fluoro-2-methylphenyl)sulfonyl]-piperazine
1-[4-(2,6-dimethylbenzyl)-1,3-thiazol-2-yl]-4-[(5-fluoro-2-methylphenyl)sulfonyl]-piperazine
1-[4-(2,3-dimethylbenzyl)-1,3-thiazol-2-yl]-4-[(5-fluoro-2-methylphenyl)sulfonyl]-piperazine
1-[4-(2,5-dimethylbenzyl)-1,3-thiazol-2-yl]-4-[(5-fluoro-2-methylphenyl)sulfonyl]-piperazine
1-[4-(2,4-dichlorobenzyl)-1,3-thiazol-2-yl]-4-[(5-fluoro-2-methylphenyl)sulfonyl]-piperazine
1-[4-(2,4-dimethoxybenzyl)-1,3-thiazol-2-yl]-4-[(5-fluoro-2-methylphenyl)sulfonyl]-piperazine
1-[4-(2,5-dimethoxybenzyl)-1,3-thiazol-2-yl]-4-[(5-fluoro-2-methylphenyl)sulfonyl]-piperazine 1-[4-(3,4-dimethoxybenzyl)-1,3-thiazol-2-yl]-4-[(5-fluoro-2-methylphenyl)sulfonyl]-piperazine
1-[4-(3,5-dimethoxybenzyl)-1,3-thiazol-2-yl]-4-[(5-fluoro-2-methylphenyl)sulfonyl]-piperazine
1-[4-(3,4-dichlorobenzyl)-1,3-thiazol-2-yl]-4-[(5-fluoro-2-methylphenyl)sulfonyl]-piperazine
1-[4-(3,4-dimethylbenzyl)-1,3-thiazol-2-yl]-4-[(5-fluoro-2-methylphenyl)sulfonyl]-piperazine
1-[4-(3,4-difluorobenzyl)-1,3-thiazol-2-yl]-4-[(5-fluoro-2-methylphenyl)sulfonyl]-piperazine
1-[4-(3,5-difluorobenzyl)-1,3-thiazol-2-yl]-4-[(5-fluoro-2-methylphenyl)sulfonyl]-piperazine
1-[4-(3,5-dichlorobenzyl)-1,3-thiazol-2-yl]-4-[(5-fluoro-2-methylphenyl)sulfonyl]-piperazine
1-[4-(3,5-dimethylbenzyl)-1,3-thiazol-2-yl]-4-[(5-fluoro-2-methylphenyl)sulfonyl]-piperazine
1-[4-(3-chloro-4-fluorobenzyl)-1,3-thiazol-2-yl]-4-[(5-fluoro-2-methylphenyl)sulfonyl]-piperazine
1-[4-(3-chloro-5-fluorobenzyl)-1,3-thiazol-2-yl]-4-[(5-fluoro-2-methylphenyl)sulfonyl]-piperazine
1-[4-(4-chloro-3-fluorobenzyl)-1,3-thiazol-2-yl]-4-[(5-fluoro-2-methylphenyl)sulfonyl]-piperazine
1-[4-(3,4,5-trimethoxybenzyl)-1,3-thiazol-2-yl]-4-[(5-fluoro-2-methylphenyl)sulfonyl]-piperazine
1-[4-(2,4,6-trimethylbenzyl)-1,3-thiazol-2-yl]-4-[(5-fluoro-2-methylphenyl)sulfonyl]-piperazine
1-[4-benzyl-1,3-thiazol-2-yl]-4-[(2,3,5,6-tetramethylphenyl)sulfonyl]-piperazine
1-[4-(2-methylbenzyl)-1,3-thiazol-2-yl]-4-[(2,3,5,6-tetramethylphenyl)sulfonyl]-piperazine
1-[4-(2-methoxybenzyl)-1,3-thiazol-2-yl]-4-[(2,3,5,6-tetramethylphenyl)sulfonyl]-piperazine
1-[4-(3-methylbenzyl)-1,3-thiazol-2-yl]-4-[(2,3,5,6-tetramethylphenyl)sulfonyl]-piperazine
1-[4-(3-methoxybenzyl)-1,3-thiazol-2-yl]-4-[(2,3,5,6-tetramethylphenyl)sulfonyl]-piperazine
1-[4-(3-bromobenzyl)-1,3-thiazol-2-yl]-4-[(2,3,5,6-tetramethylphenyl)sulfonyl]-piperazine
1-[4-(4-chlorobenzyl)-1,3-thiazol-2-yl]-4-[(2,3,5,6-tetramethylphenyl)sulfonyl]-piperazine
1-[4-(4-methoxybenzyl)-1,3-thiazol-2-yl]-4-[(2,3,5,6-tetramethylphenyl)sulfonyl]-piperazine
1-[4-(4-methylbenzyl)-1,3-thiazol-2-yl]-4-[(2,3,5,6-tetramethylphenyl)sulfonyl]-piperazine
1-[4-(4-ethylbenzyl)-1,3-thiazol-2-yl]-4-[(2,3,5,6-tetramethylphenyl)sulfonyl]-piperazine
1-[4-(4-ethoxybenzyl)-1,3-thiazol-2-yl]-4-[(2,3,5,6-tetramethylphenyl)sulfonyl]-piperazine
1-[4-(4-propylbenzyl)-1,3-thiazol-2-yl]-4-[(2,3,5,6-tetramethylphenyl)sulfonyl]-piperazine
1-[4-(2,6-dimethylbenzyl)-1,3-thiazol-2-yl]-4-[(2,3,5,6-tetramethylphenyl)sulfonyl]-piperazine
1-[4-(2,3-dimethylbenzyl)-1,3-thiazol-2-yl]-4-[(2,3,5,6-tetramethylphenyl)sulfonyl]-piperazine
1-[4-(2,5-dimethylbenzyl)-1,3-thiazol-2-yl]-4-[(2,3,5,6-tetramethylphenyl)sulfonyl]-piperazine
1-[4-(2,4-dichlorobenzyl)-1,3-thiazol-2-yl]-4-[(2,3,5,6-tetramethylphenyl)sulfonyl]-piperazine
1-[4-(2,4-dimethoxybenzyl)-1,3-thiazol-2-yl]-4-[(2,3,5,6-tetramethylphenyl)sulfonyl]-piperazine
1-[4-(2,5-dimethoxybenzyl)-1,3-thiazol-2-yl]-4-[(2,3,5,6-tetramethylphenyl)sulfonyl]-piperazine
1-[4-(3,4-dimethoxybenzyl)-1,3-thiazol-2-yl]-4-[(2,3,5,6-tetramethylphenyl)sulfonyl]-piperazine
1-[4-(3,5-dimethoxybenzyl)-1,3-thiazol-2-yl]-4-[(2,3,5,6-tetramethylphenyl)sulfonyl]-piperazine
1-[4-(3,4-dichlorobenzyl)-1,3-thiazol-2-yl]-4-[(2,3,5,6-tetramethylphenyl)sulfonyl]-piperazine
1-[4-(3,4-dimethylbenzyl)-1,3-thiazol-2-yl]-4-[(2,3,5,6-tetramethylphenyl)sulfonyl]-piperazine
1-[4-(3,4-difluorobenzyl)-1,3-thiazol-2-yl]-4-[(2,3,5,6-tetramethylphenyl)sulfonyl]-piperazine
1-[4-(3,5-difluorobenzyl)-1,3-thiazol-2-yl]-4-[(2,3,5,6-tetramethylphenyl)sulfonyl]-piperazine
1-[4-(3,5-dichlorobenzyl)-1,3-thiazol-2-yl]-4-[(2,3,5,6-tetramethylphenyl)sulfonyl]-piperazine
1-[4-(3,5-dimethylbenzyl)-1,3-thiazol-2-yl]-4-[(2,3,5,6-tetramethylphenyl)sulfonyl]-piperazine
1-[4-(3-chloro-4-fluorobenzyl)-1,3-thiazol-2-yl]-4-[(2,3,5,6-tetramethylphenyl)sulfonyl]-piperazine
1-[4-(3-chloro-5-fluorobenzyl)-1,3-thiazol-2-yl]-4-[(2,3,5,6-tetramethylphenyl)sulfonyl]-piperazine
1-[4-(4-chloro-3-fluorobenzyl)-1,3-thiazol-2-yl]-4-[(2,3,5,6-tetramethylphenyl)sulfonyl]-piperazine
1-[4-(3,4,5-trimethoxybenzyl)-1,3-thiazol-2-yl]-4-[(2,3,5,6-tetramethylphenyl)sulfonyl]-piperazine
1-[4-(2,4,6-trimethylbenzyl)-1,3-thiazol-2-yl]-4-[(2,3,5,6-tetramethylphenyl)sulfonyl]-piperazine
1-[4-benzyl-1,3-thiazol-2-yl]-4-[(2,5-dibromo-3,6-difluorophenyl)sulfonyl]-piperazine
1-[4-(2-methylbenzyl)-1,3-thiazol-2-yl]-4-[(2,5-dibromo-3,6-difluorophenyl)sulfonyl]-piperazine
1-[4-(2-methoxybenzyl)-1,3-thiazol-2-yl]-4-[(2,5-dibromo-3,6-difluorophenyl)sulfonyl]-piperazine
1-[4-(3-methylbenzyl)-1,3-thiazol-2-yl]-4-[(2,5-dibromo-3,6-difluorophenyl)sulfonyl]-piperazine
1-[4-(3-methoxybenzyl)-1,3-thiazol-2-yl]-4-[(2,5-dibromo-3,6-difluorophenyl)sulfonyl]-piperazine
1-[4-(3-bromobenzyl)-1,3-thiazol-2-yl]-4-[(2,5-dibromo-3,6-difluorophenyl)sulfonyl]-piperazine
1-[4-(4-chlorobenzyl)-1,3-thiazol-2-yl]-4-[(2,5-dibromo-3,6-difluorophenyl)sulfonyl]-piperazine
1-[4-(4-methoxybenzyl)-1,3-thiazol-2-yl]-4-[(2,5-dibromo-3,6-difluorophenyl)sulfonyl]-piperazine
1-[4-(4-methylbenzyl)-1,3-thiazol-2-yl]-4-[(2,5-dibromo-3,6-difluorophenyl)sulfonyl]-piperazine
1-[4-(4-ethylbenzyl)-1,3-thiazol-2-yl]-4-[(2,5-dibromo-3,6-difluorophenyl)sulfonyl]-piperazine
1-[4-(4-ethoxybenzyl)-1,3-thiazol-2-yl]-4-[(2,5-dibromo-3,6-difluorophenyl)sulfonyl]-piperazine
1-[4-(4-propylbenzyl)-1,3-thiazol-2-yl]-4-[(2,5-dibromo-3,6-difluorophenyl)sulfonyl]-piperazine
1-[4-(2,6-dimethylbenzyl)-1,3-thiazol-2-yl]-4-[(2,5-dibromo-3,6-difluorophenyl)sulfonyl]-piperazine
1-[4-(2,3-dimethylbenzyl)-1,3-thiazol-2-yl]-4-[(2,5-dibromo-3,6-difluorophenyl)sulfonyl]-piperazine
1-[4-(2,5-dimethylbenzyl)-1,3-thiazol-2-yl]-4-[(2,5-dibromo-3,6-difluorophenyl)sulfonyl]-piperazine
1-[4-(2,4-dichlorobenzyl)-1,3-thiazol-2-yl]-4-[(2,5-dibromo-3,6-difluorophenyl)sulfonyl]-piperazine
1-[4-(2,4-dimethoxybenzyl)-1,3-thiazol-2-yl]-4-[(2,5-dibromo-3,6-difluorophenyl)sulfonyl]-piperazine
1-[4-(2,5-dimethoxybenzyl)-1,3-thiazol-2-yl]-4-[(2,5-dibromo-3,6-difluorophenyl)sulfonyl]-piperazine
1-[4-(3,4-dimethoxybenzyl)-1,3-thiazol-2-yl]-4-[(2,5-dibromo-3,6-difluorophenyl)sulfonyl]-piperazine
1-[4-(3,5-dimethoxybenzyl)-1,3-thiazol-2-yl]-4-[(2,5-dibromo-3,6-difluorophenyl)sulfonyl]-piperazine
1-[4-(3,4-dichlorobenzyl)-1,3-thiazol-2-yl]-4-[(2,5-dibromo-3,6-difluorophenyl)sulfonyl]-piperazine
1-[4-(3,4-dimethylbenzyl)-1,3-thiazol-2-yl]-4-[(2,5-dibromo-3,6-difluorophenyl)sulfonyl]-piperazine 1-[4-(3,4-difluorobenzyl)-1,3-thiazol-2-yl]-4-[(2,5-dibromo-3,6-difluorophenyl)sulfonyl]-piperazine
1-[4-(3,5-difluorobenzyl)-1,3-thiazol-2-yl]-4-[(2,5-dibromo-3,6-difluorophenyl)sulfonyl]-piperazine
1-[4-(3,5-dichlorobenzyl)-1,3-thiazol-2-yl]-4-[(2,5-dibromo-3,6-difluorophenyl)sulfonyl]-piperazine
1-[4-(3,5-dimethylbenzyl)-1,3-thiazol-2-yl]-4-[(2,5-dibromo-3,6-difluorophenyl)sulfonyl]-piperazine
1-[4-(3-chloro-4-fluorobenzyl)-1,3-thiazol-2-yl]-4-[(2,5-dibromo-3,6-difluorophenyl)sulfonyl]-piperazine
1-[4-(3-chloro-5-fluorobenzyl)-1,3-thiazol-2-yl]-4-[(2,5-dibromo-3,6-difluorophenyl)sulfonyl]-piperazine
1-[4-(4-chloro-3-fluorobenzyl)-1,3-thiazol-2-yl]-4-[(2,5-dibromo-3,6-difluorophenyl)sulfonyl]-piperazine
1-[4-(3,4,5-trimethoxybenzyl)-1,3-thiazol-2-yl]-4-[(2,5-dibromo-3,6-difluorophenyl)sulfonyl]-piperazine
1-[4-(2,4,6-trimethylbenzyl)-1,3-thiazol-2-yl]-4-[(2,5-dibromo-3,6-difluorophenyl)sulfonyl]-piperazine
1-[4-benzyl-1,3-thiazol-2-yl]-4-[(5-bromo-2-methoxyphenyl)sulfonyl]-piperazine
1-[4-(2-methylbenzyl)-1,3-thiazol-2-yl]-4-[(5-bromo-2-methoxyphenyl)sulfonyl]-piperazine
1-[4-(2-methoxybenzyl)-1,3-thiazol-2-yl]-4-[(5-bromo-2-methoxyphenyl)sulfonyl]-piperazine
1-[4-(3-methylbenzyl)-1,3-thiazol-2-yl]-4-[(5-bromo-2-methoxyphenyl)sulfonyl]-piperazine
1-[4-(3-methoxybenzyl)-1,3-thiazol-2-yl]-4-[(5-bromo-2-methoxyphenyl)sulfonyl]-piperazine
1-[4-(3-bromobenzyl)-1,3-thiazol-2-yl]-4-[(5-bromo-2-methoxyphenyl)sulfonyl]-piperazine
1-[4-(4-chlorobenzyl)-1,3-thiazol-2-yl]-4-[(5-bromo-2-methoxyphenyl)sulfonyl]-piperazine
1-[4-(4-methoxybenzyl)-1,3-thiazol-2-yl]-4-[(5-bromo-2-methoxyphenyl)sulfonyl]-piperazine
1-[4-(4-methylbenzyl)-1,3-thiazol-2-yl]-4-[(5-bromo-2-methoxyphenyl)sulfonyl]-piperazine
1-[4-(4-ethylbenzyl)-1,3-thiazol-2-yl]-4-[(5-bromo-2-methoxyphenyl)sulfonyl]-piperazine
1-[4-(4-ethoxybenzyl)-1,3-thiazol-2-yl]-4-[(5-bromo-2-methoxyphenyl)sulfonyl]-piperazine
1-[4-(4-propylbenzyl)-1,3-thiazol-2-yl]-4-[(5-bromo-2-methoxyphenyl)sulfonyl]-piperazine
1-[4-(2,6-dimethylbenzyl)-1,3-thiazol-2-yl]-4-[(5-bromo-2-methoxyphenyl)sulfonyl]-piperazine
1-[4-(2,3-dimethylbenzyl)-1,3-thiazol-2-yl]-4-[(5-bromo-2-methoxyphenyl)sulfonyl]-piperazine
1-[4-(2,5-dimethylbenzyl)-1,3-thiazol-2-yl]-4-[(5-bromo-2-methoxyphenyl)sulfonyl]-piperazine
1-[4-(2,4-dichlorobenzyl)-1,3-thiazol-2-yl]-4-[(5-bromo-2-methoxyphenyl)sulfonyl]-piperazine
1-[4-(2,4-dimethoxybenzyl)-1,3-thiazol-2-yl]-4-[(5-bromo-2-methoxyphenyl)sulfonyl]-piperazine
1-[4-(2,5-dimethoxybenzyl)-1,3-thiazol-2-yl]-4-[(5-bromo-2-methoxyphenyl)sulfonyl]-piperazine
1-[4-(3,4-dimethoxybenzyl)-1,3-thiazol-2-yl]-4-[(5-bromo-2-methoxyphenyl)sulfonyl]-piperazine
1-[4-(3,5-dimethoxybenzyl)-1,3-thiazol-2-yl]-4-[(5-bromo-2-methoxyphenyl)sulfonyl]-piperazine
1-[4-(3,4-dichlorobenzyl)-1,3-thiazol-2-yl]-4-[(5-bromo-2-methoxyphenyl)sulfonyl]-piperazine
1-[4-(3,4-dimethylbenzyl)-1,3-thiazol-2-yl]-4-[(5-bromo-2-methoxyphenyl)sulfonyl]-piperazine
1-[4-(3,4-difluorobenzyl)-1,3-thiazol-2-yl]-4-[(5-bromo-2-methoxyphenyl)sulfonyl]-piperazine
1-[4-(3,5-difluorobenzyl)-1,3-thiazol-2-yl]-4-[(5-bromo-2-methoxyphenyl)sulfonyl]-piperazine
1-[4-(3,5-dichlorobenzyl)-1,3-thiazol-2-yl]-4-[(5-bromo-2-methoxyphenyl)sulfonyl]-piperazine
1-[4-(3,5-dimethylbenzyl)-1,3-thiazol-2-yl]-4-[(5-bromo-2-methoxyphenyl)sulfonyl]-piperazine
1-[4-(3-chloro-4-fluorobenzyl)-1,3-thiazol-2-yl]-4-[(5-bromo-2-methoxyphenyl)sulfonyl]-piperazine
1-[4-(3-chloro-5-fluorobenzyl)-1,3-thiazol-2-yl]-4-[(5-bromo-2-methoxyphenyl)sulfonyl]-piperazine
1-[4-(4-chloro-3-fluorobenzyl)-1,3-thiazol-2-yl]-4-[(5-bromo-2-methoxyphenyl)sulfonyl]-piperazine
1-[4-(3,4,5-trimethoxybenzyl)-1,3-thiazol-2-yl]-4-[(5-bromo-2-methoxyphenyl)sulfonyl]-piperazine
1-[4-(2,4,6-trimethylbenzyl)-1,3-thiazol-2-yl]-4-[(5-bromo-2-methoxyphenyl)sulfonyl]-piperazine
1-[4-benzyl-1,3-thiazol-2-yl]-4-[(4-bromo-2-chlorophenyl)sulfonyl]-piperazine
1-[4-(2-methylbenzyl)-1,3-thiazol-2-yl]-4-[(4-bromo-2-chlorophenyl)sulfonyl]-piperazine
1-[4-(2-methoxybenzyl)-1,3-thiazol-2-yl]-4-[(4-bromo-2-chlorophenyl)sulfonyl]-piperazine
1-[4-(3-methylbenzyl)-1,3-thiazol-2-yl]-4-[(4-bromo-2-chlorophenyl)sulfonyl]-piperazine
1-[4-(3-methoxybenzyl)-1,3-thiazol-2-yl]-4-[(4-bromo-2-chlorophenyl)sulfonyl]-piperazine
1-[4-(3-bromobenzyl)-1,3-thiazol-2-yl]-4-[(4-bromo-2-chlorophenyl)sulfonyl]-piperazine
1-[4-(4-chlorobenzyl)-1,3-thiazol-2-yl]-4-[(4-bromo-2-chlorophenyl)sulfonyl]-piperazine
1-[4-(4-methoxybenzyl)-1,3-thiazol-2-yl]-4-[(4-bromo-2-chlorophenyl)sulfonyl]-piperazine
1-[4-(4-methylbenzyl)-1,3-thiazol-2-yl]-4-[(4-bromo-2-chlorophenyl)sulfonyl]-piperazine
1-[4-(4-ethylbenzyl)-1,3-thiazol-2-yl]-4-[(4-bromo-2-chlorophenyl)sulfonyl]-piperazine
1-[4-(4-ethoxybenzyl)-1,3-thiazol-2-yl]-4-[(4-bromo-2-chlorophenyl)sulfonyl]-piperazine
1-[4-(4-propylbenzyl)-1,3-thiazol-2-yl]-4-[(4-bromo-2-chlorophenyl)sulfonyl]-piperazine
1-[4-(2,6-dimethylbenzyl)-1,3-thiazol-2-yl]-4-[(4-bromo-2-chlorophenyl)sulfonyl]-piperazine
1-[4-(2,3-dimethylbenzyl)-1,3-thiazol-2-yl]-4-[(4-bromo-2-chlorophenyl)sulfonyl]-piperazine
1-[4-(2,5-dimethylbenzyl)-1,3-thiazol-2-yl]-4-[(4-bromo-2-chlorophenyl)sulfonyl]-piperazine
1-[4-(2,4-dichlorobenzyl)-1,3-thiazol-2-yl]-4-[(4-bromo-2-chlorophenyl)sulfonyl]-piperazine
1-[4-(2,4-dimethoxybenzyl)-1,3-thiazol-2-yl]-4-[(4-bromo-2-chlorophenyl)sulfonyl]-piperazine
1-[4-(2,5-dimethoxybenzyl)-1,3-thiazol-2-yl]-4-[(4-bromo-2-chlorophenyl)sulfonyl]-piperazine
1-[4-(3,4-dimethoxybenzyl)-1,3-thiazol-2-yl]-4-[(4-bromo-2-chlorophenyl)sulfonyl]-piperazine
1-[4-(3,5-dimethoxybenzyl)-1,3-thiazol-2-yl]-4-[(4-bromo-2-chlorophenyl)sulfonyl]-piperazine
1-[4-(3,4-dichlorobenzyl)-1,3-thiazol-2-yl]-4-[(4-bromo-2-chlorophenyl)sulfonyl]-piperazine
1-[4-(3,4-dimethylbenzyl)-1,3-thiazol-2-yl]-4-[(4-bromo-2-chlorophenyl)sulfonyl]-piperazine
1-[4-(3,4-difluorobenzyl)-1,3-thiazol-2-yl]-4-[(4-bromo-2-chlorophenyl)sulfonyl]-piperazine
1-[4-(3,5-difluorobenzyl)-1,3-thiazol-2-yl]-4-[(4-bromo-2-chlorophenyl)sulfonyl]-piperazine
1-[4-(3,5-dichlorobenzyl)-1,3-thiazol-2-yl]-4-[(4-bromo-2-chlorophenyl)sulfonyl]-piperazine
1-[4-(3,5-dimethylbenzyl)-1,3-thiazol-2-yl]-4-[(4-bromo-2-chlorophenyl)sulfonyl]-piperazine 1-[4-(3-chloro-4-fluorobenzyl)-1,3-thiazol-2-yl]-4-[(4-bromo-2-chlorophenyl)sulfonyl]-piperazine
1-[4-(3-chloro-5-fluorobenzyl)-1,3-thiazol-2-yl]-4-[(4-bromo-2-chlorophenyl)sulfonyl]-piperazine
1-[4-(4-chloro-3-fluorobenzyl)-1,3-thiazol-2-yl]-4-[(4-bromo-2-chlorophenyl)sulfonyl]-piperazine
1-[4-(3,4,5-trimethoxybenzyl)-1,3-thiazol-2-yl]-4-[(4-bromo-2-chlorophenyl)sulfonyl]-piperazine
1-[4-(2,4,6-trimethylbenzyl)-1,3-thiazol-2-yl]-4-[(4-bromo-2-chlorophenyl)sulfonyl]-piperazine
1-[4-benzyl-1,3-thiazol-2-yl]-4-[(5-chloro-2-methoxyphenyl)sulfonyl]-piperazine
1-[4-(2-methylbenzyl)-1,3-thiazol-2-yl]-4-[(5-chloro-2-methoxyphenyl)sulfonyl]-piperazine
1-[4-(2-methoxybenzyl)-1,3-thiazol-2-yl]-4-[(5-chloro-2-methoxyphenyl)sulfonyl]-piperazine
1-[4-(3-methylbenzyl)-1,3-thiazol-2-yl]-4-[(5-chloro-2-methoxyphenyl)sulfonyl]-piperazine
1-[4-(3-methoxybenzyl)-1,3-thiazol-2-yl]-4-[(5-chloro-2-methoxyphenyl)sulfonyl]-piperazine
1-[4-(3-bromobenzyl)-1,3-thiazol-2-yl]-4-[(5-chloro-2-methoxyphenyl)sulfonyl]-piperazine
1-[4-(4-chlorobenzyl)-1,3-thiazol-2-yl]-4-[(5-chloro-2-methoxyphenyl)sulfonyl]-piperazine
1-[4-(4-methoxybenzyl)-1,3-thiazol-2-yl]-4-[(5-chloro-2-methoxyphenyl)sulfonyl]-piperazine
1-[4-(4-methylbenzyl)-1,3-thiazol-2-yl]-4-[(5-chloro-2-methoxyphenyl)sulfonyl]-piperazine
1-[4-(4-ethylbenzyl)-1,3-thiazol-2-yl]-4-[(5-chloro-2-methoxyphenyl)sulfonyl]-piperazine
1-[4-(4-ethoxybenzyl)-1,3-thiazol-2-yl]-4-[(5-chloro-2-methoxyphenyl)sulfonyl]-piperazine
1-[4-(4-propylbenzyl)-1,3-thiazol-2-yl]-4-[(5-chloro-2-methoxyphenyl)sulfonyl]-piperazine
1-[4-(2,6-dimethylbenzyl)-1,3-thiazol-2-yl]-4-[(5-chloro-2-methoxyphenyl)sulfonyl]-piperazine
1-[4-(2,3-dimethylbenzyl)-1,3-thiazol-2-yl]-4-[(5-chloro-2-methoxyphenyl)sulfonyl]-piperazine
1-[4-(2,5-dimethylbenzyl)-1,3-thiazol-2-yl]-4-[(5-chloro-2-methoxyphenyl)sulfonyl]-piperazine
1-[4-(2,4-dichlorobenzyl)-1,3-thiazol-2-yl]-4-[(5-chloro-2-methoxyphenyl)sulfonyl]-piperazine
1-[4-(2,4-dimethoxybenzyl)-1,3-thiazol-2-yl]-4-[(5-chloro-2-methoxyphenyl)sulfonyl]-piperazine
1-[4-(2,5-dimethoxybenzyl)-1,3-thiazol-2-yl]-4-[(5-chloro-2-methoxyphenyl)sulfonyl]-piperazine
1-[4-(3,4-dimethoxybenzyl)-1,3-thiazol-2-yl]-4-[(5-chloro-2-methoxyphenyl)sulfonyl]-piperazine
1-[4-(3,5-dimethoxybenzyl)-1,3-thiazol-2-yl]-4-[(5-chloro-2-methoxyphenyl)sulfonyl]-piperazine
1-[4-(3,4-dichlorobenzyl)-1,3-thiazol-2-yl]-4-[(5-chloro-2-methoxyphenyl)sulfonyl]-piperazine
1-[4-(3,4-dimethylbenzyl)-1,3-thiazol-2-yl]-4-[(5-chloro-2-methoxyphenyl)sulfonyl]-piperazine
1-[4-(3,4-difluorobenzyl)-1,3-thiazol-2-yl]-4-[(5-chloro-2-methoxyphenyl)sulfonyl]-piperazine
1-[4-(3,5-difluorobenzyl)-1,3-thiazol-2-yl]-4-[(5-chloro-2-methoxyphenyl)sulfonyl]-piperazine
1-[4-(3,5-dichlorobenzyl)-1,3-thiazol-2-yl]-4-[(5-chloro-2-methoxyphenyl)sulfonyl]-piperazine
1-[4-(3,5-dimethylbenzyl)-1,3-thiazol-2-yl]-4-[(5-chloro-2-methoxyphenyl)sulfonyl]-piperazine
1-[4-(3-chloro-4-fluorobenzyl)-1,3-thiazol-2-yl]-4-[(5-chloro-2-methoxyphenyl)sulfonyl]-piperazine
1-[4-(3-chloro-5-fluorobenzyl)-1,3-thiazol-2-yl]-4-[(5-chloro-2-methoxyphenyl)sulfonyl]-piperazine
1-[4-(4-chloro-3-fluorobenzyl)-1,3-thiazol-2-yl]-4-[(5-chloro-2-methoxyphenyl)sulfonyl]-piperazine
1-[4-(3,4,5-trimethoxybenzyl)-1,3-thiazol-2-yl]-4-[(5-chloro-2-methoxyphenyl)sulfonyl]-piperazine
1-[4-(2,4,6-trimethylbenzyl)-1,3-thiazol-2-yl]-4-[(5-chloro-2-methoxyphenyl)sulfonyl]-piperazine
1-[4-benzyl-1,3-thiazol-2-yl]-4-[(2-chloro-5-(trifluoromethyl)phenyl)sulfonyl]-piperazine
1-[4-(2-methylbenzyl)-1,3-thiazol-2-yl]-4-[(2-chloro-5-(trifluoromethyl)phenyl)sulfonyl]-piperazine
1-[4-(2-methoxybenzyl)-1,3-thiazol-2-yl]-4-[(2-chloro-5-(trifluoromethyl)phenyl)sulfonyl]-piperazine
1-[4-(3-methylbenzyl)-1,3-thiazol-2-yl]-4-[(2-chloro-5-(trifluoromethyl)phenyl)sulfonyl]-piperazine
1-[4-(3-methoxybenzyl)-1,3-thiazol-2-yl]-4-[(2-chloro-5-(trifluoromethyl)phenyl)sulfonyl]-piperazine
1-[4-(3-bromobenzyl)-1,3-thiazol-2-yl]-4-[(2-chloro-5-(trifluoromethyl)phenyl)sulfonyl]-piperazine
1-[4-(4-chlorobenzyl)-1,3-thiazol-2-yl]-4-[(2-chloro-5-(trifluoromethyl)phenyl)sulfonyl]-piperazine
1-[4-(4-methoxybenzyl)-1,3-thiazol-2-yl]-4-[(2-chloro-5-(trifluoromethyl)phenyl)sulfonyl]-piperazine
1-[4-(4-methylbenzyl)-1,3-thiazol-2-yl]-4-[(2-chloro-5-(trifluoromethyl)phenyl)sulfonyl]-piperazine
1-[4-(4-ethylbenzyl)-1,3-thiazol-2-yl]-4-[(2-chloro-5-(trifluoromethyl)phenyl)sulfonyl]-piperazine
1-[4-(4-ethoxybenzyl)-1,3-thiazol-2-yl]-4-[(2-chloro-5-(trifluoromethyl)phenyl)sulfonyl]-piperazine
1-[4-(4-propylbenzyl)-1,3-thiazol-2-yl]-4-[(2-chloro-5-(trifluoromethyl)phenyl)sulfonyl]-piperazine
1-[4-(2,6-dimethylbenzyl)-1,3-thiazol-2-yl]-4-[(2-chloro-5-(trifluoromethyl)phenyl)sulfonyl]-piperazine
1-[4-(2,3-dimethylbenzyl)-1,3-thiazol-2-yl]-4-[(2-chloro-5-(trifluoromethyl)phenyl)sulfonyl]-piperazine
1-[4-(2,5-dimethylbenzyl)-1,3-thiazol-2-yl]-4-[(2-chloro-5-(trifluoromethyl)phenyl)sulfonyl]-piperazine
1-[4-(2,4-dichlorobenzyl)-1,3-thiazol-2-yl]-4-[(2-chloro-5-(trifluoromethyl)phenyl)sulfonyl]-piperazine
1-[4-(2,4-dimethoxybenzyl)-1,3-thiazol-2-yl]-4-[(2-chloro-5-(trifluoromethyl)phenyl)sulfonyl]-piperazine
1-[4-(2,5-dimethoxybenzyl)-1,3-thiazol-2-yl]-4-[(2-chloro-5-(trifluoromethyl)phenyl)sulfonyl]-piperazine
1-[4-(3,4-dimethoxybenzyl)-1,3-thiazol-2-yl]-4-[(2-chloro-5-(trifluoromethyl)phenyl)sulfonyl]-piperazine
1-[4-(3,5-dimethoxybenzyl)-1,3-thiazol-2-yl]-4-[(2-chloro-5-(trifluoromethyl)phenyl)sulfonyl]-piperazine
1-[4-(3,4-dichlorobenzyl)-1,3-thiazol-2-yl]-4-[(2-chloro-5-(trifluoromethyl)phenyl)sulfonyl]-piperazine
1-[4-(3,4-dimethylbenzyl)-1,3-thiazol-2-yl]-4-[(2-chloro-5-(trifluoromethyl)phenyl)sulfonyl]-piperazine
1-[4-(3,4-difluorobenzyl)-1,3-thiazol-2-yl]-4-[(2-chloro-5-(trifluoromethyl)phenyl)sulfonyl]-piperazine
1-[4-(3,5-difluorobenzyl)-1,3-thiazol-2-yl]-4-[(2-chloro-5-(trifluoromethyl)phenyl)sulfonyl]-piperazine
1-[4-(3,5-dichlorobenzyl)-1,3-thiazol-2-yl]-4-[(2-chloro-5-(trifluoromethyl)phenyl)sulfonyl]-piperazine
1-[4-(3,5-dimethylbenzyl)-1,3-thiazol-2-yl]-4-[(2-chloro-5-(trifluoromethyl)phenyl)sulfonyl]-piperazine
1-[4-(3-chloro-4-fluorobenzyl)-1,3-thiazol-2-yl]-4-[(2-chloro-5-(trifluoromethyl)phenyl)sulfonyl]-piperazine
1-[4-(3-chloro-5-fluorobenzyl)-1,3-thiazol-2-yl]-4-[(2-chloro-5-(trifluoromethyl)phenyl)sulfonyl]-piperazine
1-[4-(4-chloro-3-fluorobenzyl)-1,3-thiazol-2-yl]-4-[(2-chloro-5-(trifluoromethyl)phenyl)sulfonyl]-piperazine
1-[4-(3,4,5-trimethoxybenzyl)-1,3-thiazol-2-yl]-4-[(2-chloro-5-(trifluoromethyl)phenyl)sulfonyl]-piperazine 1-[4-(2,4,6-trimethylbenzyl)-1,3-thiazol-2-yl]-4-[(2-chloro-5-(trifluoromethyl)phenyl)sulfonyl]-piperazine
1-[4-benzyl-1,3-thiazol-2-yl]-4-[(4-chloro-3-nitrophenyl)sulfonyl]-piperazine
1-[4-(2-methylbenzyl)-1,3-thiazol-2-yl]-4-[(4-chloro-3-nitrophenyl)sulfonyl]-piperazine
1-[4-(2-methoxybenzyl)-1,3-thiazol-2-yl]-4-[(4-chloro-3-nitrophenyl)sulfonyl]-piperazine
1-[4-(3-methylbenzyl)-1,3-thiazol-2-yl]-4-[(4-chloro-3-nitrophenyl)sulfonyl]-piperazine
1-[4-(3-methoxybenzyl)-1,3-thiazol-2-yl]-4-[(4-chloro-3-nitrophenyl)sulfonyl]-piperazine
1-[4-(3-bromobenzyl)-1,3-thiazol-2-yl]-4-[(4-chloro-3-nitrophenyl)sulfonyl]-piperazine
1-[4-(4-chlorobenzyl)-1,3-thiazol-2-yl]-4-[(4-chloro-3-nitrophenyl)sulfonyl]-piperazine
1-[4-(4-methoxybenzyl)-1,3-thiazol-2-yl]-4-[(4-chloro-3-nitrophenyl)sulfonyl]-piperazine
1-[4-(4-methylbenzyl)-1,3-thiazol-2-yl]-4-[(4-chloro-3-nitrophenyl)sulfonyl]-piperazine
1-[4-(4-ethylbenzyl)-1,3-thiazol-2-yl]-4-[(4-chloro-3-nitrophenyl)sulfonyl]-piperazine
1-[4-(4-ethoxybenzyl)-1,3-thiazol-2-yl]-4-[(4-chloro-3-nitrophenyl)sulfonyl]-piperazine
1-[4-(4-propylbenzyl)-1,3-thiazol-2-yl]-4-[(4-chloro-3-nitrophenyl)sulfonyl]-piperazine
1-[4-(2,6-dimethylbenzyl)-1,3-thiazol-2-yl]-4-[(4-chloro-3-nitrophenyl)sulfonyl]-piperazine
1-[4-(2,3-dimethylbenzyl)-1,3-thiazol-2-yl]-4-[(4-chloro-3-nitrophenyl)sulfonyl]-piperazine
1-[4-(2,5-dimethylbenzyl)-1,3-thiazol-2-yl]-4-[(4-chloro-3-nitrophenyl)sulfonyl]-piperazine
1-[4-(2,4-dichlorobenzyl)-1,3-thiazol-2-yl]-4-[(4-chloro-3-nitrophenyl)sulfonyl]-piperazine
1-[4-(2,4-dimethoxybenzyl)-1,3-thiazol-2-yl]-4-[(4-chloro-3-nitrophenyl)sulfonyl]-piperazine
1-[4-(2,5-dimethoxybenzyl)-1,3-thiazol-2-yl]-4-[(4-chloro-3-nitrophenyl)sulfonyl]-piperazine
1-[4-(3,4-dimethoxybenzyl)-1,3-thiazol-2-yl]-4-[(4-chloro-3-nitrophenyl)sulfonyl]-piperazine
1-[4-(3,5-dimethoxybenzyl)-1,3-thiazol-2-yl]-4-[(4-chloro-3-nitrophenyl)sulfonyl]-piperazine
1-[4-(3,4-dichlorobenzyl)-1,3-thiazol-2-yl]-4-[(4-chloro-3-nitrophenyl)sulfonyl]-piperazine
1-[4-(3,4-dimethylbenzyl)-1,3-thiazol-2-yl]-4-[(4-chloro-3-nitrophenyl)sulfonyl]-piperazine
1-[4-(3,4-difluorobenzyl)-1,3-thiazol-2-yl]-4-[(4-chloro-3-nitrophenyl)sulfonyl]-piperazine
1-[4-(3,5-difluorobenzyl)-1,3-thiazol-2-yl]-4-[(4-chloro-3-nitrophenyl)sulfonyl]-piperazine
1-[4-(3,5-dichlorobenzyl)-1,3-thiazol-2-yl]-4-[(4-chloro-3-nitrophenyl)sulfonyl]-piperazine
1-[4-(3,5-dimethylbenzyl)-1,3-thiazol-2-yl]-4-[(4-chloro-3-nitrophenyl)sulfonyl]-piperazine
1-[4-(3-chloro-4-fluorobenzyl)-1,3-thiazol-2-yl]-4-[(4-chloro-3-nitrophenyl)sulfonyl]-piperazine
1-[4-(3-chloro-5-fluorobenzyl)-1,3-thiazol-2-yl]-4-[(4-chloro-3-nitrophenyl)sulfonyl]-piperazine
1-[4-(4-chloro-3-fluorobenzyl)-1,3-thiazol-2-yl]-4-[(4-chloro-3-nitrophenyl)sulfonyl]-piperazine
1-[4-(3,4,5-trimethoxybenzyl)-1,3-thiazol-2-yl]-4-[(4-chloro-3-nitrophenyl)sulfonyl]-piperazine
1-[4-(2,4,6-trimethylbenzyl)-1,3-thiazol-2-yl]-4-[(4-chloro-3-nitrophenyl)sulfonyl]-piperazine
1-[4-benzyl-1,3-thiazol-2-yl]-4-[(2,4-dichloro-5-methylphenyl)sulfonyl]-piperazine
1-[4-(2-methylbenzyl)-1,3-thiazol-2-yl]-4-[(2,4-dichloro-5-methylphenyl)sulfonyl]-piperazine
1-[4-(2-methoxybenzyl)-1,3-thiazol-2-yl]-4-[(2,4-dichloro-5-methylphenyl)sulfonyl]-piperazine
1-[4-(3-methylbenzyl)-1,3-thiazol-2-yl]-4-[(2,4-dichloro-5-methylphenyl)sulfonyl]-piperazine
1-[4-(3-methoxybenzyl)-1,3-thiazol-2-yl]-4-[(2,4-dichloro-5-methylphenyl)sulfonyl]-piperazine
1-[4-(3-bromobenzyl)-1,3-thiazol-2-yl]-4-[(2,4-dichloro-5-methylphenyl)sulfonyl]-piperazine
1-[4-(4-chlorobenzyl)-1,3-thiazol-2-yl]-4-[(2,4-dichloro-5-methylphenyl)sulfonyl]-piperazine
1-[4-(4-methoxybenzyl)-1,3-thiazol-2-yl]-4-[(2,4-dichloro-5-methylphenyl)sulfonyl]-piperazine
1-[4-(4-methylbenzyl)-1,3-thiazol-2-yl]-4-[(2,4-dichloro-5-methylphenyl)sulfonyl]-piperazine
1-[4-(4-ethylbenzyl)-1,3-thiazol-2-yl]-4-[(2,4-dichloro-5-methylphenyl)sulfonyl]-piperazine
1-[4-(4-ethoxybenzyl)-1,3-thiazol-2-yl]-4-[(2,4-dichloro-5-methylphenyl)sulfonyl]-piperazine
1-[4-(4-propylbenzyl)-1,3-thiazol-2-yl]-4-[(2,4-dichloro-5-methylphenyl)sulfonyl]-piperazine
1-[4-(2,6-dimethylbenzyl)-1,3-thiazol-2-yl]-4-[(2,4-dichloro-5-methylphenyl)sulfonyl]-piperazine
1-[4-(2,3-dimethylbenzyl)-1,3-thiazol-2-yl]-4-[(2,4-dichloro-5-methylphenyl)sulfonyl]-piperazine
1-[4-(2,5-dimethylbenzyl)-1,3-thiazol-2-yl]-4-[(2,4-dichloro-5-methylphenyl)sulfonyl]-piperazine
1-[4-(2,4-dichlorobenzyl)-1,3-thiazol-2-yl]-4-[(2,4-dichloro-5-methylphenyl)sulfonyl]-piperazine
1-[4-(2,4-dimethoxybenzyl)-1,3-thiazol-2-yl]-4-[(2,4-dichloro-5-methylphenyl)sulfonyl]-piperazine
1-[4-(2,5-dimethoxybenzyl)-1,3-thiazol-2-yl]-4-[(2,4-dichloro-5-methylphenyl)sulfonyl]-piperazine
1-[4-(3,4-dimethoxybenzyl)-1,3-thiazol-2-yl]-4-[(2,4-dichloro-5-methylphenyl)sulfonyl]-piperazine
1-[4-(3,5-dimethoxybenzyl)-1,3-thiazol-2-yl]-4-[(2,4-dichloro-5-methylphenyl)sulfonyl]-piperazine
1-[4-(3,4-dichlorobenzyl)-1,3-thiazol-2-yl]-4-[(2,4-dichloro-5-methylphenyl)sulfonyl]-piperazine
1-[4-(3,4-dimethylbenzyl)-1,3-thiazol-2-yl]-4-[(2,4-dichloro-5-methylphenyl)sulfonyl]-piperazine
1-[4-(3,4-difluorobenzyl)-1,3-thiazol-2-yl]-4-[(2,4-dichloro-5-methylphenyl)sulfonyl]-piperazine
1-[4-(3,5-difluorobenzyl)-1,3-thiazol-2-yl]-4-[(2,4-dichloro-5-methylphenyl)sulfonyl]-piperazine
1-[4-(3,5-dichlorobenzyl)-1,3-thiazol-2-yl]-4-[(2,4-dichloro-5-methylphenyl)sulfonyl]-piperazine
1-[4-(3,5-dimethylbenzyl)-1,3-thiazol-2-yl]-4-[(2,4-dichloro-5-methylphenyl)sulfonyl]-piperazine
1-[4-(3-chloro-4-fluorobenzyl)-1,3-thiazol-2-yl]-4-[(2,4-dichloro-5-methylphenyl)sulfonyl]-piperazine
1-[4-(3-chloro-5-fluorobenzyl)-1,3-thiazol-2-yl]-4-[(2,4-dichloro-5-methylphenyl)sulfonyl]-piperazine
1-[4-(4-chloro-3-fluorobenzyl)-1,3-thiazol-2-yl]-4-[(2,4-dichloro-5-methylphenyl)sulfonyl]-piperazine
1-[4-(3,4,5-trimethoxybenzyl)-1,3-thiazol-2-yl]-4-[(2,4-dichloro-5-methylphenyl)sulfonyl]-piperazine,
1-[4-(2,4,6-trimethylbenzyl)-1,3-thiazol-2-yl]-4-[(2,4-dichloro-5-methylphenyl)sulfonyl]-piperazine
1-[4-((4-methoxyphenyl)ethyl)-1,3-thiazol-2-yl]-4-[(2,4-dichloro-5-methylphenyl)sulfonyl]-piperazine
1-[4-((4-nitrophenyl)ethyl)-1,3-thiazol-2-yl]-4-[(2,4-dichloro-5-methylphenyl)sulfonyl]-piperazine
1-[4-(phenylvinyl)-1,3-thiazol-2-yl]-4-[(2,4-dichloro-5-methylphenyl)sulfonyl]-piperazine 1-[4-(4-chloro-3-fluorobenzyl)-1,3-thiazol-2yl]-4-[(5-chloro-4-nitrothiophen-2-yl)sulfonyl]-piperazine
1-[4-((4-methoxyphenypethyl)-1,3-thiazol-2-yl]-4-[(5-chloro-4-nitrothiophen-2-yl)sulfonyl]-piperazine
1-[4-((4-nitrophenypethyl)-1,3-thiazol-2-yl]-4-[(5-chloro-4-nitrothiophen-2-yl)sulfonyl]-piperazine
1-[4-(phenylvinyl)-1,3-thiazol-2-yl]-4-[(5-chloro-4-nitrothiophen-2-yl)sulfonyl]-piperazine
1-[4-(4-chloro-3-fluorobenzyl)-1,3-thiazol-2-yl]-4-[(6-bromopyridin-3-yl)sulfonyl]-piperazine
1-[4-((4-methoxyphenypethyl)-1,3-thiazol-2-yl]-4-[(6-bromopyridin-3-yl)sulfonyl]-piperazine
1-[4-((4-nitrophenypethyl)-1,3-thiazol-2-yl]-4-[(6-bromopyridin-3-yl)sulfonyl]-piperazine
1-[4-(phenylvinyl)-1,3-thiazol-2-yl]-4-[(5-methyl-1H-imidazol-2-yl)sulfonyl]-piperazine
1-[4-(4-chloro-3-fluorobenzyl)-1,3-thiazol-2-yl]-4-[(5-methyl-1H-imidazol-2-yl)sulfonyl]-piperazine
1-[4-((4-methoxyphenypethyl)-1,3-thiazol-2-yl]-4-[(5-methyl-1H-imidazol-2-yl)sulfonyl]-piperazine
1-[4-((4-nitrophenypethyl)-1,3-thiazol-2-yl]-4-[(5-methyl-1H-imidazol-2-yl)sulfonyl]-piperazine
1-[4-(phenylvinyl)-1,3-thiazol-2-yl]-4-[(5-methyl-1H-imidazol-2-yl)sulfonyl]-piperazine
1-[4-(4-chloro-3-fluorobenzyl)-1,3-thiazol-2-yl]-4-[(2,4-dimethylpyrimidin-5-yl)sulfonyl]-piperazine
1-[4-((4-methoxyphenyl)ethyl)-1,3-thiazol-2-yl]-4-[(2,4-dimethylpyrimidin-5-yl)sulfonyl]-piperazine
1-[4-((4-nitrophenyl) ethyl)-1,3-thiazol-2-yl]-4-[(2,4-dimethylpyrimidin-5-yl)sulfonyl]-piperazine, and
1-[4-(phenylvinyl)-1,3-thiazol-2-yl]-4-[(2,4-dimethylpyrimidin-5-yl)sulfonyl]-piperazine.

Example 12

Biological Activity of Some Derivatives

Exemplary compounds of this invention are shown in table 2 below with their chemical formula, the value of $EC_{50}$ (expressed in nM) and the percentage inhibition (% inh.) in the biological assay of examples 3 and 4. The same compounds are also included in table 3 below with their official name according to IUPAC nomenclature.

TABLE 2

| Compound | Structure | $EC_{50}$ (nM) | % inh. |
|---|---|---|---|
| 10 | 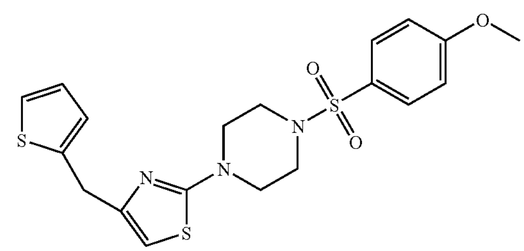 [SMILES: COc1ccc(S(=O)(=O)N2CCN(c3nc(Cc4cccs4)cs3)CC2)cc1] | 12.0 | 93 |
| 11 | 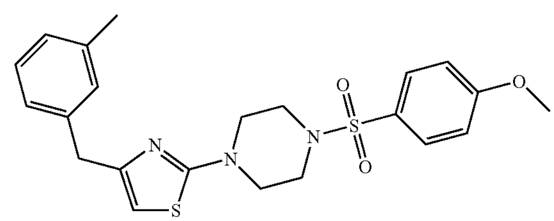 [SMILES: COc1ccc(S(=O)(=O)N2CCN(c3nc(Cc4cccc(C)c4)cs3)CC2)cc1] | 18.0 | 95 |
| 12 | 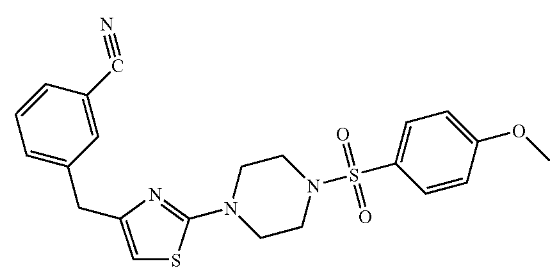 [SMILES: COc1ccc(S(=O)(=O)N2CCN(c3nc(Cc4cccc(C#N)c4)cs3)CC2)cc1] | 3.2 | 66 |
| 13 | 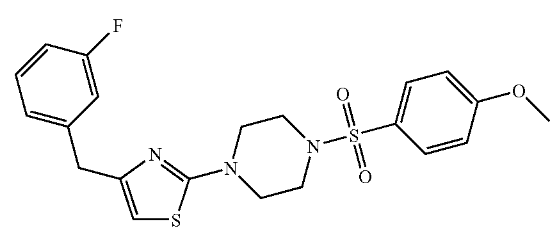 [SMILES: COc1ccc(S(=O)(=O)N2CCN(c3nc(Cc4cccc(F)c4)cs3)CC2)cc1] | 11.5 | 92 |

TABLE 2-continued

| Compound | Structure | EC$_{50}$ (nM) | % inh. |
|---|---|---|---|
| 14 | 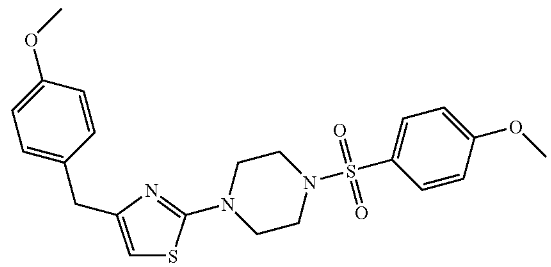 [SMILES: COc1ccc(Cc2csc(N3CCN(S(=O)(=O)c4ccc(OC)cc4)CC3)n2)cc1] | 46.6 | 90 |
| 15 | 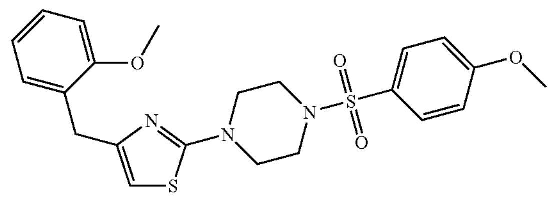 [SMILES: COc1ccc(S(=O)(=O)N2CCN(c3nc(Cc4ccccc4OC)cs3)CC2)cc1] | 17.0 | 71 |
| 16 | 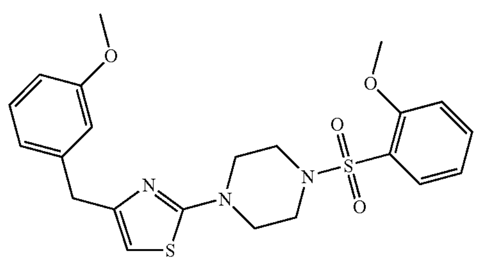 [SMILES: COc1cccc(Cc2csc(N3CCN(S(=O)(=O)c4ccccc4OC)CC3)n2)c1] | 3590 | 76 |
| 17 | 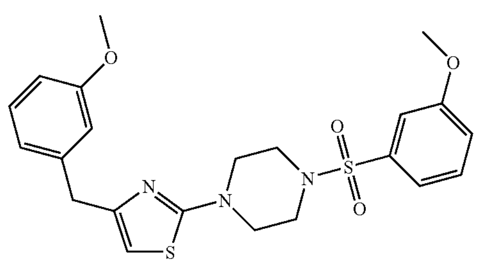 [SMILES: COc1cccc(Cc2csc(N3CCN(S(=O)(=O)c4cccc(OC)c4)CC3)n2)c1] | 4360 | 130 |
| 18 | 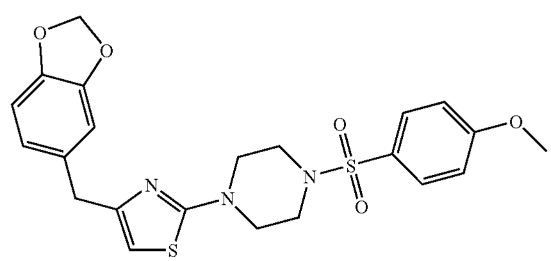 [SMILES: COc1ccc(S(=O)(=O)N2CCN(c3nc(Cc4ccc5c(c4)OCO5)cs3)CC2)cc1] | 22.8 | 19 |
| 19 | 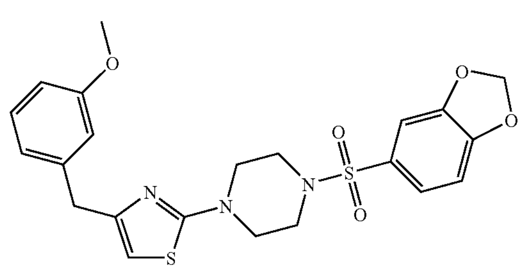 [SMILES: COc1cccc(Cc2csc(N3CCN(S(=O)(=O)c4ccc5c(c4)OCO5)CC3)n2)c1] | 251 | 84 |

TABLE 2-continued

| Compound | Structure | EC$_{50}$ (nM) | % inh. |
|---|---|---|---|
| 20 | 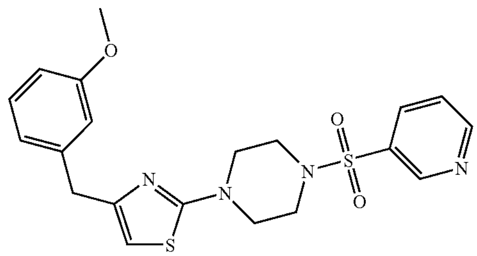 [SMILES: COc1cccc(Cc2csc(N3CCN(S(=O)(=O)c4cccnc4)CC3)n2)c1] | 1720 | 76 |
| 21 | 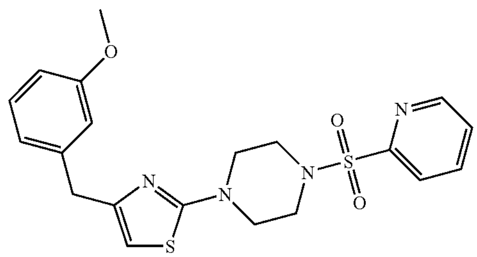 [SMILES: COc1cccc(Cc2csc(N3CCN(S(=O)(=O)c4ccccn4)CC3)n2)c1] | 2440 | 116 |
| 22 | 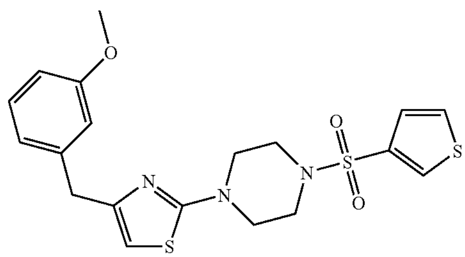 [SMILES: COc1cccc(Cc2csc(N3CCN(S(=O)(=O)c4ccsc4)CC3)n2)c1] | 1000 | 89 |
| 23 | 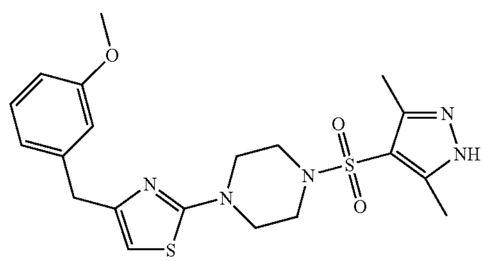 [SMILES: COc1cccc(Cc2csc(N3CCN(S(=O)(=O)c4c(C)n[nH]c4C)CC3)n2)c1] | 1290 | 95 |
| 24 | 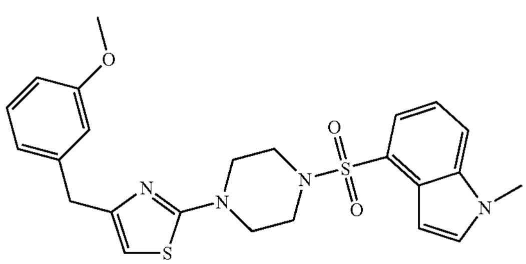 [SMILES: COc1cccc(Cc2csc(N3CCN(S(=O)(=O)c4cccc5c4ccn5C)CC3)n2)c1] | 1170 | 82 |
| 25 | 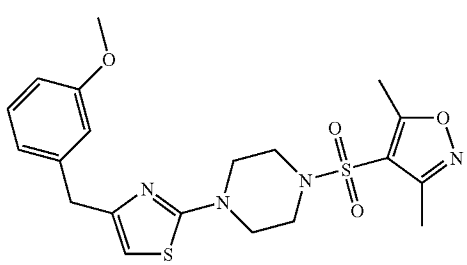 [SMILES: COc1cccc(Cc2csc(N3CCN(S(=O)(=O)c4c(C)noc4C)CC3)n2)c1] | NA | NA |

TABLE 2-continued
| Compound | Structure | EC$_{50}$ (nM) | % inh. |
|---|---|---|---|
| 26 | 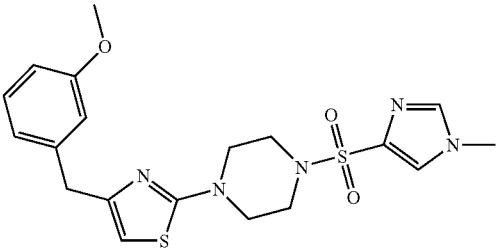 [SMILES: COc1cccc(Cc2csc(N3CCN(S(=O)(=O)c4cn(C)cn4)CC3)n2)c1] | 870 | 87 |
| 27 | 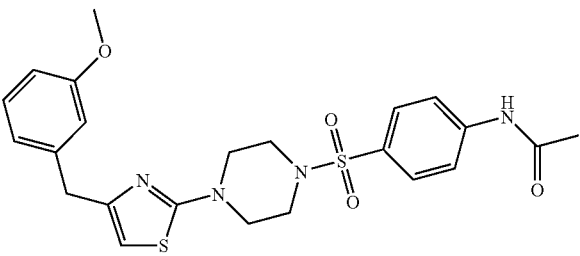 [SMILES: COc1cccc(Cc2csc(N3CCN(S(=O)(=O)c4ccc(NC(C)=O)cc4)CC3)n2)c1] | 250 | 91 |
| 28 | 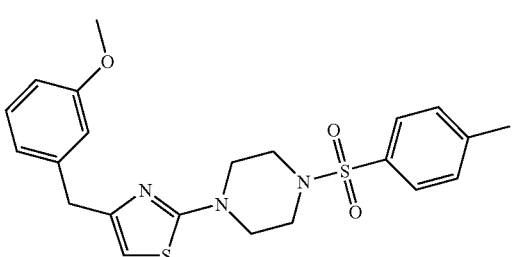 | 1890 | 165 |
| 29 | 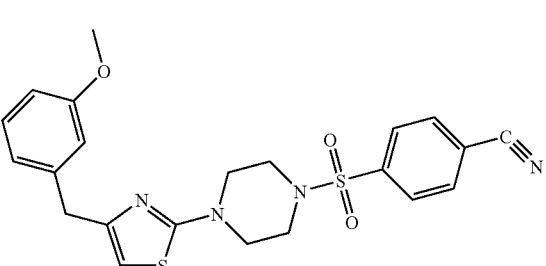 | 1270 | 42 |
| 30 | 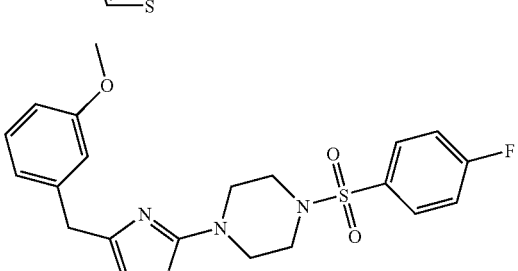 | 405 | 98 |
| 31 | 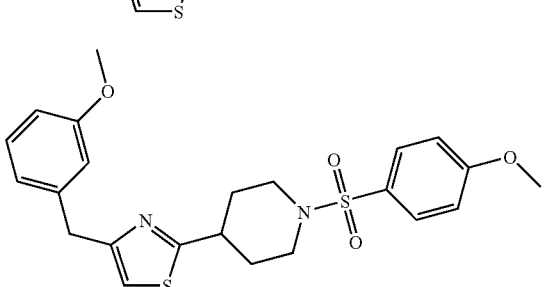 | 6.6 | 66 |

TABLE 2-continued

| Compound | Structure | EC$_{50}$ (nM) | % inh. |
|---|---|---|---|
| 32 | 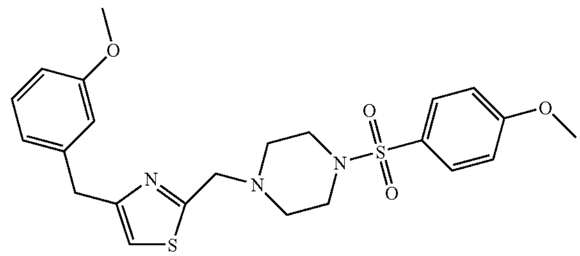 [SMILES: COc1ccc(S(=O)(=O)N2CCN(Cc3nc(Cc4cccc(OC)c4)cs3)CC2)cc1] | 159 | 95 |
| 33 | 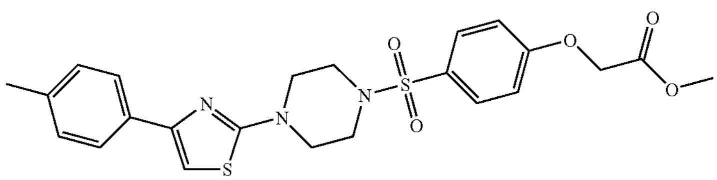 | 51.6 | 21 |
| 34 | 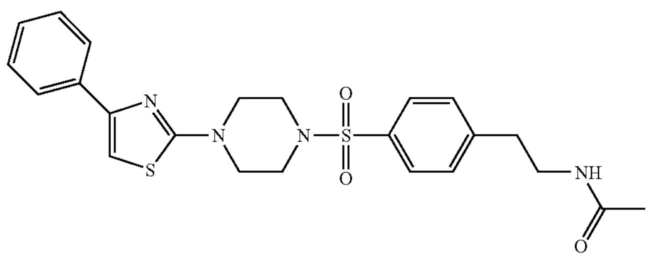 [SMILES: CC(=O)NCCc1ccc(S(=O)(=O)N2CCN(c3nc(-c4ccccc4)cs3)CC2)cc1] | 3090 | 46 |
| 35 | 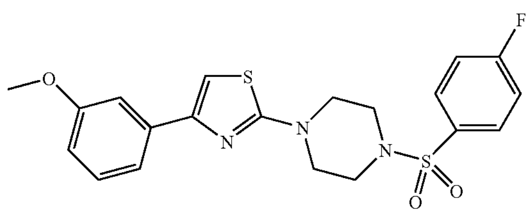 [SMILES: COc1cccc(-c2csc(N3CCN(S(=O)(=O)c4ccc(F)cc4)CC3)n2)c1] | 216 | 90 |
| 36 | 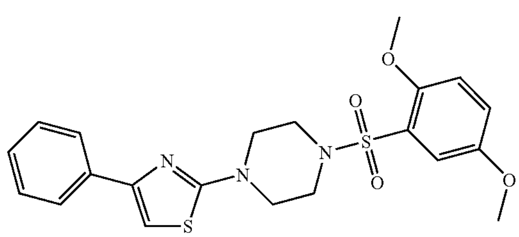 [SMILES: COc1ccc(OC)c(S(=O)(=O)N2CCN(c3nc(-c4ccccc4)cs3)CC2)c1] | 950 | 121 |
| 37 | 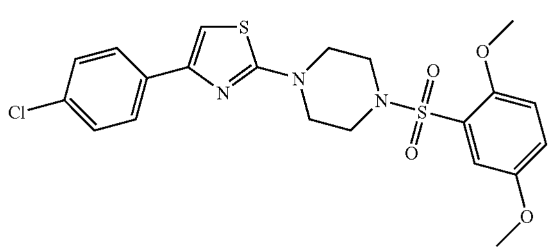 [SMILES: COc1ccc(OC)c(S(=O)(=O)N2CCN(c3nc(-c4ccc(Cl)cc4)cs3)CC2)c1] | 1290 | 74 |

TABLE 2-continued

| Compound | Structure | EC$_{50}$ (nM) | % inh. |
|---|---|---|---|
| 38 | 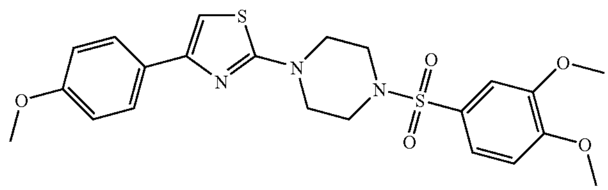 | 1060 | 65 |
| 39 | 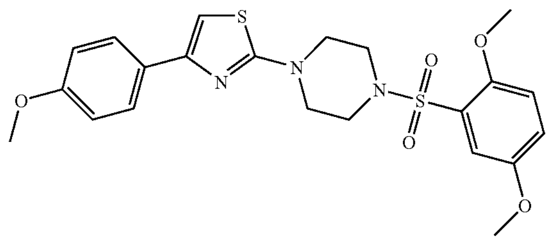 [SMILES: COc1ccc(-c2csc(N3CCN(S(=O)(=O)c4cc(OC)ccc4OC)CC3)n2)cc1] | 6750 | 107 |
| 44 | 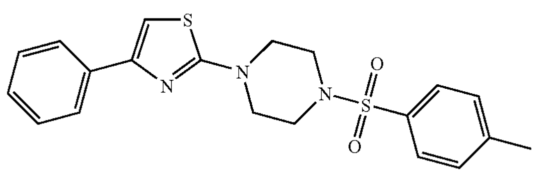 [SMILES: Cc1ccc(S(=O)(=O)N2CCN(c3nc(-c4ccccc4)cs3)CC2)cc1] | 197 | 72 |
| 47 | 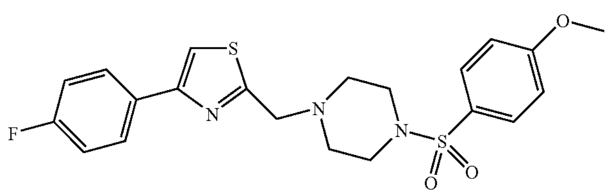 [SMILES: COc1ccc(S(=O)(=O)N2CCN(Cc3nc(-c4ccc(F)cc4)cs3)CC2)cc1] | 39.9 | 86 |
| 48 | 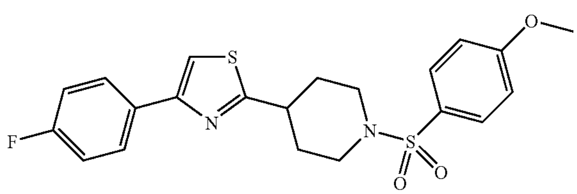 [SMILES: COc1ccc(S(=O)(=O)N2CCC(c3nc(-c4ccc(F)cc4)cs3)CC2)cc1] | 49.4 | 90 |
| 49 | 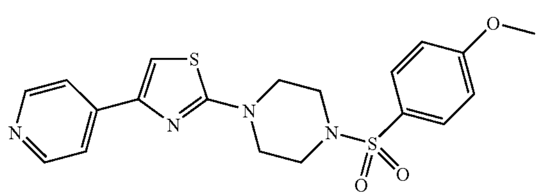 [SMILES: COc1ccc(S(=O)(=O)N2CCN(c3nc(-c4ccncc4)cs3)CC2)cc1] | 75 | 114 |
| 50 | 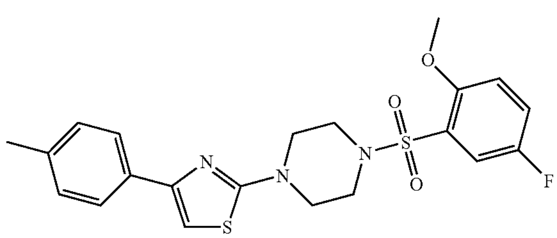 [SMILES: COc1ccc(F)cc1S(=O)(=O)N1CCN(c2nc(-c3ccc(C)cc3)cs2)CC1] | 1770 | 104 |

TABLE 2-continued
| Compound | Structure | EC$_{50}$ (nM) | % inh. |
|---|---|---|---|
| 51 | 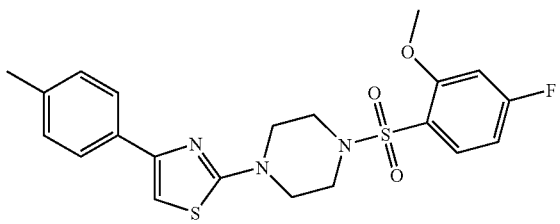 [SMILES: COc1cc(F)ccc1S(=O)(=O)N1CCN(c2nc(-c3ccc(C)cc3)cs2)CC1] | 2500 | 88 |
| 52 | 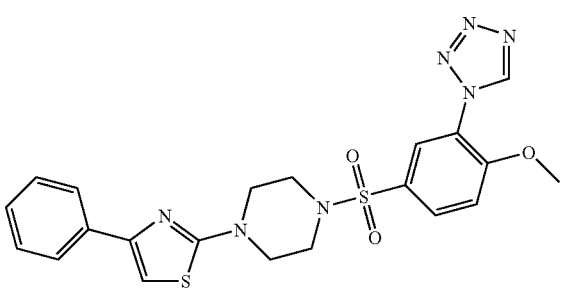 [SMILES: COc1ccc(S(=O)(=O)N2CCN(c3nc(-c4ccccc4)cs3)CC2)cc1-n1cnnn1] | 601 | 47 |
| 53 | 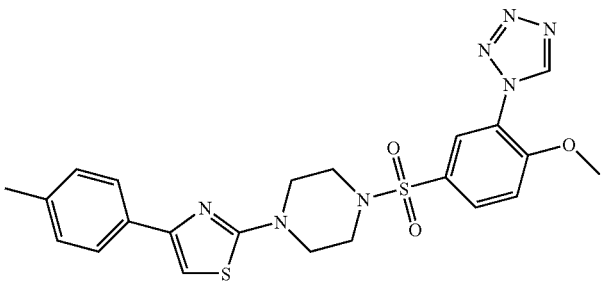 | 818 | 74 |
| 54 | 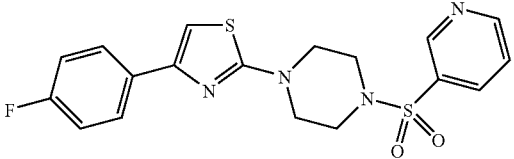 [SMILES: O=S(=O)(c1cccnc1)N1CCN(c2nc(-c3ccc(F)cc3)cs2)CC1] | 1230 | 91 |
| 55 | 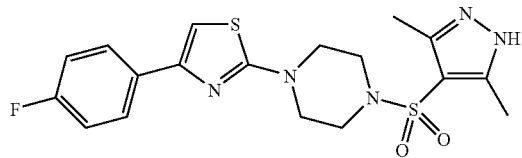 [SMILES: Cc1n[nH]c(C)c1S(=O)(=O)N1CCN(c2nc(-c3ccc(F)cc3)cs2)CC1] | 657 | 91 |
| 56 | 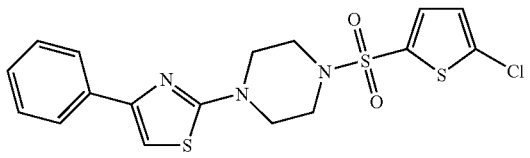 [SMILES: O=S(=O)(c1ccc(Cl)s1)N1CCN(c2nc(-c3ccccc3)cs2)CC1] | 752 | 98 |
| 57 | 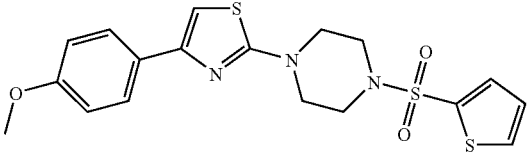 [SMILES: COc1ccc(-c2csc(N3CCN(S(=O)(=O)c4cccs4)CC3)n2)cc1] | 721 | 88 |

TABLE 2-continued

| Compound | Structure | EC$_{50}$ (nM) | % inh. |
|---|---|---|---|
| 58 | 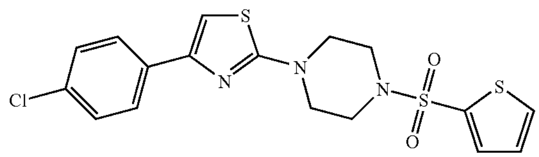 [SMILES: O=S(=O)(c1cccs1)N1CCN(c2nc(-c3ccc(Cl)cc3)cs2)CC1] | 3750 | 99 |
| 59 | 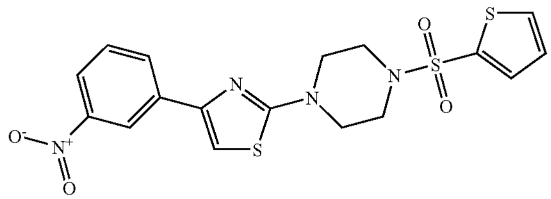 [SMILES: O=[N+]([O-])c1cccc(-c2csc(N3CCN(S(=O)(=O)c4cccs4)CC3)n2)c1] | 290 | 74 |
| 60 | 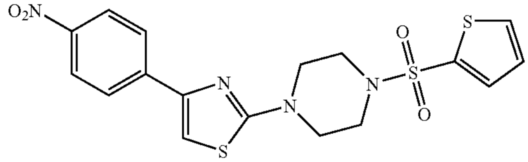 [SMILES: O=[N+]([O-])c1ccc(-c2csc(N3CCN(S(=O)(=O)c4cccs4)CC3)n2)cc1] | 1240 | 79 |
| 61 | 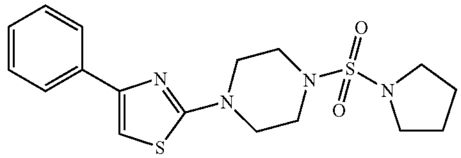 [SMILES: O=S(=O)(N1CCCC1)N1CCN(c2nc(-c3ccccc3)cs2)CC1] | 1740 | 127 |
| 62 | 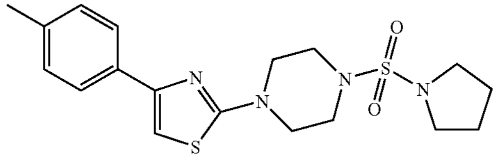 [SMILES: Cc1ccc(-c2csc(N3CCN(S(=O)(=O)N4CCCC4)CC3)n2)cc1] | 1930 | 112 |
| 63 | 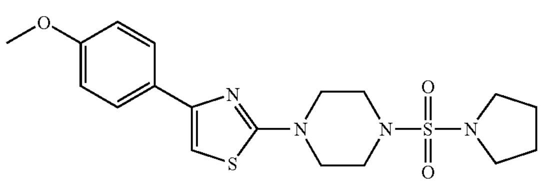 [SMILES: COc1ccc(-c2csc(N3CCN(S(=O)(=O)N4CCCC4)CC3)n2)cc1] | 3180 | 69 |
| 64 | 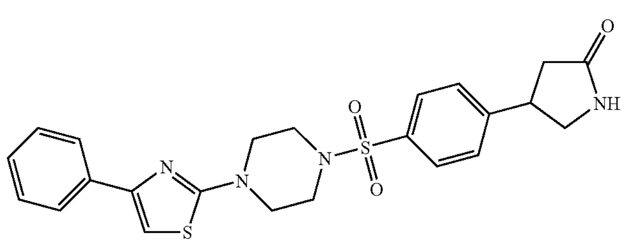 [SMILES: O=C1CC(c2ccc(S(=O)(=O)N3CCN(c4nc(-c5ccccc5)cs4)CC3)cc2)CN1] | 1440 | 83 |
| 65 | 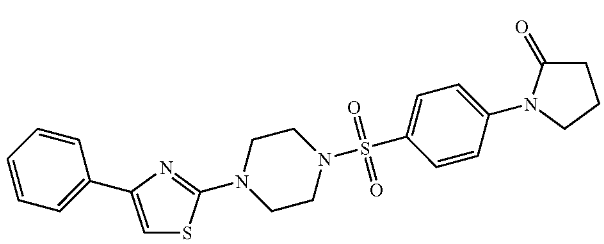 [SMILES: O=C1CCCN1c1ccc(S(=O)(=O)N2CCN(c3nc(-c4ccccc4)cs3)CC2)cc1] | 130 | 51 |

TABLE 2-continued

| Compound | Structure | EC$_{50}$ (nM) | % inh. |
|---|---|---|---|
| 66 | 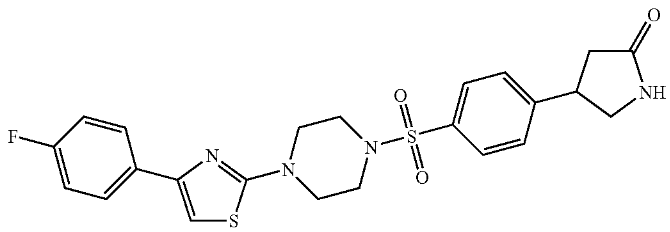 [SMILES: O=C1CC(c2ccc(S(=O)(=O)N3CCN(c4nc(-c5ccc(F)cc5)cs4)CC3)cc2)CN1] | 533 | 40 |
| 67 | 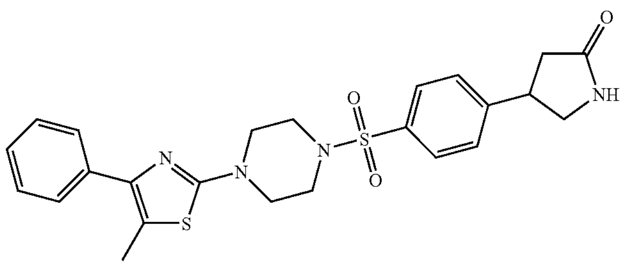 [SMILES: Cc1sc(N2CCN(S(=O)(=O)c3ccc(C4CNC(=O)C4)cc3)CC2)nc1-c1ccccc1] | 37.5 | 21 |
| 69 | 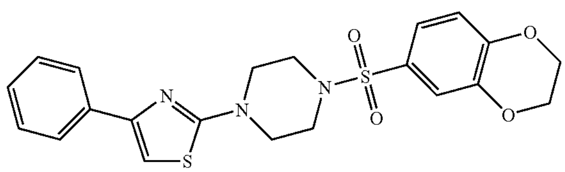 [SMILES: O=S(=O)(c1ccc2c(c1)OCCO2)N1CCN(c2nc(-c3ccccc3)cs2)CC1] | 434 | 89 |
| 70 | 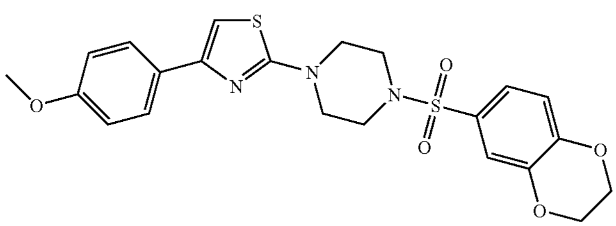 [SMILES: COc1ccc(-c2csc(N3CCN(S(=O)(=O)c4ccc5c(c4)OCCO5)CC3)n2)cc1] | 1960 | 83 |
| 71 | 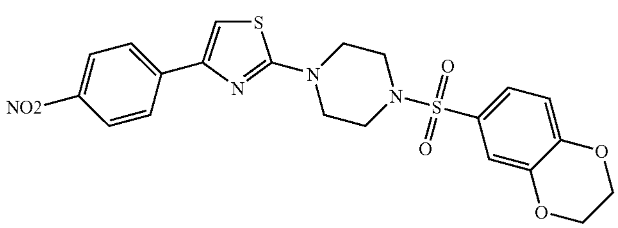 [SMILES: O=[N+]([O-])c1ccc(-c2csc(N3CCN(S(=O)(=O)c4ccc5c(c4)OCCO5)CC3)n2)cc1] | 1440 | 77 |
| 72 | 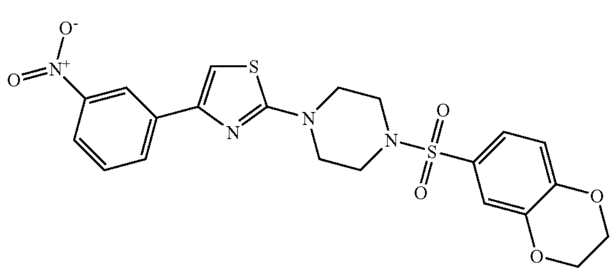 [SMILES: O=[N+]([O-])c1cccc(-c2csc(N3CCN(S(=O)(=O)c4ccc5c(c4)OCCO5)CC3)n2)c1] | 23500 | 85 |
| 73 | 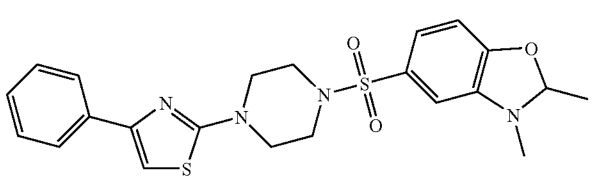 [SMILES: CC1Oc2ccc(S(=O)(=O)N3CCN(c4nc(-c5ccccc5)cs4)CC3)cc2N1C] | 172 | 16 |

TABLE 2-continued

| Compound | Structure | EC$_{50}$ (nM) | % inh. |
|---|---|---|---|
| 74 | 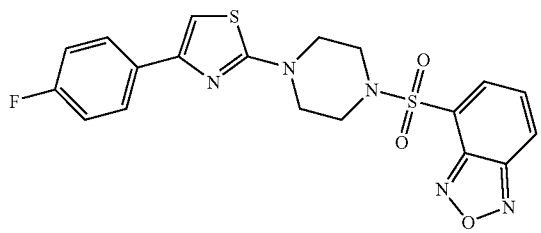 [SMILES: O=S(=O)(c1cccc2nonc12)N1CCN(c2nc(-c3ccc(F)cc3)cs2)CC1] | 233 | 41 |
| 75 | 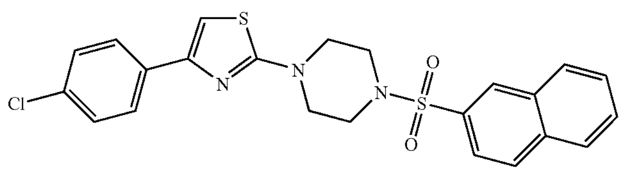 [SMILES: O=S(=O)(c1ccc2ccccc2c1)N1CCN(c2nc(-c3ccc(Cl)cc3)cs2)CC1] | 870 | 84 |
| 76 | 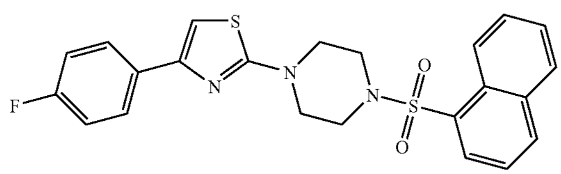 [SMILES: O=S(=O)(c1cccc2ccccc12)N1CCN(c2nc(-c3ccc(F)cc3)cs2)CC1] | 3020 | 127 |
| 77 | 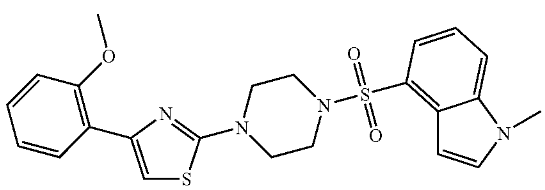 [SMILES: COc1ccccc1-c1csc(N2CCN(S(=O)(=O)c3cccc4c3ccn4C)CC2)n1] | 257 | 69 |
| 78 | 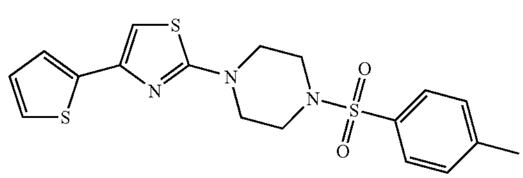 [SMILES: Cc1ccc(S(=O)(=O)N2CCN(c3nc(-c4cccs4)cs3)CC2)cc1] | 316 | 84 |

TABLE 3

| Compound | Chemical name |
|---|---|
| 10 | 1-(4-methoxyphenylsulfonyl)-4-(4-(thiophen-2-ylmethyl)thiazol-2-yl)piperazine |
| 11 | 1-(4-(4-methylbenzyl)thiazol-2-yl)-4-(4-methoxyphenylsulfonyl)piperazine |
| 12 | 3-((2-(4-(4-methoxyphenylsulfonyl)piperazin-1-yl)thiazol-4-yl)methyl)benzonitrile |
| 13 | 1-(4-(3-fluorobenzyl)thiazol-2-yl)-4-(4-methoxyphenylsulfonyl)piperazine |
| 14 | 1-(4-(4-methoxybenzyl)thiazol-2-yl)-4-(4-methoxyphenylsulfonyl)piperazine |
| 15 | 1-(4-(2-methoxybenzyl)thiazol-2-yl)-4-(4-methoxyphenylsulfonyl)piperazine |
| 16 | 1-(4-(3-methoxybenzyl)thiazol-2-yl)-4-(2-methoxyphenylsulfonyl)piperazine |
| 18 | 1-(4-(benzo[d][1,3]dioxol-5-ylmethyl)thiazol-2-yl)-4-(4-methoxyphenylsulfonyl)piperazine |
| 19 | 1-(4-(3-methoxybenzyl)thiazol-2-yl)-4-(benzo[d][1,3]dioxol-5-ylsulfonyl)piperazine |
| 20 | 1-(4-(3-methoxybenzyl)thiazol-2-yl)-4-(pyridin-3-ylsulfonyl)piperazine |
| 21 | 1-(4-(3-methoxybenzyl)thiazol-2-yl)-4-(pyridin-2-ylsulfonyl)piperazine |
| 22 | 1-(4-(3-methoxybenzyl)thiazol-2-yl)-4-(thiophen-3-ylsulfonyl)piperazine |
| 23 | 1-(4-(3-methoxybenzyl)thiazol-2-yl)-4-(3,5-dimethyl-1H-pyrazol-4-ylsulfonyl)piperazine |

TABLE 3-continued

| Compound | Chemical name |
|---|---|
| 24 | 4-(4-(4-(3-methoxybenzyl)thiazol-2-yl)piperazin-1-ylsulfonyl)-1-methyl-1H-indole |
| 25 | 1-(4-(3-methoxybenzyl)thiazol-2-yl)-4-(3,5-dimethylisoxazol-4-ylsulfonyl)piperazine |
| 26 | 1-(4-(3-methoxybenzyl)thiazol-2-yl)-4-(1-methyl-1H-imidazol-4-ylsulfonyl)piperazine |
| 27 | N-(4-(4-(4-(3-methoxybenzyl)thiazol-2-yl)piperazin-1-ylsulfonyl)phenyl)acetamide |
| 28 | 1-(4-(3-methoxybenzyl)thiazol-2-yl)-4-tosylpiperazine |
| 29 | 4-(4-(4-(3-methoxybenzyl)thiazol-2-yl)piperazin-1-ylsulfonyl)benzonitrile |
| 30 | 1-(4-(3-methoxybenzyl)thiazol-2-yl)-4-(4-fluorophenylsulfonyl)piperazine |
| 31 | 4-(4-(3-methoxybenzyl)thiazol-2-yl)-1-(4-methoxyphenylsulfonyl)piperidine |
| 32 | 1-((4-(3-methoxybenzyl)thiazol-2-yl)methyl)-4-(4-methoxyphenylsulfonyl)piperazine |
| 33 | Methyl 2-(4-(4-(4-p-tolylthiazol-2-yl)piperazin-1-ylsulfonyl)phenoxy)acetate |
| 34 | N-(4-(4-(4-phenylthiazol-2-yl)piperazin-1-ylsulfonyl)phenethyl)acetamide |
| 35 | 1-(4-fluorophenylsulfonyl)-4-(4-(3-methoxyphenyl)thiazol-2-yl)piperazine |
| 36 | 1-(2,5-dimethoxyphenylsulfonyl)-4-(4-phenylthiazol-2-yl)piperazine |
| 37 | 1-(4-(4-chlorophenyl)thiazol-2-yl)-4-(2,5-dimethoxyphenylsulfonyl)piperazine |
| 38 | 1-(3,4-dimethoxyphenylsulfonyl)-4-(4-(4-methoxyphenyl)thiazol-2-yl)piperazine |
| 39 | 1-(2,5-dimethoxyphenylsulfonyl)-4-(4-(4-methoxyphenyl)thiazol-2-yl)piperazine |
| 44 | 1-(4-phenylthiazol-2-yl)-4-tosylpiperazine |
| 47 | 1-((4-(4-fluorophenyl)thiazol-2-yl)methyl)-4-(4-methoxyphenylsulfonyl)piperazine |
| 48 | 4-(4-(4-fluorophenyl)thiazol-2-yl)-1-(4-methoxyphenylsulfonyl)piperidine |
| 49 | 1-(4-methoxyphenylsulfonyl)-4-(4-(pyridin-4-yl)thiazol-2-yl)piperazine |
| 50 | 1-(5-fluoro-2-methoxyphenylsulfonyl)-4-(4-(4-methylphenyl)thiazol-2-yl)piperazine |
| 51 | 1-(4-fluoro-2-methoxyphenylsulfonyl)-4-(4-(4-methylphenyl)thiazol-2-yl)piperazine |
| 52 | 1-(4-methoxy-3-(5H-tetrazol-5-yl)phenylsulfonyl)-4-(4-phenylthiazol-2-yl)piperazine |
| 53 | 1-(4-methoxy-3-(5H-tetrazol-5-yl)phenylsulfonyl)-4-(4-p-tolylthiazol-2-yl)piperazine |
| 54 | 1-(4-(4-fluorophenyl)thiazol-2-yl)-4-(pyridin-3-ylsulfonyl)piperazine |
| 55 | 1-(4-(4-fluorophenyl)thiazol-2-yl)-4-(3,5-dimethyl-1H-pyrazol-4-ylsulfonyl)piperazine |
| 56 | 1-(5-chlorothiophen-2-ylsulfonyl)-4-(4-phenylthiazol-2-yl)piperazine |
| 57 | 1-(thiophen-2-ylsulfonyl)-4-(4-(4-methoxyphenyl)thiazol-2-yl)piperazine |
| 58 | 1-(thiophen-2-ylsulfonyl)-4-(4-(4-chlorophenyl)thiazol-2-yl)piperazine |
| 59 | 1-(thiophen-2-ylsulfonyl)-4-(4-(2-nitrophenyl)thiazol-2-yl)piperazine |
| 60 | 1-(thiophen-2-ylsulfonyl)-4-(4-(4-nitrophenyl)thiazol-2-yl)piperazine |
| 61 | 1-(4-phenylthiazol-2-yl)-4-(pyrrolidin-1-ylsulfonyl)piperazine |
| 62 | 1-(4-(4-methylphenyl)thiazol-2-yl)-4-(pyrrolidin-1-ylsulfonyl)piperazine |
| 63 | 1-(4-(4-methoxyphenyl)thiazol-2-yl)-4-(pyrrolidin-1-ylsulfonyl)piperazine |
| 64 | 4-(4-(4-phenylthiazol-2-yl)piperazin-1-ylsulfonyl)pyrrolidin-2-one |
| 65 | 1-(4-(4-phenylthiazol-2-yl)piperazin-1-ylsulfonyl)pyrrolidin-2-one |
| 66 | 4-(4-(4-(4-fluorophenyl)thiazol-2-yl)piperazin-1-ylsulfonyl)pyrrolidin-2-one |
| 67 | 4-(4-(5-methyl-4-phenylthiazol-2-yl)piperazin-1-ylsulfonyl)pyrrolidin-2-one |
| 69 | 1-(2,3-dihydrobenzo[b][1,4]dioxin-6-ylsulfonyl)-4-(4-phenylthiazol-2-yl)piperazine |
| 70 | 1-(2,3-dihydrobenzo[b][1,4]dioxin-6-ylsulfonyl)-4-(4-(4-methoxyphenyl)thiazol-2-yl)piperazine |
| 71 | 1-(2,3-dihydrobenzo[b][1,4]dioxin-6-ylsulfonyl)-4-(4-(4-nitrophenyl)thiazol-2-yl)piperazine |
| 72 | 1-(2,3-dihydrobenzo[b][1,4]dioxin-6-ylsulfonyl)-4-(4-(3-nitrophenyl)thiazol-2-yl)piperazine |
| 73 | 3-methyl-5-(4-(4-phenylthiazol-2-yl)piperazin-1-ylsulfonyl)benzo[d]oxazol-2(3H)-one |
| 74 | 4-(4-(4-fluorophenyl)thiazol-2-yl)piperazin-1-ylsulfonyl)benzo[c][1,2,5]oxadiazole |
| 75 | 1-(4-(4-chlorophenyl)thiazol-2-yl)-4-(naphthalen-2-ylsulfonyl)piperazine |
| 76 | 1-(4-(4-fluorophenyl)thiazol-2-yl)-4-(naphthalen-1-ylsulfonyl)piperazine |
| 77 | 4-(4-(4-(2-methoxyphenyl)thiazol-2-yl)piperazin-1-ylsulfonyl)-1-methyl-1H-indole |
| 78 | 1-(4-(thiophen-2-yl)thiazol-2-yl)-4-tosylpiperazine |

Example 13

Proton Nuclear Magnetic Resonance (NMR) Characterization of Some Derivatives Exemplary compounds of this invention are shown below with the chemical shifts (ppm), multiplicity and assignment of peaks present in their proton nuclear magnetic resonance (NMR) spectra.

Compound No. 10

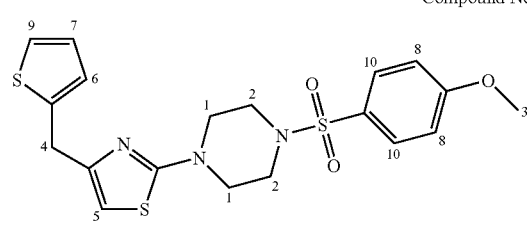

| No. | Chemical shift (ppm), multiplicity | Protons |
|---|---|---|
| 1 | 2.99, m | 3.96 |
| 2 | 3.47, m | 4.01 |
| 3 | 3.84, s | 3.01 |
| 4 | 3.99, s | 1.98 |
| 5 | 6.46, s | 0.94 |
| 6 | 6.86, m | 0.94 |
| 7 | 6.92, m | 0.95 |
| 8 | 7.17, m | 1.98 |
| 9 | 7.3, m | 0.88 |
| 10 | 7.67, m | 2.00 |

Compound No. 11

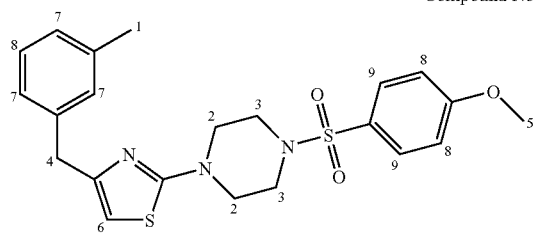

| No. | Chemical shift (ppm), multiplicity | Protons |
|---|---|---|
| 1 | 2.24, s | 3.00 |
| 2 | 3.18, m | 4.03 |
| 3 | 3.45, m | 4.09 |
| 4 | 3.72, s | 1.98 |
| 5 | 3.85, s | 3.04 |
| 6 | 6.35, s | 0.96 |
| 7 | 6.99, m | 3.00 |
| 8 | 7.16, m | 3.07 |
| 9 | 7.69, m | 2.03 |

Compound No. 12

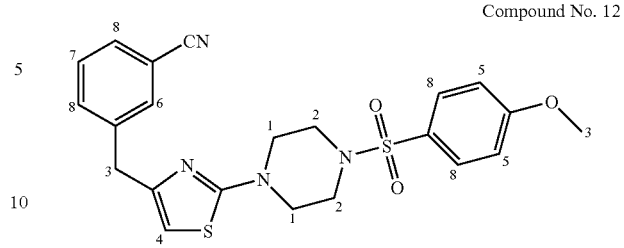

| No. | chemical shift (ppm), multiplicity | Protons |
|---|---|---|
| 1 | 2.97, m | 3.95 |
| 2 | 3.45, m | 3.97 |
| 3 | 3.85, s | 5.00 |
| 4 | 6.45, s | 0.94 |
| 5 | 7.16, m | 2.00 |
| 6 | 7.48, m | 1.02 |
| 7 | 7.57, m | 0.97 |
| 8 | 7.64, m | 3.92 |

Compound No. 13

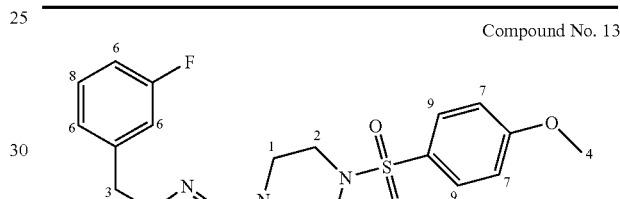

| No. | Chemical shift (ppm), multiplicity | Protons |
|---|---|---|
| 1 | 2.98, m | 4.02 |
| 2 | 3.45, m | 4.02 |
| 3 | 3.80, s | 2.00 |
| 4 | 3.85, s | 3.04 |
| 5 | 6.43, s | 0.95 |
| 6 | 7.03, m | 2.98 |
| 7 | 7.16, m | 2.00 |
| 8 | 7.30, m | 1.01 |
| 9 | 7.69, m | 2.02 |

Compound No. 14

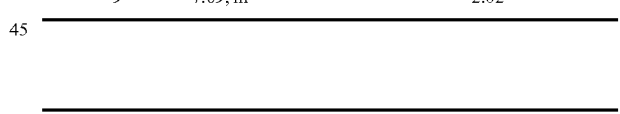

| No. | Chemical shift (ppm), multiplicity | Protons |
|---|---|---|
| 1 | 2.98, m | 4.00 |
| 2 | 3.44, m | 4.03 |
| 3 | 3.72, s | 4.99 |
| 4 | 3.86, s | 3.01 |
| 5 | 6.32, s | 0.95 |

Compound No. 14

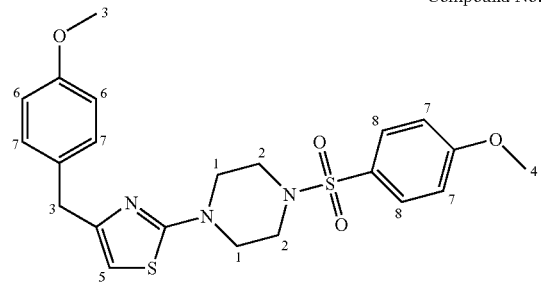

| No. | Chemical shift (ppm), multiplicity | Protons |
|---|---|---|
| 6 | 6.84, m | 1.99 |
| 7 | 7.14, m | 4.00 |
| 8 | 7.69, m | 2.00 |

Compound No. 15

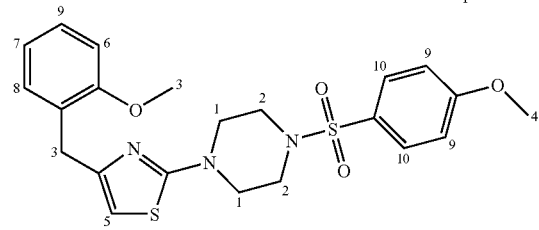

| No. | Chemical shift (ppm), multiplicity | Protons |
|---|---|---|
| 1 | 2.97, m | 3.95 |
| 2 | 3.46, m | 3.94 |
| 3 | 3.75, m | 4.96 |
| 4 | 3.86, s | 3.00 |
| 5 | 6.18, s | 0.94 |
| 6 | 6.84, m | 0.98 |
| 7 | 6.96, m | 1.06 |
| 8 | 7.05, m | 1.01 |
| 9 | 7.18, m | 3.06 |
| 10 | 7.69, m | 2.06 |

Compound No. 16

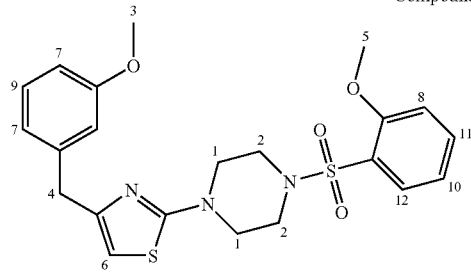

| No. | Chemical shift (ppm), multiplicity | Protons |
|---|---|---|
| 1 | 3.20, m | 3.90 |
| 2 | 3.41, m | 4.04 |
| 3 | 3.70, s | 3.01 |
| 4 | 3.76, s | 2.07 |
| 5 | 3.89, s | 3.01 |
| 6 | 6.41, s | 0.93 |
| 7 | 6.79, m | 3.00 |

Compound No. 16

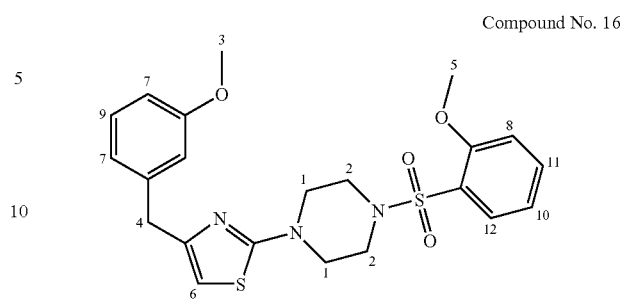

| No. | Chemical shift (ppm), multiplicity | Protons |
|---|---|---|
| 8 | 7.10, m | 0.97 |
| 9 | 7.18, m | 1.01 |
| 10 | 7.25, m | 1.01 |
| 11 | 7.64, m | 1.00 |
| 12 | 7.76, m | 0.99 |

Compound No. 17

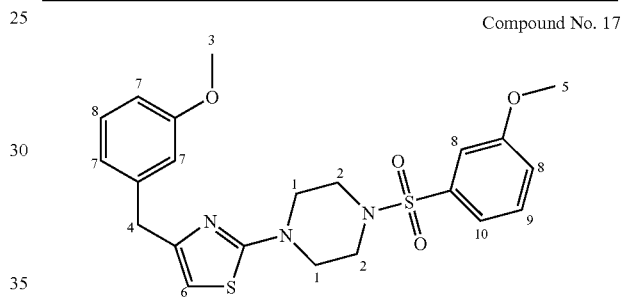

| No. | Chemical shift (ppm), multiplicity | Protons |
|---|---|---|
| 1 | 3.03, m | 3.91 |
| 2 | 3.45, m | 4.05 |
| 3 | 3.70, s | 2.98 |
| 4 | 3.74, s | 1.95 |
| 5 | 3.84, s | 3.03 |
| 6 | 6.38, s | 1.00 |
| 7 | 6.76, m | 3.03 |
| 8 | 7.17, m | 2.04 |
| 9 | 7.30, m | 2.04 |
| 10 | 7.58, m | 1.02 |

Compound No. 18

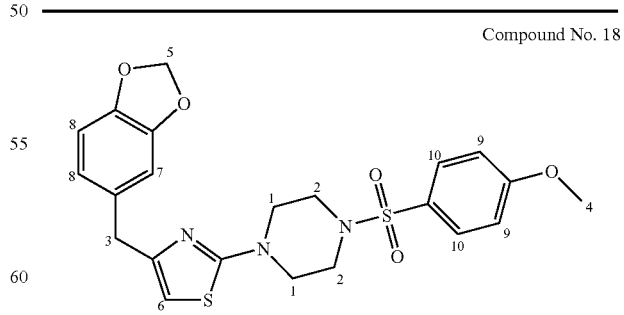

| No. | Chemical shift (ppm), multiplicity | Protons |
|---|---|---|
| 1 | 2.96, m | 3.91 |
| 2 | 3.46, m | 4.05 |
| 3 | 3.69, s | 2.98 |

Compound No. 18
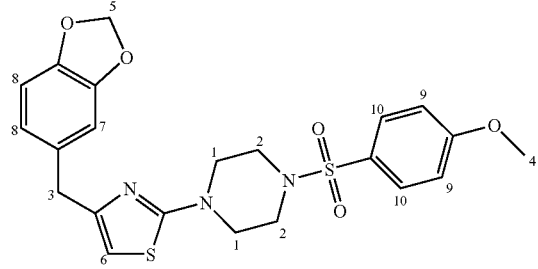 [SMILES: COc1ccc(S(=O)(=O)N2CCN(c3nc(Cc4ccc5c(c4)OCO5)cs3)CC2)cc1]
| No. | Chemical shift (ppm), multiplicity | Protons |
|---|---|---|
| 4 | 3.86, s | 1.95 |
| 5 | 5.97, s | 3.03 |
| 6 | 6.35, s | 1.00 |
| 7 | 6.66, m | 3.03 |
| 8 | 6.79, m | 2.04 |
| 9 | 7.16, m | 2.04 |
| 10 | 7.69, m | 1.02 |
Compound No. 19
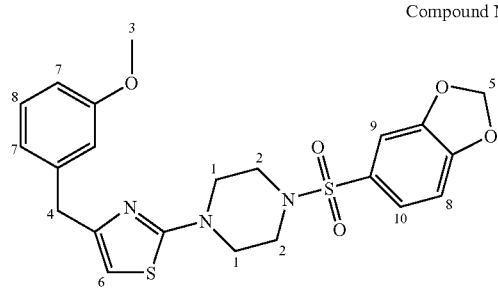
| No. | Chemical shift (ppm), multiplicity | Protons |
|---|---|---|
| 1 | 3.01, m | 3.87 |
| 2 | 3.47, m | 4.60 |
| 3 | 3.71, s | 2.95 |
| 4 | 3.76, s | 1.99 |
| 5 | 6.19, s | 1.96 |
| 6 | 6.40, s | 0.93 |
| 7 | 6.78, m | 2.99 |
| 8 | 7.15, m | 1.97 |
| 9 | 7.23, m | 0.98 |
| 10 | 7.30, m | 0.98 |
Compound No. 20
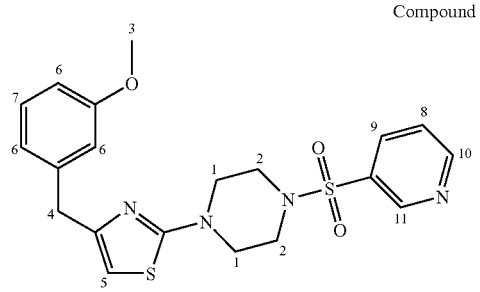
| No. | Chemical shift (ppm), multiplicity | Protons |
|---|---|---|
| 1 | 3.10, m | 3.95 |
| 2 | 3.53, m | 4.11 |
| 3 | 3.71, s | 3.01 |
Compound No. 20
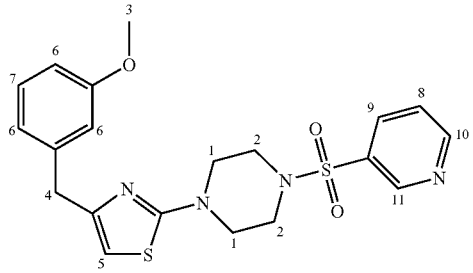 [SMILES: COc1cccc(Cc2csc(N3CCN(S(=O)(=O)c4cccnc4)CC3)n2)c1]
| No. | Chemical shift (ppm), multiplicity | Protons |
|---|---|---|
| 4 | 3.76, s | 2.05 |
| 5 | 6.40, s | 0.95 |
| 6 | 6.78, m | 3.01 |
| 7 | 7.17, m | 1.01 |
| 8 | 7.72, m | 1.00 |
| 9 | 8.16, m | 0.96 |
| 10 | 8.89, m | 0.95 |
| 11 | 8.94, m | 0.98 |
Compound No. 21
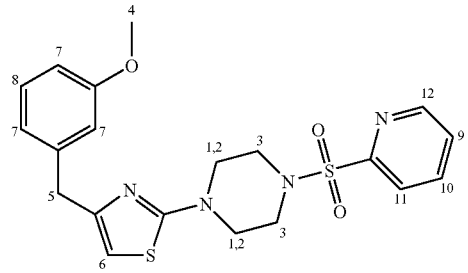 [SMILES: COc1cccc(Cc2csc(N3CCN(S(=O)(=O)c4ccccn4)CC3)n2)c1]
| No. | Chemical shift (ppm), multiplicity | Protons |
|---|---|---|
| 1 | 3.28, m | 1.86 |
| 2 | 3.32, m | 2.18 |
| 3 | 3.45, m | 3.95 |
| 4 | 3.70, s | 2.93 |
| 5 | 3.78, s | 2.06 |
| 6 | 6.42, s | 0.96 |
| 7 | 6.78, m | 2.90 |
| 8 | 7.19, m | 1.01 |
| 9 | 7.72, m | 0.99 |
| 10 | 7.96, m | 0.98 |
| 11 | 8.21, m | 0.99 |
| 12 | 8.78, m | 0.95 |

Compound No. 22
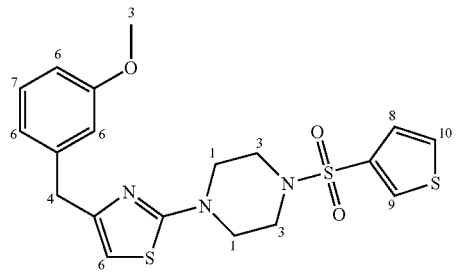 [SMILES: COc1cccc(Cc2csc(N3CCN(S(=O)(=O)c4ccsc4)CC3)n2)c1]
| No. | Chemical shift (ppm), multiplicity | Protons |
| --- | --- | --- |
| 1 | 3.05, m | 3.99 |
| 2 | 3.53, m | 3.97 |
| 3 | 3.71, s | 2.97 |
| 4 | 3.75, s | 2.01 |
| 5 | 6.40, s | 0.96 |
| 6 | 6.79, m | 3.02 |
| 7 | 7.16, m | 1.08 |
| 8 | 7.34, m | 1.08 |
| 9 | 7.86, m | 0.97 |
| 10 | 8.28, m | 0.96 |
Compound No. 23
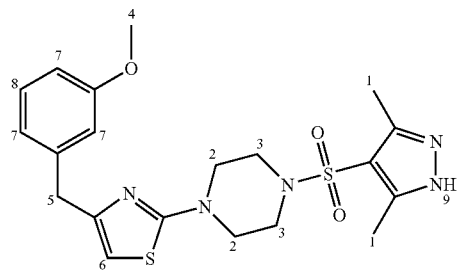 [SMILES: COc1cccc(Cc2csc(N3CCN(S(=O)(=O)c4c(C)n[nH]c4C)CC3)n2)c1]
| No. | Chemical shift (ppm), multiplicity | Protons |
| --- | --- | --- |
| 1 | 2.33, s | 6.25 |
| 2 | 3.01, m | 3.90 |
| 3 | 3.46, m | 3.99 |
| 4 | 3.71, s | 3.09 |
| 5 | 3.77, s | 2.10 |
| 6 | 6.41, s | 1.00 |
| 7 | 6.78, m | 3.09 |
| 8 | 7.19, m | 1.04 |
| 9 | 13.04, s | 0.65 |
Compound No. 24
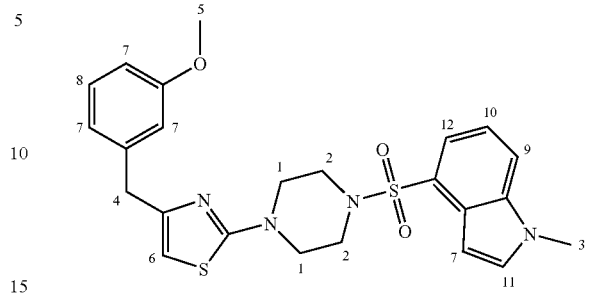
| No. | Chemical shift (ppm), multiplicity | Protons |
| --- | --- | --- |
| 1 | 3.03, m | 4.22 |
| 2 | 3.40, m | 4.28 |
| 3 | 3.68, s | 3.10 |
| 4 | 3.72, s | 2.24 |
| 5 | 3.86, s | 3.14 |
| 6 | 6.33, s | 1.00 |
| 7 | 6.77, m | 4.33 |
| 8 | 7.14, m | 1.08 |
| 9 | 7.34, m | 1.10 |
| 10 | 7.47, m | 1.08 |
| 11 | 7.58, m | 1.09 |
| 12 | 7.83, m | 1.08 |
Compound No. 25
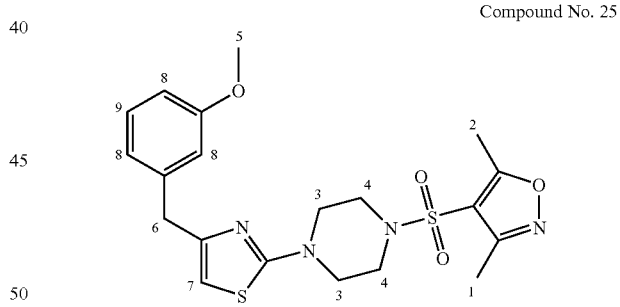
| No. | Chemical shift (ppm), multiplicity | Protons |
| --- | --- | --- |
| 1 | 2.34, s | 2.97 |
| 2 | 2.61, s | 2.96 |
| 3 | 3.07-3.23, m | 3.97 |
| 4 | 3.40-3.55, m | 3.96 |
| 5 | 3.70, s | 2.93 |
| 6 | 3.77, s | 2.02 |
| 7 | 6.42, s | 0.95 |
| 8 | 6.68-6.86, m | 2.96 |
| 9 | 7.11-7.25, m | 1.00 |

Compound No. 26
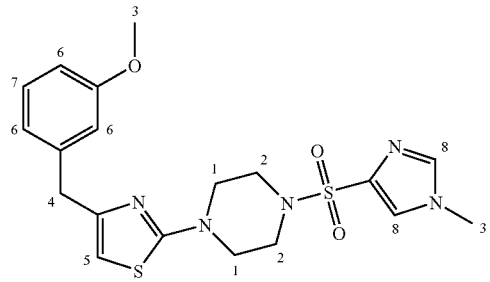 [SMILES: COc1cccc(Cc2csc(N3CCN(S(=O)(=O)c4cn(C)cn4)CC3)n2)c1]
| No. | Chemical shift (ppm), multiplicity | Protons |
|---|---|---|
| 1 | 3.09, m | 4.04 |
| 2 | 3.44, m | 4.04 |
| 3 | 3.71, s | 6.00 |
| 4 | 3.77, s | 2.12 |
| 5 | 6.39, s | 0.97 |
| 6 | 6.79, m | 3.01 |
| 7 | 7.19, m | 1.00 |
| 8 | 7.82, m | 1.99 |
Compound No. 27
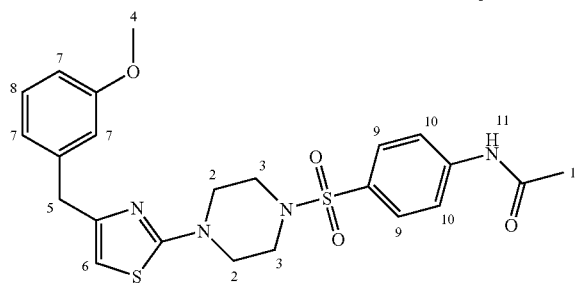
| No. | Chemical shift (ppm), multiplicity | Protons |
|---|---|---|
| 1 | 2.17, s | 2.92 |
| 2 | 2.98, m | 3.93 |
| 3 | 3.44, m | 3.97 |
| 4 | 3.71, s | 2.83 |
| 5 | 3.75, s | 2.00 |
| 6 | 6.38, s | 0.95 |
| 7 | 6.79, s | 2.97 |
| 8 | 7.17, m | 0.99 |
| 9 | 7.68, m | 2.02 |
| 10 | 7.83, m | 2.00 |
| 11 | 10.37, s | 0.99 |
Compound No. 28
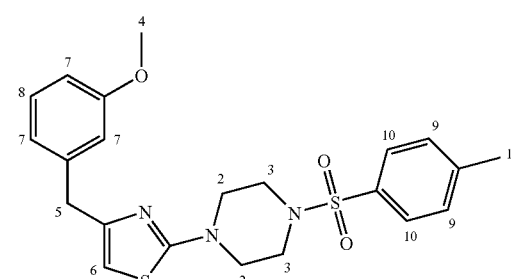
| No. | Chemical shift (ppm), multiplicity | Protons |
|---|---|---|
| 1 | 2.40, s | 3.03 |
| 2 | 2.99, m | 3.99 |
| 3 | 3.46, m | 4.02 |
| 4 | 3.69, s | 3.05 |
| 5 | 3.77, s | 2.03 |
| 6 | 6.38, s | 0.96 |
| 7 | 6.78, m | 3.00 |
| 8 | 7.15, m | 1.02 |
| 9 | 7.45, m | 2.02 |
| 10 | 7.64, m | 2.03 |
Compound No. 29
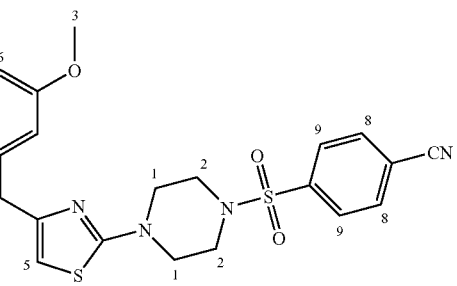
| No. | Chemical shift (ppm), multiplicity | Protons |
|---|---|---|
| 1 | 3.09, m | 4.03 |
| 2 | 3.46, m | 4.02 |
| 3 | 3.70, s | 3.00 |
| 4 | 3.75, s | 2.01 |
| 5 | 6.39, s | 0.95 |
| 6 | 6.77, m | 2.98 |
| 7 | 7.18, m | 0.99 |
| 8 | 7.93, m | 2.02 |
| 9 | 8.13, m | 1.99 |

Compound No. 30
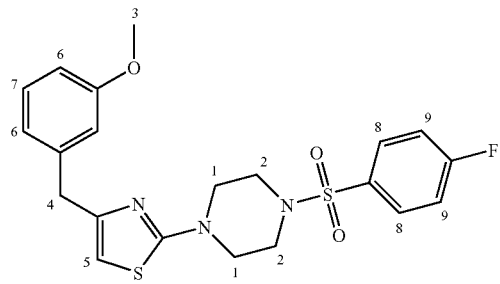 [SMILES: COc1cccc(Cc2csc(N3CCN(S(=O)(=O)c4ccc(F)cc4)CC3)n2)c1]
| No. | Chemical shift (ppm), multiplicity | Protons |
|---|---|---|
| 1 | 3.01, m | 3.99 |
| 2 | 3.47, m | 3.96 |
| 3 | 3.70, s | 2.96 |
| 4 | 3.76, s | 2.03 |
| 5 | 6.40, s | 0.99 |
| 6 | 6.78, m | 2.98 |
| 7 | 717, m | 1.01 |
| 8 | 7.49, m | 2.00 |
| 9 | 7.83, m | 1.99 |
Compound No. 31
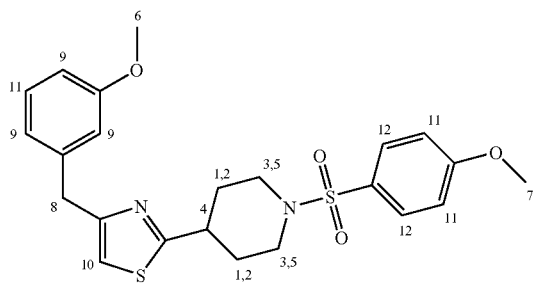 [SMILES: COc1ccc(S(=O)(=O)N2CCC(c3nc(Cc4cccc(OC)c4)cs3)CC2)cc1]
| No. | Chemical shift (ppm), multiplicity | Protons |
|---|---|---|
| 1 | 1.67, m | 2.02 |
| 2 | 2.08, m | 2.01 |
| 3 | 2.39, m | 2.01 |
| 4 | 2.97, m | 1.03 |
| 5 | 3.65, m | 2.01 |
| 6 | 3.71, s | 3.08 |
| 7 | 3.86, s | 3.01 |
| 8 | 3.97, s | 1.90 |
| 9 | 6.79, m | 3.04 |
| 10 | 7.10, s | 0.93 |
| 11 | 7.18, m | 3.05 |
| 12 | 7.70, m | 2.00 |
Compound No. 32
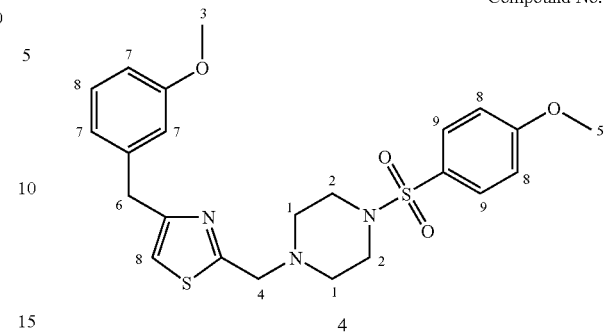
| No. | Chemical shift (ppm), multiplicity | Protons |
|---|---|---|
| 1 | 2.57, m | 3.97 |
| 2 | 2.88, m | 3.92 |
| 3 | 3.71, s | 3.01 |
| 4 | 3.77, s | 1.97 |
| 5 | 3.86, s | 3.01 |
| 6 | 3.96, s | 1.98 |
| 7 | 6.78, m | 2.96 |
| 8 | 7.17, m | 3.97 |
| 9 | 7.67, m | 2.00 |
Compound No. 47
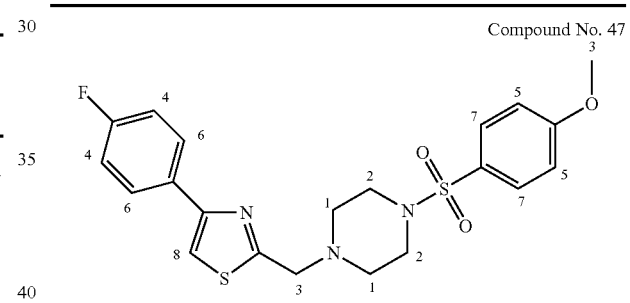
| No. | Chemical shift (ppm), multiplicity | Protons |
|---|---|---|
| 1 | 2.63, m | 4.05 |
| 2 | 2.90, m | 3.94 |
| 3 | 3.88, m | 4.87 |
| 4 | 7.18, m | 1.94 |
| 5 | 7.26, m | 2.00 |
| 6 | 7.69, m | 2.00 |
| 7 | 7.95, m | 1.94 |
| 8 | 8.00, s | 0.98 |
Compound No. 48
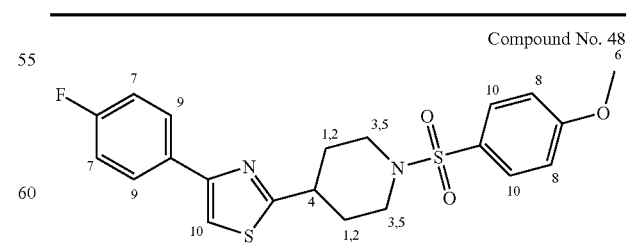
| No. | Chemical shift (ppm), multiplicity | Protons |
|---|---|---|
| 1 | 1.75, m | 1.99 |
| 2 | 2.15, m | 2.00 |

Compound No. 48

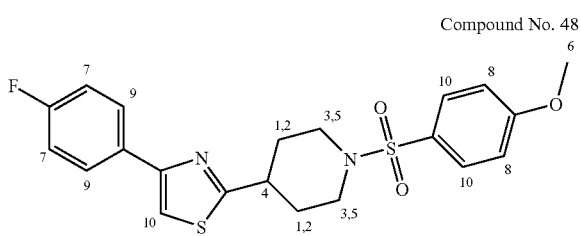

| No. | Chemical shift (ppm), multiplicity | Protons |
|---|---|---|
| 3 | 2.52, m | 2.27 |
| 4 | 3.09, m | 1.02 |
| 5 | 3.67, m | 2.00 |
| 6 | 3.87, s | 3.01 |
| 7 | 7.17, m | 1.97 |
| 8 | 7.25, m | 1.98 |
| 9 | 7.72, m | 2.00 |
| 10 | 7.92, m | 2.95 |

Compound No. 49

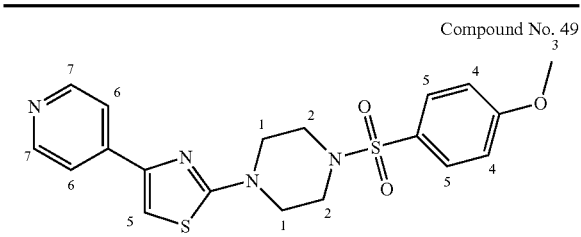

| No. | Chemical shift (ppm), multiplicity | Protons |
|---|---|---|
| 1 | 3.03, m | 3.98 |
| 2 | 3.60, m | 3.96 |
| 3 | 3.85, s | 3.00 |
| 4 | 7.16, m | 2.00 |
| 5 | 7.68, m | 3.00 |
| 6 | 7.79, m | 1.98 |
| 7 | 8.62, m | 1.97 |

Compound No. 54

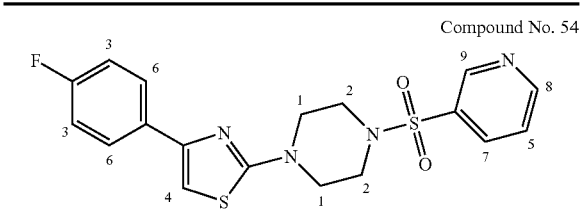

| No. | Chemical shift (ppm), multiplicity | Protons |
|---|---|---|
| 1 | 3.15, m | 4.07 |
| 2 | 3.58, m | 4.07 |
| 3 | 7.19, m | 2.06 |
| 4 | 7.28, s | 1.07 |
| 5 | 7.77, m | 1.03 |
| 6 | 7.85, m | 2.05 |
| 7 | 8.20, m | 1.03 |
| 8 | 8.88, m | 1.00 |
| 9 | 8.95, m | 1.03 |

Compound No. 55

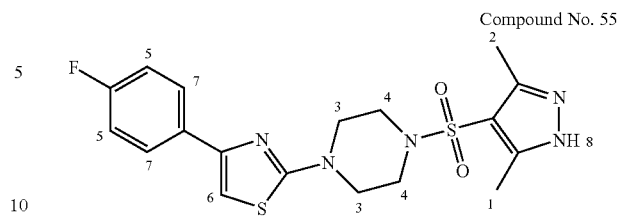

| No. | Chemical shift (ppm), multiplicity | Protons |
|---|---|---|
| 1 | 2.29, s | 3.20 |
| 2 | 2.41, s | 2.92 |
| 3 | 3.06, m | 3.98 |
| 4 | 3.59, m | 4.09 |
| 5 | 7.19, m | 1.99 |
| 6 | 7.30, s | 1.03 |
| 7 | 7.87, m | 2.01 |
| 8 | 13.16, s | 1.01 |

Compound No. 77

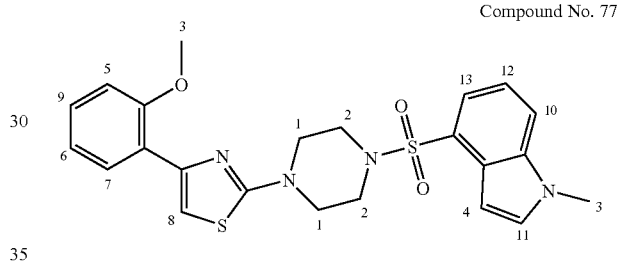

| No. | Chemical shift (ppm), multiplicity | Protons |
|---|---|---|
| 1 | 3.09, m | 3.97 |
| 2 | 3.51, m | 3.99 |
| 3 | 3.85, m | 6.00 |
| 4 | 6.82, m | 1.00 |
| 5 | 6.95, m | 0.99 |
| 6 | 7.05, m | 1.03 |
| 7 | 7.24, m | 1.00 |
| 8 | 7.30, s | 0.93 |
| 9 | 7.36, m | 1.03 |
| 10 | 7.49, m | 0.98 |
| 11 | 7.58, m | 1.01 |
| 12 | 7.81, m | 0.99 |
| 13 | 8.00, m | 0.98 |

Example 14

Production of Compound No. 26

The production of compound No. 26 proceeds according to the sequence of reaction steps shown in the following schemes:

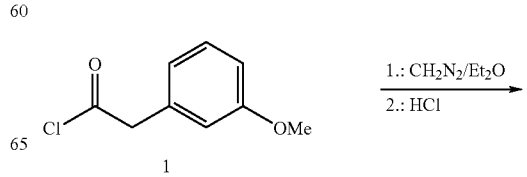

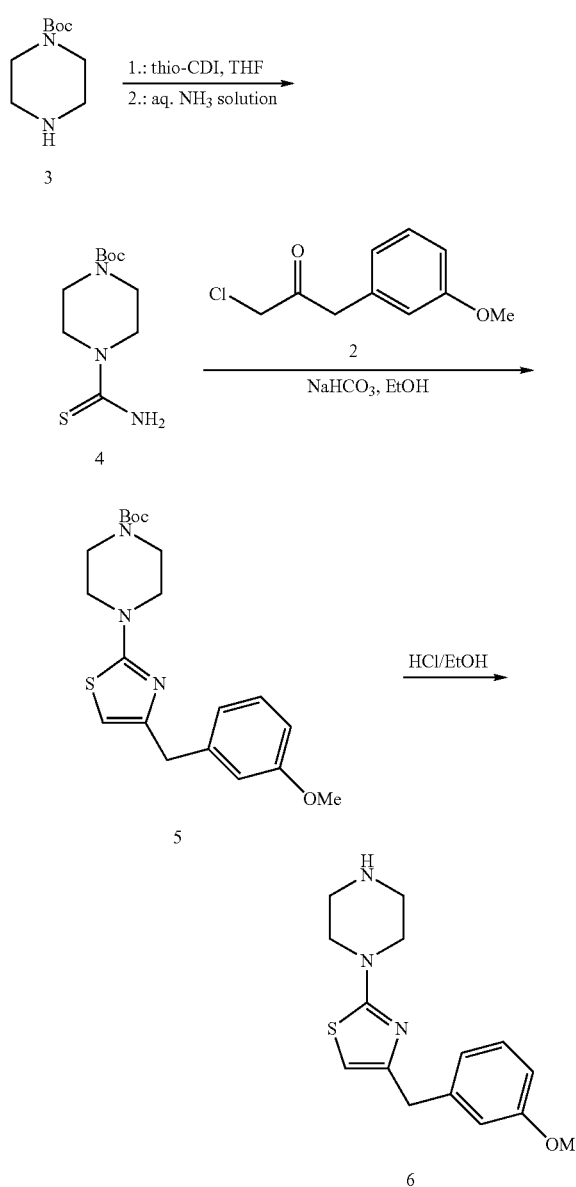

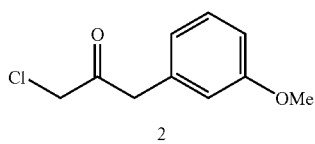

The first sub-step shown above was performed at 20° C. during 2 hours with a molar excess of CH$_2$N$_2$ (about 2 molar equivalents) in dry ether, then in a second sub-step (shown below) performed at 5° C. HCl gas was bubbled into the reaction mixture for 15 minutes, and the desired intermediate was obtained in 71% yield.

For the conversion from 3 to 4, the first sub-step shown above was performed at 20° C. during 1 hour with a molar excess of thio-carbonyldiimidazole (about 2 molar equivalents) in THF, then in a second sub-step performed at 20° C. for 12 hours a 25% aqueous NH$_3$ solution was added, and the desired intermediate was obtained in 72% yield. The conversion from 4 to 5 was performed during 6 hours with 1 molar equivalent NaHCO$_3$ at reflux in methanol, and the desired intermediate was obtained in 92% yield. The conversion from 5 to 6 was performed during 3 hours at 20° C., and the desired intermediate was obtained in 90% yield.

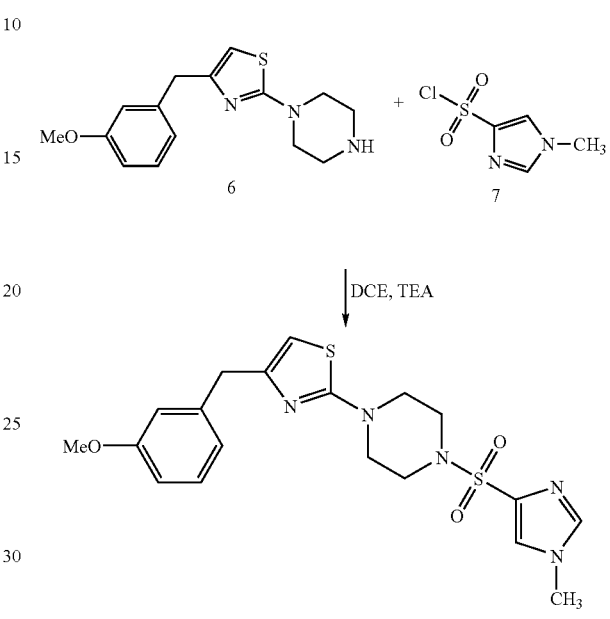

The conversion from 6 to the final compound was performed during 6 hours at 20° C. in 1,2-dichloroethane (DCE) in the presence of a molar excess of triethylamine (1.2 molar equivalents).

Example 15

Production of Compound No. 32

The production of compound No. 32 proceeds according to the sequence of reaction steps shown in FIG. 6.

The conversion from 101 to 103 can be performed at room temperature (20° C.) either during 1 hour in DCM or (as shown in FIG. 6) during 4 hours in DCE in the presence of TEA, and the desired intermediate 103 was obtained in 86% yield. The conversion from 103 to 116 was performed during 2 hours at 20° C. in the presence of a molar excess of bromoacetonitrile (1.05 molar equivalents) and 3 molar equivalents potassium carbonate, and the desired intermediate 116 was obtained in 76% yield. The conversion from 116 to 117 was performed during 24 hours at 20° C. in the presence of methanol, THF and 20% aqueous ammonium sulfide, and the desired intermediate 117 was obtained in 56% yield. The conversion from 117 to the compound 32 of this invention was performed during 8 hours at reflux in ethanol, in the presence of 1.3 molar equivalents of the 1-chloro-3-(3-methoxyphenyl)propan-2-one 118b (which can be produced similarly to reactants 105d and 105e as described in example 19 hereinafter) and 1.5 molar equivalents sodium hydrogenocarbonate.

Example 16

Production of Compounds No. 19-25 and 27-30

The production of compounds No. 27-30 proceeds according to the same sequence of reaction steps as already shown in example 14, except that in the final step intermediate 7 was replaced with a substituted arylsulfonyl chloride. In this way:

compound No. 27 was obtained in 21% yield, compound No. 28 was obtained in 43% yield;

compound No. 29 was obtained in 62% yield; and compound No. 30 was obtained in 44% yield.

The production of compounds No. 19-25 proceeds according to the same sequence of reaction steps as already shown in example 14, except that in the final step intermediate 7 was replaced with an optionally substituted heteroarylsulfonyl chloride. In this way:

compound No. 19 was obtained in 39% yield;

compound No. 20 was obtained in 52% yield;

compound No. 21 was obtained in 41% yield;

compound No. 23 was obtained in 77% yield; and compound No. 25 was obtained in 38% yield.

Example 17

Production of Compound No. 49

The production of compound No. 49 proceeds according to the sequence of reaction steps shown in the following scheme:

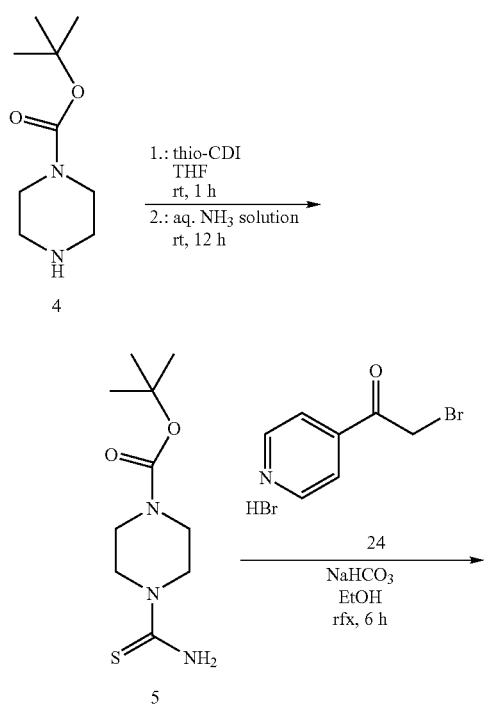

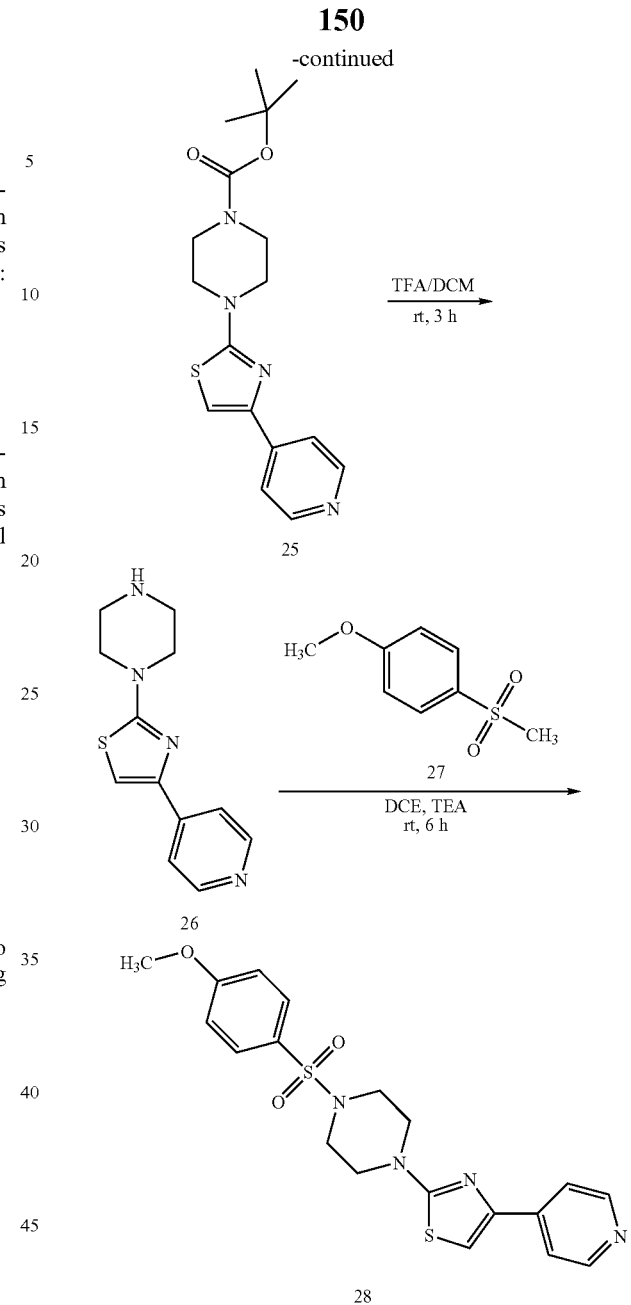

The initial step is as described in example 14. Then the conversion from 5 to 25 was performed during 6 hours at reflux in methanol in the presence of a molar equivalent of 24 and a molar equivalent of sodium hydrogenocarbonate, and the desired intermediate 25 was obtained in 81% yield. The conversion from 25 to 26 was performed during 3 hours at 20° C. in the presence of triethylamine, and the desired intermediate 26 was obtained in 73% yield. The conversion from 26 to the final compound No. 49 was performed during 6 hours at 20° C. in the presence of a molar excess of triethylamine.

Example 18

Production of Compounds No. 54-55

The production of compound No. 54-55 proceeds according to the sequence of reaction steps shown in the following scheme:

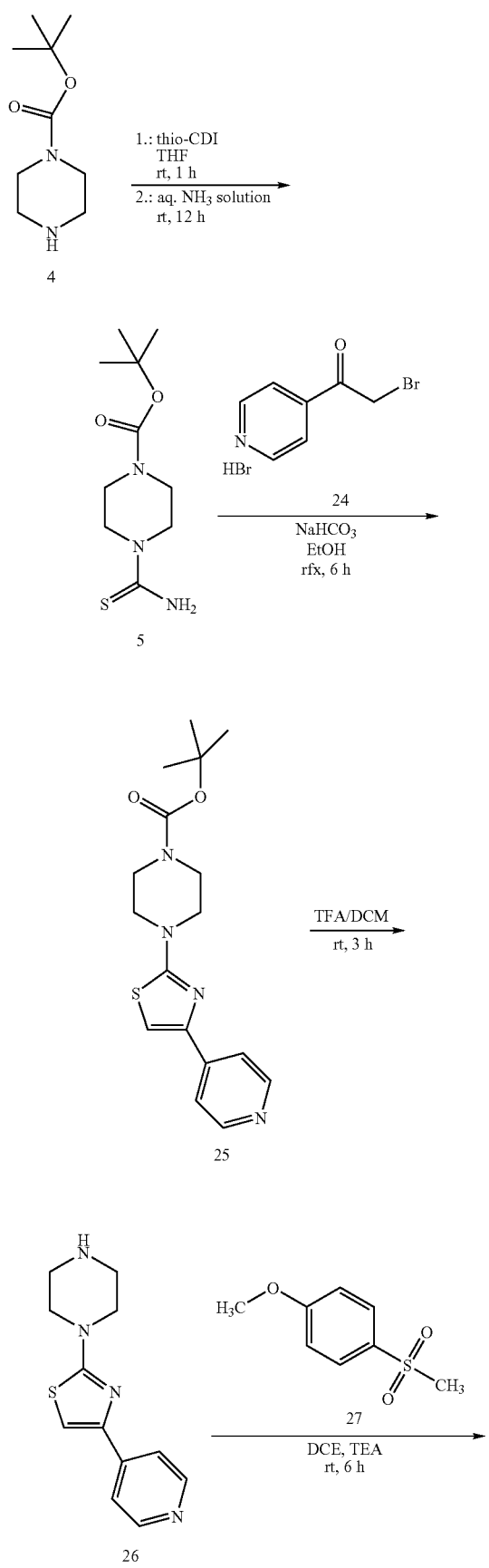

The initial step is as described in example 14. Then the conversion from 5 to 30 was performed during 6 hours at reflux in ethanol in the presence of a molar equivalent of 29 and a molar equivalent of sodium hydrogenocarbonate, and the desired intermediate 30 was obtained in 79% yield. The conversion from 30 to 31 was performed during 3 hours at 20° C., and the desired intermediate 31 was obtained in 91% yield. The conversion from 31 to the final compounds No. 54-55 was performed during 6 hours at 20° C. in the presence of a molar excess (1.1 molar equivalent) of triethylamine. In this way:

compound No. 54 was obtained in 50% yield; and
compound No. 55 was obtained in 31% yield.

Example 19

Synthesis of Compounds 10 to 15 and Compound 18

Figure 3:
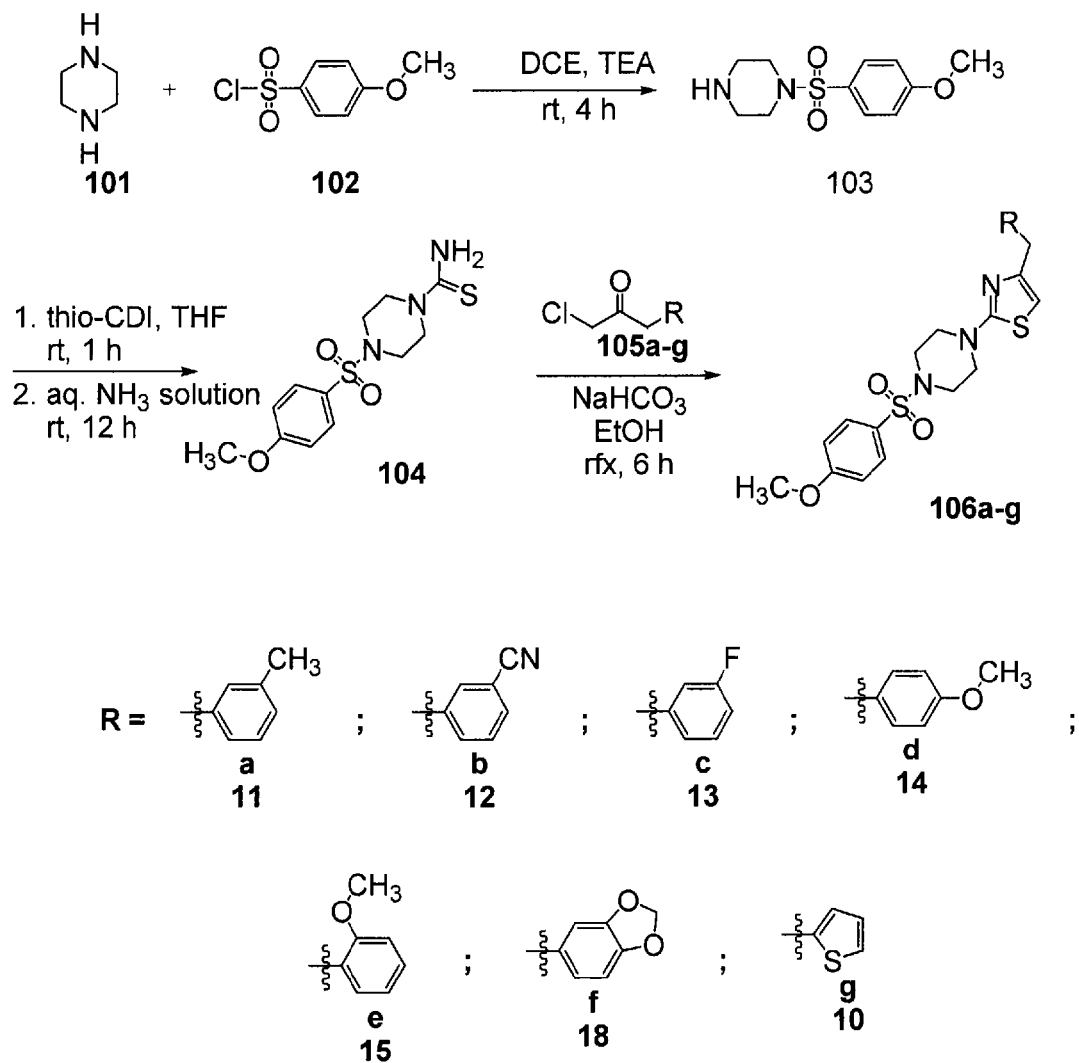
FIG. 3 shows synthetic schemes for the preparation of benzylthiazolyl-piperazine derivatives according to this invention.

The synthesis of compounds 10 to 15 and compound 18 (detailed structures shown in table 2) was performed according to the synthetic scheme detailed on FIG. 3 and involved the preparation of a series of chloro-ketone reactants denoted 105a to 105g. The latter were prepared according to the synthetic scheme detailed on FIG. 4 (reactant 105b) or the synthetic scheme detailed on FIG. 5 (reactants 105a and 105c to 105g).

Synthesis of 3-(2-diazoacetyl)benzonitrile
(Reactant XII)

With reference to FIG. 3, an Erlenmeyer flask was charged with 50% aqueous KOH (80 mL) and diethyl ether (80 mL) and cooled to 0° C. Nitrosomethyl urethane (5.1 g, 60% pure) was added portion-wise and the mixture was allowed to stand for 30 minutes at this temperature with occasional shaking. The yellow diazomethane solution was transferred into another flask containing potassium hydroxide (20 g) at 0° C., and was allowed to stand at this temperature for 1 hour. The resulting solution was transferred into a round bottomed flask followed by the addition of diethyl ether (100 mL) and TEA (1.8 g, 18.1 mmol). The reaction mixture was cooled to 0° C. and 3-cyanobenzoyl chloride (reactant XI) (3.0 g, 18 mmol) in diethyl ether (40 mL) was added drop-wise and the reaction mixture was stirred at 0° C. for 2 hours. The reaction was quenched by the careful addition of 0.5 M acetic acid (10 mL) and then a saturated aqueous $Na_2CO_3$ solution (30 mL) was added to the mixture. The phases were separated and the organic phase was washed with brine, dried over $MgSO_4$, concentrated, and dried in a vacuum dessicator to afford the crude reactant XII (2.0 g, 65% yield) which was used directly for the next step.

Synthesis of 2-(3-cyanophenyl)acetic acid
(Reactant XIII)

Reactant XII (2.0 g, 12 mmol) was dissolved in a mixture of THF (40 mL) and water (4 mL) and cooled to 25° C. A solution of silver trifluoroacetate (0.32 g, 1.45 mmol) in triethylamine (5.2 mL) was added in one portion and the reaction mixture was warmed to room temperature and stirred for 12 hours. The reaction mixture was concentrated and the residue was dissolved in 20% aqueous NaOH and washed with EtOAc (3×50 mL). The aqueous layer was acidified to pH 1 using 10% aqueous HCl and extracted with DCM (3×80 mL). The combined organic phases were dried over $MgSO_4$ and concentrated. The residue was recrystallized from water and dried in a vacuum desiccator over $P_2O_5$/KOH to afford the reactant XIII (0.64 g, 34% yield) as an off-white solid (estimated purity 60%) which was characterized as follows:
$^1$H NMR (400 MHz, DMSO-d6): δ 12.88 (1 H, br. s.), 7.69.7.77 (2 H, m), 7.62 (1 H, dt, J=7.5, 1.5 Hz), 7.53 (1 H, t, J=7.5 Hz) and 3.69 (2 H, s) ppm.

Synthesis of 2-(3-cyanophenyl)acetyl chloride
(Reactant XIV)

To a solution of reactant XIII (0.64 g, 4.0 mmol) in thionyl chloride (20 mL), was added DMF (one drop) and the reaction mixture was heated at reflux for 1 hour until gas evolution had ceased. The reaction mixture was concentrated and the residue was dissolved in DCE and concentrated again. The residue was dried in a vacuum desiccator over $P_2O_5$/KOH to afford reactant XIV (0.71 mg, 100% yield) which was used for the subsequent step without any purification.

Synthesis of 3-(3-chloro-2-oxobropyl)benzonitrile
(Reactant 105b)

An Erlenmeyer flask was charged with 50% aqueous KOH (10 mL) and diethyl ether (20 mL), and cooled to 0° C. Nitrosomethyl urethane (1.36 g; 60% pure) was added portion-wise and the mixture was allowed to stand for 30 minutes at this temperature with occasional shaking. The yellow diazomethane solution was transferred into another flask containing potassium hydroxide (5 g) at 0° C., and allowed to stand at this temperature for 1 hour. The resulting solution was transferred into a round bottomed flask at 0° C., and a solution of 2-(3-cyanophenyl)acetyl chloride (reactant XIV) (0.71 g, 4.0 mmol) in diethyl ether (5 mL) was added drop-wise. The reaction mixture was allowed to warm to room temperature and stand for 2 hours. The mixture was cooled to 0° C. and dry HCl gas was introduced for 10 minutes until the nitrogen gas evolution had ceased. Water (15 mL) was added cautiously with vigorous stirring and the phases were separated. The organic layer was washed with 5% aqueous $Na_2CO_3$ (2×15 mL), dried over $MgSO_4$, and concentrated to afford reactant 105b (0.40 g, 52% yield) which was used in the subsequent step without further purification.

Synthesis of the Phenylacetyl Chlorides XVIa, XVIc and XVIe

The arylacetyl or heteroarylacetyl chlorides XVId, XVIf and XVIg were supplied from commercial sources.

To a solution of the requisite phenylacetic acid XVa, XVc or XVSe (see FIG. 5) in thionyl chloride (30 molar equivalents) was added DMF (one drop) and the reaction mixture was heated at reflux for 1 hour until gas evolution had ceased. The reaction mixture was concentrated and the residue was dissolved in DCE and concentrated again. The residue was dried in a vacuum desiccator over $P_2O_5$/KOH to quantitatively afford the phenylacetyl chlorides reactants XVIa, XVIc, and XVIe which were used in the subsequent step without any purification.

Synthesis of the Chloro-ketone Reactants 105a and 105c to 105q

An Erlenmeyer flask was charged with 50% aqueous KOH (2-3 mL per mmol of arylacetyl chloride) and diethyl ether (3-5 mL per mmol of arylacetyl chloride) and cooled to 0° C. Nitrosomethyl urethane (2 molar equivalents, 60% pure) was added portion-wise and the mixture was allowed to stand for 30 minutes at this temperature with occasional shaking. The yellow diazomethane solution was transferred into another flask containing potassium hydroxide (50-100 g) at 0° C., and allowed to stand at this temperature for 1 hour. The resulting solution was transferred into a round bottomed flask, cooled to 0° C., and the requisite phenylacetyl chloride reactant XVIa or XVII-g) in diethyl ether (1 mL/mmol) was added drop-wise. The reaction mixture was allowed to warm to room temperature and stand for 2 hours. The mixture was cooled to 0° C. and dry HCl gas was introduced for 15 minutes until the nitrogen gas evolution had ceased. Water (80-150 mL) was added cautiously with vigorous stirring and the phases were separated. The organic layer was washed with 5% aqueous $Na_2CO_3$ (2×50 mL), dried over $MgSO_4$ and concentrated. The crude products were purified by column chromatography (silica, n-hexane/EtOAc) to afford reactants 105a and 105c-g with the following yields and characterization data:

1-chloro-3-m-tolylpropan-2-one (reactant 105a): 2-m-tolylacetyl chloride (reactant XVIa) (5.1 g, 30 mmol) was converted to reactant 105a (3.3 g, 59% yield). $^1$H NMR (400 MHz, DMSO-d6) δ 7.20 (1 H, t, J=7.5 Hz), 7.07 (1 H, d, J=7.5 Hz), 6.99 (1 H, d, J=8.0 Hz), 7.02 (1 H, s), 4.60 (2 H, s), 3.82 (2 H, s) and 2.28 (3 H, s);

1-chloro-3-(3-fluorophenyl)propan-2-one (reactant 105c): 2-(3-fluorophenyl)acetyl chloride (reactant XVIc) (1.7 g, 10 mmol) was converted to reactant 105c (0.49 g, 26% yield). $^1$H NMR (400 MHz, -d6) δ 7.28.7.40 (1 H, m), 7.03.7.13 (3 H, m), 4.63 (2 H, s) and 3.92 (2 H, s);

1-chloro-3-(4-methoxyphenyl)propan-2-one (reactant 105d): 2-(4-methoxyphenyl)-acetyl chloride (reactant XVId) (5.5 g, 30 mmol) was converted to reactant 105d (4.1 g, 69% yield). $^1$H NMR (400 MHz, DMSO-d6) 6 7.12 (2 H, d, J=8.8 Hz), 6.88 (2 H, d, J=8.8 Hz), 4.58 (2 H, s), 3.79 (2 H, s) and 3.73 (3 H, s);

1-chloro-3-(2-methoxyphenyl)propan-2-one (reactant 105e): 2-(2-methoxyphenyl)acetyl chloride (reactant XVIe) (5.6 g, 30 mmol) was converted to reactant 105e (2.9 g, 48% yield). $^1$H NMR (400 MHz, DMSO-d6) δ 7.26 (1 H, ddd, J=8.3, 7.5, 1.8 Hz), 7.15 (1 H, dd, J=7.5, 1.5 Hz), 6.97 (1 H, d, J=8.3 Hz), 6.90 (1 H, td, J=7.4, 1.0 Hz), 4.57 (2 H, s), 3.77 (2 H, s) and 3.74 (3 H, s);

1-(benzo[d][1,3]dioxol-5-yl)-3-chloropropan-2-one (reactant 105f): 2-(benzo[d][1,3]dioxol-5-yl)acetyl chloride (reactant XVIf) (0.34 g, 1.7 mmol) was converted to reactant 105f (0.21 g, 58% yield); and 1-chloro-3-(thien-2-yl)propan-2-one (reactant 105g): 2-(thien-2-yl)acetyl chloride (reactant XVIg) (4.8 g, 30 mmol) was converted to reactant 105d (4.2 g, 80% yield).

Synthesis of 1-(4-methoxyphenylsulfonyl)piperazine (Reactant 103)

With reference to FIG. 3, to a solution of piperazine (6.03 g, 70 mmol) in DCM (70 mL) at 0° C. was added dropwise a solution of 4-methoxybenzene-1-sulfonyl chloride (2.89 g, 14 mmol) in DCM (40 mL). The reaction mixture was stirred at room temperature for 1 hour and the progress of the reaction was monitored by TLC analysis (silica, 5:1:0.06 DCE/EtOH/25% aqueous $NH_3$). Upon completion of the reaction, 10% aqueous HCl (120 mL) was added and the phases were separated. The aqueous layer was washed with EtOAc (50 mL), pH adjusted to 12 using 10% aqueous NaOH, and extracted with DCM (3×80 mL). The combined organic layers were dried over $MgSO_4$ and concentrated to afford compound 103 (3.5 g, 96% yield) as a white solid which was characterized as follows:

$^1$H NMR (400 MHz, DMSO-d6): δ 7.65 (2 H, d, J=9.0 Hz), 7.16 (2 H, d, J=9.0 Hz), 3.86 (3 H, s), 2.67.2.83 (8 H, m), and 2.17 (1 H, br. s.);
APCI MS m/z 257 [M+H]+;
HPLC-MS>99% (AUC).

Synthesis of 4-(4-methoxyphenylsulfonyl)piperazine-1-carbothioamide (Reactant 104)

To a solution of thio-CDI (4.8 g, 27 mmol) in THF (80 mL) was added 1-(4-methoxyphenylsulfonyl)piperazine (reactant 103) (3.5 g, 14 mmol) portion-wise and the reaction mixture was stirred at room temperature for 1 hour. The progress of the reaction was monitored by TLC analysis (silica, 5:1:0.06 DCE/EtOH/25% aqueous $NH_3$) and upon completion of the reaction, the mixture was poured into 25% aqueous $NH_3$ (100 mL) and stirred at room temperature for 12 hours. The mixture was concentrated to half of the original volume and the precipitate was filtered, washed with water, and dried in a vacuum desiccator over $P_2O_5$/KOH to afford compound 104 (3.5 g, 81% yield) as a white powder which was characterized as follows:

APCI MS m/z 316 [M+H]+; and
HPLC-MS>99% (AUC).

Synthesis of 2-(4-(4-methoxyphenylsulfonyl)piperazin-1-yl)-4-(3-methylbenzyl)-thiazole (Compound 11)

To a solution of 4-(4-methoxyphenylsulfonyl)piperazine-1-carbothioamide (reactant 104) (160 mg, 0.50 mmol) in EtOH (5 mL) was added NaHCO3 (46 mg, 0.55 mmol) and 1-chloro-3-m-tolylpropan-2-one (reactant 105a) (100 mg, 0.55 mmol) and the reaction mixture was heated at reflux for 6 hours. The progress of the reaction was monitored by TLC analysis (silica, 5:1 DCE/EtOH) and upon completion of the reaction, 25% aqueous NH3 (2 mL) was added. The reaction mixture was concentrated and the residue was dissolved in CHCl3 (30 mL), washed with water (10 mL) and brine (10 mL), dried over MgSO4 and concentrated. The crude product was purified by column chromatography (silica, DCM/methanol) and dried under vacuum at 40° C. over P2O5/KOH to afford compound 11 (95 mg, 43% yield) as a white solid powder which was characterized as follows:

1H NMR (400 MHz, DMSO-d6): δ 7.68 (2 H, d, J=8.8 Hz), 7.11.7.20 (3 H, m), 6.96.7.04 (3 H, m), 6.35 (1 H, s), 3.85 (3 H, s), 3.73 (2 H, s), 3.37.3.49 (4 H, m), 2.92.3.03 (4 H, m), and 2.24 (3 H, s);
APCI MS m/z 444 [M+H]+; and
HPLC-MS 97.8% (AUC).

Synthesis of 3-((2-(4-(4-methoxyphenylsulfonyl) piperazin-1-yl)thiazol-4-yl)methyl)-benzonitrile (Compound 12)

To a solution of 4-(4-methoxyphenylsulfonyl)-piperazine-1-carbothioamide (reactant 104) (430 mg, 1.4 mmol) in EtOH (15 mL) was added $NaHCO_3$ (46 mg, 2.3 mmol) and 3-(3-chloro-2-oxopropyl)benzonitrile (reactant 105b) (197 mg, 2.07 mmol) and the reaction mixture was heated at reflux for 2 hours. The progress of the reaction was monitored by TLC analysis (silica, 3:2 n-hexane/EtOAc) and upon completion the reaction mixture was cooled to room temperature followed by addition of water (50 mL) and EtOAc (25 mL). The layers were separated and the aqueous layer was extracted with ethyl acetate (2×30 mL). The combined organic layers were washed with brine, dried over $MgSO_4$ and concentrated. The crude product was purified by column chromatography (silica, 3:2 n-hexane/EtOAc, then 30:1 DCE/EtOH) and dried under vacuum at 40° C. over $P_2O_5$/KOH to afford compound 12 (90 mg, 14% yield) as a light yellow powder which was characterized as follows:

$^1$H NMR (400 MHz, DMSO-d6) δ 7.64.7.71 (4 H, m), 7.57 (1 H, dt, J=8.0, 1.5 Hz), 7.48 (1 H, t, J=7.9 Hz), 7.15 (2 H, d, J=9.0 Hz), 6.44 (1 H, s), 3.85 (5 H, s), 3.37.3.48 (4 H, m), and 2.92.3.03 (4 H, m);
APCI MS m/z 455 [M+H]+; and
HPLC-MS 94.0% (AUC).

Synthesis of 4-(3-fluorobenzyl)-2-(4-(4-methoxyphenylsulfonyl)piperazin-1-yl)thiazole (Compound 13)

To a solution of 4-(4-methoxyphenylsulfonyl)-piperazine-1-carbothioamide (reactant 104) (160 mg, 0.50 mmol) in EtOH (5 mL) was added $NaHCO_3$ (50 mg, 0.60 mmol) and 1-chloro-3-(3-fluorophenyl)propan-2-one (reactant 105c) (103 mg, 0.55 mmol) and the reaction mixture was heated at reflux for 3 hours. The progress of the reaction was monitored by TLC analysis (silica, 20:1 DCE/EtOH) and upon completion the reaction mixture was concentrated and the residue was purified by column chromatography (silica, 7:3 n-hexane/EtOAc) and dried under vacuum at 40° C. over $P_2O_5$/KOH to afford compound 13 (64 mg, 29% yield) as a light yellow powder which was characterized as follows:

$^1$H NMR (400 MHz, DMSO-d6) δ 7.68 (2 H, d, J=8.8 Hz), 7.25.7.34 (1 H, m), 7.16 (2 H, d, J=9.0 Hz), 6.97.7.08 (3 H, m), 6.43 (1 H, s), 3.85 (3 H, s), 3.80 (2 H, s), 3.41.3.48 (4 H, m), and 2.92.3.03 (4 H, m);
APCI MS m/z 448 [M+H]+; and
HPLC-MS>99% (AUC).

Synthesis of 4-(4-methoxybenzyl)-2-(4-(4-methoxyphenylsulfonyl)piperazin-1-yl)-thiazole (Compound 14)

To a solution of 4-(4-methoxyphenylsulfonyl)piperazine-1-carbothioamide (reactant 104) (160 mg, 0.50 mmol) in EtOH (5 mL) was added $NaHCO_3$ (46 mg, 0.55 mmol) and 1-chloro-3-(4-methoxyphenyl)propan-2-one (reactant 105d) (109 mg, 0.55 mmol) and the reaction mixture was heated at reflux for 6 hours. The progress of the reaction was monitored by TLC analysis (silica, 5:1 DCE/EtOH) and upon completion of the reaction, 25% aqueous $NH_3$ (2 mL) was added. The reaction mixture was concentrated and the residue was dissolved in $CHCl_3$ (30 mL), washed with water (10 mL) and brine (10 mL), dried over $MgSO_4$ and concentrated. The crude product was purified by column chromatography (silica, 100:1 DCM/methanol) and dried under vacuum at 40° C. over $P_2O_5$/KOH to afford compound 14 (99 mg, 43%) as a white solid which was characterized as follows.

$^1$H NMR (400 MHz, DMSO-d6) δ 7.68 (2 H, d, J=9.0 Hz), 7.16 (2 H, d, J=9.0 Hz), 7.12 (2 H, d, J=8.8 Hz), 6.82 (2 H, d, J=8.8 Hz), 6.31 (1 H, s), 3.85 (3 H, s), 3.68.3.76 (5 H, m), 3.39.3.48 (4 H, m), and 2.92.3.03 (4 H, m);

APCI MS m/z 460 [M+H]+; and

HPLC-MS 90.7% (AUC).

Synthesis of 4-(2-methoxybenzyl)-2-(4-(4-methoxyphenylsulfonyl)piperazin-1-yl)thiazole (Compound 15)

To a solution of 4-(4-methoxyphenylsulfonyl)piperazine-1-carbothioamide (reactant 104) (160 mg, 0.50 mmol) in EtOH (5 mL) was added $NaHCO_3$ (46 mg, 0.55 mmol) and 1-chloro-3-(2-methoxyphenyl)propan-2-one (reactant 105e) (110 mg, 0.55 mmol) and the reaction mixture was heated at reflux for 6 hours. The progress of the reaction was monitored by TLC analysis (silica, 5:1 DCE/EtOH) and upon completion of the reaction, 25% aqueous $NH_3$ (2 mL) was added. The reaction mixture was concentrated and the residue was dissolved in CHCl3 (30 mL), washed with water (10 mL) and brine (10 mL), dried over $MgSO_4$ and concentrated. The crude product was purified by column chromatography (silica, DCM/methanol) and dried under vacuum at 40° C. over $P_2O_5$/KOH to afford compound 15 (84 mg, 37% yield) as a yellow oil which was characterized as follows:

$^1$H NMR (400 MHz, DMSO-d6): δ 7.68 (2 H, d, J=9.0 Hz), 7.13.7.24 (3 H, m), 7.04(1 H, dd, J=7.4, 1.6 Hz), 6.95 (1 H, dd, J=8.3, 1.0 Hz), 6.84 (1 H, td, J=7.5, 1.3 Hz), 6.18 (1 H, t, J=0.9 Hz), 3.85 (3 H, s), 3.75 (3 H, s), 3.73 (2 H, s), 3.41.3.49 (4 H, m), and 2.92.3.03 (4 H, m);

APCI MS m/z 460 [M+H]+; and

HPLC-MS 95.3% (AUC).

Synthesis of 4-(benzo[d][1,3]dioxol-5-ylmethyl)-2-(4-(4-methoxyphenylsulfonyl)-piperazin-1-yl)thiazole (Compound 18)

To a solution of 4-(4-methoxyphenyl-sulfonyl)piperazine-1-carbothioamide (reactant 104) (210 mg, 0.66 mmol) in EtOH (7 mL) was added $NaHCO_3$ (94 mg, 1.1 mmol) and 1-(benzo[d][1,3]dioxol-5-yl)-3-chloropropan-2-one (reactant 105f) (210 mg, 1.0 mmol) and the reaction mixture was heated at reflux for 6 hours. The progress of the reaction was monitored by TLC analysis (silica, 3:2 n-hexane/EtOAc) and upon completion the mixture was poured onto water (40 mL) and the resulting precipitate was filtered. The crude product was purified by column chromatography (silica, 3:2 n-hexane/EtOAc) and dried under vacuum at 40° C. over $P_2O_5$/KOH to afford compound 18 (77 mg, 25% yield) as a light yellow powder which was characterized as follows:

$^1$H NMR (400 MHz, DMSO-d6): δ 7.68 (2 H, d, J=9.0 Hz), 7.16 (2 H, d, J=9.0 Hz), 6.77 (1 H, d, J=1.5 Hz), 6.79 (1 H, d, J=8.0 Hz), 6.67 (1 H, dd, J=7.9, 1.6 Hz), 6.35 (1 H, s), 5.94 (2 H, s), 3.85 (3 H, s), 3.68 (2 H, s), 3.41.3.48 (4 H, m), and 2.92.3.03 (4 H, m);

APCI MS m/z 474 [M+H]+; and

HPLC-MS>99% (AUC).

Synthesis of 2-(4-(4-methoxyphenylsulfonyl)piperazin-1-yl)-4-(thiophen-2-ylmethyl)-thiazole (Compound 10)

To a solution of 4-(4-methoxyphenylsulfonyl)piperazine-1-carbothioamide (reactant 104) (220 mg, 0.70 mmol) in EtOH (7 mL) was added NaHCO3 (71 mg, 0.84 mmol,) and 1-chloro-3-(thiophen-2-yl)propan-2-one (reactant 105g) (150 mg, 0.84 mmol) and the reaction mixture was heated at reflux for 6 hours. The progress of the reaction was monitored by TLC analysis (silica, 5:1 DCE/EtOH) and upon completion of the reaction, 25% aqueous $NH_3$ (2 mL) was added. The reaction mixture was concentrated and the residue was dissolved in $CHCl_3$ (30 mL), washed with water (10 mL) and brine (10 mL), dried over $MgSO_4$ and concentrated. The crude product was purified by column chromatography (silica, DCM/MeOH) and dried under vacuum at 40° C. over $P_2O_5$/KOH to afford compound 10 (75 mg, 25% yield) as a yellow solid which was characterized as follows:

$^1$H NMR (400 MHz, DMSO-d6) δ 7.68 (2 H, d, J=9.0 Hz), 7.30 (1 H, dd, J=5.3, 1.3 Hz), 7.16 (2 H, d, J=9.0 Hz), 6.91 (1 H, dd, J=5.0, 3.5 Hz), 6.86 (1 H, dd, J=3.4, 1.1 Hz), 6.48 (1 H, s), 3.98 (2 H, s), 3.85 (3 H, s), 3.38.3.51 (4 H, m), and 2.93.3.04 (4 H, m);

APCI MS m/z 436 [M+H]+; and

HPLC-MS >99% (AUC).

Example 20

Synthesis of Compound 47

The synthesis of compound 47 (detailed structure shown in table 2) was performed according to the synthetic scheme detailed on FIG. 6 and involved the preparation of a series of intermediates as follows.

Synthesis of 2-(4-(4-methoxyphenylsulfonyl)piperazin-1-yl)acetonitrile (Reactant 116)

To a solution of the reactant 103 prepared in example 19 (5.0 g, 19 mmol) in acetonitrile (80 mL) was added $K_2CO_3$ (8.1 g, 58 mmol) and bromoacetonitrile (2.5 g, 20 mmol), and the reaction mixture was stirred at room temperature for 2 hours. The progress of the reaction was monitored by TLC analysis (silica, 5:1 DCE/EtOH) and upon completion the reaction mixture was concentrated. The residue was dissolved in DCM (100 mL), washed with water (30 mL), 1% aqueous HCl (30 mL) and brine (30 mL), respectively, dried over $MgSO_4$ and concentrated to afford reactant 116 (4.4 g, 76% yield) which was characterized as follows:

$^1$H NMR (400 MHz, DMSO-d6): δ 7.68 (2 H, d, J=9.0 Hz), 7.16 (2 H, d, J=9.0 Hz), 3.86 (3 H, s), 3.71 (2 H, s), 2.86.2.98 (4 H, m), and 2.51.2.55 (4 H, m);

APCI MS m/z 296 [M+H]+; and

HPLC-MS 98.6% (AUC).

Synthesis of 2-(4-(4-methoxyphenylsulfonyl)piperazin-1-yl)ethanethioamide (Reactant 117)

To a solution of reactant 116 (0.89 g, 3 mmol) in a mixture of MeOH (10 mL) and THF (10 mL) was added 20% aqueous $(NH_4)_2S$ (10 mL) and the reaction mixture was stirred at room temperature for 24 hours. The progress of the reaction was monitored by TLC analysis (silica, 40:1 $CHCl_3$/MeOH) and upon completion the reaction mixture was poured onto water (200 mL). The precipitate was filtered, washed with water and dried under vacuum over $P_2O_5$/KOH to afford reactant 117 (0.55 g, 56% yield) which was characterized as follows:
$^1$H NMR (400 MHz, DMSO-d6): δ 9.74 (1 H, br. s.), 9.02 (1 H, br. s.), 7.71 (2 H, d, J=8.8 Hz), 7.21 (2 H, d, J=9.0 Hz), 3.89 (3 H, s), 3.30 (2 H, s), 2.89.3.05 (4 H, m), and 2.47.2.53 (4 H, m);
APCI MS m/z 330 [M+H]+; HPLC-MS>99% (AUC).

Synthesis of 4-(4-fluorophenyl)-2-((4-(4-methoxyphenylsulfonyl)piperazin-1-yl)methyl)thiazole (Compound 47)

To a solution of 2-(4-(4-methoxyphenylsulfonyl)piperazin-1-yl)ethanethioamide (reactant 117) (160 mg, 0.50 mmol) in EtOH (5 mL) was added NaHCO$_3$ (46 mg, 0.55 mmol) and 4-fluorophenacyl bromide (reactant 118a in FIG. 6) (110 mg, 0.50 mmol) and the reaction mixture was heated at reflux for 2 hours. The progress of the reaction was monitored by TLC analysis (silica, 20:1 DCE/EtOH) and upon completion of the reaction, 25% aqueous NH$_3$ (2 mL) was added and the mixture was concentrated. The residue was dissolved in DCM (30 mL), washed with water (2×10 mL) and brine (10 mL), dried over MgSO$_4$ and concentrated. The crude product was purified by column chromatography (silica, n-hexane/EtOAc) and dried under vacuum at 40° C. over P$_2$O$_5$/KOH to afford compound 47 (69 mg, 31% yield) as an orange solid which was characterized as follows:.
$^1$H NMR (400 MHz, DMSO-d6): δ 7.99 (1 H, s), 7.95 (2 H, dd, J=8.9, 5.6 Hz), 7.68 (2 H, d, J=8.8 Hz), 7.25 (2 H, t, J=8.9 Hz), 7.18 (2 H, d, J=9.0 Hz), 3.88 (2 H, s), 3.87 (3 H, s), 2.82.3.00 (4 H, m), and 2.55.2.67 (4 H, m);
APCI MS m/z 448 [M+H]+; and
HPLC-MS>99% (AUC).

Example 21

Synthesis of Compounds 31 and 48

The synthesis of compounds 31 and 48 (detailed structures shown in table 2) was performed according to the synthetic scheme detailed on FIG. 7 and involved the preparation of a series of intermediates as follows.

Synthesis of 1-(4-methoxyphenylsulfonyl)piperidine-4-carbonitrile (Reactant 121)

To solution of piperidine-4-cabonitrile (reactant 120) (5.0 g, 45 mmol) in DCE (40 mL) at 0° C. was added TEA (4.8 g, 48 mmol) and a solution of 4-methoxybenzene-1-sulfonyl chloride (reactant 102) (9.8 g, 47 mmol) in DCE (90 mL) dropwise, and the reaction mixture was heated at 50° C. for 2 hours. The progress of the reaction was monitored by TLC analysis (silica, CHCl$_3$) and upon completion of the reaction the mixture was cooled to room temperature, washed with water (2×70 mL), dried over MgSO$_4$ and concentrated to afford reactant 121 (12 g, 79% yield) as a white powder which was characterized as follows:
$^1$H NMR (400 MHz, CDCl$_3$): δ 7.69 (2 H, d, J=9.0 Hz), 7.01 (2 H, d, J=9.0 Hz), 3.88 (3 H, s), 3.07.3.18 (4 H, m), 2.69.2.81 (1 H, m), and 1.89.2.05 (4 H, m);
APCI MS m/z 281 [M+H]+; and
HPLC-MS>99% (AUC).

Synthesis of 1-(4-methoxyphenylsulfonyl)piperidine-4-carbothioamide (Reactant 122)

To a solution of reactant 121 (5.0 g, 17 mmol) in a mixture of MeOH (100 mL) and THF (100 mL) was added 20% aqueous (NH$_4$)$_2$S (100 mL) and the reaction mixture was heated at 50° C. for 5 hours. The progress of the reaction was monitored by TLC analysis (silica, 20:1 CHCl$_3$/MeOH) and upon completion the reaction mixture was poured onto water (500 mL). The precipitate was filtered, washed with water and dried under vacuum over P$_2$O$_5$/KOH followed by column chromatography (silica, CHCl$_3$/methanol) to afford reactant 122 (1.4 g, 25% yield) which was characterized as follows:
$^1$H NMR (400 MHz, DMSO-d6): δ 9.40 (1 H, br. s.), 9.01 (1 H, br. s.), 7.67 (2 H, d, J=9.0 Hz), 7.15 (2 H, d, J=9.0 Hz), 3.85 (3 H, s), 3.63.3.72 (2 H, m), 2.33.2.45 (1 H, m), 2.10.2.21 (2 H, m), and 1.68.1.80 (4 H, m);
APCI MS m/z 315 [M+H]+; and
HPLC-MS>99% (AUC).

Synthesis of 4-(4-fluorophenyl)-2-(1-(4-methoxyphenylsulfonyl)piperidin-4-yl)thiazole (Compound 48)

To a solution of 1-(4-methoxyphenyl-sulfonyl)piperidine-4-carbothioamide (reactant 122) (310 mg, 1.0 mmol) in EtOH (5 mL) was added NaHCO$_3$ (92 mg, 1.1 mmol) and 4-fluorophenacyl bromide (reactant 118a in FIG. 7) (220 mg, 1.0 mmol) and the reaction mixture was heated at reflux for 2 hours. The progress of the reaction was monitored by TLC analysis (silica, 3:2 n-hexane/EtOAc) and upon completion the reaction mixture was diluted with water (15 mL). The precipitate was filtered, washed with water and diethyl ether, and dried under vacuum at 40 ° C. over P2O5/ KOH to afford compound 48 (69 mg, 31% yield) as white powder which was characterized as follows:
$^1$H NMR (400 MHz, DMSO-d6) δ 7.90.7.97 (3 H, m), 7.71 (2 H, d, J=9.0 Hz), 7.24 (2 H, t, J=8.9 Hz), 7.18 (2 H, d, J=9.0 Hz), 3.86 (3 H, s), 3.62.3.72 (2 H, m), 3.05.3.15 (1 H, m), 2.45.2.57 (2 H, m), 2.14 (2 H, dd, J=13.2, 3.1 Hz), and 1.70.1.83 (2 H, m);
APCI MS m/z 433 [M+H]+; and
HPLC-MS>99% (AUC).

Synthesis of 4-(3-methoxybenzyl)-2-(1-(4-methoxyphenylsulfonyl)piperidin-4-yl)thiazole (Compound 31)

To a solution of 1-(4-methoxyphenyl-sulfonyl)piperidine-4-carbothioamide (reactant 122) (310 mg, 1.0 mmol) in EtOH (5 mL) was added NaHCO$_3$ (130 mg, 1.5 mmol) and 1-chloro-3-(3-methoxyphenyl)-propan-2-one (reactant 118b in FIG. 7) (260 mg, 1.3 mmol) and the reaction mixture was heated at reflux for 6 hours. The progress of the reaction was monitored by TLC analysis (silica, 5:1 DCE/EtOH) and upon completion of the reaction, 25% aqueous NH$_3$ (2 mL) was added. The mixture was concentrated and the residue was dissolved in EtOAc (30 mL), washed with water (10 mL) and brine (10 mL), dried over MgSO$_4$ and concentrated. The crude product was purified by column chromatography (silica, CHCl$_3$/EtOAc) and dried under vacuum at 40° C. over P$_2$O$_5$/KOH to afford compound 31 (41 mg, 9% yield) as a light brown solid which was characterized as follows:
$^1$H NMR (400 MHz, DMSO-d6): δ 7.69 (2 H, d, J=9.0 Hz), 7.14.7.21 (3 H, m), 7.10 (1 H, s), 6.74.6.83 (3 H, m), 3.96 (2 H, s), 3.85 (3 H, s), 3.71 (3 H, s), 3.62.3.69(2 H, m), 2.92.3.03(1 H, m), 2.40 (2 H, td, J =11.9, 2.5 Hz), 2.02.2.17 (2 H, m), and 1.60.1.75 (2 H, m);
APCI MS m/z 459 [M+H]+; and
HPLC-MS 90.9% (AUC).

Example 22

Preparation of Thiazolyl-piperidine Derivatives

Using the synthetic procedure shown in FIG. 8, 1-[4-(4-fluorophenyl)-1,3-thiazol-2-yl]-4-[(4-methoxyphenyl)-sulfonyl]-piperidine) is produced in good yield starting from 4'-fluoroacetophenone, piperidine and (4-methoxyphenyl) sulfonyl chloride. Replacing 4'-fluoroacetophenone with another alkylarylketone, the following derivatives of this invention are prepared:

1-[4-phenyl-1,3-thiazol-2-yl]-4-[(4-methoxyphenyl)sulfonyl]-piperidine
1-[4-(2-methylphenyl)-1,3-thiazol-2-yl]-4-[(4-methoxyphenyl)sulfonyl]-piperidine
1-[4-(2-methoxyphenyl)-1,3-thiazol-2-yl]-4-[(4-methoxyphenyl)sulfonyl]-piperidine
1-[4-(3-methylphenyl)-1,3-thiazol-2-yl]-4-[(4-methoxyphenyl)sulfonyl]-piperidine
1-[4-(3-methoxyphenyl)-1,3-thiazol-2-yl]-4-[(4-methoxyphenyl)sulfonyl]-piperidine
1-[4-(3-bromophenyl)-1,3-thiazol-2-yl]-4-[(4-methoxyphenyl)sulfonyl]-piperidine
1-[4-(4-chlorophenyl)-1,3-thiazol-2-yl]-4-[(4-methoxyphenyl)sulfonyl]-piperidine
1-[4-(4-methoxyphenyl)-1,3-thiazol-2-yl]-4-[(4-methoxyphenyl)sulfonyl]-piperidine
1-[4-(4-methylphenyl)-1,3-thiazol-2-yl]-4-[(4-methoxyphenyl)sulfonyl]-piperidine
1-[4-(4-ethylphenyl)-1,3-thiazol-2-yl]-4-[(4-methoxyphenyl)sulfonyl]-piperidine
1-[4-(4-ethoxyphenyl)-1,3-thiazol-2-yl]-4-[(4-methoxyphenyl)sulfonyl]-piperidine
1-[4-(4-propylphenyl)-1,3-thiazol-2-yl]-4-[(4-methoxyphenyl)sulfonyl]-piperidine
1-[4-(2,6-dimethylphenyl)-1,3-thiazol-2-yl]-4-[(4-methoxyphenyl)sulfonyl]-piperidine
1-[4-(2,3-dimethylphenyl)-1,3-thiazol-2-yl]-4-[(4-methoxyphenyl)sulfonyl]-piperidine
1-[4-(2,5-dimethylphenyl)-1,3-thiazol-2-yl]-4-[(4-methoxyphenyl)sulfonyl]-piperidine
1-[4-(2,4-dichlorophenyl)-1,3-thiazol-2-yl]-4-[(4-methoxyphenyl)sulfonyl]-piperidine
1-[4-(2,4-dimethoxyphenyl)-1,3-thiazol-2-yl]-4-[(4-methoxyphenyl)sulfonyl]-piperidine
1-[4-(2,5-dimethoxyphenyl)-1,3-thiazol-2-yl]-4-[(4-methoxyphenyl)sulfonyl]-piperidine
1-[4-(3,4-dimethoxyphenyl)-1,3-thiazol-2-yl]-4-[(4-methoxyphenyl)sulfonyl]-piperidine
1-[4-(3,5-dimethoxyphenyl)-1,3-thiazol-2-yl]-4-[(4-methoxyphenyl)sulfonyl]-piperidine
1-[4-(3,4-dichlorophenyl)-1,3-thiazol-2-yl]-4-[(4-methoxyphenyl)sulfonyl]-piperidine
1-[4-(3,4-dimethylphenyl)-1,3-thiazol-2-yl]-4-[(4-methoxyphenyl)sulfonyl]-piperidine
1-[4-(3,4-difluorophenyl)-1,3-thiazol-2-yl]-4-[(4-methoxyphenyl)sulfonyl]-piperidine
1-[4-(3,5-difluorophenyl)-1,3-thiazol-2-yl]-4-[(4-methoxyphenyl)sulfonyl]-piperidine
1-[4-(3,5-dichlorophenyl)-1,3-thiazol-2-yl]-4-[(4-methoxyphenyl)sulfonyl]-piperidine
1-[4-(3,5-dimethylphenyl)-1,3-thiazol-2-yl]-4-[(4-methoxyphenyl)sulfonyl]-piperidine
1-[4-(3-chloro-4-fluorophenyl)-1,3-thiazol-2-yl]-4-[(4-methoxyphenyl)sulfonyl]-piperidine
1-[4-(3-chloro-5-fluorophenyl)-1,3-thiazol-2-yl]-4-[(4-methoxyphenyl)sulfonyl]-piperidine
1-[4-(4-chloro-3-fluorophenyl)-1,3-thiazol-2-yl]-4-[(4-methoxyphenyl)sulfonyl]-piperidine
1-[4-(3,4,5-trimethoxyphenyl)-1,3-thiazol-2-yl]-4-[(4-methoxyphenyl)sulfonyl]-piperidine, and
1-[4-(2,4,6-trimethylphenyl)-1,3-thiazol-2-yl]-4-[(4-methoxyphenyl)sulfonyl]-piperidine.

Example 23

Preparation of Thiazolyl-piperidine Derivatives wherein W is a Single Bond

Using the same synthetic procedure and the same alkylarylketones as in example 22, but replacing (4-methoxyphenyl)sulfonyl chloride with another arylsulfonylchloride, the following derivatives are prepared:

1-[4-phenyl-1,3-thiazol-2-yl]-4-[(4-fluorophenyl)sulfonyl]-piperidine
1-[4-(2-methylphenyl)-1,3-thiazol-2-yl]-4-[(4-fluorophenyl)sulfonyl]-piperidine
1-[4-(2-methoxyphenyl)-1,3-thiazol-2-yl]-4-[(4-fluorophenyl)sulfonyl]-piperidine
1-[4-(3-methylphenyl)-1,3-thiazol-2-yl]-4-[(4-fluorophenyl)sulfonyl]-piperidine
1-[4-(3-methoxyphenyl)-1,3-thiazol-2-yl]-4-[(4-fluorophenyl)sulfonyl]-piperidine
1-[4-(3-bromophenyl)-1,3-thiazol-2-yl]-4-[(4-fluorophenyl)sulfonyl]-piperidine
1-[4-(4-chlorophenyl)-1,3-thiazol-2-yl]-4-[(4-fluorophenyl)sulfonyl]-piperidine
1-[4-(4-methoxyphenyl)-1,3-thiazol-2-yl]-4-[(4-fluorophenyl)sulfonyl]-piperidine
1-[4-(4-methylphenyl)-1,3-thiazol-2-yl]-4-[(4-fluorophenyl)sulfonyl]-piperidine
1-[4-(4-ethylphenyl)-1,3-thiazol-2-yl]-4-[(4-fluorophenyl)sulfonyl]-piperidine
1-[4-(4-ethoxyphenyl)-1,3-thiazol-2-yl]-4-[(4-fluorophenyl)sulfonyl]-piperidine
1-[4-(4-propylphenyl)-1,3-thiazol-2-yl]-4-[(4-fluorophenyl)sulfonyl]-piperidine
1-[4-(2,6-dimethylphenyl)-1,3-thiazol-2-yl]-4-[(4-fluorophenyl)sulfonyl]-piperidine
1-[4-(2,3-dimethylphenyl)-1,3-thiazol-2-yl]-4-[(4-fluorophenyl)sulfonyl]-piperidine
1-[4-(2,5-dimethylphenyl)-1,3-thiazol-2-yl]-4-[(4-fluorophenyl)sulfonyl]-piperidine
1-[4-(2,4-dichlorophenyl)-1,3-thiazol-2-yl]-4-[(4-fluorophenyl)sulfonyl]-piperidine
1-[4-(2,4-dimethoxyphenyl)-1,3-thiazol-2-yl]-4-[(4-fluorophenyl)sulfonyl]-piperidine
1-[4-(2,5-dimethoxyphenyl)-1,3-thiazol-2-yl]-4-[(4-fluorophenyl)sulfonyl]-piperidine
1-[4-(3,4-dimethoxyphenyl)-1,3-thiazol-2-yl]-4-[(4-fluorophenyl)sulfonyl]-piperidine
1-[4-(3,5-dimethoxyphenyl)-1,3-thiazol-2-yl]-4-[(4-fluorophenyl)sulfonyl]-piperidine
1-[4-(3,4-dichlorophenyl)-1,3-thiazol-2-yl]-4-[(4-fluorophenyl)sulfonyl]-piperidine
1-[4-(3,4-dimethylphenyl)-1,3-thiazol-2-yl]-4-[(4-fluorophenyl)sulfonyl]-piperidine
1-[4-(3,4-difluorophenyl)-1,3-thiazol-2-yl]-4-[(4-fluorophenyl)sulfonyl]-piperidine
1-[4-(3,5-difluorophenyl)-1,3-thiazol-2-yl]-4-[(4-fluorophenyl)sulfonyl]-piperidine
1-[4-(3,5-dichlorophenyl)-1,3-thiazol-2-yl]-4-[(4-fluorophenyl)sulfonyl]-piperidine 1-[4-(3,5-dimethylphenyl)-1,3-thiazol-2-yl]-4-[(4-fluorophenyl)sulfonyl]-piperidine
1-[4-(3-chloro-4-fluorophenyl)-1,3-thiazol-2-yl]-4-[(4-fluorophenyl)sulfonyl]-piperidine
1-[4-(3-chloro-5-fluorophenyl)-1,3-thiazol-2-yl]-4-[(4-fluorophenyl)sulfonyl]-piperidine
1-[4-(4-chloro-3-fluorophenyl)-1,3-thiazol-2-yl]-4-[(4-fluorophenyl)sulfonyl]-piperidine
1-[4-(3,4,5-trimethoxyphenyl)-1,3-thiazol-2-yl]-4-[(4-fluorophenyl)sulfonyl]-piperidine
1-[4-(2,4,6-trimethylphenyl)-1,3-thiazol-2-yl]-4-[(4-fluorophenyl)sulfonyl]-piperidine
1-[4-phenyl-1,3-thiazol-2-yl]-4-[(4-bromophenyl)sulfonyl]-piperidine
1-[4-(2-methylphenyl)-1,3-thiazol-2-yl]-4-[(4-bromophenyl)sulfonyl]-piperidine
1-[4-(2-methoxyphenyl)-1,3-thiazol-2-yl]-4-[(4-bromophenyl)sulfonyl]-piperidine
1-[4-(3-methylphenyl)-1,3-thiazol-2-yl]-4-[(4-bromophenyl)sulfonyl]-piperidine
1-[4-(3-methoxyphenyl)-1,3-thiazol-2-yl]-4-[(4-bromophenyl)sulfonyl]-piperidine
1-[4-(3-bromophenyl)-1,3-thiazol-2-yl]-4-[(4-bromophenyl)sulfonyl]-piperidine
1-[4-(4-chlorophenyl)-1,3-thiazol-2-yl]-4-[(4-bromophenyl)sulfonyl]-piperidine
1-[4-(4-methoxyphenyl)-1,3-thiazol-2-yl]-4-[(4-bromophenyl)sulfonyl]-piperidine
1-[4-(4-methylphenyl)-1,3-thiazol-2-yl]-4-[(4-bromophenyl)sulfonyl]-piperidine
1-[4-(4-ethylphenyl)-1,3-thiazol-2-yl]-4-[(4-bromophenyl)sulfonyl]-piperidine
1-[4-(4-ethoxyphenyl)-1,3-thiazol-2-yl]-4-[(4-bromophenyl)sulfonyl]-piperidine
1-[4-(4-propylphenyl)-1,3-thiazol-2-yl]-4-[(4-bromophenyl)sulfonyl]-piperidine
1-[4-(2,6-dimethylphenyl)-1,3-thiazol-2-yl]-4-[(4-bromophenyl)sulfonyl]-piperidine
1-[4-(2,3-dimethylphenyl)-1,3-thiazol-2-yl]-4-[(4-bromophenyl)sulfonyl]-piperidine
1-[4-(2,5-dimethylphenyl)-1,3-thiazol-2-yl]-4-[(4-bromophenyl)sulfonyl]-piperidine
1-[4-(2,4-dichlorophenyl)-1,3-thiazol-2-yl]-4-[(4-bromophenyl)sulfonyl]-piperidine
1-[4-(2,4-dimethoxyphenyl)-1,3-thiazol-2-yl]-4-[(4-bromophenyl)sulfonyl]-piperidine
1-[4-(2,5-dimethoxyphenyl)-1,3-thiazol-2-yl]-4-[(4-bromophenyl)sulfonyl]-piperidine
1-[4-(3,4-dimethoxyphenyl)-1,3-thiazol-2-yl]-4-[(4-bromophenyl)sulfonyl]-piperidine
1-[4-(3,5-dimethoxyphenyl)-1,3-thiazol-2-yl]-4-[(4-bromophenyl)sulfonyl]-piperidine
1-[4-(3,4-dichlorophenyl)-1,3-thiazol-2-yl]-4-[(4-bromophenyl)sulfonyl]-piperidine
1-[4-(3,4-dimethylphenyl)-1,3-thiazol-2-yl]-4-[(4-bromophenyl)sulfonyl]-piperidine
1-[4-(3,4-difluorophenyl)-1,3-thiazol-2-yl]-4-[(4-bromophenyl)sulfonyl]-piperidine
1-[4-(3,5-difluorophenyl)-1,3-thiazol-2-yl]-4-[(4-bromophenyl)sulfonyl]-piperidine
1-[4-(3,5-dichlorophenyl)-1,3-thiazol-2-yl]-4-[(4-bromophenyl)sulfonyl]-piperidine
1-[4-(3,5-dimethylphenyl)-1,3-thiazol-2-yl]-4-[(4-bromophenyl)sulfonyl]-piperidine
1-[4-(3-chloro-4-fluorophenyl)-1,3-thiazol-2-yl]-4-[(4-bromophenyl)sulfonyl]-piperidine
1-[4-(3-chloro-5-fluorophenyl)-1,3-thiazol-2-yl]-4-[(4-bromophenyl)sulfonyl]-piperidine
1-[4-(4-chloro-3-fluorophenyl)-1,3-thiazol-2-yl]-4-[(4-bromophenyl)sulfonyl]-piperidine
1-[4-(3,4,5-trimethoxyphenyl)-1,3-thiazol-2-yl]-4-[(4-bromophenyl)sulfonyl]-piperidine
1-[4-(2,4,6-trimethylphenyl)-1,3-thiazol-2-yl]-4-[(4-bromophenyl)sulfonyl]-piperidine
1-[4-phenyl-1,3-thiazol-2-yl]-4-[(4-methylphenyl)sulfonyl]-piperidine
1-[4-(2-methylphenyl)-1,3-thiazol-2-yl]-4-[(4-methylphenyl)sulfonyl]-piperidine
1-[4-(2-methoxyphenyl)-1,3-thiazol-2-yl]-4-[(4-methylphenyl)sulfonyl]-piperidine
1-[4-(3-methylphenyl)-1,3-thiazol-2-yl]-4-[(4-methylphenyl)sulfonyl]-piperidine
1-[4-(3-methoxyphenyl)-1,3-thiazol-2-yl]-4-[(4-methylphenyl)sulfonyl]-piperidine
1-[4-(3-bromophenyl)-1,3-thiazol-2-yl]-4-[(4-methylphenyl)sulfonyl]-piperidine
1-[4-(4-chlorophenyl)-1,3-thiazol-2-yl]-4-[(4-methylphenyl)sulfonyl]-piperidine
1-[4-(4-methoxyphenyl)-1,3-thiazol-2-yl]-4-[(4-methylphenyl)sulfonyl]-piperidine
1-[4-(4-methylphenyl)-1,3-thiazol-2-yl]-4-[(4-methylphenyl)sulfonyl]-piperidine
1-[4-(4-ethylphenyl)-1,3-thiazol-2-yl]-4-[(4-methylphenyl)sulfonyl]-piperidine
1-[4-(4-ethoxyphenyl)-1,3-thiazol-2-yl]-4-[(4-methylphenyl)sulfonyl]-piperidine
1-[4-(4-propylphenyl)-1,3-thiazol-2-yl]-4-[(4-methylphenyl)sulfonyl]-piperidine
1-[4-(2,6-dimethylphenyl)-1,3-thiazol-2-yl]-4-[(4-methylphenyl)sulfonyl]-piperidine
1-[4-(2,3-dimethylphenyl)-1,3-thiazol-2-yl]-4-[(4-methylphenyl)sulfonyl]-piperidine
1-[4-(2,5-dimethylphenyl)-1,3-thiazol-2-yl]-4-[(4-methylphenyl)sulfonyl]-piperidine
1-[4-(2,4-dichlorophenyl)-1,3-thiazol-2-yl]-4-[(4-methylphenyl)sulfonyl]-piperidine
1-[4-(2,4-dimethoxyphenyl)-1,3-thiazol-2-yl]-4-[(4-methylphenyl)sulfonyl]-piperidine
1-[4-(2,5-dimethoxyphenyl)-1,3-thiazol-2-yl]-4-[(4-methylphenyl)sulfonyl]-piperidine
1-[4-(3,4-dimethoxyphenyl)-1,3-thiazol-2-yl]-4-[(4-methylphenyl)sulfonyl]-piperidine
1-[4-(3,5-dimethoxyphenyl)-1,3-thiazol-2-yl]-4-[(4-methylphenyl)sulfonyl]-piperidine
1-[4-(3,4-dichlorophenyl)-1,3-thiazol-2-yl]-4-[(4-methylphenyl)sulfonyl]-piperidine
1-[4-(3,4-dimethylphenyl)-1,3-thiazol-2-yl]-4-[(4-methylphenyl)sulfonyl]-piperidine
1-[4-(3,4-difluorophenyl)-1,3-thiazol-2-yl]-4-[(4-methylphenyl)sulfonyl]-piperidine
1-[4-(3,5-difluorophenyl)-1,3-thiazol-2-yl]-4-[(4-methylphenyl)sulfonyl]-piperidine
1-[4-(3,5-dichlorophenyl)-1,3-thiazol-2-yl]-4-[(4-methylphenyl)sulfonyl]-piperidine
1-[4-(3,5-dimethylphenyl)-1,3-thiazol-2-yl]-4-[(4-methylphenyl)sulfonyl]-piperidine
1-[4-(3-chloro-4-fluorophenyl)-1,3-thiazol-2-yl]-4-[(4-methylphenyl)sulfonyl]-piperidine
1-[4-(3-chloro-5-fluorophenyl)-1,3-thiazol-2-yl]-4-[(4-methylphenyl)sulfonyl]-piperidine
1-[4-(4-chloro-3-fluorophenyl)-1,3-thiazol-2-yl]-4-[(4-methylphenyl)sulfonyl]-piperidine 1-[4-(3,4,5-trimethoxyphenyl)-1,3-thiazol-2-yl]-4-[(4-methylphenyl)sulfonyl]-piperidine
1-[4-(2,4,6-trimethylphenyl)-1,3-thiazol-2-yl]-4-[(4-methylphenyl)sulfonyl]-piperidine
1-[4-phenyl-1,3-thiazol-2-yl]-4-[(4-chlorophenyl)sulfonyl]-piperidine
1-[4-(2-methylphenyl)-1,3-thiazol-2-yl]-4-[(4-chlorophenyl)sulfonyl]-piperidine
1-[4-(2-methoxyphenyl)-1,3-thiazol-2-yl]-4-[(4-chlorophenyl)sulfonyl]-piperidine
1-[4-(3-methylphenyl)-1,3-thiazol-2-yl]-4-[(4-chlorophenyl)sulfonyl]-piperidine
1-[4-(3-methoxyphenyl)-1,3-thiazol-2-yl]-4-[(4-chlorophenyl)sulfonyl]-piperidine
1-[4-(3-bromophenyl)-1,3-thiazol-2-yl]-4-[(4-chlorophenyl)sulfonyl]-piperidine
1-[4-(4-chlorophenyl)-1,3-thiazol-2-yl]-4-[(4-chlorophenyl)sulfonyl]-piperidine
1-[4-(4-methoxyphenyl)-1,3-thiazol-2-yl]-4-[(4-chlorophenyl)sulfonyl]-piperidine
1-[4-(4-methylphenyl)-1,3-thiazol-2-yl]-4-[(4-chlorophenyl)sulfonyl]-piperidine
1-[4-(4-ethylphenyl)-1,3-thiazol-2-yl]-4-[(4-chlorophenyl)sulfonyl]-piperidine
1-[4-(4-ethoxyphenyl)-1,3-thiazol-2-yl]-4-[(4-chlorophenyl)sulfonyl]-piperidine
1-[4-(4-propylphenyl)-1,3-thiazol-2-yl]-4-[(4-chlorophenyl)sulfonyl]-piperidine
1-[4-(2,6-dimethylphenyl)-1,3-thiazol-2-yl]-4-[(4-chlorophenyl)sulfonyl]-piperidine
1-[4-(2,3-dimethylphenyl)-1,3-thiazol-2-yl]-4-[(4-chlorophenyl)sulfonyl]-piperidine
1-[4-(2,5-dimethylphenyl)-1,3-thiazol-2-yl]-4-[(4-chlorophenyl)sulfonyl]-piperidine
1-[4-(2,4-dichlorophenyl)-1,3-thiazol-2-yl]-4-[(4-chlorophenyl)sulfonyl]-piperidine
1-[4-(2,4-dimethoxyphenyl)-1,3-thiazol-2-yl]-4-[(4-chlorophenyl)sulfonyl]-piperidine
1-[4-(2,5-dimethoxyphenyl)-1,3-thiazol-2-yl]-4-[(4-chlorophenyl)sulfonyl]-piperidine
1-[4-(3,4-dimethoxyphenyl)-1,3-thiazol-2-yl]-4-[(4-chlorophenyl)sulfonyl]-piperidine
1-[4-(3,5-dimethoxyphenyl)-1,3-thiazol-2-yl]-4-[(4-chlorophenyl)sulfonyl]-piperidine
1-[4-(3,4-dichlorophenyl)-1,3-thiazol-2-yl]-4-[(4-chlorophenyl)sulfonyl]-piperidine
1-[4-(3,4-dimethylphenyl)-1,3-thiazol-2-yl]-4-[(4-chlorophenyl)sulfonyl]-piperidine
1-[4-(3,4-difluorophenyl)-1,3-thiazol-2-yl]-4-[(4-chlorophenyl)sulfonyl]-piperidine
1-[4-(3,5-difluorophenyl)-1,3-thiazol-2-yl]-4-[(4-chlorophenyl)sulfonyl]-piperidine
1-[4-(3,5-dichlorophenyl)-1,3-thiazol-2-yl]-4-[(4-chlorophenyl)sulfonyl]-piperidine
1-[4-(3,5-dimethylphenyl)-1,3-thiazol-2-yl]-4-[(4-chlorophenyl)sulfonyl]-piperidine
1-[4-(3-chloro-4-fluorophenyl)-1,3-thiazol-2-yl]-4-[(4-chlorophenyl)sulfonyl]-piperidine
1-[4-(3-chloro-5-fluorophenyl)-1,3-thiazol-2-yl]-4-[(4-chlorophenyl)sulfonyl]-piperidine
1-[4-(4-chloro-3-fluorophenyl)-1,3-thiazol-2-yl]-4-[(4-chlorophenyl)sulfonyl]-piperidine
1-[4-(3,4,5-trimethoxyphenyl)-1,3-thiazol-2-yl]-4-[(4-chlorophenyl)sulfonyl]-piperidine
1-[4-(2,4,6-trimethylphenyl)-1,3-thiazol-2-yl]-4-[(4-chlorophenyl)sulfonyl]-piperidine
1-[4-phenyl-1,3-thiazol-2-yl]-4-[(4-(trifluoromethoxy)phenyl)sulfonyl]-piperidine
1-[4-(2-methylphenyl)-1,3-thiazol-2-yl]-4-[(4-(trifluoromethoxy)phenyl)sulfonyl]-piperidine
1-[4-(2-methoxyphenyl)-1,3-thiazol-2-yl]-4-[(4-(trifluoromethoxy)phenyl)sulfonyl]-piperidine
1-[4-(3-methylphenyl)-1,3-thiazol-2-yl]-4-[(4-(trifluoromethoxy)phenyl)sulfonyl]-piperidine
1-[4-(3-methoxyphenyl)-1,3-thiazol-2-yl]-4-[(4-(trifluoromethoxy)phenyl)sulfonyl]-piperidine
1-[4-(3-bromophenyl)-1,3-thiazol-2-yl]-4-[(4-(trifluoromethoxy)phenyl)sulfonyl]-piperidine
1-[4-(4-chlorophenyl)-1,3-thiazol-2-yl]-4-[(4-(trifluoromethoxy)phenyl)sulfonyl]-piperidine
1-[4-(4-methoxyphenyl)-1,3-thiazol-2-yl]-4-[(4-(trifluoromethoxy)phenyl)sulfonyl]-piperidine
1-[4-(4-methylphenyl)-1,3-thiazol-2-yl]-4-[(4-(trifluoromethoxy)phenyl)sulfonyl]-piperidine
1-[4-(4-ethylphenyl)-1,3-thiazol-2-yl]-4-[(4-(trifluoromethoxy)phenyl)sulfonyl]-piperidine
1-[4-(4-ethoxyphenyl)-1,3-thiazol-2-yl]-4-[(4-(trifluoromethoxy)phenyl)sulfonyl]-piperidine
1-[4-(4-propylphenyl)-1,3-thiazol-2-yl]-4-[(4-(trifluoromethoxy)phenyl)sulfonyl]-piperidine
1-[4-(2,6-dimethylphenyl)-1,3-thiazol-2-yl]-4-[(4-(trifluoromethoxy)phenyl)sulfonyl]-piperidine
1-[4-(2,3-dimethylphenyl)-1,3-thiazol-2-yl]-4-[(4-(trifluoromethoxy)phenyl)sulfonyl]-piperidine
1-[4-(2,5-dimethylphenyl)-1,3-thiazol-2-yl]-4-[(4-(trifluoromethoxy)phenyl)sulfonyl]-piperidine
1-[4-(2,4-dichlorophenyl)-1,3-thiazol-2-yl]-4-[(4-(trifluoromethoxy)phenyl)sulfonyl]-piperidine
1-[4-(2,4-dimethoxyphenyl)-1,3-thiazol-2-yl]-4-[(4-(trifluoromethoxy)phenyl)sulfonyl]-piperidine
1-[4-(2,5-dimethoxyphenyl)-1,3-thiazol-2-yl]-4-[(4-(trifluoromethoxy)phenyl)sulfonyl]-piperidine
1-[4-(3,4-dimethoxyphenyl)-1,3-thiazol-2-yl]-4-[(4-(trifluoromethoxy)phenyl)sulfonyl]-piperidine
1-[4-(3,5-dimethoxyphenyl)-1,3-thiazol-2-yl]-4-[(4-(trifluoromethoxy)phenyl)sulfonyl]-piperidine
1-[4-(3,4-dichlorophenyl)-1,3-thiazol-2-yl]-4-[(4-(trifluoromethoxy)phenyl)sulfonyl]-piperidine
1-[4-(3,4-dimethylphenyl)-1,3-thiazol-2-yl]-4-[(4-(trifluoromethoxy)phenyl)sulfonyl]-piperidine
1-[4-(3,4-difluorophenyl)-1,3-thiazol-2-yl]-4-[(4-(trifluoromethoxy)phenyl)sulfonyl]-piperidine
1-[4-(3,5-difluorophenyl)-1,3-thiazol-2-yl]-4-[(4-(trifluoromethoxy)phenyl)sulfonyl]-piperidine
1-[4-(3,5-dichlorophenyl)-1,3-thiazol-2-yl]-4-[(4-(trifluoromethoxy)phenyl)sulfonyl]-piperidine
1-[4-(3,5-dimethylphenyl)-1,3-thiazol-2-yl]-4-[(4-(trifluoromethoxy)phenyl)sulfonyl]-piperidine
1-[4-(3-chloro-4-fluorophenyl)-1,3-thiazol-2-yl]-4-[(4-(trifluoromethoxy)phenyl)sulfonyl]-piperidine
1-[4-(3-chloro-5-fluorophenyl)-1,3-thiazol-2-yl]-4-[(4-(trifluoromethoxy)phenyl)sulfonyl]-piperidine
1-[4-(4-chloro-3-fluorophenyl)-1,3-thiazol-2-yl]-4-[(4-(trifluoromethoxy)phenyl)sulfonyl]-piperidine
1-[4-(3,4,5-trimethoxyphenyl)-1,3-thiazol-2-yl]-4-[(4-(trifluoromethoxy)phenyl)sulfonyl]-piperidine
1-[4-(2,4,6-trimethylphenyl)-1,3-thiazol-2-yl]-4-[(4-(trifluoromethoxy)phenyl)sulfonyl]-piperidine
1-[4-phenyl-1,3-thiazol-2-yl]-4-[(4-tert-butylphenyl)sulfonyl]-piperidine
1-[4-(2-methylphenyl)-1,3-thiazol-2-yl]-4-[(4-tert-butylphenyl)sulfonyl]-piperidine 1-[4-(2-methoxyphenyl)-1,3-thiazol-2-yl]-4-[(4-tert-butylphenyl)sulfonyl]-piperidine
1-[4-(3-methylphenyl)-1,3-thiazol-2-yl]-4-[(4-tert-butylphenyl)sulfonyl]-piperidine
1-[4-(3-methoxyphenyl)-1,3-thiazol-2-yl]-4-[(4-tert-butylphenyl)sulfonyl]-piperidine
1-[4-(3-bromophenyl)-1,3-thiazol-2-yl]-4-[(4-tert-butylphenyl)sulfonyl]-piperidine
1-[4-(4-chlorophenyl)-1,3-thiazol-2-yl]-4-[(4-tert-butylphenyl)sulfonyl]-piperidine
1-[4-(4-methoxyphenyl)-1,3-thiazol-2-yl]-4-[(4-tert-butylphenyl)sulfonyl]-piperidine
1-[4-(4-methylphenyl)-1,3-thiazol-2-yl]-4-[(4-tert-butylphenyl)sulfonyl]-piperidine
1-[4-(4-ethylphenyl)-1,3-thiazol-2-yl]-4-[(4-tert-butylphenyl)sulfonyl]-piperidine
1-[4-(4-ethoxyphenyl)-1,3-thiazol-2-yl]-4-[(4-tert-butylphenyl)sulfonyl]-piperidine
1-[4-(4-propylphenyl)-1,3-thiazol-2-yl]-4-[(4-tert-butylphenyl)sulfonyl]-piperidine
1-[4-(2,6-dimethylphenyl)-1,3-thiazol-2-yl]-4-[(4-tert-butylphenyl)sulfonyl]-piperidine
1-[4-(2,3-dimethylphenyl)-1,3-thiazol-2-yl]-4-[(4-tert-butylphenyl)sulfonyl]-piperidine
1-[4-(2,5-dimethylphenyl)-1,3-thiazol-2-yl]-4-[(4-tert-butylphenyl)sulfonyl]-piperidine
1-[4-(2,4-dichlorophenyl)-1,3-thiazol-2-yl]-4-[(4-tert-butylphenyl)sulfonyl]-piperidine
1-[4-(2,4-dimethoxyphenyl)-1,3-thiazol-2-yl]-4-[(4-tert-butylphenyl)sulfonyl]-piperidine
1-[4-(2,5-dimethoxyphenyl)-1,3-thiazol-2-yl]-4-[(4-tert-butylphenyl)sulfonyl]-piperidine
1-[4-(3,4-dimethoxyphenyl)-1,3-thiazol-2-yl]-4-[(4-tert-butylphenyl)sulfonyl]-piperidine
1-[4-(3,5-dimethoxyphenyl)-1,3-thiazol-2-yl]-4-[(4-tert-butylphenyl)sulfonyl]-piperidine
1-[4-(3,4-dichlorophenyl)-1,3-thiazol-2-yl]-4-[(4-tert-butylphenyl)sulfonyl]-piperidine
1-[4-(3,4-dimethylphenyl)-1,3-thiazol-2-yl]-4-[(4-tert-butylphenyl)sulfonyl]-piperidine
1-[4-(3,4-difluorophenyl)-1,3-thiazol-2-yl]-4-[(4-tert-butylphenyl)sulfonyl]-piperidine
1-[4-(3,5-difluorophenyl)-1,3-thiazol-2-yl]-4-[(4-tert-butylphenyl)sulfonyl]-piperidine
1-[4-(3,5-dichlorophenyl)-1,3-thiazol-2-yl]-4-[(4-tert-butylphenyl)sulfonyl]-piperidine
1-[4-(3,5-dimethylphenyl)-1,3-thiazol-2-yl]-4-[(4-tert-butylphenyl)sulfonyl]-piperidine
1-[4-(3-chloro-4-fluorophenyl)-1,3-thiazol-2-yl]-4-[(4-tert-butylphenyl)sulfonyl]-piperidine
1-[4-(3-chloro-5-fluorophenyl)-1,3-thiazol-2-yl]-4-[(4-tert-butylphenyl)sulfonyl]-piperidine
1-[4-(4-chloro-3-fluorophenyl)-1,3-thiazol-2-yl]-4-[(4-tert-butylphenyl)sulfonyl]-piperidine
1-[4-(3,4,5-trimethoxyphenyl)-1,3-thiazol-2-yl]-4-[(4-tert-butylphenyl)sulfonyl]-piperidine
1-[4-(2,4,6-trimethylphenyl)-1,3-thiazol-2-yl]-4-[(4-tert-butylphenyl)sulfonyl]-piperidine
1-[4-phenyl-1,3-thiazol-2-yl]-4-[(pentafluorophenyl)sulfonyl]-piperidine
1-[4-(2-methylphenyl)-1,3-thiazol-2-yl]-4-[(pentafluorophenyl)sulfonyl]-piperidine
1-[4-(2-methoxyphenyl)-1,3-thiazol-2-yl]-4-[(pentafluorophenyl)sulfonyl]-piperidine
1-[4-(3-methylphenyl)-1,3-thiazol-2-yl]-4-[(pentafluorophenyl)sulfonyl]-piperidine
1-[4-(3-methoxyphenyl)-1,3-thiazol-2-yl]-4-[(pentafluorophenyl)sulfonyl]-piperidine
1-[4-(3-bromophenyl)-1,3-thiazol-2-yl]-4-[(pentafluorophenyl)sulfonyl]-piperidine
1-[4-(4-chlorophenyl)-1,3-thiazol-2-yl]-4-[(pentafluorophenyl)sulfonyl]-piperidine
1-[4-(4-methoxyphenyl)-1,3-thiazol-2-yl]-4-[(pentafluorophenyl)sulfonyl]-piperidine
1-[4-(4-methylphenyl)-1,3-thiazol-2-yl]-4-[(pentafluorophenyl)sulfonyl]-piperidine
1-[4-(4-ethylphenyl)-1,3-thiazol-2-yl]-4-[(pentafluorophenyl)sulfonyl]-piperidine
1-[4-(4-ethoxyphenyl)-1,3-thiazol-2-yl]-4-[(pentafluorophenyl)sulfonyl]-piperidine
1-[4-(4-propylphenyl)-1,3-thiazol-2-yl]-4-[(pentafluorophenyl)sulfonyl]-piperidine
1-[4-(2,6-dimethylphenyl)-1,3-thiazol-2-yl]-4-[(pentafluorophenyl)sulfonyl]-piperidine
1-[4-(2,3-dimethylphenyl)-1,3-thiazol-2-yl]-4-[(pentafluorophenyl)sulfonyl]-piperidine
1-[4-(2,5-dimethylphenyl)-1,3-thiazol-2-yl]-4-[(pentafluorophenyl)sulfonyl]-piperidine
1-[4-(2,4-dichlorophenyl)-1,3-thiazol-2-yl]-4-[(pentafluorophenyl)sulfonyl]-piperidine
1-[4-(2,4-dimethoxyphenyl)-1,3-thiazol-2-yl]-4-[(pentafluorophenyl)sulfonyl]-piperidine
1-[4-(2,5-dimethoxyphenyl)-1,3-thiazol-2-yl]-4-[(pentafluorophenyl)sulfonyl]-piperidine
1-[4-(3,4-dimethoxyphenyl)-1,3-thiazol-2-yl]-4-[(pentafluorophenyl)sulfonyl]-piperidine
1-[4-(3,5-dimethoxyphenyl)-1,3-thiazol-2-yl]-4-[(pentafluorophenyl)sulfonyl]-piperidine
1-[4-(3,4-dichlorophenyl)-1,3-thiazol-2-yl]-4-[(pentafluorophenyl)sulfonyl]-piperidine
1-[4-(3,4-dimethylphenyl)-1,3-thiazol-2-yl]-4-[(pentafluorophenyl)sulfonyl]-piperidine
1-[4-(3,4-difluorophenyl)-1,3-thiazol-2-yl]-4-[(pentafluorophenyl)sulfonyl]-piperidine
1-[4-(3,5-difluorophenyl)-1,3-thiazol-2-yl]-4-[(pentafluorophenyl)sulfonyl]-piperidine
1-[4-(3,5-dichlorophenyl)-1,3-thiazol-2-yl]-4-[(pentafluorophenyl)sulfonyl]-piperidine
1-[4-(3,5-dimethylphenyl)-1,3-thiazol-2-yl]-4-[(pentafluorophenyl)sulfonyl]-piperidine
1-[4-(3-chloro-4-fluorophenyl)-1,3-thiazol-2-yl]-4-[(pentafluorophenyl)sulfonyl]-piperidine
1-[4-(3-chloro-5-fluorophenyl)-1,3-thiazol-2-yl]-4-[(pentafluorophenyl)sulfonyl]-piperidine
1-[4-(4-chloro-3-fluorophenyl)-1,3-thiazol-2-yl]-4-[(pentafluorophenyl)sulfonyl]-piperidine
1-[4-(3,4,5-trimethoxyphenyl)-1,3-thiazol-2-yl]-4-[(pentafluorophenyl)sulfonyl]-piperidine
1-[4-(2,4,6-trimethylphenyl)-1,3-thiazol-2-yl]-4-[(pentafluorophenyl)sulfonyl]-piperidine
1-[4-phenyl-1,3-thiazol-2-yl]-4-[(2,4,6-trimethylphenyl)sulfonyl]-piperidine
1-[4-(2-methylphenyl)-1,3-thiazol-2-yl]-4-[(2,4,6-trimethylphenyl)sulfonyl]-piperidine
1-[4-(2-methoxyphenyl)-1,3-thiazol-2-yl]-4-[(2,4,6-trimethylphenyl)sulfonyl]-piperidine
1-[4-(3-methylphenyl)-1,3-thiazol-2-yl]-4-[(2,4,6-trimethylphenyl)sulfonyl]-piperidine
1-[4-(3-methoxyphenyl)-1,3-thiazol-2-yl]-4-[(2,4,6-trimethylphenyl)sulfonyl]-piperidine
1-[4-(3-bromophenyl)-1,3-thiazol-2-yl]-4-[(2,4,6-trimethylphenyl)sulfonyl]-piperidine 1-[4-(4-chlorophenyl)-1,3-thiazol-2-yl]-4-[(2,4,6-trimethylphenyl)sulfonyl]-piperidine
1-[4-(4-methoxyphenyl)-1,3-thiazol-2-yl]-4-[(2,4,6-trimethylphenyl)sulfonyl]-piperidine
1-[4-(4-methylphenyl)-1,3-thiazol-2-yl]-4-[(2,4,6-trimethylphenyl)sulfonyl]-piperidine
1-[4-(4-ethylphenyl)-1,3-thiazol-2-yl]-4-[(2,4,6-trimethylphenyl)sulfonyl]-piperidine
1-[4-(4-ethoxyphenyl)-1,3-thiazol-2-yl]-4-[(2,4,6-trimethylphenyl)sulfonyl]-piperidine
1-[4-(4-propylphenyl)-1,3-thiazol-2-yl]-4-[(2,4,6-trimethylphenyl)sulfonyl]-piperidine
1-[4-(2,6-dimethylphenyl)-1,3-thiazol-2-yl]-4-[(2,4,6-trimethylphenyl)sulfonyl]-piperidine
1-[4-(2,3-dimethylphenyl)-1,3-thiazol-2-yl]-4-[(2,4,6-trimethylphenyl)sulfonyl]-piperidine
1-[4-(2,5-dimethylphenyl)-1,3-thiazol-2-yl]-4-[(2,4,6-trimethylphenyl)sulfonyl]-piperidine
1-[4-(2,4-dichlorophenyl)-1,3-thiazol-2-yl]-4-[(2,4,6-trimethylphenyl)sulfonyl]-piperidine
1-[4-(2,4-dimethoxyphenyl)-1,3-thiazol-2-yl]-4-[(2,4,6-trimethylphenyl)sulfonyl]-piperidine
1-[4-(2,5-dimethoxyphenyl)-1,3-thiazol-2-yl]-4-[(2,4,6-trimethylphenyl)sulfonyl]-piperidine
1-[4-(3,4-dimethoxyphenyl)-1,3-thiazol-2-yl]-4-[(2,4,6-trimethylphenyl)sulfonyl]-piperidine
1-[4-(3,5-dimethoxyphenyl)-1,3-thiazol-2-yl]-4-[(2,4,6-trimethylphenyl)sulfonyl]-piperidine
1-[4-(3,4-dichlorophenyl)-1,3-thiazol-2-yl]-4-[(2,4,6-trimethylphenyl)sulfonyl]-piperidine
1-[4-(3,4-dimethylphenyl)-1,3-thiazol-2-yl]-4-[(2,4,6-trimethylphenyl)sulfonyl]-piperidine
1-[4-(3,4-difluorophenyl)-1,3-thiazol-2-yl]-4-[(2,4,6-trimethylphenyl)sulfonyl]-piperidine
1-[4-(3,5-difluorophenyl)-1,3-thiazol-2-yl]-4-[(2,4,6-trimethylphenyl)sulfonyl]-piperidine
1-[4-(3,5-dichlorophenyl)-1,3-thiazol-2-yl]-4-[(2,4,6-trimethylphenyl)sulfonyl]-piperidine
1-[4-(3,5-dimethylphenyl)-1,3-thiazol-2-yl]-4-[(2,4,6-trimethylphenyl)sulfonyl]-piperidine
1-[4-(3-chloro-4-fluorophenyl)-1,3-thiazol-2-yl]-4-[(2,4,6-trimethylphenyl)sulfonyl]-piperidine
1-[4-(3-chloro-5-fluorophenyl)-1,3-thiazol-2-yl]-4-[(2,4,6-trimethylphenyl)sulfonyl]-piperidine
1-[4-(4-chloro-3-fluorophenyl)-1,3-thiazol-2-yl]-4-[(2,4,6-trimethylphenyl)sulfonyl]-piperidine
1-[4-(3,4,5-trimethoxyphenyl)-1,3-thiazol-2-yl]-4-[(2,4,6-trimethylphenyl)sulfonyl]-piperidine
1-[4-(2,4,6-trimethylphenyl)-1,3-thiazol-2-yl]-4-[(2,4,6-trimethylphenyl)sulfonyl]-piperidine
1-[4-phenyl-1,3-thiazol-2-yl]-4-[(2,4,6-tri-iso-propylphenyl)sulfonyl]-piperidine
1-[4-(2-methylphenyl)-1,3-thiazol-2-yl]-4-[(2,4,6-tri-iso-propylphenyl)sulfonyl]-piperidine
1-[4-(2-methoxyphenyl)-1,3-thiazol-2-yl]-4-[(2,4,6-tri-iso-propylphenyl)sulfonyl]-piperidine
1-[4-(3-methylphenyl)-1,3-thiazol-2-yl]-4-[(2,4,6-tri-iso-propylphenyl)sulfonyl]-piperidine
1-[4-(3-methoxyphenyl)-1,3-thiazol-2-yl]-4-[(2,4,6-tri-iso-propylphenyl)sulfonyl]-piperidine
1-[4-(3-bromophenyl)-1,3-thiazol-2-yl]-4-[(2,4,6-tri-iso-propylphenyl)sulfonyl]-piperidine
1-[4-(4-chlorophenyl)-1,3-thiazol-2-yl]-4-[(2,4,6-tri-iso-propylphenyl)sulfonyl]-piperidine
1-[4-(4-methoxyphenyl)-1,3-thiazol-2-yl]-4-[(2,4,6-tri-iso-propylphenyl)sulfonyl]-piperidine
1-[4-(4-methylphenyl)-1,3-thiazol-2-yl]-4-[(2,4,6-tri-iso-propylphenyl)sulfonyl]-piperidine
1-[4-(4-ethylphenyl)-1,3-thiazol-2-yl]-4-[(2,4,6-tri-iso-propylphenyl)sulfonyl]-piperidine
1-[4-(4-ethoxyphenyl)-1,3-thiazol-2-yl]-4-[(2,4,6-tri-iso-propylphenyl)sulfonyl]-piperidine
1-[4-(4-propylphenyl)-1,3-thiazol-2-yl]-4-[(2,4,6-tri-iso-propylphenyl)sulfonyl]-piperidine
1-[4-(2,6-dimethylphenyl)-1,3-thiazol-2-yl]-4-[(2,4,6-tri-iso-propylphenyl)sulfonyl]-piperidine
1-[4-(2,3-dimethylphenyl)-1,3-thiazol-2-yl]-4-[(2,4,6-tri-iso-propylphenyl)sulfonyl]-piperidine
1-[4-(2,5-dimethylphenyl)-1,3-thiazol-2-yl]-4-[(2,4,6-tri-iso-propylphenyl)sulfonyl]-piperidine
1-[4-(2,4-dichlorophenyl)-1,3-thiazol-2-yl]-4-[(2,4,6-tri-iso-propylphenyl)sulfonyl]-piperidine
1-[4-(2,4-dimethoxyphenyl)-1,3-thiazol-2-yl]-4-[(2,4,6-tri-iso-propylphenyl)sulfonyl]-piperidine
1-[4-(2,5-dimethoxyphenyl)-1,3-thiazol-2-yl]-4-[(2,4,6-tri-iso-propylphenyl)sulfonyl]-piperidine
1-[4-(3,4-dimethoxyphenyl)-1,3-thiazol-2-yl]-4-[(2,4,6-tri-iso-propylphenyl)sulfonyl]-piperidine
1-[4-(3,5-dimethoxyphenyl)-1,3-thiazol-2-yl]-4-[(2,4,6-tri-iso-propylphenyl)sulfonyl]-piperidine
1-[4-(3,4-dichlorophenyl)-1,3-thiazol-2-yl]-4-[(2,4,6-tri-iso-propylphenyl)sulfonyl]-piperidine
1-[4-(3,4-dimethylphenyl)-1,3-thiazol-2-yl]-4-[(2,4,6-tri-iso-propylphenyl)sulfonyl]-piperidine
1-[4-(3,4-difluorophenyl)-1,3-thiazol-2-yl]-4-[(2,4,6-tri-iso-propylphenyl)sulfonyl]-piperidine
1-[4-(3,5-difluorophenyl)-1,3-thiazol-2-yl]-4-[(2,4,6-tri-iso-propylphenyl)sulfonyl]-piperidine
1-[4-(3,5-dichlorophenyl)-1,3-thiazol-2-yl]-4-[(2,4,6-tri-iso-propylphenyl)sulfonyl]-piperidine
1-[4-(3,5-dimethylphenyl)-1,3-thiazol-2-yl]-4-[(2,4,6-tri-iso-propylphenyl)sulfonyl]-piperidine
1-[4-(3-chloro-4-fluorophenyl)-1,3-thiazol-2-yl]-4-[(2,4,6-tri-iso-propylphenyl)sulfonyl]-piperidine
1-[4-(3-chloro-5-fluorophenyl)-1,3-thiazol-2-yl]-4-[(2,4,6-tri-iso-propylphenyl)sulfonyl]-piperidine
1-[4-(4-chloro-3-fluorophenyl)-1,3-thiazol-2-yl]-4-[(2,4,6-tri-iso-propylphenyl)sulfonyl]-piperidine
1-[4-(3,4,5-trimethoxyphenyl)-1,3-thiazol-2-yl]-4-[(2,4,6-tri-iso-propylphenyl)sulfonyl]-piperidine
1-[4-(2,4,6-trimethylphenyl)-1,3-thiazol-2-yl]-4-[(2,4,6-tri-iso-propylphenyl)sulfonyl]-piperidine
1-[4-phenyl-1,3-thiazol-2-yl]-4-[(2,4-dichlorophenyl)sulfonyl]-piperidine
1-[4-(2-methylphenyl)-1,3-thiazol-2-yl]-4-[(2,4-dichlorophenyl)sulfonyl]-piperidine
1-[4-(2-methoxyphenyl)-1,3-thiazol-2-yl]-4-[(2,4-dichlorophenyl)sulfonyl]-piperidine
1-[4-(3-methylphenyl)-1,3-thiazol-2-yl]-4-[(2,4-dichlorophenyl)sulfonyl]-piperidine
1-[4-(3-methoxyphenyl)-1,3-thiazol-2-yl]-4-[(2,4-dichlorophenyl)sulfonyl]-piperidine
1-[4-(3-bromophenyl)-1,3-thiazol-2-yl]-4-[(2,4-dichlorophenyl)sulfonyl]-piperidine
1-[4-(4-chlorophenyl)-1,3-thiazol-2-yl]-4-[(2,4-dichlorophenyl)sulfonyl]-piperidine
1-[4-(4-methoxyphenyl)-1,3-thiazol-2-yl]-4-[(2,4-dichlorophenyl)sulfonyl]-piperidine
1-[4-(4-methylphenyl)-1,3-thiazol-2-yl]-4-[(2,4-dichlorophenyl)sulfonyl]-piperidine
1-[4-(4-ethylphenyl)-1,3-thiazol-2-yl]-4-[(2,4-dichlorophenyl)sulfonyl]-piperidine 1-[4-(4-ethoxyphenyl)-1,3-thiazol-2-yl]-4-[(2,4-dichlorophenyl)sulfonyl]-piperidine
1-[4-(4-propylphenyl)-1,3-thiazol-2-yl]-4-[(2,4-dichlorophenyl)sulfonyl]-piperidine
1-[4-(2,6-dimethylphenyl)-1,3-thiazol-2-yl]-4-[(2,4-dichlorophenyl)sulfonyl]-piperidine
1-[4-(2,3-dimethylphenyl)-1,3-thiazol-2-yl]-4-[(2,4-dichlorophenyl)sulfonyl]-piperidine
1-[4-(2,5-dimethylphenyl)-1,3-thiazol-2-yl]-4-[(2,4-dichlorophenyl)sulfonyl]-piperidine
1-[4-(2,4-dichlorophenyl)-1,3-thiazol-2-yl]-4-[(2,4-dichlorophenyl)sulfonyl]-piperidine
1-[4-(2,4-dimethoxyphenyl)-1,3-thiazol-2-yl]-4-[(2,4-dichlorophenyl)sulfonyl]-piperidine
1-[4-(2,5-dimethoxyphenyl)-1,3-thiazol-2-yl]-4-[(2,4-dichlorophenyl)sulfonyl]-piperidine
1-[4-(3,4-dimethoxyphenyl)-1,3-thiazol-2-yl]-4-[(2,4-dichlorophenyl)sulfonyl]-piperidine
1-[4-(3,5-dimethoxyphenyl)-1,3-thiazol-2-yl]-4-[(2,4-dichlorophenyl)sulfonyl]-piperidine
1-[4-(3,4-dichlorophenyl)-1,3-thiazol-2-yl]-4-[(2,4-dichlorophenyl)sulfonyl]-piperidine
1-[4-(3,4-dimethylphenyl)-1,3-thiazol-2-yl]-4-[(2,4-dichlorophenyl)sulfonyl]-piperidine
1-[4-(3,4-difluorophenyl)-1,3-thiazol-2-yl]-4-[(2,4-dichlorophenyl)sulfonyl]-piperidine
1-[4-(3,5-difluorophenyl)-1,3-thiazol-2-yl]-4-[(2,4-dichlorophenyl)sulfonyl]-piperidine
1-[4-(3,5-dichlorophenyl)-1,3-thiazol-2-yl]-4-[(2,4-dichlorophenyl)sulfonyl]-piperidine
1-[4-(3,5-dimethylphenyl)-1,3-thiazol-2-yl]-4-[(2,4-dichlorophenyl)sulfonyl]-piperidine
1-[4-(3-chloro-4-fluorophenyl)-1,3-thiazol-2-yl]-4-[(2,4-dichlorophenyl)sulfonyl]-piperidine
1-[4-(3-chloro-5-fluorophenyl)-1,3-thiazol-2-yl]-4-[(2,4-dichlorophenyl)sulfonyl]-piperidine
1-[4-(4-chloro-3-fluorophenyl)-1,3-thiazol-2-yl]-4-[(2,4-dichlorophenyl)sulfonyl]-piperidine
1-[4-(3,4,5-trimethoxyphenyl)-1,3-thiazol-2-yl]-4-[(2,4-dichlorophenyl)sulfonyl]-piperidine
1-[4-(2,4,6-trimethylphenyl)-1,3-thiazol-2-yl]-4-[(2,4-dichlorophenyl)sulfonyl]-piperidine
1-[4-phenyl-1,3-thiazol-2-yl]-4-[(2,5-dichlorophenyl)sulfonyl]-piperidine
1-[4-(2-methylphenyl)-1,3-thiazol-2-yl]-4-[(2,5-dichlorophenyl)sulfonyl]-piperidine
1-[4-(2-methoxyphenyl)-1,3-thiazol-2-yl]-4-[(2,5-dichlorophenyl)sulfonyl]-piperidine
1-[4-(3-methylphenyl)-1,3-thiazol-2-yl]-4-[(2,5-dichlorophenyl)sulfonyl]-piperidine
1-[4-(3-methoxyphenyl)-1,3-thiazol-2-yl]-4-[(2,5-dichlorophenyl)sulfonyl]-piperidine
1-[4-(3-bromophenyl)-1,3-thiazol-2-yl]-4-[(2,5-dichlorophenyl)sulfonyl]-piperidine
1-[4-(4-chlorophenyl)-1,3-thiazol-2-yl]-4-[(2,5-dichlorophenyl)sulfonyl]-piperidine
1-[4-(4-methoxyphenyl)-1,3-thiazol-2-yl]-4-[(2,5-dichlorophenyl)sulfonyl]-piperidine
1-[4-(4-methylphenyl)-1,3-thiazol-2-yl]-4-[(2,5-dichlorophenyl)sulfonyl]-piperidine
1-[4-(4-ethylphenyl)-1,3-thiazol-2-yl]-4-[(2,5-dichlorophenyl)sulfonyl]-piperidine
1-[4-(4-ethoxyphenyl)-1,3-thiazol-2-yl]-4-[(2,5-dichlorophenyl)sulfonyl]-piperidine
1-[4-(4-propylphenyl)-1,3-thiazol-2-yl]-4-[(2,5-dichlorophenyl)sulfonyl]-piperidine
1-[4-(2,6-dimethylphenyl)-1,3-thiazol-2-yl]-4-[(2,5-dichlorophenyl)sulfonyl]-piperidine
1-[4-(2,3-dimethylphenyl)-1,3-thiazol-2-yl]-4-[(2,5-dichlorophenyl)sulfonyl]-piperidine
1-[4-(2,5-dimethylphenyl)-1,3-thiazol-2-yl]-4-[(2,5-dichlorophenyl)sulfonyl]-piperidine
1-[4-(2,4-dichlorophenyl)-1,3-thiazol-2-yl]-4-[(2,5-dichlorophenyl)sulfonyl]-piperidine
1-[4-(2,4-dimethoxyphenyl)-1,3-thiazol-2-yl]-4-[(2,5-dichlorophenyl)sulfonyl]-piperidine
1-[4-(2,5-dimethoxyphenyl)-1,3-thiazol-2-yl]-4-[(2,5-dichlorophenyl)sulfonyl]-piperidine
1-[4-(3,4-dimethoxyphenyl)-1,3-thiazol-2-yl]-4-[(2,5-dichlorophenyl)sulfonyl]-piperidine
1-[4-(3,5-dimethoxyphenyl)-1,3-thiazol-2-yl]-4-[(2,5-dichlorophenyl)sulfonyl]-piperidine
1-[4-(3,4-dichlorophenyl)-1,3-thiazol-2-yl]-4-[(2,5-dichlorophenyl)sulfonyl]-piperidine
1-[4-(3,4-dimethylphenyl)-1,3-thiazol-2-yl]-4-[(2,5-dichlorophenyl)sulfonyl]-piperidine
1-[4-(3,4-difluorophenyl)-1,3-thiazol-2-yl]-4-[(2,5-dichlorophenyl)sulfonyl]-piperidine
1-[4-(3,5-difluorophenyl)-1,3-thiazol-2-yl]-4-[(2,5-dichlorophenyl)sulfonyl]-piperidine
1-[4-(3,5-dichlorophenyl)-1,3-thiazol-2-yl]-4-[(2,5-dichlorophenyl)sulfonyl]-piperidine
1-[4-(3,5-dimethylphenyl)-1,3-thiazol-2-yl]-4-[(2,5-dichlorophenyl)sulfonyl]-piperidine
1-[4-(3-chloro-4-fluorophenyl)-1,3-thiazol-2-yl]-4-[(2,5-dichlorophenyl)sulfonyl]-piperidine
1-[4-(3-chloro-5-fluorophenyl)-1,3-thiazol-2-yl]-4-[(2,5-dichlorophenyl)sulfonyl]-piperidine
1-[4-(4-chloro-3-fluorophenyl)-1,3-thiazol-2-yl]-4-[(2,5-dichlorophenyl)sulfonyl]-piperazine
1-[4-(3,4,5-trimethoxylphenyl)-1,3-thiazol-2-yl]-4-[(2,5-dichlorophenyl)sulfonyl]-piperidine
1-[4-(2,4,6-trimethylphenyl)-1,3-thiazol-2-yl]-4-[(2,5-dichlorophenyl)sulfonyl]-piperidine
1-[4-phenyl-1,3-thiazol-2-yl]-4-[(3,4-dichlorophenyl)sulfonyl]-piperidine
1-[4-(2-methylphenyl)-1,3-thiazol-2-yl]-4-[(3,4-dichlorophenyl)sulfonyl]-piperidine
1-[4-(2-methoxyphenyl)-1,3-thiazol-2-yl]-4-[(3,4-dichlorophenyl)sulfonyl]-piperidine
1-[4-(3-methylphenyl)-1,3-thiazol-2-yl]-4-[(3,4-dichlorophenyl)sulfonyl]-piperidine
1-[4-(3-methoxyphenyl)-1,3-thiazol-2-yl]-4-[(3,4-dichlorophenyl)sulfonyl]-piperidine
1-[4-(3-bromophenyl)-1,3-thiazol-2-yl]-4-[(3,4-dichlorophenyl)sulfonyl]-piperidine
1-[4-(4-chlorophenyl)-1,3-thiazol-2-yl]-4-[(3,4-dichlorophenyl)sulfonyl]-piperidine
1-[4-(4-methoxyphenyl)-1,3-thiazol-2-yl]-4-[(3,4-dichlorophenyl)sulfonyl]-piperidine
1-[4-(4-methylphenyl)-1,3-thiazol-2-yl]-4-[(3,4-dichlorophenyl)sulfonyl]-piperidine
1-[4-(4-ethylphenyl)-1,3-thiazol-2-yl]-4-[(3,4-dichlorophenyl)sulfonyl]-piperidine
1-[4-(4-ethoxyphenyl)-1,3-thiazol-2-yl]-4-[(3,4-dichlorophenyl)sulfonyl]-piperidine
1-[4-(4-propylphenyl)-1,3-thiazol-2-yl]-4-[(3,4-dichlorophenyl)sulfonyl]-piperidine
1-[4-(2,6-dimethylphenyl)-1,3-thiazol-2-yl]-4-[(3,4-dichlorophenyl)sulfonyl]-piperidine
1-[4-(2,3-dimethylphenyl)-1,3-thiazol-2-yl]-4-[(3,4-dichlorophenyl)sulfonyl]-piperidine 1-[4-(2,5-dimethylphenyl)-1,3-thiazol-2-yl]-4-[(3,4-dichlorophenyl)sulfonyl]-piperidine
1-[4-(2,4-dichlorophenyl)-1,3-thiazol-2-yl]-4-[(3,4-dichlorophenyl)sulfonyl]-piperidine
1-[4-(2,4-dimethoxyphenyl)-1,3-thiazol-2-yl]-4-[(3,4-dichlorophenyl)sulfonyl]-piperidine
1-[4-(2,5-dimethoxyphenyl)-1,3-thiazol-2-yl]-4-[(3,4-dichlorophenyl)sulfonyl]-piperidine
1-[4-(3,4-dimethoxyphenyl)-1,3-thiazol-2-yl]-4-[(3,4-dichlorophenyl)sulfonyl]-piperidine
1-[4-(3,5-dimethoxyphenyl)-1,3-thiazol-2-yl]-4-[(3,4-dichlorophenyl)sulfonyl]-piperidine
1-[4-(3,4-dichlorophenyl)-1,3-thiazol-2-yl]-4-[(3,4-dichlorophenyl)sulfonyl]-piperidine
1-[4-(3,4-dimethylphenyl)-1,3-thiazol-2-yl]-4-[(3,4-dichlorophenyl)sulfonyl]-piperidine
1-[4-(3,4-difluorophenyl)-1,3-thiazol-2-yl]-4-[(3,4-dichlorophenyl)sulfonyl]-piperidine
1-[4-(3,5-difluorophenyl)-1,3-thiazol-2-yl]-4-[(3,4-dichlorophenyl)sulfonyl]-piperidine
1-[4-(3,5-dichlorophenyl)-1,3-thiazol-2-yl]-4-[(3,4-dichlorophenyl)sulfonyl]-piperidine
1-[4-(3,5-dimethylphenyl)-1,3-thiazol-2-yl]-4-[(3,4-dichlorophenyl)sulfonyl]-piperidine
1-[4-(3-chloro-4-fluorophenyl)-1,3-thiazol-2-yl]-4-[(3,4-dichlorophenyl)sulfonyl]-piperidine
1-[4-(3-chloro-5-fluorophenyl)-1,3-thiazol-2-yl]-4-[(3,4-dichlorophenyl)sulfonyl]-piperidine
1-[4-(4-chloro-3-fluorophenyl)-1,3-thiazol-2-yl]-4-[(3,4-dichlorophenyl)sulfonyl]-piperidine
1-[4-(3,4,5-trimethoxyphenyl)-1,3-thiazol-2-yl]-4-[(3,4-dichlorophenyl)sulfonyl]-piperidine
1-[4-(3,4,6-trimethylphenyl)-1,3-thiazol-2-yl]-4-[(3,4-dichlorophenyl)sulfonyl]-piperidine
1-[4-phenyl-1,3-thiazol-2-yl]-4-[(3,4-dimethoxyphenyl)sulfonyl]-piperidine
1-[4-(2-methylphenyl)-1,3-thiazol-2-yl]-4-[(3,4-dimethoxyphenyl)sulfonyl]-piperidine
1-[4-(2-methoxyphenyl)-1,3-thiazol-2-yl]-4-[(3,4-dimethoxyphenyl)sulfonyl]-piperidine
1-[4-(3-methylphenyl)-1,3-thiazol-2-yl]-4-[(3,4-dimethoxyphenyl)sulfonyl]-piperidine
1-[4-(3-methoxyphenyl)-1,3-thiazol-2-yl]-4-[(3,4-dimethoxyphenyl)sulfonyl]-piperidine
1-[4-(3-bromophenyl)-1,3-thiazol-2-yl]-4-[(3,4-dimethoxyphenyl)sulfonyl]-piperidine
1-[4-(4-chlorophenyl)-1,3-thiazol-2-yl]-4-[(3,4-dimethoxyphenyl)sulfonyl]-piperidine
1-[4-(4-methoxyphenyl)-1,3-thiazol-2-yl]-4-[(3,4-dimethoxyphenyl)sulfonyl]-piperidine
1-[4-(4-methylphenyl)-1,3-thiazol-2-yl]-4-[(3,4-dimethoxyphenyl)sulfonyl]-piperidine
1-[4-(4-ethylphenyl)-1,3-thiazol-2-yl]-4-[(3,4-dimethoxyphenyl)sulfonyl]-piperidine
1-[4-(4-ethoxyphenyl)-1,3-thiazol-2-yl]-4-[(3,4-dimethoxyphenyl)sulfonyl]-piperidine
1-[4-(4-propylphenyl)-1,3-thiazol-2-yl]-4-[(3,4-dimethoxyphenyl)sulfonyl]-piperidine
1-[4-(2,6-dimethylphenyl)-1,3-thiazol-2-yl]-4-[(3,4-dimethoxyphenyl)sulfonyl]-piperidine
1-[4-(2,3-dimethylphenyl)-1,3-thiazol-2-yl]-4-[(3,4-dimethoxyphenyl)sulfonyl]-piperidine
1-[4-(2,5-dimethylphenyl)-1,3-thiazol-2-yl]-4-[(3,4-dimethoxyphenyl)sulfonyl]-piperidine
1-[4-(2,4-dichlorophenyl)-1,3-thiazol-2-yl]-4-[(3,4-dimethoxyphenyl)sulfonyl]-piperidine
1-[4-(2,4-dimethoxyphenyl)-1,3-thiazol-2-yl]-4-[(3,4-dimethoxyphenyl)sulfonyl]-piperidine
1-[4-(2,5-dimethoxyphenyl)-1,3-thiazol-2-yl]-4-[(3,4-dimethoxyphenyl)sulfonyl]-piperidine
1-[4-(3,4-dimethoxyphenyl)-1,3-thiazol-2-yl]-4-[(3,4-dimethoxyphenyl)sulfonyl]-piperidine
1-[4-(3,5-dimethoxyphenyl)-1,3-thiazol-2-yl]-4-[(3,4-dimethoxyphenyl)sulfonyl]-piperidine
1-[4-(3,4-dichlorophenyl)-1,3-thiazol-2-yl]-4-[(3,4-dimethoxyphenyl)sulfonyl]-piperidine
1-[4-(3,4-dimethylphenyl)-1,3-thiazol-2-yl]-4-[(3,4-dimethoxyphenyl)sulfonyl]-piperidine
1-[4-(3,4-difluorophenyl)-1,3-thiazol-2-yl]-4-[(3,4-dimethoxyphenyl)sulfonyl]-piperidine
1-[4-(3,5-difluorophenyl)-1,3-thiazol-2-yl]-4-[(3,4-dimethoxyphenyl)sulfonyl]-piperidine
1-[4-(3,5-dichlorophenyl)-1,3-thiazol-2-yl]-4-[(3,4-dimethoxyphenyl)sulfonyl]-piperidine
1-[4-(3,5-dimethylphenyl)-1,3-thiazol-2-yl]-4-[(3,4-dimethoxyphenyl)sulfonyl]-piperidine
1-[4-(3-chloro-4-fluorophenyl)-1,3-thiazol-2-yl]-4-[(3,4-dimethoxyphenyl)sulfonyl]-piperidine
1-[4-(3-chloro-5-fluorophenyl)-1,3-thiazol-2-yl]-4-[(3,4-dimethoxyphenyl)sulfonyl]-piperidine
1-[4-(4-chloro-3-fluorophenyl)-1,3-thiazol-2-yl]-4-[(3,4-dimethoxyphenyl)sulfonyl]-piperidine
1-[4-(3,4,5-trimethoxyphenyl)-1,3-thiazol-2-yl]-4-[(3,4-dimethoxyphenyl)sulfonyl]-piperidine
1-[4-(2,4,6-trimethylphenyl)-1,3-thiazol-2-yl]-4-[(3,4-dimethoxyphenyl)sulfonyl]-piperidine
1-[4-phenyl-1,3-thiazol-2-yl]-4-[(2,4-dimethoxyphenyl)sulfonyl]-piperidine
1-[4-(2-methylphenyl)-1,3-thiazol-2-yl]-4-[(2,4-dimethoxyphenyl)sulfonyl]-piperidine
1-[4-(2-methoxyphenyl)-1,3-thiazol-2-yl]-4-[(2,4-dimethoxyphenyl)sulfonyl]-piperidine
1-[4-(3-methylphenyl)-1,3-thiazol-2-yl]-4-[(2,4-dimethoxyphenyl)sulfonyl]-piperidine
1-[4-(3-methoxyphenyl)-1,3-thiazol-2-yl]-4-[(2,4-dimethoxyphenyl)sulfonyl]-piperidine
1-[4-(3-bromophenyl)-1,3-thiazol-2-yl]-4-[(2,4-dimethoxyphenyl)sulfonyl]-piperidine
1-[4-(4-chlorophenyl)-1,3-thiazol-2-yl]-4-[(2,4-dimethoxyphenyl)sulfonyl]-piperidine
1-[4-(4-methoxyphenyl)-1,3-thiazol-2-yl]-4-[(2,4-dimethoxyphenyl)sulfonyl]-piperidine
1-[4-(4-methylphenyl)-1,3-thiazol-2-yl]-4-[(2,4-dimethoxyphenyl)sulfonyl]-piperidine
1-[4-(4-ethylphenyl)-1,3-thiazol-2-yl]-4-[(2,4-dimethoxyphenyl)sulfonyl]-piperidine
1-[4-(4-ethoxyphenyl)-1,3-thiazol-2-yl]-4-[(2,4-dimethoxyphenyl)sulfonyl]-piperidine
1-[4-(4-propylphenyl)-1,3-thiazol-2-yl]-4-[(2,4-dimethoxyphenyl)sulfonyl]-piperidine
1-[4-(2,6-dimethylphenyl)-1,3-thiazol-2-yl]-4-[(2,4-dimethoxyphenyl)sulfonyl]-piperidine
1-[4-(2,3-dimethylphenyl)-1,3-thiazol-2-yl]-4-[(2,4-dimethoxyphenyl)sulfonyl]-piperidine
1-[4-(2,5-dimethylphenyl)-1,3-thiazol-2-yl]-4-[(2,4-dimethoxyphenyl)sulfonyl]-piperidine
1-[4-(2,4-dichlorophenyl)-1,3-thiazol-2-yl]-4-[(2,4-dimethoxyphenyl)sulfonyl]-piperidine
1-[4-(2,4-dimethoxyphenyl)-1,3-thiazol-2-yl]-4-[(2,4-dimethoxyphenyl)sulfonyl]-piperidine
1-[4-(2,5-dimethoxyphenyl)-1,3-thiazol-2-yl]-4-[(2,4-dimethoxyphenyl)sulfonyl]-piperidine 1-[4-(3,4-dimethoxyphenyl)-1,3-thiazol-2-yl]-4-[(2,4-dimethoxyphenyl)sulfonyl]-piperidine
1-[4-(3,5-dimethoxyphenyl)-1,3-thiazol-2-yl]-4-[(2,4-dimethoxyphenyl)sulfonyl]-piperidine
1-[4-(3,4-dichlorophenyl)-1,3-thiazol-2-yl]-4-[(2,4-dimethoxyphenyl)sulfonyl]-piperidine
1-[4-(3,4-dimethylphenyl)-1,3-thiazol-2-yl]-4-[(2,4-dimethoxyphenyl)sulfonyl]-piperidine
1-[4-(3,4-difluorophenyl)-1,3-thiazol-2-yl]-4-[(2,4-dimethoxyphenyl)sulfonyl]-piperidine
1-[4-(3,5-difluorophenyl)-1,3-thiazol-2-yl]-4-[(2,4-dimethoxyphenyl)sulfonyl]-piperidine
1-[4-(3,5-dichlorophenyl)-1,3-thiazol-2-yl]-4-[(2,4-dimethoxyphenyl)sulfonyl]-piperidine
1-[4-(3,5-dimethylphenyl)-1,3-thiazol-2-yl]-4-[(2,4-dimethoxyphenyl)sulfonyl]-piperidine
1-[4-(3-chloro-4-fluorophenyl)-1,3-thiazol-2-yl]-4-[(2,4-dimethoxyphenyl)sulfonyl]-piperidine
1-[4-(3-chloro-5-fluorophenyl)-1,3-thiazol-2-yl]-4-[(2,4-dimethoxyphenyl)sulfonyl]-piperidine
1-[4-(4-chloro-3-fluorophenyl)-1,3-thiazol-2-yl]-4-[(2,4-dimethoxyphenyl)sulfonyl]-piperidine
1-[4-(3,4,5-trimethoxyphenyl)-1,3-thiazol-2-yl]-4-[(2,4-dimethoxyphenyl)sulfonyl]-piperidine
1-[4-(2,4,6-trimethylphenyl)-1,3-thiazol-2-yl]-4-[(2,4-dimethoxyphenyl)sulfonyl]-piperidine
1-[4-phenyl-1,3-thiazol-2-yl]-4-[(2,5-dimethoxyphenyl)sulfonyl]-piperidine
1-[4-(2-methylphenyl)-1,3-thiazol-2-yl]-4-[(2,5-dimethoxyphenyl)sulfonyl]-piperidine
1-[4-(2-methoxyphenyl)-1,3-thiazol-2-yl]-4-[(2,5-dimethoxyphenyl)sulfonyl]-piperidine
1-[4-(3-methylphenyl)-1,3-thiazol-2-yl]-4-[(2,5-dimethoxyphenyl)sulfonyl]-piperidine
1-[4-(3-methoxyphenyl)-1,3-thiazol-2-yl]-4-[(2,5-dimethoxyphenyl)sulfonyl]-piperidine
1-[4-(3-bromophenyl)-1,3-thiazol-2-yl]-4-[(2,5-dimethoxyphenyl)sulfonyl]-piperidine
1-[4-(4-chlorophenyl)-1,3-thiazol-2-yl]-4-[(2,5-dimethoxyphenyl)sulfonyl]-piperidine
1-[4-(4-methoxyphenyl)-1,3-thiazol-2-yl]-4-[(2,5-dimethoxyphenyl)sulfonyl]-piperidine
1-[4-(4-methylphenyl)-1,3-thiazol-2-yl]-4-[(2,5-dimethoxyphenyl)sulfonyl]-piperidine
1-[4-(4-ethylphenyl)-1,3-thiazol-2-yl]-4-[(2,5-dimethoxyphenyl)sulfonyl]-piperidine
1-[4-(4-ethoxyphenyl)-1,3-thiazol-2-yl]-4-[(2,5-dimethoxyphenyl)sulfonyl]-piperidine
1-[4-(4-propylphenyl)-1,3-thiazol-2-yl]-4-[(2,5-dimethoxyphenyl)sulfonyl]-piperidine
1-[4-(2,6-dimethylphenyl)-1,3-thiazol-2-yl]-4-[(2,5-dimethoxyphenyl)sulfonyl]-piperidine
1-[4-(2,3-dimethylphenyl)-1,3-thiazol-2-yl]-4-[(2,5-dimethoxyphenyl)sulfonyl]-piperidine
1-[4-(2,5-dimethylphenyl)-1,3-thiazol-2-yl]-4-[(2,5-dimethoxyphenyl)sulfonyl]-piperidine
1-[4-(2,4-dichlorophenyl)-1,3-thiazol-2-yl]-4-[(2,5-dimethoxyphenyl)sulfonyl]-piperidine
1-[4-(2,4-dimethoxyphenyl)-1,3-thiazol-2-yl]-4-[(2,5-dimethoxyphenyl)sulfonyl]-piperidine
1-[4-(2,5-dimethoxyphenyl)-1,3-thiazol-2-yl]-4-[(2,5-dimethoxyphenyl)sulfonyl]-piperidine
1-[4-(3,4-dimethoxyphenyl)-1,3-thiazol-2-yl]-4-[(2,5-dimethoxyphenyl)sulfonyl]-piperidine
1-[4-(3,5-dimethoxyphenyl)-1,3-thiazol-2-yl]-4-[(2,5-dimethoxyphenyl)sulfonyl]-piperidine
1-[4-(3,4-dichlorophenyl)-1,3-thiazol-2-yl]-4-[(2,5-dimethoxyphenyl)sulfonyl]-piperidine
1-[4-(3,4-dimethylphenyl)-1,3-thiazol-2-yl]-4-[(2,5-dimethoxyphenyl)sulfonyl]-piperidine
1-[4-(3,4-difluorophenyl)-1,3-thiazol-2-yl]-4-[(2,5-dimethoxyphenyl)sulfonyl]-piperidine
1-[4-(3,5-difluorophenyl)-1,3-thiazol-2-yl]-4-[(2,5-dimethoxyphenyl)sulfonyl]-piperidine
1-[4-(3,5-dichlorophenyl)-1,3-thiazol-2-yl]-4-[(2,5-dimethoxyphenyl)sulfonyl]-piperidine
1-[4-(3,5-dimethylphenyl)-1,3-thiazol-2-yl]-4-[(2,5-dimethoxyphenyl)sulfonyl]-piperidine
1-[4-(3-chloro-4-fluorophenyl)-1,3-thiazol-2-yl]-4-[(2,5-dimethoxyphenyl)sulfonyl]-piperidine
1-[4-(3-chloro-5-fluorophenyl)-1,3-thiazol-2-yl]-4-[(2,5-dimethoxyphenyl)sulfonyl]-piperidine
1-[4-(4-chloro-3-fluorophenyl)-1,3-thiazol-2-yl]-4-[(2,5-dimethoxyphenyl)sulfonyl]-piperidine
1-[4-(3,4,5-trimethoxyphenyl)-1,3-thiazol-2-yl]-4-[(2,5-dimethoxyphenyl)sulfonyl]-piperidine
1-[4-(2,4,6-trimethylphenyl)-1,3-thiazol-2-yl]-4-[(2,5-dimethoxyphenyl)sulfonyl]-piperidine
1-[4-phenyl-1,3-thiazol-2-yl]-4-[(3,5-dichlorophenyl)sulfonyl]-piperidine
1-[4-(2-methylphenyl)-1,3-thiazol-2-yl]-4-[(3,5-dichlorophenyl)sulfonyl]-piperidine
1-[4-(2-methoxyphenyl)-1,3-thiazol-2-yl]-4-[(3,5-dichlorophenyl)sulfonyl]-piperidine
1-[4-(3-methylphenyl)-1,3-thiazol-2-yl]-4-[(3,5-dichlorophenyl)sulfonyl]-piperidine
1-[4-(3-methoxyphenyl)-1,3-thiazol-2-yl]-4-[(3,5-dichlorophenyl)sulfonyl]-piperidine
1-[4-(3-bromophenyl)-1,3-thiazol-2-yl]-4-[(3,5-dichlorophenyl)sulfonyl]-piperidine
1-[4-(4-chlorophenyl)-1,3-thiazol-2-yl]-4-[(3,5-dichlorophenyl)sulfonyl]-piperidine
1-[4-(4-methoxyphenyl)-1,3-thiazol-2-yl]-4-[(3,5-dichlorophenyl)sulfonyl]-piperidine
1-[4-(4-methylphenyl)-1,3-thiazol-2-yl]-4-[(3,5-dichlorophenyl)sulfonyl]-piperidine
1-[4-(4-ethylphenyl)-1,3-thiazol-2-yl]-4-[(3,5-dichlorophenyl)sulfonyl]-piperidine
1-[4-(4-ethoxyphenyl)-1,3-thiazol-2-yl]-4-[(3,5-dichlorophenyl)sulfonyl]-piperidine
1-[4-(4-propylphenyl)-1,3-thiazol-2-yl]-4-[(3,5-dichlorophenyl)sulfonyl]-piperidine
1-[4-(2,6-dimethylphenyl)-1,3-thiazol-2-yl]-4-[(3,5-dichlorophenyl)sulfonyl]-piperidine
1-[4-(2,3-dimethylphenyl)-1,3-thiazol-2-yl]-4-[(3,5-dichlorophenyl)sulfonyl]-piperidine
1-[4-(2,5-dimethylphenyl)-1,3-thiazol-2-yl]-4-[(3,5-dichlorophenyl)sulfonyl]-piperidine
1-[4-(2,4-dichlorophenyl)-1,3-thiazol-2-yl]-4-[(3,5-dichlorophenyl)sulfonyl]-piperidine
1-[4-(2,4-dimethoxyphenyl)-1,3-thiazol-2-yl]-4-[(3,5-dichlorophenyl)sulfonyl]-piperidine
1-[4-(2,5-dimethoxyphenyl)-1,3-thiazol-2-yl]-4-[(3,5-dichlorophenyl)sulfonyl]-piperidine
1-[4-(3,4-dimethoxyphenyl)-1,3-thiazol-2-yl]-4-[(3,5-dichlorophenyl)sulfonyl]-piperidine
1-[4-(3,5-dimethoxyphenyl)-1,3-thiazol-2-yl]-4-[(3,5-dichlorophenyl)sulfonyl]-piperidine
1-[4-(3,4-dichlorophenyl)-1,3-thiazol-2-yl]-4-[(3,5-dichlorophenyl)sulfonyl]-piperidine
1-[4-(3,4-dimethylphenyl)-1,3-thiazol-2-yl]-4-[(3,5-dichlorophenyl)sulfonyl]-piperidine 1-[4-(3,4-difluorophenyl)-1,3-thiazol-2-yl]-4-[(3,5-dichlorophenyl)sulfonyl]-piperidine
1-[4-(3,5-difluorophenyl)-1,3-thiazol-2-yl]-4-[(3,5-dichlorophenyl)sulfonyl]-piperidine
1-[4-(3,5-dichlorophenyl)-1,3-thiazol-2-yl]-4-[(3,5-dichlorophenyl)sulfonyl]-piperidine
1-[4-(3,5-dimethylphenyl)-1,3-thiazol-2-yl]-4-[(3,5-dichlorophenyl)sulfonyl]-piperidine
1-[4-(3-chloro-4-fluorophenyl)-1,3-thiazol-2-yl]-4-[(3,5-dichlorophenyl)sulfonyl]-piperidine
1-[4-(3-chloro-5-fluorophenyl)-1,3-thiazol-2-yl]-4-[(3,5-dichlorophenyl)sulfonyl]-piperidine
1-[4-(4-chloro-3-fluorophenyl)-1,3-thiazol-2-yl]-4-[(3,5-dichlorophenyl)sulfonyl]-piperidine
1-[4-(3,4,5-trimethoxyphenyl)-1,3-thiazol-2-yl]-4-[(3,5-dichlorophenyl)sulfonyl]-piperidine
1-[4-(2,4,6-trimethylphenyl)-1,3-thiazol-2-yl]-4-[(3,5-dichlorophenyl)sulfonyl]-piperidine
1-[4-phenyl-1,3-thiazol-2-yl]-4-[(2,3-dichlorophenyl)sulfonyl]-piperidine
1-[4-(2-methylphenyl)-1,3-thiazol-2-yl]-4-[(2,3-dichlorophenyl)sulfonyl]-piperidine
1-[4-(2-methoxyphenyl)-1,3-thiazol-2-yl]-4-[(2,3-dichlorophenyl)sulfonyl]-piperidine
1-[4-(3-methylphenyl)-1,3-thiazol-2-yl]-4-[(2,3-dichlorophenyl)sulfonyl]-piperidine
1-[4-(3-methoxyphenyl)-1,3-thiazol-2-yl]-4-[(2,3-dichlorophenyl)sulfonyl]-piperidine
1-[4-(3-bromophenyl)-1,3-thiazol-2-yl]-4-[(2,3-dichlorophenyl)sulfonyl]-piperidine
1-[4-(4-chlorophenyl)-1,3-thiazol-2-yl]-4-[(2,3-dichlorophenyl)sulfonyl]-piperidine
1-[4-(4-methoxyphenyl)-1,3-thiazol-2-yl]-4-[(2,3-dichlorophenyl)sulfonyl]-piperidine
1-[4-(4-methylphenyl)-1,3-thiazol-2-yl]-4-[(2,3-dichlorophenyl)sulfonyl]-piperidine
1-[4-(4-ethylphenyl)-1,3-thiazol-2-yl]-4-[(2,3-dichlorophenyl)sulfonyl]-piperidine
1-[4-(4-ethoxyphenyl)-1,3-thiazol-2-yl]-4-[(2,3-dichlorophenyl)sulfonyl]-piperidine
1-[4-(4-propylphenyl)-1,3-thiazol-2-yl]-4-[(2,3-dichlorophenyl)sulfonyl]-piperidine
1-[4-(2,6-dimethylphenyl)-1,3-thiazol-2-yl]-4-[(2,3-dichlorophenyl)sulfonyl]-piperidine
1-[4-(2,3-dimethylphenyl)-1,3-thiazol-2-yl]-4-[(2,3-dichlorophenyl)sulfonyl]-piperidine
1-[4-(2,5-dimethylphenyl)-1,3-thiazol-2-yl]-4-[(2,3-dichlorophenyl)sulfonyl]-piperidine
1-[4-(2,4-dichlorophenyl)-1,3-thiazol-2-yl]-4-[(2,3-dichlorophenyl)sulfonyl]-piperidine
1-[4-(2,4-dimethoxyphenyl)-1,3-thiazol-2-yl]-4-[(2,3-dichlorophenyl)sulfonyl]-piperidine
1-[4-(2,5-dimethoxyphenyl)-1,3-thiazol-2-yl]-4-[(2,3-dichlorophenyl)sulfonyl]-piperidine
1-[4-(3,4-dimethoxyphenyl)-1,3-thiazol-2-yl]-4-[(2,3-dichlorophenyl)sulfonyl]-piperidine
1-[4-(3,5-dimethoxyphenyl)-1,3-thiazol-2-yl]-4-[(2,3-dichlorophenyl)sulfonyl]-piperidine
1-[4-(3,4-dichlorophenyl)-1,3-thiazol-2-yl]-4-[(2,3-dichlorophenyl)sulfonyl]-piperidine
1-[4-(3,4-dimethylphenyl)-1,3-thiazol-2-yl]-4-[(2,3-dichlorophenyl)sulfonyl]-piperidine
1-[4-(3,4-difluorophenyl)-1,3-thiazol-2-yl]-4-[(2,3-dichlorophenyl)sulfonyl]-piperidine
1-[4-(3,5-difluorophenyl)-1,3-thiazol-2-yl]-4-[(2,3-dichlorophenyl)sulfonyl]-piperidine
1-[4-(3,5-dichlorophenyl)-1,3-thiazol-2-yl]-4-[(2,3-dichlorophenyl)sulfonyl]-piperidine
1-[4-(3,5-dimethylphenyl)-1,3-thiazol-2-yl]-4-[(2,3-dichlorophenyl)sulfonyl]-piperidine
1-[4-(3-chloro-4-fluorophenyl)-1,3-thiazol-2-yl]-4-[(2,3-dichlorophenyl)sulfonyl]-piperidine
1-[4-(3-chloro-5-fluorophenyl)-1,3-thiazol-2-yl]-4-[(2,3-dichlorophenyl)sulfonyl]-piperidine
1-[4-(4-chloro-3-fluorophenyl)-1,3-thiazol-2-yl]-4-[(2,3-dichlorophenyl)sulfonyl]-piperidine
1-[4-(3,4,5-trimethoxyphenyl)-1,3-thiazol-2-yl]-4-[(2,3-dichlorophenyl)sulfonyl]-piperidine
1-[4-(2,4,6-trimethylphenyl)-1,3-thiazol-2-yl]-4-[(2,3-dichlorophenyl)sulfonyl]-piperidine
1-[4-phenyl-1,3-thiazol-2-yl]-4-[(2,6-difluorophenyl)sulfonyl]-piperidine
1-[4-(2-methylphenyl)-1,3-thiazol-2-yl]-4-[(2,6-difluorophenyl)sulfonyl]-piperidine
1-[4-(2-methoxyphenyl)-1,3-thiazol-2-yl]-4-[(2,6-difluorophenyl)sulfonyl]-piperidine
1-[4-(3-methylphenyl)-1,3-thiazol-2-yl]-4-[(2,6-difluorophenyl)sulfonyl]-piperidine
1-[4-(3-methoxyphenyl)-1,3-thiazol-2-yl]-4-[(2,6-difluorophenyl)sulfonyl]-piperidine
1-[4-(3-bromophenyl)-1,3-thiazol-2-yl]-4-[(2,6-difluorophenyl)sulfonyl]-piperidine
1-[4-(4-chlorophenyl)-1,3-thiazol-2-yl]-4-[(2,6-difluorophenyl)sulfonyl]-piperidine
1-[4-(4-methoxyphenyl)-1,3-thiazol-2-yl]-4-[(2,6-difluorophenyl)sulfonyl]-piperidine
1-[4-(4-methylphenyl)-1,3-thiazol-2-yl]-4-[(2,6-difluorophenyl)sulfonyl]-piperidine
1-[4-(4-ethylphenyl)-1,3-thiazol-2-yl]-4-[(2,6-difluorophenyl)sulfonyl]-piperidine
1-[4-(4-ethoxyphenyl)-1,3-thiazol-2-yl]-4-[(2,6-difluorophenyl)sulfonyl]-piperidine
1-[4-(4-propylphenyl)-1,3-thiazol-2-yl]-4-[(2,6-difluorophenyl)sulfonyl]-piperidine
1-[4-(2,6-dimethylphenyl)-1,3-thiazol-2-yl]-4-[(2,6-difluorophenyl)sulfonyl]-piperidine
1-[4-(2,3-dimethylphenyl)-1,3-thiazol-2-yl]-4-[(2,6-difluorophenyl)sulfonyl]-piperidine
1-[4-(2,5-dimethylphenyl)-1,3-thiazol-2-yl]-4-[(2,6-difluorophenyl)sulfonyl]-piperidine
1-[4-(2,4-dichlorophenyl)-1,3-thiazol-2-yl]-4-[(2,6-difluorophenyl)sulfonyl]-piperidine
1-[4-(2,4-dimethoxyphenyl)-1,3-thiazol-2-yl]-4-[(2,6-difluorophenyl)sulfonyl]-piperidine
1-[4-(2,5-dimethoxyphenyl)-1,3-thiazol-2-yl]-4-[(2,6-difluorophenyl)sulfonyl]-piperidine
1-[4-(3,4-dimethoxyphenyl)-1,3-thiazol-2-yl]-4-[(2,6-difluorophenyl)sulfonyl]-piperidine
1-[4-(3,5-dimethoxyphenyl)-1,3-thiazol-2-yl]-4-[(2,6-difluorophenyl)sulfonyl]-piperidine
1-[4-(3,4-dichlorophenyl)-1,3-thiazol-2-yl]-4-[(2,6-difluorophenyl)sulfonyl]-piperidine
1-[4-(3,4-dimethylphenyl)-1,3-thiazol-2-yl]-4-[(2,6-difluorophenyl)sulfonyl]-piperidine
1-[4-(3,4-difluorophenyl)-1,3-thiazol-2-yl]-4-[(2,6-difluorophenyl)sulfonyl]-piperidine
1-[4-(3,5-difluorophenyl)-1,3-thiazol-2-yl]-4-[(2,6-difluorophenyl)sulfonyl]-piperidine
1-[4-(3,5-dichlorophenyl)-1,3-thiazol-2-yl]-4-[(2,6-difluorophenyl)sulfonyl]-piperidine
1-[4-(3,5-dimethylphenyl)-1,3-thiazol-2-yl]-4-[(2,6-difluorophenyl)sulfonyl]-piperidine 1-[4-(3-chloro-4-fluorophenyl)-1,3-thiazol-2-yl]-4-[(2,6-difluorophenyl)sulfonyl]-piperidine
1-[4-(3-chloro-5-fluorophenyl)-1,3-thiazol-2-yl]-4-[(2,6-difluorophenyl)sulfonyl]-piperidine
1-[4-(4-chloro-3-fluorophenyl)-1,3-thiazol-2-yl]-4-[(2,6-difluorophenyl)sulfonyl]-piperidine
1-[4-(3,4,5-trimethoxyphenyl)-1,3-thiazol-2-yl]-4-[(2,6-difluorophenyl)sulfonyl]-piperidine
1-[4-(2,4,6-trimethylphenyl)-1,3-thiazol-2-yl]-4-[(2,6-difluorophenyl)sulfonyl]-piperidine
1-[4-phenyl-1,3-thiazol-2-yl]-4-[(2,4-difluorophenyl)sulfonyl]-piperidine
1-[4-(2-methylphenyl)-1,3-thiazol-2-yl]-4-[(2,4-difluorophenyl)sulfonyl]-piperidine
1-[4-(2-methoxyphenyl)-1,3-thiazol-2-yl]-4-[(2,4-difluorophenyl)sulfonyl]-piperidine
1-[4-(3-methylphenyl)-1,3-thiazol-2-yl]-4-[(2,4-difluorophenyl)sulfonyl]-piperidine
1-[4-(3-methoxyphenyl)-1,3-thiazol-2-yl]-4-[(2,4-difluorophenyl)sulfonyl]-piperidine
1-[4-(3-bromophenyl)-1,3-thiazol-2-yl]-4-[(2,4-difluorophenyl)sulfonyl]-piperidine
1-[4-(4-chlorophenyl)-1,3-thiazol-2-yl]-4-[(2,4-difluorophenyl)sulfonyl]-piperidine
1-[4-(4-methoxyphenyl)-1,3-thiazol-2-yl]-4-[(2,4-difluorophenyl)sulfonyl]-piperidine
1-[4-(4-methylphenyl)-1,3-thiazol-2-yl]-4-[(2,4-difluorophenyl)sulfonyl]-piperidine
1-[4-(4-ethylphenyl)-1,3-thiazol-2-yl]-4-[(2,4-difluorophenyl)sulfonyl]-piperidine
1-[4-(4-ethoxyphenyl)-1,3-thiazol-2-yl]-4-[(2,4-difluorophenyl)sulfonyl]-piperidine
1-[4-(4-propylphenyl)-1,3-thiazol-2-yl]-4-[(2,4-difluorophenyl)sulfonyl]-piperidine
1-[4-(2,6-dimethylphenyl)-1,3-thiazol-2-yl]-4-[(2,4-difluorophenyl)sulfonyl]-piperidine
1-[4-(2,3-dimethylphenyl)-1,3-thiazol-2-yl]-4-[(2,4-difluorophenyl)sulfonyl]-piperidine
1-[4-(2,5-dimethylphenyl)-1,3-thiazol-2-yl]-4-[(2,4-difluorophenyl)sulfonyl]-piperidine
1-[4-(2,4-dichlorophenyl)-1,3-thiazol-2-yl]-4-[(2,4-difluorophenyl)sulfonyl]-piperidine
1-[4-(2,4-dimethoxyphenyl)-1,3-thiazol-2-yl]-4-[(2,4-difluorophenyl)sulfonyl]-piperidine
1-[4-(2,5-dimethoxyphenyl)-1,3-thiazol-2-yl]-4-[(2,4-difluorophenyl)sulfonyl]-piperidine
1-[4-(3,4-dimethoxyphenyl)-1,3-thiazol-2-yl]-4-[(2,4-difluorophenyl)sulfonyl]-piperidine
1-[4-(3,5-dimethoxyphenyl)-1,3-thiazol-2-yl]-4-[(2,4-difluorophenyl)sulfonyl]-piperidine
1-[4-(3,4-dichlorophenyl)-1,3-thiazol-2-yl]-4-[(2,4-difluorophenyl)sulfonyl]-piperidine
1-[4-(3,4-dimethylphenyl)-1,3-thiazol-2-yl]-4-[(2,4-difluorophenyl)sulfonyl]-piperidine
1-[4-(3,4-difluorophenyl)-1,3-thiazol-2-yl]-4-[(2,4-difluorophenyl)sulfonyl]-piperidine
1-[4-(3,5-difluorophenyl)-1,3-thiazol-2-yl]-4-[(2,4-difluorophenyl)sulfonyl]-piperidine
1-[4-(3,5-dichlorophenyl)-1,3-thiazol-2-yl]-4-[(2,4-difluorophenyl)sulfonyl]-piperidine
1-[4-(3,5-dimethylphenyl)-1,3-thiazol-2-yl]-4-[(2,4-difluorophenyl)sulfonyl]-piperidine
1-[4-(3-chloro-4-fluorophenyl)-1,3-thiazol-2-yl]-4-[(2,4-difluorophenyl)sulfonyl]-piperidine
1-[4-(3-chloro-5-fluorophenyl)-1,3-thiazol-2-yl]-4-[(2,4-difluorophenyl)sulfonyl]-piperidine
1-[4-(4-chloro-3-fluorophenyl)-1,3-thiazol-2-yl]-4-[(2,4-difluorophenyl)sulfonyl]-piperidine
1-[4-(3,4,5-trimethoxyphenyl)-1,3-thiazol-2-yl]-4-[(2,4-difluorophenyl)sulfonyl]-piperidine
1-[4-(2,4,6-trimethylphenyl)-1,3-thiazol-2-yl]-4-[(2,4-difluorophenyl)sulfonyl]-piperidine
1-[4-phenyl-1,3-thiazol-2-yl]-4-[(4-(bromomethyl)phenyl)sulfonyl]piperidine
1-[4-(2-methylphenyl)-1,3-thiazol-2-yl]-4-[(4-(bromomethyl)phenyl)sulfonyl]piperidine
1-[4-(2-methoxyphenyl)-1,3-thiazol-2-yl]-4-[(4-(bromomethyl)phenyl)sulfonyl]-piperidine
1-[4-(3-methylphenyl)-1,3-thiazol-2-yl]-4-[(4-(bromomethyl)phenyl)sulfonyl]piperidine
1-[4-(3-methoxyphenyl)-1,3-thiazol-2-yl]-4-[(4-(bromomethyl)phenyl)sulfonyl]-piperidine
1-[4-(3-bromophenyl)-1,3-thiazol-2-yl]-4-[(4-(bromomethyl)phenyl)sulfonyl]-piperidine
1-[4-(4-chlorophenyl)-1,3-thiazol-2-yl]-4-[(4-(bromomethyl)phenyl)sulfonyl]-piperidine
1-[4-(4-methoxyphenyl)-1,3-thiazol-2-yl]-4-[(4-(bromomethyl)phenyl)sulfonyl]-piperidine
1-[4-(4-methylphenyl)-1,3-thiazol-2-yl]-4-[(4-(bromomethyl)phenyl)sulfonyl]-piperidine
1-[4-(4-ethylphenyl)-1,3-thiazol-2-yl]-4-[(4-(bromomethyl)phenyl)sulfonyl]-piperidine
1-[4-(4-ethoxyphenyl)-1,3-thiazol-2-yl]-4-[(4-(bromomethyl)phenyl)sulfonyl]-piperidine
1-[4-(4-propylphenyl)-1,3-thiazol-2-yl]-4-[(4-(bromomethyl)phenyl)sulfonyl]-piperidine
1-[4-(2,6-dimethylphenyl)-1,3-thiazol-2-yl]-4-[(4-(bromomethyl)phenyl)sulfonyl]-piperidine
1-[4-(2,3-dimethylphenyl)-1,3-thiazol-2-yl]-4-[(4-(bromomethyl)phenyl)sulfonyl]-piperidine
1-[4-(2,5-dimethylphenyl)-1,3-thiazol-2-yl]-4-[(4-(bromomethyl)phenyl)sulfonyl]-piperidine
1-[4-(2,4-dichlorophenyl)-1,3-thiazol-2-yl]-4-[(4-(bromomethyl)phenyl)sulfonyl]-piperidine
1-[4-(2,4-dimethoxyphenyl)-1,3-thiazol-2-yl]-4-[(4-(bromomethyl)phenyl)sulfonyl]-piperidine
1-[4-(2,5-dimethoxyphenyl)-1,3-thiazol-2-yl]-4-[(4-(bromomethyl)phenyl)sulfonyl]-piperidine
1-[4-(3,4-dimethoxyphenyl)-1,3-thiazol-2-yl]-4-[(4-(bromomethyl)phenyl)sulfonyl]-piperidine
1-[4-(3,5-dimethoxyphenyl)-1,3-thiazol-2-yl]-4-[(4-(bromomethyl)phenyl)sulfonyl]-piperidine
1-[4-(3,4-dichlorophenyl)-1,3-thiazol-2-yl]-4-[(4-(bromomethyl)phenyl)sulfonyl]-piperidine
1-[4-(3,4-dimethylphenyl)-1,3-thiazol-2-yl]-4-[(4-(bromomethyl)phenyl)sulfonyl]-piperidine
1-[4-(3,4-difluorophenyl)-1,3-thiazol-2-yl]-4-[(4-(bromomethyl)phenyl)sulfonyl]-piperidine
1-[4-(3,5-difluorophenyl)-1,3-thiazol-2-yl]-4-[(4-(bromomethyl)phenyl)sulfonyl]-piperidine
1-[4-(3,5-dichlorophenyl)-1,3-thiazol-2-yl]-4-[(4-(bromomethyl)phenyl)sulfonyl]-piperidine
1-[4-(3,5-dimethylphenyl)-1,3-thiazol-2-yl]-4-[(4-(bromomethyl)phenyl)sulfonyl]-piperidine
1-[4-(3-chloro-4-fluorophenyl)-1,3-thiazol-2-yl]-4-[(4-(bromomethyl)phenyl)sulfonyl]-piperidine
1-[4-(3-chloro-5-fluorophenyl)-1,3-thiazol-2-yl]-4-[(4-(bromomethyl)phenyl)sulfonyl]-piperidine
1-[4-(4-chloro-3-fluorophenyl)-1,3-thiazol-2-yl]-4-[(4-(bromomethyl)phenyl)sulfonyl]-piperidine
1-[4-(3,4,5-trimethoxyphenyl)-1,3-thiazol-2-yl]-4-[(4-(bromomethyl)phenyl)sulfonyl]-piperidine 1-[4-(2,4,6-trimethylphenyl)-1,3-thiazol-2-yl]-4-[(4-(bromomethyl)phenyl)sulfonyl]-piperidine
1-[4-phenyl-1,3-thiazol-2-yl]-4-[(3-(trifluoromethyl)phenyl)sulfonyl]-piperidine
1-[4-(2-methylphenyl)-1,3-thiazol-2-yl]-4-[(3-(trifluoromethyl)phenyl)sulfonyl]-piperidine
1-[4-(2-methoxyphenyl)-1,3-thiazol-2-yl]-4-[(3-(trifluoromethyl)phenyl)sulfonyl]-piperidine
1-[4-(3-methylphenyl)-1,3-thiazol-2-yl]-4-[(3-(trifluoromethyl)phenyl)sulfonyl]-piperidine
1-[4-(3-methoxyphenyl)-1,3-thiazol-2-yl]-4-[(3-(trifluoromethyl)phenyl)sulfonyl]-piperidine
1-[4-(3-bromophenyl)-1,3-thiazol-2-yl]-4-[(3-(trifluoromethyl)phenyl)sulfonyl]-piperidine
1-[4-(4-chlorophenyl)-1,3-thiazol-2-yl]-4-[(3-(trifluoromethyl)phenyl)sulfonyl]-piperidine
1-[4-(4-methoxyphenyl)-1,3-thiazol-2-yl]-4-[(3-(trifluoromethyl)phenyl)sulfonyl]-piperidine
1-[4-(4-methylphenyl)-1,3-thiazol-2-yl]-4-[(3-(trifluoromethyl)phenyl)sulfonyl]-piperidine
1-[4-(4-ethylphenyl)-1,3-thiazol-2-yl]-4-[(3-(trifluoromethyl)phenyl)sulfonyl]-piperidine
1-[4-(4-ethoxyphenyl)-1,3-thiazol-2-yl]-4-[(3-(trifluoromethyl)phenyl)sulfonyl]-piperidine
1-[4-(4-propylphenyl)-1,3-thiazol-2-yl]-4-[(3-(trifluoromethyl)phenyl)sulfonyl]-piperidine
1-[4-(2,6-dimethylphenyl)-1,3-thiazol-2-yl]-4-[(3-(trifluoromethyl)phenyl)sulfonyl]-piperidine
1-[4-(2,3-dimethylphenyl)-1,3-thiazol-2-yl]-4-[(3-(trifluoromethyl)phenyl)sulfonyl]-piperidine
1-[4-(2,5-dimethylphenyl)-1,3-thiazol-2-yl]-4-[(3-(trifluoromethyl)phenyl)sulfonyl]-piperidine
1-[4-(2,4-dichlorophenyl)-1,3-thiazol-2-yl]-4-[(3-(trifluoromethyl)phenyl)sulfonyl]-piperidine
1-[4-(2,4-dimethoxyphenyl)-1,3-thiazol-2-yl]-4-[(3-(trifluoromethyl)phenyl)sulfonyl]-piperidine
1-[4-(2,5-dimethoxyphenyl)-1,3-thiazol-2-yl]-4-[(3-(trifluoromethyl)phenyl)sulfonyl]-piperidine
1-[4-(3,4-dimethoxyphenyl)-1,3-thiazol-2-yl]-4-[(3-(trifluoromethyl)phenyl)sulfonyl]-piperidine
1-[4-(3,5-dimethoxyphenyl)-1,3-thiazol-2-yl]-4-[(3-(trifluoromethyl)phenyl)sulfonyl]-piperidine
1-[4-(3,4-dichlorophenyl)-1,3-thiazol-2-yl]-4-[(3-(trifluoromethyl)phenyl)sulfonyl]-piperidine
1-[4-(3,4-dimethylphenyl)-1,3-thiazol-2-yl]-4-[(3-(trifluoromethyl)phenyl)sulfonyl]-piperidine
1-[4-(3,4-difluorophenyl)-1,3-thiazol-2-yl]-4-[(3-(trifluoromethyl)phenyl)sulfonyl]-piperidine
1-[4-(3,5-difluorophenyl)-1,3-thiazol-2-yl]-4-[(3-(trifluoromethyl)phenyl)sulfonyl]-piperidine
1-[4-(3,5-dichlorophenyl)-1,3-thiazol-2-yl]-4-[(3-(trifluoromethyl)phenyl)sulfonyl]-piperidine
1-[4-(3,5-dimethylphenyl)-1,3-thiazol-2-yl]-4-[(3-(trifluoromethyl)phenyl)sulfonyl]-piperidine
1-[4-(3-chloro-4-fluorophenyl)-1,3-thiazol-2-yl]-4-[(3-(trifluoromethyl)phenyl)sulfonyl]-piperidine
1-[4-(3-chloro-5-fluorophenyl)-1,3-thiazol-2-yl]-4-[(3-(trifluoromethyl)phenyl)sulfonyl]-piperidine
1-[4-(4-chloro-3-fluorophenyl)-1,3-thiazol-2-yl]-4-[(3-(trifluoromethyl)phenyl)sulfonyl]-piperidine
1-[4-(3,4,5-trimethoxyphenyl)-1,3-thiazol-2-yl]-4-[(3-(trifluoromethyl)phenyl)sulfonyl]-piperidine
1-[4-(2,4,6-trimethylphenyl)-1,3-thiazol-2-yl]-4-[(3-(trifluoromethyl)phenyl)sulfonyl]-piperidine
1-[4-phenyl-1,3-thiazol-2-yl]-4-[(2-(trifluoromethyl)phenyl)sulfonyl]-piperidine
1-[4-(2-methylphenyl)-1,3-thiazol-2-yl]-4-[(2-(trifluoromethyl)phenyl)sulfonyl]-piperidine
1-[4-(2-methoxyphenyl)-1,3-thiazol-2-yl]-4-[(2-(trifluoromethyl)phenyl)sulfonyl]-piperidine
1-[4-(3-methylphenyl)-1,3-thiazol-2-yl]-4-[(2-(trifluoromethyl)phenyl)sulfonyl]-piperidine
1-[4-(3-methoxyphenyl)-1,3-thiazol-2-yl]-4-[(2-(trifluoromethyl)phenyl)sulfonyl]-piperidine
1-[4-(3-bromophenyl)-1,3-thiazol-2-yl]-4-[(2-(trifluoromethyl)phenyl)sulfonyl]-piperidine
1-[4-(4-chlorophenyl)-1,3-thiazol-2-yl]-4-[(2-(trifluoromethyl)phenyl)sulfonyl]-piperidine
1-[4-(4-methoxyphenyl)-1,3-thiazol-2-yl]-4-[(2-(trifluoromethyl)phenyl)sulfonyl]-piperidine
1-[4-(4-methylphenyl)-1,3-thiazol-2-yl]-4-[(2-(trifluoromethyl)phenyl)sulfonyl]-piperidine
1-[4-(4-ethylphenyl)-1,3-thiazol-2-yl]-4-[(2-(trifluoromethyl)phenyl)sulfonyl]-piperidine
1-[4-(4-ethoxyphenyl)-1,3-thiazol-2-yl]-4-[(2-(trifluoromethyl)phenyl)sulfonyl]-piperidine
1-[4-(4-propylphenyl)-1,3-thiazol-2-yl]-4-[(2-(trifluoromethyl)phenyl)sulfonyl]-piperidine
1-[4-(2,6-dimethylphenyl)-1,3-thiazol-2-yl]-4-[(2-(trifluoromethyl)phenyl)sulfonyl]-piperidine
1-[4-(2,3-dimethylphenyl)-1,3-thiazol-2-yl]-4-[(2-(trifluoromethyl)phenyl)sulfonyl]-piperidine
1-[4-(2,5-dimethylphenyl)-1,3-thiazol-2-yl]-4-[(2-(trifluoromethyl)phenyl)sulfonyl]-piperidine
1-[4-(2,4-dichlorophenyl)-1,3-thiazol-2-yl]-4-[(2-(trifluoromethyl)phenyl)sulfonyl]-piperidine
1-[4-(2,4-dimethoxyphenyl)-1,3-thiazol-2-yl]-4-[(2-(trifluoromethyl)phenyl)sulfonyl]-piperidine
1-[4-(2,5-dimethoxyphenyl)-1,3-thiazol-2-yl]-4-[(2-(trifluoromethyl)phenyl)sulfonyl]-piperidine
1-[4-(3,4-dimethoxyphenyl)-1,3-thiazol-2-yl]-4-[(2-(trifluoromethyl)phenyl)sulfonyl]-piperidine
1-[4-(3,5-dimethoxyphenyl)-1,3-thiazol-2-yl]-4-[(2-(trifluoromethyl)phenyl)sulfonyl]-piperidine
1-[4-(3,4-dichlorophenyl)-1,3-thiazol-2-yl]-4-[(2-(trifluoromethyl)phenyl)sulfonyl]-piperidine
1-[4-(3,4-dimethylphenyl)-1,3-thiazol-2-yl]-4-[(2-(trifluoromethyl)phenyl)sulfonyl]-piperidine
1-[4-(3,4-difluorophenyl)-1,3-thiazol-2-yl]-4-[(2-(trifluoromethyl)phenyl)sulfonyl]-piperidine
1-[4-(3,5-difluorophenyl)-1,3-thiazol-2-yl]-4-[(2-(trifluoromethyl)phenyl)sulfonyl]-piperidine
1-[4-(3,5-dichlorophenyl)-1,3-thiazol-2-yl]-4-[(2-(trifluoromethyl)phenyl)sulfonyl]-piperidine
1-[4-(3,5-dimethylphenyl)-1,3-thiazol-2-yl]-4-[(2-(trifluoromethyl)phenyl)sulfonyl]-piperidine
1-[4-(3-chloro-4-fluorophenyl)-1,3-thiazol-2-yl]-4-[(2-(trifluoromethyl)phenyl)sulfonyl]-piperidine
1-[4-(3-chloro-5-fluorophenyl)-1,3-thiazol-2-yl]-4-[(2-(trifluoromethyl)phenyl)sulfonyl]-piperidine
1-[4-(4-chloro-3-fluorophenyl)-1,3-thiazol-2-yl]-4-[(2-(trifluoromethyl)phenyl)sulfonyl]-piperidine
1-[4-(3,4,5-trimethoxyphenyl)-1,3-thiazol-2-yl]-4-[(2-(trifluoromethyl)phenyl)sulfonyl]-piperidine
1-[4-(2,4,6-trimethylphenyl)-1,3-thiazol-2-yl]-4-[(2-(trifluoromethyl)phenyl)sulfonyl]-piperidine
1-[4-phenyl-1,3-thiazol-2-yl]-4-[(4-nitrophenyl)sulfonyl]-piperidine
1-[4-(2-methylphenyl)-1,3-thiazol-2-yl]-4-[(4-nitrophenyl)sulfonyl]-piperidine
1-[4-(2-methoxyphenyl)-1,3-thiazol-2-yl]-4-[(4-nitrophenyl)sulfonyl]-piperidine 1-[4-(3-methylphenyl)-1,3-thiazol-2-yl]-4-[(4-nitrophenyl)sulfonyl]-piperidine
1-[4-(3-methoxyphenyl)-1,3-thiazol-2-yl]-4-[(4-nitrophenyl)sulfonyl]-piperidine
1-[4-(3-bromophenyl)-1,3-thiazol-2-yl]-4-[(4-nitrophenyl)sulfonyl]-piperidine
1-[4-(4-chlorophenyl)-1,3-thiazol-2-yl]-4-[(4-nitrophenyl)sulfonyl]-piperidine
1-[4-(4-methoxyphenyl)-1,3-thiazol-2-yl]-4-[(4-nitrophenyl)sulfonyl]-piperidine
1-[4-(4-methylphenyl)-1,3-thiazol-2-yl]-4-[(4-nitrophenyl)sulfonyl]-piperidine
1-[4-(4-ethylphenyl)-1,3-thiazol-2-yl]-4-[(4-nitrophenyl)sulfonyl]-piperidine
1-[4-(4-ethoxyphenyl)-1,3-thiazol-2-yl]-4-[(4-nitrophenyl)sulfonyl]-piperidine
1-[4-(4-propylphenyl)-1,3-thiazol-2-yl]-4-[(4-nitrophenyl)sulfonyl]-piperidine
1-[4-(2,6-dimethylphenyl)-1,3-thiazol-2-yl]-4-[(4-nitrophenyl)sulfonyl]-piperidine
1-[4-(2,3-dimethylphenyl)-1,3-thiazol-2-yl]-4-[(4-nitrophenyl)sulfonyl]-piperidine
1-[4-(2,5-dimethylphenyl)-1,3-thiazol-2-yl]-4-[(4-nitrophenyl)sulfonyl]-piperidine
1-[4-(2,4-dichlorophenyl)-1,3-thiazol-2-yl]-4-[(4-nitrophenyl)sulfonyl]-piperidine
1-[4-(2,4-dimethoxyphenyl)-1,3-thiazol-2-yl]-4-[(4-nitrophenyl)sulfonyl]-piperidine
1-[4-(2,5-dimethoxyphenyl)-1,3-thiazol-2-yl]-4-[(4-nitrophenyl)sulfonyl]-piperidine
1-[4-(3,4-dimethoxyphenyl)-1,3-thiazol-2-yl]-4-[(4-nitrophenyl)sulfonyl]-piperidine
1-[4-(3,5-dimethoxyphenyl)-1,3-thiazol-2-yl]-4-[(4-nitrophenyl)sulfonyl]-piperidine
1-[4-(3,4-dichlorophenyl)-1,3-thiazol-2-yl]-4-[(4-nitrophenyl)sulfonyl]-piperidine
1-[4-(3,4-dimethylphenyl)-1,3-thiazol-2-yl]-4-[(4-nitrophenyl)sulfonyl]-piperidine
1-[4-(3,4-difluorophenyl)-1,3-thiazol-2-yl]-4-[(4-nitrophenyl)sulfonyl]-piperidine
1-[4-(3,5-difluorophenyl)-1,3-thiazol-2-yl]-4-[(4-nitrophenyl)sulfonyl]-piperidine
1-[4-(3,5-dichlorophenyl)-1,3-thiazol-2-yl]-4-[(4-nitrophenyl)sulfonyl]-piperidine
1-[4-(3,5-dimethylphenyl)-1,3-thiazol-2-yl]-4-[(4-nitrophenyl)sulfonyl]-piperidine
1-[4-(3-chloro-4-fluorophenyl)-1,3-thiazol-2-yl]-4-[(4-nitrophenyl)sulfonyl]-piperidine
1-[4-(3-chloro-5-fluorophenyl)-1,3-thiazol-2-yl]-4-[(4-nitrophenyl)sulfonyl]-piperidine
1-[4-(4-chloro-3-fluorophenyl)-1,3-thiazol-2-yl]-4-[(4-nitrophenyl)sulfonyl]-piperidine
1-[4-(3,4,5-trimethoxyphenyl)-1,3-thiazol-2-yl]-4-[(4-nitrophenyl)sulfonyl]-piperidine
1-[4-(2,4,6-trimethylphenyl)-1,3-thiazol-2-yl]-4-[(4-nitrophenyl)sulfonyl]-piperidine
1-[4-phenyl-1,3-thiazol-2-yl]-4-[(2-bromophenyl)sulfonyl]-piperidine
1-[4-(2-methylphenyl)-1,3-thiazol-2-yl]-4-[(2-bromophenyl)sulfonyl]-piperidine
1-[4-(2-methoxyphenyl)-1,3-thiazol-2-yl]-4-[(2-bromophenyl)sulfonyl]-piperidine
1-[4-(3-methylphenyl)-1,3-thiazol-2-yl]-4-[(2-bromophenyl)sulfonyl]-piperidine
1-[4-(3-methoxyphenyl)-1,3-thiazol-2-yl]-4-[(2-bromophenyl)sulfonyl]-piperidine
1-[4-(3-bromophenyl)-1,3-thiazol-2-yl]-4-[(2-bromophenyl)sulfonyl]-piperidine
1-[4-(4-chlorophenyl)-1,3-thiazol-2-yl]-4-[(2-bromophenyl)sulfonyl]-piperidine
1-[4-(4-methoxyphenyl)-1,3-thiazol-2-yl]-4-[(2-bromophenyl)sulfonyl]-piperidine
1-[4-(4-methylphenyl)-1,3-thiazol-2-yl]-4-[(2-bromophenyl)sulfonyl]-piperidine
1-[4-(4-ethylphenyl)-1,3-thiazol-2-yl]-4-[(2-bromophenyl)sulfonyl]-piperidine
1-[4-(4-ethoxyphenyl)-1,3-thiazol-2-yl]-4-[(2-bromophenyl)sulfonyl]-piperidine
1-[4-(4-propylphenyl)-1,3-thiazol-2-yl]-4-[(2-bromophenyl)sulfonyl]-piperidine
1-[4-(2,6-dimethylphenyl)-1,3-thiazol-2-yl]-4-[(2-bromophenyl)sulfonyl]-piperidine
1-[4-(2,3-dimethylphenyl)-1,3-thiazol-2-yl]-4-[(2-bromophenyl)sulfonyl]-piperidine
1-[4-(2,5-dimethylphenyl)-1,3-thiazol-2-yl]-4-[(2-bromophenyl)sulfonyl]-piperidine
1-[4-(2,4-dichlorophenyl)-1,3-thiazol-2-yl]-4-[(2-bromophenyl)sulfonyl]-piperidine
1-[4-(2,4-dimethoxyphenyl)-1,3-thiazol-2-yl]-4-[(2-bromophenyl)sulfonyl]-piperidine
1-[4-(2,5-dimethoxyphenyl)-1,3-thiazol-2-yl]-4-[(2-bromophenyl)sulfonyl]-piperidine
1-[4-(3,4-dimethoxyphenyl)-1,3-thiazol-2-yl]-4-[(2-bromophenyl)sulfonyl]-piperidine
1-[4-(3,5-dimethoxyphenyl)-1,3-thiazol-2-yl]-4-[(2-bromophenyl)sulfonyl]-piperidine
1-[4-(3,4-dichlorophenyl)-1,3-thiazol-2-yl]-4-[(2-bromophenyl)sulfonyl]-piperidine
1-[4-(3,4-dimethylphenyl)-1,3-thiazol-2-yl]-4-[(2-bromophenyl)sulfonyl]-piperidine
1-[4-(3,4-difluorophenyl)-1,3-thiazol-2-yl]-4-[(2-bromophenyl)sulfonyl]-piperidine
1-[4-(3,5-difluorophenyl)-1,3-thiazol-2-yl]-4-[(2-bromophenyl)sulfonyl]-piperidine
1-[4-(3,5-dichlorophenyl)-1,3-thiazol-2-yl]-4-[(2-bromophenyl)sulfonyl]-piperidine
1-[4-(3,5-dimethylphenyl)-1,3-thiazol-2-yl]-4-[(2-bromophenyl)sulfonyl]-piperidine
1-[4-(3-chloro-4-fluorophenyl)-1,3-thiazol-2-yl]-4-[(2-bromophenyl)sulfonyl]-piperidine
1-[4-(3-chloro-5-fluorophenyl)-1,3-thiazol-2-yl]-4-[(2-bromophenyl)sulfonyl]-piperidine
1-[4-(4-chloro-3-fluorophenyl)-1,3-thiazol-2-yl]-4-[(2-bromophenyl)sulfonyl]-piperidine
1-[4-(3,4,5-trimethoxyphenyl)-1,3-thiazol-2-yl]-4-[(2-bromophenyl)sulfonyl]-piperidine
1-[4-(2,4,6-trimethylphenyl)-1,3-thiazol-2-yl]-4-[(2-bromophenyl)sulfonyl]-piperidine
1-[4-phenyl-1,3-thiazol-2-yl]-4-[(2-chlorophenyl)sulfonyl]-piperidine
1-[4-(2-methylphenyl)-1,3-thiazol-2-yl]-4-[(2-chlorophenyl)sulfonyl]-piperidine
1-[4-(2-methoxyphenyl)-1,3-thiazol-2-yl]-4-[(2-chlorophenyl)sulfonyl]-piperidine
1-[4-(3-methylphenyl)-1,3-thiazol-2-yl]-4-[(2-chlorophenyl)sulfonyl]-piperidine
1-[4-(3-methoxyphenyl)-1,3-thiazol-2-yl]-4-[(2-chlorophenyl)sulfonyl]-piperidine
1-[4-(3-bromophenyl)-1,3-thiazol-2-yl]-4-[(2-chlorophenyl)sulfonyl]-piperidine
1-[4-(4-chlorophenyl)-1,3-thiazol-2-yl]-4-[(2-chlorophenyl)sulfonyl]-piperidine 1-[4-(4-methoxyphenyl)-1,3-thiazol-2-yl]-4-[(2-chlorophenyl)sulfonyl]-piperidine
1-[4-(4-methylphenyl)-1,3-thiazol-2-yl]-4-[(2-chlorophenyl)sulfonyl]-piperidine
1-[4-(4-ethylphenyl)-1,3-thiazol-2-yl]-4-[(2-chlorophenyl)sulfonyl]-piperidine
1-[4-(4-ethoxyphenyl)-1,3-thiazol-2-yl]-4-[(2-chlorophenyl)sulfonyl]-piperidine
1-[4-(4-propylphenyl)-1,3-thiazol-2-yl]-4-[(2-chlorophenyl)sulfonyl]-piperidine
1-[4-(2,6-dimethylphenyl)-1,3-thiazol-2-yl]-4-[(2-chlorophenyl)sulfonyl]-piperidine
1-[4-(2,3-dimethylphenyl)-1,3-thiazol-2-yl]-4-[(2-chlorophenyl)sulfonyl]-piperidine
1-[4-(2,5-dimethylphenyl)-1,3-thiazol-2-yl]-4-[(2-chlorophenyl)sulfonyl]-piperidine
1-[4-(2,4-dichlorophenyl)-1,3-thiazol-2-yl]-4-[(2-chlorophenyl)sulfonyl]-piperidine
1-[4-(2,4-dimethoxyphenyl)-1,3-thiazol-2-yl]-4-[(2-chlorophenyl)sulfonyl]-piperidine
1-[4-(2,5-dimethoxyphenyl)-1,3-thiazol-2-yl]-4-[(2-chlorophenyl)sulfonyl]-piperidine
1-[4-(3,4-dimethoxyphenyl)-1,3-thiazol-2-yl]-4-[(2-chlorophenyl)sulfonyl]-piperidine
1-[4-(3,5-dimethoxyphenyl)-1,3-thiazol-2-yl]-4-[(2-chlorophenyl)sulfonyl]-piperidine
1-[4-(3,4-dichlorophenyl)-1,3-thiazol-2-yl]-4-[(2-chlorophenyl)sulfonyl]-piperidine
1-[4-(3,4-dimethylphenyl)-1,3-thiazol-2-yl]-4-[(2-chlorophenyl)sulfonyl]-piperidine
1-[4-(3,4-difluorophenyl)-1,3-thiazol-2-yl]-4-[(2-chlorophenyl)sulfonyl]-piperidine
1-[4-(3,5-difluorophenyl)-1,3-thiazol-2-yl]-4-[(2-chlorophenyl)sulfonyl]-piperidine
1-[4-(3,5-dichlorophenyl)-1,3-thiazol-2-yl]-4-[(2-chlorophenyl)sulfonyl]-piperidine
1-[4-(3,5-dimethylphenyl)-1,3-thiazol-2-yl]-4-[(2-chlorophenyl)sulfonyl]-piperidine
1-[4-(3-chloro-4-fluorophenyl)-1,3-thiazol-2-yl]-4-[(2-chlorophenyl)sulfonyl]-piperidine
1-[4-(3-chloro-5-fluorophenyl)-1,3-thiazol-2-yl]-4-[(2-chlorophenyl)sulfonyl]-piperidine
1-[4-(4-chloro-3-fluorophenyl)-1,3-thiazol-2-yl]-4-[(2-chlorophenyl)sulfonyl]-piperidine
1-[4-(3,4,5-trimethoxyphenyl)-1,3-thiazol-2-yl]-4-[(2-chlorophenyl)sulfonyl]-piperidine
1-[4-(2,4,6-trimethylphenyl)-1,3-thiazol-2-yl]-4-[(2-chlorophenyl)sulfonyl]-piperidine
1-[4-phenyl-1,3-thiazol-2-yl]-4-[(2-cyanophenyl)sulfonyl]-piperidine
1-[4-(2-methylphenyl)-1,3-thiazol-2-yl]-4-[(2-cyanophenyl)sulfonyl]-piperidine
1-[4-(2-methoxyphenyl)-1,3-thiazol-2-yl]-4-[(2-cyanophenyl)sulfonyl]-piperidine
1-[4-(3-methylphenyl)-1,3-thiazol-2-yl]-4-[(2-cyanophenyl)sulfonyl]-piperidine
1-[4-(3-methoxyphenyl)-1,3-thiazol-2-yl]-4-[(2-cyanophenyl)sulfonyl]-piperidine
1-[4-(3-bromophenyl)-1,3-thiazol-2-yl]-4-[(2-cyanophenyl)sulfonyl]-piperidine
1-[4-(4-chlorophenyl)-1,3-thiazol-2-yl]-4-[(2-cyanophenyl)sulfonyl]-piperidine
1-[4-(4-methoxyphenyl)-1,3-thiazol-2-yl]-4-[(2-cyanophenyl)sulfonyl]-piperidine
1-[4-(4-methylphenyl)-1,3-thiazol-2-yl]-4-[(2-cyanophenyl)sulfonyl]-piperidine
1-[4-(4-ethylphenyl)-1,3-thiazol-2-yl]-4-[(2-cyanophenyl)sulfonyl]-piperidine
1-[4-(4-ethoxyphenyl)-1,3-thiazol-2-yl]-4-[(2-cyanophenyl)sulfonyl]-piperidine
1-[4-(4-propylphenyl)-1,3-thiazol-2-yl]-4-[(2-cyanophenyl)sulfonyl]-piperidine
1-[4-(2,6-dimethylphenyl)-1,3-thiazol-2-yl]-4-[(2-cyanophenyl)sulfonyl]-piperidine
1-[4-(2,3-dimethylphenyl)-1,3-thiazol-2-yl]-4-[(2-cyanophenyl)sulfonyl]-piperidine
1-[4-(2,5-dimethylphenyl)-1,3-thiazol-2-yl]-4-[(2-cyanophenyl)sulfonyl]-piperidine
1-[4-(2,4-dichlorophenyl)-1,3-thiazol-2-yl]-4-[(2-cyanophenyl)sulfonyl]-piperidine
1-[4-(2,4-dimethoxyphenyl)-1,3-thiazol-2-yl]-4-[(2-cyanophenyl)sulfonyl]-piperidine
1-[4-(2,5-dimethoxyphenyl)-1,3-thiazol-2-yl]-4-[(2-cyanophenyl)sulfonyl]-piperidine
1-[4-(3,4-dimethoxyphenyl)-1,3-thiazol-2-yl]-4-[(2-cyanophenyl)sulfonyl]-piperidine
1-[4-(3,5-dimethoxyphenyl)-1,3-thiazol-2-yl]-4-[(2-cyanophenyl)sulfonyl]-piperidine
1-[4-(3,4-dichlorophenyl)-1,3-thiazol-2-yl]-4-[(2-cyanophenyl)sulfonyl]-piperidine
1-[4-(3,4-dimethylphenyl)-1,3-thiazol-2-yl]-4-[(2-cyanophenyl)sulfonyl]-piperidine
1-[4-(3,4-difluorophenyl)-1,3-thiazol-2-yl]-4-[(2-cyanophenyl)sulfonyl]-piperidine
1-[4-(3,5-difluorophenyl)-1,3-thiazol-2-yl]-4-[(2-cyanophenyl)sulfonyl]-piperidine
1-[4-(3,5-dichlorophenyl)-1,3-thiazol-2-yl]-4-[(2-cyanophenyl)sulfonyl]-piperidine
1-[4-(3,5-dimethylphenyl)-1,3-thiazol-2-yl]-4-[(2-cyanophenyl)sulfonyl]-piperidine
1-[4-(3-chloro-4-fluorophenyl)-1,3-thiazol-2-yl]-4-[(2-cyanophenyl)sulfonyl]-piperidine
1-[4-(3-chloro-5-fluorophenyl)-1,3-thiazol-2-yl]-4-[(2-cyanophenyl)sulfonyl]-piperidine
1-[4-(4-chloro-3-fluorophenyl)-1,3-thiazol-2-yl]-4-[(2-cyanophenyl)sulfonyl]-piperidine
1-[4-(3,4,5-trimethoxyphenyl)-1,3-thiazol-2-yl]-4-[(2-cyanophenyl)sulfonyl]-piperidine
1-[4-(2,4,6-trimethylphenyl)-1,3-thiazol-2-yl]-4-[(2-cyanophenyl)sulfonyl]-piperidine
1-[4-phenyl-1,3-thiazol-2-yl]-4-[(3-nitrophenyl)sulfonyl]-piperidine
1-[4-(2-methylphenyl)-1,3-thiazol-2-yl]-4-[(3-nitrophenyl)sulfonyl]-piperidine
1-[4-(2-methoxyphenyl)-1,3-thiazol-2-yl]-4-[(3-nitrophenyl)sulfonyl]-piperidine
1-[4-(3-methylphenyl)-1,3-thiazol-2-yl]-4-[(3-nitrophenyl)sulfonyl]-piperidine
1-[4-(3-methoxyphenyl)-1,3-thiazol-2-yl]-4-[(3-nitrophenyl)sulfonyl]-piperidine
1-[4-(3-bromophenyl)-1,3-thiazol-2-yl]-4-[(3-nitrophenyl)sulfonyl]-piperidine
1-[4-(4-chlorophenyl)-1,3-thiazol-2-yl]-4-[(3-nitrophenyl)sulfonyl]-piperidine
1-[4-(4-methoxyphenyl)-1,3-thiazol-2-yl]-4-[(3-nitrophenyl)sulfonyl]-piperidine
1-[4-(4-methylphenyl)-1,3-thiazol-2-yl]-4-[(3-nitrophenyl)sulfonyl]-piperidine
1-[4-(4-ethylphenyl)-1,3-thiazol-2-yl]-4-[(3-nitrophenyl)sulfonyl]-piperidine
1-[4-(4-ethoxyphenyl)-1,3-thiazol-2-yl]-4-[(3-nitrophenyl)sulfonyl]-piperidine 1-[4-(4-propylphenyl)-1,3-thiazol-2-yl]-4-[(3-nitrophenyl)sulfonyl]-piperidine
1-[4-(2,6-dimethylphenyl)-1,3-thiazol-2-yl]-4-[(3-nitrophenyl)sulfonyl]-piperidine
1-[4-(2,3-dimethylphenyl)-1,3-thiazol-2-yl]-4-[(3-nitrophenyl)sulfonyl]-piperidine
1-[4-(2,5-dimethylphenyl)-1,3-thiazol-2-yl]-4-[(3-nitrophenyl)sulfonyl]-piperidine
1-[4-(2,4-dichlorophenyl)-1,3-thiazol-2-yl]-4-[(3-nitrophenyl)sulfonyl]-piperidine
1-[4-(2,4-dimethoxyphenyl)-1,3-thiazol-2-yl]-4-[(3-nitrophenyl)sulfonyl]-piperidine
1-[4-(2,5-dimethoxyphenyl)-1,3-thiazol-2-yl]-4-[(3-nitrophenyl)sulfonyl]-piperidine
1-[4-(3,4-dimethoxyphenyl)-1,3-thiazol-2-yl]-4-[(3-nitrophenyl)sulfonyl]-piperidine
1-[4-(3,5-dimethoxyphenyl)-1,3-thiazol-2-yl]-4-[(3-nitrophenyl)sulfonyl]-piperidine
1-[4-(3,4-dichlorophenyl)-1,3-thiazol-2-yl]-4-[(3-nitrophenyl)sulfonyl]-piperidine
1-[4-(3,4-dimethylphenyl)-1,3-thiazol-2-yl]-4-[(3-nitrophenyl)sulfonyl]-piperidine
1-[4-(3,4-difluorophenyl)-1,3-thiazol-2-yl]-4-[(3-nitrophenyl)sulfonyl]-piperidine
1-[4-(3,5-difluorophenyl)-1,3-thiazol-2-yl]-4-[(3-nitrophenyl)sulfonyl]-piperidine
1-[4-(3,5-dichlorophenyl)-1,3-thiazol-2-yl]-4-[(3-nitrophenyl)sulfonyl]-piperidine
1-[4-(3,5-dimethylphenyl)-1,3-thiazol-2-yl]-4-[(3-nitrophenyl)sulfonyl]-piperidine
1-[4-(3-chloro-4-fluorophenyl)-1,3-thiazol-2-yl]-4-[(3-nitrophenyl)sulfonyl]-piperidine
1-[4-(3-chloro-5-fluorophenyl)-1,3-thiazol-2-yl]-4-[(3-nitrophenyl)sulfonyl]-piperidine
1-[4-(4-chloro-3-fluorophenyl)-1,3-thiazol-2-yl]-4-[(3-nitrophenyl)sulfonyl]-piperidine
1-[4-(3,4,5-trimethoxyphenyl)-1,3-thiazol-2-yl]-4-[(3-nitrophenyl)sulfonyl]-piperidine
1-[4-(2,4,6-trimethylphenyl)-1,3-thiazol-2-yl]-4-[(3-nitrophenyl)sulfonyl]-piperidine
1-[4-phenyl-1,3-thiazol-2-yl]-4-[(3-chlorophenyl)sulfonyl]-piperidine
1-[4-(2-methylphenyl)-1,3-thiazol-2-yl]-4-[(3-chlorophenyl)sulfonyl]-piperidine
1-[4-(2-methoxyphenyl)-1,3-thiazol-2-yl]-4-[(3-chlorophenyl)sulfonyl]-piperidine
1-[4-(3-methylphenyl)-1,3-thiazol-2-yl]-4-[(3-chlorophenyl)sulfonyl]-piperidine
1-[4-(3-methoxyphenyl)-1,3-thiazol-2-yl]-4-[(3-chlorophenyl)sulfonyl]-piperidine
1-[4-(3-bromophenyl)-1,3-thiazol-2-yl]-4-[(3-chlorophenyl)sulfonyl]-piperidine
1-[4-(4-chlorophenyl)-1,3-thiazol-2-yl]-4-[(3-chlorophenyl)sulfonyl]-piperidine
1-[4-(4-methoxyphenyl)-1,3-thiazol-2-yl]-4-[(3-chlorophenyl)sulfonyl]-piperidine
1-[4-(4-methylphenyl)-1,3-thiazol-2-yl]-4-[(3-chlorophenyl)sulfonyl]-piperidine
1-[4-(4-ethylphenyl)-1,3-thiazol-2-yl]-4-[(3-chlorophenyl)sulfonyl]-piperidine
1-[4-(4-ethoxyphenyl)-1,3-thiazol-2-yl]-4-[(3-chlorophenyl)sulfonyl]-piperidine
1-[4-(4-propylphenyl)-1,3-thiazol-2-yl]-4-[(3-chlorophenyl)sulfonyl]-piperidine
1-[4-(2,6-dimethylphenyl)-1,3-thiazol-2-yl]-4-[(3-chlorophenyl)sulfonyl]-piperidine
1-[4-(2,3-dimethylphenyl)-1,3-thiazol-2-yl]-4-[(3-chlorophenyl)sulfonyl]-piperidine
1-[4-(2,5-dimethylphenyl)-1,3-thiazol-2-yl]-4-[(3-chlorophenyl)sulfonyl]-piperidine
1-[4-(2,4-dichlorophenyl)-1,3-thiazol-2-yl]-4-[(3-chlorophenyl)sulfonyl]-piperidine
1-[4-(2,4-dimethoxyphenyl)-1,3-thiazol-2-yl]-4-[(3-chlorophenyl)sulfonyl]-piperidine
1-[4-(2,5-dimethoxyphenyl)-1,3-thiazol-2-yl]-4-[(3-chlorophenyl)sulfonyl]-piperidine
1-[4-(3,4-dimethoxyphenyl)-1,3-thiazol-2-yl]-4-[(3-chlorophenyl)sulfonyl]-piperidine
1-[4-(3,5-dimethoxyphenyl)-1,3-thiazol-2-yl]-4-[(3-chlorophenyl)sulfonyl]-piperidine
1-[4-(3,4-dichlorophenyl)-1,3-thiazol-2-yl]-4-[(3-chlorophenyl)sulfonyl]-piperidine
1-[4-(3,4-dimethylphenyl)-1,3-thiazol-2-yl]-4-[(3-chlorophenyl)sulfonyl]-piperidine
1-[4-(3,4-difluorophenyl)-1,3-thiazol-2-yl]-4-[(3-chlorophenyl)sulfonyl]-piperidine
1-[4-(3,5-difluorophenyl)-1,3-thiazol-2-yl]-4-[(3-chlorophenyl)sulfonyl]-piperidine
1-[4-(3,5-dichlorophenyl)-1,3-thiazol-2-yl]-4-[(3-chlorophenyl)sulfonyl]-piperidine
1-[4-(3,5-dimethylphenyl)-1,3-thiazol-2-yl]-4-[(3-chlorophenyl)sulfonyl]-piperidine
1-[4-(3-chloro-4-fluorophenyl)-1,3-thiazol-2-yl]-4-[(3-chlorophenyl)sulfonyl]-piperidine
1-[4-(3-chloro-5-fluorophenyl)-1,3-thiazol-2-yl]-4-[(3-chlorophenyl)sulfonyl]-piperidine
1-[4-(4-chloro-3-fluorophenyl)-1,3-thiazol-2-yl]-4-[(3-chlorophenyl)sulfonyl]-piperidine
1-[4-(3,4,5-trimethoxyphenyl)-1,3-thiazol-2-yl]-4-[(3-chlorophenyl)sulfonyl]-piperidine
1-[4-(2,4,6-trimethylphenyl)-1,3-thiazol-2-yl]-4-[(3-chlorophenyl)sulfonyl]-piperidine
1-[4-phenyl-1,3-thiazol-2-yl]-4-[(3-bromophenyl)sulfonyl]-piperidine
1-[4-(2-methylphenyl)-1,3-thiazol-2-yl]-4-[(3-bromophenyl)sulfonyl]-piperidine
1-[4-(2-methoxyphenyl)-1,3-thiazol-2-yl]-4-[(3-bromophenyl)sulfonyl]-piperidine
1-[4-(3-methylphenyl)-1,3-thiazol-2-yl]-4-[(3-bromophenyl)sulfonyl]-piperidine
1-[4-(3-methoxyphenyl)-1,3-thiazol-2-yl]-4-[(3-bromophenyl)sulfonyl]-piperidine
1-[4-(3-bromophenyl)-1,3-thiazol-2-yl]-4-[(3-bromophenyl)sulfonyl]-piperidine
1-[4-(4-chlorophenyl)-1,3-thiazol-2-yl]-4-[(3-bromophenyl)sulfonyl]-piperidine
1-[4-(4-methoxyphenyl)-1,3-thiazol-2-yl]-4-[(3-bromophenyl)sulfonyl]-piperidine
1-[4-(4-methylphenyl)-1,3-thiazol-2-yl]-4-[(3-bromophenyl)sulfonyl]-piperidine
1-[4-(4-ethylphenyl)-1,3-thiazol-2-yl]-4-[(3-bromophenyl)sulfonyl]-piperidine
1-[4-(4-ethoxyphenyl)-1,3-thiazol-2-yl]-4-[(3-bromophenyl)sulfonyl]-piperidine
1-[4-(4-propylphenyl)-1,3-thiazol-2-yl]-4-[(3-bromophenyl)sulfonyl]-piperidine
1-[4-(2,6-dimethylphenyl)-1,3-thiazol-2-yl]-4-[(3-bromophenyl)sulfonyl]-piperidine
1-[4-(2,3-dimethylphenyl)-1,3-thiazol-2-yl]-4-[(3-bromophenyl)sulfonyl]-piperidine
1-[4-(2,5-dimethylphenyl)-1,3-thiazol-2-yl]-4-[(3-bromophenyl)sulfonyl]-piperidine 1-[4-(2,4-dichlorophenyl)-1,3-thiazol-2-yl]-4-[(3-bromophenyl)sulfonyl]-piperidine
1-[4-(2,4-dimethoxyphenyl)-1,3-thiazol-2-yl]-4-[(3-bromophenyl)sulfonyl]-piperidine
1-[4-(2,5-dimethoxyphenyl)-1,3-thiazol-2-yl]-4-[(3-bromophenyl)sulfonyl]-piperidine
1-[4-(3,4-dimethoxyphenyl)-1,3-thiazol-2-yl]-4-[(3-bromophenyl)sulfonyl]-piperidine
1-[4-(3,5-dimethoxyphenyl)-1,3-thiazol-2-yl]-4-[(3-bromophenyl)sulfonyl]-piperidine
1-[4-(3,4-dichlorophenyl)-1,3-thiazol-2-yl]-4-[(3-bromophenyl)sulfonyl]-piperidine
1-[4-(3,4-dimethylphenyl)-1,3-thiazol-2-yl]-4-[(3-bromophenyl)sulfonyl]-piperidine
1-[4-(3,4-difluorophenyl)-1,3-thiazol-2-yl]-4-[(3-bromophenyl)sulfonyl]-piperidine
1-[4-(3,5-difluorophenyl)-1,3-thiazol-2-yl]-4-[(3-bromophenyl)sulfonyl]-piperidine
1-[4-(3,5-dichlorophenyl)-1,3-thiazol-2-yl]-4-[(3-bromophenyl)sulfonyl]-piperidine
1-[4-(3,5-dimethylphenyl)-1,3-thiazol-2-yl]-4-[(3-bromophenyl)sulfonyl]-piperidine
1-[4-(3-chloro-4-fluorophenyl)-1,3-thiazol-2-yl]-4-[(3-bromophenyl)sulfonyl]-piperidine
1-[4-(3-chloro-5-fluorophenyl)-1,3-thiazol-2-yl]-4-[(3-bromophenyl)sulfonyl]-piperidine
1-[4-(4-chloro-3-fluorophenyl)-1,3-thiazol-2-yl]-4-[(3-bromophenyl)sulfonyl]-piperidine
1-[4-(3,4,5-trimethoxyphenyl)-1,3-thiazol-2-yl]-4-[(3-bromophenyl)sulfonyl]-piperidine
1-[4-(2,4,6-trimethylphenyl)-1,3-thiazol-2-yl]-4-[(3-bromophenyl)sulfonyl]-piperidine
1-[4-phenyl-1,3-thiazol-2-yl]-4-[(3-fluorophenyl)sulfonyl]-piperidine
1-[4-(2-methylphenyl)-1,3-thiazol-2-yl]-4-[(3-fluorophenyl)sulfonyl]-piperidine
1-[4-(2-methoxyphenyl)-1,3-thiazol-2-yl]-4-[(3-fluorophenyl)sulfonyl]-piperidine
1-[4-(3-methylphenyl)-1,3-thiazol-2-yl]-4-[(3-fluorophenyl)sulfonyl]-piperidine
1-[4-(3-methoxyphenyl)-1,3-thiazol-2-yl]-4-[(3-fluorophenyl)sulfonyl]-piperidine
1-[4-(3-bromophenyl)-1,3-thiazol-2-yl]-4-[(3-fluorophenyl)sulfonyl]-piperidine
1-[4-(4-chlorophenyl)-1,3-thiazol-2-yl]-4-[(3-fluorophenyl)sulfonyl]-piperidine
1-[4-(4-methoxyphenyl)-1,3-thiazol-2-yl]-4-[(3-fluorophenyl)sulfonyl]-piperidine
1-[4-(4-methylphenyl)-1,3-thiazol-2-yl]-4-[(3-fluorophenyl)sulfonyl]-piperidine
1-[4-(4-ethylphenyl)-1,3-thiazol-2-yl]-4-[(3-fluorophenyl)sulfonyl]-piperidine
1-[4-(4-ethoxyphenyl)-1,3-thiazol-2-yl]-4-[(3-fluorophenyl)sulfonyl]-piperidine
1-[4-(4-propylphenyl)-1,3-thiazol-2-yl]-4-[(3-fluorophenyl)sulfonyl]-piperidine
1-[4-(2,6-dimethylphenyl)-1,3-thiazol-2-yl]-4-[(3-fluorophenyl)sulfonyl]-piperidine
1-[4-(2,3-dimethylphenyl)-1,3-thiazol-2-yl]-4-[(3-fluorophenyl)sulfonyl]-piperidine
1-[4-(2,5-dimethylphenyl)-1,3-thiazol-2-yl]-4-[(3-fluorophenyl)sulfonyl]-piperidine
1-[4-(2,4-dichlorophenyl)-1,3-thiazol-2-yl]-4-[(3-fluorophenyl)sulfonyl]-piperidine
1-[4-(2,4-dimethoxyphenyl)-1,3-thiazol-2-yl]-4-[(3-fluorophenyl)sulfonyl]-piperidine
1-[4-(2,5-dimethoxyphenyl)-1,3-thiazol-2-yl]-4-[(3-fluorophenyl)sulfonyl]-piperidine
1-[4-(3,4-dimethoxyphenyl)-1,3-thiazol-2-yl]-4-[(3-fluorophenyl)sulfonyl]-piperidine
1-[4-(3,5-dimethoxyphenyl)-1,3-thiazol-2-yl]-4-[(3-fluorophenyl)sulfonyl]-piperidine
1-[4-(3,4-dichlorophenyl)-1,3-thiazol-2-yl]-4-[(3-fluorophenyl)sulfonyl]-piperidine
1-[4-(3,4-dimethylphenyl)-1,3-thiazol-2-yl]-4-[(3-fluorophenyl)sulfonyl]-piperidine
1-[4-(3,4-difluorophenyl)-1,3-thiazol-2-yl]-4-[(3-fluorophenyl)sulfonyl]-piperidine
1-[4-(3,5-difluorophenyl)-1,3-thiazol-2-yl]-4-[(3-fluorophenyl)sulfonyl]-piperidine
1-[4-(3,5-dichlorophenyl)-1,3-thiazol-2-yl]-4-[(3-fluorophenyl)sulfonyl]-piperidine
1-[4-(3,5-dimethylphenyl)-1,3-thiazol-2-yl]-4-[(3-fluorophenyl)sulfonyl]-piperidine
1-[4-(3-chloro-4-fluorophenyl)-1,3-thiazol-2-yl]-4-[(3-fluorophenyl)sulfonyl]-piperidine
1-[4-(3-chloro-5-fluorophenyl)-1,3-thiazol-2-yl]-4-[(3-fluorophenyl)sulfonyl]-piperidine
1-[4-(4-chloro-3-fluorophenyl)-1,3-thiazol-2-yl]-4-[(3-fluorophenyl)sulfonyl]-piperidine
1-[4-(3,4,5-trimethoxyphenyl)-1,3-thiazol-2-yl]-4-[(3-fluorophenyl)sulfonyl]-piperidine
1-[4-(2,4,6-trimethylphenyl)-1,3-thiazol-2-yl]-4-[(3-fluorophenyl)sulfonyl]-piperidine
1-[4-phenyl-1,3-thiazol-2-yl]-4-[(3-chloro-4-fluorophenyl)sulfonyl]-piperidine
1-[4-(2-methylphenyl)-1,3-thiazol-2-yl]-4-[(3-chloro-4-fluorophenyl)sulfonyl]-piperidine
1-[4-(2-methoxyphenyl)-1,3-thiazol-2-yl]-4-[(3-chloro-4-fluorophenyl)sulfonyl]-piperidine
1-[4-(3-methylphenyl)-1,3-thiazol-2-yl]-4-[(3-chloro-4-fluorophenyl)sulfonyl]-piperidine
1-[4-(3-methoxyphenyl)-1,3-thiazol-2-yl]-4-[(3-chloro-4-fluorophenyl)sulfonyl]-piperidine
1-[4-bromophenyl)-1,3-thiazol-2-yl]-4-[(3-chloro-4-fluorophenyl)sulfonyl]-piperidine
1-[3-chlorophenyl)-1,3-thiazol-2-yl]-4-[(3-chloro-4-fluorophenyl)sulfonyl]-piperidine
1-[4-(4-methoxyphenyl)-1,3-thiazol-2-yl]-4-[(3-chloro-4-fluorophenyl)sulfonyl]-piperidine
1-[4-(4-methylphenyl)-1,3-thiazol-2-yl]-4-[(3-chloro-4-fluorophenyl)sulfonyl]-piperidine
1-[4-(4-ethylphenyl)-1,3-thiazol-2-yl]-4-[(3-chloro-4-fluorophenyl)sulfonyl]-piperidine
1-[4-(4-ethoxyphenyl)-1,3-thiazol-2-yl]-4-[(3-chloro-4-fluorophenyl)sulfonyl]-piperidine
1-[4-(4-propylphenyl)-1,3-thiazol-2-yl]-4-[(3-chloro-4-fluorophenyl)sulfonyl]-piperidine
1-[4-(2,6-dimethylphenyl)-1,3-thiazol-2-yl]-4-[(3-chloro-4-fluorophenyl)sulfonyl]-piperidine
1-[4-(2,3-dimethylphenyl)-1,3-thiazol-2-yl]-4-[(3-chloro-4-fluorophenyl)sulfonyl]-piperidine
1-[4-(2,5-dimethylphenyl)-1,3-thiazol-2-yl]-4-[(3-chloro-4-fluorophenyl)sulfonyl]-piperidine
1-[4-(2,4-dichlorophenyl)-1,3-thiazol-2-yl]-4-[(3-chloro-4-fluorophenyl)sulfonyl]-piperidine
1-[4-(2,4-dimethoxyphenyl)-1,3-thiazol-2-yl]-4-[(3-chloro-4-fluorophenyl)sulfonyl]-piperidine
1-[4-(2,5-dimethoxyphenyl)-1,3-thiazol-2-yl]-4-[(3-chloro-4-fluorophenyl)sulfonyl]-piperidine
1-[4-(3,4-dimethoxyphenyl)-1,3-thiazol-2-yl]-4-[(3-chloro-4-fluorophenyl)sulfonyl]-piperidine 1-[4-(3,5-dimethoxyphenyl)-1,3-thiazol-2-yl]-4-[(3-chloro-4-fluorophenyl)sulfonyl]-piperidine
1-[4-(3,4-dichlorophenyl)-1,3-thiazol-2-yl]-4-[(3-chloro-4-fluorophenyl)sulfonyl]-piperidine
1-[4-(3,4-dimethylphenyl)-1,3-thiazol-2-yl]-4-[(3-chloro-4-fluorophenyl)sulfonyl]-piperidine
1-[4-(3,4-difluorophenyl)-1,3-thiazol-2-yl]-4-[(3-chloro-4-fluorophenyl)sulfonyl]-piperidine
1-[4-(3,5-difluorophenyl)-1,3-thiazol-2-yl]-4-[(3-chloro-4-fluorophenyl)sulfonyl]-piperidine
1-[4-(3,5-dichlorophenyl)-1,3-thiazol-2-yl]-4-[(3-chloro-4-fluorophenyl)sulfonyl]-piperidine
1-[4-(3,5-dimethylphenyl)-1,3-thiazol-2-yl]-4-[(3-chloro-4-fluorophenyl)sulfonyl]-piperidine
1-[4-(3-chloro-4-fluorophenyl)-1,3-thiazol-2-yl]-4-[(3-chloro-4-fluorophenyl)sulfonyl]-piperidine
1-[4-(3-chloro-5-fluorophenyl)-1,3-thiazol-2-yl]-4-[(3-chloro-4-fluorophenyl)sulfonyl]-piperidine
1-[4-(4-chloro-3-fluorophenyl)-1,3-thiazol-2-yl]-4-[(3-chloro-4-fluorophenyl)sulfonyl]-piperidine
1-[4-(3,4,5-trimethoxyphenyl)-1,3-thiazol-2-yl]-4-[(3-chloro-4-fluorophenyl)sulfonyl]-piperidine
1-[4-(2,4,6-trimethylphenyl)-1,3-thiazol-2-yl]-4-[(3-chloro-4-fluorophenyl)sulfonyl]-piperidine
1-[4-phenyl-1,3-thiazol-2-yl]-4-[(2-chloro-4-fluorophenyl)sulfonyl]-piperidine
1-[4-(2-methylphenyl)-1,3-thiazol-2-yl]-4-[(2-chloro-4-fluorophenyl)sulfonyl]-piperidine
1-[4-(2-methoxyphenyl)-1,3-thiazol-2-yl]-4-[(2-chloro-4-fluorophenyl)sulfonyl]-piperidine
1-[4-(3-methylphenyl)-1,3-thiazol-2-yl]-4-[(2-chloro-4-fluorophenyl)sulfonyl]-piperidine
1-[4-(3-methoxyphenyl)-1,3-thiazol-2-yl]-4-[(2-chloro-4-fluorophenyl)sulfonyl]-piperidine
1-[4-(3-bromophenyl)-1,3-thiazol-2-yl]-4-[(2-chloro-4-fluorophenyl)sulfonyl]-piperidine
1-[4-(4-chlorophenyl)-1,3-thiazol-2-yl]-4-[(2-chloro-4-fluorophenyl)sulfonyl]-piperidine
1-[4-(4-methoxyphenyl)-1,3-thiazol-2-yl]-4-[(2-chloro-4-fluorophenyl)sulfonyl]-piperidine
1-[4-(4-methylphenyl)-1,3-thiazol-2-yl]-4-[(2-chloro-4-fluorophenyl)sulfonyl]-piperidine
1-[4-(4-ethylphenyl)-1,3-thiazol-2-yl]-4-[(2-chloro-4-fluorophenyl)sulfonyl]-piperidine
1-[4-(4-ethoxyphenyl)-1,3-thiazol-2-yl]-4-[(2-chloro-4-fluorophenyl)sulfonyl]-piperidine
1-[4-(4-propylphenyl)-1,3-thiazol-2-yl]-4-[(2-chloro-4-fluorophenyl)sulfonyl]-piperidine
1-[4-(2,6-dimethylphenyl)-1,3-thiazol-2-yl]-4-[(2-chloro-4-fluorophenyl)sulfonyl]-piperidine
1-[4-(2,3-dimethylphenyl)-1,3-thiazol-2-yl]-4-[(2-chloro-4-fluorophenyl)sulfonyl]-piperidine
1-[4-(2,5-dimethylphenyl)-1,3-thiazol-2-yl]-4-[(2-chloro-4-fluorophenyl)sulfonyl]-piperidine
1-[4-(2,4-dichlorophenyl)-1,3-thiazol-2-yl]-4-[(2-chloro-4-fluorophenyl)sulfonyl]-piperidine
1-[4-(2,4-dimethoxyphenyl)-1,3-thiazol-2-yl]-4-[(2-chloro-4-fluorophenyl)sulfonyl]-piperidine
1-[4-(2,5-dimethoxyphenyl)-1,3-thiazol-2-yl]-4-[(2-chloro-4-fluorophenyl)sulfonyl]-piperidine
1-[4-(3,4-dimethoxyphenyl)-1,3-thiazol-2-yl]-4-[(2-chloro-4-fluorophenyl)sulfonyl]-piperidine
1-[4-(3,5-dimethoxyphenyl)-1,3-thiazol-2-yl]-4-[(2-chloro-4-fluorophenyl)sulfonyl]-piperidine
1-[4-(3,4-dichlorophenyl)-1,3-thiazol-2-yl]-4-[(2-chloro-4-fluorophenyl)sulfonyl]-piperidine
1-[4-(3,4-dimethylphenyl)-1,3-thiazol-2-yl]-4-[(2-chloro-4-fluorophenyl)sulfonyl]-piperidine
1-[4-(3,4-difluorophenyl)-1,3-thiazol-2-yl]-4-[(2-chloro-4-fluorophenyl)sulfonyl]-piperidine
1-[4-(3,5-difluorophenyl)-1,3-thiazol-2-yl]-4-[(2-chloro-4-fluorophenyl)sulfonyl]-piperidine
1-[4-(3,5-dichlorophenyl)-1,3-thiazol-2-yl]-4-[(2-chloro-4-fluorophenyl)sulfonyl]-piperidine
1-[4-(3,5-dimethylphenyl)-1,3-thiazol-2-yl]-4-[(2-chloro-4-fluorophenyl)sulfonyl]-piperidine
1-[4-(3-chloro-4-fluorophenyl)-1,3-thiazol-2-yl]-4-[(2-chloro-4-fluorophenyl)sulfonyl]-piperidine
1-[4-(3-chloro-5-fluorophenyl)-1,3-thiazol-2-yl]-4-[(2-chloro-4-fluorophenyl)sulfonyl]-piperidine
1-[4-(4-chloro-3-fluorophenyl)-1,3-thiazol-2-yl]-4-[(2-chloro-4-fluorophenyl)sulfonyl]-piperidine
1-[4-(3,4,5-trimethoxyphenyl)-1,3-thiazol-2-yl]-4-[(2-chloro-4-fluorophenyl)sulfonyl]-piperidine
1-[4-(2,4,6-trimethylphenyl)-1,3-thiazol-2-yl]-4-[(2-chloro-4-fluorophenyl)sulfonyl]-piperidine
1-[4-phenyl-1,3-thiazol-2-yl]-4-[(2-chloro-2-methylphenyl)sulfonyl]-piperidine
1-[4-(2-methylphenyl)-1,3-thiazol-2-yl]-4-[(2-chloro-2-methylphenyl)sulfonyl]-piperidine
1-[4-(2-methoxyphenyl)-1,3-thiazol-2-yl]-4-[(2-chloro-2-methylphenyl)sulfonyl]-piperidine
1-[4-(3-methylphenyl)-1,3-thiazol-2-yl]-4-[(2-chloro-2-methylphenyl)sulfonyl]-piperidine
1-[4-(3-methoxyphenyl)-1,3-thiazol-2-yl]-4-[(2-chloro-2-methylphenyl)sulfonyl]-piperidine
1-[4-(3-bromophenyl)-1,3-thiazol-2-yl]-4-[(2-chloro-2-methylphenyl)sulfonyl]-piperidine
1-[4-(4-chlorophenyl)-1,3-thiazol-2-yl]-4-[(2-chloro-2-methylphenyl)sulfonyl]-piperidine
1-[4-(4-methoxyphenyl)-1,3-thiazol-2-yl]-4-[(2-chloro-2-methylphenyl)sulfonyl]-piperidine
1-[4-(4-methylphenyl)-1,3-thiazol-2-yl]-4-[(2-chloro-2-methylphenyl)sulfonyl]-piperidine
1-[4-(4-ethylphenyl)-1,3-thiazol-2-yl]-4-[(2-chloro-2-methylphenyl)sulfonyl]-piperidine
1-[4-(4-ethoxyphenyl)-1,3-thiazol-2-yl]-4-[(2-chloro-2-methylphenyl)sulfonyl]-piperidine
1-[4-(4-propylphenyl)-1,3-thiazol-2-yl]-4-[(2-chloro-2-methylphenyl)sulfonyl]-piperidine
1-[4-(2,6-dimethylphenyl)-1,3-thiazol-2-yl]-4-[(2-chloro-2-methylphenyl)sulfonyl]-piperidine
1-[4-(2,3-dimethylphenyl)-1,3-thiazol-2-yl]-4-[(2-chloro-2-methylphenyl)sulfonyl]-piperidine
1-[4-(2,5-dimethylphenyl)-1,3-thiazol-2-yl]-4-[(2-chloro-2-methylphenyl)sulfonyl]-piperidine
1-[4-(2,4-dichlorophenyl)-1,3-thiazol-2-yl]-4-[(2-chloro-2-methylphenyl)sulfonyl]-piperidine
1-[4-(2,4-dimethoxyphenyl)-1,3-thiazol-2-yl]-4-[(2-chloro-2-methylphenyl)sulfonyl]-piperidine
1-[4-(2,5-dimethoxyphenyl)-1,3-thiazol-2-yl]-4-[(2-chloro-2-methylphenyl)sulfonyl]-piperidine
1-[4-(3,4-dimethoxyphenyl)-1,3-thiazol-2-yl]-4-[(2-chloro-2-methylphenyl)sulfonyl]-piperidine
1-[4-(3,5-dimethoxyphenyl)-1,3-thiazol-2-yl]-4-[(2-chloro-2-methylphenyl)sulfonyl]-piperidine
1-[4-(3,4-dichlorophenyl)-1,3-thiazol-2-yl]-4-[(2-chloro-2-methylphenyl)sulfonyl]-piperidine
1-[4-(3,4-dimethylphenyl)-1,3-thiazol-2-yl]-4-[(2-chloro-2-methylphenyl)sulfonyl]-piperidine
1-[4-(3,4-difluorophenyl)-1,3-thiazol-2-yl]-4-[(2-chloro-2-methylphenyl)sulfonyl]-piperidine 1-[4-(3,5-difluorophenyl)-1,3-thiazol-2-yl]-4-[(2-chloro-2-methylphenyl)sulfonyl]-piperidine
1-[4-(3,5-dichlorophenyl)-1,3-thiazol-2-yl]-4-[(2-chloro-2-methylphenyl)sulfonyl]-piperidine
1-[4-(3,5-dimethylphenyl)-1,3-thiazol-2-yl]-4-[(2-chloro-2-methylphenyl)sulfonyl]-piperidine
1-[4-(3-chloro-4-fluorophenyl)-1,3-thiazol-2-yl]-4-[(2-chloro-2-methylphenyl)sulfonyl]-piperidine
1-[4-(3-chloro-5-fluorophenyl)-1,3-thiazol-2-yl]-4-[(2-chloro-2-methylphenyl)sulfonyl]-piperidine
1-[4-(4-chloro-3-fluorophenyl)-1,3-thiazol-2-yl]-4-[(2-chloro-2-methylphenyl)sulfonyl]-piperidine
1-[4-(3,4,5-trimethoxyphenyl)-1,3-thiazol-2-yl]-4-[(2-chloro-2-methylphenyl)sulfonyl]-piperidine
1-[4-(2,4,6-trimethylphenyl)-1,3-thiazol-2-yl]-4-[(2-chloro-2-methylphenyl)sulfonyl]-piperidine
1-[4-phenyl-1,3-thiazol-2-yl]-4-[(5-fluoro-2-methylphenyl)sulfonyl]-piperidine
1-[4-(2-methylphenyl)-1,3-thiazol-2-yl]-4-[(5-fluoro-2-methylphenyl)sulfonyl]-piperidine
1-[4-(2-methoxyphenyl)-1,3-thiazol-2-yl]-4-[(5-fluoro-2-methylphenyl)sulfonyl]-piperidine
1-[4-(3-methylphenyl)-1,3-thiazol-2-yl]-4-[(5-fluoro-2-methylphenyl)sulfonyl]-piperidine
1-[4-(3-methoxyphenyl)-1,3-thiazol-2-yl]-4-[(5-fluoro-2-methylphenyl)sulfonyl]-piperidine
1-[4-(3-bromophenyl)-1,3-thiazol-2-yl]-4-[(5-fluoro-2-methylphenyl)sulfonyl]-piperidine
1-[4-(4-chlorophenyl)-1,3-thiazol-2-yl]-4-[(5-fluoro-2-methylphenyl)sulfonyl]-piperidine
1-[4-(4-methoxyphenyl)-1,3-thiazol-2-yl]-4-[(5-fluoro-2-methylphenyl)sulfonyl]-piperidine
1-[4-(4-methylphenyl)-1,3-thiazol-2-yl]-4-[(5-fluoro-2-methylphenyl)sulfonyl]-piperidine
1-[4-(4-ethylphenyl)-1,3-thiazol-2-yl]-4-[(5-fluoro-2-methylphenyl)sulfonyl]-piperidine
1-[4-(4-ethoxyphenyl)-1,3-thiazol-2-yl]-4-[(5-fluoro-2-methylphenyl)sulfonyl]-piperidine
1-[4-(4-propylphenyl)-1,3-thiazol-2-yl]-4-[(5-fluoro-2-methylphenyl)sulfonyl]-piperidine
1-[4-(2,6-dimethylphenyl)-1,3-thiazol-2-yl]-4-[(5-fluoro-2-methylphenyl)sulfonyl]-piperidine
1-[4-(2,3-dimethylphenyl)-1,3-thiazol-2-yl]-4-[(5-fluoro-2-methylphenyl)sulfonyl]-piperidine
1-[4-(2,5-dimethylphenyl)-1,3-thiazol-2-yl]-4-[(5-fluoro-2-methylphenyl)sulfonyl]-piperidine
1-[4-(2,4-dichlorophenyl)-1,3-thiazol-2-yl]-4-[(5-fluoro-2-methylphenyl)sulfonyl]-piperidine
1-[4-(2,4-dimethoxyphenyl)-1,3-thiazol-2-yl]-4-[(5-fluoro-2-methylphenyl)sulfonyl]-piperidine
1-[4-(2,5-dimethoxyphenyl)-1,3-thiazol-2-yl]-4-[(5-fluoro-2-methylphenyl)sulfonyl]-piperidine
1-[4-(3,4-dimethoxyphenyl)-1,3-thiazol-2-yl]-4-[(5-fluoro-2-methylphenyl)sulfonyl]-piperidine
1-[4-(3,5-dimethoxyphenyl)-1,3-thiazol-2-yl]-4-[(5-fluoro-2-methylphenyl)sulfonyl]-piperidine
1-[4-(3,4-dichlorophenyl)-1,3-thiazol-2-yl]-4-[(5-fluoro-2-methylphenyl)sulfonyl]-piperidine
1-[4-(3,4-dimethylphenyl)-1,3-thiazol-2-yl]-4-[(5-fluoro-2-methylphenyl)sulfonyl]-piperidine
1-[4-(3,4-difluorophenyl)-1,3-thiazol-2-yl]-4-[(5-fluoro-2-methylphenyl)sulfonyl]-piperidine
1-[4-(3,5-difluorophenyl)-1,3-thiazol-2-yl]-4-[(5-fluoro-2-methylphenyl)sulfonyl]-piperidine
1-[4-(3,5-dichlorophenyl)-1,3-thiazol-2-yl]-4-[(5-fluoro-2-methylphenyl)sulfonyl]-piperidine
1-[4-(3,5-dimethylphenyl)-1,3-thiazol-2-yl]-4-[(5-fluoro-2-methylphenyl)sulfonyl]-piperidine
1-[4-(3-chloro-4-fluorophenyl)-1,3-thiazol-2-yl]-4-[(5-fluoro-2-methylphenyl)sulfonyl]-piperidine
1-[4-(3-chloro-5-fluorophenyl)-1,3-thiazol-2-yl]-4-[(5-fluoro-2-methylphenyl)sulfonyl]-piperidine
1-[4-(4-chloro-3-fluorophenyl)-1,3-thiazol-2-yl]-4-[(5-fluoro-2-methylphenyl)sulfonyl]-piperidine
1-[4-(3,4,5-trimethoxyphenyl)-1,3-thiazol-2-yl]-4-[(5-fluoro-2-methylphenyl)sulfonyl]-piperidine
1-[4-(2,4,6-trimethylphenyl)-1,3-thiazol-2-yl]-4-[(5-fluoro-2-methylphenyl)sulfonyl]-piperidine
1-[4-phenyl-1,3-thiazol-2-yl]-4-[(2,3,5,6-tetramethylphenyl)sulfonyl]-piperidine
1-[4-(2-methylphenyl)-1,3-thiazol-2-yl]-4-[(2,3,5,6-tetramethylphenyl)sulfonyl]-piperidine
1-[4-(2-methoxyphenyl)-1,3-thiazol-2-yl]-4-[(2,3,5,6-tetramethylphenyl)sulfonyl]-piperidine
1-[4-(3-methylphenyl)-1,3-thiazol-2-yl]-4-[(2,3,5,6-tetramethylphenyl)sulfonyl]-piperidine
1-[4-(3-methoxyphenyl)-1,3-thiazol-2-yl]-4-[(2,3,5,6-tetramethylphenyl)sulfonyl]-piperidine
1-[4-(3-bromophenyl)-1,3-thiazol-2-yl]-4-[(2,3,5,6-tetramethylphenyl)sulfonyl]-piperidine
1-[4-(4-chlorophenyl)-1,3-thiazol-2-yl]-4-[(2,3,5,6-tetramethylphenyl)sulfonyl]-piperidine
1-[4-(4-methoxyphenyl)-1,3-thiazol-2-yl]-4-[(2,3,5,6-tetramethylphenyl)sulfonyl]-piperidine
1-[4-(4-methylphenyl)-1,3-thiazol-2-yl]-4-[(2,3,5,6-tetramethylphenyl)sulfonyl]-piperidine
1-[4-(4-ethylphenyl)-1,3-thiazol-2-yl]-4-[(2,3,5,6-tetramethylphenyl)sulfonyl]-piperidine
1-[4-(4-ethoxyphenyl)-1,3-thiazol-2-yl]-4-[(2,3,5,6-tetramethylphenyl)sulfonyl]-piperidine
1-[4-(4-propylphenyl)-1,3-thiazol-2-yl]-4-[(2,3,5,6-tetramethylphenyl)sulfonyl]-piperidine
1-[4-(2,6-dimethylphenyl)-1,3-thiazol-2-yl]-4-[(2,3,5,6-tetramethylphenyl)sulfonyl]-piperidine
1-[4-(2,3-dimethylphenyl)-1,3-thiazol-2-yl]-4-[(2,3,5,6-tetramethylphenyl)sulfonyl]-piperidine
1-[4-(2,5-dimethylphenyl)-1,3-thiazol-2-yl]-4-[(2,3,5,6-tetramethylphenyl)sulfonyl]-piperidine
1-[4-(2,4-dichlorophenyl)-1,3-thiazol-2-yl]-4-[(2,3,5,6-tetramethylphenyl)sulfonyl]-piperidine
1-[4-(2,4-dimethoxyphenyl)-1,3-thiazol-2-yl]-4-[(2,3,5,6-tetramethylphenyl)sulfonyl]-piperidine
1-[4-(2,5-dimethoxyphenyl)-1,3-thiazol-2-yl]-4-[(2,3,5,6-tetramethylphenyl)sulfonyl]-piperidine
1-[4-(3,4-dimethoxyphenyl)-1,3-thiazol-2-yl]-4-[(2,3,5,6-tetramethylphenyl)sulfonyl]-piperidine
1-[4-(3,5-dimethoxyphenyl)-1,3-thiazol-2-yl]-4-[(2,3,5,6-tetramethylphenyl)sulfonyl]-piperidine
1-[4-(3,4-dichlorophenyl)-1,3-thiazol-2-yl]-4-[(2,3,5,6-tetramethylphenyl)sulfonyl]-piperidine
1-[4-(3,4-dimethylphenyl)-1,3-thiazol-2-yl]-4-[(2,3,5,6-tetramethylphenyl)sulfonyl]-piperidine
1-[4-(3,4-difluorophenyl)-1,3-thiazol-2-yl]-4-[(2,3,5,6-tetramethylphenyl)sulfonyl]-piperidine
1-[4-(3,5-difluorophenyl)-1,3-thiazol-2-yl]-4-[(2,3,5,6-tetramethylphenyl)sulfonyl]-piperidine
1-[4-(3,5-dichlorophenyl)-1,3-thiazol-2-yl]-4-[(2,3,5,6-tetramethylphenyl)sulfonyl]-piperidine
1-[4-(3,5-dimethyhenyl)-1,3-thiazol-2-yl]-4-[(2,3,5,6-tetramethylphenyl)sulfonyl]-piperidine
1-[4-(3-chloro-4-fluorophenyl)-1,3-thiazol-2-yl]-4-[(2,3,5,6-tetramethylphenyl)sulfonyl]-piperidine 1-[4-(3-chloro-5-fluorophenyl)-1,3-thiazol-2-yl]-4-[(2,3,5,6-tetramethylphenyl)sulfonyl]-piperidine
1-[4-(4-chloro-3-fluorophenyl)-1,3-thiazol-2-yl]-4-[(2,3,5,6-tetramethylphenyl)sulfonyl]-piperidine
1-[4-(3,4,5-trimethoxyphenyl)-1,3-thiazol-2-yl]-4-[(2,3,5,6-tetramethylphenyl)sulfonyl]-piperidine
1-[4-(2,4,6-trimethylphenyl)-1,3-thiazol-2-yl]-4-[(2,3,5,6-tetramethylphenyl)sulfonyl]-piperidine
1-[4-phenyl-1,3-thiazol-2-yl]-4-[(2,5-dibromo-3,6-difluorophenyl)sulfonyl]-piperidine
1-[4-(2-methylphenyl)-1,3-thiazol-2-yl]-4-[(2,5-dibromo-3,6-difluorophenyl)sulfonyl]-piperidine
1-[4-(2-methoxyphenyl)-1,3-thiazol-2-yl]-4-[(2,5-dibromo-3,6-difluorophenyl)sulfonyl]-piperidine
1-[4-(3-methylphenyl)-1,3-thiazol-2-yl]-4-[(2,5-dibromo-3,6-difluorophenyl)sulfonyl]-piperidine
1-[4-(3-methoxyphenyl)-1,3-thiazol-2-yl]-4-[(2,5-dibromo-3,6-difluorophenyl)sulfonyl]-piperidine
1-[4-(3-bromophenyl)-1,3-thiazol-2-yl]-4-[(2,5-dibromo-3,6-difluorophenyl)sulfonyl]-piperidine
1-[4-(4-chlorophenyl)-1,3-thiazol-2-yl]-4-[(2,5-dibromo-3,6-difluorophenyl)sulfonyl]-piperidine
1-[4-(4-methoxyphenyl)-1,3-thiazol-2-yl]-4-[(2,5-dibromo-3,6-difluorophenyl)sulfonyl]-piperidine
1-[4-(4-methylphenyl)-1,3-thiazol-2-yl]-4-[(2,5-dibromo-3,6-difluorophenyl)sulfonyl]-piperidine
1-[4-(4-ethylphenyl)-1,3-thiazol-2-yl]-4-[(2,5-dibromo-3,6-difluorophenyl)sulfonyl]-piperidine
1-[4-(4-ethoxyphenyl)-1,3-thiazol-2-yl]-4-[(2,5-dibromo-3,6-difluorophenyl)sulfonyl]-piperidine
1-[4-(4-propylphenyl)-1,3-thiazol-2-yl]-4-[(2,5-dibromo-3,6-difluorophenyl)sulfonyl]-piperidine
1-[4-(2,6-dimethylphenyl)-1,3-thiazol-2-yl]-4-[(2,5-dibromo-3,6-difluorophenyl)sulfonyl]-piperidine
1-[4-(2,3-dimethylphenyl)-1,3-thiazol-2-yl]-4-[(2,5-dibromo-3,6-difluorophenyl)sulfonyl]-piperidine
1-[4-(2,5-dimethylphenyl))-1,3-thiazol-2-yl]-4-[(2,5-dibromo-3,6-difluorophenyl)sulfonyl]-piperidine
1-[4-(2,4-dichlorophenyl))-1,3-thiazol-2-yl]-4-[(2,5-dibromo-3,6-difluorophenyl)sulfonyl]-piperidine
1-[4-(2,4-dimethoxyphenyl))-1,3-thiazol-2-yl]-4-[(2,5-dibromo-3,6-difluorophenyl)sulfonyl]-piperidine
1-[4-(2,5-dimethoxyphenyl))-1,3-thiazol-2-yl]-4-[(2,5-dibromo-3,6-difluorophenyl)sulfonyl]-piperidine
1-[4-(3,4-dimethoxyphenyl))-1,3-thiazol-2-yl]-4-[(2,5-dibromo-3,6-difluorophenyl)sulfonyl]-piperidine
1-[4-(3,5-dimethoxyphenyl))-1,3-thiazol-2-yl]-4-[(2,5-dibromo-3,6-difluorophenyl)sulfonyl]-piperidine
1-[4-(3,4-dichlorophenyl))-1,3-thiazol-2-yl]-4-[(2,5-dibromo-3,6-difluorophenyl)sulfonyl]-piperidine
1-[4-(3,4-dimethylphenyl))-1,3-thiazol-2-yl]-4-[(2,5-dibromo-3,6-difluorophenyl)sulfonyl]-piperidine
1-[4-(3,4-difluorophenyl)-1,3-thiazol-2-yl]-4-[(2,5-dibromo-3,6-difluorophenyl)sulfonyl]-piperidine
1-[4-(3,5-difluorophenyl)-1,3-thiazol-2-yl]-4-[(2,5-dibromo-3,6-difluorophenyl)sulfonyl]-piperidine
1-[4-(3,5-dichlorophenyl))-1,3-thiazol-2-yl]-4-[(2,5-dibromo-3,6-difluorophenyl)sulfonyl]-piperidine
1-[4-(3,5-dimethylphenyl))-1,3-thiazol-2-yl]-4-[(2,5-dibromo-3,6-difluorophenyl)sulfonyl]-piperidine
1-[4-(3-chloro-4-fluorophenyl)-1,3-thiazol-2-yl]-4-[(2,5-dibromo-3,6-difluorophenyl)sulfonyl]-piperidine
1-[4-(3-chloro-5-fluorophenyl)-1,3-thiazol-2-yl]-4-[(2,5-dibromo-3,6-difluorophenyl)sulfonyl]-piperidine
1-[4-(4-chloro-3-fluorophenyl)-1,3-thiazol-2-yl]-4-[(2,5-dibromo-3,6-difluorophenyl)sulfonyl]-piperidine
1-[4-(3,4,5-trimethoxyphenyl)-1,3-thiazol-2-yl]-4-[(2,5-dibromo-3,6-difluorophenyl)sulfonyl]-piperidine
1-[4-(2,4,6-trimethylphenyl)-1,3-thiazol-2-yl]-4-[(2,5-dibromo-3,6-difluorophenyl)sulfonyl]-piperidine
1-[4-phenyl-1,3-thiazol-2-yl]-4-[(5-bromo-2-methoxyphenyl)sulfonyl]-piperidine
1-[4-(2-methylphenyl))-1,3-thiazol-2-yl]-4-[(5-bromo-2-methoxyphenyl)sulfonyl]-piperidine
1-[4-(2-methoxyphenyl)-1,3-thiazol-2-yl]-4-[(5-bromo-2-methoxyphenyl)sulfonyl]-piperidine
1-[4-(3-methylphenyl)-1,3-thiazol-2-yl]-4-[(5-bromo-2-methoxyphenyl)sulfonyl]-piperidine
1-[4-(3-methoxyphenyl)-1,3-thiazol-2-yl]-4-[(5-bromo-2-methoxyphenyl)sulfonyl]-piperidine
1-[4-(3-bromophenyl)-1,3-thiazol-2-yl]-4-[(5-bromo-2-methoxyphenyl)sulfonyl]-piperidine
1-[4-(4-chlorophenyl)-1,3-thiazol-2-yl]-4-[(5-bromo-2-methoxyphenyl)sulfonyl]-piperidine
1-[4-(4-methoxyphenyl)-1,3-thiazol-2-yl]-4-[(5-bromo-2-methoxyphenyl)sulfonyl]-piperidine
1-[4-(4-methylphenyl)-1,3-thiazol-2-yl]-4-[(5-bromo-2-methoxyphenyl)sulfonyl]-piperidine
1-[4-(4-ethylphenyl)-1,3-thiazol-2-yl]-4-[(5-bromo-2-methoxyphenyl)sulfonyl]-piperidine
1-[4-(4-ethoxyphenyl)-1,3-thiazol-2-yl]-4-[(5-bromo-2-methoxyphenyl)sulfonyl]-piperidine
1-[4-(4-propylphenyl)-1,3-thiazol-2-yl]-4-[(5-bromo-2-methoxyphenyl)sulfonyl]-piperidine
1-[4-(2,6-dimethylphenyl)-1,3-thiazol-2-yl]-4-[(5-bromo-2-methoxyphenyl)sulfonyl]-piperidine
1-[4-(2,3-dimethylphenyl)-1,3-thiazol-2-yl]-4-[(5-bromo-2-methoxyphenyl)sulfonyl]-piperidine
1-[4-(2,5-dimethylphenyl)-1,3-thiazol-2-yl]-4-[(5-bromo-2-methoxyphenyl)sulfonyl]-piperidine
1-[4-(2,4-dichlorophenyl)-1,3-thiazol-2-yl]-4-[(5-bromo-2-methoxyphenyl)sulfonyl]-piperidine
1-[4-(2,4-dimethoxyphenyl)-1,3-thiazol-2-yl]-4-[(5-bromo-2-methoxyphenyl)sulfonyl]-piperidine
1-[4-(2,5-dimethoxyphenyl)-1,3-thiazol-2-yl]-4-[(5-bromo-2-methoxyphenyl)sulfonyl]-piperidine
1-[4-(3,4-dimethoxyphenyl)-1,3-thiazol-2-yl]-4-[(5-bromo-2-methoxyphenyl)sulfonyl]-piperidine
1-[4-(3,5-dimethoxyphenyl)-1,3-thiazol-2-yl]-4-[(5-bromo-2-methoxyphenyl)sulfonyl]-piperidine
1-[4-(3,4-dichlorophenyl)-1,3-thiazol-2-yl]-4-[(5-bromo-2-methoxyphenyl)sulfonyl]-piperidine
1-[4-(3,4-dimethylphenyl)-1,3-thiazol-2-yl]-4-[(5-bromo-2-methoxyphenyl)sulfonyl]-piperidine
1-[4-(3,4-difluorophenyl)-1,3-thiazol-2-yl]-4-[(5-bromo-2-methoxyphenyl)sulfonyl]-piperidine
1-[4-(3,5-difluorophenyl)-1,3-thiazol-2-yl]-4-[(5-bromo-2-methoxyphenyl)sulfonyl]-piperidine
1-[4-(3,5-dichlorophenyl)-1,3-thiazol-2-yl]-4-[(5-bromo-2-methoxyphenyl)sulfonyl]-piperidine
1-[4-(3,5-dimethylphenyl)-1,3-thiazol-2-yl]-4-[(5-bromo-2-methoxyphenyl)sulfonyl]-piperidine
1-[4-(3-chloro-4-fluorophenyl)-1,3-thiazol-2-yl]-4-[(5-bromo-2-methoxyphenyl)sulfonyl]-piperidine
1-[4-(3-chloro-5-fluorophenyl)-1,3-thiazol-2-yl]-4-[(5-bromo-2-methoxyphenyl)sulfonyl]-piperidine
1-[4-(4-chloro-3-fluorophenyl)-1,3-thiazol-2-yl]-4-[(5-bromo-2-methoxyphenyl)sulfonyl]-piperidine
1-[4-(3,4,5-trimethoxyphenyl)-1,3-thiazol-2-yl]-4-[(5-bromo-2-methoxyphenyl)sulfonyl]-piperidine
1-[4-(2,4,6-trimethylphenyl)-1,3-thiazol-2-yl]-4-[(5-bromo-2-methoxyphenyl)sulfonyl]-piperidine 1-[4-phenyl-1,3-thiazol-2-yl]-4-[(4-bromo-2-chlorophenyl)sulfonyl]-piperidine
1-[4-(2-methylphenyl)-1,3-thiazol-2-yl]-4-[(4-bromo-2-chlorophenyl)sulfonyl]-piperidine
1-[4-(2-methoxyphenyl)-1,3-thiazol-2-yl]-4-[(4-bromo-2-chlorophenyl)sulfonyl]-piperidine
1-[4-(3-methylphenyl)-1,3-thiazol-2-yl]-4-[(4-bromo-2-chlorophenyl)sulfonyl]-piperidine
1-[4-(3-methoxyphenyl)-1,3-thiazol-2-yl]-4-[(4-bromo-2-chlorophenyl)sulfonyl]-piperidine
1-[4-(3-bromophenyl)-1,3-thiazol-2-yl]-4-[(4-bromo-2-chlorophenyl)sulfonyl]-piperidine
1-[4-(4-chlorophenyl)-1,3-thiazol-2-yl]-4-[(4-bromo-2-chlorophenyl)sulfonyl]-piperidine
1-[4-(4-methoxyphenyl)-1,3-thiazol-2-yl]-4-[(4-bromo-2-chlorophenyl)sulfonyl]-piperidine
1-[4-(4-methylphenyl)-1,3-thiazol-2-yl]-4-[(4-bromo-2-chlorophenyl)sulfonyl]-piperidine
1-[4-(4-ethylphenyl)-1,3-thiazol-2-yl]-4-[(4-bromo-2-chlorophenyl)sulfonyl]-piperidine
1-[4-(4-ethoxyphenyl)-1,3-thiazol-2-yl]-4-[(4-bromo-2-chlorophenyl)sulfonyl]-piperidine
1-[4-(4-propylphenyl)-1,3-thiazol-2-yl]-4-[(4-bromo-2-chlorophenyl)sulfonyl]-piperidine
1-[4-(2,6-dimethylphenyl)-1,3-thiazol-2-yl]-4-[(4-bromo-2-chlorophenyl)sulfonyl]-piperidine
1-[4-(2,3-dimethylphenyl)-1,3-thiazol-2-yl]-4-[(4-bromo-2-chlorophenyl)sulfonyl]-piperidine
1-[4-(2,5-dimethylphenyl)-1,3-thiazol-2-yl]-4-[(4-bromo-2-chlorophenyl)sulfonyl]-piperidine
1-[4-(2,4-dichlorophenyl)-1,3-thiazol-2-yl]-4-[(4-bromo-2-chlorophenyl)sulfonyl]-piperidine
1-[4-(2,4-dimethoxyphenyl)-1,3-thiazol-2-yl]-4-[(4-bromo-2-chlorophenyl)sulfonyl]-piperidine
1-[4-(2,5-dimethoxyphenyl)-1,3-thiazol-2-yl]-4-[(4-bromo-2-chlorophenyl)sulfonyl]-piperidine
1-[4-(3,4-dimethoxyphenyl)-1,3-thiazol-2-yl]-4-[(4-bromo-2-chlorophenyl)sulfonyl]-piperidine
1-[4-(3,5-dimethoxyphenyl)-1,3-thiazol-2-yl]-4-[(4-bromo-2-chlorophenyl)sulfonyl]-piperidine
1-[4-(3,4-dichlorophenyl)-1,3-thiazol-2-yl]-4-[(4-bromo-2-chlorophenyl)sulfonyl]-piperidine
1-[4-(3,4-dimethylphenyl)-1,3-thiazol-2-yl]-4-[(4-bromo-2-chlorophenyl)sulfonyl]-piperidine
1-[4-(3,4-difluorophenyl)-1,3-thiazol-2-yl]-4-[(4-bromo-2-chlorophenyl)sulfonyl]-piperidine
1-[4-(3,5-difluorophenyl)-1,3-thiazol-2-yl]-4-[(4-bromo-2-chlorophenyl)sulfonyl]-piperidine
1-[4-(3,5-dichlorophenyl)-1,3-thiazol-2-yl]-4-[(4-bromo-2-chlorophenyl)sulfonyl]-piperidine
1-[4-(3,5-dimethylphenyl)-1,3-thiazol-2-yl]-4-[(4-bromo-2-chlorophenyl)sulfonyl]-piperidine
1-[4-(3-chloro-4-fluorophenyl)-1,3-thiazol-2-yl]-4-[(4-bromo-2-chlorophenyl)sulfonyl]-piperidine
1-[4-(3-chloro-5-fluorophenyl)-1,3-thiazol-2-yl]-4-[(4-bromo-2-chlorophenyl)sulfonyl]-piperidine
1-[4-(4-chloro-3-fluorophenyl)-1,3-thiazol-2-yl]-4-[(4-bromo-2-chlorophenyl)sulfonyl]-piperidine
1-[4-(3,4,5-trimethoxyphenyl)-1,3-thiazol-2-yl]-4-[(4-bromo-2-chlorophenyl)sulfonyl]-piperidine
1-[4-(2,4,6-trimethylphenyl)-1,3-thiazol-2-yl]-4-[(4-bromo-2-chlorophenyl)sulfonyl]-piperidine
1-[4-phenyl-1,3-thiazol-2-yl]-4-[(5-chloro-2-methoxyphenyl)sulfonyl]-piperidine
1-[4-(2-methylphenyl)-1,3-thiazol-2-yl]-4-[(5-chloro-2-methoxyphenyl)sulfonyl]-piperidine
1-[4-(2-methoxyphenyl)-1,3-thiazol-2-yl]-4-[(5-chloro-2-methoxyphenyl)sulfonyl]-piperidine
1-[4-(3-methylphenyl)-1,3-thiazol-2-yl]-4-[(5-chloro-2-methoxyphenyl)sulfonyl]-piperidine
1-[4-(3-methoxyphenyl)-1,3-thiazol-2-yl]-4-[(5-chloro-2-methoxyphenyl)sulfonyl]-piperidine
1-[4-(3-bromophenyl)-1,3-thiazol-2-yl]-4-[(5-chloro-2-methoxyphenyl)sulfonyl]-piperidine
1-[4-(4-chlorophenyl)-1,3-thiazol-2-yl]-4-[(5-chloro-2-methoxyphenyl)sulfonyl]-piperidine
1-[4-(4-methoxyphenyl)-1,3-thiazol-2-yl]-4-[(5-chloro-2-methoxyphenyl)sulfonyl]-piperidine
1-[4-(4-methylphenyl)-1,3-thiazol-2-yl]-4-[(5-chloro-2-methoxyphenyl)sulfonyl]-piperidine
1-[4-(4-ethylphenyl)-1,3-thiazol-2-yl]-4-[(5-chloro-2-methoxyphenyl)sulfonyl]-piperidine
1-[4-(4-ethoxyphenyl)-1,3-thiazol-2-yl]-4-[(5-chloro-2-methoxyphenyl)sulfonyl]-piperidine
1-[4-(4-propylphenyl)-1,3-thiazol-2-yl]-4-[(5-chloro-2-methoxyphenyl)sulfonyl]-piperidine
1-[4-(2,6-dimethylphenyl)-1,3-thiazol-2-yl]-4-[(5-chloro-2-methoxyphenyl)sulfonyl]-piperidine
1-[4-(2,3-dimethylphenyl)-1,3-thiazol-2-yl]-4-[(5-chloro-2-methoxyphenyl)sulfonyl]-piperidine
1-[4-(2,5-dimethylphenyl)-1,3-thiazol-2-yl]-4-[(5-chloro-2-methoxyphenyl)sulfonyl]-piperidine
1-[4-(2,4-dichlorophenyl)-1,3-thiazol-2-yl]-4-[(5-chloro-2-methoxyphenyl)sulfonyl]-piperidine
1-[4-(2,4-dimethoxyphenyl)-1,3-thiazol-2-yl]-4-[(5-chloro-2-methoxyphenyl)sulfonyl]-piperidine
1-[4-(2,5-dimethoxyphenyl)-1,3-thiazol-2-yl]-4-[(5-chloro-2-methoxyphenyl)sulfonyl]-piperidine
1-[4-(3,4-dimethoxyphenyl)-1,3-thiazol-2-yl]-4-[(5-chloro-2-methoxyphenyl)sulfonyl]-piperidine
1-[4-(3,5-dimethoxyphenyl)-1,3-thiazol-2-yl]-4-[(5-chloro-2-methoxyphenyl)sulfonyl]-piperidine
1-[4-(3,4-dichlorophenyl)-1,3-thiazol-2-yl]-4-[(5-chloro-2-methoxyphenyl)sulfonyl]-piperidine
1-[4-(3,4-dimethylphenyl)-1,3-thiazol-2-yl]-4-[(5-chloro-2-methoxyphenyl)sulfonyl]-piperidine
1-[4-(3,4-difluorophenyl)-1,3-thiazol-2-yl]-4-[(5-chloro-2-methoxyphenyl)sulfonyl]-piperidine
1-[4-(3,5-difluorophenyl)-1,3-thiazol-2-yl]-4-[(5-chloro-2-methoxyphenyl)sulfonyl]-piperidine
1-[4-(3,5-dichlorophenyl)-1,3-thiazol-2-yl]-4-[(5-chloro-2-methoxyphenyl)sulfonyl]-piperidine
1-[4-(3,5-dimethylphenyl)-1,3-thiazol-2-yl]-4-[(5-chloro-2-methoxyphenyl)sulfonyl]-piperidine
1-[4-(3-chloro-4-fluorophenyl)-1,3-thiazol-2-yl]-4-[(5-chloro-2-methoxyphenyl)sulfonyl]-piperidine
1-[4-(3-chloro-5-fluorophenyl)-1,3-thiazol-2-yl]-4-[(5-chloro-2-methoxyphenyl)sulfonyl]-piperidine
1-[4-(4-chloro-3-fluorophenyl)-1,3-thiazol-2-yl]-4-[(5-chloro-2-methoxyphenyl)sulfonyl]-piperidine
1-[4-(3,4,5-trimethoxyphenyl)-1,3-thiazol-2-yl]-4-[(5-chloro-2-methoxyphenyl)sulfonyl]-piperidine
1-[4-(2,4,6-trimethylphenyl)-1,3-thiazol-2-yl]-4-[(5-chloro-2-methoxyphenyl)sulfonyl]-piperidine
1-[4-phenyl-1,3-thiazol-2-yl]-4-[(2-chloro-5-(trifluoromethyl)phenyl)sulfonyl]-piperidine
1-[4-(2-methylphenyl)-1,3-thiazol-2-yl]-4-[(2-chloro-5-(trifluoromethyl)phenyl)sulfonyl]-piperidine
1-[4-(2-methoxyphenyl)-1,3-thiazol-2-yl]-4-[(2-chloro-5-(trifluoromethyl)phenyl)sulfonyl]-piperidine
1-[4-(3-methylphenyl)-1,3-thiazol-2-yl]-4-[(2-chloro-5-(trifluoromethyl)phenyl)sulfonyl]-piperidine 1-[4-(3-methoxyphenyl)-1,3-thiazol-2-yl]-4-[(2-chloro-5-(trifluoromethyl)phenyl)sulfonyl]-piperidine
1-[4-(3-bromophenyl)-1,3-thiazol-2-yl]-4-[(2-chloro-5-(trifluoromethyl)phenyl)sulfonyl]-piperidine
1-[4-(4-chlorophenyl)-1,3-thiazol-2-yl]-4-[(2-chloro-5-(trifluoromethyl)phenyl)sulfonyl]-piperidine
1-[4-(4-methoxyphenyl)-1,3-thiazol-2-yl]-4-[(2-chloro-5-(trifluoromethyl)phenyl)sulfonyl]-piperidine
1-[4-(4-methylphenyl)-1,3-thiazol-2-yl]-4-[(2-chloro-5-(trifluoromethyl)phenyl)sulfonyl]-piperidine
1-[4-(4-ethylphenyl)-1,3-thiazol-2-yl]-4-[(2-chloro-5-(trifluoromethyl)phenyl)sulfonyl]-piperidine
1-[4-(4-ethoxyphenyl)-1,3-thiazol-2-yl]-4-[(2-chloro-5-(trifluoromethyl)phenyl)sulfonyl]-piperidine
1-[4-(4-propylphenyl)-1,3-thiazol-2-yl]-4-[(2-chloro-5-(trifluoromethyl)phenyl)sulfonyl]-piperidine
1-[4-(2,6-dimethylphenyl)-1,3-thiazol-2-yl]-4-[(2-chloro-5-(trifluoromethyl)phenyl)sulfonyl]-piperidine
1-[4-(2,3-dimethylphenyl)-1,3-thiazol-2-yl]-4-[(2-chloro-5-(trifluoromethyl)phenyl)sulfonyl]-piperidine
1-[4-(2,5-dimethylphenyl)-1,3-thiazol-2-yl]-4-[(2-chloro-5-(trifluoromethyl)phenyl)sulfonyl]-piperidine
1-[4-(2,4-dichlorophenyl)-1,3-thiazol-2-yl]-4-[(2-chloro-5-(trifluoromethyl)phenyl)sulfonyl]-piperidine
1-[4-(2,4-dimethoxyphenyl)-1,3-thiazol-2-yl]-4-[(2-chloro-5-(trifluoromethyl)phenyl)sulfonyl]-piperidine
1-[4-(2,5-dimethoxyphenyl)-1,3-thiazol-2-yl]-4-[(2-chloro-5-(trifluoromethyl)phenyl)sulfonyl]-piperidine
1-[4-(3,4-dimethoxyphenyl)-1,3-thiazol-2-yl]-4-[(2-chloro-5-(trifluoromethyl)phenyl)sulfonyl]-piperidine
1-[4-(3,5-dimethoxyphenyl)-1,3-thiazol-2-yl]-4-[(2-chloro-5-trifluoromethyl)phenyl)sulfonyl]-piperidine
1-[4-(3,4-dichlorophenyl)-1,3-thiazol-2-yl]-4-[(2-chloro-5-(trifluoromethyl)phenyl)sulfonyl]-piperidine
1-[4-(3,4-dimethylphenyl)-1,3-thiazol-2-yl]-4-[(2-chloro-5-(trifluoromethyl)phenyl)sulfonyl]-piperidine
1-[4-(3,4-difluorophenyl)-1,3-thiazol-2-yl]-4-[(2-chloro-5-(trifluoromethyl)phenyl)sulfonyl]-piperidine
1-[4-(3,5-difluorophenyl)-1,3-thiazol-2-yl]-4-[(2-chloro-5-(trifluoromethyl)phenyl)sulfonyl]-piperidine
1-[4-(3,5-dichlorophenyl))-1,3-thiazol-2-yl]-4-[(2-chloro-5-(trifluoromethyl)phenyl)sulfonyl]-piperidine
1-[4-(3,5-dimethylphenyl))-1,3-thiazol-2-yl]-4-[(2-chloro-5-(trifluoromethyl)phenyl)sulfonyl]-piperidine
1-[4-(3-chloro-4-fluorophenyl)-1,3-thiazol-2-yl]-4-[(2-chloro-5-(trifluoromethyl)phenyl)sulfonyl]-piperidine
1-[4-(3-chloro-5-fluorophenyl)-1,3-thiazol-2-yl]-4-[(2-chloro-5-(trifluoromethyl)phenyl)sulfonyl]-piperidine
1-[4-(4-chloro-3-fluorophenyl)-1,3-thiazol-2-yl]-4-[(2-chloro-5-(trifluoromethyl)phenyl)sulfonyl]-piperidine
1-[4-(3,4,5-trimethoxyphenyl))-1,3-thiazol-2-yl]-4-[(2-chloro-5-(trifluoromethyl)phenyl)sulfonyl]-piperidine
1-[4-(2,4,6-trimethylphenyl))-1,3-thiazol-2-yl]-4-[(2-chloro-5-(trifluoromethyl)phenyl)sulfonyl]-piperidine
1-[4-phenyl-1,3-thiazol-2-yl]-4-[(4-chloro-3-nitrophenyl)sulfonyl]-piperidine
1-[4-(2-methylphenyl))-1,3-thiazol-2-yl]-4-[(4-chloro-3-nitrophenyl)sulfonyl]-piperidine
1-[4-(2-methoxyphenyl))-1,3-thiazol-2-yl]-4-[(4-chloro-3-nitrophenyl)sulfonyl]-piperidine
1-[4-(3-methylphenyl))-1,3-thiazol-2-yl]-4-[(4-chloro-3-nitrophenyl)sulfonyl]-piperidine
1-[4-(3-methoxyphenyl))-1,3-thiazol-2-yl]-4-[(4-chloro-3-nitrophenyl)sulfonyl]-piperidine
1-[4-(3-bromophenyl))-1,3-thiazol-2-yl]-4-[(4-chloro-3-nitrophenyl)sulfonyl]-piperidine
1-[4-(4-chlorophenyl))-1,3-thiazol-2-yl]-4-[(4-chloro-3-nitrophenyl)sulfonyl]-piperidine
1-[4-(4-methoxyphenyl))-1,3-thiazol-2-yl]-4-[(4-chloro-3-nitrophenyl)sulfonyl]-piperidine
1-[4-(4-methylphenyl))-1,3-thiazol-2-yl]-4-[(4-chloro-3-nitrophenyl)sulfonyl]-piperidine
1-[4-(4-ethylphenyl))-1,3-thiazol-2-yl]-4-[(4-chloro-3-nitrophenyl)sulfonyl]-piperidine
1-[4-(4-ethoxyphenyl))-1,3-thiazol-2-yl]-4-[(4-chloro-3-nitrophenyl)sulfonyl]-piperidine
1-[4-(4-propylphenyl))-1,3-thiazol-2-yl]-4-[(4-chloro-3-nitrophenyl)sulfonyl]-piperidine
1-[4-(2,6-dimethylphenyl))-1,3-thiazol-2-yl]-4-[(4-chloro-3-nitrophenyl)sulfonyl]-piperidine
1-[4-(2,3-dimethylphenyl))-1,3-thiazol-2-yl]-4-[(4-chloro-3-nitrophenyl)sulfonyl]-piperidine
1-[4-(2,5-dimethylphenyl))-1,3-thiazol-2-yl]-4-[(4-chloro-3-nitrophenyl)sulfonyl]-piperidine
1-[4-(2,4-dichlorophenyl))-1,3-thiazol-2-yl]-4-[(4-chloro-3-nitrophenyl)sulfonyl]-piperidine
1-[4-(2,4-dimethoxyphenyl))-1,3-thiazol-2-yl]-4-[(4-chloro-3-nitrophenyl)sulfonyl]-piperidine
1-[4-(2,5-dimethoxyphenyl)-1,3-thiazol-2-yl]-4-[(4-chloro-3-nitrophenyl)sulfonyl]-piperidine
1-[4-(3,4-dimethoxyphenyl)-1,3-thiazol-2-yl]-4-[(4-chloro-3-nitrophenyl)sulfonyl]-piperidine
1-[4-(3,5-dimethoxyphenyl)-1,3-thiazol-2-yl]-4-[(4-chloro-3-nitrophenyl)sulfonyl]-piperidine
1-[4-(3,4-dichlorophenyl)-1,3-thiazol-2-yl]-4-[(4-chloro-3-nitrophenyl)sulfonyl]-piperidine
1-[4-(3,4-dimethylphenyl)-1,3-thiazol-2-yl]-4-[(4-chloro-3-nitrophenyl)sulfonyl]-piperidine
1-[4-(3,4-difluorophenyl)-1,3-thiazol-2-yl]-4-[(4-chloro-3-nitrophenyl)sulfonyl]-piperidine
1-[4-(3,5-difluorophenyl)-1,3-thiazol-2-yl]-4-[(4-chloro-3-nitrophenyl)sulfonyl]-piperidine
1-[4-(3,5-dichlorophenyl)-1,3-thiazol-2-yl]-4-[(4-chloro-3-nitrophenyl)sulfonyl]-piperidine
1-[4-(3,5-dimethylphenyl)-1,3-thiazol-2-yl]-4-[(4-chloro-3-nitrophenyl)sulfonyl]-piperidine
1-[4-(3-chloro-4-fluorophenyl)-1,3-thiazol-2-yl]-4-[(4-chloro-3-nitrophenyl)sulfonyl]-piperidine
1-[4-(3-chloro-5-fluorophenyl)-1,3-thiazol-2-yl]-4-[(4-chloro-3-nitrophenyl)sulfonyl]-piperidine
1-[4-(4-chloro-3-fluorophenyl)-1,3-thiazol-2-yl]-4-[(4-chloro-3-nitrophenyl)sulfonyl]-piperidine
1-[4-(3,4,5-trimethoxyphenyl)-1,3-thiazol-2-yl]-4-[(4-chloro-3-nitrophenyl)sulfonyl]-piperidine
1-[4-(2,4,6-trimethylphenyl)-1,3-thiazol-2-yl]-4-[(4-chloro-3-nitrophenyl)sulfonyl]-piperidine
1-[4-phenyl-1,3-thiazol-2-yl]-4-[(2,4-dichloro-5-methylphenyl)sulfonyl]-piperidine
1-[4-(2-methylphenyl)-1,3-thiazol-2-yl]-4-[(2,4-dichloro-5-methylphenyl)sulfonyl]-piperidine
1-[4-(2-methoxyphenyl)-1,3-thiazol-2-yl]-4-[(2,4-dichloro-5-methylphenyl)sulfonyl]-piperidine
1-[4-(3-methylphenyl)-1,3-thiazol-2-yl]-4-[(2,4-dichloro-5-methylphenyl)sulfonyl]-piperidine
1-[4-(3-methoxyphenyl)-1,3-thiazol-2-yl]-4-[(2,4-dichloro-5-methylphenyl)sulfonyl]-piperidine
1-[4-(3-bromophenyl)-1,3-thiazol-2-yl]-4-[(2,4-dichloro-5-methylphenyl)sulfonyl]-piperidine
1-[4-(4-chlorophenyl)-1,3-thiazol-2-yl]-4-[(2,4-dichloro-5-methylphenyl)sulfonyl]-piperidine
1-[4-(4-methoxyphenyl)-1,3-thiazol-2-yl]-4-[(2,4-dichloro-5-methylphenyl)sulfonyl]-piperidine 1-[4-(4-methylphenyl)-1,3-thiazol-2-yl]-4-[(2,4-dichloro-5-methylphenyl)sulfonyl]-piperidine
1-[4-(4-ethylphenyl)-1,3-thiazol-2-yl]-4-[(2,4-dichloro-5-methylphenyl)sulfonyl]-piperidine
1-[4-(4-ethoxyphenyl)-1,3-thiazol-2-yl]-4-[(2,4-dichloro-5-methylphenyl)sulfonyl]-piperidine
1-[4-(4-propylphenyl)-1,3-thiazol-2-yl]-4-[(2,4-dichloro-5-methylphenyl)sulfonyl]-piperidine
1-[4-(2,6-dimethylphenyl)-1,3-thiazol-2-yl]-4-[(2,4-dichloro-5-methylphenyl)sulfonyl]-piperidine
1-[4-(2,3-dimethylphenyl)-1,3-thiazol-2-yl]-4-[(2,4-dichloro-5-methylphenyl)sulfonyl]-piperidine
1-[4-(2,5-dimethylphenyl)-1,3-thiazol-2-yl]-4-[(2,4-dichloro-5-methylphenyl)sulfonyl]-piperidine
1-[4-(2,4-dichlorophenyl)-1,3-thiazol-2-yl]-4-[(2,4-dichloro-5-methylphenyl)sulfonyl]-piperidine
1-[4-(2,4-dimethoxyphenyl)-1,3-thiazol-2-yl]-4-[(2,4-dichloro-5-methylphenyl)sulfonyl]-piperidine
1-[4-(2,5-dimethoxyphenyl)-1,3-thiazol-2-yl]-4-[(2,4-dichloro-5-methylphenyl)sulfonyl]-piperidine
1-[4-(3,4-dimethoxyphenyl)-1,3-thiazol-2-yl]-4-[(2,4-dichloro-5-methylphenyl)sulfonyl]-piperidine
1-[4-(3,5-dimethoxyphenyl)-1,3-thiazol-2-yl]-4-[(2,4-dichloro-5-methylphenyl)sulfonyl]-piperidine
1-[4-(3,4-dichlorophenyl)-1,3-thiazol-2-yl]-4-[(2,4-dichloro-5-methylphenyl)sulfonyl]-piperidine
1-[4-(3,4-dimethylphenyl)-1,3-thiazol-2-yl]-4-[(2,4-dichloro-5-methylphenyl)sulfonyl]-piperidine
1-[4-(3,4-difluorophenyl)-1,3-thiazol-2-yl]-4-[(2,4-dichloro-5-methylphenyl)sulfonyl]-piperidine
1-[4-(3,5-difluorophenyl)-1,3-thiazol-2-yl]-4-[(2,4-dichloro-5-methylphenyl)sulfonyl]-piperidine
1-[4-(3,5-dichlorophenyl)-1,3-thiazol-2-yl]-4-[(2,4-dichloro-5-methylphenyl)sulfonyl]-piperidine
1-[4-(3,5-dimethylphenyl)-1,3-thiazol-2-yl]-4-[(2,4-dichloro-5-methylphenyl)sulfonyl]-piperidine
1-[4-(3-chloro-4-fluorophenyl)-1,3-thiazol-2-yl]-4-[(2,4-dichloro-5-methylphenyl)sulfonyl]-piperidine
1-[4-(3-chloro-5-fluorophenyl)-1,3-thiazol-2-yl]-4-[(2,4-dichloro-5-methylphenyl)sulfonyl]-piperidine
1-[4-(4-chloro-3-fluorophenyl)-1,3-thiazol-2-yl]-4-[(2,4-dichloro-5-methylphenyl)sulfonyl]-piperidine
1-[4-(3,4,5-trimethoxyphenyl)-1,3-thiazol-2-yl]-4-[(2,4-dichloro-5-methylphenyl)sulfonyl]-piperidine
1-[4-(2,4,6-trimethylphenyl)-1,3-thiazol-2-yl]-4-[(2,4-dichloro-5-methylphenyl)sulfonyl]-piperidine
1-[4-(piridin-2-yl)-1,3-thiazol-2-yl]-4-[(4-bromophenyl)sulfonyl]-piperidine
1-[4-(thien-3-yl)-1,3-thiazol-2-yl]-4-[(4-bromophenyl)sulfonyl]-piperidine
1-[4-(piridin-2-yl)-1,3-thiazol-2-yl]-4-[(5-chloro-4-nitrothiophen-2-yl)sulfonyl]-piperidine
1-[4-(thien-3-yl)-1,3-thiazol-2-yl]-4-[(5-chloro-4-nitrothiophen-2-yl)sulfonyl]-piperidine
1-[4-(2,4,6-trimethylphenyl)-1,3-thiazol-2-yl]-4-[(5-chloro-4-nitrothiophen-2-yl)sulfonyl]-piperidine
1-[4-(piridin-2-yl)-1,3-thiazol-2-yl]-4-[(6-bromopyridin-3-yl)sulfonyl]-piperidine
1-[4-(thien-3-yl)-1,3-thiazol-2-yl]-4-[(6-bromopyridin-3-yl)sulfonyl]-piperidine
1-[4-(2,4,6-trimethylphenyl)-1,3-thiazol-2-yl]-4-[(6-bromopyridin-3-yl)sulfonyl]-piperidine
1-[4-(piridin-2-yl)-1,3-thiazol-2-yl]-4-[(5-methyl-1H-imidazol-2-yl)sulfonyl]-piperidine
1-[4-(thien-3-yl)-1,3-thiazol-2-yl]-4-[(5-methyl-1H-imidazol-2-yl)sulfonyl]-piperidine
1-[4-(2,4,6-trimethylphenyl)-1,3-thiazol-2-yl]-4-[(5-methyl-1H-imdazol-2-yl)sulfonyl]-piperidine
1-[4-(piridin-2-yl)-1,3-thiazol-2-yl]-4-[(2,4-dimethylpyrimidin-5-yl)sulfonyl]-piperidine
1-[4-(thien-3-yl)-1,3-thiazol-2-yl]-4-[(2,4-dimethylpyrimidin-5-yl)sulfonyl]-piperidine, and
1-[4-(2,4,6-trimethylphenyl)-1,3-thiazol-2-yl]-4-[(2,4-dimethylpyrimidin-5-yl)sulfonyl]-piperidine.

Example 24

Preparation of Thiazolyl-piperidine Derivatives Wherein W is Methylene

1-[4-(4-methylbenzyl-1,3-thiazol-2-yl]-4-[(4-propylphenyl)sulfonyl]-piperidine is prepared using the synthetic scheme shown in FIG. 2 (wherein W is methylene), starting from 4-methylbenzylmagnesium chloride, piperidine and 4-propylbenzene-1-sulfonyl chloride.

Using the same procedure, the following compounds are prepared:
1-[4-benzyl-1,3-thiazol-2-yl]-4-[(4-fluorophenyl)sulfonyl]-piperidine
1-[4-(2-methylbenzyl)-1,3-thiazol-2-yl]-4-[(4-fluorophenyl)sulfonyl]-piperidine
1-[4-(2-methoxybenzyl)-1,3-thiazol-2-yl]-4-[(4-fluorophenyl)sulfonyl]-piperidine
1-[4-(3-methylbenzyl)-1,3-thiazol-2-yl]-4-[(4-fluorophenyl)sulfonyl]-piperidine
1-[4-(3-methoxybenzyl)-1,3-thiazol-2-yl]-4-[(4-fluorophenyl)sulfonyl]-piperidine
1-[4-(3-bromobenzyl)-1,3-thiazol-2-yl]-4-[(4-fluorophenyl)sulfonyl]-piperidine
1-[4-(4-chlorobenzyl)-1,3-thiazol-2-yl]-4-[(4-fluorophenyl)sulfonyl]-piperidine
1-[4-(4-methoxybenzyl)-1,3-thiazol-2-yl]-4-[(4-fluorophenyl)sulfonyl]-piperidine
1-[4-(4-methylbenzyl)-1,3-thiazol-2-yl]-4-[(4-fluorophenyl)sulfonyl]-piperidine
1-[4-(4-ethylbenzyl)-1,3-thiazol-2-yl]-4-[(4-fluorophenyl)sulfonyl]-piperidine
1-[4-(4-ethoxybenzyl)-1,3-thiazol-2-yl]-4-[(4-fluorophenyl)sulfonyl]-piperidine
1-[4-(4-propylbenzyl)-1,3-thiazol-2-yl]-4-[(4-fluorophenyl)sulfonyl]-piperidine
1-[4-(2,6-dimethylbenzyl)-1,3-thiazol-2-yl]-4-[(4-fluorophenyl)sulfonyl]-piperidine
1-[4-(2,3-dimethylbenzyl)-1,3-thiazol-2-yl]-4-[(4-fluorophenyl)sulfonyl]-piperidine
1-[4-(2,5-dimethylbenzyl)-1,3-thiazol-2-yl]-4-[(4-fluorophenyl)sulfonyl]-piperidine
1-[4-(2,4-dichlorobenzyl)-1,3-thiazol-2-yl]-4-[(4-fluorophenyl)sulfonyl]-piperidine
1-[4-(2,4-dimethoxybenzyl)-1,3-thiazol-2-yl]-4-[(4-fluorophenyl)sulfonyl]-piperidine
1-[4-(2,5-dimethoxybenzyl)-1,3-thiazol-2-yl]-4-[(4-fluorophenyl)sulfonyl]-piperidine
1-[4-(3,4-dimethoxybenzyl)-1,3-thiazol-2-yl]-4-[(4-fluorophenyl)sulfonyl]-piperidine
1-[4-(3,5-dimethoxybenzyl)-1,3-thiazol-2-yl]-4-[(4-fluorophenyl)sulfonyl]-piperidine
1-[4-(3,4-dichlorobenzyl)-1,3-thiazol-2-yl]-4-[(4-fluorophenyl)sulfonyl]-piperidine
1-[4-(3,4-dimethylbenzyl)-1,3-thiazol-2-yl]-4-[(4-fluorophenyl)sulfonyl]-piperidine
1-[4-(3,4-difluorobenzyl)-1,3-thiazol-2-yl]-4-[(4-fluorophenyl)sulfonyl]-piperidine 1-[4-(3,5-difluorobenzyl)-1,3-thiazol-2-yl]-4-[(4-fluorophenyl)sulfonyl]-piperidine
1-[4-(3,5-dichlorobenzyl)-1,3-thiazol-2-yl]-4-[(4-fluorophenyl)sulfonyl]-piperidine
1-[4-(3,5-dimethylbenzyl)-1,3-thiazol-2-yl]-4-[(4-fluorophenyl)sulfonyl]-piperidine
1-[4-(3-chloro-4-fluorobenzyl)-1,3-thiazol-2-yl]-4-[(4-fluorophenyl)sulfonyl]-piperidine
1-[4-(3-chloro-5-fluorobenzyl)-1,3-thiazol-2-yl]-4-[(4-fluorophenyl)sulfonyl]-piperidine
1-[4-(4-chloro-3-fluorobenzyl)-1,3-thiazol-2-yl]-4-[(4-fluorophenyl)sulfonyl]-piperidine
1-[4-(3,4,5-trimethoxybenzyl)-1,3-thiazol-2-yl]-4-[(4-fluorophenyl)sulfonyl]-piperidine
1-[4-(2,4,6-trimethylbenzyl)-1,3-thiazol-2-yl]-4-[(4-fluorophenyl)sulfonyl]-piperidine
1-[4-benzyl-1,3-thiazol-2-yl]-4-[(4-bromophenyl)sulfonyl]-piperidine
1-[4-(2-methylbenzyl)-1,3-thiazol-2-yl]-4-[(4-bromophenyl)sulfonyl]-piperidine
1-[4-(2-methoxybenzyl)-1,3-thiazol-2-yl]-4-[(4-bromophenyl)sulfonyl]-piperidine
1-[4-(3-methylbenzyl)-1,3-thiazol-2-yl]-4-[(4-bromophenyl)sulfonyl]-piperidine
1-[4-(3-methoxybenzyl)-1,3-thiazol-2-yl]-4-[(4-bromophenyl)sulfonyl]-piperidine
1-[4-(3-bromobenzyl)-1,3-thiazol-2-yl]-4-[(4-bromophenyl)sulfonyl]-piperidine
1-[4-(4-chlorobenzyl)-1,3-thiazol-2-yl]-4-[(4-bromophenyl)sulfonyl]-piperidine
1-[4-(4-methoxybenzyl)-1,3-thiazol-2-yl]-4-[(4-bromophenyl)sulfonyl]-piperidine
1-[4-(4-methylbenzyl)-1,3-thiazol-2-yl]-4-[(4-bromophenyl)sulfonyl]-piperidine
1-[4-(4-ethylbenzyl)-1,3-thiazol-2-yl]-4-[(4-bromophenyl)sulfonyl]-piperidine
1-[4-(4-ethoxybenzyl)-1,3-thiazol-2-yl]-4-[(4-bromophenyl)sulfonyl]-piperidine
1-[4-(4-propylbenzyl)-1,3-thiazol-2-yl]-4-[(4-bromophenyl)sulfonyl]-piperidine
1-[4-(2,6-dimethylbenzyl)-1,3-thiazol-2-yl]-4-[(4-bromophenyl)sulfonyl]-piperidine
1-[4-(2,3-dimethylbenzyl)-1,3-thiazol-2-yl]-4-[(4-bromophenyl)sulfonyl]-piperidine
1-[4-(2,5-dimethylbenzyl)-1,3-thiazol-2-yl]-4-[(4-bromophenyl)sulfonyl]-piperidine
1-[4-(2,4-dichlorobenzyl)-1,3-thiazol-2-yl]-4-[(4-bromophenyl)sulfonyl]-piperidine
1-[4-(2,4-dimethoxybenzyl)-1,3-thiazol-2-yl]-4-[(4-bromophenyl)sulfonyl]-piperidine
1-[4-(2,5-dimethoxybenzyl)-1,3-thiazol-2-yl]-4-[(4-bromophenyl)sulfonyl]-piperidine
1-[4-(3,4-dimethoxybenzyl)-1,3-thiazol-2-yl]-4-[(4-bromophenyl)sulfonyl]-piperidine
1-[4-(3,5-dimethoxybenzyl)-1,3-thiazol-2-yl]-4-[(4-bromophenyl)sulfonyl]-piperidine
1-[4-(3,4-dichlorobenzyl)-1,3-thiazol-2-yl]-4-[(4-bromophenyl)sulfonyl]-piperidine
1-[4-(3,4-dimethylbenzyl)-1,3-thiazol-2-yl]-4-[(4-bromophenyl)sulfonyl]-piperidine
1-[4-(3,4-difluorobenzyl)-1,3-thiazol-2-yl]-4-[(4-bromophenyl)sulfonyl]-piperidine
1-[4-(3,5-difluorobenzyl)-1,3-thiazol-2-yl]-4-[(4-bromophenyl)sulfonyl]-piperidine
1-[4-(3,5-dichlorobenzyl)-1,3-thiazol-2-yl]-4-[(4-bromophenyl)sulfonyl]-piperidine
1-[4-(3,5-dimethylbenzyl)-1,3-thiazol-2-yl]-4-[(4-bromophenyl)sulfonyl]-piperidine
1-[4-(3-chloro-4-fluorobenzyl)-1,3-thiazol-2-yl]-4-[(4-bromophenyl)sulfonyl]-piperidine
1-[4-(3-chloro-5-fluorobenzyl)-1,3-thiazol-2-yl]-4-[(4-bromophenyl)sulfonyl]-piperidine
1-[4-(4-chloro-3-fluorobenzyl)-1,3-thiazol-2-yl]-4-[(4-bromophenyl)sulfonyl]-piperidine
1-[4-(3,4,5-trimethoxybenzyl)-1,3-thiazol-2-yl]-4-[(4-bromophenyl)sulfonyl]-piperidine
1-[4-(2,4,6-trimethylbenzyl)-1,3-thiazol-2-yl]-4-[(4-bromophenyl)sulfonyl]-piperidine
1-[4-benzyl-1,3-thiazol-2-yl]-4-[(4-methylphenyl)sulfonyl]-piperidine
1-[4-(2-methylbenzyl)-1,3-thiazol-2-yl]-4-[(4-methylphenyl)sulfonyl]-piperidine
1-[4-(2-methoxybenzyl)-1,3-thiazol-2-yl]-4-[(4-methylphenyl)sulfonyl]-piperidine
1-[4-(3-methylbenzyl)-1,3-thiazol-2-yl]-4-[(4-methylphenyl)sulfonyl]-piperidine
1-[4-(3-methoxybenzyl)-1,3-thiazol-2-yl]-4-[(4-methylphenyl)sulfonyl]-piperidine
1-[4-(3-bromobenzyl)-1,3-thiazol-2-yl]-4-[(4-methylphenyl)sulfonyl]-piperidine
1-[4-(4-chlorobenzyl)-1,3-thiazol-2-yl]-4-[(4-methylphenyl)sulfonyl]-piperidine
1-[4-(4-methoxybenzyl)-1,3-thiazol-2-yl]-4-[(4-methylphenyl)sulfonyl]-piperidine
1-[4-(4-methylbenzyl)-1,3-thiazol-2-yl]-4-[(4-methylphenyl)sulfonyl]-piperidine
1-[4-(4-ethylbenzyl)-1,3-thiazol-2-yl]-4-[(4-methylphenyl)sulfonyl]-piperidine
1-[4-(4-ethoxybenzyl)-1,3-thiazol-2-yl]-4-[(4-methylphenyl)sulfonyl]-piperidine
1-[4-(4-propylbenzyl)-1,3-thiazol-2-yl]-4-[(4-methylphenyl)sulfonyl]-piperidine
1-[4-(2,6-dimethylbenzyl)-1,3-thiazol-2-yl]-4-[(4-methylphenyl)sulfonyl]-piperidine
1-[4-(2,3-dimethylbenzyl)-1,3-thiazol-2-yl]-4-[(4-methylphenyl)sulfonyl]-piperidine
1-[4-(2,5-dimethylbenzyl)-1,3-thiazol-2-yl]-4-[(4-methylphenyl)sulfonyl]-piperidine
1-[4-(2,4-dichlorobenzyl)-1,3-thiazol-2-yl]-4-[(4-methylphenyl)sulfonyl]-piperidine
1-[4-(2,4-dimethoxybenzyl)-1,3-thiazol-2-yl]-4-[(4-methylphenyl)sulfonyl]-piperidine
1-[4-(2,5-dimethoxybenzyl)-1,3-thiazol-2-yl]-4-[(4-methylphenyl)sulfonyl]-piperidine
1-[4-(3,4-dimethoxybenzyl)-1,3-thiazol-2-yl]-4-[(4-methylphenyl)sulfonyl]-piperidine
1-[4-(3,5-dimethoxybenzyl)-1,3-thiazol-2-yl]-4-[(4-methylphenyl)sulfonyl]-piperidine
1-[4-(3,4-dichlorobenzyl)-1,3-thiazol-2-yl]-4-[(4-methylphenyl)sulfonyl]-piperidine
1-[4-(3,4-dimethylbenzyl)-1,3-thiazol-2-yl]-4-[(4-methylphenyl)sulfonyl]-piperidine
1-[4-(3,4-difluorobenzyl)-1,3-thiazol-2-yl]-4-[(4-methylphenyl)sulfonyl]-piperidine
1-[4-(3,5-difluorobenzyl)-1,3-thiazol-2-yl]-4-[(4-methylphenyl)sulfonyl]-piperidine
1-[4-(3,5-dichlorobenzyl)-1,3-thiazol-2-yl]-4-[(4-methylphenyl)sulfonyl]-piperidine
1-[4-(3,5-dimethylbenzyl)-1,3-thiazol-2-yl]-4-[(4-methylphenyl)sulfonyl]-piperidine
1-[4-(3-chloro-4-fluorobenzyl)-1,3-thiazol-2-yl]-4-[(4-methylphenyl)sulfonyl]-piperidine 1-[4-(3-chloro-5-fluorobenzyl)-1,3-thiazol-2-yl]-4-[(4-methylphenyl)sulfonyl]-piperidine
1-[4-(4-chloro-3-fluorobenzyl)-1,3-thiazol-2-yl]-4-[(4-methylphenyl)sulfonyl]-piperidine
1-[4-(3,4,5-trimethoxybenzyl)-1,3-thiazol-2-yl]-4-[(4-methylphenyl)sulfonyl]-piperidine
1-[4-(2,4,6-trimethylbenzyl)-1,3-thiazol-2-yl]-4-[(4-methylphenyl)sulfonyl]-piperidine
1-[4-benzyl-1,3-thiazol-2-yl]-4-[(4-chlorophenyl)sulfonyl]-piperidine
1-[4-(2-methylbenzyl)-1,3-thiazol-2-yl]-4-[(4-chlorophenyl)sulfonyl]-piperidine
1-[4-(2-methoxybenzyl)-1,3-thiazol-2-yl]-4-[(4-chlorophenyl)sulfonyl]-piperidine
1-[4-(3-methylbenzyl)-1,3-thiazol-2-yl]-4-[(4-chlorophenyl)sulfonyl]-piperidine
1-[4-(3-methoxybenzyl)-1,3-thiazol-2-yl]-4-[(4-chlorophenyl)sulfonyl]-piperidine
1-[4-(3-bromobenzyl)-1,3-thiazol-2-yl]-4-[(4-chlorophenyl)sulfonyl]-piperidine
1-[4-(4-chlorobenzyl)-1,3-thiazol-2-yl]-4-[(4-chlorophenyl)sulfonyl]-piperidine
1-[4-(4-methoxybenzyl)-1,3-thiazol-2-yl]-4-[(4-chlorophenyl)sulfonyl]-piperidine
1-[4-(4-methylbenzyl)-1,3-thiazol-2-yl]-4-[(4-chlorophenyl)sulfonyl]-piperidine
1-[4-(4-ethylbenzyl)-1,3-thiazol-2-yl]-4-[(4-chlorophenyl)sulfonyl]-piperidine
1-[4-(4-ethoxybenzyl)-1,3-thiazol-2-yl]-4-[(4-chlorophenyl)sulfonyl]-piperidine
1-[4-(4-propylbenzyl)-1,3-thiazol-2-yl]-4-[(4-chlorophenyl)sulfonyl]-piperidine
1-[4-(2,6-dimethylbenzyl)-1,3-thiazol-2-yl]-4-[(4-chlorophenyl)sulfonyl]-piperidine
1-[4-(2,3-dimethylbenzyl)-1,3-thiazol-2-yl]-4-[(4-chlorophenyl)sulfonyl]-piperidine
1-[4-(2,5-dimethylbenzyl)-1,3-thiazol-2-yl]-4-[(4-chlorophenyl)sulfonyl]-piperidine
1-[4-(2,4-dichlorobenzyl)-1,3-thiazol-2-yl]-4-[(4-chlorophenyl)sulfonyl]-piperidine
1-[4-(2,4-dimethoxybenzyl)-1,3-thiazol-2-yl]-4-[(4-chlorophenyl)sulfonyl]-piperidine
1-[4-(2,5-dimethoxybenzyl)-1,3-thiazol-2-yl]-4-[(4-chlorophenyl)sulfonyl]-piperidine
1-[4-(3,4-dimethoxybenzyl)-1,3-thiazol-2-yl]-4-[(4-chlorophenyl)sulfonyl]-piperidine
1-[4-(3,5-dimethoxybenzyl)-1,3-thiazol-2-yl]-4-[(4-chlorophenyl)sulfonyl]-piperidine
1-[4-(3,4-dichlorobenzyl)-1,3-thiazol-2-yl]-4-[(4-chlorophenyl)sulfonyl]-piperidine
1-[4-(3,4-dimethylbenzyl)-1,3-thiazol-2-yl]-4-[(4-chlorophenyl)sulfonyl]-piperidine
1-[4-(3,4-difluorobenzyl)-1,3-thiazol-2-yl]-4-[(4-chlorophenyl)sulfonyl]-piperidine
1-[4-(3,5-difluorobenzyl)-1,3-thiazol-2-yl]-4-[(4-chlorophenyl)sulfonyl]-piperidine
1-[4-(3,5-dichlorobenzyl)-1,3-thiazol-2-yl]-4-[(4-chlorophenyl)sulfonyl]-piperidine
1-[4-(3,5-dimethylbenzyl)-1,3-thiazol-2-yl]-4-[(4-chlorophenyl)sulfonyl]-piperidine
1-[4-(3-chloro-4-fluorobenzyl)-1,3-thiazol-2-yl]-4-[(4-chlorophenyl)sulfonyl]-piperidine
1-[4-(3-chloro-5-fluorobenzyl)-1,3-thiazol-2-yl]-4-[(4-chlorophenyl)sulfonyl]-piperidine
1-[4-(4-chloro-3-fluorobenzyl)-1,3-thiazol-2-yl]-4-[(4-chlorophenyl)sulfonyl]-piperidine
1-[4-(3,4,5-trimethoxybenzyl)-1,3-thiazol-2-yl]-4-[(4-chlorophenyl)sulfonyl]-piperidine
1-[4-(2,4,6-trimethylbenzyl)-1,3-thiazol-2-yl]-4-[(4-chlorophenyl)sulfonyl]-piperidine
1-[4-benzyl-1,3-thiazol-2-yl]-4-[(4-(trifluoromethoxy)phenyl)sulfonyl]-piperidine
1-[4-(2-methylbenzyl)-1,3-thiazol-2-yl]-4-[(4-(trifluoromethoxy)phenyl)sulfonyl]-piperidine
1-[4-(2-methoxybenzyl)-1,3-thiazol-2-yl]-4-[(4-(trifluoromethoxy)phenyl)sulfonyl]-piperidine
1-[4-(3-methylbenzyl)-1,3-thiazol-2-yl]-4-[(4-(trifluoromethoxy)phenyl)sulfonyl]-piperidine
1-[4-(3-methoxybenzyl)-1,3-thiazol-2-yl]-4-[(4-(trifluoromethoxy)phenyl)sulfonyl]-piperidine
1-[4-(3-bromobenzyl)-1,3-thiazol-2-yl]-4-[(4-(trifluoromethoxy)phenyl)sulfonyl]-piperidine
1-[4-(4-chlorobenzyl)-1,3-thiazol-2-yl]-4-[(4-(trifluoromethoxy)phenyl)sulfonyl]-piperidine
1-[4-(4-methoxybenzyl)-1,3-thiazol-2-yl]-4-[(4-(trifluoromethoxy)phenyl)sulfonyl]-piperidine
1-[4-(4-methylbenzyl)-1,3-thiazol-2-yl]-4-[(4-(trifluoromethoxy)phenyl)sulfonyl]-piperidine
1-[4-(4-ethylbenzyl)-1,3-thiazol-2-yl]-4-[(4-(trifluoromethoxy)phenyl)sulfonyl]-piperidine
1-[4-(4-ethoxybenzyl)-1,3-thiazol-2-yl]-4-[(4-(trifluoromethoxy)phenyl)sulfonyl]-piperidine
1-[4-(4-propylbenzyl)-1,3-thiazol-2-yl]-4-[(4-(trifluoromethoxy)phenyl)sulfonyl]-piperidine
1-[4-(2,6-dimethylbenzyl)-1,3-thiazol-2-yl]-4-[(4-(trifluoromethoxy)phenyl)sulfonyl]-piperidine
1-[4-(2,3-dimethylbenzyl)-1,3-thiazol-2-yl]-4-[(4-(trifluoromethoxy)phenyl)sulfonyl]-piperidine
1-[4-(2,5-dimethylbenzyl)-1,3-thiazol-2-yl]-4-[(4-(trifluoromethoxy)phenyl)sulfonyl]-piperidine
1-[4-(2,4-dichlorobenzyl)-1,3-thiazol-2-yl]-4-[(4-(trifluoromethoxy)phenyl)sulfonyl]-piperidine
1-[4-(2,4-dimethoxybenzyl)-1,3-thiazol-2-yl]-4-[(4-(trifluoromethoxy)phenyl)sulfonyl]-piperidine
1-[4-(2,5-dimethoxybenzyl)-1,3-thiazol-2-yl]-4-[(4-(trifluoromethoxy)phenyl)sulfonyl]-piperidine
1-[4-(3,4-dimethoxybenzyl)-1,3-thiazol-2-yl]-4-[(4-(trifluoromethoxy)phenyl)sulfonyl]-piperidine
1-[4-(3,5-dimethoxybenzyl)-1,3-thiazol-2-yl]-4-[(4-(trifluoromethoxy)phenyl)sulfonyl]-piperidine
1-[4-(3,4-dichlorobenzyl)-1,3-thiazol-2-yl]-4-[(4-(trifluoromethoxy)phenyl)sulfonyl]-piperidine
1-[4-(3,4-dimethylbenzyl)-1,3-thiazol-2-yl]-4-[(4-(trifluoromethoxy)phenyl)sulfonyl]-piperidine
1-[4-(3,4-difluorobenzyl)-1,3-thiazol-2-yl]-4-[(4-(trifluoromethoxy)phenyl)sulfonyl]-piperidine
1-[4-(3,5-difluorobenzyl)-1,3-thiazol-2-yl]-4-[(4-(trifluoromethoxy)phenyl)sulfonyl]-piperidine
1-[4-(3,5-dichlorobenzyl)-1,3-thiazol-2-yl]-4-[(4-(trifluoromethoxy)phenyl)sulfonyl]-piperidine
1-[4-(3,5-dimethylbenzyl)-1,3-thiazol-2-yl]-4-[(4-(trifluoromethoxy)phenyl)sulfonyl]-piperidine
1-[4-(3-chloro-4-fluorobenzyl)-1,3-thiazol-2-yl]-4-[(4-(trifluoromethoxy)phenyl)sulfonyl]-piperidine
1-[4-(3-chloro-5-fluorobenzyl)-1,3-thiazol-2-yl]-4-[(4-(trifluoromethoxy)phenyl)sulfonyl]-piperidine
1-[4-(4-chloro-3-fluorobenzyl)-1,3-thiazol-2-yl]-4-[(4-(trifluoromethoxy)phenyl)sulfonyl]-piperidine
1-[4-(3,4,5-trimethoxybenzyl)-1,3-thiazol-2-yl]-4-[(4-(trifluoromethoxy)phenyl)sulfonyl]-piperidine
1-[4-(2,4,6-trimethylbenzyl)-1,3-thiazol-2-yl]-4-[(4-(trifluoromethoxy)phenyl)sulfonyl]-piperidine 1-[4-benzyl-1,3-thiazol-2-yl]-4-[(4-tert-butylphenyl)sulfonyl]-piperidine
1-[4-(2-methylbenzyl)-1,3-thiazol-2-yl]-4-[(4-tert-butylphenyl)sulfonyl]-piperidine
1-[4-(2-methoxybenzyl)-1,3-thiazol-2-yl]-4-[(4-tert-butylphenyl)sulfonyl]-piperidine
1-[4-(3-methylbenzyl)-1,3-thiazol-2-yl]-4-[(4-tert-butylphenyl)sulfonyl]-piperidine
1-[4-(3-methoxybenzyl)-1,3-thiazol-2-yl]-4-[(4-tert-butylphenyl)sulfonyl]-piperidine
1-[4-(3-bromobenzyl)-1,3-thiazol-2-yl]-4-[(4-tert-butylphenyl)sulfonyl]-piperidine
1-[4-(4-chlorobenzyl)-1,3-thiazol-2-yl]-4-[(4-tert-butylphenyl)sulfonyl]-piperidine
1-[4-(4-methoxybenzyl)-1,3-thiazol-2-yl]-4-[(4-tert-butylphenyl)sulfonyl]-piperidine
1-[4-(4-methylbenzyl)-1,3-thiazol-2-yl]-4-[(4-tert-butylphenyl)sulfonyl]-piperidine
1-[4-(4-ethylbenzyl)-1,3-thiazol-2-yl]-4-[(4-tert-butylphenyl)sulfonyl]-piperidine
1-[4-(4-ethoxybenzyl)-1,3-thiazol-2-yl]-4-[(4-tert-butylphenyl)sulfonyl]-piperidine
1-[4-(4-propylbenzyl)-1,3-thiazol-2-yl]-4-[(4-tert-butylphenyl)sulfonyl]-piperidine
1-[4-(2,6-dimethylbenzyl)-1,3-thiazol-2-yl]-4-[(4-tert-butylphenyl)sulfonyl]-piperidine
1-[4-(2,3-dimethylbenzyl)-1,3-thiazol-2-yl]-4-[(4-tert-butylphenyl)sulfonyl]-piperidine
1-[4-(2,5-dimethylbenzyl)-1,3-thiazol-2-yl]-4-[(4-tert-butylphenyl)sulfonyl]-piperidine
1-[4-(2,4-dichlorobenzyl)-1,3-thiazol-2-yl]-4-[(4-tert-butylphenyl)sulfonyl]-piperidine
1-[4-(2,4-dimethoxybenzyl)-1,3-thiazol-2-yl]-4-[(4-tert-butylphenyl)sulfonyl]-piperidine
1-[4-(2,5-dimethoxybenzyl)-1,3-thiazol-2-yl]-4-[(4-tert-butylphenyl)sulfonyl]-piperidine
1-[4-(3,4-dimethoxybenzyl)-1,3-thiazol-2-yl]-4-[(4-tert-butylphenyl)sulfonyl]-piperidine
1-[4-(3,5-dimethoxybenzyl)-1,3-thiazol-2-yl]-4-[(4-tert-butylphenyl)sulfonyl]-piperidine
1-[4-(3,4-dichlorobenzyl)-1,3-thiazol-2-yl]-4-[(4-tert-butylphenyl)sulfonyl]-piperidine
1-[4-(3,4-dimethylbenzyl)-1,3-thiazol-2-yl]-4-[(4-tert-butylphenyl)sulfonyl]-piperidine
1-[4-(3,4-difluorobenzyl)-1,3-thiazol-2-yl]-4-[(4-tert-butylphenyl)sulfonyl]-piperidine
1-[4-(3,5-difluorobenzyl)-1,3-thiazol-2-yl]-4-[(4-tert-butylphenyl)sulfonyl]-piperidine
1-[4-(3,5-dichlorobenzyl)-1,3-thiazol-2-yl]-4-[(4-tert-butylphenyl)sulfonyl]-piperidine
1-[4-(3,5-dimethylbenzyl)-1,3-thiazol-2-yl]-4-[(4-tert-butylphenyl)sulfonyl]-piperidine
1-[4-(3-chloro-4-fluorobenzyl)-1,3-thiazol-2-yl]-4-[(4-tert-butylphenyl)sulfonyl]-piperidine
1-[4-(3-chloro-5-fluorobenzyl)-1,3-thiazol-2-yl]-4-[(4-tert-butylphenyl)sulfonyl]-piperidine
1-[4-(4-chloro-3-fluorobenzyl)-1,3-thiazol-2-yl]-4-[(4-tert-butylphenyl)sulfonyl]-piperidine
1-[4-(3,4,5-trimethoxybenzyl)-1,3-thiazol-2-yl]-4-[(4-tert-butylphenyl)sulfonyl]-piperidine
1-[4-(2,4,6-trimethylbenzyl)-1,3-thiazol-2-yl]-4-[(4-tert-butylphenyl)sulfonyl]-piperidine
1-[4-benzyl-1,3-thiazol-2-yl]-4-[(pentafluorophenyl)sulfonyl]-piperidine
1-[4-(2-methylbenzyl)-1,3-thiazol-2-yl]-4-[(pentafluorophenyl)sulfonyl]-piperidine
1-[4-(2-methoxybenzyl)-1,3-thiazol-2-yl]-4-[(pentafluorophenyl)sulfonyl]-piperidine
1-[4-(3-methylbenzyl)-1,3-thiazol-2-yl]-4-[(pentafluorophenyl)sulfonyl]-piperidine
1-[4-(3-methoxybenzyl)-1,3-thiazol-2-yl]-4-[(pentafluorophenyl)sulfonyl]-piperidine
1-[4-(3-bromobenzyl)-1,3-thiazol-2-yl]-4-[(pentafluorophenyl)sulfonyl]-piperidine
1-[4-(4-chlorobenzyl)-1,3-thiazol-2-yl]-4-[(pentafluorophenyl)sulfonyl]-piperidine
1-[4-(4-methoxybenzyl)-1,3-thiazol-2-yl]-4-[(pentafluorophenyl)sulfonyl]-piperidine
1-[4-(4-methylbenzyl)-1,3-thiazol-2-yl]-4-[(pentafluorophenyl)sulfonyl]-piperidine
1-[4-(4-ethylbenzyl)-1,3-thiazol-2-yl]-4-[(pentafluorophenyl)sulfonyl]-piperidine
1-[4-(4-ethoxybenzyl)-1,3-thiazol-2-yl]-4-[(pentafluorophenyl)sulfonyl]-piperidine
1-[4-(4-propylbenzyl)-1,3-thiazol-2-yl]-4-[(pentafluorophenyl)sulfonyl]-piperidine
1-[4-(2,6-dimethylbenzyl)-1,3-thiazol-2-yl]-4-[(pentafluorophenyl)sulfonyl]-piperidine
1-[4-(2,3-dimethylbenzyl)-1,3-thiazol-2-yl]-4-[(pentafluorophenyl)sulfonyl]-piperidine
1-[4-(2,5-dimethylbenzyl)-1,3-thiazol-2-yl]-4-[(pentafluorophenyl)sulfonyl]-piperidine
1-[4-(2,4-dichlorobenzyl)-1,3-thiazol-2-yl]-4-[(pentafluorophenyl)sulfonyl]-piperidine
1-[4-(2,4-dimethoxybenzyl)-1,3-thiazol-2-yl]-4-[(pentafluorophenyl)sulfonyl]-piperidine
1-[4-(2,5-dimethoxybenzyl)-1,3-thiazol-2-yl]-4-[(pentafluorophenyl)sulfonyl]-piperidine
1-[4-(3,4-dimethoxybenzyl)-1,3-thiazol-2-yl]-4-[(pentafluorophenyl)sulfonyl]-piperidine
1-[4-(3,5-dimethoxybenzyl)-1,3-thiazol-2-yl]-4-[(pentafluorophenyl)sulfonyl]-piperidine
1-[4-(3,4-dichlorobenzyl)-1,3-thiazol-2-yl]-4-[(pentafluorophenyl)sulfonyl]-piperidine
1-[4-(3,4-dimethylbenzyl)-1,3-thiazol-2-yl]-4-[(pentafluorophenyl)sulfonyl]-piperidine
1-[4-(3,4-difluorobenzyl)-1,3-thiazol-2-yl]-4-[(pentafluorophenyl)sulfonyl]-piperidine
1-[4-(3,5-difluorobenzyl)-1,3-thiazol-2-yl]-4-[(pentafluorophenyl)sulfonyl]-piperidine
1-[4-(3,5-dichlorobenzyl)-1,3-thiazol-2-yl]-4-[(pentafluorophenyl)sulfonyl]-piperidine
1-[4-(3,5-dimethylbenzyl)-1,3-thiazol-2-yl]-4-[(pentafluorophenyl)sulfonyl]-piperidine
1-[4-(3-chloro-4-fluorobenzyl)-1,3-thiazol-2-yl]-4-[(pentafluorophenyl)sulfonyl]-piperidine
1-[4-(3-chloro-5-fluorobenzyl)-1,3-thiazol-2-yl]-4-[(pentafluorophenyl)sulfonyl]-piperidine
1-[4-(4-chloro-3-fluorobenzyl)-1,3-thiazol-2-yl]-4-[(pentafluorophenyl)sulfonyl]-piperidine
1-[4-(3,4,5-trimethoxybenzyl)-1,3-thiazol-2-yl]-4-[(pentafluorophenyl)sulfonyl]-piperidine
1-[4-(2,4,6-trimethylbenzyl)-1,3-thiazol-2-yl]-4-[(pentafluorophenyl)sulfonyl]-piperidine
1-[4-benzyl-1,3-thiazol-2-yl]-4-[(2,4,6-trimethylphenyl)sulfonyl]-piperidine
1-[4-(2-methylbenzyl)-1,3-thiazol-2-yl]-4-[(2,4,6-trimethylphenyl)sulfonyl]-piperidine
1-[4-(2-methoxybenzyl)-1,3-thiazol-2-yl]-4-[(2,4,6-trimethylphenyl)sulfonyl]-piperidine
1-[4-(3-methylbenzyl)-1,3-thiazol-2-yl]-4-[(2,4,6-trimethylphenyl)sulfonyl]-piperidine 1-[4-(3-methoxybenzyl)-1,3-thiazol-2-yl]-4-[(2,4,6-trimethylphenyl)sulfonyl]-piperidine
1-[4-(3-bromobenzyl)-1,3-thiazol-2-yl]-4-[(2,4,6-trimethylphenyl)sulfonyl]-piperidine
1-[4-(4-chlorobenzyl)-1,3-thiazol-2-yl]-4-[(2,4,6-trimethylphenyl)sulfonyl]-piperidine
1-[4-(4-methoxybenzyl)-1,3-thiazol-2-yl]-4-[(2,4,6-trimethylphenyl)sulfonyl]-piperidine
1-[4-(4-methylbenzyl)-1,3-thiazol-2-yl]-4-[(2,4,6-trimethylphenyl)sulfonyl]-piperidine
1-[4-(4-ethylbenzyl)-1,3-thiazol-2-yl]-4-[(2,4,6-trimethylphenyl)sulfonyl]-piperidine
1-[4-(4-ethoxybenzyl)-1,3-thiazol-2-yl]-4-[(2,4,6-trimethylphenyl)sulfonyl]-piperidine
1-[4-(4-propylbenzyl)-1,3-thiazol-2-yl]-4-[(2,4,6-trimethylphenyl)sulfonyl]-piperidine
1-[4-(2,6-dimethylbenzyl)-1,3-thiazol-2-yl]-4-[(2,4,6-trimethylphenyl)sulfonyl]-piperidine
1-[4-(2,3-dimethylbenzyl)-1,3-thiazol-2-yl]-4-[(2,4,6-trimethylphenyl)sulfonyl]-piperidine
1-[4-(2,5-dimethylbenzyl)-1,3-thiazol-2-yl]-4-[(2,4,6-trimethylphenyl)sulfonyl]-piperidine
1-[4-(2,4-dichlorobenzyl)-1,3-thiazol-2-yl]-4-[(2,4,6-trimethylphenyl)sulfonyl]-piperidine
1-[4-(2,4-dimethoxybenzyl)-1,3-thiazol-2-yl]-4-[(2,4,6-trimethylphenyl)sulfonyl]-piperidine
1-[4-(2,5-dimethoxybenzyl)-1,3-thiazol-2-yl]-4-[(2,4,6-trimethylphenyl)sulfonyl]-piperidine
1-[4-(3,4-dimethoxybenzyl)-1,3-thiazol-2-yl]-4-[(2,4,6-trimethylphenyl)sulfonyl]-piperidine
1-[4-(3,5-dimethoxybenzyl)-1,3-thiazol-2-yl]-4-[(2,4,6-trimethylphenyl)sulfonyl]-piperidine
1-[4-(3,4-dichlorobenzyl)-1,3-thiazol-2-yl]-4-[(2,4,6-trimethylphenyl)sulfonyl]-piperidine
1-[4-(3,4-dimethylbenzyl)-1,3-thiazol-2-yl]-4-[(2,4,6-trimethylphenyl)sulfonyl]-piperidine
1-[4-(3,4-difluorobenzyl)-1,3-thiazol-2-yl]-4-[(2,4,6-trimethylphenyl)sulfonyl]-piperidine
1-[4-(3,5-difluorobenzyl)-1,3-thiazol-2-yl]-4-[(2,4,6-trimethylphenyl)sulfonyl]-piperidine
1-[4-(3,5-dichlorobenzyl)-1,3-thiazol-2-yl]-4-[(2,4,6-trimethylphenyl)sulfonyl]-piperidine
1-[4-(3,5-dimethylbenzyl)-1,3-thiazol-2-yl]-4-[(2,4,6-trimethylphenyl)sulfonyl]-piperidine
1-[4-(3-chloro-4-fluorobenzyl)-1,3-thiazol-2-yl]-4-[(2,4,6-trimethylphenyl)sulfonyl]-piperidine
1-[4-(3-chloro-5-fluorobenzyl)-1,3-thiazol-2-yl]-4-[(2,4,6-trimethylphenyl)sulfonyl]-piperidine
1-[4-(4-chloro-3-fluorobenzyl)-1,3-thiazol-2-yl]-4-[(2,4,6-trimethylphenyl)sulfonyl]-piperidine
1-[4-(3,4,5-trimethoxybenzyl)-1,3-thiazol-2-yl]-4-[(2,4,6-trimethylphenyl)sulfonyl]-piperidine
1-[4-(2,4,6-trimethylbenzyl)-1,3-thiazol-2-yl]-4-[(2,4,6-trimethylphenyl)sulfonyl]-piperidine
1-[4-benzyl-1,3-thiazol-2-yl]-4-[(2,4,6-tri-iso-propylphenyl)sulfonyl]-piperidine
1-[4-(2-methylbenzyl)-1,3-thiazol-2-yl]-4-[(2,4,6-tri-iso-propylphenyl)sulfonyl]-piperidine
1-[4-(2-methoxybenzyl)-1,3-thiazol-2-yl]-4-[(2,4,6-tri-iso-propylphenyl)sulfonyl]-piperidine
1-[4-(3-methylbenzyl)-1,3-thiazol-2-yl]-4-[(2,4,6-tri-iso-propylphenyl)sulfonyl]-piperidine
1-[4-(3-methoxybenzyl)-1,3-thiazol-2-yl]-4-[(2,4,6-tri-iso-propylphenyl)sulfonyl]-piperidine
1-[4-(3-bromobenzyl)-1,3-thiazol-2-yl]-4-[(2,4,6-tri-iso-propylphenyl)sulfonyl]-piperidine
1-[4-(4-chlorobenzyl)-1,3-thiazol-2-yl]-4-[(2,4,6-tri-iso-propylphenyl)sulfonyl]-piperidine
1-[4-(4-methoxybenzyl)-1,3-thiazol-2-yl]-4-[(2,4,6-tri-iso-propylphenyl)sulfonyl]-piperidine
1-[4-(4-methylbenzyl)-1,3-thiazol-2-yl]-4-[(2,4,6-tri-iso-propylphenyl)sulfonyl]-piperidine
1-[4-(4-ethylbenzyl)-1,3-thiazol-2-yl]-4-[(2,4,6-tri-iso-propylphenyl)sulfonyl]-piperidine
1-[4-(4-ethoxybenzyl)-1,3-thiazol-2-yl]-4-[(2,4,6-tri-iso-propylphenyl)sulfonyl]-piperidine
1-[4-(4-propylbenzyl)-1,3-thiazol-2-yl]-4-[(2,4,6-tri-iso-propylphenyl)sulfonyl]-piperidine
1-[4-(2,6-dimethylbenzyl)-1,3-thiazol-2-yl]-4-[(2,4,6-tri-iso-propylphenyl)sulfonyl]-piperidine
1-[4-(2,3-dimethylbenzyl)-1,3-thiazol-2-yl]-4-[(2,4,6-tri-iso-propylphenyl)sulfonyl]-piperidine
1-[4-(2,5-dimethylbenzyl)-1,3-thiazol-2-yl]-4-[(2,4,6-tri-iso-propylphenyl)sulfonyl]-piperidine
1-[4-(2,4-dichlorobenzyl)-1,3-thiazol-2-yl]-4-[(2,4,6-tri-iso-propylphenyl)sulfonyl]-piperidine
1-[4-(2,4-dimethoxybenzyl)-1,3-thiazol-2-yl]-4-[(2,4,6-tri-iso-propylphenyl)sulfonyl]-piperidine
1-[4-(2,5-dimethoxybenzyl)-1,3-thiazol-2-yl]-4-[(2,4,6-tri-iso-propylphenyl)sulfonyl]-piperidine
1-[4-(3,4-dimethoxybenzyl)-1,3-thiazol-2-yl]-4-[(2,4,6-tri-iso-propylphenyl)sulfonyl]-piperidine
1-[4-(3,5-dimethoxybenzyl)-1,3-thiazol-2-yl]-4-[(2,4,6-tri-iso-propylphenyl)sulfonyl]-piperidine
1-[4-(3,4-dichlorobenzyl)-1,3-thiazol-2-yl]-4-[(2,4,6-tri-iso-propylphenyl)sulfonyl]-piperidine
1-[4-(3,4-dimethylbenzyl)-1,3-thiazol-2-yl]-4-[(2,4,6-tri-iso-propylphenyl)sulfonyl]-piperidine
1-[4-(3,4-difluorobenzyl)-1,3-thiazol-2-yl]-4-[(2,4,6-tri-iso-propylphenyl)sulfonyl]-piperidine
1-[4-(3,5-difluorobenzyl)-1,3-thiazol-2-yl]-4-[(2,4,6-tri-iso-propylphenyl)sulfonyl]-piperidine
1-[4-(3,5-dichlorobenzyl)-1,3-thiazol-2-yl]-4-[(2,4,6-tri-iso-propylphenyl)sulfonyl]-piperidine
1-[4-(3,5-dimethylbenzyl)-1,3-thiazol-2-yl]-4-[(2,4,6-tri-iso-propylphenyl)sulfonyl]-piperidine
1-[4-(3-chloro-4-fluorobenzyl)-1,3-thiazol-2-yl]-4-[(2,4,6-tri-iso-propylphenyl)sulfonyl]-piperidine
1-[4-(3-chloro-5-fluorobenzyl)-1,3-thiazol-2-yl]-4-[(2,4,6-tri-iso-propylphenyl)sulfonyl]-piperidine
1-[4-(4-chloro-3-fluorobenzyl)-1,3-thiazol-2-yl]-4-[(2,4,6-tri-iso-propylphenyl)sulfonyl]-piperidine
1-[4-(3,4,5-trimethoxybenzyl)-1,3-thiazol-2-yl]-4-[(2,4,6-tri-iso-propylphenyl)sulfonyl]-piperidine
1-[4-(2,4,6-trimethylbenzyl)-1,3-thiazol-2-yl]-4-[(2,4,6-tri-iso-propylphenyl)sulfonyl]-piperidine
1-[4-benzyl-1,3-thiazol-2-yl]-4-[(2,4-dichlorophenyl)sulfonyl]-piperidine
1-[4-(2-methylbenzyl)-1,3-thiazol-2-yl]-4-[(2,4-dichlorophenyl)sulfonyl]-piperidine
1-[4-(2-methoxybenzyl)-1,3-thiazol-2-yl]-4-[(2,4-dichlorophenyl)sulfonyl]-piperidine
1-[4-(3-methylbenzyl)-1,3-thiazol-2-yl]-4-[(2,4-dichlorophenyl)sulfonyl]-piperidine
1-[4-(3-methoxybenzyl)-1,3-thiazol-2-yl]-4-[(2,4-dichlorophenyl)sulfonyl]-piperidine
1-[4-(3-bromobenzyl)-1,3-thiazol-2-yl]-4-[(2,4-dichlorophenyl)sulfonyl]-piperidine
1-[4-(4-chlorobenzyl)-1,3-thiazol-2-yl]-4-[(2,4-dichlorophenyl)sulfonyl]-piperidine
1-[4-(4-methoxybenzyl)-1,3-thiazol-2-yl]-4-[(2,4-dichlorophenyl)sulfonyl]-piperidine 1-[4-(4-methylbenzyl)-1,3-thiazol-2-yl]-4-[(2,4-dichlorophenyl)sulfonyl]-piperidine
1-[4-(4-ethylbenzyl)-1,3-thiazol-2-yl]-4-[(2,4-dichlorophenyl)sulfonyl]-piperidine
1-[4-(4-ethoxybenzyl)-1,3-thiazol-2-yl]-4-[(2,4-dichlorophenyl)sulfonyl]-piperidine
1-[4-(4-propylbenzyl)-1,3-thiazol-2-yl]-4-[(2,4-dichlorophenyl)sulfonyl]-piperidine
1-[4-(2,6-dimethylbenzyl)-1,3-thiazol-2-yl]-4-[(2,4-dichlorophenyl)sulfonyl]-piperidine
1-[4-(2,3-dimethylbenzyl)-1,3-thiazol-2-yl]-4-[(2,4-dichlorophenyl)sulfonyl]-piperidine
1-[4-(2,5-dimethylbenzyl)-1,3-thiazol-2-yl]-4-[(2,4-dichlorophenyl)sulfonyl]-piperidine
1-[4-(2,4-dichlorobenzyl)-1,3-thiazol-2-yl]-4-[(2,4-dichlorophenyl)sulfonyl]-piperidine
1-[4-(2,4-dimethoxybenzyl)-1,3-thiazol-2-yl]-4-[(2,4-dichlorophenyl)sulfonyl]-piperidine
1-[4-(2,5-dimethoxybenzyl)-1,3-thiazol-2-yl]-4-[(2,4-dichlorophenyl)sulfonyl]-piperidine
1-[4-(3,4-dimethoxybenzyl)-1,3-thiazol-2-yl]-4-[(2,4-dichlorophenyl)sulfonyl]-piperidine
1-[4-(3,5-dimethoxybenzyl)-1,3-thiazol-2-yl]-4-[(2,4-dichlorophenyl)sulfonyl]-piperidine
1-[4-(3,4-dichlorobenzyl)-1,3-thiazol-2-yl]-4-[(2,4-dichlorophenyl)sulfonyl]-piperidine
1-[4-(3,4-dimethylbenzyl)-1,3-thiazol-2-yl]-4-[(2,4-dichlorophenyl)sulfonyl]-piperidine
1-[4-(3,4-difluorobenzyl)-1,3-thiazol-2-yl]-4-[(2,4-dichlorophenyl)sulfonyl]-piperidine
1-[4-(3,5-difluorobenzyl)-1,3-thiazol-2-yl]-4-[(2,4-dichlorophenyl)sulfonyl]-piperidine
1-[4-(3,5-dichlorobenzyl)-1,3-thiazol-2-yl]-4-[(2,4-dichlorophenyl)sulfonyl]-piperidine
1-[4-(3,5-dimethylbenzyl)-1,3-thiazol-2-yl]-4-[(2,4-dichlorophenyl)sulfonyl]-piperidine
1-[4-(3-chloro-4-fluorobenzyl)-1,3-thiazol-2-yl]-4-[(2,4-dichlorophenyl)sulfonyl]-piperidine
1-[4-(3-chloro-5-fluorobenzyl)-1,3-thiazol-2-yl]-4-[(2,4-dichlorophenyl)sulfonyl]-piperidine
1-[4-(4-chloro-3-fluorobenzyl)-1,3-thiazol-2-yl]-4-[(2,4-dichlorophenyl)sulfonyl]-piperidine
1-[4-(3,4,5-trimethoxybenzyl)-1,3-thiazol-2-yl]-4-[(2,4-dichlorophenyl)sulfonyl]-piperidine
1-[4-(2,4,6-trimethylbenzyl)-1,3-thiazol-2-yl]-4-[(2,4-dichlorophenyl)sulfonyl]-piperidine
1-[4-benzyl-1,3-thiazol-2-yl]-4-[(2,5-dichlorophenyl)sulfonyl]-piperidine
1-[4-(2-methylbenzyl)-1,3-thiazol-2-yl]-4-[(2,5-dichlorophenyl)sulfonyl]-piperidine
1-[4-(2-methoxybenzyl)-1,3-thiazol-2-yl]-4-[(2,5-dichlorophenyl)sulfonyl]-piperidine
1-[4-(3-methylbenzyl)-1,3-thiazol-2-yl]-4-[(2,5-dichlorophenyl)sulfonyl]-piperidine
1-[4-(3-methoxybenzyl)-1,3-thiazol-2-yl]-4-[(2,5-dichlorophenyl)sulfonyl]-piperidine
1-[4-(3-bromobenzyl)-1,3-thiazol-2-yl]-4-[(2,5-dichlorophenyl)sulfonyl]-piperidine
1-[4-(4-chlorobenzyl)-1,3-thiazol-2-yl]-4-[(2,5-dichlorophenyl)sulfonyl]-piperidine
1-[4-(4-methoxybenzyl)-1,3-thiazol-2-yl]-4-[(2,5-dichlorophenyl)sulfonyl]-piperidine
1-[4-(4-methylbenzyl)-1,3-thiazol-2-yl]-4-[(2,5-dichlorophenyl)sulfonyl]-piperidine
1-[4-(4-ethylbenzyl)-1,3-thiazol-2-yl]-4-[(2,5-dichlorophenyl)sulfonyl]-piperidine
1-[4-(4-ethoxybenzyl)-1,3-thiazol-2-yl]-4-[(2,5-dichlorophenyl)sulfonyl]-piperidine
1-[4-(4-propylbenzyl)-1,3-thiazol-2-yl]-4-[(2,5-dichlorophenyl)sulfonyl]-piperidine
1-[4-(2,6-dimethylbenzyl)-1,3-thiazol-2-yl]-4-[(2,5-dichlorophenyl)sulfonyl]-piperidine
1-[4-(2,3-dimethylbenzyl)-1,3-thiazol-2-yl]-4-[(2,5-dichlorophenyl)sulfonyl]-piperidine
1-[4-(2,5-dimethylbenzyl)-1,3-thiazol-2-yl]-4-[(2,5-dichlorophenyl)sulfonyl]-piperidine
1-[4-(2,4-dichlorobenzyl)-1,3-thiazol-2-yl]-4-[(2,5-dichlorophenyl)sulfonyl]-piperidine
1-[4-(2,4-dimethoxybenzyl)-1,3-thiazol-2-yl]-4-[(2,5-dichlorophenyl)sulfonyl]-piperidine
1-[4-(2,5-dimethoxybenzyl)-1,3-thiazol-2-yl]-4-[(2,5-dichlorophenyl)sulfonyl]-piperidine
1-[4-(3,4-dimethoxybenzyl)-1,3-thiazol-2-yl]-4-[(2,5-dichlorophenyl)sulfonyl]-piperidine
1-[4-(3,5-dimethoxybenzyl)-1,3-thiazol-2-yl]-4-[(2,5-dichlorophenyl)sulfonyl]-piperidine
1-[4-(3,4-dichlorobenzyl)-1,3-thiazol-2-yl]-4-[(2,5-dichlorophenyl)sulfonyl]-piperidine
1-[4-(3,4-dimethylbenzyl)-1,3-thiazol-2-yl]-4-[(2,5-dichlorophenyl)sulfonyl]-piperidine
1-[4-(3,4-difluorobenzyl)-1,3-thiazol-2-yl]-4-[(2,5-dichlorophenyl)sulfonyl]-piperidine
1-[4-(3,5-difluorobenzyl)-1,3-thiazol-2-yl]-4-[(2,5-dichlorophenyl)sulfonyl]-piperidine
1-[4-(3,5-dichlorobenzyl)-1,3-thiazol-2-yl]-4-[(2,5-dichlorophenyl)sulfonyl]-piperidine
1-[4-(3,5-dimethylbenzyl)-1,3-thiazol-2-yl]-4-[(2,5-dichlorophenyl)sulfonyl]-piperidine
1-[4-(3-chloro-4-fluorobenzyl)-1,3-thiazol-2-yl]-4-[(2,5-dichlorophenyl)sulfonyl]-piperidine
1-[4-(3-chloro-5-fluorobenzyl)-1,3-thiazol-2-yl]-4-[(2,5-dichlorophenyl)sulfonyl]-piperidine
1-[4-(4-chloro-3-fluorobenzyl)-1,3-thiazol-2-yl]-4-[(2,5-dichlorophenyl)sulfonyl]-piperidine
1-[4-(3,4,5-trimethoxybenzyl)-1,3-thiazol-2-yl]-4-[(2,5-dichlorophenyl)sulfonyl]-piperidine
1-[4-(2,4,6-trimethylbenzyl)-1,3-thiazol-2-yl]-4-[(2,5-dichlorophenyl)sulfonyl]-piperidine
1-[4-benzyl-1,3-thiazol-2-yl]-4-[(3,4-dichlorophenyl)sulfonyl]-piperidine
1-[4-(2-methylbenzyl)-1,3-thiazol-2-yl]-4-[(3,4-dichlorophenyl)sulfonyl]-piperidine
1-[4-(2-methoxybenzyl)-1,3-thiazol-2-yl]-4-[(3,4-dichlorophenyl)sulfonyl]-piperidine
1-[4-(3-methylbenzyl)-1,3-thiazol-2-yl]-4-[(3,4-dichlorophenyl)sulfonyl]-piperidine
1-[4-(3-methoxybenzyl)-1,3-thiazol-2-yl]-4-[(3,4-dichlorophenyl)sulfonyl]-piperidine
1-[4-(3-bromobenzyl)-1,3-thiazol-2-yl]-4-[(3,4-dichlorophenyl)sulfonyl]-piperidine
1-[4-(4-chlorobenzyl)-1,3-thiazol-2-yl]-4-[(3,4-dichlorophenyl)sulfonyl]-piperidine
1-[4-(4-methoxybenzyl)-1,3-thiazol-2-yl]-4-[(3,4-dichlorophenyl)sulfonyl]-piperidine
1-[4-(4-methylbenzyl)-1,3-thiazol-2-yl]-4-[(3,4-dichlorophenyl)sulfonyl]-piperidine
1-[4-(4-ethylbenzyl)-1,3-thiazol-2-yl]-4-[(3,4-dichlorophenyl)sulfonyl]-piperidine
1-[4-(4-ethoxybenzyl)-1,3-thiazol-2-yl]-4-[(3,4-dichlorophenyl)sulfonyl]-piperidine
1-[4-(4-propylbenzyl)-1,3-thiazol-2-yl]-4-[(3,4-dichlorophenyl)sulfonyl]-piperidine 1-[4-(2,6-dimethylbenzyl)-1,3-thiazol-2-yl]-4-[(3,4-dichlorophenyl)sulfonyl]-piperidine
1-[4-(2,3-dimethylbenzyl)-1,3-thiazol-2-yl]-4-[(3,4-dichlorophenyl)sulfonyl]-piperidine
1-[4-(2,5-dimethylbenzyl)-1,3-thiazol-2-yl]-4-[(3,4-dichlorophenyl)sulfonyl]-piperidine
1-[4-(2,4-dichlorobenzyl)-1,3-thiazol-2-yl]-4-[(3,4-dichlorophenyl)sulfonyl]-piperidine
1-[4-(2,4-dimethoxybenzyl)-1,3-thiazol-2-yl]-4-[(3,4-dichlorophenyl)sulfonyl]-piperidine
1-[4-(2,5-dimethoxybenzyl)-1,3-thiazol-2-yl]-4-[(3,4-dichlorophenyl)sulfonyl]-piperidine
1-[4-(3,4-dimethoxybenzyl)-1,3-thiazol-2-yl]-4-[(3,4-dichlorophenyl)sulfonyl]-piperidine
1-[4-(3,5-dimethoxybenzyl)-1,3-thiazol-2-yl]-4-[(3,4-dichlorophenyl)sulfonyl]-piperidine
1-[4-(3,4-dichlorobenzyl)-1,3-thiazol-2-yl]-4-[(3,4-dichlorophenyl)sulfonyl]-piperidine
1-[4-(3,4-dimethylbenzyl)-1,3-thiazol-2-yl]-4-[(3,4-dichlorophenyl)sulfonyl]-piperidine
1-[4-(3,4-difluorobenzyl)-1,3-thiazol-2-yl]-4-[(3,4-dichlorophenyl)sulfonyl]-piperidine
1-[4-(3,5-difluorobenzyl)-1,3-thiazol-2-yl]-4-[(3,4-dichlorophenyl)sulfonyl]-piperidine
1-[4-(3,5-dichlorobenzyl)-1,3-thiazol-2-yl]-4-[(3,4-dichlorophenyl)sulfonyl]-piperidine
1-[4-(3,5-dimethylbenzyl)-1,3-thiazol-2-yl]-4-[(3,4-dichlorophenyl)sulfonyl]-piperidine
1-[4-(3-chloro-4-fluorobenzyl)-1,3-thiazol-2-yl]-4-[(3,4-dichlorophenyl)sulfonyl]-piperidine
1-[4-(3-chloro-5-fluorobenzyl)-1,3-thiazol-2-yl]-4-[(3,4-dichlorophenyl)sulfonyl]-piperidine
1-[4-(4-chloro-3-fluorobenzyl)-1,3-thiazol-2-yl]-4-[(3,4-dichlorophenyl)sulfonyl]-piperidine
1-[4-(3,4,5-trimethoxybenzyl)-1,3-thiazol-2-yl]-4-[(3,4-dichlorophenyl)sulfonyl]-piperidine
1-[4-(2,4,6-trimethylbenzyl)-1,3-thiazol-2-yl]-4-[(3,4-dichlorophenyl)sulfonyl]-piperidine
1-[4-benzyl-1,3-thiazol-2-yl]-4-[(3,4-dimethoxyphenyl)sulfonyl]-piperidine
1-[4-(2-methylbenzyl)-1,3-thiazol-2-yl]-4-[(3,4-dimethoxyphenyl)sulfonyl]-piperidine
1-[4-(2-methoxybenzyl)-1,3-thiazol-2-yl]-4-[(3,4-dimethoxyphenyl)sulfonyl]-piperidine
1-[4-(3-methylbenzyl)-1,3-thiazol-2-yl]-4-[(3,4-dimethoxyphenyl)sulfonyl]-piperidine
1-[4-(3-methoxybenzyl)-1,3-thiazol-2-yl]-4-[(3,4-dimethoxyphenyl)sulfonyl]-piperidine
1-[4-(3-bromobenzyl)-1,3-thiazol-2-yl]-4-[(3,4-dimethoxyphenyl)sulfonyl]-piperidine
1-[4-(4-chlorobenzyl)-1,3-thiazol-2-yl]-4-[(3,4-dimethoxyphenyl)sulfonyl]-piperidine
1-[4-(4-methoxybenzyl)-1,3-thiazol-2-yl]-4-[(3,4-dimethoxyphenyl)sulfonyl]-piperidine
1-[4-(4-methylbenzyl)-1,3-thiazol-2-yl]-4-[(3,4-dimethoxyphenyl)sulfonyl]-piperidine
1-[4-(4-ethylbenzyl)-1,3-thiazol-2-yl]-4-[(3,4-dimethoxyphenyl)sulfonyl]-piperidine
1-[4-(4-ethoxybenzyl)-1,3-thiazol-2-yl]-4-[(3,4-dimethoxyphenyl)sulfonyl]-piperidine
1-[4-(4-propylbenzyl)-1,3-thiazol-2-yl]-4-[(3,4-dimethoxyphenyl)sulfonyl]-piperidine
1-[4-(2,6-dimethylbenzyl)-1,3-thiazol-2-yl]-4-[(3,4-dimethoxyphenyl)sulfonyl]-piperidine
1-[4-(2,3-dimethylbenzyl)-1,3-thiazol-2-yl]-4-[(3,4-dimethoxyphenyl)sulfonyl]-piperidine
1-[4-(2,5-dimethylbenzyl)-1,3-thiazol-2-yl]-4-[(3,4-dimethoxyphenyl)sulfonyl]-piperidine
1-[4-(2,4-dichlorobenzyl)-1,3-thiazol-2-yl]-4-[(3,4-dimethoxyphenyl)sulfonyl]-piperidine
1-[4-(2,4-dimethoxybenzyl)-1,3-thiazol-2-yl]-4-[(3,4-dimethoxyphenyl)sulfonyl]-piperidine
1-[4-(2,5-dimethoxybenzyl)-1,3-thiazol-2-yl]-4-[(3,4-dimethoxyphenyl)sulfonyl]-piperidine
1-[4-(3,4-dimethoxybenzyl)-1,3-thiazol-2-yl]-4-[(3,4-dimethoxyphenyl)sulfonyl]-piperidine
1-[4-(3,5-dimethoxybenzyl)-1,3-thiazol-2-yl]-4-[(3,4-dimethoxyphenyl)sulfonyl]-piperidine
1-[4-(3,4-dichlorobenzyl)-1,3-thiazol-2-yl]-4-[(3,4-dimethoxyphenyl)sulfonyl]-piperidine
1-[4-(3,4-dimethylbenzyl)-1,3-thiazol-2-yl]-4-[(3,4-dimethoxyphenyl)sulfonyl]-piperidine
1-[4-(3,4-difluorobenzyl)-1,3-thiazol-2-yl]-4-[(3,4-dimethoxyphenyl)sulfonyl]-piperidine
1-[4-(3,5-difluorobenzyl)-1,3-thiazol-2-yl]-4-[(3,4-dimethoxyphenyl)sulfonyl]-piperidine
1-[4-(3,5-dichlorobenzyl)-1,3-thiazol-2-yl]-4-[(3,4-dimethoxyphenyl)sulfonyl]-piperidine
1-[4-(3,5-dimethylbenzyl)-1,3-thiazol-2-yl]-4-[(3,4-dimethoxyphenyl)sulfonyl]-piperidine
1-[4-(3-chloro-4-fluorobenzyl)-1,3-thiazol-2-yl]-4-[(3,4-dimethoxyphenyl)sulfonyl]-piperidine
1-[4-(3-chloro-5-fluorobenzyl)-1,3-thiazol-2-yl]-4-[(3,4-dimethoxyphenyl)sulfonyl]-piperidine
1-[4-(4-chloro-3-fluorobenzyl)-1,3-thiazol-2-yl]-4-[(3,4-dimethoxyphenyl)sulfonyl]-piperidine
1-[4-(3,4,5-trimethoxybenzyl)-1,3-thiazol-2-yl]-4-[(3,4-dimethoxyphenyl)sulfonyl]-piperidine
1-[4-(2,4,6-trimethylbenzyl)-1,3-thiazol-2-yl]-4-[(3,4-dimethoxyphenyl)sulfonyl]-piperidine
1-[4-benzyl-1,3-thiazol-2-yl]-4-[(2,4-dimethoxyphenyl)sulfonyl]-piperidine
1-[4-(2-methylbenzyl)-1,3-thiazol-2-yl]-4-[(2,4-dimethoxyphenyl)sulfonyl]-piperidine
1-[4-(2-methoxybenzyl)-1,3-thiazol-2-yl]-4-[(2,4-dimethoxyphenyl)sulfonyl]-piperidine
1-[4-(3-methylbenzyl)-1,3-thiazol-2-yl]-4-[(2,4-dimethoxyphenyl)sulfonyl]-piperidine
1-[4-(3-methoxybenzyl)-1,3-thiazol-2-yl]-4-[(2,4-dimethoxyphenyl)sulfonyl]-piperidine
1-[4-(3-bromobenzyl)-1,3-thiazol-2-yl]-4-[(2,4-dimethoxyphenyl)sulfonyl]-piperidine
1-[4-(4-chlorobenzyl)-1,3-thiazol-2-yl]-4-[(2,4-dimethoxyphenyl)sulfonyl]-piperidine
1-[4-(4-methoxybenzyl)-1,3-thiazol-2-yl]-4-[(2,4-dimethoxyphenyl)sulfonyl]-piperidine
1-[4-(4-methylbenzyl)-1,3-thiazol-2-yl]-4-[(2,4-dimethoxyphenyl)sulfonyl]-piperidine
1-[4-(4-ethylbenzyl)-1,3-thiazol-2-yl]-4-[(2,4-dimethoxyphenyl)sulfonyl]-piperidine
1-[4-(4-ethoxybenzyl)-1,3-thiazol-2-yl]-4-[(2,4-dimethoxyphenyl)sulfonyl]-piperidine
1-[4-(4-propylbenzyl)-1,3-thiazol-2-yl]-4-[(2,4-dimethoxyphenyl)sulfonyl]-piperidine
1-[4-(2,6-dimethylbenzyl)-1,3-thiazol-2-yl]-4-[(2,4-dimethoxyphenyl)sulfonyl]-piperidine
1-[4-(2,3-dimethylbenzyl)-1,3-thiazol-2-yl]-4-[(2,4-dimethoxyphenyl)sulfonyl]-piperidine
1-[4-(2,5-dimethylbenzyl)-1,3-thiazol-2-yl]-4-[(2,4-dimethoxyphenyl)sulfonyl]-piperidine
1-[4-(2,4-dichlorobenzyl)-1,3-thiazol-2-yl]-4-[(2,4-dimethoxyphenyl)sulfonyl]-piperidine 1-[4-(2,4-dimethoxybenzyl)-1,3-thiazol-2-yl]-4-[(2,4-dimethoxyphenyl)sulfonyl]-piperidine
1-[4-(2,5-dimethoxybenzyl)-1,3-thiazol-2-yl]-4-[(2,4-dimethoxyphenyl)sulfonyl]-piperidine
1-[4-(3,4-dimethoxybenzyl)-1,3-thiazol-2-yl]-4-[(2,4-dimethoxyphenyl)sulfonyl]-piperidine
1-[4-(3,5-dimethoxybenzyl)-1,3-thiazol-2-yl]-4-[(2,4-dimethoxyphenyl)sulfonyl]-piperidine
1-[4-(3,4-dichlorobenzyl)-1,3-thiazol-2-yl]-4-[(2,4-dimethoxyphenyl)sulfonyl]-piperidine
1-[4-(3,4-dimethylbenzyl)-1,3-thiazol-2-yl]-4-[(2,4-dimethoxyphenyl)sulfonyl]-piperidine
1-[4-(3,4-difluorobenzyl)-1,3-thiazol-2-yl]-4-[(2,4-dimethoxyphenyl)sulfonyl]-piperidine
1-[4-(3,5-difluorobenzyl)-1,3-thiazol-2-yl]-4-[(2,4-dimethoxyphenyl)sulfonyl]-piperidine
1-[4-(3,5-dichlorobenzyl)-1,3-thiazol-2-yl]-4-[(2,4-dimethoxyphenyl)sulfonyl]-piperidine
1-[4-(3,5-dimethylbenzyl)-1,3-thiazol-2-yl]-4-[(2,4-dimethoxyphenyl)sulfonyl]-piperidine
1-[4-(3-chloro-4-fluorobenzyl)-1,3-thiazol-2-yl]-4-[(2,4-dimethoxyphenyl)sulfonyl]-piperidine
1-[4-(3-chloro-5-fluorobenzyl)-1,3-thiazol-2-yl]-4-[(2,4-dimethoxyphenyl)sulfonyl]-piperidine
1-[4-(4-chloro-3-fluorobenzyl)-1,3-thiazol-2-yl]-4-[(2,4-dimethoxyphenyl)sulfonyl]-piperidine
1-[4-(3,4,5-trimethoxybenzyl)-1,3-thiazol-2-yl]-4-[(2,4-dimethoxyphenyl)sulfonyl]-piperidine
1-[4-(2,4,6-trimethylbenzyl)-1,3-thiazol-2-yl]-4-[(2,4-dimethoxyphenyl)sulfonyl]-piperidine
1-[4-benzyl-1,3-thiazol-2-yl]-4-[(2,5-dimethoxyphenyl)sulfonyl]-piperidine
1-[4-(2-methylbenzyl)-1,3-thiazol-2-yl]-4-[(2,5-dimethoxyphenyl)sulfonyl]-piperidine
1-[4-(2-methoxybenzyl)-1,3-thiazol-2-yl]-4-[(2,5-dimethoxyphenyl)sulfonyl]-piperidine
1-[4-(3-methylbenzyl)-1,3-thiazol-2-yl]-4-[(2,5-dimethoxyphenyl)sulfonyl]-piperidine
1-[4-(3-methoxybenzyl)-1,3-thiazol-2-yl]-4-[(2,5-dimethoxyphenyl)sulfonyl]-piperidine
1-[4-(3-bromobenzyl)-1,3-thiazol-2-yl]-4-[(2,5-dimethoxyphenyl)sulfonyl]-piperidine
1-[4-(4-chlorobenzyl)-1,3-thiazol-2-yl]-4-[(2,5-dimethoxyphenyl)sulfonyl]-piperidine
1-[4-(4-methoxybenzyl)-1,3-thiazol-2-yl]-4-[(2,5-dimethoxyphenyl)sulfonyl]-piperidine
1-[4-(4-methylbenzyl)-1,3-thiazol-2-yl]-4-[(2,5-dimethoxyphenyl)sulfonyl]-piperidine
1-[4-(4-ethylbenzyl)-1,3-thiazol-2-yl]-4-[(2,5-dimethoxyphenyl)sulfonyl]-piperidine
1-[4-(4-ethoxybenzyl)-1,3-thiazol-2-yl]-4-[(2,5-dimethoxyphenyl)sulfonyl]-piperidine
1-[4-(4-propylbenzyl)-1,3-thiazol-2-yl]-4-[(2,5-dimethoxyphenyl)sulfonyl]-piperidine
1-[4-(2,6-dimethylbenzyl)-1,3-thiazol-2-yl]-4-[(2,5-dimethoxyphenyl)sulfonyl]-piperidine
1-[4-(2,3-dimethylbenzyl)-1,3-thiazol-2-yl]-4-[(2,5-dimethoxyphenyl)sulfonyl]-piperidine
1-[4-(2,5-dimethylbenzyl)-1,3-thiazol-2-yl]-4-[(2,5-dimethoxyphenyl)sulfonyl]-piperidine
1-[4-(2,4-dichlorobenzyl)-1,3-thiazol-2-yl]-4-[(2,5-dimethoxyphenyl)sulfonyl]-piperidine
1-[4-(2,4-dimethoxybenzyl)-1,3-thiazol-2-yl]-4-[(2,5-dimethoxyphenyl)sulfonyl]-piperidine
1-[4-(2,5-dimethoxybenzyl)-1,3-thiazol-2-yl]-4-[(2,5-dimethoxyphenyl)sulfonyl]-piperidine
1-[4-(3,4-dimethoxybenzyl)-1,3-thiazol-2-yl]-4-[(2,5-dimethoxyphenyl)sulfonyl]-piperidine
1-[4-(3,5-dimethoxybenzyl)-1,3-thiazol-2-yl]-4-[(2,5-dimethoxyphenyl)sulfonyl]-piperidine
1-[4-(3,4-dichlorobenzyl)-1,3-thiazol-2-yl]-4-[(2,5-dimethoxyphenyl)sulfonyl]-piperidine
1-[4-(3,4-dimethylbenzyl)-1,3-thiazol-2-yl]-4-[(2,5-dimethoxyphenyl)sulfonyl]-piperidine
1-[4-(3,4-difluorobenzyl)-1,3-thiazol-2-yl]-4-[(2,5-dimethoxyphenyl)sulfonyl]-piperidine
1-[4-(3,5-difluorobenzyl)-1,3-thiazol-2-yl]-4-[(2,5-dimethoxyphenyl)sulfonyl]-piperidine
1-[4-(3,5-dichlorobenzyl)-1,3-thiazol-2-yl]-4-[(2,5-dimethoxyphenyl)sulfonyl]-piperidine
1-[4-(3,5-dimethylbenzyl)-1,3-thiazol-2-yl]-4-[(2,5-dimethoxyphenyl)sulfonyl]-piperidine
1-[4-(3-chloro-4-fluorobenzyl)-1,3-thiazol-2-yl]-4-[(2,5-dimethoxyphenyl)sulfonyl]-piperidine
1-[4-(3-chloro-5-fluorobenzyl)-1,3-thiazol-2-yl]-4-[(2,5-dimethoxyphenyl)sulfonyl]-piperidine
1-[4-(4-chloro-3-fluorobenzyl)-1,3-thiazol-2-yl]-4-[(2,5-dimethoxyphenyl)sulfonyl]-piperidine
1-[4-(3,4,5-trimethoxybenzyl)-1,3-thiazol-2-yl]-4-[(2,5-dimethoxyphenyl)sulfonyl]-piperidine
1-[4-(2,4,6-trimethylbenzyl)-1,3-thiazol-2-yl]-4-[(2,5-dimethoxyphenyl)sulfonyl]-piperidine
1-[4-benzyl-1,3-thiazol-2-yl]-4-[(3,5-dichlorophenyl)sulfonyl]-piperidine
1-[4-(2-methylbenzyl)-1,3-thiazol-2-yl]-4-[(3,5-dichlorophenyl)sulfonyl]-piperidine
1-[4-(2-methoxybenzyl)-1,3-thiazol-2-yl]-4-[(3,5-dichlorophenyl)sulfonyl]-piperidine
1-[4-(3-methylbenzyl)-1,3-thiazol-2-yl]-4-[(3,5-dichlorophenyl)sulfonyl]-piperidine
1-[4-(3-methoxybenzyl)-1,3-thiazol-2-yl]-4-[(3,5-dichlorophenyl)sulfonyl]-piperidine
1-[4-(3-bromobenzyl)-1,3-thiazol-2-yl]-4-[(3,5-dichlorophenyl)sulfonyl]-piperidine
1-[4-(4-chlorobenzyl)-1,3-thiazol-2-yl]-4-[(3,5-dichlorophenyl)sulfonyl]-piperidine
1-[4-(4-methoxybenzyl)-1,3-thiazol-2-yl]-4-[(3,5-dichlorophenyl)sulfonyl]-piperidine
1-[4-(4-methylbenzyl)-1,3-thiazol-2-yl]-4-[(3,5-dichlorophenyl)sulfonyl]-piperidine
1-[4-(4-ethylbenzyl)-1,3-thiazol-2-yl]-4-[(3,5-dichlorophenyl)sulfonyl]-piperidine
1-[4-(4-ethoxybenzyl)-1,3-thiazol-2-yl]-4-[(3,5-dichlorophenyl)sulfonyl]-piperidine
1-[4-(4-propylbenzyl)-1,3-thiazol-2-yl]-4-[(3,5-dichlorophenyl)sulfonyl]-piperidine
1-[4-(2,6-dimethylbenzyl)-1,3-thiazol-2-yl]-4-[(3,5-dichlorophenyl)sulfonyl]-piperidine
1-[4-(2,3-dimethylbenzyl)-1,3-thiazol-2-yl]-4-[(3,5-dichlorophenyl)sulfonyl]-piperidine
1-[4-(2,5-dimethylbenzyl)-1,3-thiazol-2-yl]-4-[(3,5-dichlorophenyl)sulfonyl]-piperidine
1-[4-(2,4-dichlorobenzyl)-1,3-thiazol-2-yl]-4-[(3,5-dichlorophenyl)sulfonyl]-piperidine
1-[4-(2,4-dimethoxybenzyl)-1,3-thiazol-2-yl]-4-[(3,5-dichlorophenyl)sulfonyl]-piperidine
1-[4-(2,5-dimethoxybenzyl)-1,3-thiazol-2-yl]-4-[(3,5-dichlorophenyl)sulfonyl]-piperidine
1-[4-(3,4-dimethoxybenzyl)-1,3-thiazol-2-yl]-4-[(3,5-dichlorophenyl)sulfonyl]-piperidine
1-[4-(3,5-dimethoxybenzyl)-1,3-thiazol-2-yl]-4-[(3,5-dichlorophenyl)sulfonyl]-piperidine 1-[4-(3,4-dichlorobenzyl)-1,3-thiazol-2-yl]-4-[(3,5-dichlorophenyl)sulfonyl]-piperidine
1-[4-(3,4-dimethylbenzyl)-1,3-thiazol-2-yl]-4-[(3,5-dichlorophenyl)sulfonyl]-piperidine
1-[4-(3,4-difluorobenzyl)-1,3-thiazol-2-yl]-4-[(3,5-dichlorophenyl)sulfonyl]-piperidine
1-[4-(3,5-difluorobenzyl)-1,3-thiazol-2-yl]-4-[(3,5-dichlorophenyl)sulfonyl]-piperidine
1-[4-(3,5-dichlorobenzyl)-1,3-thiazol-2-yl]-4-[(3,5-dichlorophenyl)sulfonyl]-piperidine
1-[4-(3,5-dimethylbenzyl)-1,3-thiazol-2-yl]-4-[(3,5-dichlorophenyl)sulfonyl]-piperidine
1-[4-(3-chloro-4-fluorobenzyl)-1,3-thiazol-2-yl]-4-[(3,5-dichlorophenyl)sulfonyl]-piperidine
1-[4-(3-chloro-5-fluorobenzyl)-1,3-thiazol-2-yl]-4-[(3,5-dichlorophenyl)sulfonyl]-piperidine
1-[4-(4-chloro-3-fluorobenzyl)-1,3-thiazol-2-yl]-4-[(3,5-dichlorophenyl)sulfonyl]-piperidine
1-[4-(3,4,5-trimethoxybenzyl)-1,3-thiazol-2-yl]-4-[(3,5-dichlorophenyl)sulfonyl]-piperidine
1-[4-(2,4,6-trimethylbenzyl)-1,3-thiazol-2-yl]-4-[(3,5-dichlorophenyl)sulfonyl]-piperidine
1-[4-benzyl-1,3-thiazol-2-yl]-4-[(2,3-dichlorophenyl)sulfonyl]-piperidine
1-[4-(2-methylbenzyl)-1,3-thiazol-2-yl]-4-[(2,3-dichlorophenyl)sulfonyl]-piperidine
1-[4-(2-methoxybenzyl)-1,3-thiazol-2-yl]-4-[(2,3-dichlorophenyl)sulfonyl]-piperidine
1-[4-(3-methylbenzyl)-1,3-thiazol-2-yl]-4-[(2,3-dichlorophenyl)sulfonyl]-piperidine
1-[4-(3-methoxybenzyl)-1,3-thiazol-2-yl]-4-[(2,3-dichlorophenyl)sulfonyl]-piperidine
1-[4-(3-bromobenzyl)-1,3-thiazol-2-yl]-4-[(2,3-dichlorophenyl)sulfonyl]-piperidine
1-[4-(4-chlorobenzyl)-1,3-thiazol-2-yl]-4-[(2,3-dichlorophenyl)sulfonyl]-piperidine
1-[4-(4-methoxybenzyl)-1,3-thiazol-2-yl]-4-[(2,3-dichlorophenyl)sulfonyl]-piperidine
1-[4-(4-methylbenzyl)-1,3-thiazol-2-yl]-4-[(2,3-dichlorophenyl)sulfonyl]-piperidine
1-[4-(4-ethylbenzyl)-1,3-thiazol-2-yl]-4-[(2,3-dichlorophenyl)sulfonyl]-piperidine
1-[4-(4-ethoxybenzyl)-1,3-thiazol-2-yl]-4-[(2,3-dichlorophenyl)sulfonyl]-piperidine
1-[4-(4-propylbenzyl)-1,3-thiazol-2-yl]-4-[(2,3-dichlorophenyl)sulfonyl]-piperidine
1-[4-(2,6-dimethylbenzyl)-1,3-thiazol-2-yl]-4-[(2,3-dichlorophenyl)sulfonyl]-piperidine
1-[4-(2,3-dimethylbenzyl)-1,3-thiazol-2-yl]-4-[(2,3-dichlorophenyl)sulfonyl]-piperidine
1-[4-(2,5-dimethylbenzyl)-1,3-thiazol-2-yl]-4-[(2,3-dichlorophenyl)sulfonyl]-piperidine
1-[4-(2,4-dichlorobenzyl)-1,3-thiazol-2-yl]-4-[(2,3-dichlorophenyl)sulfonyl]-piperidine
1-[4-(2,4-dimethoxybenzyl)-1,3-thiazol-2-yl]-4-[(2,3-dichlorophenyl)sulfonyl]-piperidine
1-[4-(2,5-dimethoxybenzyl)-1,3-thiazol-2-yl]-4-[(2,3-dichlorophenyl)sulfonyl]-piperidine
1-[4-(3,4-dimethoxybenzyl)-1,3-thiazol-2-yl]-4-[(2,3-dichlorophenyl)sulfonyl]-piperidine
1-[4-(3,5-dimethoxybenzyl)-1,3-thiazol-2-yl]-4-[(2,3-dichlorophenyl)sulfonyl]-piperidine
1-[4-(3,4-dichlorobenzyl)-1,3-thiazol-2-yl]-4-[(2,3-dichlorophenyl)sulfonyl]-piperidine
1-[4-(3,4-dimethylbenzyl)-1,3-thiazol-2-yl]-4-[(2,3-dichlorophenyl)sulfonyl]-piperidine
1-[4-(3,4-difluorobenzyl)-1,3-thiazol-2-yl]-4-[(2,3-dichlorophenyl)sulfonyl]-piperidine
1-[4-(3,5-difluorobenzyl)-1,3-thiazol-2-yl]-4-[(2,3-dichlorophenyl)sulfonyl]-piperidine
1-[4-(3,5-dichlorobenzyl)-1,3-thiazol-2-yl]-4-[(2,3-dichlorophenyl)sulfonyl]-piperidine
1-[4-(3,5-dimethylbenzyl)-1,3-thiazol-2-yl]-4-[(2,3-dichlorophenyl)sulfonyl]-piperidine
1-[4-(3-chloro-4-fluorobenzyl)-1,3-thiazol-2-yl]-4-[(2,3-dichlorophenyl)sulfonyl]-piperidine
1-[4-(3-chloro-5-fluorobenzyl)-1,3-thiazol-2-yl]-4-[(2,3-dichlorophenyl)sulfonyl]-piperidine
1-[4-(4-chloro-3-fluorobenzyl)-1,3-thiazol-2-yl]-4-[(2,3-dichlorophenyl)sulfonyl]-piperidine
1-[4-(3,4,5-trimethoxybenzyl)-1,3-thiazol-2-yl]-4-[(2,3-dichlorophenyl)sulfonyl]-piperidine
1-[4-(2,4,6-trimethylbenzyl)-1,3-thiazol-2-yl]-4-[(2,3-dichlorophenyl)sulfonyl]-piperidine
1-[4-benzyl-1,3-thiazol-2-yl]-4-[(2,6-difluorophenyl)sulfonyl]-piperidine
1-[4-(2-methylbenzyl)-1,3-thiazol-2-yl]-4-[(2,6-difluorophenyl)sulfonyl]-piperidine
1-[4-(2-methoxybenzyl)-1,3-thiazol-2-yl]-4-[(2,6-difluorophenyl)sulfonyl]-piperidine
1-[4-(3-methylbenzyl)-1,3-thiazol-2-yl]-4-[(2,6-difluorophenyl)sulfonyl]-piperidine
1-[4-(3-methoxybenzyl)-1,3-thiazol-2-yl]-4-[(2,6-difluorophenyl)sulfonyl]-piperidine
1-[4-(3-bromobenzyl)-1,3-thiazol-2-yl]-4-[(2,6-difluorophenyl)sulfonyl]-piperidine
1-[4-(4-chlorobenzyl)-1,3-thiazol-2-yl]-4-[(2,6-difluorophenyl)sulfonyl]-piperidine
1-[4-(4-methoxybenzyl)-1,3-thiazol-2-yl]-4-[(2,6-difluorophenyl)sulfonyl]-piperidine
1-[4-(4-methylbenzyl)-1,3-thiazol-2-yl]-4-[(2,6-difluorophenyl)sulfonyl]-piperidine
1-[4-(4-ethylbenzyl)-1,3-thiazol-2-yl]-4-[(2,6-difluorophenyl)sulfonyl]-piperidine
1-[4-(4-ethoxybenzyl)-1,3-thiazol-2-yl]-4-[(2,6-difluorophenyl)sulfonyl]-piperidine
1-[4-(4-propylbenzyl)-1,3-thiazol-2-yl]-4-[(2,6-difluorophenyl)sulfonyl]-piperidine
1-[4-(2,6-dimethylbenzyl)-1,3-thiazol-2-yl]-4-[(2,6-difluorophenyl)sulfonyl]-piperidine
1-[4-(2,3-dimethylbenzyl)-1,3-thiazol-2-yl]-4-[(2,6-difluorophenyl)sulfonyl]-piperidine
1-[4-(2,5-dimethylbenzyl)-1,3-thiazol-2-yl]-4-[(2,6-difluorophenyl)sulfonyl]-piperidine
1-[4-(2,4-dichlorobenzyl)-1,3-thiazol-2-yl]-4-[(2,6-difluorophenyl)sulfonyl]-piperidine
1-[4-(2,4-dimethoxybenzyl)-1,3-thiazol-2-yl]-4-[(2,6-difluorophenyl)sulfonyl]-piperidine
1-[4-(2,5-dimethoxybenzyl)-1,3-thiazol-2-yl]-4-[(2,6-difluorophenyl)sulfonyl]-piperidine
1-[4-(3,4-dimethoxybenzyl)-1,3-thiazol-2-yl]-4-[(2,6-difluorophenyl)sulfonyl]-piperidine
1-[4-(3,5-dimethoxybenzyl)-1,3-thiazol-2-yl]-4-[(2,6-difluorophenyl)sulfonyl]-piperidine
1-[4-(3,4-dichlorobenzyl)-1,3-thiazol-2-yl]-4-[(2,6-difluorophenyl)sulfonyl]-piperidine
1-[4-(3,4-dimethylbenzyl)-1,3-thiazol-2-yl]-4-[(2,6-difluorophenyl)sulfonyl]-piperidine
1-[4-(3,4-difluorobenzyl)-1,3-thiazol-2-yl]-4-[(2,6-difluorophenyl)sulfonyl]-piperidine
1-[4-(3,5-difluorobenzyl)-1,3-thiazol-2-yl]-4-[(2,6-difluorophenyl)sulfonyl]-piperidine 1-[4-(3,5-dichlorobenzyl)-1,3-thiazol-2-yl]-4-[(2,6-difluorophenyl)sulfonyl]-piperidine
1-[4-(3,5-dimethylbenzyl)-1,3-thiazol-2-yl]-4-[(2,6-difluorophenyl)sulfonyl]-piperidine
1-[4-(3-chloro-4-fluorobenzyl)-1,3-thiazol-2-yl]-4-[(2,6-difluorophenyl)sulfonyl]-piperidine
1-[4-(3-chloro-5-fluorobenzyl)-1,3-thiazol-2-yl]-4-[(2,6-difluorophenyl)sulfonyl]-piperidine
1-[4-(4-chloro-3-fluorobenzyl)-1,3-thiazol-2-yl]-4-[(2,6-difluorophenyl)sulfonyl]-piperidine
1-[4-(3,4,5-trimethoxybenzyl)-1,3-thiazol-2-yl]-4-[(2,6-difluorophenyl)sulfonyl]-piperidine
1-[4-(2,4,6-trimethylbenzyl)-1,3-thiazol-2-yl]-4-[(2,6-difluorophenyl)sulfonyl]-piperidine
1-[4-benzyl-1,3-thiazol-2-yl]-4-[(2,4-difluorophenyl)sulfonyl]-piperidine
1-[4-(2-methylbenzyl)-1,3-thiazol-2-yl]-4-[(2,4-difluorophenyl)sulfonyl]-piperidine
1-[4-(2-methoxybenzyl)-1,3-thiazol-2-yl]-4-[(2,4-difluorophenyl)sulfonyl]-piperidine
1-[4-(3-methylbenzyl)-1,3-thiazol-2-yl]-4-[(2,4-difluorophenyl)sulfonyl]-piperidine
1-[4-(3-methoxybenzyl)-1,3-thiazol-2-yl]-4-[(2,4-difluorophenyl)sulfonyl]-piperidine
1-[4-(3-bromobenzyl)-1,3-thiazol-2-yl]-4-[(2,4-difluorophenyl)sulfonyl]-piperidine
1-[4-(4-chlorobenzyl)-1,3-thiazol-2-yl]-4-[(2,4-difluorophenyl)sulfonyl]-piperidine
1-[4-(4-methoxybenzyl)-1,3-thiazol-2-yl]-4-[(2,4-difluorophenyl)sulfonyl]-piperidine
1-[4-(4-methylbenzyl)-1,3-thiazol-2-yl]-4-[(2,4-difluorophenyl)sulfonyl]-piperidine
1-[4-(4-ethylbenzyl)-1,3-thiazol-2-yl]-4-[(2,4-difluorophenyl)sulfonyl]-piperidine
1-[4-(4-ethoxybenzyl)-1,3-thiazol-2-yl]-4-[(2,4-difluorophenyl)sulfonyl]-piperidine
1-[4-(4-propylbenzyl)-1,3-thiazol-2-yl]-4-[(2,4-difluorophenyl)sulfonyl]-piperidine
1-[4-(2,6-dimethylbenzyl)-1,3-thiazol-2-yl]-4-[(2,4-difluorophenyl)sulfonyl]-piperidine
1-[4-(2,3-dimethylbenzyl)-1,3-thiazol-2-yl]-4-[(2,4-difluorophenyl)sulfonyl]-piperidine
1-[4-(2,5-dimethylbenzyl)-1,3-thiazol-2-yl]-4-[(2,4-difluorophenyl)sulfonyl]-piperidine
1-[4-(2,4-dichlorobenzyl)-1,3-thiazol-2-yl]-4-[(2,4-difluorophenyl)sulfonyl]-piperidine
1-[4-(2,4-dimethoxybenzyl)-1,3-thiazol-2-yl]-4-[(2,4-difluorophenyl)sulfonyl]-piperidine
1-[4-(2,5-dimethoxybenzyl)-1,3-thiazol-2-yl]-4-[(2,4-difluorophenyl)sulfonyl]-piperidine
1-[4-(3,4-dimethoxybenzyl)-1,3-thiazol-2-yl]-4-[(2,4-difluorophenyl)sulfonyl]-piperidine
1-[4-(3,5-dimethoxybenzyl)-1,3-thiazol-2-yl]-4-[(2,4-difluorophenyl)sulfonyl]-piperidine
1-[4-(3,4-dichlorobenzyl)-1,3-thiazol-2-yl]-4-[(2,4-difluorophenyl)sulfonyl]-piperidine
1-[4-(3,4-dimethylbenzyl)-1,3-thiazol-2-yl]-4-[(2,4-difluorophenyl)sulfonyl]-piperidine
1-[4-(3,4-difluorobenzyl)-1,3-thiazol-2-yl]-4-[(2,4-difluorophenyl)sulfonyl]-piperidine
1-[4-(3,5-difluorobenzyl)-1,3-thiazol-2-yl]-4-[(2,4-difluorophenyl)sulfonyl]-piperidine
1-[4-(3,5-dichlorobenzyl)-1,3-thiazol-2-yl]-4-[(2,4-difluorophenyl)sulfonyl]-piperidine
1-[4-(3,5-dimethylbenzyl)-1,3-thiazol-2-yl]-4-[(2,4-difluorophenyl)sulfonyl]-piperidine
1-[4-(3-chloro-4-fluorobenzyl)-1,3-thiazol-2-yl]-4-[(2,4-difluorophenyl)sulfonyl]-piperidine
1-[4-(3-chloro-5-fluorobenzyl)-1,3-thiazol-2-yl]-4-[(2,4-difluorophenyl)sulfonyl]-piperidine
1-[4-(4-chloro-3-fluorobenzyl)-1,3-thiazol-2-yl]-4-[(2,4-difluorophenyl)sulfonyl]-piperidine
1-[4-(3,4,5-trimethoxybenzyl)-1,3-thiazol-2-yl]-4-[(2,4-difluorophenyl)sulfonyl]-piperidine
1-[4-(2,4,6-trimethylbenzyl)-1,3-thiazol-2-yl]-4-[(2,4-difluorophenyl)sulfonyl]-piperidine
1-[4-benzyl-1,3-thiazol-2-yl]-4-[(4-(bromomethyl)phenyl)sulfonyl]-piperidine
1-[4-(2-methylbenzyl)-1,3-thiazol-2-yl]-4-[(4-(bromomethyl)phenyl)sulfonyl]-piperidine
1-[4-(2-methoxybenzyl)-1,3-thiazol-2-yl]-4-[(4-(bromomethyl)phenyl)sulfonyl]-piperidine
1-[4-(3-methylbenzyl)-1,3-thiazol-2-yl]-4-[(4-(bromomethyl)phenyl)sulfonyl]-piperidine
1-[4-(3-methoxybenzyl)-1,3-thiazol-2-yl]-4-[(4-(bromomethyl)phenyl)sulfonyl]-piperidine
1-[4-(3-bromobenzyl)-1,3-thiazol-2-yl]-4-[(4-(bromomethyl)phenyl)sulfonyl]-piperidine
1-[4-(4-chlorobenzyl)-1,3-thiazol-2-yl]-4-[(4-(bromomethyl)phenyl)sulfonyl]-piperidine
1-[4-(4-methoxybenzyl)-1,3-thiazol-2-yl]-4-[(4-(bromomethyl)phenyl)sulfonyl]-piperidine
1-[4-(4-methylbenzyl)-1,3-thiazol-2-yl]-4-[(4-(bromomethyl)phenyl)sulfonyl]-piperidine
1-[4-(4-ethylbenzyl)-1,3-thiazol-2-yl]-4-[(4-(bromomethyl)phenyl)sulfonyl]-piperidine
1-[4-(4-ethoxybenzyl)-1,3-thiazol-2-yl]-4-[(4-(bromomethyl)phenyl)sulfonyl]-piperidine
1-[4-(4-propylbenzyl)-1,3-thiazol-2-yl]-4-[(4-(bromomethyl)phenyl)sulfonyl]-piperidine
1-[4-(2,6-dimethylbenzyl)-1,3-thiazol-2-yl]-4-[(4-(bromomethyl)phenyl)sulfonyl]-piperidine
1-[4-(2,3-dimethylbenzyl)-1,3-thiazol-2-yl]-4-[(4-(bromomethyl)phenyl)sulfonyl]-piperidine
1-[4-(2,5-dimethylbenzyl)-1,3-thiazol-2-yl]-4-[(4-(bromomethyl)phenyl)sulfonyl]-piperidine
1-[4-(2,4-dichlorobenzyl)-1,3-thiazol-2-yl]-4-[(4-(bromomethyl)phenyl)sulfonyl]-piperidine
1-[4-(2,4-dimethoxybenzyl)-1,3-thiazol-2-yl]-4-[(4-(bromomethyl)phenyl)sulfonyl]-piperidine
1-[4-(2,5-dimethoxybenzyl)-1,3-thiazol-2-yl]-4-[(4-(bromomethyl)phenyl)sulfonyl]-piperidine
1-[4-(3,4-dimethoxybenzyl)-1,3-thiazol-2-yl]-4-[(4-(bromomethyl)phenyl)sulfonyl]-piperidine
1-[4-(3,5-dimethoxybenzyl)-1,3-thiazol-2-yl]-4-[(4-(bromomethyl)phenyl)sulfonyl]-piperidine
1-[4-(3,4-dichlorobenzyl)-1,3-thiazol-2-yl]-4-[(4-(bromomethyl)phenyl)sulfonyl]-piperidine
1-[4-(3,4-dimethylbenzyl)-1,3-thiazol-2-yl]-4-[(4-(bromomethyl)phenyl)sulfonyl]-piperidine
1-[4-(3,4-difluorobenzyl)-1,3-thiazol-2-yl]-4-[(4-(bromomethyl)phenyl)sulfonyl]-piperidine
1-[4-(3,5-difluorobenzyl)-1,3-thiazol-2-yl]-4-[(4-(bromomethyl)phenyl)sulfonyl]-piperidine
1-[4-(3,5-dichlorobenzyl)-1,3-thiazol-2-yl]-4-[(4-(bromomethyl)phenyl)sulfonyl]-piperidine
1-[4-(3,5-dimethylbenzyl)-1,3-thiazol-2-yl]-4-[(4-(bromomethyl)phenyl)sulfonyl]-piperidine
1-[4-(3-chloro-4-fluorobenzyl)-1,3-thiazol-2-yl]-4-[(4-(bromomethyl)phenyl)sulfonyl]-piperidine
1-[4-(3-chloro-5-fluorobenzyl)-1,3-thiazol-2-yl]-4-[(4-(bromomethyl)phenyl)sulfonyl]-piperidine 1-[4-(4-chloro-3-fluorobenzyl)-1,3-thiazol-2-yl]-4-[(4-(bromomethyl)phenyl)sulfonyl]-piperidine
1-[4-(3,4,5-trimethoxybenzyl)-1,3-thiazol-2-yl]-4-[(4-(bromomethyl)phenyl)sulfonyl]-piperidine
1-[4-(2,4,6-trimethylbenzyl)-1,3-thiazol-2-yl]-4-[(4-(bromomethyl)phenyl)sulfonyl]-piperidine
1-[4-benzyl-1,3-thiazol-2-yl]-4-[(3-(trifluoromethyl)phenyl)sulfonyl]-piperidine
1-[4-(2-methylbenzyl)-1,3-thiazol-2-yl]-4-[(3-(trifluoromethyl)phenyl)sulfonyl]-piperidine
1-[4-(2-methoxybenzyl)-1,3-thiazol-2-yl]-4-[(3-(trifluoromethyl)phenyl)sulfonyl]-piperidine
1-[4-(3-methylbenzyl)-1,3-thiazol-2-yl]-4-[(3-(trifluoromethyl)phenyl)sulfonyl]-piperidine
1-[4-(3-methoxybenzyl)-1,3-thiazol-2-yl]-4-[(3-(trifluoromethyl)phenyl)sulfonyl]-piperidine
1-[4-(3-bromobenzyl)-1,3-thiazol-2-yl]-4-[(3-(trifluoromethyl)phenyl)sulfonyl]-piperidine
1-[4-(4-chlorobenzyl)-1,3-thiazol-2-yl]-4-[(3-(trifluoromethyl)phenyl)sulfonyl]-piperidine
1-[4-(4-methoxybenzyl)-1,3-thiazol-2-yl]-4-[(3-(trifluoromethyl)phenyl)sulfonyl]-piperidine
1-[4-(4-methylbenzyl)-1,3-thiazol-2-yl]-4-[(3-(trifluoromethyl)phenyl)sulfonyl]-piperidine
1-[4-(4-ethylbenzyl)-1,3-thiazol-2-yl]-4-[(3-(trifluoromethyl)phenyl)sulfonyl]-piperidine
1-[4-(4-ethoxybenzyl)-1,3-thiazol-2-yl]-4-[(3-(trifluoromethyl)phenyl)sulfonyl]-piperidine
1-[4-(4-propylbenzyl)-1,3-thiazol-2-yl]-4-[(3-(trifluoromethyl)phenyl)sulfonyl]-piperidine
1-[4-(2,6-dimethylbenzyl)-1,3-thiazol-2-yl]-4-[(3-(trifluoromethyl)phenyl)sulfonyl]-piperidine
1-[4-(2,3-dimethylbenzyl)-1,3-thiazol-2-yl]-4-[(3-(trifluoromethyl)phenyl)sulfonyl]-piperidine
1-[4-(2,5-dimethylbenzyl)-1,3-thiazol-2-yl]-4-[(3-(trifluoromethyl)phenyl)sulfonyl]-piperidine
1-[4-(2,4-dichlorobenzyl)-1,3-thiazol-2-yl]-4-[(3-(trifluoromethyl)phenyl)sulfonyl]-piperidine
1-[4-(2,4-dimethoxybenzyl)-1,3-thiazol-2-yl]-4-[(3-(trifluoromethyl)phenyl)sulfonyl]-piperidine
1-[4-(2,5-dimethoxybenzyl)-1,3-thiazol-2-yl]-4-[(3-(trifluoromethyl)phenyl)sulfonyl]-piperidine
1-[4-(3,4-dimethoxybenzyl)-1,3-thiazol-2-yl]-4-[(3-(trifluoromethyl)phenyl)sulfonyl]-piperidine
1-[4-(3,5-dimethoxybenzyl)-1,3-thiazol-2-yl]-4-[(3-(trifluoromethyl)phenyl)sulfonyl]-piperidine
1-[4-(3,4-dichlorobenzyl)-1,3-thiazol-2-yl]-4-[(3-(trifluoromethyl)phenyl)sulfonyl]-piperidine
1-[4-(3,4-dimethylbenzyl)-1,3-thiazol-2-yl]-4-[(3-(trifluoromethyl)phenyl)sulfonyl]-piperidine
1-[4-(3,4-difluorobenzyl)-1,3-thiazol-2-yl]-4-[(3-(trifluoromethyl)phenyl)sulfonyl]-piperidine
1-[4-(3,5-difluorobenzyl)-1,3-thiazol-2-yl]-4-[(3-(trifluoromethyl)phenyl)sulfonyl]-piperidine
1-[4-(3,5-dichlorobenzyl)-1,3-thiazol-2-yl]-4-[(3-(trifluoromethyl)phenyl)sulfonyl]-piperidine
1-[4-(3,5-dimethylbenzyl)-1,3-thiazol-2-yl]-4-[(3-(trifluoromethyl)phenyl)sulfonyl]-piperidine
1-[4-(3-chloro-4-fluorobenzyl)-1,3-thiazol-2-yl]-4-[(3-(trifluoromethyl)phenyl)sulfonyl]-piperidine
1-[4-(3-chloro-5-fluorobenzyl)-1,3-thiazol-2-yl]-4-[(3-(trifluoromethyl)phenyl)sulfonyl]-piperidine
1-[4-(4-chloro-3-fluorobenzyl)-1,3-thiazol-2-yl]-4-[(3-(trifluoromethyl)phenyl)sulfonyl]-piperidine
1-[4-(3,4,5-trimethoxybenzyl)-1,3-thiazol-2-yl]-4-[(3-(trifluoromethyl)phenyl)sulfonyl]-piperidine
1-[4-(2,4,6-trimethylbenzyl)-1,3-thiazol-2-yl]-4-[(3-(trifluoromethyl)phenyl)sulfonyl]-piperidine
1-[4-benzyl-1,3-thiazol-2-yl]-4-[(2-(trifluoromethyl)phenyl)sulfonyl]-piperidine
1-[4-(2-methylbenzyl)-1,3-thiazol-2-yl]-4-[(2-(trifluoromethyl)phenyl)sulfonyl]-piperidine
1-[4-(2-methoxybenzyl)-1,3-thiazol-2-yl]-4-[(2-(trifluoromethyl)phenyl)sulfonyl]-piperidine
1-[4-(3-methylbenzyl)-1,3-thiazol-2-yl]-4-[(2-(trifluoromethyl)phenyl)sulfonyl]-piperidine
1-[4-(3-methoxybenzyl)-1,3-thiazol-2-yl]-4-[(2-(trifluoromethyl)phenyl)sulfonyl]-piperidine
1-[4-(3-bromobenzyl)-1,3-thiazol-2-yl]-4-[(2-(trifluoromethyl)phenyl)sulfonyl]-piperidine
1-[4-(4-chlorobenzyl)-1,3-thiazol-2-yl]-4-[(2-(trifluoromethyl)phenyl)sulfonyl]-piperidine
1-[4-(4-methoxybenzyl)-1,3-thiazol-2-yl]-4-[(2-(trifluoromethyl)phenyl)sulfonyl]-piperidine
1-[4-(4-methylbenzyl)-1,3-thiazol-2-yl]-4-[(2-(trifluoromethyl)phenyl)sulfonyl]-piperidine
1-[4-(4-ethylbenzyl)-1,3-thiazol-2-yl]-4-[(2-(trifluoromethyl)phenyl)sulfonyl]-piperidine
1-[4-(4-ethoxybenzyl)-1,3-thiazol-2-yl]-4-[(2-(trifluoromethyl)phenyl)sulfonyl]-piperidine
1-[4-(4-propylbenzyl)-1,3-thiazol-2-yl]-4-[(2-(trifluoromethyl)phenyl)sulfonyl]-piperidine
1-[4-(2,6-dimethylbenzyl)-1,3-thiazol-2-yl]-4-[(2-(trifluoromethyl)phenyl)sulfonyl]-piperidine
1-[4-(2,3-dimethylbenzyl)-1,3-thiazol-2-yl]-4-[(2-(trifluoromethyl)phenyl)sulfonyl]-piperidine
1-[4-(2,5-dimethylbenzyl)-1,3-thiazol-2-yl]-4-[(2-(trifluoromethyl)phenyl)sulfonyl]-piperidine
1-[4-(2,4-dichlorobenzyl)-1,3-thiazol-2-yl]-4-[(2-(trifluoromethyl)phenyl)sulfonyl]-piperidine
1-[4-(2,4-dimethoxybenzyl)-1,3-thiazol-2-yl]-4-[(2-(trifluoromethyl)phenyl)sulfonyl]-piperidine
1-[4-(2,5-dimethoxybenzyl)-1,3-thiazol-2-yl]-4-[(2-(trifluoromethyl)phenyl)sulfonyl]-piperidine
1-[4-(3,4-dimethoxybenzyl)-1,3-thiazol-2-yl]-4-[(2-(trifluoromethyl)phenyl)sulfonyl]-piperidine
1-[4-(3,5-dimethoxybenzyl)-1,3-thiazol-2-yl]-4-[(2-(trifluoromethyl)phenyl)sulfonyl]-piperidine
1-[4-(3,4-dichlorobenzyl)-1,3-thiazol-2-yl]-4-[(2-(trifluoromethyl)phenyl)sulfonyl]-piperidine
1-[4-(3,4-dimethylbenzyl)-1,3-thiazol-2-yl]-4-[(2-(trifluoromethyl)phenyl)sulfonyl]-piperidine
1-[4-(3,4-difluorobenzyl)-1,3-thiazol-2-yl]-4-[(2-(trifluoromethyl)phenyl)sulfonyl]-piperidine
1-[4-(3,5-difluorobenzyl)-1,3-thiazol-2-yl]-4-[(2-(trifluoromethyl)phenyl)sulfonyl]-piperidine
1-[4-(3,5-dichlorobenzyl)-1,3-thiazol-2-yl]-4-[(2-(trifluoromethyl)phenyl)sulfonyl]-piperidine
1-[4-(3,5-dimethylbenzyl)-1,3-thiazol-2-yl]-4-[(2-(trifluoromethyl)phenyl)sulfonyl]-piperidine
1-[4-(3-chloro-4-fluorobenzyl)-1,3-thiazol-2-yl]-4-[(2-(trifluoromethyl)phenyl)sulfonyl]-piperidine
1-[4-(3-chloro-5-fluorobenzyl)-1,3-thiazol-2-yl]-4-[(2-(trifluoromethyl)phenyl)sulfonyl]-piperidine
1-[4-(4-chloro-3-fluorobenzyl)-1,3-thiazol-2-yl]-4-[(2-(trifluoromethyl)phenyl)sulfonyl]-piperidine
1-[4-(3,4,5-trimethoxybenzyl)-1,3-thiazol-2-yl]-4-[(2-(trifluoromethyl)phenyl)sulfonyl]-piperidine
1-[4-(2,4,6-trimethylbenzyl)-1,3-thiazol-2-yl]-4-[(2-(trifluoromethyl)phenyl)sulfonyl]-piperidine
1-[4-benzyl-1,3-thiazol-2-yl]-4-[(4-nitrophenyl)sulfonyl]-piperidine 1-[4-(2-methylbenzyl)-1,3-thiazol-2-yl]-4-[(4-nitrophenyl)sulfonyl]-piperidine
1-[4-(2-methoxybenzyl)-1,3-thiazol-2-yl]-4-[(4-nitrophenyl)sulfonyl]-piperidine
1-[4-(3-methylbenzyl)-1,3-thiazol-2-yl]-4-[(4-nitrophenyl)sulfonyl]-piperidine
1-[4-(3-methoxybenzyl)-1,3-thiazol-2-yl]-4-[(4-nitrophenyl)sulfonyl]-piperidine
1-[4-(3-bromobenzyl)-1,3-thiazol-2-yl]-4-[(4-nitrophenyl)sulfonyl]-piperidine
1-[4-(4-chlorobenzyl)-1,3-thiazol-2-yl]-4-[(4-nitrophenyl)sulfonyl]-piperidine
1-[4-(4-methoxybenzyl)-1,3-thiazol-2-yl]-4-[(4-nitrophenyl)sulfonyl]-piperidine
1-[4-(4-methylbenzyl)-1,3-thiazol-2-yl]-4-[(4-nitrophenyl)sulfonyl]-piperidine
1-[4-(4-ethylbenzyl)-1,3-thiazol-2-yl]-4-[(4-nitrophenyl)sulfonyl]-piperidine
1-[4-(4-ethoxybenzyl)-1,3-thiazol-2-yl]-4-[(4-nitrophenyl)sulfonyl]-piperidine
1-[4-(4-propylbenzyl)-1,3-thiazol-2-yl]-4-[(4-nitrophenyl)sulfonyl]-piperidine
1-[4-(2,6-dimethylbenzyl)-1,3-thiazol-2-yl]-4-[(4-nitrophenyl)sulfonyl]-piperidine
1-[4-(2,3-dimethylbenzyl)-1,3-thiazol-2-yl]-4-[(4-nitrophenyl)sulfonyl]-piperidine
1-[4-(2,5-dimethylbenzyl)-1,3-thiazol-2-yl]-4-[(4-nitrophenyl)sulfonyl]-piperidine
1-[4-(2,4-dichlorobenzyl)-1,3-thiazol-2-yl]-4-[(4-nitrophenyl)sulfonyl]-piperidine
1-[4-(2,4-dimethoxybenzyl)-1,3-thiazol-2-yl]-4-[(4-nitrophenyl)sulfonyl]-piperidine
1-[4-(2,5-dimethoxybenzyl)-1,3-thiazol-2-yl]-4-[(4-nitrophenyl)sulfonyl]-piperidine
1-[4-(3,4-dimethoxybenzyl)-1,3-thiazol-2-yl]-4-[(4-nitrophenyl)sulfonyl]-piperidine
1-[4-(3,5-dimethoxybenzyl)-1,3-thiazol-2-yl]-4-[(4-nitrophenyl)sulfonyl]-piperidine
1-[4-(3,4-dichlorobenzyl)-1,3-thiazol-2-yl]-4-[(4-nitrophenyl)sulfonyl]-piperidine
1-[4-(3,4-dimethylbenzyl)-1,3-thiazol-2-yl]-4-[(4-nitrophenyl)sulfonyl]-piperidine
1-[4-(3,4-difluorobenzyl)-1,3-thiazol-2-yl]-4-[(4-nitrophenyl)sulfonyl]-piperidine
1-[4-(3,5-difluorobenzyl)-1,3-thiazol-2-yl]-4-[(4-nitrophenyl)sulfonyl]-piperidine
1-[4-(3,5-dichlorobenzyl)-1,3-thiazol-2-yl]-4-[(4-nitrophenyl)sulfonyl]-piperidine
1-[4-(3,5-dimethylbenzyl)-1,3-thiazol-2-yl]-4-[(4-nitrophenyl)sulfonyl]-piperidine
1-[4-(3-chloro-4-fluorobenzyl)-1,3-thiazol-2-yl]-4-[(4-nitrophenyl)sulfonyl]-piperidine
1-[4-(3-chloro-5-fluorobenzyl)-1,3-thiazol-2-yl]-4-[(4-nitrophenyl)sulfonyl]-piperidine
1-[4-(4-chloro-3-fluorobenzyl)-1,3-thiazol-2-yl]-4-[(4-nitrophenyl)sulfonyl]-piperidine
1-[4-(3,4,5-trimethoxybenzyl)-1,3-thiazol-2-yl]-4-[(4-nitrophenyl)sulfonyl]-piperidine
1-[4-(2,4,6-trimethylbenzyl)-1,3-thiazol-2-yl]-4-[(4-nitrophenyl)sulfonyl]-piperidine
1-[4-benzyl-1,3-thiazol-2-yl]-4-[(2-bromophenyl)sulfonyl]-piperidine
1-[4-(2-methylbenzyl)-1,3-thiazol-2-yl]-4-[(2-bromophenyl)sulfonyl]-piperidine
1-[4-(2-methoxybenzyl)-1,3-thiazol-2-yl]-4-[(2-bromophenyl)sulfonyl]-piperidine
1-[4-(3-methylbenzyl)-1,3-thiazol-2-yl]-4-[(2-bromophenyl)sulfonyl]-piperidine
1-[4-(3-methoxybenzyl)-1,3-thiazol-2-yl]-4-[(2-bromophenyl)sulfonyl]-piperidine
1-[4-(3-bromobenzyl)-1,3-thiazol-2-yl]-4-[(2-bromophenyl)sulfonyl]-piperidine
1-[4-(4-chlorobenzyl)-1,3-thiazol-2-yl]-4-[(2-bromophenyl)sulfonyl]-piperidine
1-[4-(4-methoxybenzyl)-1,3-thiazol-2-yl]-4-[(2-bromophenyl)sulfonyl]-piperidine
1-[4-(4-methylbenzyl)-1,3-thiazol-2-yl]-4-[(2-bromophenyl)sulfonyl]-piperidine
1-[4-(4-ethylbenzyl)-1,3-thiazol-2-yl]-4-[(2-bromophenyl)sulfonyl]-piperidine
1-[4-(4-ethoxybenzyl)-1,3-thiazol-2-yl]-4-[(2-bromophenyl)sulfonyl]-piperidine
1-[4-(4-propylbenzyl)-1,3-thiazol-2-yl]-4-[(2-bromophenyl)sulfonyl]-piperidine
1-[4-(2,6-dimethylbenzyl)-1,3-thiazol-2-yl]-4-[(2-bromophenyl)sulfonyl]-piperidine
1-[4-(2,3-dimethylbenzyl)-1,3-thiazol-2-yl]-4-[(2-bromophenyl)sulfonyl]-piperidine
1-[4-(2,5-dimethylbenzyl)-1,3-thiazol-2-yl]-4-[(2-bromophenyl)sulfonyl]-piperidine
1-[4-(2,4-dichlorobenzyl)-1,3-thiazol-2-yl]-4-[(2-bromophenyl)sulfonyl]-piperidine
1-[4-(2,4-dimethoxybenzyl)-1,3-thiazol-2-yl]-4-[(2-bromophenyl)sulfonyl]-piperidine
1-[4-(2,5-dimethoxybenzyl)-1,3-thiazol-2-yl]-4-[(2-bromophenyl)sulfonyl]-piperidine
1-[4-(3,4-dimethoxybenzyl)-1,3-thiazol-2-yl]-4-[(2-bromophenyl)sulfonyl]-piperidine
1-[4-(3,5-dimethoxybenzyl)-1,3-thiazol-2-yl]-4-[(2-bromophenyl)sulfonyl]-piperidine
1-[4-(3,4-dichlorobenzyl)-1,3-thiazol-2-yl]-4-[(2-bromophenyl)sulfonyl]-piperidine
1-[4-(3,4-dimethylbenzyl)-1,3-thiazol-2-yl]-4-[(2-bromophenyl)sulfonyl]-piperidine
1-[4-(3,4-difluorobenzyl)-1,3-thiazol-2-yl]-4-[(2-bromophenyl)sulfonyl]-piperidine
1-[4-(3,5-difluorobenzyl)-1,3-thiazol-2-yl]-4-[(2-bromophenyl)sulfonyl]-piperidine
1-[4-(3,5-dichlorobenzyl)-1,3-thiazol-2-yl]-4-[(2-bromophenyl)sulfonyl]-piperidine
1-[4-(3,5-dimethylbenzyl)-1,3-thiazol-2-yl]-4-[(2-bromophenyl)sulfonyl]-piperidine
1-[4-(3-chloro-4-fluorobenzyl)-1,3-thiazol-2-yl]-4-[(2-bromophenyl)sulfonyl]-piperidine
1-[4-(3-chloro-5-fluorobenzyl)-1,3-thiazol-2-yl]-4-[(2-bromophenyl)sulfonyl]-piperidine
1-[4-(4-chloro-3-fluorobenzyl)-1,3-thiazol-2-yl]-4-[(2-bromophenyl)sulfonyl]-piperidine
1-[4-(3,4,5-trimethoxybenzyl)-1,3-thiazol-2-yl]-4-[(2-bromophenyl)sulfonyl]-piperidine
1-[4-(2,4,6-trimethylbenzyl)-1,3-thiazol-2-yl]-4-[(2-bromophenyl)sulfonyl]-piperidine
1-[4-benzyl-1,3-thiazol-2-yl]-4-[(2-chlorophenyl)sulfonyl]-piperidine
1-[4-(2-methylbenzyl)-1,3-thiazol-2-yl]-4-[(2-chlorophenyl)sulfonyl]-piperidine
1-[4-(2-methoxybenzyl)-1,3-thiazol-2-yl]-4-[(2-chlorophenyl)sulfonyl]-piperidine
1-[4-(3-methylbenzyl)-1,3-thiazol-2-yl]-4-[(2-chlorophenyl)sulfonyl]-piperidine
1-[4-(3-methoxybenzyl)-1,3-thiazol-2-yl]-4-[(2-chlorophenyl)sulfonyl]-piperidine 1-[4-(3-bromobenzyl)-1,3-thiazol-2-yl]-4-[(2-chlorophenyl)sulfonyl]-piperidine
1-[4-(4-chlorobenzyl)-1,3-thiazol-2-yl]-4-[(2-chlorophenyl)sulfonyl]-piperidine
1-[4-(4-methoxybenzyl)-1,3-thiazol-2-yl]-4-[(2-chlorophenyl)sulfonyl]-piperidine
1-[4-(4-methylbenzyl)-1,3-thiazol-2-yl]-4-[(2-chlorophenyl)sulfonyl]-piperidine
1-[4-(4-ethylbenzyl)-1,3-thiazol-2-yl]-4-[(2-chlorophenyl)sulfonyl]-piperidine
1-[4-(4-ethoxybenzyl)-1,3-thiazol-2-yl]-4-[(2-chlorophenyl)sulfonyl]-piperidine
1-[4-(4-propylbenzyl)-1,3-thiazol-2-yl]-4-[(2-chlorophenyl)sulfonyl]-piperidine
1-[4-(2,6-dimethylbenzyl)-1,3-thiazol-2-yl]-4-[(2-chlorophenyl)sulfonyl]-piperidine
1-[4-(2,3-dimethylbenzyl)-1,3-thiazol-2-yl]-4-[(2-chlorophenyl)sulfonyl]-piperidine
1-[4-(2,5-dimethylbenzyl)-1,3-thiazol-2-yl]-4-[(2-chlorophenyl)sulfonyl]-piperidine
1-[4-(2,4-dichlorobenzyl)-1,3-thiazol-2-yl]-4-[(2-chlorophenyl)sulfonyl]-piperidine
1-[4-(2,4-dimethoxybenzyl)-1,3-thiazol-2-yl]-4-[(2-chlorophenyl)sulfonyl]-piperidine
1-[4-(2,5-dimethoxybenzyl)-1,3-thiazol-2-yl]-4-[(2-chlorophenyl)sulfonyl]-piperidine
1-[4-(3,4-dimethoxybenzyl)-1,3-thiazol-2-yl]-4-[(2-chlorophenyl)sulfonyl]-piperidine
1-[4-(3,5-dimethoxybenzyl)-1,3-thiazol-2-yl]-4-[(2-chlorophenyl)sulfonyl]-piperidine
1-[4-(3,4-dichlorobenzyl)-1,3-thiazol-2-yl]-4-[(2-chlorophenyl)sulfonyl]-piperidine
1-[4-(3,4-dimethylbenzyl)-1,3-thiazol-2-yl]-4-[(2-chlorophenyl)sulfonyl]-piperidine
1-[4-(3,4-difluorobenzyl)-1,3-thiazol-2-yl]-4-[(2-chlorophenyl)sulfonyl]-piperidine
1-[4-(3,5-difluorobenzyl)-1,3-thiazol-2-yl]-4-[(2-chlorophenyl)sulfonyl]-piperidine
1-[4-(3,5-dichlorobenzyl)-1,3-thiazol-2-yl]-4-[(2-chlorophenyl)sulfonyl]-piperidine
1-[4-(3,5-dimethylbenzyl)-1,3-thiazol-2-yl]-4-[(2-chlorophenyl)sulfonyl]-piperidine
1-[4-(3-chloro-4-fluorobenzyl)-1,3-thiazol-2-yl]-4-[(2-chlorophenyl)sulfonyl]-piperidine
1-[4-(3-chloro-5-fluorobenzyl)-1,3-thiazol-2-yl]-4-[(2-chlorophenyl)sulfonyl]-piperidine
1-[4-(4-chloro-3-fluorobenzyl)-1,3-thiazol-2-yl]-4-[(2-chlorophenyl)sulfonyl]-piperidine
1-[4-(3,4,5-trimethoxybenzyl)-1,3-thiazol-2-yl]-4-[(2-chlorophenyl)sulfonyl]-piperidine
1-[4-(2,4,6-trimethylbenzyl)-1,3-thiazol-2-yl]-4-[(2-chlorophenyl)sulfonyl]-piperidine
1-[4-benzyl-1,3-thiazol-2-yl]-4-[(2-cyanophenyl)sulfonyl]-piperidine
1-[4-(2-methylbenzyl)-1,3-thiazol-2-yl]-4-[(2-cyanophenyl)sulfonyl]-piperidine
1-[4-(2-methoxybenzyl)-1,3-thiazol-2-yl]-4-[(2-cyanophenyl)sulfonyl]-piperidine
1-[4-(3-methylbenzyl)-1,3-thiazol-2-yl]-4-[(2-cyanophenyl)sulfonyl]-piperidine
1-[4-(3-methoxybenzyl)-1,3-thiazol-2-yl]-4-[(2-cyanophenyl)sulfonyl]-piperidine
1-[4-(3-bromobenzyl)-1,3-thiazol-2-yl]-4-[(2-cyanophenyl)sulfonyl]-piperidine
1-[4-(4-chlorobenzyl)-1,3-thiazol-2-yl]-4-[(2-cyanophenyl)sulfonyl]-piperidine
1-[4-(4-methoxybenzyl)-1,3-thiazol-2-yl]-4-[(2-cyanophenyl)sulfonyl]-piperidine
1-[4-(4-methylbenzyl)-1,3-thiazol-2-yl]-4-[(2-cyanophenyl)sulfonyl]-piperidine
1-[4-(4-ethylbenzyl)-1,3-thiazol-2-yl]-4-[(2-cyanophenyl)sulfonyl]-piperidine
1-[4-(4-ethoxybenzyl)-1,3-thiazol-2-yl]-4-[(2-cyanophenyl)sulfonyl]-piperidine
1-[4-(4-propylbenzyl)-1,3-thiazol-2-yl]-4-[(2-cyanophenyl)sulfonyl]-piperidine
1-[4-(2,6-dimethylbenzyl)-1,3-thiazol-2-yl]-4-[(2-cyanophenyl)sulfonyl]-piperidine
1-[4-(2,3-dimethylbenzyl)-1,3-thiazol-2-yl]-4-[(2-cyanophenyl)sulfonyl]-piperidine
1-[4-(2,5-dimethylbenzyl)-1,3-thiazol-2-yl]-4-[(2-cyanophenyl)sulfonyl]-piperidine
1-[4-(2,4-dichlorobenzyl)-1,3-thiazol-2-yl]-4-[(2-cyanophenyl)sulfonyl]-piperidine
1-[4-(2,4-dimethoxybenzyl)-1,3-thiazol-2-yl]-4-[(2-cyanophenyl)sulfonyl]-piperidine
1-[4-(2,5-dimethoxybenzyl)-1,3-thiazol-2-yl]-4-[(2-cyanophenyl)sulfonyl]-piperidine
1-[4-(3,4-dimethoxybenzyl)-1,3-thiazol-2-yl]-4-[(2-cyanophenyl)sulfonyl]-piperidine
1-[4-(3,5-dimethoxybenzyl)-1,3-thiazol-2-yl]-4-[(2-cyanophenyl)sulfonyl]-piperidine
1-[4-(3,4-dichlorobenzyl)-1,3-thiazol-2-yl]-4-[(2-cyanophenyl)sulfonyl]-piperidine
1-[4-(3,4-dimethylbenzyl)-1,3-thiazol-2-yl]-4-[(2-cyanophenyl)sulfonyl]-piperidine
1-[4-(3,4-difluorobenzyl)-1,3-thiazol-2-yl]-4-[(2-cyanophenyl)sulfonyl]-piperidine
1-[4-(3,5-difluorobenzyl)-1,3-thiazol-2-yl]-4-[(2-cyanophenyl)sulfonyl]-piperidine
1-[4-(3,5-dichlorobenzyl)-1,3-thiazol-2-yl]-4-[(2-cyanophenyl)sulfonyl]-piperidine
1-[4-(3,5-dimethylbenzyl)-1,3-thiazol-2-yl]-4-[(2-cyanophenyl)sulfonyl]-piperidine
1-[4-(3-chloro-4-fluorobenzyl)-1,3-thiazol-2-yl]-4-[(2-cyanophenyl)sulfonyl]-piperidine
1-[4-(3-chloro-5-fluorobenzyl)-1,3-thiazol-2-yl]-4-[(2-cyanophenyl)sulfonyl]-piperidine
1-[4-(4-chloro-3-fluorobenzyl)-1,3-thiazol-2-yl]-4-[(2-cyanophenyl)sulfonyl]-piperidine
1-[4-(3,4,5-trimethoxybenzyl)-1,3-thiazol-2-yl]-4-[(2-cyanophenyl)sulfonyl]-piperidine
1-[4-(2,4,6-trimethylbenzyl)-1,3-thiazol-2-yl]-4-[(2-cyanophenyl)sulfonyl]-piperidine
1-[4-benzyl-1,3-thiazol-2-yl]-4-[(3-nitrophenyl)sulfonyl]-piperidine
1-[4-(2-methylbenzyl)-1,3-thiazol-2-yl]-4-[(3-nitrophenyl)sulfonyl]-piperidine
1-[4-(2-methoxybenzyl)-1,3-thiazol-2-yl]-4-[(3-nitrophenyl)sulfonyl]-piperidine
1-[4-(3-methylbenzyl)-1,3-thiazol-2-yl]-4-[(3-nitrophenyl)sulfonyl]-piperidine
1-[4-(3-methoxybenzyl)-1,3-thiazol-2-yl]-4-[(3-nitrophenyl)sulfonyl]-piperidine
1-[4-(3-bromobenzyl)-1,3-thiazol-2-yl]-4-[(3-nitrophenyl)sulfonyl]-piperidine
1-[4-(4-chlorobenzyl)-1,3-thiazol-2-yl]-4-[(3-nitrophenyl)sulfonyl]-piperidine
1-[4-(4-methoxybenzyl)-1,3-thiazol-2-yl]-4-[(3-nitrophenyl)sulfonyl]-piperidine
1-[4-(4-methylbenzyl)-1,3-thiazol-2-yl]-4-[(3-nitrophenyl)sulfonyl]-piperidine 1-[4-(4-ethylbenzyl)-1,3-thiazol-2-yl]-4-[(3-nitrophenyl)sulfonyl]-piperidine
1-[4-(4-ethoxybenzyl)-1,3-thiazol-2-yl]-4-[(3-nitrophenyl)sulfonyl]-piperidine
1-[4-(4-propylbenzyl)-1,3-thiazol-2-yl]-4-[(3-nitrophenyl)sulfonyl]-piperidine
1-[4-(2,6-dimethylbenzyl)-1,3-thiazol-2-yl]-4-[(3-nitrophenyl)sulfonyl]-piperidine
1-[4-(2,3-dimethylbenzyl)-1,3-thiazol-2-yl]-4-[(3-nitrophenyl)sulfonyl]-piperidine
1-[4-(2,5-dimethylbenzyl)-1,3-thiazol-2-yl]-4-[(3-nitrophenyl)sulfonyl]-piperidine
1-[4-(2,4-dichlorobenzyl)-1,3-thiazol-2-yl]-4-[(3-nitrophenyl)sulfonyl]-piperidine
1-[4-(2,4-dimethoxybenzyl)-1,3-thiazol-2-yl]-4-[(3-nitrophenyl)sulfonyl]-piperidine
1-[4-(2,5-dimethoxybenzyl)-1,3-thiazol-2-yl]-4-[(3-nitrophenyl)sulfonyl]-piperidine
1-[4-(3,4-dimethoxybenzyl)-1,3-thiazol-2-yl]-4-[(3-nitrophenyl)sulfonyl]-piperidine
1-[4-(3,5-dimethoxybenzyl)-1,3-thiazol-2-yl]-4-[(3-nitrophenyl)sulfonyl]-piperidine
1-[4-(3,4-dichlorobenzyl)-1,3-thiazol-2-yl]-4-[(3-nitrophenyl)sulfonyl]-piperidine
1-[4-(3,4-dimethylbenzyl)-1,3-thiazol-2-yl]-4-[(3-nitrophenyl)sulfonyl]-piperidine
1-[4-(3,4-difluorobenzyl)-1,3-thiazol-2-yl]-4-[(3-nitrophenyl)sulfonyl]-piperidine
1-[4-(3,5-difluorobenzyl)-1,3-thiazol-2-yl]-4-[(3-nitrophenyl)sulfonyl]-piperidine
1-[4-(3,5-dichlorobenzyl)-1,3-thiazol-2-yl]-4-[(3-nitrophenyl)sulfonyl]-piperidine
1-[4-(3,5-dimethylbenzyl)-1,3-thiazol-2-yl]-4-[(3-nitrophenyl)sulfonyl]-piperidine
1-[4-(3-chloro-4-fluorobenzyl)-1,3-thiazol-2-yl]-4-[(3-nitrophenyl)sulfonyl]-piperidine
1-[4-(3-chloro-5-fluorobenzyl)-1,3-thiazol-2-yl]-4-[(3-nitrophenyl)sulfonyl]-piperidine
1-[4-(4-chloro-3-fluorobenzyl)-1,3-thiazol-2-yl]-4-[(3-nitrophenyl)sulfonyl]-piperidine
1-[4-(3,4,5-trimethoxybenzyl)-1,3-thiazol-2-yl]-4-[(3-nitrophenyl)sulfonyl]-piperidine
1-[4-(2,4,6-trimethylbenzyl)-1,3-thiazol-2-yl]-4-[(3-nitrophenyl)sulfonyl]-piperidine
1-[4-benzyl-1,3-thiazol-2-yl]-4-[(3-chlorophenyl)sulfonyl]-piperidine
1-[4-(2-methylbenzyl)-1,3-thiazol-2-yl]-4-[(3-chlorophenyl)sulfonyl]-piperidine
1-[4-(2-methoxybenzyl)-1,3-thiazol-2-yl]-4-[(3-chlorophenyl)sulfonyl]-piperidine
1-[4-(3-methylbenzyl)-1,3-thiazol-2-yl]-4-[(3-chlorophenyl)sulfonyl]-piperidine
1-[4-(3-methoxybenzyl)-1,3-thiazol-2-yl]-4-[(3-chlorophenyl)sulfonyl]-piperidine
1-[4-(3-bromobenzyl)-1,3-thiazol-2-yl]-4-[(3-chlorophenyl)sulfonyl]-piperidine
1-[4-(4-chlorobenzyl)-1,3-thiazol-2-yl]-4-[(3-chlorophenyl)sulfonyl]-piperidine
1-[4-(4-methoxybenzyl)-1,3-thiazol-2-yl]-4-[(3-chlorophenyl)sulfonyl]-piperidine
1-[4-(4-methylbenzyl)-1,3-thiazol-2-yl]-4-[(3-chlorophenyl)sulfonyl]-piperidine
1-[4-(4-ethylbenzyl)-1,3-thiazol-2-yl]-4-[(3-chlorophenyl)sulfonyl]-piperidine
1-[4-(4-ethoxybenzyl)-1,3-thiazol-2-yl]-4-[(3-chlorophenyl)sulfonyl]-piperidine
1-[4-(4-propylbenzyl)-1,3-thiazol-2-yl]-4-[(3-chlorophenyl)sulfonyl]-piperidine
1-[4-(2,6-dimethylbenzyl)-1,3-thiazol-2-yl]-4-[(3-chlorophenyl)sulfonyl]-piperidine
1-[4-(2,3-dimethylbenzyl)-1,3-thiazol-2-yl]-4-[(3-chlorophenyl)sulfonyl]-piperidine
1-[4-(2,5-dimethylbenzyl)-1,3-thiazol-2-yl]-4-[(3-chlorophenyl)sulfonyl]-piperidine
1-[4-(2,4-dichlorobenzyl)-1,3-thiazol-2-yl]-4-[(3-chlorophenyl)sulfonyl]-piperidine
1-[4-(2,4-dimethoxybenzyl)-1,3-thiazol-2-yl]-4-[(3-chlorophenyl)sulfonyl]-piperidine
1-[4-(2,5-dimethoxybenzyl)-1,3-thiazol-2-yl]-4-[(3-chlorophenyl)sulfonyl]-piperidine
1-[4-(3,4-dimethoxybenzyl)-1,3-thiazol-2-yl]-4-[(3-chlorophenyl)sulfonyl]-piperidine
1-[4-(3,5-dimethoxybenzyl)-1,3-thiazol-2-yl]-4-[(3-chlorophenyl)sulfonyl]-piperidine
1-[4-(3,4-dichlorobenzyl)-1,3-thiazol-2-yl]-4-[(3-chlorophenyl)sulfonyl]-piperidine
1-[4-(3,4-dimethylbenzyl)-1,3-thiazol-2-yl]-4-[(3-chlorophenyl)sulfonyl]-piperidine
1-[4-(3,4-difluorobenzyl)-1,3-thiazol-2-yl]-4-[(3-chlorophenyl)sulfonyl]-piperidine
1-[4-(3,5-difluorobenzyl)-1,3-thiazol-2-yl]-4-[(3-chlorophenyl)sulfonyl]-piperidine
1-[4-(3,5-dichlorobenzyl)-1,3-thiazol-2-yl]-4-[(3-chlorophenyl)sulfonyl]-piperidine
1-[4-(3,5-dimethylbenzyl)-1,3-thiazol-2-yl]-4-[(3-chlorophenyl)sulfonyl]-piperidine
1-[4-(3-chloro-4-fluorobenzyl)-1,3-thiazol-2-yl]-4-[(3-chlorophenyl)sulfonyl]-piperidine
1-[4-(3-chloro-5-fluorobenzyl)-1,3-thiazol-2-yl]-4-[(3-chlorophenyl)sulfonyl]-piperidine
1-[4-(4-chloro-3-fluorobenzyl)-1,3-thiazol-2-yl]-4-[(3-chlorophenyl)sulfonyl]-piperidine
1-[4-(3,4,5-trimethoxybenzyl)-1,3-thiazol-2-yl]-4-[(3-chlorophenyl)sulfonyl]-piperidine
1-[4-(2,4,6-trimethylbenzyl)-1,3-thiazol-2-yl]-4-[(3-chlorophenyl)sulfonyl]-piperidine
1-[4-benzyl-1,3-thiazol-2-yl]-4-[(3-bromophenyl)sulfonyl]-piperidine
1-[4-(2-methylbenzyl)-1,3-thiazol-2-yl]-4-[(3-bromophenyl)sulfonyl]-piperidine
1-[4-(2-methoxybenzyl)-1,3-thiazol-2-yl]-4-[(3-bromophenyl)sulfonyl]-piperidine
1-[4-(3-methylbenzyl)-1,3-thiazol-2-yl]-4-[(3-bromophenyl)sulfonyl]-piperidine
1-[4-(3-methoxybenzyl)-1,3-thiazol-2-yl]-4-[(3-bromophenyl)sulfonyl]-piperidine
1-[4-(3-bromobenzyl)-1,3-thiazol-2-yl]-4-[(3-bromophenyl)sulfonyl]-piperidine
1-[4-(4-chlorobenzyl)-1,3-thiazol-2-yl]-4-[(3-bromophenyl)sulfonyl]-piperidine
1-[4-(4-methoxybenzyl)-1,3-thiazol-2-yl]-4-[(3-bromophenyl)sulfonyl]-piperidine
1-[4-(4-methylbenzyl)-1,3-thiazol-2-yl]-4-[(3-bromophenyl)sulfonyl]-piperidine
1-[4-(4-ethylbenzyl)-1,3-thiazol-2-yl]-4-[(3-bromophenyl)sulfonyl]-piperidine
1-[4-(4-ethoxybenzyl)-1,3-thiazol-2-yl]-4-[(3-bromophenyl)sulfonyl]-piperidine
1-[4-(4-propylbenzyl)-1,3-thiazol-2-yl]-4-[(3-bromophenyl)sulfonyl]-piperidine
1-[4-(2,6-dimethylbenzyl)-1,3-thiazol-2-yl]-4-[(3-bromophenyl)sulfonyl]-piperidine 1-[4-(2,3-dimethylbenzyl)-1,3-thiazol-2-yl]-4-[(3-bromophenyl)sulfonyl]-piperidine
1-[4-(2,5-dimethylbenzyl)-1,3-thiazol-2-yl]-4-[(3-bromophenyl)sulfonyl]-piperidine
1-[4-(2,4-dichlorobenzyl)-1,3-thiazol-2-yl]-4-[(3-bromophenyl)sulfonyl]-piperidine
1-[4-(2,4-dimethoxybenzyl)-1,3-thiazol-2-yl]-4-[(3-bromophenyl)sulfonyl]-piperidine
1-[4-(2,5-dimethoxybenzyl)-1,3-thiazol-2-yl]-4-[(3-bromophenyl)sulfonyl]-piperidine
1-[4-(3,4-dimethoxybenzyl)-1,3-thiazol-2-yl]-4-[(3-bromophenyl)sulfonyl]-piperidine
1-[4-(3,5-dimethoxybenzyl)-1,3-thiazol-2-yl]-4-[(3-bromophenyl)sulfonyl]-piperidine
1-[4-(3,4-dichlorobenzyl)-1,3-thiazol-2-yl]-4-[(3-bromophenyl)sulfonyl]-piperidine
1-[4-(3,4-dimethylbenzyl)-1,3-thiazol-2-yl]-4-[(3-bromophenyl)sulfonyl]-piperidine
1-[4-(3,4-difluorobenzyl)-1,3-thiazol-2-yl]-4-[(3-bromophenyl)sulfonyl]-piperidine
1-[4-(3,5-difluorobenzyl)-1,3-thiazol-2-yl]-4-[(3-bromophenyl)sulfonyl]-piperidine
1-[4-(3,5-dichlorobenzyl)-1,3-thiazol-2-yl]-4-[(3-bromophenyl)sulfonyl]-piperidine
1-[4-(3,5-dimethylbenzyl)-1,3-thiazol-2-yl]-4-[(3-bromophenyl)sulfonyl]-piperidine
1-[4-(3-chloro-4-fluorobenzyl)-1,3-thiazol-2-yl]-4-[(3-bromophenyl)sulfonyl]-piperidine
1-[4-(3-chloro-5-fluorobenzyl)-1,3-thiazol-2-yl]-4-[(3-bromophenyl)sulfonyl]-piperidine
1-[4-(4-chloro-3-fluorobenzyl)-1,3-thiazol-2-yl]-4-[(3-bromophenyl)sulfonyl]-piperidine
1-[4-(3,4,5-trimethoxybenzyl)-1,3-thiazol-2-yl]-4-[(3-bromophenyl)sulfonyl]-piperidine
1-[4-(2,4,6-trimethylbenzyl)-1,3-thiazol-2-yl]-4-[(3-bromophenyl)sulfonyl]-piperidine
1-[4-benzyl-1,3-thiazol-2-yl]-4-[(3-fluorophenyl)sulfonyl]-piperidine
1-[4-(2-methylbenzyl)-1,3-thiazol-2-yl]-4-[(3-fluorophenyl)sulfonyl]-piperidine
1-[4-(2-methoxybenzyl)-1,3-thiazol-2-yl]-4-[(3-fluorophenyl)sulfonyl]-piperidine
1-[4-(3-methylbenzyl)-1,3-thiazol-2-yl]-4-[(3-fluorophenyl)sulfonyl]-piperidine
1-[4-(3-methoxybenzyl)-1,3-thiazol-2-yl]-4-[(3-fluorophenyl)sulfonyl]-piperidine
1-[4-(3-bromobenzyl)-1,3-thiazol-2-yl]-4-[(3-fluorophenyl)sulfonyl]-piperidine
1-[4-(4-chlorobenzyl)-1,3-thiazol-2-yl]-4-[(3-fluorophenyl)sulfonyl]-piperidine
1-[4-(4-methoxybenzyl)-1,3-thiazol-2-yl]-4-[(3-fluorophenyl)sulfonyl]-piperidine
1-[4-(4-methylbenzyl)-1,3-thiazol-2-yl]-4-[(3-fluorophenyl)sulfonyl]-piperidine
1-[4-(4-ethylbenzyl)-1,3-thiazol-2-yl]-4-[(3-fluorophenyl)sulfonyl]-piperidine
1-[4-(4-ethoxybenzyl)-1,3-thiazol-2-yl]-4-[(3-fluorophenyl)sulfonyl]-piperidine
1-[4-(4-propylbenzyl)-1,3-thiazol-2-yl]-4-[(3-fluorophenyl)sulfonyl]-piperidine
1-[4-(2,6-dimethylbenzyl)-1,3-thiazol-2-yl]-4-[(3-fluorophenyl)sulfonyl]-piperidine
1-[4-(2,3-dimethylbenzyl)-1,3-thiazol-2-yl]-4-[(3-fluorophenyl)sulfonyl]-piperidine
1-[4-(2,5-dimethylbenzyl)-1,3-thiazol-2-yl]-4-[(3-fluorophenyl)sulfonyl]-piperidine
1-[4-(2,4-dichlorobenzyl)-1,3-thiazol-2-yl]-4-[(3-fluorophenyl)sulfonyl]-piperidine
1-[4-(2,4-dimethoxybenzyl)-1,3-thiazol-2-yl]-4-[(3-fluorophenyl)sulfonyl]-piperidine
1-[4-(2,5-dimethoxybenzyl)-1,3-thiazol-2-yl]-4-[(3-fluorophenyl)sulfonyl]-piperidine
1-[4-(3,4-dimethoxybenzyl)-1,3-thiazol-2-yl]-4-[(3-fluorophenyl)sulfonyl]-piperidine
1-[4-(3,5-dimethoxybenzyl)-1,3-thiazol-2-yl]-4-[(3-fluorophenyl)sulfonyl]-piperidine
1-[4-(3,4-dichlorobenzyl)-1,3-thiazol-2-yl]-4-[(3-fluorophenyl)sulfonyl]-piperidine
1-[4-(3,4-dimethylbenzyl)-1,3-thiazol-2-yl]-4-[(3-fluorophenyl)sulfonyl]-piperidine
1-[4-(3,4-difluorobenzyl)-1,3-thiazol-2-yl]-4-[(3-fluorophenyl)sulfonyl]-piperidine
1-[4-(3,5-difluorobenzyl)-1,3-thiazol-2-yl]-4-[(3-fluorophenyl)sulfonyl]-piperidine
1-[4-(3,5-dichlorobenzyl)-1,3-thiazol-2-yl]-4-[(3-fluorophenyl)sulfonyl]-piperidine
1-[4-(3,5-dimethylbenzyl)-1,3-thiazol-2-yl]-4-[(3-fluorophenyl)sulfonyl]-piperidine
1-[4-(3-chloro-4-fluorobenzyl)-1,3-thiazol-2-yl]-4-[(3-fluorophenyl)sulfonyl]-piperidine
1-[4-(3-chloro-5-fluorobenzyl)-1,3-thiazol-2-yl]-4-[(3-fluorophenyl)sulfonyl]-piperidine
1-[4-(4-chloro-3-fluorobenzyl)-1,3-thiazol-2-yl]-4-[(3-fluorophenyl)sulfonyl]-piperidine
1-[4-(3,4,5-trimethoxybenzyl)-1,3-thiazol-2-yl]-4-[(3-fluorophenyl)sulfonyl]-piperidine
1-[4-(2,4,6-trimethylbenzyl)-1,3-thiazol-2-yl]-4-[(3-fluorophenyl)sulfonyl]-piperidine
1-[4-benzyl-1,3-thiazol-2-yl]-4-[(3-chloro-4-fluorophenyl)sulfonyl]-piperidine
1-[4-(2-methylbenzyl)-1,3-thiazol-2-yl]-4-[(3-chloro-4-fluorophenyl)sulfonyl]-piperidine
1-[4-(2-methoxybenzyl)-1,3-thiazol-2-yl]-4-[(3-chloro-4-fluorophenyl)sulfonyl]-piperidine
1-[4-(3-methylbenzyl)-1,3-thiazol-2-yl]-4-[(3-chloro-4-fluorophenyl)sulfonyl]-piperidine
1-[4-(3-methoxybenzyl)-1,3-thiazol-2-yl]-4-[(3-chloro-4-fluorophenyl)sulfonyl]-piperidine
1-[4-(3-bromobenzyl)-1,3-thiazol-2-yl]-4-[(3-chloro-4-fluorophenyl)sulfonyl]-piperidine
1-[4-(4-chlorobenzyl)-1,3-thiazol-2-yl]-4-[(3-chloro-4-fluorophenyl)sulfonyl]-piperidine
1-[4-(4-methoxybenzyl)-1,3-thiazol-2-yl]-4-[(3-chloro-4-fluorophenyl)sulfonyl]-piperidine
1-[4-(4-methylbenzyl)-1,3-thiazol-2-yl]-4-[(3-chloro-4-fluorophenyl)sulfonyl]-piperidine
1-[4-(4-ethylbenzyl)-1,3-thiazol-2-yl]-4-[(3-chloro-4-fluorophenyl)sulfonyl]-piperidine
1-[4-(4-ethoxybenzyl)-1,3-thiazol-2-yl]-4-[(3-chloro-4-fluorophenyl)sulfonyl]-piperidine
1-[4-(4-propylbenzyl)-1,3-thiazol-2-yl]-4-[(3-chloro-4-fluorophenyl)sulfonyl]-piperidine
1-[4-(2,6-dimethylbenzyl)-1,3-thiazol-2-yl]-4-[(3-chloro-4-fluorophenyl)sulfonyl]-piperidine
1-[4-(2,3-dimethylbenzyl)-1,3-thiazol-2-yl]-4-[(3-chloro-4-fluorophenyl)sulfonyl]-piperidine
1-[4-(2,5-dimethylbenzyl)-1,3-thiazol-2-yl]-4-[(3-chloro-4-fluorophenyl)sulfonyl]-piperidine
1-[4-(2,4-dichlorobenzyl)-1,3-thiazol-2-yl]-4-[(3-chloro-4-fluorophenyl)sulfonyl]-piperidine
1-[4-(2,4-dimethoxybenzyl)-1,3-thiazol-2-yl]-4-[(3-chloro-4-fluorophenyl)sulfonyl]-piperidine 1-[4-(2,5-dimethoxybenzyl)-1,3-thiazol-2-yl]-4-[(3-chloro-4-fluorophenyl)sulfonyl]-piperidine
1-[4-(3,4-dimethoxybenzyl)-1,3-thiazol-2-yl]-4-[(3-chloro-4-fluorophenyl)sulfonyl]-piperidine
1-[4-(3,5-dimethoxybenzyl)-1,3-thiazol-2-yl]-4-[(3-chloro-4-fluorophenyl)sulfonyl]-piperidine
1-[4-(3,4-dichlorobenzyl)-1,3-thiazol-2-yl]-4-[(3-chloro-4-fluorophenyl)sulfonyl]-piperidine
1-[4-(3,4-dimethylbenzyl)-1,3-thiazol-2-yl]-4-[(3-chloro-4-fluorophenyl)sulfonyl]-piperidine
1-[4-(3,4-difluorobenzyl)-1,3-thiazol-2-yl]-4-[(3-chloro-4-fluorophenyl)sulfonyl]-piperidine
1-[4-(3,5-difluorobenzyl)-1,3-thiazol-2-yl]-4-[(3-chloro-4-fluorophenyl)sulfonyl]-piperidine
1-[4-(3,5-dichlorobenzyl)-1,3-thiazol-2-yl]-4-[(3-chloro-4-fluorophenyl)sulfonyl]-piperidine
1-[4-(3,5-dimethylbenzyl)-1,3-thiazol-2-yl]-4-[(3-chloro-4-fluorophenyl)sulfonyl]-piperidine
1-[4-(3-chloro-4-fluorobenzyl)-1,3-thiazol-2-yl]-4-[(3-chloro-4-fluorophenyl)sulfonyl]-piperidine
1-[4-(3-chloro-5-fluorobenzyl)-1,3-thiazol-2-yl]-4-[(3-chloro-4-fluorophenyl)sulfonyl]-piperidine
1-[4-(4-chloro-3-fluorobenzyl)-1,3-thiazol-2-yl]-4-[(3-chloro-4-fluorophenyl)sulfonyl]-piperidine
1-[4-(3,4,5-trimethoxybenzyl)-1,3-thiazol-2-yl]-4-[(3-chloro-4-fluorophenyl)sulfonyl]-piperidine
1-[4-(2,4,6-trimethylbenzyl)-1,3-thiazol-2-yl]-4-[(3-chloro-4-fluorophenyl)sulfonyl]-piperidine
1-[4-benzyl-1,3-thiazol-2-yl]-4-[(2-chloro-4-fluorophenyl)sulfonyl]-piperidine
1-[4-(2-methylbenzyl)-1,3-thiazol-2-yl]-4-[(2-chloro-4-fluorophenyl)sulfonyl]-piperidine
1-[4-(2-methoxybenzyl)-1,3-thiazol-2-yl]-4-[(2-chloro-4-fluorophenyl)sulfonyl]-piperidine
1-[4-(3-methylbenzyl)-1,3-thiazol-2-yl]-4-[(2-chloro-4-fluorophenyl)sulfonyl]-piperidine
1-[4-(3-methoxybenzyl)-1,3-thiazol-2-yl]-4-[(2-chloro-4-fluorophenyl)sulfonyl]-piperidine
1-[4-(3-bromobenzyl)-1,3-thiazol-2-yl]-4-[(2-chloro-4-fluorophenyl)sulfonyl]-piperidine
1-[4-(4-chlorobenzyl)-1,3-thiazol-2-yl]-4-[(2-chloro-4-fluorophenyl)sulfonyl]-piperidine
1-[4-(4-methoxybenzyl)-1,3-thiazol-2-yl]-4-[(2-chloro-4-fluorophenyl)sulfonyl]-piperidine
1-[4-(4-methylbenzyl)-1,3-thiazol-2-yl]-4-[(2-chloro-4-fluorophenyl)sulfonyl]-piperidine
1-[4-(4-ethylbenzyl)-1,3-thiazol-2-yl]-4-[(2-chloro-4-fluorophenyl)sulfonyl]-piperidine
1-[4-(4-ethoxybenzyl)-1,3-thiazol-2-yl]-4-[(2-chloro-4-fluorophenyl)sulfonyl]-piperidine
1-[4-(4-propylbenzyl)-1,3-thiazol-2-yl]-4-[(2-chloro-4-fluorophenyl)sulfonyl]-piperidine
1-[4-(2,6-dimethylbenzyl)-1,3-thiazol-2-yl]-4-[(2-chloro-4-fluorophenyl)sulfonyl]-piperidine
1-[4-(2,3-dimethylbenzyl)-1,3-thiazol-2-yl]-4-[(2-chloro-4-fluorophenyl)sulfonyl]-piperidine
1-[4-(2,5-dimethylbenzyl)-1,3-thiazol-2-yl]-4-[(2-chloro-4-fluorophenyl)sulfonyl]-piperidine
1-[4-(2,4-dichlorobenzyl)-1,3-thiazol-2-yl]-4-[(2-chloro-4-fluorophenyl)sulfonyl]-piperidine
1-[4-(2,4-dimethoxybenzyl)-1,3-thiazol-2-yl]-4-[(2-chloro-4-fluorophenyl)sulfonyl]-piperidine
1-[4-(2,5-dimethoxybenzyl)-1,3-thiazol-2-yl]-4-[(2-chloro-4-fluorophenyl)sulfonyl]-piperidine
1-[4-(3,4-dimethoxybenzyl)-1,3-thiazol-2-yl]-4-[(2-chloro-4-fluorophenyl)sulfonyl]-piperidine
1-[4-(3,5-dimethoxybenzyl)-1,3-thiazol-2-yl]-4-[(2-chloro-4-fluorophenyl)sulfonyl]-piperidine
1-[4-(3,4-dichlorobenzyl)-1,3-thiazol-2-yl]-4-[(2-chloro-4-fluorophenyl)sulfonyl]-piperidine
1-[4-(3,4-dimethylbenzyl)-1,3-thiazol-2-yl]-4-[(2-chloro-4-fluorophenyl)sulfonyl]-piperidine
1-[4-(3,4-difluorobenzyl)-1,3-thiazol-2-yl]-4-[(2-chloro-4-fluorophenyl)sulfonyl]-piperidine
1-[4-(3,5-difluorobenzyl)-1,3-thiazol-2-yl]-4-[(2-chloro-4-fluorophenyl)sulfonyl]-piperidine
1-[4-(3,5-dichlorobenzyl)-1,3-thiazol-2-yl]-4-[(2-chloro-4-fluorophenyl)sulfonyl]-piperidine
1-[4-(3,5-dimethylbenzyl)-1,3-thiazol-2-yl]-4-[(2-chloro-4-fluorophenyl)sulfonyl]-piperidine
1-[4-(3-chloro-4-fluorobenzyl)-1,3-thiazol-2-yl]-4-[(2-chloro-4-fluorophenyl)sulfonyl]-piperidine
1-[4-(3-chloro-5-fluorobenzyl)-1,3-thiazol-2-yl]-4-[(2-chloro-4-fluorophenyl)sulfonyl]-piperidine
1-[4-(4-chloro-3-fluorobenzyl)-1,3-thiazol-2-yl]-4-[(2-chloro-4-fluorophenyl)sulfonyl]-piperidine
1-[4-(3,4,5-trimethoxybenzyl)-1,3-thiazol-2-yl]-4-[(2-chloro-4-fluorophenyl)sulfonyl]-piperidine
1-[4-(2,4,6-trimethylbenzyl)-1,3-thiazol-2-yl]-4-[(2-chloro-4-fluorophenyl)sulfonyl]-piperidine
1-[4-benzyl-1,3-thiazol-2-yl]-4-[(2-chloro-2-methylphenyl)sulfonyl]-piperidine
1-[4-(2-methylbenzyl)-1,3-thiazol-2-yl]-4-[(2-chloro-2-methylphenyl)sulfonyl]-piperidine
1-[4-(2-methoxybenzyl)-1,3-thiazol-2-yl]-4-[(2-chloro-2-methylphenyl)sulfonyl]-piperidine
1-[4-(3-methylbenzyl)-1,3-thiazol-2-yl]-4-[(2-chloro-2-methylphenyl)sulfonyl]-piperidine
1-[4-(3-methoxybenzyl)-1,3-thiazol-2-yl]-4-[(2-chloro-2-methylphenyl)sulfonyl]-piperidine
1-[4-(3-bromobenzyl)-1,3-thiazol-2-yl]-4-[(2-chloro-2-methylphenyl)sulfonyl]-piperidine
1-[4-(4-chlorobenzyl)-1,3-thiazol-2-yl]-4-[(2-chloro-2-methylphenyl)sulfonyl]-piperidine
1-[4-(4-methoxybenzyl)-1,3-thiazol-2-yl]-4-[(2-chloro-2-methylphenyl)sulfonyl]-piperidine
1-[4-(4-methylbenzyl)-1,3-thiazol-2-yl]-4-[(2-chloro-2-methylphenyl)sulfonyl]-piperidine
1-[4-(4-ethylbenzyl)-1,3-thiazol-2-yl]-4-[(2-chloro-2-methylphenyl)sulfonyl]-piperidine
1-[4-(4-ethoxybenzyl)-1,3-thiazol-2-yl]-4-[(2-chloro-2-methylphenyl)sulfonyl]-piperidine
1-[4-(4-propylbenzyl)-1,3-thiazol-2-yl]-4-[(2-chloro-2-methylphenyl)sulfonyl]-piperidine
1-[4-(2,6-dimethylbenzyl)-1,3-thiazol-2-yl]-4-[(2-chloro-2-methylphenyl)sulfonyl]-piperidine
1-[4-(2,3-dimethylbenzyl)-1,3-thiazol-2-yl]-4-[(2-chloro-2-methylphenyl)sulfonyl]-piperidine
1-[4-(2,5-dimethylbenzyl)-1,3-thiazol-2-yl]-4-[(2-chloro-2-methylphenyl)sulfonyl]-piperidine
1-[4-(2,4-dichlorobenzyl)-1,3-thiazol-2-yl]-4-[(2-chloro-2-methylphenyl)sulfonyl]-piperidine
1-[4-(2,4-dimethoxybenzyl)-1,3-thiazol-2-yl]-4-[(2-chloro-2-methylphenyl)sulfonyl]-piperidine
1-[4-(2,5-dimethoxybenzyl)-1,3-thiazol-2-yl]-4-[(2-chloro-2-methylphenyl)sulfonyl]-piperidine
1-[4-(3,4-dimethoxybenzyl)-1,3-thiazol-2-yl]-4-[(2-chloro-2-methylphenyl)sulfonyl]-piperidine
1-[4-(3,5-dimethoxybenzyl)-1,3-thiazol-2-yl]-4-[(2-chloro-2-methylphenyl)sulfonyl]-piperidine
1-[4-(3,4-dichlorobenzyl)-1,3-thiazol-2-yl]-4-[(2-chloro-2-methylphenyl)sulfonyl]-piperidine 1-[4-(3,4-dimethylbenzyl)-1,3-thiazol-2-yl]-4-[(2-chloro-2-methylphenyl)sulfonyl]-piperidine
1-[4-(3,4-difluorobenzyl)-1,3-thiazol-2-yl]-4-[(2-chloro-2-methylphenyl)sulfonyl]-piperidine
1-[4-(3,5-difluorobenzyl)-1,3-thiazol-2-yl]-4-[(2-chloro-2-methylphenyl)sulfonyl]-piperidine
1-[4-(3,5-dichlorobenzyl)-1,3-thiazol-2-yl]-4-[(2-chloro-2-methylphenyl)sulfonyl]-piperidine
1-[4-(3,5-dimethylbenzyl)-1,3-thiazol-2-yl]-4-[(2-chloro-2-methylphenyl)sulfonyl]-piperidine
1-[4-(3-chloro-4-fluorobenzyl)-1,3-thiazol-2-yl]-4-[(2-chloro-2-methylphenyl)sulfonyl]-piperidine
1-[4-(3-chloro-5-fluorobenzyl)-1,3-thiazol-2-yl]-4-[(2-chloro-2-methylphenyl)sulfonyl]-piperidine
1-[4-(4-chloro-3-fluorobenzyl)-1,3-thiazol-2-yl]-4-[(2-chloro-2-methylphenyl)sulfonyl]-piperidine
1-[4-(3,4,5-trimethoxybenzyl)-1,3-thiazol-2-yl]-4-[(2-chloro-2-methylphenyl)sulfonyl]-piperidine
1-[4-(2,4,6-trimethylbenzyl)-1,3-thiazol-2-yl]-4-[(2-chloro-2-methylphenyl)sulfonyl]-piperidine
1-[4-benzyl-1,3-thiazol-2-yl]-4-[(5-fluoro-2-methylphenyl)sulfonyl]-piperidine
1-[4-(2-methylbenzyl)-1,3-thiazol-2-yl]-4-[(5-fluoro-2-methylphenyl)sulfonyl]-piperidine
1-[4-(2-methoxybenzyl)-1,3-thiazol-2-yl]-4-[(5-fluoro-2-methylphenyl)sulfonyl]-piperidine
1-[4-(3-methylbenzyl)-1,3-thiazol-2-yl]-4-[(5-fluoro-2-methylphenyl)sulfonyl]-piperidine
1-[4-(3-methoxybenzyl)-1,3-thiazol-2-yl]-4-[(5-fluoro-2-methylphenyl)sulfonyl]-piperidine
1-[4-(3-bromobenzyl)-1,3-thiazol-2-yl]-4-[(5-fluoro-2-methylphenyl)sulfonyl]-piperidine
1-[4-(4-chlorobenzyl)-1,3-thiazol-2-yl]-4-[(5-fluoro-2-methylphenyl)sulfonyl]-piperidine
1-[4-(4-methoxybenzyl)-1,3-thiazol-2-yl]-4-[(5-fluoro-2-methylphenyl)sulfonyl]-piperidine
1-[4-(4-methylbenzyl)-1,3-thiazol-2-yl]-4-[(5-fluoro-2-methylphenyl)sulfonyl]-piperidine
1-[4-(4-ethylbenzyl)-1,3-thiazol-2-yl]-4-[(5-fluoro-2-methylphenyl)sulfonyl]-piperidine
1-[4-(4-ethoxybenzyl)-1,3-thiazol-2-yl]-4-[(5-fluoro-2-methylphenyl)sulfonyl]-piperidine
1-[4-(4-propylbenzyl)-1,3-thiazol-2-yl]-4-[(5-fluoro-2-methylphenyl)sulfonyl]-piperidine
1-[4-(2,6-dimethylbenzyl)-1,3-thiazol-2-yl]-4-[(5-fluoro-2-methylphenyl)sulfonyl]-piperidine
1-[4-(2,3-dimethylbenzyl)-1,3-thiazol-2-yl]-4-[(5-fluoro-2-methylphenyl)sulfonyl]-piperidine
1-[4-(2,5-dimethylbenzyl)-1,3-thiazol-2-yl]-4-[(5-fluoro-2-methylphenyl)sulfonyl]-piperidine
1-[4-(2,4-dichlorobenzyl)-1,3-thiazol-2-yl]-4-[(5-fluoro-2-methylphenyl)sulfonyl]-piperidine
1-[4-(2,4-dimethoxybenzyl)-1,3-thiazol-2-yl]-4-[(5-fluoro-2-methylphenyl)sulfonyl]-piperidine
1-[4-(2,5-dimethoxybenzyl)-1,3-thiazol-2-yl]-4-[(5-fluoro-2-methylphenyl)sulfonyl]-piperidine
1-[4-(3,4-dimethoxybenzyl)-1,3-thiazol-2-yl]-4-[(5-fluoro-2-methylphenyl)sulfonyl]-piperidine
1-[4-(3,5-dimethoxybenzyl)-1,3-thiazol-2-yl]-4-[(5-fluoro-2-methylphenyl)sulfonyl]-piperidine
1-[4-(3,4-dichlorobenzyl)-1,3-thiazol-2-yl]-4-[(5-fluoro-2-methylphenyl)sulfonyl]-piperidine
1-[4-(3,4-dimethylbenzyl)-1,3-thiazol-2-yl]-4-[(5-fluoro-2-methylphenyl)sulfonyl]-piperidine
1-[4-(3,4-difluorobenzyl)-1,3-thiazol-2-yl]-4-[(5-fluoro-2-methylphenyl)sulfonyl]-piperidine
1-[4-(3,5-difluorobenzyl)-1,3-thiazol-2-yl]-4-[(5-fluoro-2-methylphenyl)sulfonyl]-piperidine
1-[4-(3,5-dichlorobenzyl)-1,3-thiazol-2-yl]-4-[(5-fluoro-2-methylphenyl)sulfonyl]-piperidine
1-[4-(3,5-dimethylbenzyl)-1,3-thiazol-2-yl]-4-[(5-fluoro-2-methylphenyl)sulfonyl]-piperidine
1-[4-(3-chloro-4-fluorobenzyl)-1,3-thiazol-2-yl]-4-[(5-fluoro-2-methylphenyl)sulfonyl]-piperidine
1-[4-(3-chloro-5-fluorobenzyl)-1,3-thiazol-2-yl]-4-[(5-fluoro-2-methylphenyl)sulfonyl]-piperidine
1-[4-(4-chloro-3-fluorobenzyl)-1,3-thiazol-2-yl]-4-[(5-fluoro-2-methylphenyl)sulfonyl]-piperidine
1-[4-(3,4,5-trimethoxybenzyl)-1,3-thiazol-2-yl]-4-[(5-fluoro-2-methylphenyl)sulfonyl]-piperidine
1-[4-(2,4,6-trimethylbenzyl)-1,3-thiazol-2-yl]-4-[(5-fluoro-2-methylphenyl)sulfonyl]-piperidine
1-[4-benzyl-1,3-thiazol-2-yl]-4-[(2,3,5,6-tetramethylphenyl)sulfonyl]-piperidine
1-[4-(2-methylbenzyl)-1,3-thiazol-2-yl]-4-[(2,3,5,6-tetramethylphenyl)sulfonyl]-piperidine
1-[4-(2-methoxybenzyl)-1,3-thiazol-2-yl]-4-[(2,3,5,6-tetramethylphenyl)sulfonyl]-piperidine
1-[4-(3-methylbenzyl)-1,3-thiazol-2-yl]-4-[(2,3,5,6-tetramethylphenyl)sulfonyl]-piperidine
1-[4-(3-methoxybenzyl)-1,3-thiazol-2-yl]-4-[(2,3,5,6-tetramethylphenyl)sulfonyl]-piperidine
1-[4-(3-bromobenzyl)-1,3-thiazol-2-yl]-4-[(2,3,5,6-tetramethylphenyl)sulfonyl]-piperidine
1-[4-(4-chlorobenzyl)-1,3-thiazol-2-yl]-4-[(2,3,5,6-tetramethylphenyl)sulfonyl]-piperidine
1-[4-(4-methoxybenzyl)-1,3-thiazol-2-yl]-4-[(2,3,5,6-tetramethylphenyl)sulfonyl]-piperidine
1-[4-(4-methylbenzyl)-1,3-thiazol-2-yl]-4-[(2,3,5,6-tetramethylphenyl)sulfonyl]-piperidine
1-[4-(4-ethylbenzyl)-1,3-thiazol-2-yl]-4-[(2,3,5,6-tetramethylphenyl)sulfonyl]-piperidine
1-[4-(4-ethoxybenzyl)-1,3-thiazol-2-yl]-4-[(2,3,5,6-tetramethylphenyl)sulfonyl]-piperidine
1-[4-(4-propylbenzyl)-1,3-thiazol-2-yl]-4-[(2,3,5,6-tetramethylphenyl)sulfonyl]-piperidine
1-[4-(2,6-dimethylbenzyl)-1,3-thiazol-2-yl]-4-[(2,3,5,6-tetramethylphenyl)sulfonyl]-piperidine
1-[4-(2,3-dimethylbenzyl)-1,3-thiazol-2-yl]-4-[(2,3,5,6-tetramethylphenyl)sulfonyl]-piperidine
1-[4-(2,5-dimethylbenzyl)-1,3-thiazol-2-yl]-4-[(2,3,5,6-tetramethylphenyl)sulfonyl]-piperidine
1-[4-(2,4-dichlorobenzyl)-1,3-thiazol-2-yl]-4-[(2,3,5,6-tetramethylphenyl)sulfonyl]-piperidine
1-[4-(2,4-dimethoxybenzyl)-1,3-thiazol-2-yl]-4-[(2,3,5,6-tetramethylphenyl)sulfonyl]-piperidine
1-[4-(2,5-dimethoxybenzyl)-1,3-thiazol-2-yl]-4-[(2,3,5,6-tetramethylphenyl)sulfonyl]-piperidine
1-[4-(3,4-dimethoxybenzyl)-1,3-thiazol-2-yl]-4-[(2,3,5,6-tetramethylphenyl)sulfonyl]-piperidine
1-[4-(3,5-dimethoxybenzyl)-1,3-thiazol-2-yl]-4-[(2,3,5,6-tetramethylphenyl)sulfonyl]-piperidine
1-[4-(3,4-dichlorobenzyl)-1,3-thiazol-2-yl]-4-[(2,3,5,6-tetramethylphenyl)sulfonyl]-piperidine
1-[4-(3,4-dimethylbenzyl)-1,3-thiazol-2-yl]-4-[(2,3,5,6-tetramethylphenyl)sulfonyl]-piperidine
1-[4-(3,4-difluorobenzyl)-1,3-thiazol-2-yl]-4-[(2,3,5,6-tetramethylphenyl)sulfonyl]-piperidine
1-[4-(3,5-difluorobenzyl)-1,3-thiazol-2-yl]-4-[(2,3,5,6-tetramethylphenyl)sulfonyl]-piperidine
1-[4-(3,5-dichlorobenzyl)-1,3-thiazol-2-yl]-4-[(2,3,5,6-tetramethylphenyl)sulfonyl]-piperidine 1-[4-(3,5-dimethylbenzyl)-1,3-thiazol-2-yl]-4-[(2,3,5,6-tetramethylphenyl)sulfonyl]-piperidine
1-[4-(3-chloro-4-fluorobenzyl)-1,3-thiazol-2-yl]-4-[(2,3,5,6-tetramethylphenyl)sulfonyl]-piperidine
1-[4-(3-chloro-5-fluorobenzyl)-1,3-thiazol-2-yl]-4-[(2,3,5,6-tetramethylphenyl)sulfonyl]-piperidine
1-[4-(4-chloro-3-fluorobenzyl)-1,3-thiazol-2-yl]-4-[(2,3,5,6-tetramethylphenyl)sulfonyl]-piperidine
1-[4-(3,4,5-trimethoxybenzyl)-1,3-thiazol-2-yl]-4-[(2,3,5,6-tetramethylphenyl)sulfonyl]-piperidine
1-[4-(2,4,6-trimethylbenzyl)-1,3-thiazol-2-yl]-4-[(2,3,5,6-tetramethylphenyl)sulfonyl]-piperidine
1-[4-benzyl-1,3-thiazol-2-yl]-4-[(2,5-dibromo-3,6-difluorophenyl)sulfonyl]-piperidine
1-[4-(2-methylbenzyl)-1,3-thiazol-2-yl]-4-[(2,5-dibromo-3,6-difluorophenyl)sulfonyl]-piperidine
1-[4-(2-methoxybenzyl)-1,3-thiazol-2-yl]-4-[(2,5-dibromo-3,6-difluorophenyl)sulfonyl]-piperidine
1-[4-(3-methylbenzyl)-1,3-thiazol-2-yl]-4-[(2,5-dibromo-3,6-difluorophenyl)sulfonyl]-piperidine
1-[4-(3-methoxybenzyl)-1,3-thiazol-2-yl]-4-[(2,5-dibromo-3,6-difluorophenyl)sulfonyl]-piperidine
1-[4-(3-bromobenzyl)-1,3-thiazol-2-yl]-4-[(2,5-dibromo-3,6-difluorophenyl)sulfonyl]-piperidine
1-[4-(4-chlorobenzyl)-1,3-thiazol-2-yl]-4-[(2,5-dibromo-3,6-difluorophenyl)sulfonyl]-piperidine
1-[4-(4-methoxybenzyl)-1,3-thiazol-2-yl]-4-[(2,5-dibromo-3,6-difluorophenyl)sulfonyl]-piperidine
1-[4-(4-methylbenzyl)-1,3-thiazol-2-yl]-4-[(2,5-dibromo-3,6-difluorophenyl)sulfonyl]-piperidine
1-[4-(4-ethylbenzyl)-1,3-thiazol-2-yl]-4-[(2,5-dibromo-3,6-difluorophenyl)sulfonyl]-piperidine
1-[4-(4-ethoxybenzyl)-1,3-thiazol-2-yl]-4-[(2,5-dibromo-3,6-difluorophenyl)sulfonyl]-piperidine
1-[4-(4-propylbenzyl)-1,3-thiazol-2-yl]-4-[(2,5-dibromo-3,6-difluorophenyl)sulfonyl]-piperidine
1-[4-(2,6-dimethylbenzyl)-1,3-thiazol-2-yl]-4-[(2,5-dibromo-3,6-difluorophenyl)sulfonyl]-piperidine
1-[4-(2,3-dimethylbenzyl)-1,3-thiazol-2-yl]-4-[(2,5-dibromo-3,6-difluorophenyl)sulfonyl]-piperidine
1-[4-(2,5-dimethylbenzyl)-1,3-thiazol-2-yl]-4-[(2,5-dibromo-3,6-difluorophenyl)sulfonyl]-piperidine
1-[4-(2,4-dichlorobenzyl)-1,3-thiazol-2-yl]-4-[(2,5-dibromo-3,6-difluorophenyl)sulfonyl]-piperidine
1-[4-(2,4-dimethoxybenzyl)-1,3-thiazol-2-yl]-4-[(2,5-dibromo-3,6-difluorophenyl)sulfonyl]-piperidine
1-[4-(2,5-dimethoxybenzyl)-1,3-thiazol-2-yl]-4-[(2,5-dibromo-3,6-difluorophenyl)sulfonyl]-piperidine
1-[4-(3,4-dimethoxybenzyl)-1,3-thiazol-2-yl]-4-[(2,5-dibromo-3,6-difluorophenyl)sulfonyl]-piperidine
1-[4-(3,5-dimethoxybenzyl)-1,3-thiazol-2-yl]-4-[(2,5-dibromo-3,6-difluorophenyl)sulfonyl]-piperidine
1-[4-(3,4-dichlorobenzyl)-1,3-thiazol-2-yl]-4-[(2,5-dibromo-3,6-difluorophenyl)sulfonyl]-piperidine
1-[4-(3,4-dimethylbenzyl)-1,3-thiazol-2-yl]-4-[(2,5-dibromo-3,6-difluorophenyl)sulfonyl]-piperidine
1-[4-(3,4-difluorobenzyl)-1,3-thiazol-2-yl]-4-[(2,5-dibromo-3,6-difluorophenyl)sulfonyl]-piperidine
1-[4-(3,5-difluorobenzyl)-1,3-thiazol-2-yl]-4-[(2,5-dibromo-3,6-difluorophenyl)sulfonyl]-piperidine
1-[4-(3,5-dichlorobenzyl)-1,3-thiazol-2-yl]-4-[(2,5-dibromo-3,6-difluorophenyl)sulfonyl]-piperidine
1-[4-(3,5-dimethylbenzyl)-1,3-thiazol-2-yl]-4-[(2,5-dibromo-3,6-difluorophenyl)sulfonyl]-piperidine
1-[4-(3-chloro-4-fluorobenzyl)-1,3-thiazol-2-yl]-4-[(2,5-dibromo-3,6-difluorophenyl)sulfonyl]-piperidine
1-[4-(3-chloro-5-fluorobenzyl)-1,3-thiazol-2-yl]-4-[(2,5-dibromo-3,6-difluorophenyl)sulfonyl]-piperidine
1-[4-(4-chloro-3-fluorobenzyl)-1,3-thiazol-2-yl]-4-[(2,5-dibromo-3,6-difluorophenyl)sulfonyl]-piperidine
1-[4-(3,4,5-trimethoxybenzyl)-1,3-thiazol-2-yl]-4-[(2,5-dibromo-3,6-difluorophenyl)sulfonyl]-piperidine
1-[4-(2,4,6-trimethylbenzyl)-1,3-thiazol-2-yl]-4-[(2,5-dibromo-3,6-difluorophenyl)sulfonyl]-piperidine
1-[4-benzyl-1,3-thiazol-2-yl]-4-[(5-bromo-2-methoxyphenyl)sulfonyl]-piperidine
1-[4-(2-methylbenzyl)-1,3-thiazol-2-yl]-4-[(5-bromo-2-methoxyphenyl)sulfonyl]-piperidine
1-[4-(2-methoxybenzyl)-1,3-thiazol-2-yl]-4-[(5-bromo-2-methoxyphenyl)sulfonyl]-piperidine
1-[4-(3-methylbenzyl)-1,3-thiazol-2-yl]-4-[(5-bromo-2-methoxyphenyl)sulfonyl]-piperidine
1-[4-(3-methoxybenzyl)-1,3-thiazol-2-yl]-4-[(5-bromo-2-methoxyphenyl)sulfonyl]-piperidine
1-[4-(3-bromobenzyl)-1,3-thiazol-2-yl]-4-[(5-bromo-2-methoxyphenyl)sulfonyl]-piperidine
1-[4-(4-chlorobenzyl)-1,3-thiazol-2-yl]-4-[(5-bromo-2-methoxyphenyl)sulfonyl]-piperidine
1-[4-(4-methoxybenzyl)-1,3-thiazol-2-yl]-4-[(5-bromo-2-methoxyphenyl)sulfonyl]-piperidine
1-[4-(4-methylbenzyl)-1,3-thiazol-2-yl]-4-[(5-bromo-2-methoxyphenyl)sulfonyl]-piperidine
1-[4-(4-ethylbenzyl)-1,3-thiazol-2-yl]-4-[(5-bromo-2-methoxyphenyl)sulfonyl]-piperidine
1-[4-(4-ethoxybenzyl)-1,3-thiazol-2-yl]-4-[(5-bromo-2-methoxyphenyl)sulfonyl]-piperidine
1-[4-(4-propylbenzyl)-1,3-thiazol-2-yl]-4-[(5-bromo-2-methoxyphenyl)sulfonyl]-piperidine
1-[4-(2,6-dimethylbenzyl)-1,3-thiazol-2-yl]-4-[(5-bromo-2-methoxyphenyl)sulfonyl]-piperidine
1-[4-(2,3-dimethylbenzyl)-1,3-thiazol-2-yl]-4-[(5-bromo-2-methoxyphenyl)sulfonyl]-piperidine
1-[4-(2,5-dimethylbenzyl)-1,3-thiazol-2-yl]-4-[(5-bromo-2-methoxyphenyl)sulfonyl]-piperidine
1-[4-(2,4-dichlorobenzyl)-1,3-thiazol-2-yl]-4-[(5-bromo-2-methoxyphenyl)sulfonyl]-piperidine
1-[4-(2,4-dimethoxybenzyl)-1,3-thiazol-2-yl]-4-[(5-bromo-2-methoxyphenyl)sulfonyl]-piperidine
1-[4-(2,5-dimethoxybenzyl)-1,3-thiazol-2-yl]-4-[(5-bromo-2-methoxyphenyl)sulfonyl]-piperidine
1-[4-(3,4-dimethoxybenzyl)-1,3-thiazol-2-yl]-4-[(5-bromo-2-methoxyphenyl)sulfonyl]-piperidine
1-[4-(3,5-dimethoxybenzyl)-1,3-thiazol-2-yl]-4-[(5-bromo-2-methoxyphenyl)sulfonyl]-piperidine
1-[4-(3,4-dichlorobenzyl)-1,3-thiazol-2-yl]-4-[(5-bromo-2-methoxyphenyl)sulfonyl]-piperidine
1-[4-(3,4-dimethylbenzyl)-1,3-thiazol-2-yl]-4-[(5-bromo-2-methoxyphenyl)sulfonyl]-piperidine
1-[4-(3,4-difluorobenzyl)-1,3-thiazol-2-yl]-4-[(5-bromo-2-methoxyphenyl)sulfonyl]-piperidine
1-[4-(3,5-difluorobenzyl)-1,3-thiazol-2-yl]-4-[(5-bromo-2-methoxyphenyl)sulfonyl]-piperidine
1-[4-(3,5-dichlorobenzyl)-1,3-thiazol-2-yl]-4-[(5-bromo-2-methoxyphenyl)sulfonyl]-piperidine
1-[4-(3,5-dimethylbenzyl)-1,3-thiazol-2-yl]-4-[(5-bromo-2-methoxyphenyl)sulfonyl]-piperidine
1-[4-(3-chloro-4-fluorobenzyl)-1,3-thiazol-2-yl]-4-[(5-bromo-2-methoxyphenyl)sulfonyl]-piperidine
1-[4-(3-chloro-5-fluorobenzyl)-1,3-thiazol-2-yl]-4-[(5-bromo-2-methoxyphenyl)sulfonyl]-piperidine
1-[4-(4-chloro-3-fluorobenzyl)-1,3-thiazol-2-yl]-4-[(5-bromo-2-methoxyphenyl)sulfonyl]-piperidine 1-[4-(3,4,5-trimethoxybenzyl)-1,3-thiazol-2-yl]-4-[(5-bromo-2-methoxyphenyl)sulfonyl]-piperidine
1-[4-(2,4,6-trimethylbenzyl)-1,3-thiazol-2-yl]-4-[(5-bromo-2-methoxyphenyl)sulfonyl]-piperidine
1-[4-benzyl-1,3-thiazol-2-yl]-4-[(4-bromo-2-chlorophenyl)sulfonyl]-piperidine
1-[4-(2-methylbenzyl)-1,3-thiazol-2-yl]-4-[(4-bromo-2-chlorophenyl)sulfonyl]-piperidine
1-[4-(2-methoxybenzyl)-1,3-thiazol-2-yl]-4-[(4-bromo-2-chlorophenyl)sulfonyl]-piperidine
1-[4-(3-methylbenzyl)-1,3-thiazol-2-yl]-4-[(4-bromo-2-chlorophenyl)sulfonyl]-piperidine
1-[4-(3-methoxybenzyl)-1,3-thiazol-2-yl]-4-[(4-bromo-2-chlorophenyl)sulfonyl]-piperidine
1-[4-(3-bromobenzyl)-1,3-thiazol-2-yl]-4-[(4-bromo-2-chlorophenyl)sulfonyl]-piperidine
1-[4-(4-chlorobenzyl)-1,3-thiazol-2-yl]-4-[(4-bromo-2-chlorophenyl)sulfonyl]-piperidine
1-[4-(4-methoxybenzyl)-1,3-thiazol-2-yl]-4-[(4-bromo-2-chlorophenyl)sulfonyl]-piperidine
1-[4-(4-methylbenzyl)-1,3-thiazol-2-yl]-4-[(4-bromo-2-chlorophenyl)sulfonyl]-piperidine
1-[4-(4-ethylbenzyl)-1,3-thiazol-2-yl]-4-[(4-bromo-2-chlorophenyl)sulfonyl]-piperidine
1-[4-(4-ethoxybenzyl)-1,3-thiazol-2-yl]-4-[(4-bromo-2-chlorophenyl)sulfonyl]-piperidine
1-[4-(4-propylbenzyl)-1,3-thiazol-2-yl]-4-[(4-bromo-2-chlorophenyl)sulfonyl]-piperidine
1-[4-(2,6-dimethylbenzyl)-1,3-thiazol-2-yl]-4-[(4-bromo-2-chlorophenyl)sulfonyl]-piperidine
1-[4-(2,3-dimethylbenzyl)-1,3-thiazol-2-yl]-4-[(4-bromo-2-chlorophenyl)sulfonyl]-piperidine
1-[4-(2,5-dimethylbenzyl)-1,3-thiazol-2-yl]-4-[(4-bromo-2-chlorophenyl)sulfonyl]-piperidine
1-[4-(2,4-dichlorobenzyl)-1,3-thiazol-2-yl]-4-[(4-bromo-2-chlorophenyl)sulfonyl]-piperidine
1-[4-(2,4-dimethoxylbenzyl)-1,3-thiazol-2-yl]-4-[(4-bromo-2-chlorophenyl)sulfonyl]-piperidine
1-[4-(2,5-dimethoxybenzyl)-1,3-thiazol-2-yl]-4-[(4-bromo-2-chlorophenyl)sulfonyl]-piperidine
1-[4-(3,4-dimethoxybenzyl)-1,3-thiazol-2-yl]-4-[(4-bromo-2-chlorophenyl)sulfonyl]-piperidine
1-[4-(3,5-dimethoxybenzyl)-1,3-thiazol-2-yl]-4-[(4-bromo-2-chlorophenyl)sulfonyl]-piperidine
1-[4-(3,4-dichlorobenzyl)-1,3-thiazol-2-yl]-4-[(4-bromo-2-chlorophenyl)sulfonyl]-piperidine
1-[4-(3,4-dimethylbenzyl)-1,3-thiazol-2-yl]-4-[(4-bromo-2-chlorophenyl)sulfonyl]-piperidine
1-[4-(3,4-difluorobenzyl)-1,3-thiazol-2-yl]-4-[(4-bromo-2-chlorophenyl)sulfonyl]-piperidine
1-[4-(3,5-difluorobenzyl)-1,3-thiazol-2-yl]-4-[(4-bromo-2-chlorophenyl)sulfonyl]-piperidine
1-[4-(3,5-dichlorobenzyl)-1,3-thiazol-2-yl]-4-[(4-bromo-2-chlorophenyl)sulfonyl]-piperidine
1-[4-(3,5-dimethylbenzyl)-1,3-thiazol-2-yl]-4-[(4-bromo-2-chlorophenyl)sulfonyl]-piperidine
1-[4-(3-chloro-4-fluorobenzyl)-1,3-thiazol-2-yl]-4-[(4-bromo-2-chlorophenyl)sulfonyl]-piperidine
1-[4-(3-chloro-5-fluorobenzyl)-1,3-thiazol-2-yl]-4-[(4-bromo-2-chlorophenyl)sulfonyl]-piperidine
1-[4-(4-chloro-3-fluorobenzyl)-1,3-thiazol-2-yl]-4-[(4-bromo-2-chlorophenyl)sulfonyl]-piperidine
1-[4-(3,4,5-trimethoxybenzyl)-1,3-thiazol-2-yl]-4-[(4-bromo-2-chlorophenyl)sulfonyl]-piperidine
1-[4-(2,4,6-trimethylbenzyl)-1,3-thiazol-2-yl]-4-[(4-bromo-2-chlorophenyl)sulfonyl]-piperidine
1-[4-benzyl-1,3-thiazol-2-yl]-4-[(5-chloro-2-methoxyphenyl)sulfonyl]-piperidine
1-[4-(2-methylbenzyl)-1,3-thiazol-2-yl]-4-[(5-chloro-2-methoxyphenyl)sulfonyl]-piperidine
1-[4-(2-methoxybenzyl)-1,3-thiazol-2-yl]-4-[(5-chloro-2-methoxyphenyl)sulfonyl]-piperidine
1-[4-(3-methylbenzyl)-1,3-thiazol-2-yl]-4-[(5-chloro-2-methoxyphenyl)sulfonyl]-piperidine
1-[4-(3-methoxylbenzyl)-1,3-thiazol-2-yl]-4-[(5-chloro-2-methoxyphenyl)sulfonyl]-piperidine
1-[4-(3-bromobenzyl)-1,3-thiazol-2-yl]-4-[(5-chloro-2-methoxyphenyl)sulfonyl]-piperidine
1-[4-(4-chlorobenzyl)-1,3-thiazol-2-yl]-4-[(5-chloro-2-methoxyphenyl)sulfonyl]-piperidine
1-[4-(4-methoxybenzyl)-1,3-thiazol-2-yl]-4-[(5-chloro-2-methoxyphenyl)sulfonyl]-piperidine
1-[4-(4-methylbenzyl)-1,3-thiazol-2-yl]-4-[(5-chloro-2-methoxyphenyl)sulfonyl]-piperidine
1-[4-(4-ethylbenzyl)-1,3-thiazol-2-yl]-4-[(5-chloro-2-methoxyphenyl)sulfonyl]-piperidine
1-[4-(4-ethoxybenzyl)-1,3-thiazol-2-yl]-4-[(5-chloro-2-methoxyphenyl)sulfonyl]-piperidine
1-[4-(4-propylbenzyl)-1,3-thiazol-2-yl]-4-[(5-chloro-2-methoxyphenyl)sulfonyl]-piperidine
1-[4-(2,6-dimethylbenzyl)-1,3-thiazol-2-yl]-4-[(5-chloro-2-methoxyphenyl)sulfonyl]-piperidine
1-[4-(2,3-dimethylbenzyl)-1,3-thiazol-2-yl]-4-[(5-chloro-2-methoxyphenyl)sulfonyl]-piperidine
1-[4-(2,5-dimethylbenzyl)-1,3-thiazol-2-yl]-4-[(5-chloro-2-methoxyphenyl)sulfonyl]-piperidine
1-[4-(2,4-dichlorobenzyl)-1,3-thiazol-2-yl]-4-[(5-chloro-2-methoxyphenyl)sulfonyl]-piperidine
1-[4-(2,4-dimethoxybenzyl)-1,3-thiazol-2-yl]-4-[(5-chloro-2-methoxyphenyl)sulfonyl]-piperidine
1-[4-(2,5-dimethoxybenzyl)-1,3-thiazol-2-yl]-4-[(5-chloro-2-methoxyphenyl)sulfonyl]-piperidine
1-[4-(3,4-dimethoxybenzyl)-1,3-thiazol-2-yl]-4-[(5-chloro-2-methoxyphenyl)sulfonyl]-piperidine
1-[4-(3,5-dimethoxybenzyl)-1,3-thiazol-2-yl]-4-[(5-chloro-2-methoxyphenyl)sulfonyl]-piperidine
1-[4-(3,4-dichlorobenzyl)-1,3-thiazol-2-yl]-4-[(5-chloro-2-methoxyphenyl)sulfonyl]-piperidine
1-[4-(3,4-dimethylbenzyl)-1,3-thiazol-2-yl]-4-[(5-chloro-2-methoxyphenyl)sulfonyl]-piperidine
1-[4-(3,4-difluorobenzyl)-1,3-thiazol-2-yl]-4-[(5-chloro-2-methoxyphenyl)sulfonyl]-piperidine
1-[4-(3,5-difluorobenzyl)-1,3-thiazol-2-yl]-4-[(5-chloro-2-methoxyphenyl)sulfonyl]-piperidine
1-[4-(3,5-dichlorobenzyl)-1,3-thiazol-2-yl]-4-[(5-chloro-2-methoxyphenyl)sulfonyl]-piperidine
1-[4-(3,5-dimethylbenzyl)-1,3-thiazol-2-yl]-4-[(5-chloro-2-methoxyphenyl)sulfonyl]-piperidine
1-[4-(3-chloro-4-fluorobenzyl)-1,3-thiazol-2-yl]-4-[(5-chloro-2-methoxyphenyl)sulfonyl]-piperidine
1-[4-(3-chloro-5-fluorobenzyl)-1,3-thiazol-2-yl]-4-[(5-chloro-2-methoxyphenyl)sulfonyl]-piperidine
1-[4-(4-chloro-3-fluorobenzyl)-1,3-thiazol-2-yl]-4-[(5-chloro-2-methoxyphenyl)sulfonyl]-piperidine
1-[4-(3,4,5-trimethoxybenzyl)-1,3-thiazol-2-yl]-4-[(5-chloro-2-methoxyphenyl)sulfonyl]-piperidine
1-[4-(2,4,6-trimethylbenzyl)-1,3-thiazol-2-yl]-4-[(5-chloro-2-methoxyphenyl)sulfonyl]-piperidine
1-[4-benzyl-1,3-thiazol-2-yl]-4-[(2-chloro-5-(trifluoromethyl)phenyl)sulfonyl]-piperidine
1-[4-(2-methylbenzyl)-1,3-thiazol-2-yl]-4-[(2-chloro-5-(trifluoromethyl)phenyl)sulfonyl]-piperidine 1-[4-(2-methoxybenzyl)-1,3-thiazol-2-yl]-4-[(2-chloro-5-(trifluoromethyl)phenyl)sulfonyl]-piperidine
1-[4-(3-methylbenzyl)-1,3-thiazol-2-yl]-4-[(2-chloro-5-(trifluoromethyl)phenyl)sulfonyl]-piperidine
1-[4-(3-methoxybenzyl)-1,3-thiazol-2-yl]-4-[(2-chloro-5-(trifluoromethyl)phenyl)sulfonyl]-piperidine
1-[4-(3-bromobenzyl)-1,3-thiazol-2-yl]-4-[(2-chloro-5-(trifluoromethyl)phenyl)sulfonyl]-piperidine
1-[4-(4-chlorobenzyl)-1,3-thiazol-2-yl]-4-[(2-chloro-5-(trifluoromethyl)phenyl)sulfonyl]-piperidine
1-[4-(4-methoxybenzyl)-1,3-thiazol-2-yl]-4-[(2-chloro-5-(trifluoromethyl)phenyl)sulfonyl]-piperidine
1-[4-(4-methylbenzyl)-1,3-thiazol-2-yl]-4-[(2-chloro-5-(trifluoromethyl)phenyl)sulfonyl]-piperidine
1-[4-(4-ethylbenzyl)-1,3-thiazol-2-yl]-4-[(2-chloro-5-(trifluoromethyl)phenyl)sulfonyl]-piperidine
1-[4-(4-ethoxybenzyl)-1,3-thiazol-2-yl]-4-[(2-chloro-5-(trifluoromethyl)phenyl)sulfonyl]-piperidine
1-[4-(4-propylbenzyl)-1,3-thiazol-2-yl]-4-[(2-chloro-5-(trifluoromethyl)phenyl)sulfonyl]-piperidine
1-[4-(2,6-dimethylbenzyl))-1,3-thiazol-2-yl]-4-[(2-chloro-5-(trifluoromethyl)phenyl)sulfonyl]-piperidine
1-[4-(2,3-dimethylbenzyl))-1,3-thiazol-2-yl]-4-[(2-chloro-5-(trifluoromethyl)phenyl)sulfonyl]-piperidine
1-[4-(2,5-dimethylbenzyl))-1,3-thiazol-2-yl]-4-[(2-chloro-5-(trifluoromethyl)phenyl)sulfonyl]-piperidine
1-[4-(2,4-dichlorobenzyl))-1,3-thiazol-2-yl]-4-[(2-chloro-5-(trifluoromethyl)phenyl)sulfonyl]-piperidine
1-[4-(2,4-dimethoxybenzyl))-1,3-thiazol-2-yl]-4-[(2-chloro-5-(trifluoromethyl)phenyl)sulfonyl]-piperidine
1-[4-(2,5-dimethoxybenzyl))-1,3-thiazol-2-yl]-4-[(2-chloro-5-(trifluoromethyl)phenyl)sulfonyl]-piperidine
1-[4-(3,4-dimethoxybenzyl))-1,3-thiazol-2-yl]-4-[(2-chloro-5-(trifluoromethyl)phenyl)sulfonyl]-piperidine
1-[4-(3,5-dimethoxybenzyl))-1,3-thiazol-2-yl]-4-[(2-chloro-5-(trifluoromethyl)phenyl)sulfonyl]-piperidine
1-[4-(3,4-dichlorobenzyl))-1,3-thiazol-2-yl]-4-[(2-chloro-5-(trifluoromethyl)phenyl)sulfonyl]-piperidine
1-[4-(3,4-dimethylbenzyl))-1,3-thiazol-2-yl]-4-[(2-chloro-5-(trifluoromethyl)phenyl)sulfonyl]-piperidine
1-[4-(3,4-difluorobenzyl)-1,3-thiazol-2-yl]-4-[(2-chloro-5-(trifluoromethyl)phenyl)sulfonyl]-piperidine
1-[4-(3,5-difluorobenzyl)-1,3-thiazol-2-yl]-4-[(2-chloro-5-(trifluoromethyl)phenyl)sulfonyl]-piperidine
1-[4-(3,5-dichlorobenzyl))-1,3-thiazol-2-yl]-4-[(2-chloro-5-(trifluoromethyl)phenyl)sulfonyl]-piperidine
1-[4-(3,5-dimethylbenzyl))-1,3-thiazol-2-yl]-4-[(2-chloro-5-(trifluoromethyl)phenyl)sulfonyl]-piperidine
1-[4-(3-chloro-4-fluorobenzyl))-1,3-thiazol-2-yl]-4-[(2-chloro-5-(trifluoromethyl)phenyl)sulfonyl]-piperidine
1-[4-(3-chloro-5-fluorobenzyl))-1,3-thiazol-2-yl]-4-[(2-chloro-5-(trifluoromethyl)phenyl)sulfonyl]-piperidine
1-[4-(4-chloro-3-fluorobenzyl))-1,3-thiazol-2-yl]-4-[(2-chloro-5-(trifluoromethyl)phenyl)sulfonyl]-piperidine
1-[4-(3,4,5-trimethoxybenzyl))-1,3-thiazol-2-yl]-4-[(2-chloro-5-(trifluoromethyl)phenyl)sulfonyl]-piperidine
1-[4-(2,4,6-trimethylbenzyl)-1,3-thiazol-2-yl]-4-[(2-chloro-5-(trifluoromethyl)phenyl)sulfonyl]-piperidine
1-[4-benzyl-1,3-thiazol-2-yl]-4-[(4-chloro-3-nitrophenyl)sulfonyl]-piperidine
1-[4-(2-methylbenzyl)-1,3-thiazol-2-yl]-4-[(4-chloro-3-nitrophenyl)sulfonyl]-piperidine
1-[4-(2-methoxybenzyl)-1,3-thiazol-2-yl]-4-[(4-chloro-3-nitrophenyl)sulfonyl]-piperidine
1-[4-(3-methylbenzyl)-1,3-thiazol-2-yl]-4-[(4-chloro-3-nitrophenyl)sulfonyl]-piperidine
1-[4-(3-methoxybenzyl)-1,3-thiazol-2-yl]-4-[(4-chloro-3-nitrophenyl)sulfonyl]-piperidine
1-[4-(3-bromobenzyl)-1,3-thiazol-2-yl]-4-[(4-chloro-3-nitrophenyl)sulfonyl]-piperidine
1-[4-(4-chlorobenzyl)-1,3-thiazol-2-yl]-4-[(4-chloro-3-nitrophenyl)sulfonyl]-piperidine
1-[4-(4-methoxybenzyl)-1,3-thiazol-2-yl]-4-[(4-chloro-3-nitrophenyl)sulfonyl]-piperidine
1-[4-(4-methylbenzyl)-1,3-thiazol-2-yl]-4-[(4-chloro-3-nitrophenyl)sulfonyl]-piperidine
1-[4-(4-ethylbenzyl)-1,3-thiazol-2-yl]-4-[(4-chloro-3-nitrophenyl)sulfonyl]-piperidine
1-[4-(4-ethoxybenzyl)-1,3-thiazol-2-yl]-4-[(4-chloro-3-nitrophenyl)sulfonyl]-piperidine
1-[4-(4-propylbenzyl)-1,3-thiazol-2-yl]-4-[(4-chloro-3-nitrophenyl)sulfonyl]-piperidine
1-[4-(2,6-dimethylbenzyl)-1,3-thiazol-2-yl]-4-[(4-chloro-3-nitrophenyl)sulfonyl]-piperidine
1-[4-(2,3-dimethylbenzyl)-1,3-thiazol-2-yl]-4-[(4-chloro-3-nitrophenyl)sulfonyl]-piperidine
1-[4-(2,5-dimethylbenzyl)-1,3-thiazol-2-yl]-4-[(4-chloro-3-nitrophenyl)sulfonyl]-piperidine
1-[4-(2,4-dichlorobenzyl)-1,3-thiazol-2-yl]-4-[(4-chloro-3-nitrophenyl)sulfonyl]-piperidine
1-[4-(2,4-dimethoxybenzyl)-1,3-thiazol-2-yl]-4-[(4-chloro-3-nitrophenyl)sulfonyl]-piperidine
1-[4-(2,5-dimethoxybenzyl)-1,3-thiazol-2-yl]-4-[(4-chloro-3-nitrophenyl)sulfonyl]-piperidine
1-[4-(3,4-dimethoxybenzyl)-1,3-thiazol-2-yl]-4-[(4-chloro-3-nitrophenyl)sulfonyl]-piperidine
1-[4-(3,5-dimethoxybenzyl)-1,3-thiazol-2-yl]-4-[(4-chloro-3-nitrophenyl)sulfonyl]-piperidine
1-[4-(3,4-dichlorobenzyl)-1,3-thiazol-2-yl]-4-[(4-chloro-3-nitrophenyl)sulfonyl]-piperidine
1-[4-(3,4-dimethylbenzyl)-1,3-thiazol-2-yl]-4-[(4-chloro-3-nitrophenyl)sulfonyl]-piperidine
1-[4-(3,4-difluorobenzyl)-1,3-thiazol-2-yl]-4-[(4-chloro-3-nitrophenyl)sulfonyl]-piperidine
1-[4-(3,5-difluorobenzyl)-1,3-thiazol-2-yl]-4-[(4-chloro-3-nitrophenyl)sulfonyl]-piperidine
1-[4-(3,5-dichlorobenzyl)-1,3-thiazol-2-yl]-4-[(4-chloro-3-nitrophenyl)sulfonyl]-piperidine
1-[4-(3,5-dimethylbenzyl)-1,3-thiazol-2-yl]-4-[(4-chloro-3-nitrophenyl)sulfonyl]-piperidine
1-[4-(3-chloro-4-fluorobenzyl)-1,3-thiazol-2-yl]-4-[(4-chloro-3-nitrophenyl)sulfonyl]-piperidine
1-[4-(3-chloro-5-fluorobenzyl)-1,3-thiazol-2-yl]-4-[(4-chloro-3-nitrophenyl)sulfonyl]-piperidine
1-[4-(4-chloro-3-fluorobenzyl)-1,3-thiazol-2-yl]-4-[(4-chloro-3-nitrophenyl)sulfonyl]-piperidine
1-[4-(3,4,5-trimethoxybenzyl)-1,3-thiazol-2-yl]-4-[(4-chloro-3-nitrophenyl)sulfonyl]-piperidine
1-[4-(2,4,6-trimethylbenzyl)-1,3-thiazol-2-yl]-4-[(4-chloro-3-nitrophenyl)sulfonyl]-piperidine
1-[4-benzyl-1,3-thiazol-2-yl]-4-[(2,4-dichloro-5-methylphenyl)sulfonyl]-piperidine
1-[4-(2-methylbenzyl)-1,3-thiazol-2-yl]-4-[(2,4-dichloro-5-methylphenyl)sulfonyl]-piperidine
1-[4-(2-methoxybenzyl)-1,3-thiazol-2-yl]-4-[(2,4-dichloro-5-methylphenyl)sulfonyl]-piperidine
1-[4-(3-methylbenzyl)-1,3-thiazol-2-yl]-4-[(2,4-dichloro-5-methylphenyl)sulfonyl]-piperidine
1-[4-(3-methoxybenzyl)-1,3-thiazol-2-yl]-4-[(2,4-dichloro-5-methylphenyl)sulfonyl]-piperidine
1-[4-(3-bromobenzyl)-1,3-thiazol-2-yl]-4-[(2,4-dichloro-5-methylphenyl)sulfonyl]-piperidine 1-[4-(4-chlorobenzyl)-1,3-thiazol-2-yl]-4-[(2,4-dichloro-5-methylphenyl)sulfonyl]-piperidine
1-[4-(4-methoxybenzyl)-1,3-thiazol-2-yl]-4-[(2,4-dichloro-5-methylphenyl)sulfonyl]-piperidine
1-[4-(4-methylbenzyl)-1,3-thiazol-2-yl]-4-[(2,4-dichloro-5-methylphenyl)sulfonyl]-piperidine
1-[4-(4-ethylbenzyl)-1,3-thiazol-2-yl]-4-[(2,4-dichloro-5-methylphenyl)sulfonyl]-piperidine
1-[4-(4-ethoxylbenzyl)-1,3-thiazol-2-yl]-4-[(2,4-dichloro-5-methylphenyl)sulfonyl]-piperidine
1-[4-(4-propylbenzyl)-1,3-thiazol-2-yl]-4-[(2,4-dichloro-5-methylphenyl)sulfonyl]-piperidine
1-[4-(2,6-dimethylbenzyl)-1,3-thiazol-2-yl]-4-[(2,4-dichloro-5-methylphenyl)sulfonyl]-piperidine
1-[4-(2,3-dimethylbenzyl)-1,3-thiazol-2-yl]-4-[(2,4-dichloro-5-methylphenyl)sulfonyl]-piperidine
1-[4-(2,5-dimethylbenzyl)-1,3-thiazol-2-yl]-4-[(2,4-dichloro-5-methylphenyl)sulfonyl]-piperidine
1-[4-(2,4-dichlorobenzyl)-1,3-thiazol-2-yl]-4-[(2,4-dichloro-5-methylphenyl)sulfonyl]-piperidine
1-[4-(2,4-dimethoxybenzyl)-1,3-thiazol-2-yl]-4-[(2,4-dichloro-5-methylphenyl)sulfonyl]-piperidine
1-[4-(2,5-dimethoxybenzyl)-1,3-thiazol-2-yl]-4-[(2,4-dichloro-5-methylphenyl)sulfonyl]-piperidine
1-[4-(3,4-dimethoxybenzyl)-1,3-thiazol-2-yl]-4-[(2,4-dichloro-5-methylphenyl)sulfonyl]-piperidine
1-[4-(3,5-dimethoxybenzyl)-1,3-thiazol-2-yl]-4-[(2,4-dichloro-5-methylphenyl)sulfonyl]-piperidine
1-[4-(3,4-dichlorobenzyl)-1,3-thiazol-2-yl]-4-[(2,4-dichloro-5-methylphenyl)sulfonyl]-piperidine
1-[4-(3,4-dimethylbenzyl)-1,3-thiazol-2-yl]-4-[(2,4-dichloro-5-methylphenyl)sulfonyl]-piperidine
1-[4-(3,4-difluorobenzyl)-1,3-thiazol-2-yl]-4-[(2,4-dichloro-5-methylphenyl)sulfonyl]-piperidine
1-[4-(3,5-difluorobenzyl)-1,3-thiazol-2-yl]-4-[(2,4-dichloro-5-methylphenyl)sulfonyl]-piperidine
1-[4-(3,5-dichlorobenzyl)-1,3-thiazol-2-yl]-4-[(2,4-dichloro-5-methylphenyl)sulfonyl]-piperidine
1-[4-(3,5-dimethylbenzyl)-1,3-thiazol-2-yl]-4-[(2,4-dichloro-5-methylphenyl)sulfonyl]-piperidine
1-[4-(3-chloro-4-fluorobenzyl)-1,3-thiazol-2-yl]-4-[(2,4-dichloro-5-methylphenyl)sulfonyl]-piperidine
1-[4-(3-chloro-5-fluorobenzyl)-1,3-thiazol-2-yl]-4-[(2,4-dichloro-5-methylphenyl)sulfonyl]-piperidine
1-[4-(4-chloro-3-fluorobenzyl)-1,3-thiazol-2-yl]-4-[(2,4-dichloro-5-methylphenyl)sulfonyl]-piperidine
1-[4-(3,4,5-trimethoxybenzyl)-1,3-thiazol-2-yl]-4-[(2,4-dichloro-5-methylphenyl)sulfonyl]-piperidine,
1-[4-(2,4,6-trimethylbenzyl)-1,3-thiazol-2-yl]-4-[(2,4-dichloro-5-methylphenyl)sulfonyl]-piperidine
1-[4-((4-methoxyphenypethyl)-1,3-thiazol-2-yl]-4-[(2,4-dichloro-5-methylphenyl)sulfonyl]-piperidine
1-[4-((4-nitrophenypethyl)-1,3-thiazol-2-yl]-4-[(2,4-dichloro-5-methylphenyl)sulfonyl]-piperidine
1-[4-(phenylvinyl)-1,3-thiazol-2-yl]-4-[(2,4-dichloro-5-methylphenyl)sulfonyl]-piperidine
1-[4-(4-chloro-3-fluorobenzyl)-1,3-thiazol-2-yl]4-[(5-chloro-4-nitrothiophen-2-yl)sulfonyl]-piperidine
1-[4-((4-methoxyphenypethyl)-1,3-thiazol-2-yl]-4-[(5-chloro-4-nitrothiophen-2-yl)sulfonyl]-piperidine
1-[4-((4-nitrophenypethyl)-1,3-thiazol-2-yl]-4-[(5-chloro-4-nitrothiophen-2-yl)sulfonyl]-piperidine
1-[4-(phenylvinyl)-1,3-thiazol-2-yl]4-[(5-chloro-4-nitrothiophen-2-yl)sulfonyl]-piperidine
1-[4-(4-chloro-3-fluorobenzyl)-1,3-thiazol-2-yl]-4-[(6-bromopyridin-3-yl)sulfonyl]-piperidine
1-[4-((4-methoxyphenypethyl)-1,3-thiazol-2-yl]-4-[(6-bromopyridin-3-yl)sulfonyl]-piperidine
1-[4-((4-nitrophenypethyl)-1,3-thiazol-2-yl]-4-[(6-bromopyridin-3-yl)sulfonyl]-piperidine
1-[4-(phenylvinyl)-1,3-thiazol-2-yl]4-[(5-methyl-1H-imidazol-2-yl)sulfonyl]-piperidine
1-[4-(4-chloro-3-fluorobenzyl)-1,3-thiazol-2-yl]-4-[(5-methyl-1H-imidazol-2-yl)sulfonyl]-piperidine
1-[4-((4-methoxyphenypethyl)-1,3-thiazol-2-yl]-4-[(5-methyl-1H-imidazol-2-yl)sulfonyl]-piperidine
1-[4-((4-nitrophenypethyl)-1,3-thiazol-2-yl]-4-[(5-methyl-1H-imidazol-2-yl)sulfonyl]-piperidine
1-[4-(phenylvinyl)-1,3-thiazol-2-yl]4-[(5-methyl-1H-imidazol-2-yl)sulfonyl]-piperidine
1-[4-(4-chloro-3-fluorobenzyl)-1,3-thiazol-2-yl]-4-[(2,4-dimethylpyrimidin-5-yl)sulfonyl]-piperidine
1-[4-((4-methoxyphenypethyl)-1,3-thiazol-2-yl]-4-[(2,4-dimethylpyrimidin-5-yl)sulfonyl]-piperidine
1-[4-((4-nitrophenypethyl)-1,3-thiazol-2-yl]-4-[(2,4-dimethylpyrimidin-5-yl)sulfonyl]-piperidine, and
1-[4-(phenylvinyl)-1,3-thiazol-2-yl]4-[(2,4-dimethylpyrimidin-5-yl)sulfonyl]-piperidine.

Such thiazolyl-piperidine derivatives are useful in the treatment of synucleopathies such as, but not limited to, Parkinson's disease, Down syndrome and Alzheimer's disease.

All publications, patents and patent applications are herein incorporated by reference in their entirety to the same extent as if each individual publication, patent or patent application was specifically and individually indicated to be incorporated by reference in its entirety.

Other embodiments are in the claims.

What is claimed is:
1. A thiazolyl-piperazine derivative represented by the structural formula (I)

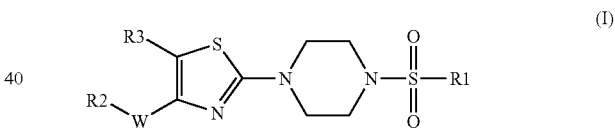

wherein:
W is a single bond or $CH_2$;
$R_1$ is a phenyl ring substituted with two or three halogens or with one or more substituents independently selected from the group consisting of $C_{1-6}$ alkyl, $C_{1-6}$ alkoxy and trifluoromethyl, or any two adjacent substituents of said phenyl ring form, together with the phenyl ring carbon atoms to which they are attached, a saturated ring fused to said phenyl ring and having 5 ring members, said saturated ring comprising one or two heteroatoms independently selected from the group consisting of oxygen and nitrogen; and each of said $C_{1-6}$ alkyl or $C_{1-6}$ alkoxy is optionally substituted with one or more halogen atoms; or $R_1$ is a monocyclic saturated or mono-unsaturated heterocyclyl having 5 or 6 members and comprising one or more atoms selected from the group consisting of nitrogen, oxygen, and sulfur and optionally substituted with one or more substituents independently selected from $R_8$ and $R_9$; or $R_1$ is a monocyclic polyunsaturated heterocyclyl having 5 or 6 members and comprising one or more atoms selected from the group consisting of nitrogen and oxygen and optionally substituted with one or more substituents independently selected from $R_8$ and $R_9$;

$R_2$ is a phenyl ring optionally substituted with one or more substituents independently selected from the group consisting of $C_{1-6}$ alkyl, $C_{1-6}$ alkoxy, trifluoromethyl and halogen; or any two adjacent substituents of said phenyl ring form, together with the phenyl ring carbon atoms to which they are attached, a saturated ring fused to said phenyl ring and having 5 ring members, said saturated ring comprising one or two heteroatoms independently selected from the group consisting of oxygen and nitrogen; and each of said $C_{1-6}$ alkyl and $C_{1-6}$ alkoxy is optionally substituted with one or more halogen atoms, or $R_2$ is a monocyclic heterocyclyl having 5 or 6 members and comprising one or more atoms selected from the group consisting of nitrogen, oxygen, and sulfur and optionally substituted with one or more substituents independently selected from $R_8$ and $R_9$, said heterocyclyl including more than one oxygen atom or including one or more heteroatoms selected from the group consisting of nitrogen and sulfur;

$R_3$ is hydrogen;

each $R_8$ is independently selected from the group consisting of $C_{1-10}$ alkyl and $C_{1-6}$ alkoxy; and each $R_9$ is independently selected from the group consisting of OH, $NO_2$ and halogen, or a stereoisomer thereof, or an enantiomer thereof, or a N-oxide thereof, or a pharmaceutically acceptable salt thereof, provided that said derivative is not:

1-[4-(4-fluorophenyl)-1,3-thiazol-2-yl]-4-[(4-methoxyphenyl)sulfonyl]-piperazine; or 1-[4-(4-fluorophenyl)-1,3-thiazol-2-yl]-4-[(4-methylphenyl)sulfonyl]-piperazine.

2. A thiazolyl-piperazine derivative selected from the group listed in the following table:

| Compound | chemical name |
|---|---|
| 10 | 1-(4-methoxyphenylsulfonyl)-4-(4-(thiophen-2-ylmethyl)thiazol-2-yl)piperazine |
| 11 | 1-(4-(4-methylbenzyl)thiazol-2-yl)-4-(4-methoxyphenylsulfonyl)piperazine |
| 12 | 3-((2-(4-(4-methoxyphenylsulfonyl)piperazin-1-yl)thiazol-4-yl)methyl)benzonitrile |
| 13 | 1-(4-(3-fluorobenzyl)thiazol-2-yl)-4-(4-methoxyphenylsulfonyl)piperazine |
| 14 | 1-(4-(4-methoxybenzyl)thiazol-2-yl)-4-(4-methoxyphenylsulfonyl)piperazine |
| 15 | 1-(4-(2-methoxybenzyl)thiazol-2-yl)-4-(4-methoxyphenylsulfonyl)piperazine |
| 16 | 1-(4-(3-methoxybenzyl)thiazol-2-yl)-4-(2-methoxyphenylsulfonyl)piperazine |
| 17 | 1-(4-(3-methoxybenzyl)thiazol-2-yl)-4-(3-methoxyphenylsulfonyl)piperazine |
| 18 | 1-(4-(benzo[d][1,3]dioxol-5-ylmethyl)thiazol-2-yl)-4-(4-methoxyphenylsulfonyl)piperazine |
| 19 | 1-(4-(3-methoxybenzyl)thiazol-2-yl)-4-(benzo[d][1,3]dioxol-5-ylsulfonyl)piperazine |
| 20 | 1-(4-(3-methoxybenzyl)thiazol-2-yl)-4-(pyridin-3-ylsulfonyl)piperazine |
| 21 | 1-(4-(3-methoxybenzyl)thiazol-2-yl)-4-(pyridin-2-ylsulfonyl)piperazine |
| 22 | 1-(4-(3-methoxybenzyl)thiazol-2-yl)-4-(thiophen-3-ylsulfonyl)piperazine |
| 23 | 1-(4-(3-methoxybenzyl)thiazol-2-yl)-4-(3,5-dimethyl-1H-pyrazol-4-ylsulfonyl)piperazine |
| 24 | 4-(4-(4-(3-methoxybenzyl)thiazol-2-yl)piperazin-1-ylsulfonyl)-1-methyl-1H-indole |
| 25 | 1-(4-(3-methoxybenzyl)thiazol-2-yl)-4-(3,5-dimethylisoxazol-4-ylsulfonyl)piperazine |
| 26 | 1-(4-(3-methoxybenzyl)thiazol-2-yl)-4-(1-methyl-1H-imidazol-4-ylsulfonyl)piperazine |
| 27 | N-(4-(4-(4-(3-methoxybenzyl)thiazol-2-yl)piperazin-1-ylsulfonyl)phenyl)acetamide |
| 28 | 1-(4-(3-methoxybenzyl)thiazol-2-yl)-4-tosylpiperazine |
| 29 | 4-(4-(4-(3-methoxybenzyl)thiazol-2-yl)piperazin-1-ylsulfonyl)benzonitrile |
| 30 | 1-(4-(3-methoxybenzyl)thiazol-2-yl)-4-(4-fluorophenylsulfonyl)piperazine |
| 49 | 1-(4-methoxyphenylsulfonyl)-4-(4-(pyridin-4-yl)thiazol-2-yl)piperazine |
| 54 | 1-(4-(4-fluorophenyl)thiazol-2-yl)-4-(pyridin-3-ylsulfonyl)piperazine |
| 55 | 1-(4-(4-fluorophenyl)thiazol-2-yl)-4-(3,5-dimethyl-1H-pyrazol-4-ylsulfonyl)piperazine |
| 77 | 4-(4-(4-(2-methoxyphenyl)thiazol-2-yl)piperazin-1-ylsulfonyl)-1-methyl-1H-indole. |

3. A pharmaceutical composition comprising one or more pharmaceutically acceptable excipients and a therapeutically effective amount of a thiazolyl-piperazine derivative represented by the structural formula (I)

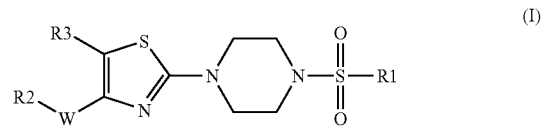

wherein:
W is a single bond or $CH_2$;
$R_1$ is a phenyl ring substituted with one or more substituents independently selected from the group consisting of $C_{1-6}$ alkyl, $C_{1-6}$ alkoxy, trifluoromethyl and halogen; or any two adjacent substituents of said phenyl ring form, together with the phenyl ring carbon atoms to which they are attached, a saturated ring fused to said phenyl ring and having 5 ring members, said saturated ring comprising one or two heteroatoms independently selected from the group consisting of oxygen and nitrogen; and each of said $C_{1-6}$ alkyl and $C_{1-6}$ alkoxy is optionally substituted with one or more halogen atoms; or $R_1$ is a monocyclic heterocyclyl having 5 or 6 members and comprising one or more atoms selected from the group consisting of nitrogen, oxygen and sulfur and optionally substituted with one or more substituents independently selected from $R_8$ and $R_9$;

$R_2$ is a phenyl ring optionally substituted with one or more substituents independently selected from the group consisting of $C_{1-6}$ alkyl, $C_{1-6}$ alkoxy, trifluoromethyl and halogen; or any two adjacent substituents of said phenyl ring form, together with the phenyl ring carbon atoms to which they are attached, a saturated ring fused to said phenyl ring and having 5 ring members, said saturated ring comprising one or two heteroatoms independently selected from the group consisting of oxygen and nitrogen; and each of said $C_{1-6}$ alkyl and $C_{1-6}$ alkoxy is optionally substituted with one or more halogen atoms, or $R_2$ is a monocyclic heterocyclyl having 5 or 6 members and comprising one or more atoms selected from the group consisting of nitrogen, oxygen and sulfur and optionally substituted with one or more substituents independently selected from $R_8$ and $R_9$, said heterocyclyl including more than one oxygen atom or including one or more heteroatoms selected from the group consisting of nitrogen and sulfur;

$R_3$ is hydrogen;

each $R_8$ is independently selected from the group consisting of $C_{1-10}$ alkyl and $C_{1-8}$ alkoxy; and each $R_9$ is independently selected from the group consisting of OH, $NO_2$ and halogen, or a stereoisomer thereof, or an enantiomer thereof, or a N-oxide thereof, or a pharmaceutically acceptable salt thereof.

4. A pharmaceutical composition comprising one or more pharmaceutically acceptable excipients and a therapeutically effective amount of a thiazolyl-piperazine derivative selected from the group listed in the following table:

| Compound | chemical name |
| --- | --- |
| 10 | 1-(4-methoxyphenylsulfonyl)-4-(4-(thiophen-2-ylmethyl)thiazol-2-yl)piperazine |
| 11 | 1-(4-(4-methylbenzyl)thiazol-2-yl)-4-(4-methoxyphenylsulfonyl)piperazine |
| 12 | 3-((2-(4-(4-methoxyphenylsulfonyl)piperazin-1-yl)thiazol-4-yl)methyl)benzonitrile |
| 13 | 1-(4-(3-fluorobenzyl)thiazol-2-yl)-4-(4-methoxyphenylsulfonyl)piperazine |
| 14 | 1-(4-(4-methoxybenzyl)thiazol-2-yl)-4-(4-methoxyphenylsulfonyl)piperazine |
| 15 | 1-(4-(2-methoxybenzyl)thiazol-2-yl)-4-(4-methoxyphenylsulfonyl)piperazine |
| 16 | 1-(4-(3-methoxybenzyl)thiazol-2-yl)-4-(2-methoxyphenylsulfonyl)piperazine |
| 17 | 1-(4-(3-methoxybenzyl)thiazol-2-yl)-4-(3-methoxyphenylsulfonyl)piperazine |
| 18 | 1-(4-(benzo[d][1,3]dioxol-5-ylmethyl)thiazol-2-yl)-4-(4-methoxyphenylsulfonyl)piperazine |
| 19 | 1-(4-(3-methoxybenzyl)thiazol-2-yl)-4-(benzo[d][1,3]dioxol-5-ylsulfonyl)piperazine |
| 20 | 1-(4-(3-methoxybenzyl)thiazol-2-yl)-4-(pyridin-3-ylsulfonyl)piperazine |
| 21 | 1-(4-(3-methoxybenzyl)thiazol-2-yl)-4-(pyridin-2-ylsulfonyl)piperazine |
| 22 | 1-(4-(3-methoxybenzyl)thiazol-2-yl)-4-(thiophen-3-ylsulfonyl)piperazine |
| 23 | 1-(4-(3-methoxybenzyl)thiazol-2-yl)-4-(3,5-dimethyl-1H-pyrazol-4-ylsulfonyl)piperazine |
| 24 | 4-(4-(4-(3-methoxybenzyl)thiazol-2-yl)piperazin-1-ylsulfonyl)-1-methyl-1H-indole |
| 25 | 1-(4-(3-methoxybenzyl)thiazol-2-yl)-4-(3,5-dimethylisoxazol-4-ylsulfonyl)piperazine |
| 26 | 1-(4-(3-methoxybenzyl)thiazol-2-yl)-4-(1-methyl-1H-imidazol-4-ylsulfonyl)piperazine |
| 27 | N-(4-(4-(4-(3-methoxybenzyl)thiazol-2-yl)piperazin-1-ylsulfonyl)phenyl)acetamide |
| 28 | 1-(4-(3-methoxybenzyl)thiazol-2-yl)-4-tosylpiperazine |
| 29 | 4-(4-(4-(3-methoxybenzyl)thiazol-2-yl)piperazin-1-ylsulfonyl)benzonitrile |
| 30 | 1-(4-(3-methoxybenzyl)thiazol-2-yl)-4-(4-fluorophenylsulfonyl)piperazine |
| 33 | Methyl 2-(4-(4-(4-p-tolylthiazol-2-yl)piperazin-1-ylsulfonyl)phenoxy)acetate |
| 34 | N-(4-(4-(4-phenylthiazol-2-yl)piperazin-1-ylsulfonyl)phenethyl)acetamide |
| 35 | 1-(4-fluorophenylsulfonyl)-4-(4-(3-methoxyphenyl)thiazol-2-yl)piperazine |
| 36 | 1-(2,5-dimethoxyphenylsulfonyl)-4-(4-phenylthiazol-2-yl)piperazine |
| 37 | 1-(4-(4-chlorophenyl)thiazol-2-yl)-4-(2,5-dimethoxyphenylsulfonyl)piperazine |
| 38 | 1-(3,4-dimethoxyphenylsulfonyl)-4-(4-(4-methoxyphenyl)thiazol-2-yl)piperazine |
| 39 | 1-(2,5-dimethoxyphenylsulfonyl)-4-(4-(4-methoxyphenyl)thiazol-2-yl)piperazine |

-continued

| Compound | chemical name |
|---|---|
| 40 | 1-(4-(4-fluorophenyl)thiazol-2-yl)-4-(4-fluorophenylsulfonyl)piperazine |
| 41 | 1-(4-chlorophenylsulfonyl)-4-(4-(4-fluorophenyl)thiazol-2-yl)piperazine |
| 42 | 1-(4-bromophenylsulfonyl)-4-(4-(4-fluorophenyl)thiazol-2-yl)piperazine |
| 43 | 1-(2-bromophenylsulfonyl)-4-(4-(4-fluorophenyl)thiazol-2-yl)piperazine |
| 44 | 1-(4-phenylthiazol-2-yl)-4-tosylpiperazine |
| 45 | 1-(4-(4-fluorophenyl)thiazol-2-yl)-4-tosylpiperazine |
| 46 | 1-(4-(4-fluorophenyl)thiazol-2-yl)-4-(4-methoxyphenylsulfonyl)piperazine |
| 47 | 1-((4-(4-fluorophenyl)thiazol-2-yl)methyl)-4-(4-methoxyphenylsulfonyl)piperazine |
| 49 | 1-(4-methoxyphenylsulfonyl)-4-(4-(pyridin-4-yl)thiazol-2-yl)piperazine |
| 50 | 1-(5-fluoro-2-methoxyphenylsulfonyl)-4-(4-(4-methylphenyl)thiazol-2-yl)piperazine |
| 51 | 1-(4-fluoro-2-methoxyphenylsulfonyl)-4-(4-(4-methylphenyl)thiazol-2-yl)piperazine |
| 52 | 1-(4-methoxy-3-(5H-tetrazol-5-yl)phenylsulfonyl)-4-(4-phenylthiazol-2-yl)piperazine |
| 53 | 1-(4-methoxy-3-(5H-tetrazol-5-yl)phenylsulfonyl)-4-(4-p-tolylthiazol-2-yl)piperazine |
| 54 | 1-(4-(4-fluorophenyl)thiazol-2-yl)-4-(pyridin-3-ylsulfonyl)piperazine |
| 55 | 1-(4-(4-fluorophenyl)thiazol-2-yl)-4-(3,5-dimethyl-1H-pyrazol-4-ylsulfonyl)piperazine |
| 56 | 1-(5-chlorothiophen-2-ylsulfonyl)-4-(4-phenylthiazol-2-yl)piperazine |
| 57 | 1-(thiophen-2-ylsulfonyl)-4-(4-(4-methoxyphenyl)thiazol-2-yl)piperazine |
| 58 | 1-(thiophen-2-ylsulfonyl)-4-(4-(4-chlorophenyl)thiazol-2-yl)piperazine |
| 59 | 1-(thiophen-2-ylsulfonyl)-4-(4-(2-nitrophenyl)thiazol-2-yl)piperazine |
| 60 | 1-(thiophen-2-ylsulfonyl)-4-(4-(4-nitrophenyl)thiazol-2-yl)piperazine |
| 61 | 1-(4-phenylthiazol-2-yl)-4-(pyrrolidin-1-ylsulfonyl)piperazine |
| 62 | 1-(4-(4-methylphenyl)thiazol-2-yl)-4-(pyrrolidin-1-ylsulfonyl)piperazine |
| 63 | 1-(4-(4-methoxyphenyl)thiazol-2-yl)-4-(pyrrolidin-1-ylsulfonyl)piperazine |
| 64 | 4-(4-(4-phenylthiazol-2-yl)piperazin-1-ylsulfonyl)pyrrolidin-2-one |
| 65 | 1-(4-(4-phenylthiazol-2-yl)piperazin-1-ylsulfonyl)pyrrolidin-2-one |
| 66 | 4-(4-(4-(4-fluorophenyl)thiazol-2-yl)piperazin-1-ylsulfonyl)pyrrolidin-2-one |
| 67 | 4-(4-(5-methyl-4-phenylthiazol-2-yl)piperazin-1-ylsulfonyl)pyrrolidin-2-one |
| 68 | 1-(4-phenyl-5-propylthiazol-2-yl)-4-tosylpiperazine |
| 69 | 1-(2,3-dihydrobenzo[b][1,4]dioxin-6-ylsulfonyl)-4-(4-phenylthiazol-2-yl)piperazine |
| 70 | 1-(2,3-dihydrobenzo[b][1,4]dioxin-6-ylsulfonyl)-4-(4-(4-methoxyphenyl)thiazol-2-yl)piperazine |
| 71 | 1-(2,3-dihydrobenzo[b][1,4]dioxin-6-ylsulfonyl)-4-(4-(4-nitrophenyl)thiazol-2-yl)piperazine |
| 72 | 1-(2,3-dihydrobenzo[b][1,4]dioxin-6-ylsulfonyl)-4-(4-(3-nitrophenyl)thiazol-2-yl)piperazine |
| 73 | 3-methyl-5-(4-(4-phenylthiazol-2-yl)piperazin-1-ylsulfonyl)benzo[d]oxazol-2(3H)-one |
| 74 | 4-(4-(4-(4-fluorophenyl)thiazol-2-yl)piperazin-1-ylsulfonyl)benzo[c][1,2,5]oxadiazole |
| 75 | 1-(4-(4-chlorophenyl)thiazol-2-yl)-4-(naphthalen-2-ylsulfonyl)piperazine |
| 76 | 1-(4-(4-fluorophenyl)thiazol-2-yl)-4-(naphthalen-1-ylsulfonyl)piperazine |
| 77 | 4-(4-(4-(2-methoxyphenyl)thiazol-2-yl)piperazin-1-ylsulfonyl)-1-methyl-1H-indole |
| 78 | 1-(4-(thiophen-2-yl)thiazol-2-yl)-4-tosylpiperazine. |

5. A thiazolyl-piperazine derivative according to claim 1, wherein W is a single bond and $R_2$ is not substituted in ortho position with respect to the thiazolyl ring.

6. A thiazolyl-piperazine derivative according to claim 1, wherein $R_1$ is phenyl substituted with $C_{1-6}$ alkyl or $C_{1-6}$ alkoxy in para position with respect to the sulfonyl moiety.

7. A thiazolyl-piperazine derivative according to claim 5, wherein $R_1$ is phenyl substituted with $C_{1-6}$ alkyl or $C_{1-6}$ alkoxy in para position with respect to the sulfonyl moiety.

8. A pharmaceutical composition according to claim 3, wherein W is a single bond and $R_2$ is not substituted in ortho position with respect to the thiazolyl ring.

9. A pharmaceutical composition according to claim 3, wherein $R_1$ is phenyl substituted with $C_{1-6}$ alkyl or $C_{1-6}$ alkoxy in para position with respect to the sulfonyl moiety.

10. A pharmaceutical composition according to claim 8, wherein $R_1$ is phenyl substituted with $C_{1-6}$ alkyl or $C_{1-6}$ alkoxy in para position with respect to the sulfonyl moiety.

11. A thiazolyl-piperazine derivative according to claim 1, wherein W is $CH_2$ and $R_2$ is a substituted phenyl ring.

12. A pharmaceutical composition according to claim 3, wherein W is $CH_2$ and $R_2$ is a substituted phenyl ring.

13. A N-sulfonyl heterocyclic derivative selected from the group listed in the following table:

| Compound | chemical name |
|---|---|
| 32 | 1-((4-(3-methoxybenzyl)thiazol-2-yl)methyl)-4-(4-methoxyphenylsulfonyl)piperazine |
| 47 | 1-((4-(4-fluorophenyl)thiazol-2-yl)methyl)-4-(4-methoxyphenylsulfonyl)piperazine. |

14. A pharmaceutical composition comprising one or more pharmaceutically acceptable excipients and a therapeutically effective amount of a N-sulfonyl heterocyclic derivative represented by the structural formula (IV)

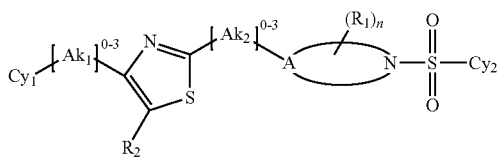

wherein:
A is N and the divalent group schematically represented by the structural formula (G)

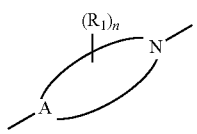

is selected from the group consisting of piperazine, 2-piperazinone, 2,6-piperazinedione, 2-phenylpiperazine, 2-vinylpiperazine, 2-ethynylpiperazine, 2-(methoxymethyl)-pipera-zine, 2-(phenoxymethyl)piperazine, 2-(hexyloxymethyl)piperazine, 2-(dodecyloxy-methyl)piperazine, 2-[(1-methyl-ethoxy)methyl]piperazine, 2-(3-methyl-2-thienyl)-piperazine, 2-(fluoromethyl)piperazine, 2-(2-furanyl)piperazine, 2-(5-methyl-2-furanyl)-piperazine, 2-(2-benzofuranyl)piperazine, 2-(3,5-dimethyl-2-furanyl)-piperazine, 2-(3-thienyl)piperazine, 2-(4-methyl-2-thienyl)piperazine, 2-(5-methyl-2-thienyl)piperazine, 2-(2,5-dimethyl-3-thienyl)piperazine, 2-(1H-pyrrol-1-ylmethyl)piperazine and 3-(1-methyl-1H-pyrazol-3-yl)-piperazine;

each $R_1$ is independently selected from the group consisting of $C_{1-4}$ alkyl;

n is 0, 1, or 2;

$R_2$ is hydrogen or $C_{1-6}$ alkyl;

$Ak_1$ and $Ak_2$ are independently selected from the group consisting of a single bond, methylene ($CH_2$), bis-methylene ($CH_2$—$CH_2$) and vinylene (CH=CH);

$Cy_1$ is a phenyl ring optionally substituted with one or more substituents independently selected from the group consisting of $C_{1-6}$ alkyl, $C_{1-6}$ alkoxy, and halogen; or any two adjacent substituents of said phenyl ring form, together with the phenyl ring carbon atoms to which they are attached, a saturated ring fused to said phenyl ring and having 5 ring members, said saturated ring comprising one or two heteroatoms independently selected from the group consisting of O and N; and each of said $C_{1-6}$ alkyl or $C_{1-6}$ alkoxy is optionally substituted with one or more substituents selected from the group consisting of $C_{1-6}$ alkyl, oxo and halogen; or $Cy_1$ is a monocyclic heterocyclyl having 5 or 6 members and comprising one or more atoms selected from the group consisting of nitrogen, oxygen and sulfur and optionally substituted with one or more $R_3$, said heterocyclyl including more than one oxygen atom or including one or more heteroatoms selected from the group consisting of nitrogen and sulfur;

$Cy_2$ is a phenyl ring substituted with two or three halogens or with one or more substituents independently selected from the group consisting of $C_{1-6}$ alkyl and $C_{1-6}$ alkoxy; or any two adjacent substituents of said phenyl ring form, together with the phenyl ring carbon atoms to which they are attached, a saturated ring fused to said phenyl ring and having 5 ring members, said saturated ring comprising one or two heteroatoms independently selected from the group consisting of O and N; and each of said $C_{1-6}$ alkyl and $C_{1-6}$ alkoxy is optionally substituted with one or more halogen; and each $R_3$ is independently selected from the group consisting of $C_{1-6}$ alkyl, $C_{1-6}$ alkoxy, hydroxyl, cyano and halogen;

or a stereoisomer thereof, or an enantiomer thereof, or a N-oxide thereof, or a pharmaceutically acceptable salt thereof.

15. A pharmaceutical composition comprising one or more pharmaceutically acceptable excipients and a therapeutically effective amount of a N-sulfonyl heterocyclic derivative according to claim 13.

* * * * *

UNITED STATES PATENT AND TRADEMARK OFFICE
CERTIFICATE OF CORRECTION

Page 1 of 1

PATENT NO.       : 8,722,681 B2
APPLICATION NO.  : 12/701361
DATED            : May 13, 2014
INVENTOR(S)      : Griffioen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this
Eleventh Day of August, 2015

Michelle K. Lee
*Director of the United States Patent and Trademark Office*